US008597923B2

(12) United States Patent
Ness et al.

(10) Patent No.: US 8,597,923 B2
(45) **Date of Patent: *Dec. 3, 2013**

(54) **OXIDATION OF COMPOUNDS USING GENETICALLY MODIFIED *CANDIDA***

(75) Inventors: Jon E. Ness, Redwood City, CA (US); Jeremy Minshull, Palo Alto, CA (US)

(73) Assignee: SyntheZyme, LLC, Brooklyn, NY (US)

(*) Notice: Subject to any disclaimer, the term of this patent is extended or adjusted under 35 U.S.C. 154(b) by 498 days.

This patent is subject to a terminal disclaimer.

(21) Appl. No.: 12/775,306

(22) Filed: May 6, 2010

(65) Prior Publication Data

US 2010/0291653 A1 Nov. 18, 2010

Related U.S. Application Data

(63) Continuation-in-part of application No. 12/436,729, filed on May 6, 2009, now Pat. No. 8,158,391.

(60) Provisional application No. 61/176,064, filed on May 6, 2009.

(51) Int. Cl.

| | |
|---|---|
| ***C12P 7/64*** | (2006.01) |
| ***C12P 1/02*** | (2006.01) |
| ***C12N 9/00*** | (2006.01) |
| ***C12N 1/00*** | (2006.01) |
| ***C12N 15/00*** | (2006.01) |
| ***C12N 15/74*** | (2006.01) |
| ***C07H 21/04*** | (2006.01) |

(52) U.S. Cl.
USPC ...... 435/171; 435/134; 435/183; 435/254.22; 435/320.1; 435/471

(58) Field of Classification Search
None
See application file for complete search history.

(56) References Cited

U.S. PATENT DOCUMENTS

| | | | |
|---|---|---|---|
| 5,254,466 A | 10/1993 | Picataggio et al. | |
| 5,849,524 A | 12/1998 | Kondo et al. | |
| 8,158,391 B2 * | 4/2012 | Gross et al. | 435/134 |
| 2003/0233675 A1 | 12/2003 | Cao et al. | |

FOREIGN PATENT DOCUMENTS

| | | |
|---|---|---|
| JP | 07059576 A | 8/1993 |

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Seffernick et al. J Bacteriol. Apr. 2001; 183 (8): 2405-10.*
ISA/US, PCT Invitation to Pay Additional Fees and, Where Applicable, Protest Fee dated Feb. 11, 2011 for PCT/US10/01361.
Eschenfeldt et al., "Transformation of Fatty Acids Catalyzed by Cytochrome P450 Monooxygenase Enzymes of *Candida tropicalis," Applied and Environmental Microbiology*, 2003;69:5992-5999.
Kusunose et al., "Enzymatic *w* -Oxidation of Fatty Acids," *The Journal of Biological Chemistry*, 1964;239:2135-2139.
Mukherjee et al., "Alcohol Dehydrogenase Restricts the Ability of the Pathogen *Candida albicans* To Form a Biofilm on Catheter Surfaces through an Ethanol-Based Mechanism," *Infection and Immunity*, Jul. 2006;74(7):3804-3816.
NCBI, "adhA4 NADP-dependent alcohol dehydrogenase [*Streptomyces avermitilis* MA-4680]," retrieved from the internet Feb. 8, 2011 from <http://www.ncbi.nim.nih.gov/sites/entrez>.
Okazaki et al., "Two acyl-coenzyme A oxidases in peroxisomes of the yeast *Candida tropicalis*: Primary structures deduced from genomic DNA sequence," *Proc. Natl. Acad. Sci. USA*, 1986; 83:1232-1236.
Umemura et al., "A novel promoter, derived from the isocitrate lyase gene of *Candida tropicalis*, inducible with acetate in *Saccharomyces cerevisae*," Appl Microbiol Biotechnol., Jul. 1995;43(3):489-92 (Abstract only from PubMed).
Waché et al., "role of β-Oxidation Enzymes in γ-Declactone Production by the Yeast *Yarrowia lipolytica," Applied and Environmental Microbiology*, 2001; 67:5700-5704.

* cited by examiner

*Primary Examiner* — Christian Fronda
(74) *Attorney, Agent, or Firm* — Laurence P. Colton; Smith Risley Tempel Santos LLC

(57) ABSTRACT

A substantially pure *Candida* host cell is provided for the biotransformation of a substrate to a product wherein the host cell is characterized by a first genetic modification class that comprises one or more genetic modifications that collectively or individually disrupt at least one alcohol dehydrogenase gene in the substantially pure *Candida* host cell.

23 Claims, 28 Drawing Sheets

Figure 1:
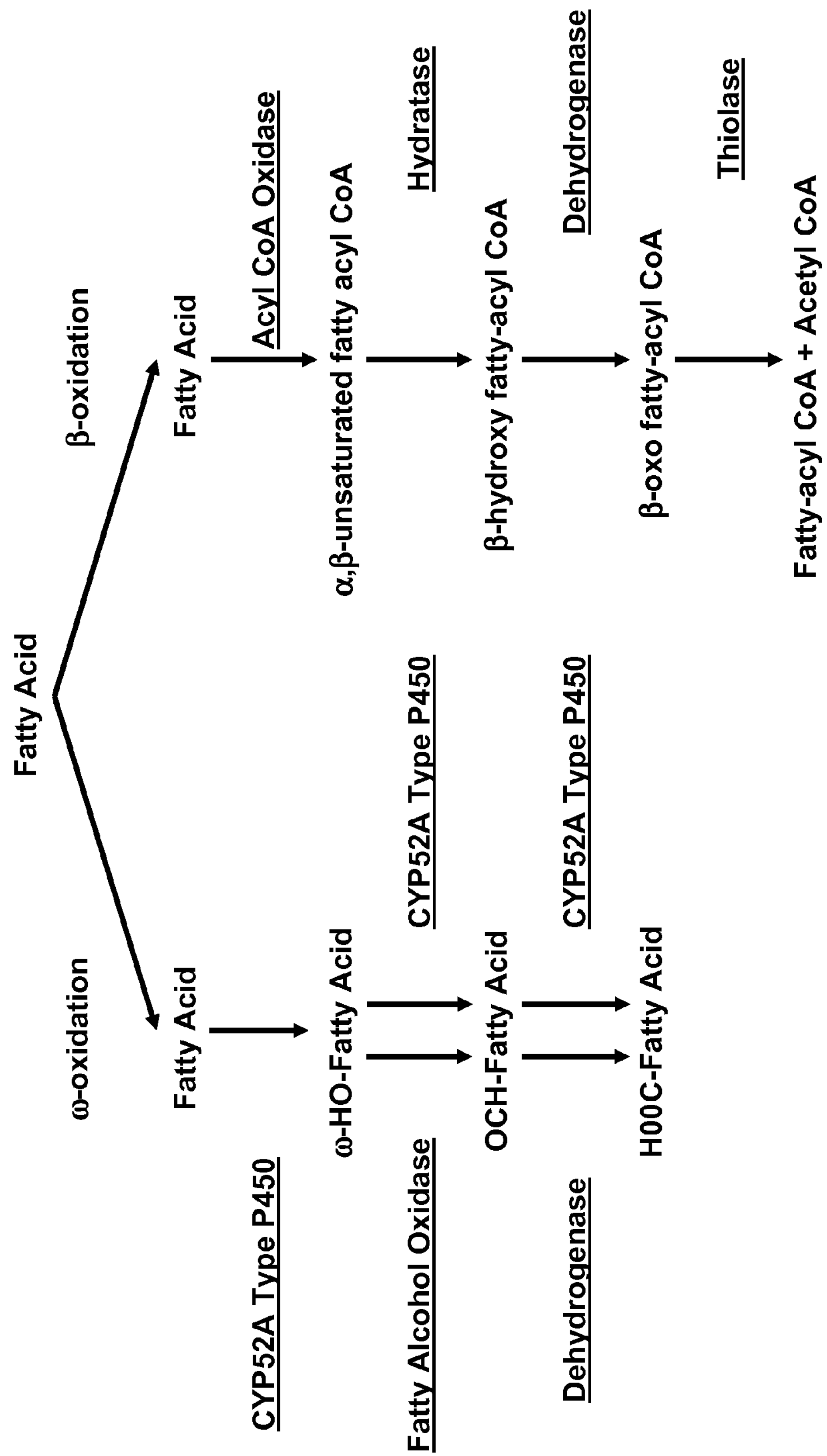

```
C.albicans_ADH_1A          MQASLFRIFRGASLTTTTAAASFTATATAGATTAKTLSGSTVLRKSYKRTYSSSVLSSPE
C.albicans_ADH_1B          MEARFFRIFKGGSLTTTTAAASFTATATAGATTAKTLSGSTVLRKSYKRTYSSSVLSSPE
C.tropicalis_ADH_A4        ------------------------------------------------------------
C.albicans_ADH_2A          ------------------------------------------------------------
C.albicans_ADH_2B          ------------------------------------------------------------
C.tropicalis_ADH_B4        ------------------------------------------------------------
C.tropicalis_ADH_A10       ------------------------------------------------------------
C.tropicalis_ADH_B11       ------------------------------------------------------------

C.albicans_ADH_1A          LFFFHQFNNNKRYCHTTTTTNTKTIMSEQIPKTQKAVVFDTNGGQLVYKDYPVPTPKPNE
C.albicans_ADH_1B          LFFFHQFNNNKRYCHTTTTTNTKTIMSEQIPKTQKAVVFDTNGGQLVYKDYPVPTPKPNE
C.tropicalis_ADH_A4        --------------------------------------------ELEYKDIPVPTPKANE
C.albicans_ADH_2A          ---------------------------MSVPTTQKAVIFETNGGKLEYKDIPVPKPKANE
C.albicans_ADH_2B          ---------------------------MSVPTTQKAVIFETNGGKLEYKDIPVPKPKANE
C.tropicalis_ADH_B4        --------------------------------------------KLEYKDIPVPKPKPNE
C.tropicalis_ADH_A10       --------------------------------------------KLEYKDVPVPVPKPNE
C.tropicalis_ADH_B11       --------------------------------------------PLQYTDIPVPVPKPNE
                                     * *.* *** **.**

C.albicans_ADH_1A          LLIHVKYSGVCHTDLHAWKGDWPLATKLPLVGGHEGAGVVVGMGENVKGWKIGDFAGIKW
C.albicans_ADH_1B          LLINVKYSGVCHTDLHAWKGDWPLATKLPLVGGHEGAGVVVGMGENVKGWKIGDFAGIKW
C.tropicalis_ADH_A4        LLINVKYSGVCHTDLHAWKGDWPLATKLPLVGGHEGAGVVVGMGENVKGWKIGDFAGIKW
C.albicans_ADH_2A          LLINVKYSGVCHTDLHAWKGDWPLATKLPLVGGHEGAGVVVALGENVKGWKVGDYAGVKW
C.albicans_ADH_2B          LLINVKYSGVCHTDLHAWKGDWPLATKLPLVGGHEGAGVVVALGENVKGWKVGDYAGVKW
C.tropicalis_ADH_B4        LLINVKYSGVCHTDLHAWKGDWPLDTKLPLVGGHEGAGVVVAIGDNVKGWKVGDLAGVKW
C.tropicalis_ADH_A10       LLVNVKYSGVCHSDLHVWKGDWPIPAKLPLVGGHEGAGVVVGMGDNVKGWKVGDLAGIKW
C.tropicalis_ADH_B11       LLVHVKYSGVCHSDIHVWKGDWFPASKLPVVGGHEGAGVVVAIGENVQGWKVGDLAGIKM
             **::********:*:*.*****    :***:***********.:*:**:***:** **:*

C.albicans_ADH_1A          LNGSCMSCEFCQQGAEPNCGEADLSGYTHDGSFEQYATADAVQAAKIPAGTDLANVAPIL
C.albicans_ADH_1B          LNGSCMSCEFCQQGAEPNCGEADLSGYTHDGSFEQYATADAVQAAKIPAGTDLANVAPIL
C.tropicalis_ADH_A4        LNGSCMSCEFCQQGAEPNCGEADLSGYTHDGSFEQYATADAVQAARIPAGTDLAEVAPIL
C.albicans_ADH_2A          LNGSCLNCEYCQSGAEPNCAEADLSGYTHDGSFQQYATADAVQAARIPAGTDLANVAPIL
C.albicans_ADH_2B          LNGSCLNCEYCQSGAEPNCAEADLSGYTHDGSFQQYATADAVQAARIPAGTDLANVAPIL
C.tropicalis_ADH_B4        LNGSCMNCEYCQQGAEPNCPQADLSGYTHDGSFQQYATADAVQAARIPAGTDLANVAPIL
C.tropicalis_ADH_A10       LNGSCMNCEFCQQGAEPNCSRADMSGYTHDGTFQQYATADAVQAAKIPEGADMASIAPIL
C.tropicalis_ADH_B11       LNGSCMNCEYCQQGAEPNCPHADVSGYSHDGTFQQYATADAVQAAKFPAGSDLASIAPIS
             *****:.**:**.****** .**:***:***:*:***********::* *:*:*.:***

C.albicans_ADH_1A          CAGVTVYKALKTADLAAGQWVAISGAGGGLGSLAVQYARAMGLRVVAIDGGDEKGEFVKS
C.albicans_ADH_1B          CAGVTVYKALKTADLAAGQWVAISGAGGGLGSLAVQYARAMGLRVVAIDGGDEKGEFVKS
C.tropicalis_ADH_A4        CAGVTVYKALKTADLAAGQWVAISGAGGGLGSLAVQYAVAMGLRVVAIDGGDEKGAFVKS
C.albicans_ADH_2A          CAGVTVYKALKTAELEAGQWVAISGAAGGLGSLAVQYAKAMGYRVLAIDGGEDKGEFVKS
C.albicans_ADH_2B          CAGVTVYKALKTAELEAGQWVAISGAAGGLGSLAVQYAKAMGYRVLAIDGGEDKGEFVKS
```

Figure 3A

```
C.tropicalis_ADH_B4       CAGVTVYKALKTADLQPGQWVAISGAAGGLGSLAVQYAKAMGYRVVAIDGGADKGEFVKS
C.tropicalis_ADH_A10      CAGVTVYKALKNADLLAGQWVAISGAGGGLGSLGVQYAKAMGYRVLAIDGGDERGEFVKS
C.tropicalis_ADH_B11      CAGVTVYKALKTAGLQPGQWVAISGAAGGLGSLAVQYAKAMGLRVVAIDGGDERGVFVKS
                          ***********.* * .*********.******.**** *** **:***** ::* ****

C.albicans_ADH_1A         LGAEAYVDFTKDKDIVEAVKKATDGGPHGAINVSVSEKAIDQSVEYVRPLGKVVLVGLPA
C.albicans_ADH_1B         LGAEAYVDFTKDKDIVEAVKKATDGGPHGAINVSVSEKAIDQSVEYVRPLGKVVLVGLPA
C.tropicalis_ADH_A4       LGAEAYIDFLKEKDIVSAVKKATDGGPHGAINVSVSEKAIDQSVEYVRPLGKVVLVGLPA
C.albicans_ADH_2A         LGAETFIDFTKEKDVVEAVKKATNGGPHGVINVSVSERAIGQSTEYVRTLGKVVLVGLPA
C.albicans_ADH_2B         LGAETFIDFTKEKDVVEAVKKATNGGPHGVINVSVSERAIGQSTEYVRTLGKVVLVGLPA
C.tropicalis_ADH_B4       LGAEVFVDFLKEKDIVGAVKKATDGGPHGAVNVSISEKAINQSVDYVRTLGKVVLVGLPA
C.tropicalis_ADH_A10      LGAEVYIDFLKEQDIVSAIRKATGGGPHGVINVSVSEKAINQSVEYVRTLGKVVLVSLPA
C.tropicalis_ADH_B11      LGAEVFVDFTKEANVSEAIIKATDGGAHGVINVSISEKAINQSVEYVRTLGTVVLVGLPA
                          ****.::** *: ::  *: ***.**.**.:***:**:**.**.:***.**.****.***

C.albicans_ADH_1A         HAKVTAPVFDAVVKSIEIKGSYVGNRKDTAEAIDFFSRGLIKCPIKIVGLSDLPEVFKLM
C.albicans_ADH_1B         HAKVTAPVFDAVVKSIEIKGSYVGNRKDTAEAIDFFSRGLIKCPIKIVGLSDLPEVFKLM
C.tropicalis_ADH_A4       GSKVTAGVFEAVVKSIEIKGSYVGNRKDTAEAVDFFSRGLIKCPIKIVGLSELPQVFKLM
C.albicans_ADH_2A         GAKISTPVFDAVIKTIQIKGSYVGNRKDTAEAVDFFTRGLIKCPIKIVGLSELPEVYKLM
C.albicans_ADH_2B         GAKISTPVFDAVIKTIQIKGSYVGNRKDTAEAVDFFTRGLIKCPIKIVGLSELPEVYKLM
C.tropicalis_ADH_B4       GSKVSAPVFDSVVKSIQIKGSYVGNRKDTAEAVDFFSRGLIKCPIKVVGLSELPEVYKLM
C.tropicalis_ADH_A10      GGKLTAPLFESVARSIQIRTTCVGNRKDTTEAIDFFVRGLIDCPIKVAGLSEVPEIFDLM
C.tropicalis_ADH_B11      GAKLEAPIFNAVAKSIQIKGSYVGNRRDTAEAVDFFARGLVKCPIKVVGLSELPEIFKLL
                           .*: : :*::* ::*:*: : ****:**:**:*** ***:.****:.***::*:::.*:

        C.albicans_ADH_1A         EEGKILSRYVLDTS- SEQ ID NO:172
        C.albicans_ADH_1B         EEGKILGRYVLDTSK SEQ ID NO:173
        C.tropicalis_ADH_A4       --------------- SEQ ID NO:155
        C.albicans_ADH_2A         EEGKILGRYVLDNDK SEQ ID NO:174
        C.albicans_ADH_2B         EEGKILGRYVLDNDK SEQ ID NO:175
        C.tropicalis_ADH_B4       --------------- SEQ ID NO:154
        C.tropicalis_ADH_A10      --------------- SEQ ID NO:152
        C.tropicalis_ADH_B11      --------------- SEQ ID NO:151
```

Figure 3B

Targeting sequence

Selective marker

Targeting sequence

Figure 11

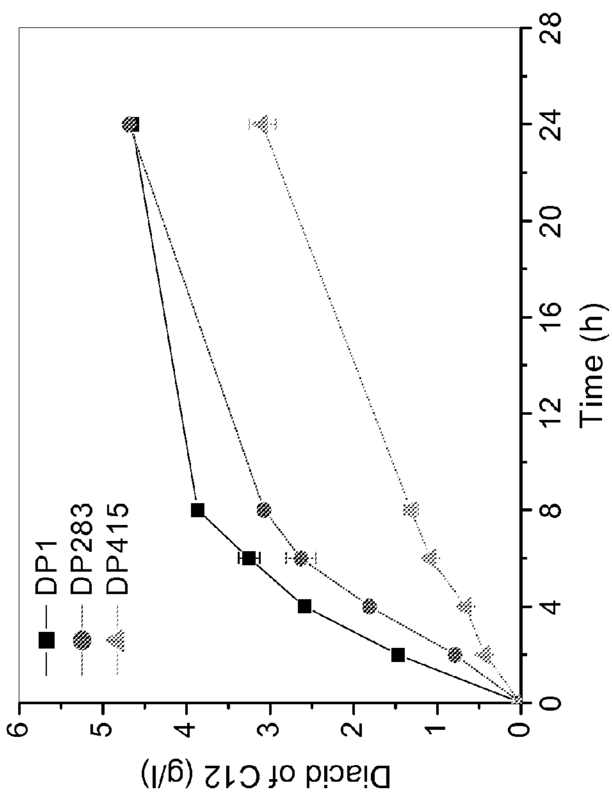
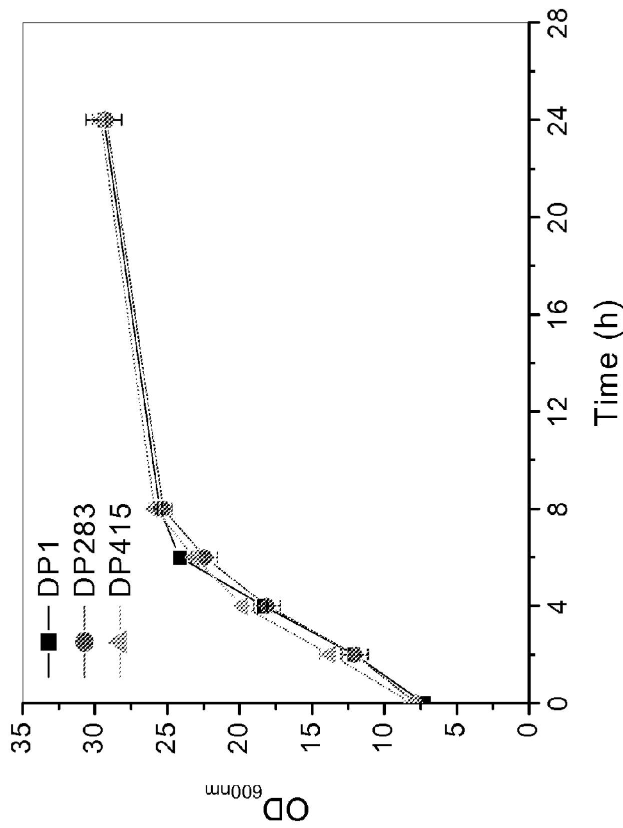
Figure 19

OXIDATION OF COMPOUNDS USING GENETICALLY MODIFIED *CANDIDA*

RELATED APPLICATIONS

This application is a continuation-in-part of U.S. patent application Ser. No. 12/436,729, entitled "BIOSYNTHETIC ROUTES TO LONG-CHAIN ALPHA, OMEGA-HYDROXYACIDS, DIACIDS AND THEIR CONVERSION TO OLIGOMERS AND POLYMERS," filed May 6, 2009 now U.S. Pat. No. 8,158,391. This application also claims priority to U.S. Provisional Patent Application No. 61/176,064, entitled "BIOSYNTHETIC ROUTES TO ENERGY RICH MOLECULES USING GENETICALLY MODIFIED *CANDID,* " filed May 6, 2009. The disclosures of the above-referenced applications are incorporated by reference herein in their entirety.

STATEMENT REGARDING FEDERALLY SPONSORED RESEARCH OR DEVELOPMENT

This invention was made with government support under grant number DAAD19-03-1-0091, W911QY-04-C-0082 and NBCH1070004 awarded by the Defense Advanced Research Projects Agency (DARPA) to Richard A. Gross. The United States Government has certain rights in this invention.

SEQUENCE LISTING

This application includes a Sequence Listing submitted as filename Sequence_Listing__11548__024__999.TXT, of size 323,000 bytes, created May 6, 2010. The Sequence Listing is incorporated by reference herein in its entirety.

1. FIELD

Methods for biological production of α,ω-hydroxyacids using genetically modified strains of the yeast *Candida* are provided. Also provided are methods for the genetic modification of the yeast *Candida*. Also provided are DNA constructs for removal of genes that can interfere with the production of energy rich molecules by *Candida*. Also provided are DNA constructs for insertion of genes for expression into the *Candida* genome.

2. BACKGROUND

Genes that encode proteins that catalyze chemical transformations of alkanes, alkenes, fatty acids, fatty alcohols, fatty aldehydes, aldehydes and alcohols may aid in the biosynthesis of energy rich molecules, or in the conversion of such compounds to compounds better suited to specific applications. Such molecules include hydrocarbons (alkane, alkene and isoprenoid), fatty acids, fatty alcohols, fatty aldehydes, esters, ethers, lipids, triglycerides, and waxes, and can be produced from plant derived substrates, such as plant cell walls (lignocellulose, cellulose, hemicellulose, and pectin) starch, and sugar. These molecules are of particular interest as potential sources of energy from biological sources, and thus as possible replacements from energy sources derived from crude oil and its distillates. These molecules are also of interest as potential sources of chemical intermediates, and thus as possible replacements for chemicals derived from crude oil and its distillates.

Yeasts from the genus *Candida* are industrially important, they tolerate high concentrations of fatty acids and hydrocarbons in their growth media and have been used to produce long chain fatty diacids (Picataggio et al. (1992), Biotechnology (NY): 10, 894-8.) However they frequently lack enzymes that would facilitate conversion of plant cell wall material (cellulose, hemicellulose, pectins and lignins) into sugar monomers for use in biofuel production. Methods for addition of genes encoding proteins capable of catalyzing such conversion into the *Candida* genome are thus of commercial interest. Further, because yeasts do not always contain enzymatic systems for uptake and metabolism of all of the sugar monomers derived from plant cell wall material, genes encoding enzymes that enable *Candida* to utilize sugars that it does not normally use, and methods for adding these genes to the *Candida* genome, are thus of commercial interest.

Currently, α,ω-dicarboxylic acids are almost exclusively produced by chemical conversion processes. However, the chemical processes for production of α,ω-dicarboxylic acids from non-renewable petrochemical feedstocks usually produces numerous unwanted byproducts, requires extensive purification and gives low yields (Picataggio et al., 1992, Bio/Technology 10, 894-898). Moreover, α,ω-dicarboxylic acids with carbon chain lengths greater than 13 are not readily available by chemical synthesis. While several chemical routes to synthesize long-chain α,ω-dicarboxylic acids are available, their synthesis is difficult, costly and requires toxic reagents. Furthermore, most methods result in mixtures containing shorter chain lengths. Furthermore, other than four-carbon α,ω-unsaturated diacids (e.g. maleic acid and fumaric acid), longer chain unsaturated α,ω-dicarboxylic acids or those with other functional groups are currently unavailable since chemical oxidation cleaves unsaturated bonds or modifies them resulting in cis-trans isomerization and other byproducts.

Many microorganisms have the ability to produce α,ω-dicarboxylic acids when cultured in n-alkanes and fatty acids, including *Candida tropicalis, Candida cloacae, Cryptococcus neoforman* and *Corynebacterium* sp. (Shiio et al., 1971, Agr. Biol. Chem. 35, 2033-2042; Hill et al., 1986, Appl. Microbiol. Biotech. 24: 168-174; and Broadway et al., 1993, J. Gen. Microbiol. 139, 1337-1344). *Candida tropicalis* and similar yeasts are known to produce α,ω-dicarboxylic acids with carbon lengths from C12 to C22 via an ω-oxidation pathway. The terminal methyl group of n-alkanes or fatty acids is first hydroxylated by a membrane-bound enzyme complex consisting of cytochrome P450 monooxygenase and associated NADPH cytochrome reductase that is the rate-limiting step in the ω-oxidation pathway. Two additional enzymes, the fatty alcohol oxidase and fatty aldehyde dehydrogenase, further oxidize the alcohol to create ω-aldehyde acid and then the corresponding α,ω-dicarboxylic acid (Eschenfeldt et al., 2003, Appl. Environ. Microbiol. 69, 5992-5999). However, there is also a β-oxidation pathway for fatty acid oxidation that exists within *Candida tropicalis*. Both fatty acids and α,ω-dicarboxylic acids in wild type *Candida tropicalis* are efficiently degraded after activation to the corresponding acyl-CoA ester through the β-oxidation pathway, leading to carbon-chain length shortening, which results in the low yields of α,ω-dicarboxylic acids and numerous byproducts.

Mutants of *C. tropicalis* in which the β-oxidation of fatty acids is impaired may be used to improve the production of α,ω-dicarboxylic acids (Uemura et al., 1988, J. Am. Oil. Chem. Soc. 64, 1254-1257; and Yi et al., 1989, Appl. Microbiol. Biotech. 30, 327-331). Recently, genetically modified strains of the yeast *Candida tropicalis* have been developed to increase the production of α,ω-dicarboxylic acids. An engineered *Candida tropicalis* (Strain H5343, ATCC No. 20962)

with the POX4 and POX5 genes that code for enzymes in the first step of fatty acid β-oxidation disrupted was generated so that it can prevent the strain from metabolizing fatty acids, which directs the metabolic flux toward ω-oxidation and results in the accumulation of α,ω-dicarboxylic acids (FIG. 3). See U.S. Pat. No. 5,254,466 and Picataggio et al., 1992, Bio/Technology 10: 894-898, each of which is hereby incorporated by reference herein. Furthermore, by introduction of multiple copies of cytochrome P450 and reductase genes into *C. tropicalis* in which the β-oxidation pathway is blocked, the *C. tropicalis* strain AR40 was generated with increased ω-hydroxylase activity and higher specific productivity of diacids from long-chain fatty acids. See, Picataggio et al., 1992, Bio/Technology 10: 894-898 (1992); and U.S. Pat. No. 5,620,878, each of which is hereby incorporated by reference herein. Genes encoding proteins that catalyze chemical transformations of alkanes, alkenes, fatty acids, fatty alcohols, fatty aldehydes, aldehydes and alcohols may also reduce the usefulness of these compounds as energy sources, for example by oxidizing them or further metabolizing them. Methods for identifying and eliminating from the *Candida* genome genes encoding enzymes that oxidize or metabolize alkanes, alkenes, fatty acids, fatty alcohols, fatty aldehydes, aldehydes and alcohols are thus of commercial interest. For example fatty alcohols cannot be prepared using any described strain of *Candida* because the hydroxy fatty acid is oxidized to form a dicarboxylic acid, which has reduced energy content relative to the hydroxy fatty acid. Furthermore, neither the general classes nor the specific sequences of the *Candida* enzymes responsible for the oxidation from hydroxy fatty acids to dicarboxylic acids have been identified. There is therefore a need in the art for methods to prevent the oxidation of hydroxy fatty acids to diacids during fermentative production.

3. SUMMARY

Methods for the genetic modification of *Candida* species to produce strains improved for the production of biofuels are disclosed. Methods by which yeast strains may be engineered by the addition or removal of genes to modify the oxidation of compounds of interest as biofuels are disclosed. Enzymes to facilitate conversion of plant cell wall material (cellulose, hemicellulose, pectins and lignins) into sugar monomers and enzymes to enable *Candida* to utilize such sugars for use in biofuel production and methods for addition of genes encoding such enzymes into the *Candida* genome are disclosed.

One embodiment provides a substantially pure *Candida* host cell for the production of an α-carboxyl-ω-hydroxy fatty acid having a carbon chain length in the range from C6 to C22, an α,ω-dicarboxylic fatty acid having a carbon chain length in the range from C6 to C22, or mixtures thereof. The *Candida* host cell is characterized by a first genetic modification class and a second genetic modification class. The first genetic modification class comprises one or more genetic modifications that disrupt the β-oxidation pathway in the substantially pure *Candida* host cell. The second genetic modification class comprises one or more genetic modifications that collectively or individually disrupt at least one gene in the substantially pure *Candida* host cell selected from the group consisting of a CYP52A type cytochrome P450, a fatty alcohol oxidase, and an alcohol dehydrogenase.

Another embodiment provides a method for producing an α-carboxyl-ω-hydroxy fatty acid having a carbon chain length in the range from C6 to C22, an α,ω-dicarboxylic fatty acid having a carbon chain length in the range from C6 to C22, or mixtures thereof in a *Candida* host cell. The method comprises (A) making one or more first genetic modifications in a first genetic modification class to the *Candida* host cell. The method further comprises (B) making one or more second genetic modifications in a second genetic modification class to the *Candida* host cell, where steps (A) and (B) collectively form a genetically modified *Candida* host cell. The method further comprises (C) producing an α-carboxyl-ω-hydroxy fatty acid having a carbon chain length in the range from C6 to C22, an α,ω-dicarboxylic fatty acid having a carbon chain length in the range from C6 to C22, or mixtures thereof, by fermenting the genetically modified *Candida* host cell in a culture medium comprising a nitrogen source, an organic substrate having a carbon chain length in the range from C6 to C22, and a cosubstrate. Here, the first genetic modification class comprises one or more genetic modifications that disrupt the β-oxidation pathway of the *Candida* host cell. Also, the second genetic modification class comprises one or more genetic modifications that collectively or individually disrupt at least one gene selected from the group consisting of a CYP52A type cytochrome P450, a fatty alcohol oxidase, and an alcohol dehydrogenase in the *Candida* host cell.

One embodiment provides a substantially pure *Candida* host cell for the production of energy rich molecules. The *Candida* host cell is characterized by a first genetic modification class and a second genetic modification class. The first genetic modification class comprises one or more genetic modifications that collectively or individually disrupt at least one gene in the substantially pure *Candida* host cell selected from the group consisting of a fatty alcohol oxidase, and an alcohol dehydrogenase. The second genetic modification class comprises one or more genetic modifications that collectively or individually add to the host cell genome at least one gene selected from the group consisting of a lipase, a cellulase, a ligninase or a cytochrome P450 that is not identical to a naturally occurring counterpart gene in the *Candida* host cell; or a lipase, a cellulase, a ligninase or a cytochrome P450 that is expressed under control of a promoter other than the promoter that controls expression of the naturally occurring counterpart gene in the *Candida* host cell.

One embodiment provides a substantially pure *Candida* host cell for the biotransformation of organic molecules. The *Candida* host cell is characterized by a first genetic modification class and a second genetic modification class. The first genetic modification class comprises one or more genetic modifications that collectively or individually disrupt at least one alcohol dehydrogenase gene in the substantially pure *Candida* host cell. The second genetic modification class comprises one or more genetic modifications that collectively or individually add to the host cell genome at least one gene that is not identical to a naturally occurring counterpart gene in the *Candida* host cell; or at least one gene that is identical to a naturally occurring counterpart gene in the *Candida* host cell, but that is expressed under control of a promoter other than the promoter that controls expression of the naturally occurring counterpart gene in the *Candida* host cell.

In some embodiments the first genetic modification class comprises disruption of at least one alcohol dehydrogenase gene selected from the group consisting of ADH-A4, ADH-A4B, ADH-B4, ADH-B4B, ADH-A10, ADH-A10B, ADH-B11 and ADH-B11B.

In some embodiments the first genetic modification class comprises disruption of at least one alcohol dehydrogenase gene whose nucleotide sequence is at least 95% identical to a stretch of at least 50, at least 60, at least 70, at least 80, at least 90, at least 100, at least 110 at least 120 contiguous nucleotides of SEQ ID NO: 39, SEQ ID NO: 40, SEQ ID NO: 42, SEQ ID NO: 43, or SEQ ID NO: 56, or at least 90% identical to a stretch of at least 50, at least 60, at least 70, at least 80, at least 90, at least 100, at least 110 at least 120 contiguous nucleotides of SEQ ID NO: 39, SEQ ID NO: 40, SEQ ID NO: 42, SEQ ID NO: 43, or SEQ ID NO: 56, or at least 85% identical to a stretch of at least 50, at least 60, at least 70, at least 80, at least 90, at least 100, at least 110 at least 120 contiguous nucleotides of SEQ ID NO: 39, SEQ ID NO: 40, SEQ ID NO: 42, SEQ ID NO: 43, or SEQ ID NO: 56, or at least 80% identical to a stretch of at least 50, at least 60, at least 70, at least 80, at least 90, at least 100, at least 110 at least 120 contiguous nucleotides of SEQ ID NO: 39, SEQ ID NO: 40, SEQ ID NO: 42, SEQ ID NO: 43, or SEQ ID NO: 56, or at least 75% identical to a stretch of at least 50, at least 60, at least 70, at least 80, at least 90, at least 100, at least 110 at least 120 contiguous nucleotides of SEQ ID NO: 39, SEQ ID NO: 40, SEQ ID NO: 42, SEQ ID NO: 43, or SEQ ID NO: 56, or at least 70% identical to a stretch of at least 50, at least 60, at least 70, at least 80, at least 90, at least 100, at least 110 at least 120 contiguous nucleotides of SEQ ID NO: 39, SEQ ID NO: 40, SEQ ID NO: 42, SEQ ID NO: 43, or SEQ ID NO: 56, or at least 65% identical to a stretch of at least 50, at least 60, at least 70, at least 80, at least 90, at least 100, at least 110 at least 120 contiguous nucleotides of SEQ ID NO: 39, SEQ ID NO: 40, SEQ ID NO: 42, SEQ ID NO: 43, or SEQ ID NO: 56, or at least 60% identical to a stretch of at least 50, at least 60, at least 70, at least 80, at least 90, at least 100, at least 110 at least 120 contiguous nucleotides of SEQ ID NO: 39, SEQ ID NO: 40, SEQ ID NO: 42, SEQ ID NO: 43, or SEQ ID NO: 56, or at least 50% identical to a stretch of at least 50, at least 60, at least 70, at least 80, at least 90, at least 100, at least 110 at least 120 contiguous nucleotides of SEQ ID NO: 39, SEQ ID NO: 40, SEQ ID NO: 42, SEQ ID NO: 43, or SEQ ID NO: 56, or at least 40% identical to a stretch of at least 50, at least 60, at least 70, at least 80, at least 90, at least 100, at least 110 at least 120 contiguous nucleotides of SEQ ID NO: 39, SEQ ID NO: 40, SEQ ID NO: 42, SEQ ID NO: 43, or SEQ ID NO: 56, or at least 30% identical to a stretch of at least 50, at least 60, at least 70, at least 80, at least 90, at least 100, at least 110 at least 120 contiguous nucleotides of SEQ ID NO: 39, SEQ ID NO: 40, SEQ ID NO: 42, SEQ ID NO: 43, or SEQ ID NO: 56, or at least 20% identical to a stretch of at least 50, at least 60, at least 70, at least 80, at least 90, at least 100, at least 110 at least 120 contiguous nucleotides of SEQ ID NO: 39, SEQ ID NO: 40, SEQ ID NO: 42, SEQ ID NO: 43, or SEQ ID NO: 56, or at least 10% identical to a stretch of at least 50, at least 60, at least 70, at least 80, at least 90, at least 100, at least 110 at least 120 contiguous nucleotides of any one of SEQ ID NO: 39, SEQ ID NO: 40, SEQ ID NO: 42, SEQ ID NO: 43, or SEQ ID NO: 56.

In some embodiments the first genetic modification class comprises disruption of at least one alcohol dehydrogenase gene whose amino acid sequence, predicted from translation of the gene that encodes it, comprises a first peptide. In some embodiments the first peptide has the sequence VKYSGVCH (SEQ ID NO: 156). In some embodiments, the first peptide has the sequence VKYSGVCHxxxxxWKGDW (SEQ ID NO: 162). In some embodiments the first peptide has the sequence VKYSGVCHxxxxxWKGDWxxxxKLPxVGGHEGAGVVV (SEQ ID NO: 163). It will be understood that in amino acid sequences presented herein, each "x" represents a placeholder for a residue of any of the naturally occurring amino acids.

In some embodiments the first genetic modification class comprises disruption of at least one alcohol dehydrogenase gene whose amino acid sequence, predicted from translation of the gene that encodes it, comprises a second peptide. In some embodiments the second peptide has the sequence QYATADAVQAA (SEQ ID NO: 158). In some embodiments the second peptide has the sequence SGYxHDGxFxQYATADAVQAA (SEQ ID NO: 164). In some embodiments the second peptide has the sequence GAEPNCxxADxSGYxHDGxFxQYATADAVQAA (SEQ ID NO: 165).

In some embodiments the first genetic modification class comprises disruption of at least one alcohol dehydrogenase gene whose amino acid sequence, predicted from translation of the gene that encodes it, comprises a third peptide. In some embodiments the third peptide has the sequence CAGVTVYKALK (SEQ ID NO: 159). In some embodiments the third peptide has the sequence APIxCAGVTVYKALK (SEQ ID NO: 166).

In some embodiments the first genetic modification class comprises disruption of at least one alcohol dehydrogenase gene whose amino acid sequence, predicted from translation of the gene that encodes it, comprises a fourth peptide. In some embodiments the fourth peptide has the sequence GQWVAISGA (SEQ ID NO: 160). In some embodiments the fourth peptide has the sequence GQWVAISGAxGGLGSL (SEQ ID NO: 167). In some embodiments the fourth peptide has the sequence GQWVAISGAxGGLGSLxVQYA (SEQ ID NO: 168). In some embodiments, the fourth peptide has the sequence GQWVAISGAxGGLGSLxVQYAxAMG (SEQ ID NO: 169). In some embodiments the fourth peptide has the sequence GQWVAISGAxGGLGSLxVQYAxAMGxRVxAIDGG (SEQ ID NO: 170).

In some embodiments the first genetic modification class comprises disruption of at least one alcohol dehydrogenase gene whose amino acid sequence, predicted from translation of the gene that encodes it, comprises a fifth peptide. In some embodiments the fifth peptide has the sequence VGGHEGAGVVV (SEQ ID NO: 157).

In some embodiments the first genetic modification class comprises disruption of at least one alcohol dehydrogenase gene whose amino acid sequence, predicted from translation of the gene that encodes it, comprises at least one, two, three, four or five peptides selected from the group consisting of a first peptide having the sequence VKYSGVCH (SEQ ID NO: 156), a second peptide having the sequence QYATADAVQAA (SEQ ID NO: 158), a third peptide having the sequence CAGVTVYKALK (SEQ ID NO: 159), a fourth peptide having the sequence GQWVAISGA (SEQ ID NO: 160) and a fifth peptide having the sequence VGGHEGAGVVV (SEQ ID NO: 157).

In some embodiments the first genetic modification class comprises disruption of at least one alcohol dehydrogenase gene whose amino acid sequence, predicted from translation of the gene that encodes it has at least 65 percent sequence identity, at least 70 percent sequence identity, at least 75 percent sequence identity, at least 80 percent sequence identity, at least 85 percent sequence identity, at least 90 percent sequence identity, or at least 95 percent sequence identity to a stretch of at least 20, at least 30, at least 40, at least 50, at least 60, at least 70, at least 80, at least 90, or at least 100 contiguous residues of any one of SEQ ID NO:151, SEQ ID NO:152, SEQ ID NO:153, SEQ ID NO:154, or SEQ ID NO:155.

In some embodiments the first genetic modification class comprises disruption of at least one alcohol dehydrogenase gene whose amino acid sequence, predicted from translation of the gene that encodes it, has at least 65 percent sequence identity, at least 70 percent sequence identity, at least 75 percent sequence identity, at least 80 percent sequence identity, at least 85 percent sequence identity, at least 90 percent sequence identity, or at least 95 percent sequence identity to a stretch of between 5 and 120 contiguous residues, between 40 and 100 contiguous residues, between 50 and 90 contiguous residues, between 60 and 80 contiguous residues of any one of SEQ ID NO:151, SEQ ID NO:152, SEQ ID NO:153, SEQ ID NO:154, or SEQ ID NO:155.

In some embodiments the first genetic modification class comprises disruption of at least one alcohol dehydrogenase gene whose amino acid sequence, predicted from translation of the gene that encodes it, has at least 90 percent sequence identity to a stretch of between 10 and 100 contiguous residues of any one of SEQ ID NO:151, SEQ ID NO:152, SEQ ID NO:153, SEQ ID NO:154, or SEQ ID NO:155.

In some embodiments, the first genetic modification class causes disruption of an alcohol dehydrogenase in a *Candida* host cell. In some embodiments disruption of an alcohol dehydrogenase is measured by incubating the *Candida* host cell in a mixture comprising a substrate possessing a hydroxyl group and measuring the rate of conversion of the substrate to a more oxidized product such as an aldehyde or a carboxyl group. The rate of conversion of the substrate by the *Candida* host cell is compared with the rate of conversion produced by a second host cell that does not contain the disrupted gene but contains a wild type counterpart of the gene, when the *Candida* host cell and the second host cell are under the same environmental conditions (e.g., same temperature, same media, etc.). The rate of formation of the product can be measured using colorimetric assays, or chromatographic assays, or mass spectroscopy assays. In some embodiments the alcohol dehydrogenase is deemed disrupted if the rate of conversion is at least 5% lower, at least 10% lower, at least 15% lower, at least 20% lower, at least 25% lower, or at least 30% lower in the *Candida* host cell than the second host cell.

In some embodiments, disruption of an alcohol dehydrogenase in a *Candida* host cell is measured by incubating the *Candida* host cell in a mixture comprising a substrate possessing a hydroxyl group and measuring the rate of conversion of the substrate to a more oxidized product such as an aldehyde or a carboxyl group. The amount of the substrate converted to product by the *Candida* host cell in a specified time is compared with the amount of substrate converted to product by a second host cell that does not contain the disrupted gene but contains a wild type counterpart of the gene, when the *Candida* host cell and the second host cell are under the same environmental conditions (e.g., same temperature, same media, etc.). The amount of product can be measured using colorimetric assays, or chromatographic assays, or mass spectroscopy assays. In some embodiments the alcohol dehydrogenase is deemed disrupted if the amount of product is at least 5%, at least 10%, at least 15%, at least 20%, at least 25%, or at least 25% lower in the *Candida* host cell than the second host cell.

In some embodiments, the first genetic modification class causes an alcohol dehydrogenases to have decreased function relative to the function of the wild-type counterpart in the *Candida* host cell.

In some embodiments, decreased function of an alcohol dehydrogenase in a *Candida* host cell is measured by incubating the *Candida* host cell in a mixture comprising a substrate possessing a hydroxyl group and measuring the rate of conversion of the substrate to a more oxidized product such as an aldehyde or a carboxyl group. The rate of conversion of the substrate by the *Candida* host cell is compared with the rate of conversion produced by a second host cell that does not contain the disrupted gene but contains a wild type counterpart of the gene, when the *Candida* host cell and the second host cell are under the same environmental conditions (e.g., same temperature, same media, etc.). The rate of formation of the product can be measured using colorimetric assays, or chromatographic assays, or mass spectroscopy assays. In some embodiments the alcohol dehydrogenase is deemed to have decreased function if the rate of conversion is at least 5% lower, at least 10% lower, at least 15% lower, at least 20% lower, at least 25% lower, or at least 30% lower in the *Candida* host cell than the second host cell In some embodiments, decreased function of an alcohol dehydrogenase in a *Candida* host cell is measured by incubating the *Candida* host cell in a mixture comprising a substrate possessing a hydroxyl group and measuring the rate of conversion of the substrate to a more oxidized product such as an aldehyde or a carboxyl group. The amount of the substrate converted to product by the *Candida* host cell in a specified time is compared with the amount of substrate converted to product by a second host cell that does not contain the disrupted gene but contains a wild type counterpart of the gene, when the *Candida* host cell and the second host cell are under the same environmental conditions (e.g., same temperature, same media, etc.). The amount of product can be measured using colorimetric assays, or chromatographic assays, or mass spectroscopy assays. In some embodiments the alcohol dehydrogenase is deemed to have decreased function if the amount of product is at least 5% lower, at least 10% lower, at least 15% lower, at least 20% lower, at least 25% lower, or at least 30% lower in the *Candida* host cell than the second host cell.

In some embodiments, the first genetic modification class causes an alcohol dehydrogenases to have a modified activity spectrum relative to an activity spectrum of the wild-type counterpart.

In some embodiments, activity of an alcohol dehydrogenase in a *Candida* host cell is measured by incubating the *Candida* host cell in a mixture comprising a substrate possessing a hydroxyl group and measuring the rate of conversion of the substrate to a more oxidized product such as an aldehyde or a carboxyl group. The rate of conversion of the substrate by the *Candida* host cell is compared with the rate of conversion produced by a second host cell that does not contain the disrupted gene but contains a wild type counterpart of the gene, when the *Candida* host cell and the second host cell are under the same environmental conditions (e.g., same temperature, same media, etc.). The rate of formation of the product can be measured using colorimetric assays, or chromatographic assays, or mass spectroscopy assays. In some embodiments the alcohol dehydrogenase is deemed to have a modified activity spectrum if the rate of conversion is at least 5% lower, at least 10% lower, at least 15% lower, at least 20% lower, or at least 25% lower in the *Candida* host cell than the second host cell.

In some embodiments, activity of an alcohol dehydrogenase in a *Candida* host cell is measured by incubating the *Candida* host cell in a mixture comprising a substrate possessing a hydroxyl group and measuring the rate of conversion of the substrate to a more oxidized product such as an aldehyde or a carboxyl group. The amount of the substrate converted to product by the *Candida* host cell in a specified time is compared with the amount of substrate converted to product by a second host cell that does not contain the disrupted gene but contains a wild type counterpart of the gene, when the *Candida* host cell and the second host cell are under the same environmental conditions (e.g., same temperature, same media, etc.). The amount of product can be measured using colorimetric assays, or chromatographic assays, or mass spectroscopy assays. In some embodiments the alcohol dehydrogenase is deemed to have a modified activity spectrum if the amount of product is at least 5% lower, at least 10% lower, at least 15% lower, at least 20% lower, at least 25% lower in the *Candida* host cell than the second host cell.

In some embodiments the second genetic modification class comprises addition of at least one modified CYP52A type cytochrome P450 selected from the group consisting of CYP52A13, CYP52A14, CYP52A17, CYP52A18, CYP52A12, and CYP52A12B.

Disclosed are biosynthetic routes that convert (oxidize) fatty acids to their corresponding α-carboxyl-ω-hydroxyl fatty acids. This is accomplished by culturing fatty acid substrates with a yeast, preferably a strain of *Candida* and more preferably a strain of *Candida tropicalis*. The yeast converts fatty acids to long-chain ω-hydroxy fatty acids and α,ω-dicarboxylic acids, and mixtures thereof. Methods by which yeast strains may be engineered by the addition or removal of genes to modify the oxidation products formed are disclosed. Fermentations are conducted in liquid media containing fatty acids as substrates. Biological conversion methods for these compounds use readily renewable resources such as fatty acids as starting materials rather than non-renewable petrochemicals—For example, ω-hydroxy fatty acids and α,ω-dicarboxylic acids can be produced from inexpensive long-chain fatty acids, which are readily available from renewable agricultural and forest products such as soybean oil, corn oil and tallow. Moreover, a wide range of α-carboxyl-ω-hydroxyl fatty acids with different carbon length can be prepared because the biocatalyst accepts a wide range of fatty acid substrates. Products described herein produced by the biocatalytic methods described herein are new and not commercially available since chemical methods are impractical to prepare the compounds and biocatalytic methods to these products were previously unknown.

4. BRIEF DESCRIPTION OF THE FIGURES

FIG. 1 shows two pathways for metabolism of fatty acids, ω-oxidation and β-oxidation, both of which exist in yeasts of the genus *Candida* including *Candida tropicalis*. The names of classes of compounds are shown, arrows indicate transformations from one compound to another, and the names of classes of enzymes that perform these conversions are indicated by underlined names adjacent to the arrows.

Figure 2:
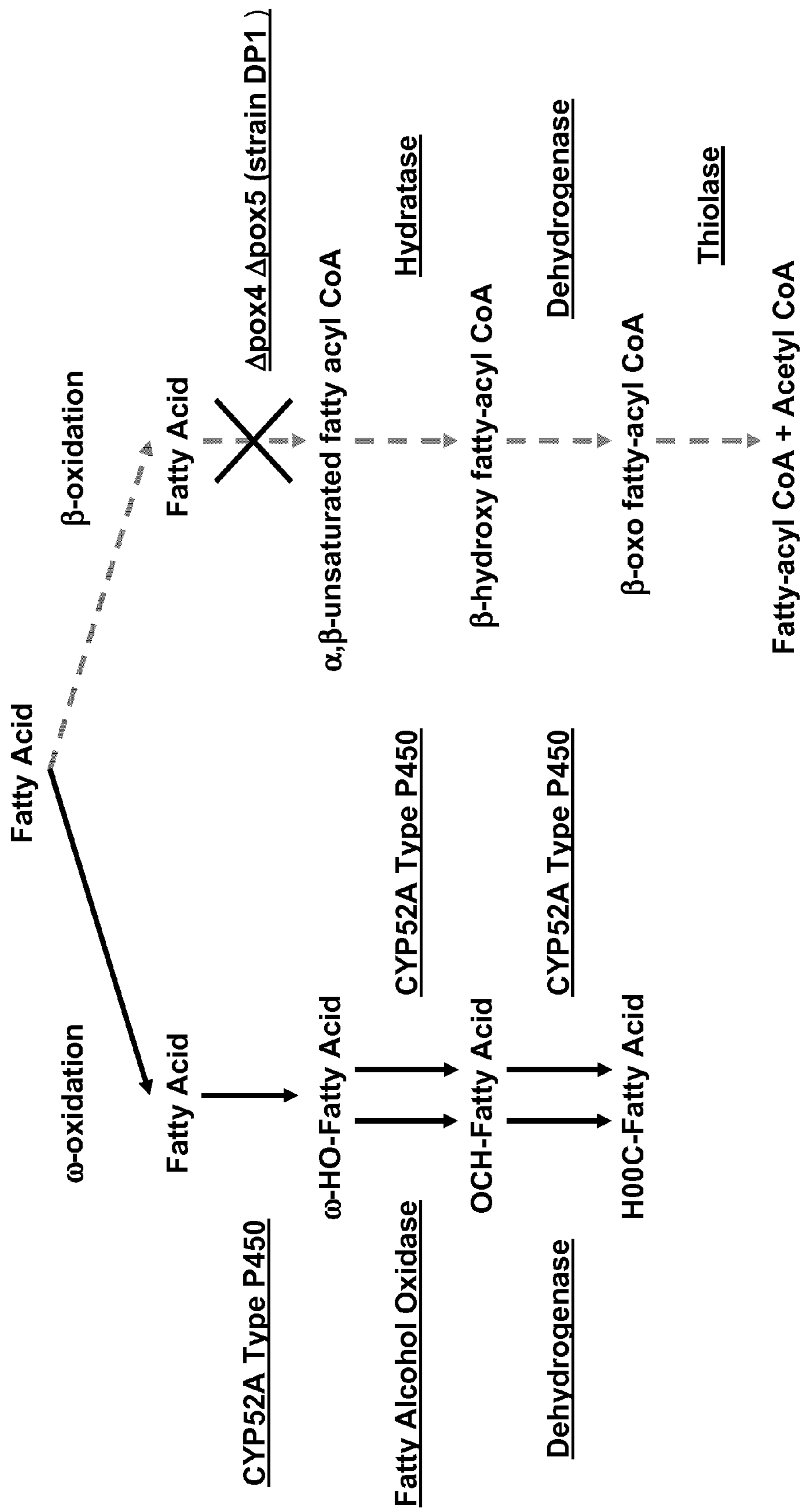

FIG. 2 shows two pathways for metabolism of fatty acids, ω-oxidation and β-oxidation, both of which exist in yeasts of the genus *Candida* including *Candida tropicalis*. The names of classes of compounds are shown, arrows indicate transformations from one compound to another, and the names of classes of enzymes that perform these conversions are indicated by underlined names adjacent to the arrows. By inactivating the genes encoding acyl coA oxidase (pox4 and pox5), the β-oxidation pathway is blocked (indicated by broken arrows), so that fatty acids are not used as substrates for growth. This genetic modification allows *Candida* species of yeast including *Candida tropicalis* to be used as a biocatalyst for the production of α,ω-diacids. See, for example, Picataggio et al., 1991, Mol Cell Biol 11, 4333-4339; and Picataggio et al., 1992, Biotechnology 10, 894-898. The β-oxidation pathway may be disrupted by any genetic modification or treatment of the host cells with a chemical for example an inhibitor that substantially reduces or eliminates the activity of one or more enzymes in the β-oxidation pathway, including the hydratase, dehydrogenase or thiolase enzymes, and thereby reduces the flux through that pathway and thus the utilization of fatty acids as growth substrates.

FIG. 3 shows an alignment, using ClustalW, of the amino acid sequences of alcohol dehydrogenase proteins predicted from the sequences of genes from *Candida albicans* and *Candida tropicalis*. The genes from *Candida tropicalis* were isolated as partial genes by PCR with degenerate primers, so the nucleic acid sequences of the genes and the predicted amino acid sequences of the encoded proteins are incomplete. Amino acid sequences of the partial genes are predicted and provided: SEQ ID NO:155 (ADH-A4), SEQ ID NO:154 (ADH-B4), SEQ ID NO:152 (ADH-A10), SEQ ID NO:153 (ADH-A10B) and SEQ ID NO:151 (ADH-B11).

Figure 4:
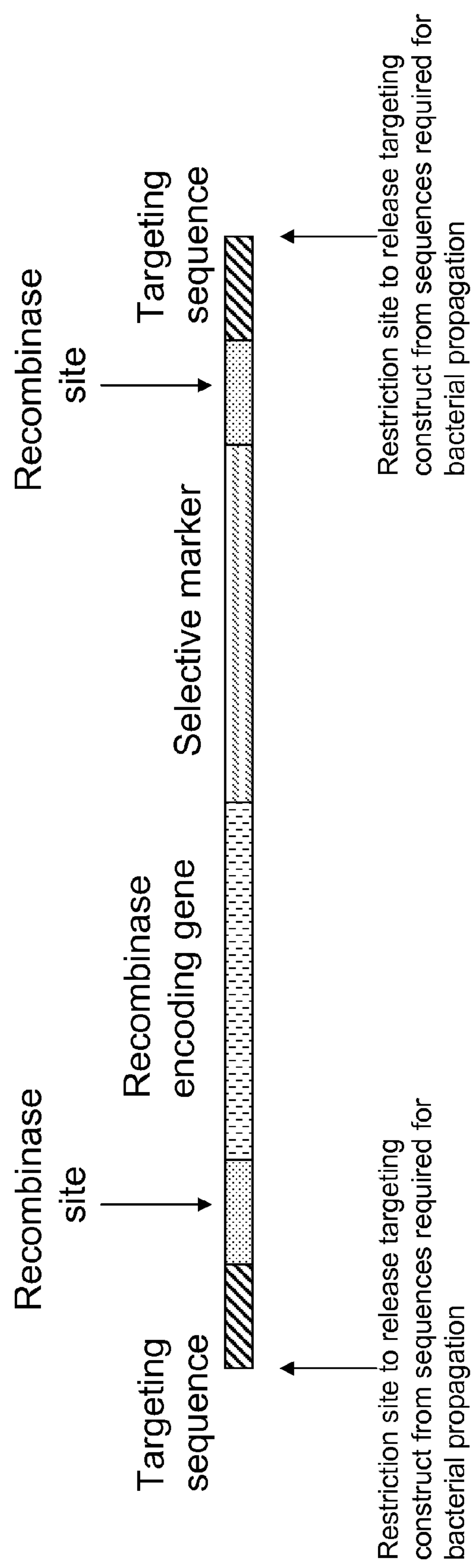

FIG. 4 shows a schematic representation of a DNA "genomic targeting" construct for deleting sequences from the genome of yeasts. The general structure is that the construct has two targeting sequences that are homologous to the sequences of two regions of the target yeast chromosome. Between these targeting sequences are two sites recognized by a site-specific recombinase (indicated as "recombinase site"). Between the two site specific recombinase sites are sequence elements, one of which encodes a selective marker and the other of which (optionally) encodes the site-specific recombinase that recognizes the recombinase sites. In one embodiment the sequences of the DNA construct between the targeting sequences is the "SAT1 flipper", a DNA construct for inserting and deleting sequences into the chromosome of *Candida* (Reuss et al., (2004), Gene: 341, 119-27.). In the "SAT1 flipper", the recombinase is the flp recombinase from *Saccharomyces cerevisiae* (Vetter et al., 1983, Proc Natl Acad Sci USA: 80, 7284-8) (FLP) and the flanking sequences recognized by the recombinase are recognition sites for the flp recombinase (FRT). The selective marker is the gene encoding resistance to the Nourseothricin resistance marker from transposon Tn1825 (Tietze et al., 1988, J Basic Microbiol: 28, 129-36.). The DNA sequence of the SAT1-flipper is given as SEQ ID NO: 1. The genomic targeting sequence can be propagated in bacteria, for example *E coli*, in which case the complete plasmid will also contain sequences required for propagation in bacteria, comprising a bacterial origin of replication and a bacterial selective marker such as a gene conferring antibiotic resistance. The targeting construct can be released from this plasmid in a linear form by digestion with one or more restriction enzymes with recognition sites that flank the targeting sequences.

Figure 5:
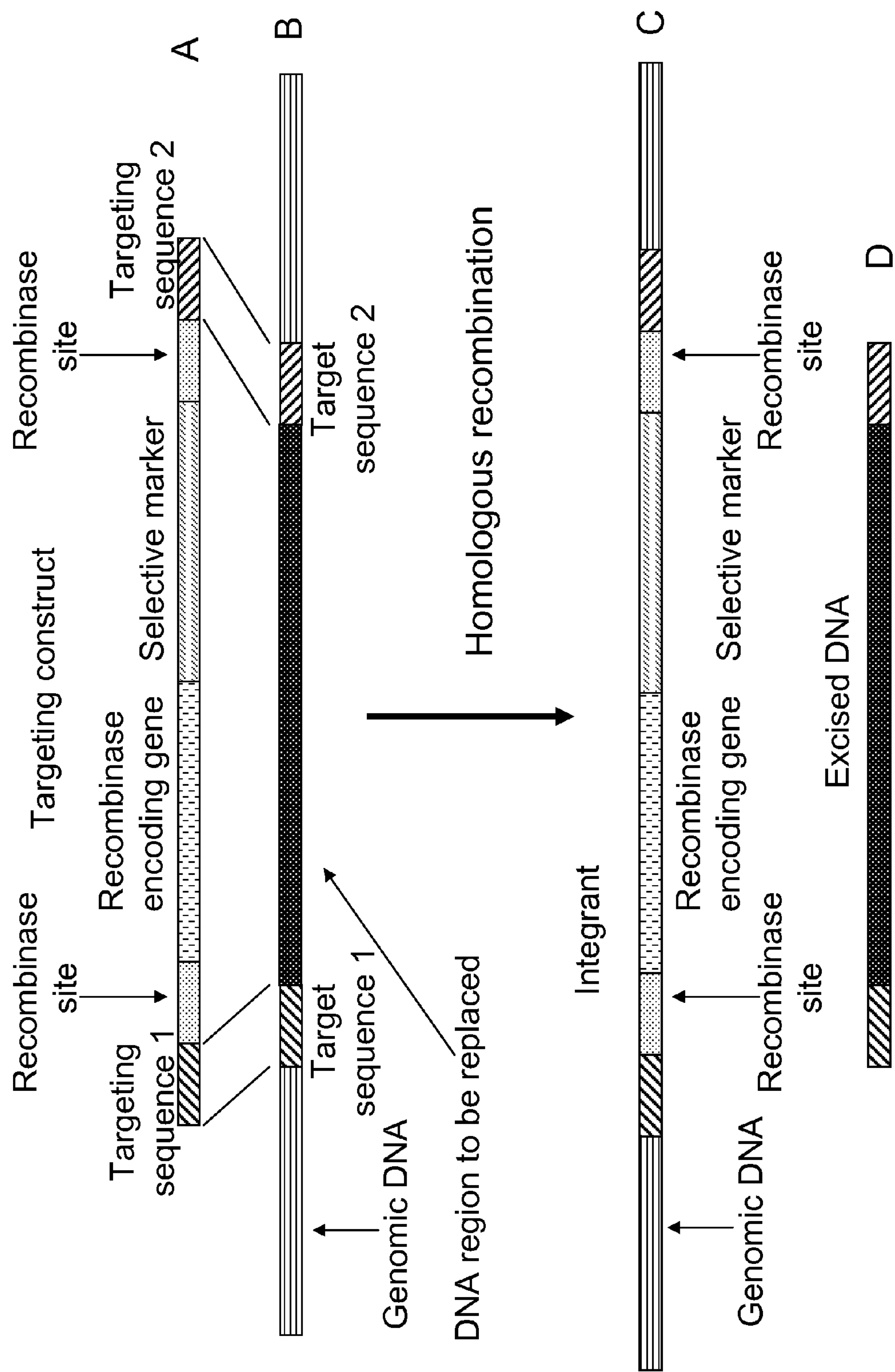

FIG. 5 shows a schematic representation of the homologous recombination between a "genomic targeting" construct of the form shown in FIG. 4, with the DNA contained in a yeast genome (either in the chromosome or in the mitochondrial DNA). The targeting construct (A) contains two regions of sequence homology to the genomic sequence (B); the corresponding sequences in the genomic sequence flank the DNA region to be replaced. Introduction of the targeting construct into the host cell is followed by homologous recombination catalyzed by host cell enzymes. The result is an integrant of the targeting construct into the genomic DNA (C) and the excised DNA (D) which will generally be lost from the cell.

Figure 6:
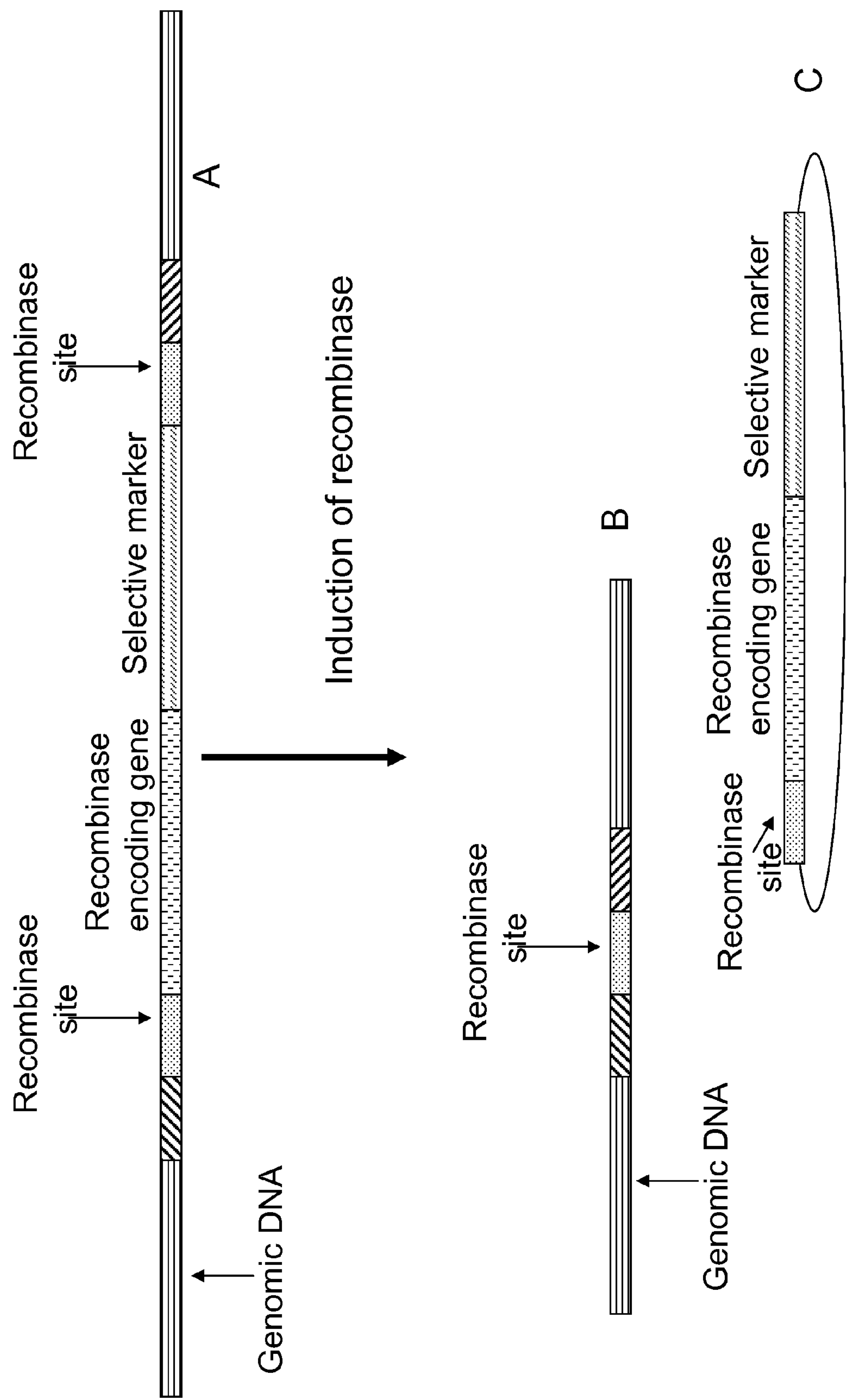

FIG. 6 shows a schematic representation of excision of the targeting construct from the yeast genome that occurs when expression of the recombinase in the targeting construct is induced in the integrant (A) shown in FIG. 5. Induction of the site-specific recombinase causes recombination between the two recombinase recognition sites. The result is the excision of the sequences between the two recombinase sites (C) leaving a single recombinase site in the genomic DNA (B).

Figure 7:
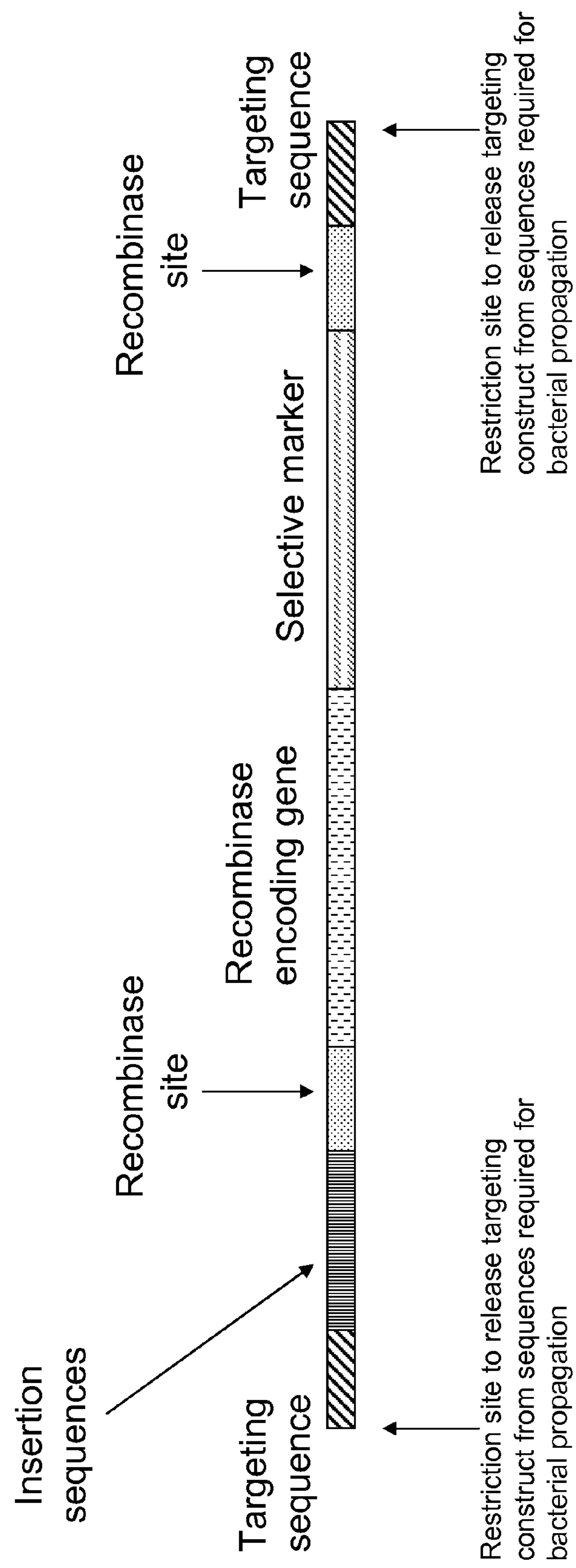

FIG. 7 shows a schematic representation of a DNA "genomic targeting" construct for inserting sequences into the genome of yeasts. The general structure is that the construct has two targeting sequences that are homologous to the sequences of two regions of the target yeast chromosome. Between these targeting sequences are two sites recognized by a site-specific recombinase (indicated as "recombinase site"). Between the two site specific recombinase sites are sequence elements, one of which encodes a selective marker and the other of which (optionally) encodes the site-specific recombinase that recognizes the recombinase sites. Insertion of additional sequences between one of the targeting sequences and its closest recombinase recognition site will result in those sequences being inserted into the chromosome after excision of the targeting construct ("Insertion sequences"). The genomic targeting sequence can be propagated in bacteria, for example *E coli*, in which case the complete plasmid will also contain sequences required for propagation in bacteria, comprising a bacterial origin of replication and a bacterial selective marker such as a gene conferring antibiotic resistance. The targeting construct can be released from this plasmid in a linear form by digestion with one or more restriction enzymes with recognition sites that flank the targeting sequences.

Figure 8:
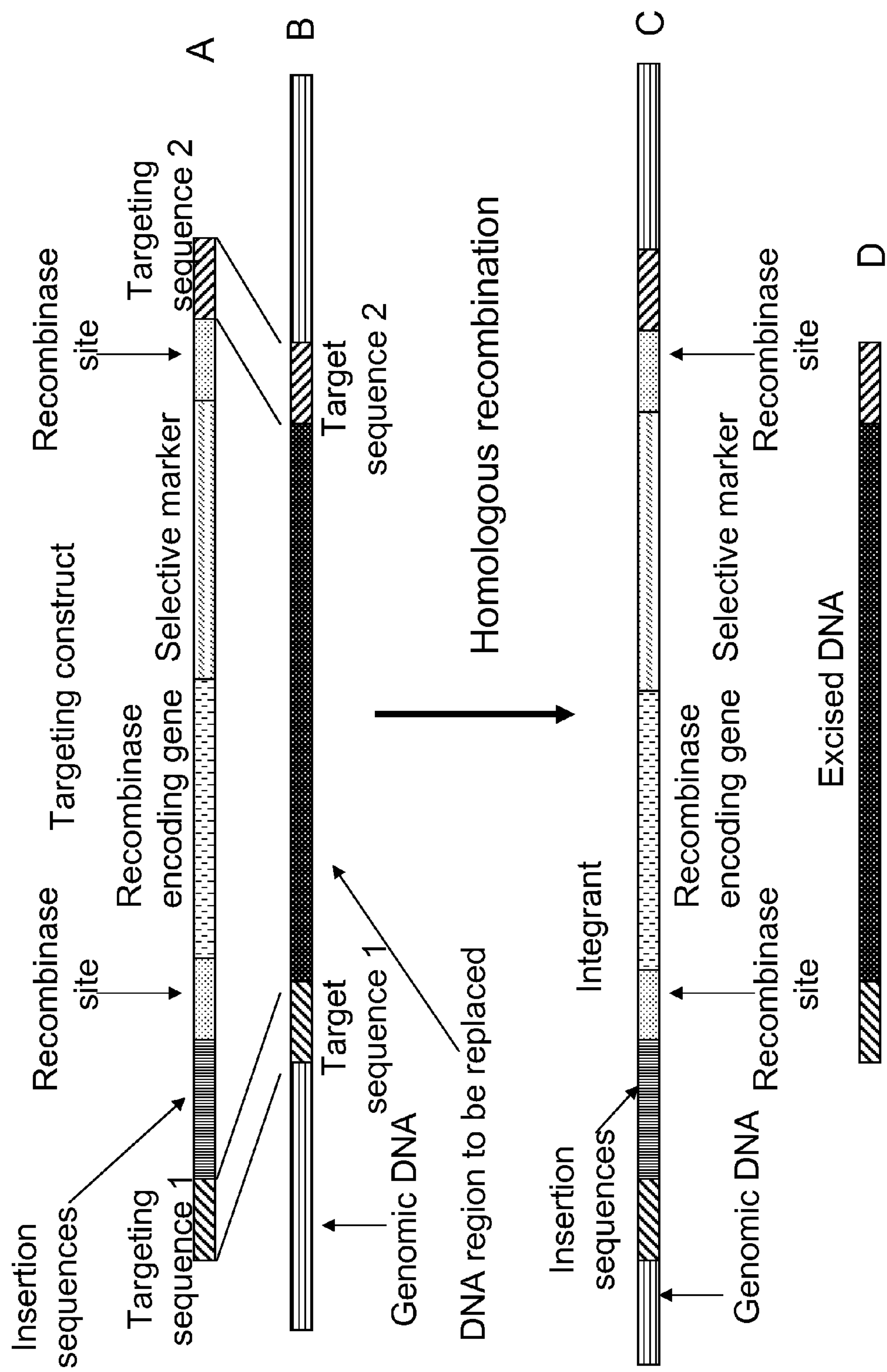

FIG. 8 shows a schematic representation of the homologous recombination between a "genomic targeting" construct of the form shown in FIG. 7, with the DNA contained in a yeast genome (either in the chromosome or in the mitochondrial DNA). The targeting construct (A) contains two regions of sequence homology to the genomic sequence (B); the corresponding sequences in the genomic sequence flank the DNA region to be replaced. Introduction of the targeting construct into the host cell is followed by homologous recombination catalyzed by host cell enzymes. The result is an integrant of the targeting construct into the genomic DNA (C) and the excised DNA (D) which will generally be lost from the cell.

Figure 9:
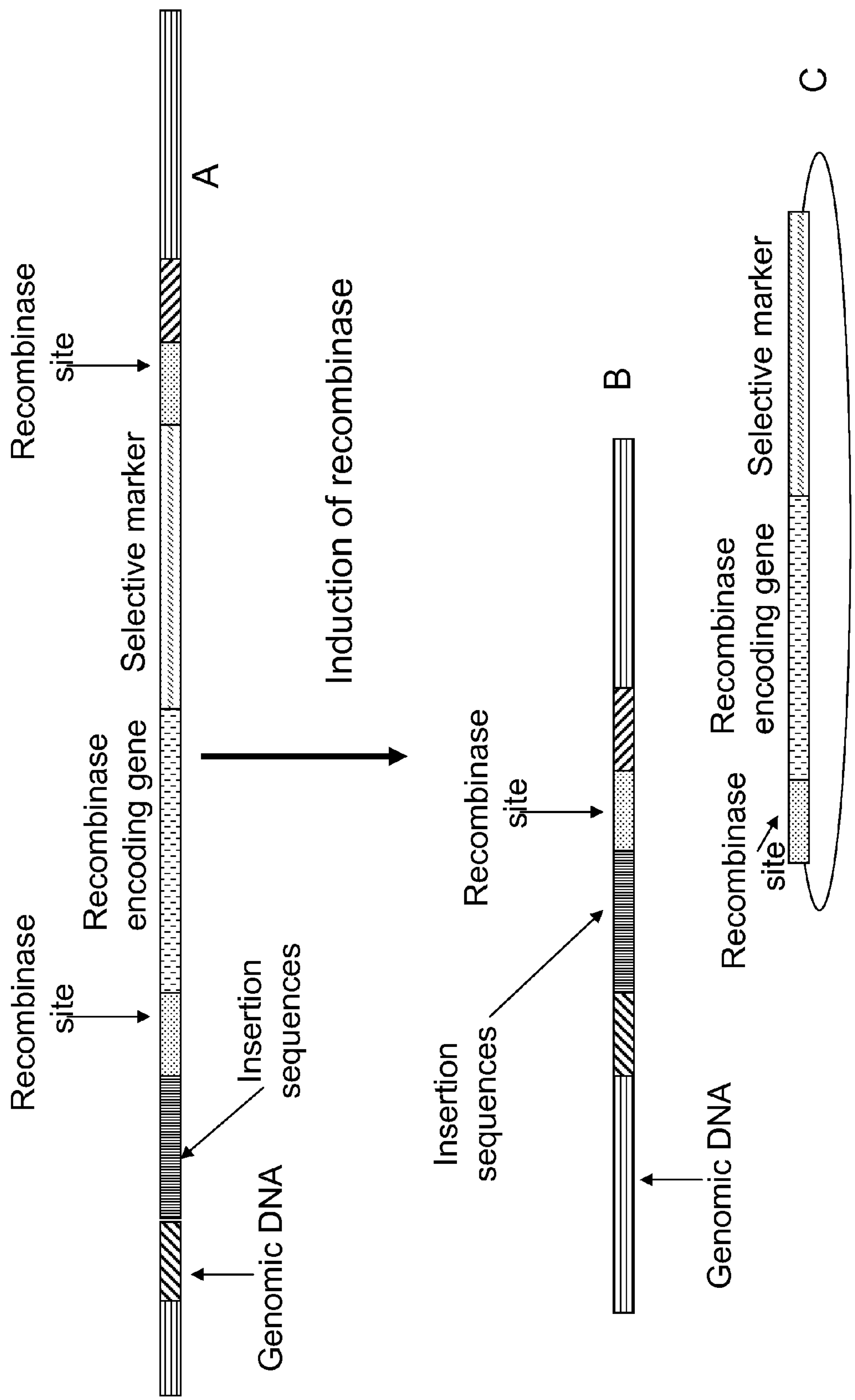

FIG. 9 shows a schematic representation of excision of the targeting construct from the yeast genome that occurs when expression of the recombinase in the targeting construct is induced in the integrant (A) shown in FIG. 8. Induction of the site-specific recombinase causes recombination between the two recombinase recognition sites. The result is the excision of the sequences between the two recombinase sites (C) leaving a single recombinase site together with the additional sequences that were included between the targeting sequences and the recombinase site (see FIG. 7) in the genomic DNA (B).

Figure 10:
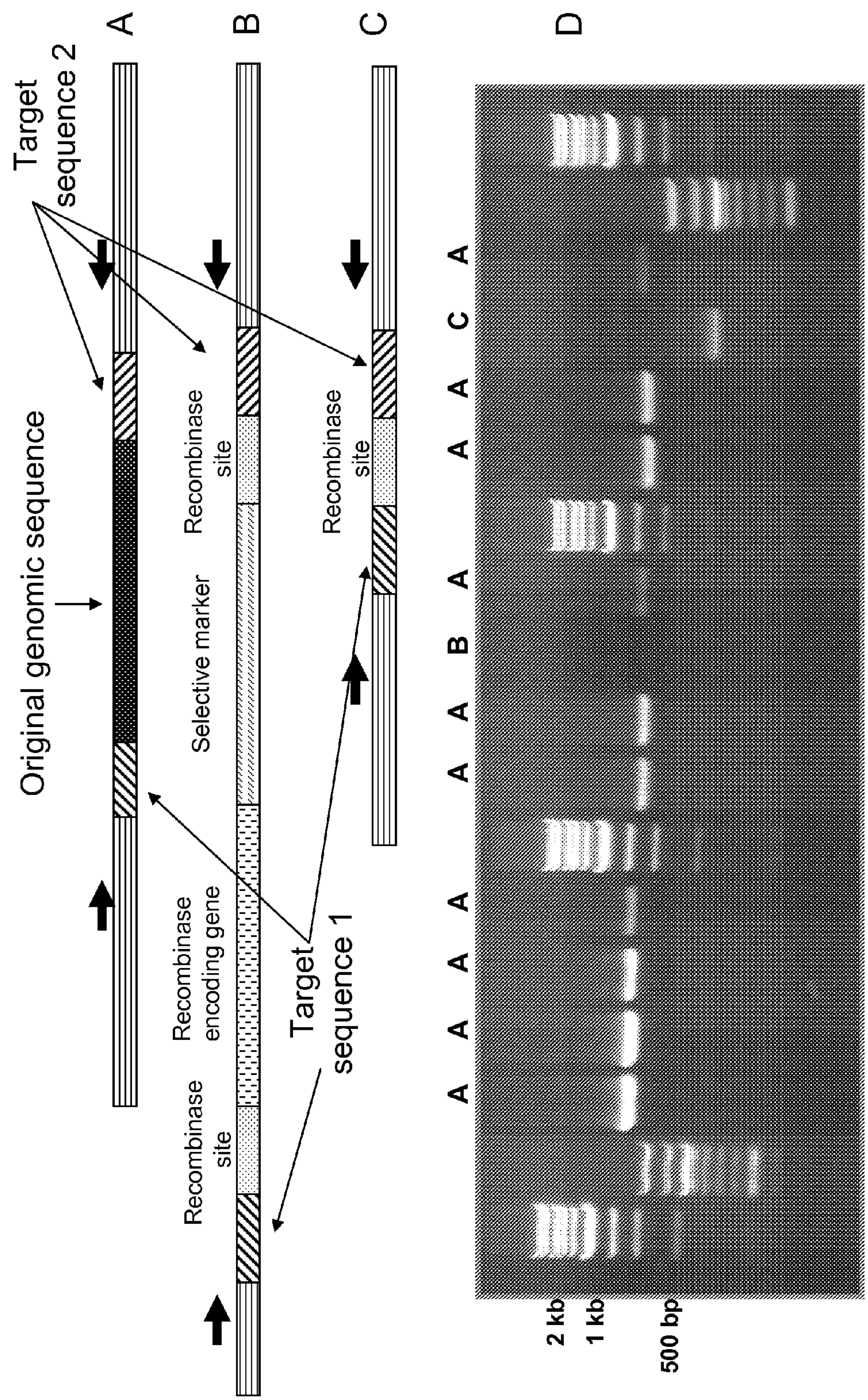

FIG. 10 shows a schematic representation of three stages in generation of a targeted deletion in a yeast genome (either in the chromosome or in the mitochondrial DNA), and the results of a PCR test to distinguish between the three stages. (A) PCR primers (thick arrows) are designed to flank the targeted region. (B) Insertion of a genomic targeting construct into the genome inserts two recombinase sites, a recombinase gene and a selection marker between the two target sequences. This changes the size of the DNA segment between the two PCR primers; in the case shown the size is increased. (C) Induction of the recombinase results in excision of the recombinase encoding gene, the selective marker and one of the recombinase sites. This again changes the size of the DNA segment between the two PCR primers. (D) PCR amplification from yeast genomic DNA unmodified (gel lanes marked A), with integrated genomic targeting vector (gel lanes marked B) or after excision of the genomic targeting vector (gel lanes marked C).

Figure 11:
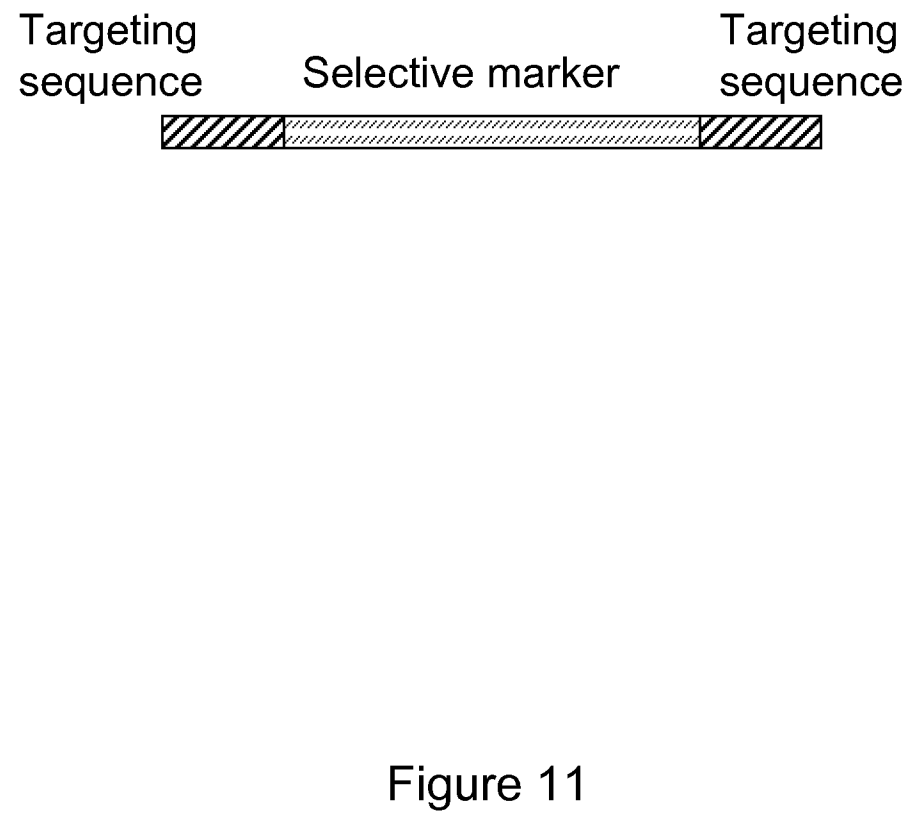

FIG. 11 shows a schematic representation of a DNA "genomic targeting" construct for inserting or deleting sequences in the genome of yeasts. The general structure is that the construct has two targeting sequences that are homologous to the sequences of two regions of the target yeast chromosome. Between these targeting sequences is a sequence that encodes a selective marker.

Figure 12:
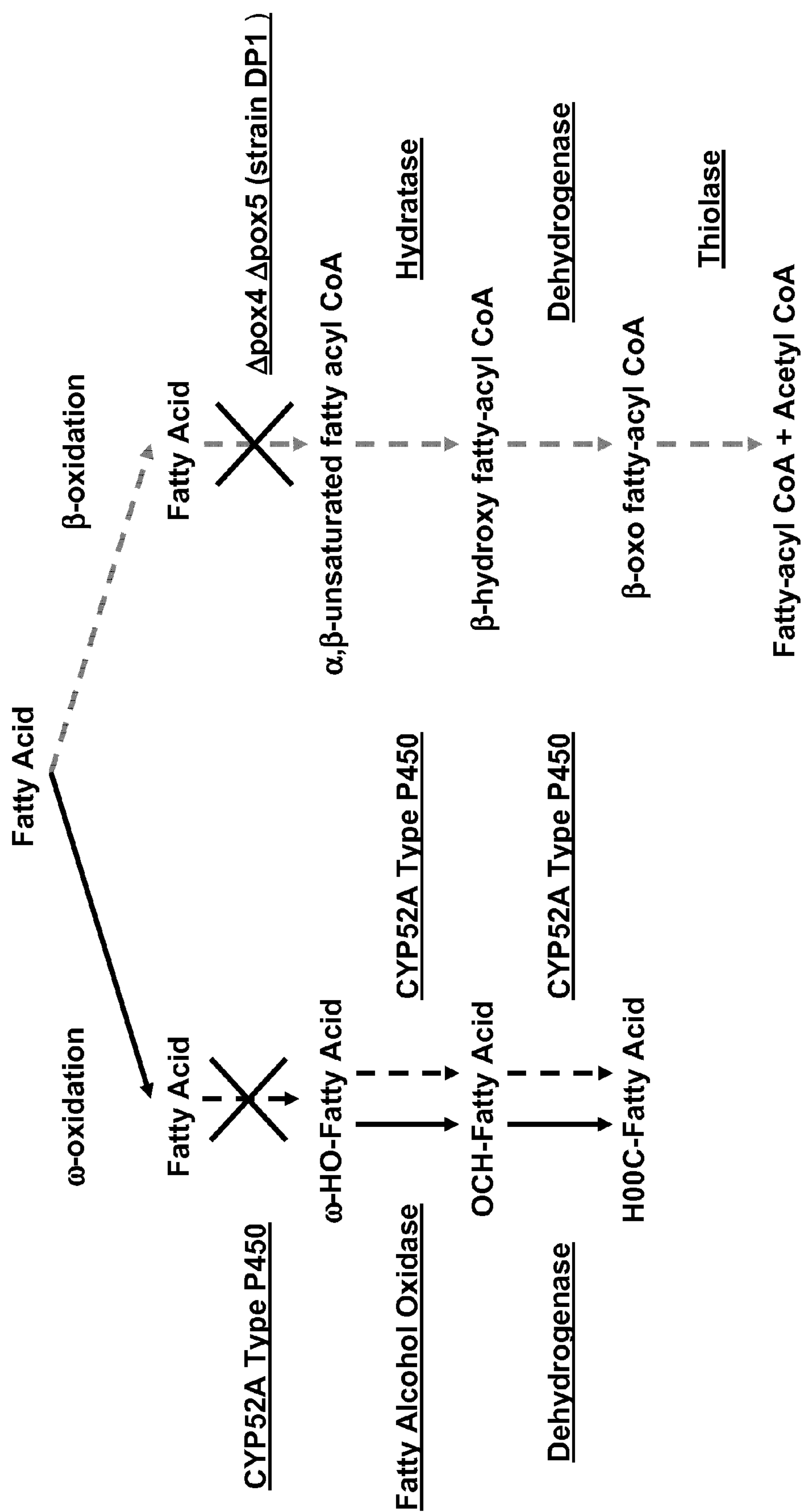

FIG. 12 shows two pathways for metabolism of fatty acids, ω-oxidation and β-oxidation, both of which exist in *Candida* species of yeast including *Candida tropicalis*. The names of classes of compounds are shown, arrows indicate transformations from one compound to another, and the names of classes of enzymes that perform these conversions are indicated by underlined names adjacent to the arrows. By inactivating the *Candida tropicalis* genes pox4 and pox5 (or their functional homologs in other *Candida* species), the β-oxidation pathway is blocked (indicated by broken arrows), so that fatty acids are not used as substrates for growth. Furthermore, inactivation of CYP52A type cytochrome P450 enzymes, as illustrated in the Figure, prevents the ω-oxidation of these fatty acids. These enzymes may also be responsible for some or all of the transformations involved in oxidizing ω-hydroxy fatty acids to α,ω-dicarboxylic acids. See Eschenfeldt et al., 2003, "Transformation of fatty acids catalyzed by cytochrome P450 monooxygenase enzymes of *Candida tropicalis*." Appli. Environ. Microbiol. 69: 5992-5999, which is hereby incorporated by reference herein.

Figure 13:
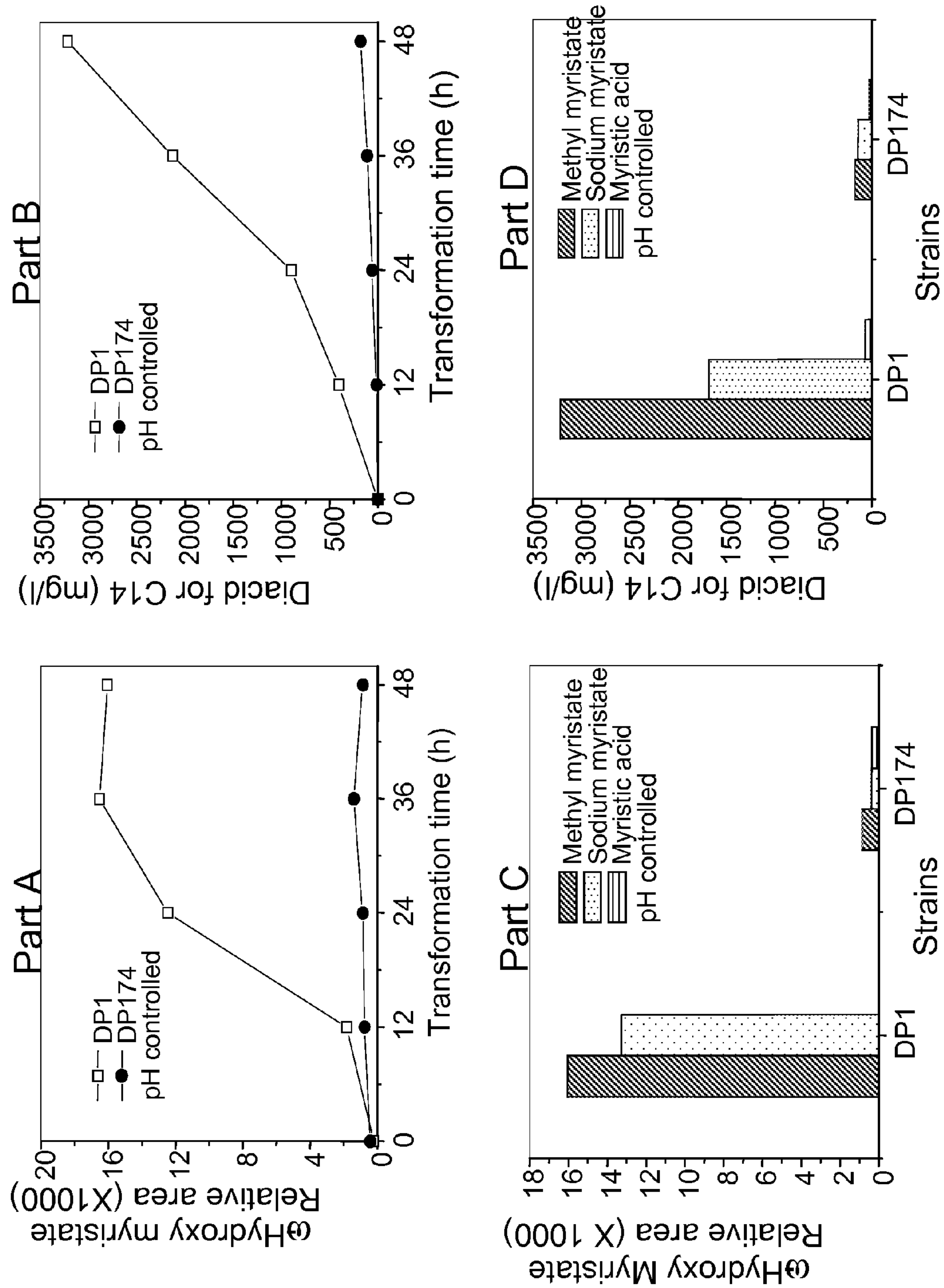

FIG. 13 shows the levels of ω-hydroxy myristate and the over-oxidized C14 diacid produced by *Candida tropicalis* strains DP1 (ura3A/ura3B pox5A::ura3A/pox5B::ura3A pox4A::ura3A/pox4B::URA3A) and DP174 (ura3A/ura3B pox5A::ura3A/pox5B::ura3A pox4A::ura3A/pox4B::URA3A ΔCYP52A17/ΔCYP52A18 ΔCYP52A13/ΔCYP52A14). Cultures of the yeast strains were grown at 30° C. and 250 rpm for 16 hours in a 500 ml flask containing 30 ml of media F (media F is peptone 3 g/l, yeast extract 6 g/l, yeast nitrogen base 6.7 g/l, sodium acetate 3 g/l, $K_2HPO_4$ 7.2 g/l, $KH_2PO_4$ 9.3 g/l) plus 30 g/l glucose. After 16 hours 0.5 ml of culture was added to 4.5 ml fresh media F plus 60 g/l glucose in a 125 ml flask, and grown at 30° C. and 250 rpm for 12 hours before addition of substrate. After addition of substrates growth was continued at 30° C. and 250 rpm. Parts A and B: the substrate methyl myristate was then added to a final concentration of 10 g/l and the pH was adjusted to between 7.5 and 8. The culture was pH controlled by adding 2 mol/l NaOH every 12 hours and glucose was fed as a cosubstrate by adding 400 g/l glucose every 8 hours. Samples were taken at the times indicated, cell culture was acidified to pH~1.0 by addition of 6 N HCl, products were extracted from the cell culture by diethyl ether and the concentrations of ω-hydroxy myristate and of the C14 diacid produced by oxidation of the ω-hydroxy myristate were measured by LC-MS (liquid chromatography mass spectroscopy). The diacid was quantified relative to a known standard. No such standard was available for the ω-hydroxy myristate, so it was quantified by measuring the area under the peak in the MS chromatogram. Parts C and D: the substrates methyl myristate, sodium myristate or myristic acid were added to a final concentration of 10 g/l and the pH was adjusted to between 7.5 and 8. The culture was pH controlled by adding 2 mol/l NaOH every 12 hours and glucose was fed as a cosubstrate by adding 400 g/l glucose every 8 hours. Samples were taken after 48 hours, cell culture was acidified to pH~1.0 by addition of 6 N HCl, products were extracted from the cell culture by diethyl ether and the concentrations of ω-hydroxy myristate and of the C14 diacid produced by oxidation of the ω-hydroxy myristate were measured by LC-MS (liquid chromatography mass spectroscopy).

Figure 14:
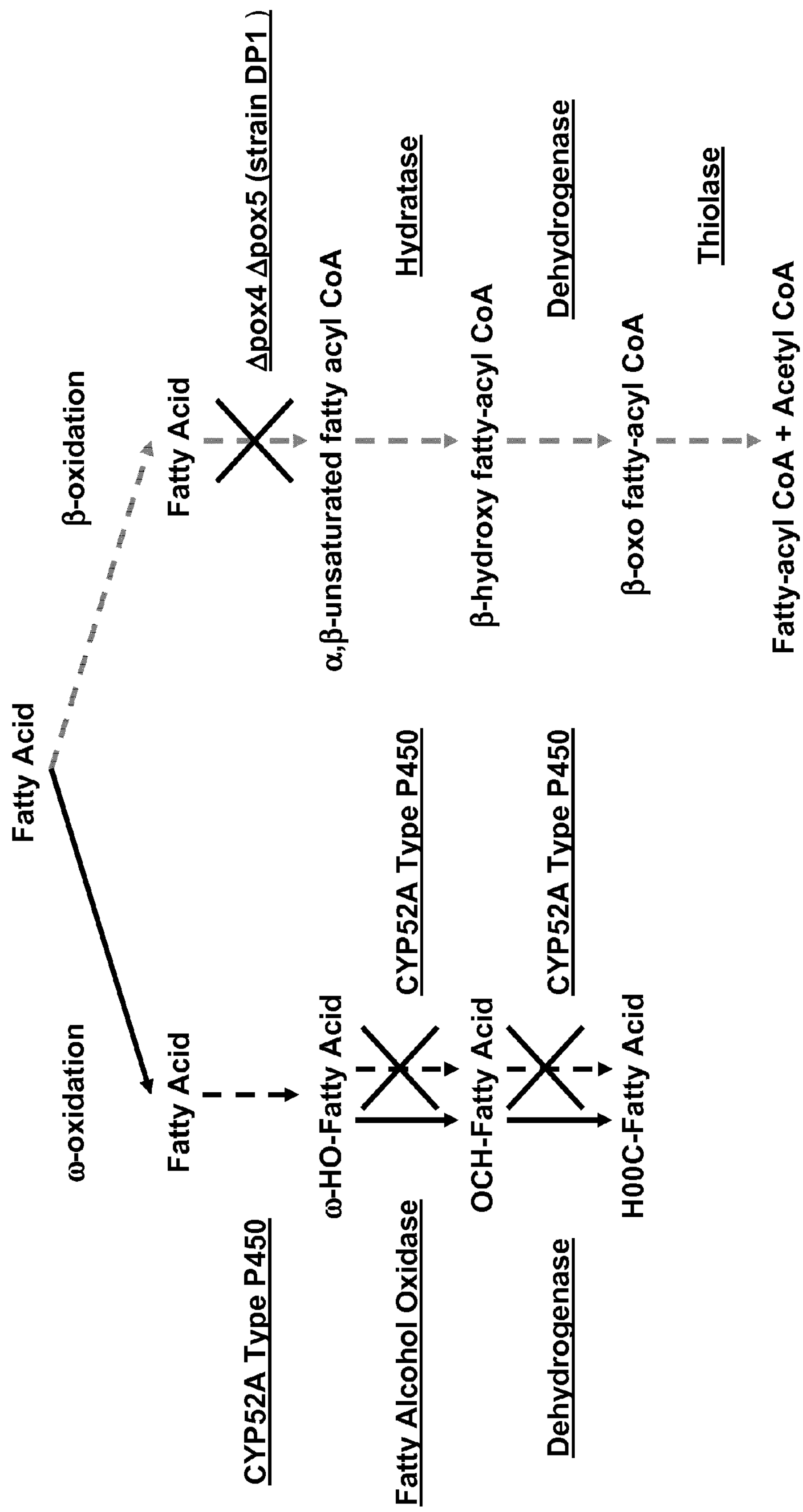

FIG. 14 shows two pathways for metabolism of fatty acids, ω-oxidation and β-oxidation, both of which exist in *Candida* species of yeast including *Candida tropicalis*. The names of classes of compounds are shown, arrows indicate transformations from one compound to another, and the names of classes of enzymes that perform these conversions are indicated by underlined names adjacent to the arrows. By inactivating the *Candida tropicalis* genes pox4 and pox5 (or their functional homologs in other *Candida* species), the β-oxidation pathway is blocked (indicated by broken arrows), so that fatty acids are not used as substrates for growth. Furthermore, inactivation of CYP52A type cytochrome P450 enzymes prevents the ω-oxidation of fatty acids. Several enzymes including, but not limited to CYP52A type P450s, are responsible for transformations involved in oxidizing ω-hydroxy fatty acids to α,ω-dicarboxylic acids. If other enzymes involved in oxidation of ω-hydroxy fatty acids are present in the strain, then the strain will convert ω-hydroxy fatty acids fed in the media to α,ω-dicarboxylic acids. If other enzymes involved in oxidation of ω-hydroxy fatty acids have been eliminated from the strain, then the strain will convert ω-hydroxy fatty acids fed in the media to α,ω-dicarboxylic acids.

Figure 15:
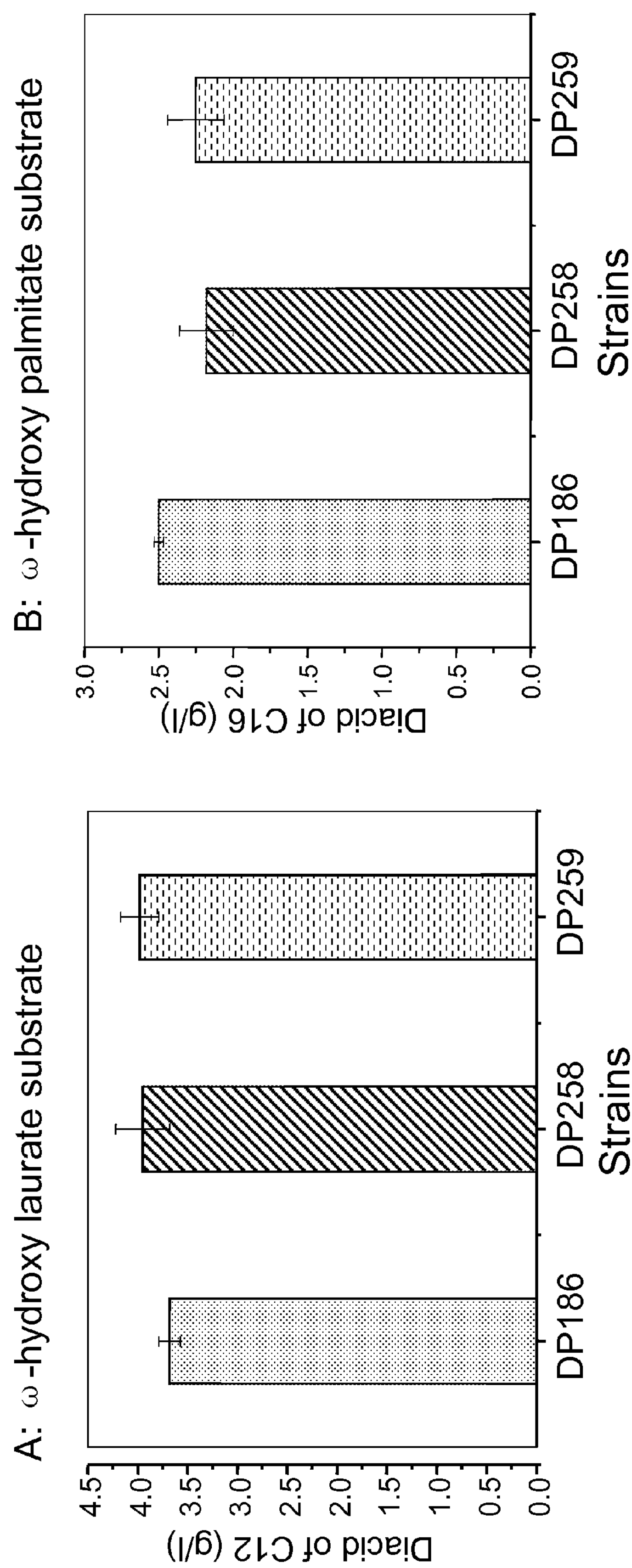

FIG. 15 shows the levels of α,ω-dicarboxylic acids produced by *Candida tropicalis* strains DP186, DP258 and DP259 (see Table 3 for genotypes). Cultures of the yeast strains were grown at 30° C. and 250 rpm for 16 hours in a 500 ml flask containing 30 ml of media F (media F is peptone 3 g/l, yeast extract 6 g/l, yeast nitrogen base 6.7 g/l, sodium acetate 3 g/l, $K_2HPO_4$ 7.2 g/l, $KH_2PO_4$ 9.3 g/l) plus 20 g/l glycerol. After 16 hours 0.5 ml of culture was added to 4.5 ml fresh media F plus 20 g/l glycerol in a 125 ml flask, and grown at 30° C. and 250 rpm for 12 hours before addition of substrate. After addition of substrates growth was continued at 30° C. and 250 rpm. Part A: the substrate ω-hydroxy laurate was then added to a final concentration of 5 g/l and the pH was adjusted to between 7.5 and 8. Samples were taken after 24 hours, cell culture was acidified to pH~1.0 by addition of 6 N HCl, products were extracted from the cell culture by diethyl ether and the concentrations of α,ω-dicarboxy laurate were measured by LC-MS (liquid chromatography mass spectroscopy). Part B: the substrate ω-hydroxy palmitate was then added to a final concentration of 5 g/l and the pH was adjusted to between 7.5 and 8. Samples were taken after 24 hours, cell culture was acidified to pH~1.0 by addition of 6 N HCl, products were extracted from the cell culture by diethyl ether and the concentrations of α,ω-dicarboxy laurate were measured by LC-MS (liquid chromatography mass spectroscopy).

Figure 16:
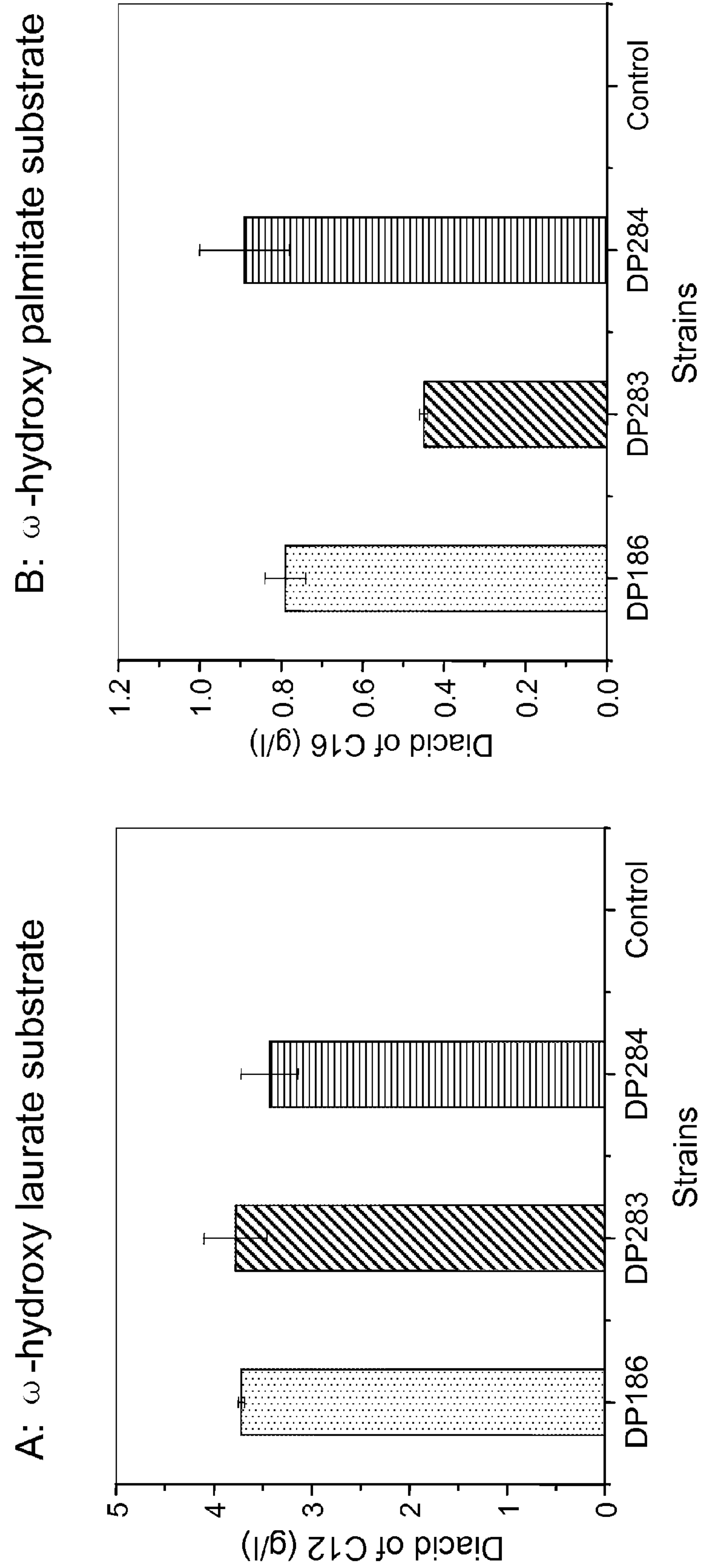

FIG. 16 shows the levels of α,ω-dicarboxylic acids produced by *Candida tropicalis* strains DP186, DP283 and DP284 (see Table 3 for genotypes). Cultures of the yeast strains were grown at 30° C. and 250 rpm for 16 hours in a 500 ml flask containing 30 ml of media F (media F is peptone 3 g/l, yeast extract 6 g/l, yeast nitrogen base 6.7 g/l, sodium acetate 3 g/l, $K_2HPO_4$ 7.2 g/l, $KH_2PO_4$ 9.3 g/l) plus 20 g/l glycerol. After 16 hours 0.5 ml of culture was added to 4.5 ml fresh media F plus 20 g/l glycerol in a 125 ml flask, and grown at 30° C. and 250 rpm for 12 hours before addition of substrate. After addition of substrates growth was continued at 30° C. and 250 rpm. Part A: the substrate ω-hydroxy laurate was then added to a final concentration of 5 g/l and the pH was adjusted to between 7.5 and 8. Samples were taken after 24 hours, cell culture was acidified to pH~1.0 by addition of 6 N HCl, products were extracted from the cell culture by diethyl ether and the concentrations of α,ω-dicarboxy laurate were measured by LC-MS (liquid chromatography mass spectroscopy). Part B: the substrate ω-hydroxy palmitate was then added to a final concentration of 5 g/l and the pH was adjusted to between 7.5 and 8. Samples were taken after 24 hours, cell culture was acidified to pH~1.0 by addition of 6 N HCl, products were extracted from the cell culture by diethyl ether and the concentrations of α,ω-dicarboxy laurate were measured by LC-MS (liquid chromatography mass spectroscopy).

Figure 17:
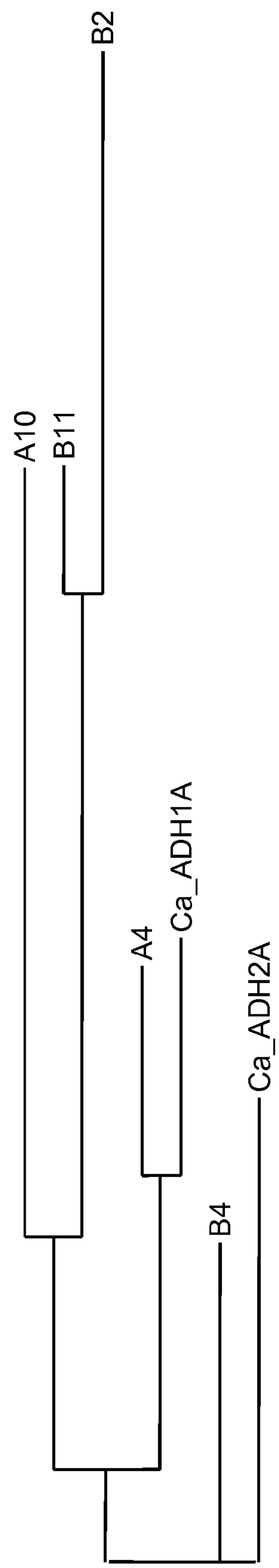

FIG. 17 shows a phylogenetic tree with five *Candida tropicalis* alcohol dehydrogenase sequences (A10, B11, B2, A4 and B4) and two alcohol dehydrogenases from *Candida albicans* (Ca_ADH1A and Ca_ADH2A).

Figure 18:
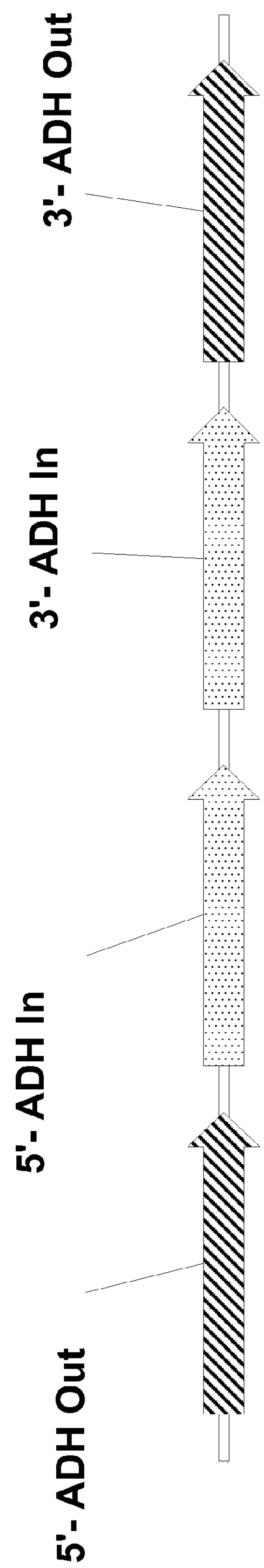

FIG. 18 shows a schematic design for selecting two sets of nested targeting sequences for the deletion of two alleles of a gene whose sequences are very similar, for example the alcohol dehydrogenase genes. The construct for the first allele uses ~200 base pair at the 5' end and ~200 base pair at the 3' end as targeting sequences (5'-ADH Out and 3'-ADH Out). The construct for the second allele uses two sections of ~200 base pair between the first two targeting sequences (5'-ADH In and 3'-ADH In). These sequences are eliminated by the first targeting construct from the first allele of the gene and will thus serve as a targeting sequence for the second allele of the gene.

FIG. 19 shows the levels of α,ω-dicarboxylic acids produced by *Candida tropicalis* strains DP1, DP283 and DP415 (see Table 3 for genotypes). Cultures of the yeast strains were grown at 30° C. and 250 rpm for 18 hours in a 500 ml flask containing 30 ml of media F (media F is peptone 3 g/l, yeast extract 6 g/l, yeast nitrogen base 6.7 g/l, sodium acetate 3 g/l, $K_2HPO_4$ 7.2 g/l, $KH_2PO_4$ 9.3 g/l) plus 20 g/l glycerol. After 18 hours the preculture was diluted in fresh media to $A_{600}$=1.0. This culture was shaken until the $A_{600}$ reached between 5.0 and 6.0. Biocatalytic conversion was initiated by adding 5 ml culture to a 125 ml flask together with 50 mg of ω-hydroxy lauric acid, and pH adjusted to ~7.5 with 2M NaOH. Part A: cell growth was followed by measuring the $A_{600}$ every 2 hours. Part B: formation of diacid; every 2 hours a sample of the cell culture was taken, acidified to pH~1.0 by addition of 6 N HCl, products were extracted from the cell culture by diethyl ether and the concentrations of α,ω-dicarboxy laurate were measured by LC-MS (liquid chromatography mass spectroscopy).

Figure 20:
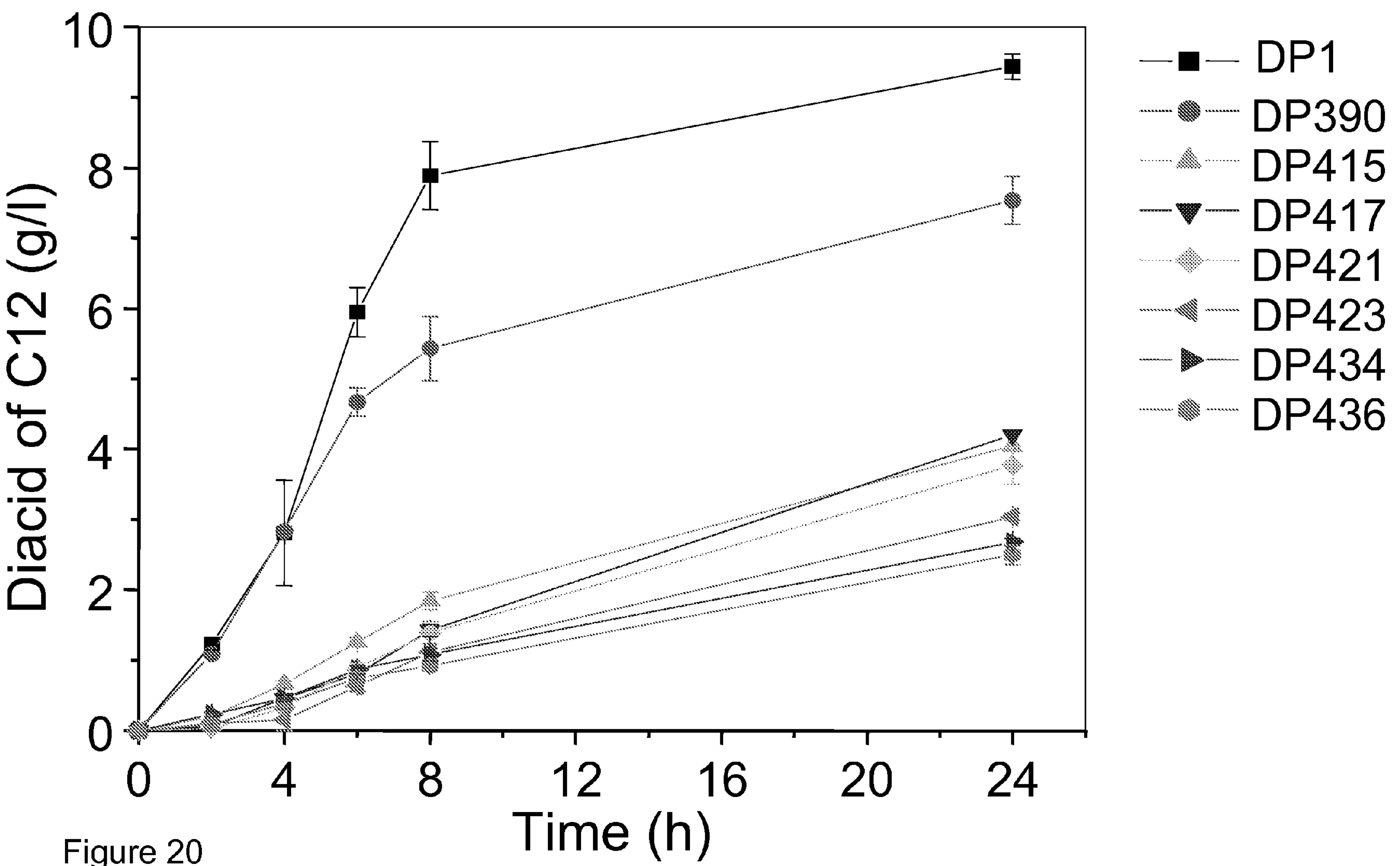

FIG. 20 shows the levels of α,ω-dicarboxylic acids produced by *Candida tropicalis* strains DP1, DP390, DP415, DP417, DP421, DP423, DP434 and DP436 (see Table 3 for genotypes). Cultures of the yeast strains were grown at 30° C. and 250 rpm for 18 hours in a 500 ml flask containing 30 ml of media F (media F is peptone 3 g/l, yeast extract 6 g/l, yeast nitrogen base 6.7 g/l, sodium acetate 3 g/l, $K_2HPO_4$ 7.2 g/l, $KH_2PO_4$ 9.3 g/l) plus 20 g/l glycerol. After 18 hours the preculture was diluted in fresh media to $A_{600}$=1.0. This culture was shaken until the $A_{600}$ reached between 5.0 and 6.0. Biocatalytic conversion was initiated by adding 5 ml culture to a 125 ml flask together with 50 mg of ω-hydroxy lauric acid, and pH adjusted to ~7.5 with 2M NaOH. Formation of diacid was measured at the indicated intervals by taking a sample of the cell culture and acidifying to pH~1.0 by addition of 6 N HCl, products were extracted from the cell culture by diethyl ether and the concentrations of α,ω-dicarboxy laurate were measured by LC-MS (liquid chromatography mass spectroscopy).

Figure 21:
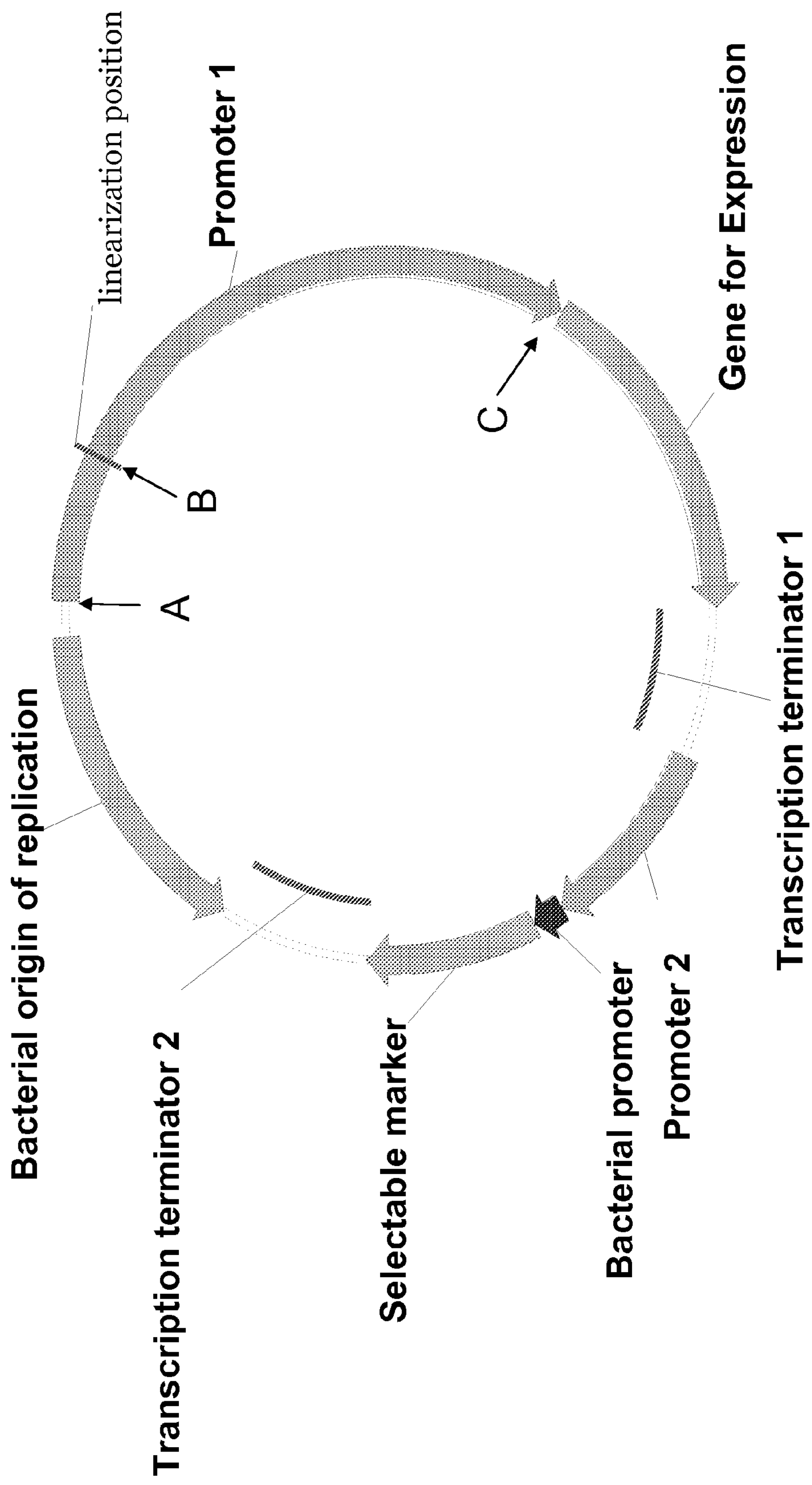

FIG. 21 shows a schematic representation of a DNA "genomic insertion" construct for inserting sequences to be expressed into the genome of yeasts. The general structure is that the construct has a gene for expression which is preceded by a promoter that is active in the yeast (Promoter 1). Promoter 1 comprises a linearization position which may be a site recognized by a restriction enzyme which cleaves the genomic insertion construct once to linearize it, or an annealing site for PCR primers to amplify a linear molecule from the construct. Three positions (A, B and C) are marked in Promoter 1 for reference in FIG. 22 when the construct is linearized. The gene for expression is optionally followed by a transcription terminator (Transcription terminator 1). The genomic insertion construct also comprises a selectable marker. The selectable marker is preferably one that is active in both bacterial and yeast hosts. To achieve this, the selectable marker may be preceded by a yeast promoter (promoter 2) and a bacterial promoter, and optionally it may be followed by a transcription terminator (transcription terminator 2). The genomic insertion construct also comprises a bacterial origin of replication.

Figure 22:
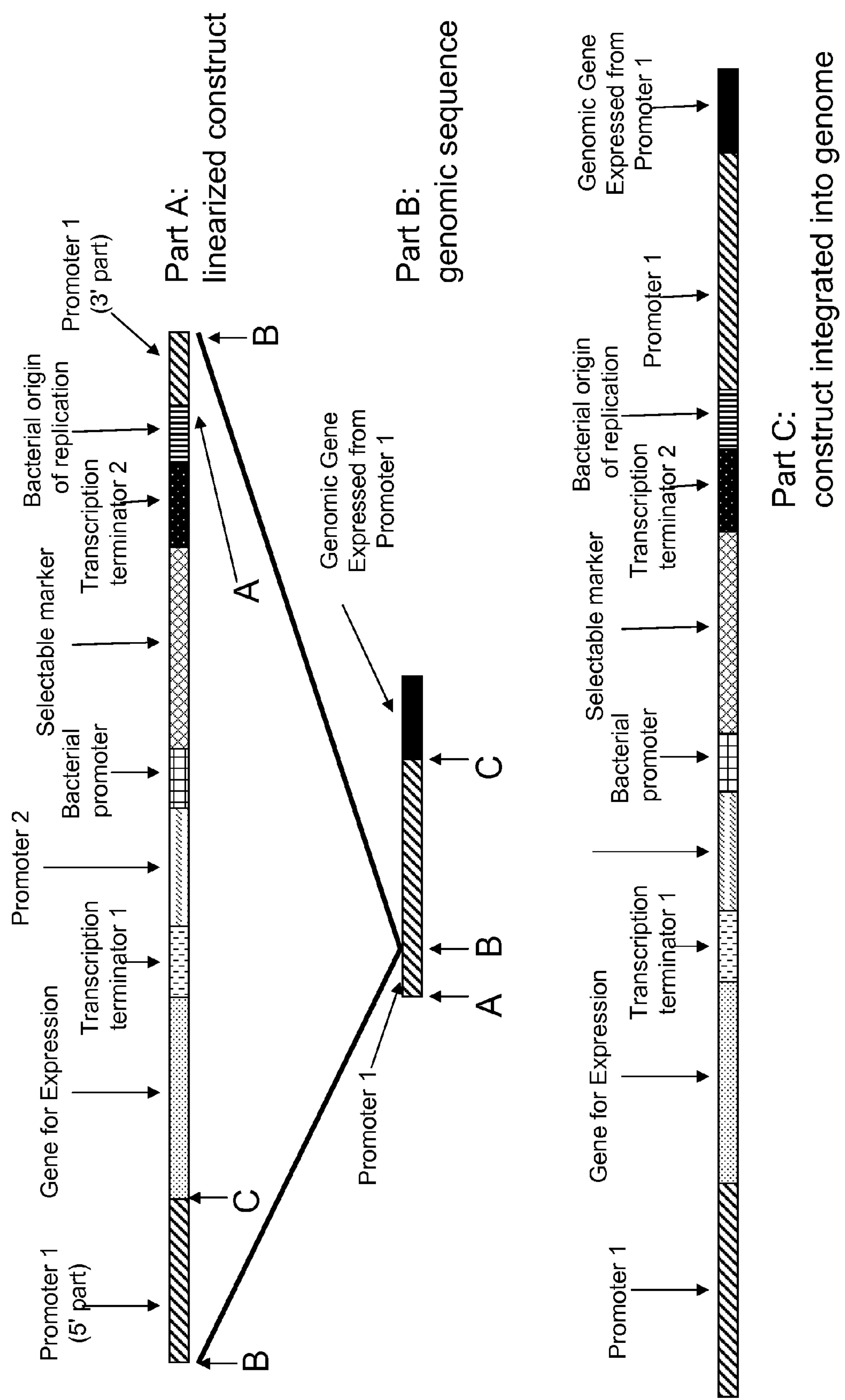

FIG. 22 shows a schematic representation of the integration of a DNA "genomic insertion" construct into the DNA of a yeast genome. Part A shows an integration construct of the structure shown in FIG. 22, with parts marked. The construct is linearized, for example by digesting with an enzyme that recognizes a unique restriction site within promoter 1, or by PCR amplification, or by any other method, so that a portion of promoter 1 is at one end of the linearized construct (5' part), and the remainder at the other end (3' end). Three positions (A, B and C) are marked in Promoter 1, these refer to the positions in FIG. 21. Part B shows the intact Promoter 1 in the yeast genome, followed by the gene that is normally transcribed from Promoter 1 (genomic gene expressed from promoter 1). Three positions (A, B and C) are also marked in the genomic copy of Promoter 1. Part C shows the genome after integration of the construct. The construct integrates at position B in Promoter 1, the site at which the construct was linearized. This results in a duplication of promoter 1 in the genome, with one copy of the promoter driving transcription of the introduced gene for expression and the other copy driving the transcription of the genomic gene expressed from promoter 1.

Figure 23:
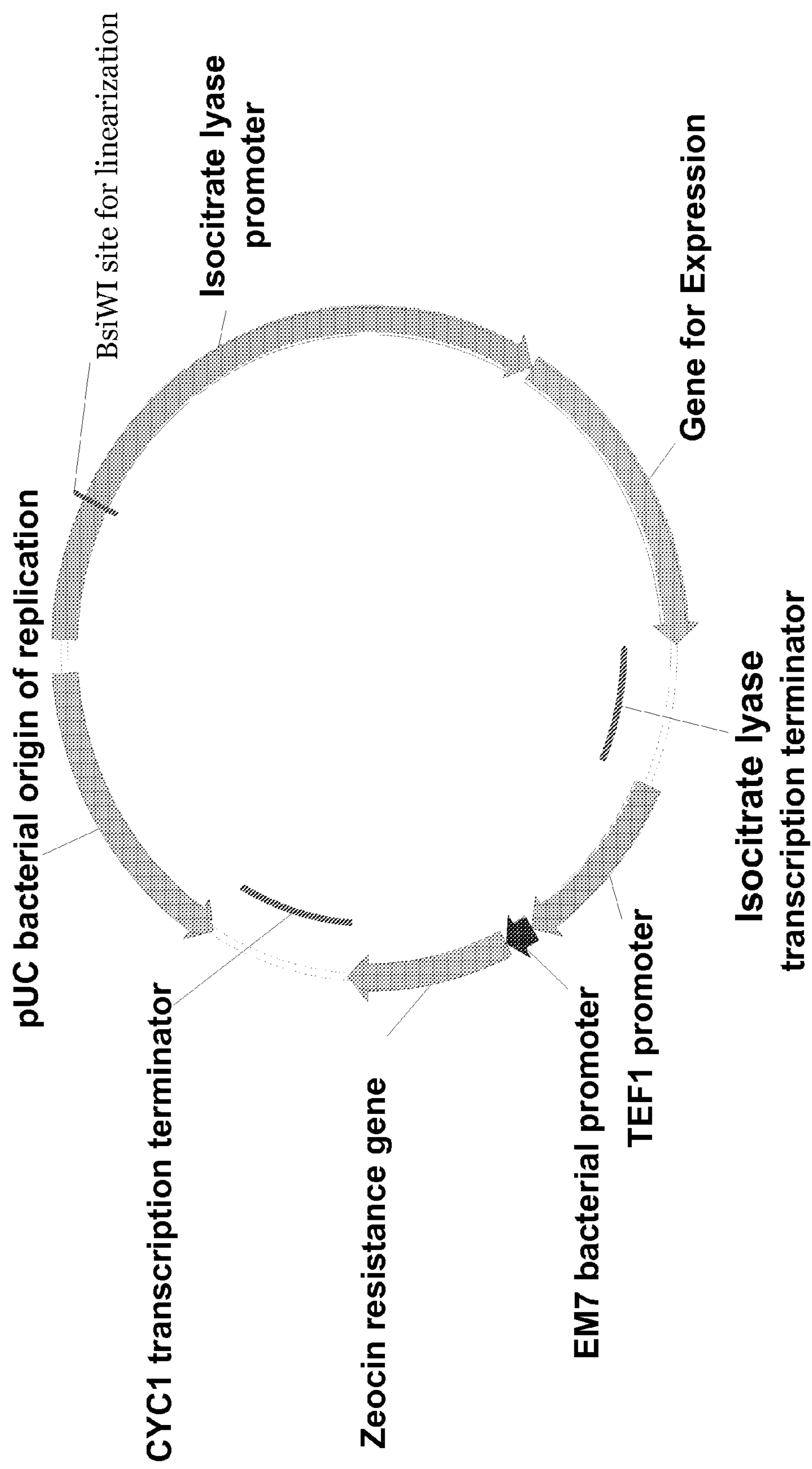

FIG. 23 shows a specific embodiment of the DNA "genomic insertion" construct shown in FIG. 21. The general structure is that the construct has a gene for expression which is preceded by a promoter that is active in the yeast (the *Candida tropicalis* isocitrate lyase promoter). The isocitrate lyase promoter comprises a unique BsiWI site whereby the construct may be cleaved by endocunclease BsiWI once to linearize it. The gene for expression is followed by a transcription terminator (isocitrate lyase transcription terminator). The genomic insertion construct also comprises a selectable marker conferring resistance to the antibiotic zeocin. This selectable marker is active in both bacterial and yeast hosts and preceded by a yeast promoter (the TEF1 promoter) and a Bacterial promoter (the EM7 promoter), and followed by a transcription terminator (the CYC1 transcription terminator 2). The genomic insertion construct also comprises a bacterial origin of replication (the pUC origin of replication).

Figure 24:
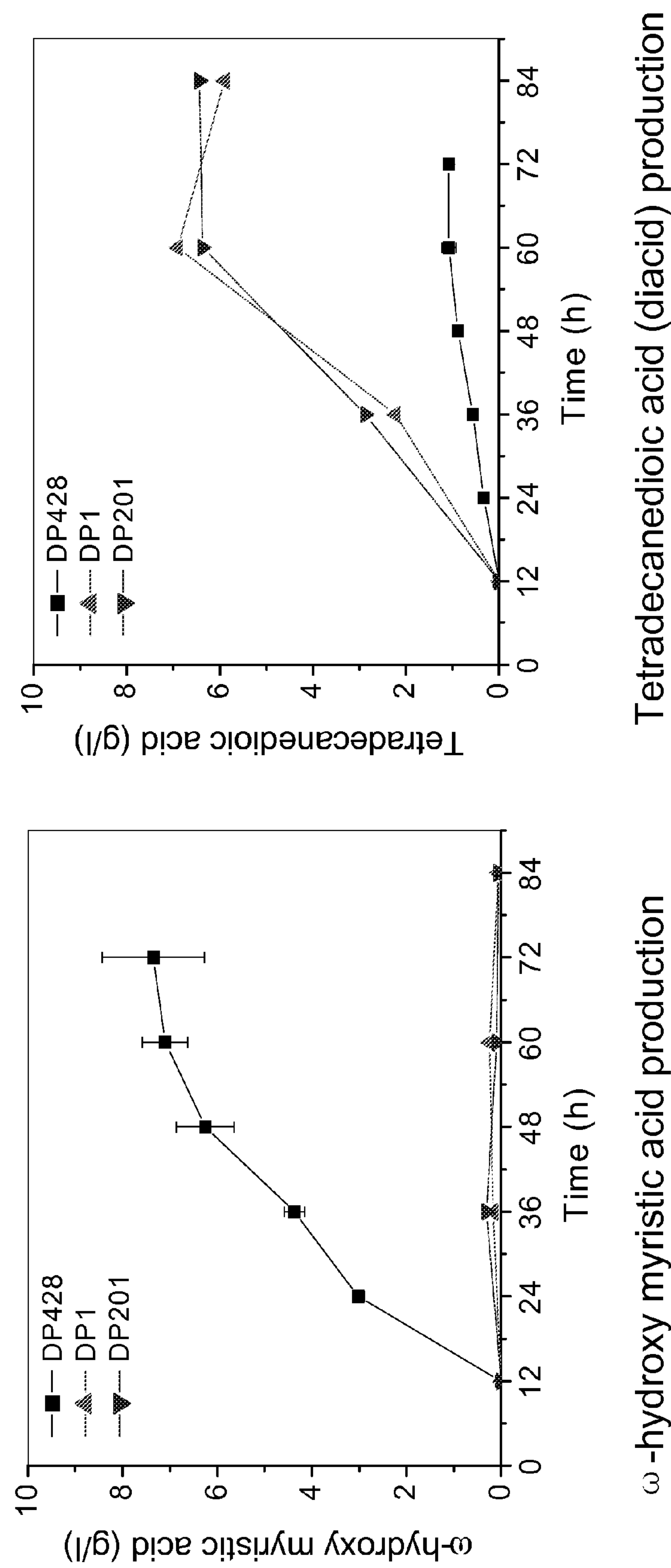

FIG. 24 shows the levels of α,ω-dicarboxylic acids and ω-hydroxy fatty acids produced by *Candida tropicalis* strains dp1, dp201 and dp428 (see table 3 for genotypes). Cultures of the yeast strains were grown at 30° C. and 250 rpm for 18 hours in a 500 ml flask containing 30 ml of media f (media f is peptone 3 g/l, yeast extract 6 g/l, yeast nitrogen base 6.7 g/l, sodium acetate 3 g/l, $k_2hpo_4$ 7.2 g/l, $kh_2po_4$ 9.3 g/l) plus 20 g/l glucose plus 5 g/l ethanol. After 18 hours 3 ml of preculture was added to 27 ml fresh media f plus 20 g/l glucose plus 5 g/l ethanol in a 500 ml flask, and grown at 30° C. and 250 rpm for 20 hours before addition of substrate. Biocatalytic conversion was initiated by adding 40 g/l of methyl myristate, the ph was adjusted to ~7.8 with 2 m naoh. The culture was ph controlled by adding 2 mol/l naoh every 12 hours, glycerol was fed as cosubstrate by adding 500 g/l glycerol and ethanol was fed as a inducer by adding 50% ethanol every 12 hours. Samples were taken at the times indicated, cell culture was acidified to ph ~1.0 by addition of 6 n hcl, products were extracted from the cell culture by diethyl ether and the concentrations of ω-hydroxy myristate and α,ω-dicarboxymyristate were measured by lc-ms (liquid chromatography mass spectroscopy).

Figure 25:
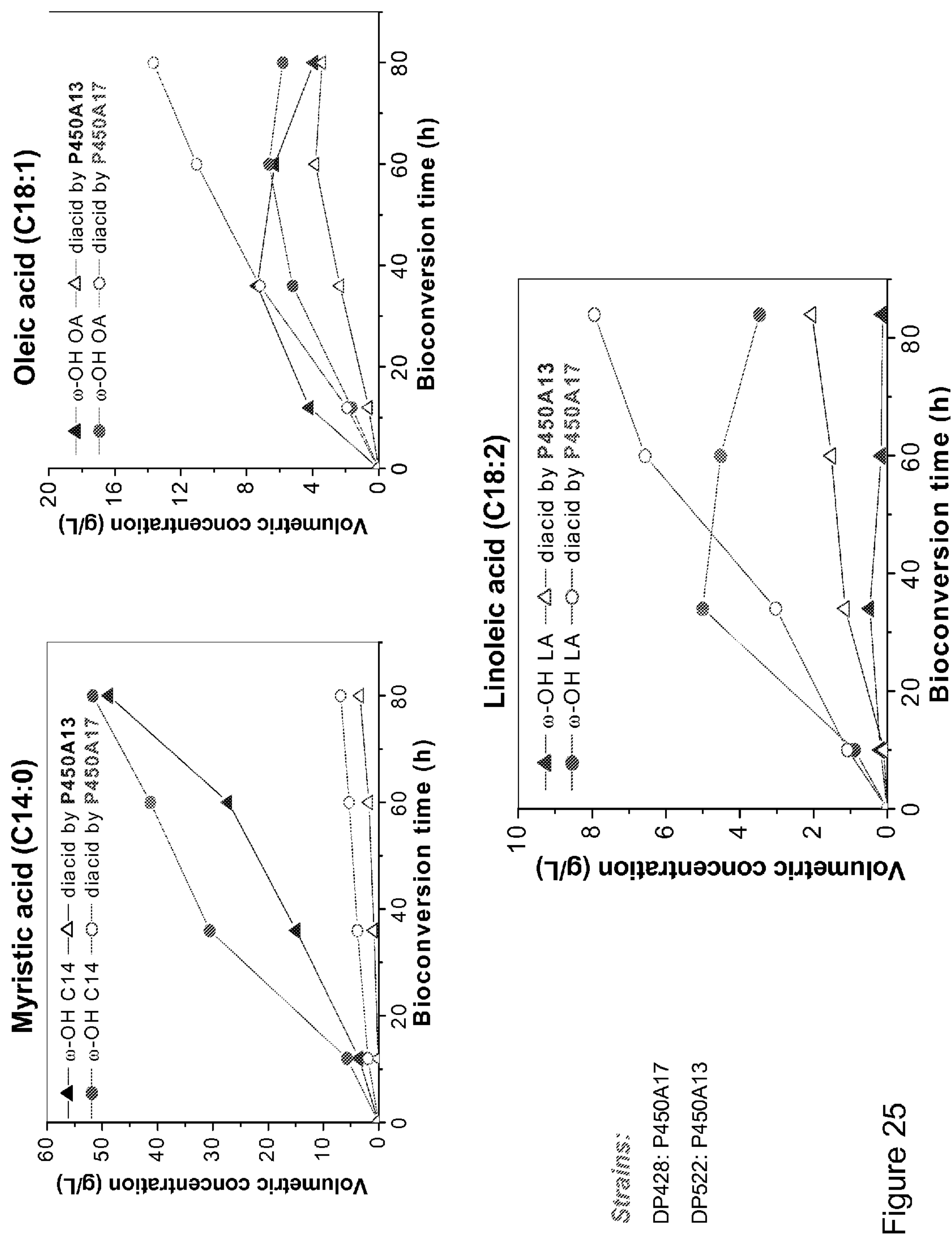

FIG. 25 shows the levels of α,ω-dicarboxylic acids and ω-hydroxy fatty acids produced by *Candida tropicalis* strains dp428 and dp522 (see table 3 for genotypes). Cultures of the yeast strains were grown at 30° C. in a dasgip parallel fermentor containing 200 ml of media f (media f is peptone 3 g/l, yeast extract 6 g/l, yeast nitrogen base 6.7 g/l, sodium acetate 3 g/l, $k_2hpo_4$ 7.2 g/l, $kh_2po_4$ 9.3 g/l) plus 30 g/l glucose. The ph was maintained at 6.0 by automatic addition of 6 m naoh or 2 m $h_2so_4$ solution. Dissolved oxygen was kept at 70% by agitation and $o_2$-cascade control mode. After 6 hour growth, ethanol was fed into the cell culture to 5 g/l. After 12 h growth, biocatalytic conversion was initiated by adding (a) 20 g/l of methyl myristate, (b) 20 g/l oleic acid or (c) 10 g/l linoleic acid. During the conversion phase, 80% glycerol was fed as co-substrate for conversion of methyl myristate and 500 g/l glucose was fed as co-substrate for conversion of oleic acid and linoleic acid by dissolved oxygen-stat control mode (the high limit of dissolved oxygen was 75% and low limit of dissolved oxygen was 70%, which means glycerol feeding was initiated when dissolved oxygen is higher than 75% and stopped when dissolved oxygen was lower than 70%). Every 12 hour, ethanol was added into cell culture to 2 g/l, and fatty acid substrate was added to 20 g/l until the total substrate concentration added was (a) 60 g/l of methyl myristate, (b) 60 g/l oleic acid or (c) 30 g/l linoleic acid. Formation of products was measured at the indicated intervals by taking samples and acidifying to ph~1.0 by addition of 6 n hcl; products were extracted from the cell culture by diethyl ether and the concentrations of ω-hydroxy fatty acids and α,ω-dicarboxylic acids were measured by lc-ms (liquid chromatography mass spectroscopy).

Figure 26:
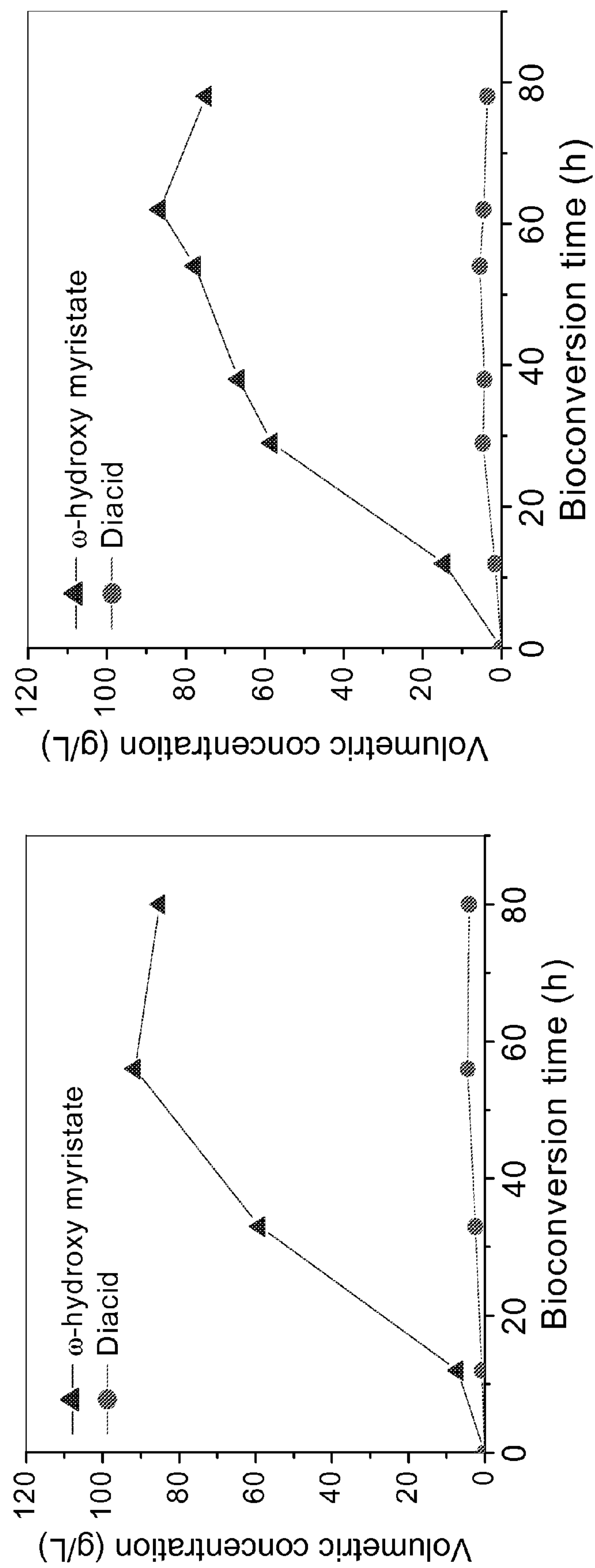

FIG. 26 shows the levels of α,ω-dicarboxylic acids and ω-hydroxy fatty acids produced by *Candida tropicalis* strain dp428 (see table 3 for genotype) in two separate fermentor runs. *C. Tropicalis* dp428 was taken from a glycerol stock or fresh agar plate and inoculated into 500 ml shake flask containing 30 ml of ypd medium (20 g/l glucose, 20 g/l peptone and 10 g/l yeast extract) and shaken at 30° C., 250 rpm for 20 hours. Cells were collected by centrifugation and re-suspended in fm3 medium for inoculation. (fm3 medium is 30 g/l glucose, 7 g/l ammonium sulfate, 5.1 g/l potassium phosphate, monobasic, 0.5 g/l magnesium sulfate, 0.1 g/l calcium chloride, 0.06 g/l citric acid, 0.023 g/l ferric chloride, 0.0002 g/l biotin and 1 ml/l of a trace elements solution. The trace elements solution contains 0.9 g/l boric acid, 0.07 g/l cupric sulfate, 0.18 g/l potassium iodide, 0.36 g/l ferric chloride, 0.72 g/l manganese sulfate, 0.36 g/l sodium molybdate, 0.72 g/l zinc sulfate.) Conversion was performed by inoculating 15 ml of preculture into 135 ml fm3 medium, methyl myristate was added to 20 g/l and the temperature was kept at 30° C. The ph was maintained at 6.0 by automatic addition of 6 m naoh or 2 m $h_2so_4$ solution. Dissolved oxygen was kept at 70% by agitation and $o_2$-cascade control mode. After six hour growth, ethanol was fed into the cell culture to 5 g/l. During the conversion phase, 80% glycerol was fed as co-substrate by dissolved oxygen-stat control mode (the high limit of dissolved oxygen was 75% and low limit of dissolved oxygen was 70%, which means glycerol feeding was initiated when dissolved oxygen is higher than 75% and stopped when dissolved oxygen was lower than 70%). Every 12 hour, ethanol was added into cell culture to 2 g/l, and methyl myristate was added to 40 g/l until the total methyl myristate added was 140 g/l (e.g. the initial 20 g/l plus 3 subsequent 40 g/l additions). Formation of products was measured at the indicated intervals by taking samples and acidifying to ph~1.0 by addition of 6 n hcl; products were extracted from the cell culture by diethyl ether and the concentrations of ω-hydroxy myristate and α,ω-dicarboxymyristate were measured by lc-ms (liquid chromatography mass spectroscopy).

Figure 27:
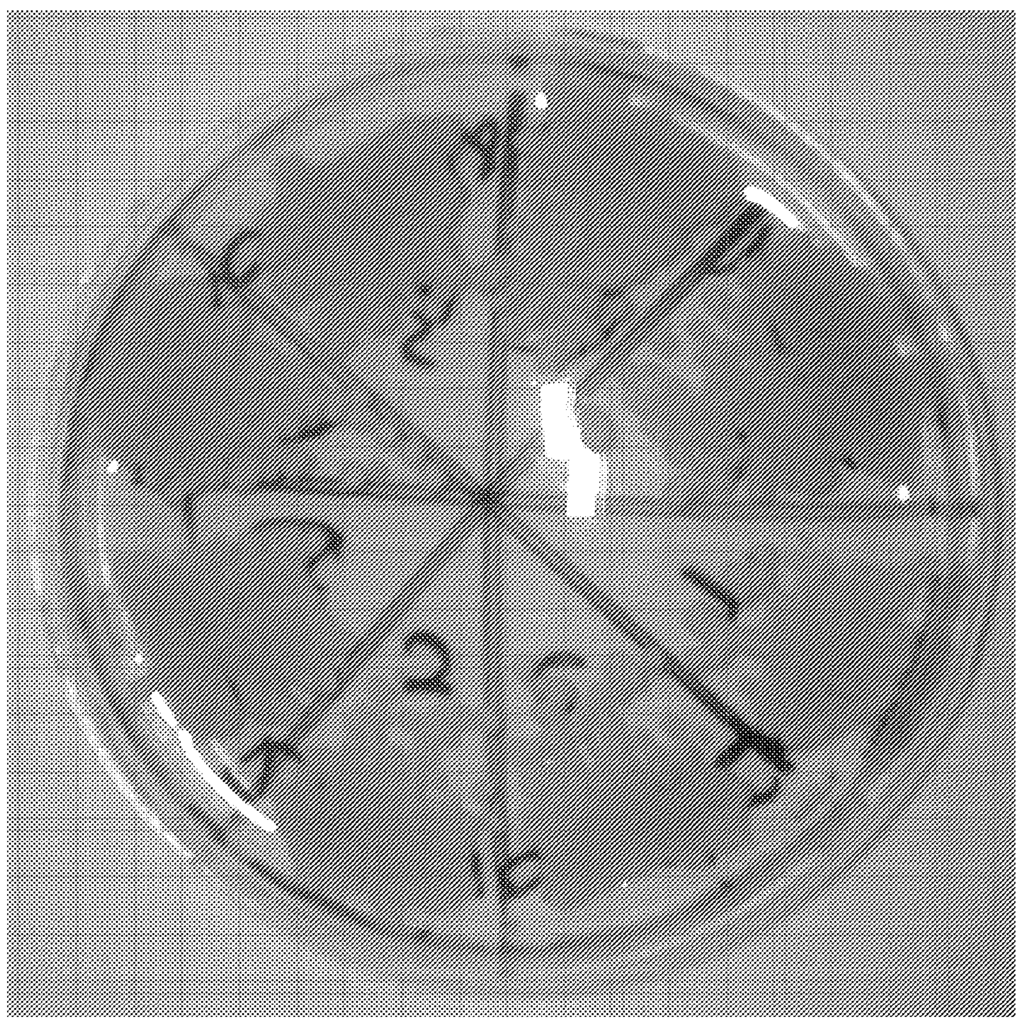

FIG. 27 shows the red fluorescent protein mCherry produced by *Candida tropicalis* strain DP197 (see Table 3 for genotypes). Cultures of the yeast strains were grown at 30° C. on plates containing Buffered Minimal Medium+0.5% Glucose, 0.5% Glycerol, and 0.5% EtOH.

5. DETAILED DESCRIPTION

It is to be understood that what is disclosed herein is not limited to the particular methodology, devices, solutions or apparatuses described, as such methods, devices, solutions or apparatuses can, of course, vary.

5.1. Definitions

Use of the singular forms "a," "an," and "the" include plural references unless the context clearly dictates otherwise. Thus, for example, reference to "a polynucleotide" includes a plurality of polynucleotides, reference to "a substrate" includes a plurality of such substrates, reference to "a variant" includes a plurality of variants, and the like.

Terms such as "connected," "attached," "linked," and "conjugated" are used interchangeably herein and encompass direct as well as indirect connection, attachment, linkage or conjugation unless the context clearly dictates otherwise. Where a range of values is recited, it is to be understood that each intervening integer value, and each fraction thereof, between the recited upper and lower limits of that range is also specifically disclosed, along with each subrange between such values. The upper and lower limits of any range can independently be included in or excluded from the range, and each range where either, neither or both limits are included is also encompassed in the disclosed embodiments. Where a value being discussed has inherent limits, for example where a component can be present at a concentration of from 0 to 100%, or where the pH of an aqueous solution can range from 1 to 14, those inherent limits are specifically disclosed. Where a value is explicitly recited, it is to be understood that values which are about the same quantity or amount as the recited value are also encompassed. Where a combination is disclosed, each subcombination of the elements of that combination is also specifically disclosed and is within the scope of the disclosed embodiments. Conversely, where different elements or groups of elements are individually disclosed, combinations thereof are also disclosed. Where any embodiment is disclosed as having a plurality of alternatives, examples of that embodiment in which each alternative is excluded singly or in any combination with the other alternatives are also hereby disclosed; more than one element of a disclosed embodiment can have such exclusions, and all combinations of elements having such exclusions are hereby disclosed.

Unless defined otherwise herein, all technical and scientific terms used herein have the same meaning as commonly understood by one of ordinary skill in the art. Singleton et al., *Dictionary of Microbiology and Molecular Biology,* 2nd Ed., John Wiley and Sons, New York, 1994, and Hale & Marham, *The Harper Collins Dictionary of Biology*, Harper Perennial, NY, 1991, provide one of ordinary skill in the art with a general dictionary of many of the terms used herein. Although any methods and materials similar or equivalent to those described herein can be used in the practice or testing of the disclosed embodiments, the preferred methods and materials are described. Unless otherwise indicated, nucleic acids are written left to right in 5' to 3' orientation; amino acid sequences are written left to right in amino to carboxy orientation, respectively. The terms defined immediately below are more fully defined by reference to the specification as a whole.

As used, herein, computation of percent identity takes full weight of any insertions in two sequences for which percent identity is computed. To compute percent identity between two sequences, they are aligned and any necessary insertions in either sequence being compared are then made in accordance with sequence alignment algorithms known in the art. Then, the percent identity is computed, where each insertion in either sequence necessary to make the optimal alignment between the two sequences is counted as a mismatch.

The terms "polynucleotide," "oligonucleotide," "nucleic acid" and "nucleic acid molecule" and "gene" are used interchangeably herein to refer to a polymeric form of nucleotides of any length, and may comprise ribonucleotides, deoxyribonucleotides, analogs thereof, or mixtures thereof. This term refers only to the primary structure of the molecule. Thus, the term includes triple-, double- and single-stranded deoxyribonucleic acid ("DNA"), as well as triple-, double- and single-stranded ribonucleic acid ("RNA"). It also includes modified, for example by alkylation, and/or by capping, and unmodified forms of the polynucleotide. More particularly, the terms "polynucleotide," "oligonucleotide," "nucleic acid" and "nucleic acid molecule" include polydeoxyribonucleotides (containing 2-deoxy-D-ribose), polyribonucleotides (containing D-ribose), including tRNA, rRNA, hRNA, siRNA and mRNA, whether spliced or unspliced, any other type of polynucleotide which is an N- or C-glycoside of a purine or pyrimidine base, and other polymers containing nonnucleotidic backbones, for example, polyamide (e.g., peptide nucleic acids ("PNAs")) and polymorpholino (commercially available from the Anti-Virals, Inc., Corvallis, Oreg., as Neugene) polymers, and other synthetic sequence-specific nucleic acid polymers providing that the polymers contain nucleobases in a configuration which allows for base pairing and base stacking, such as is found in DNA and RNA. There is no intended distinction in length between the terms "polynucleotide," "oligonucleotide," "nucleic acid" and "nucleic acid molecule," and these terms are used interchangeably herein. These terms refer only to the primary structure of the molecule. Thus, these terms include, for example, 3'-deoxy-2',5'-DNA, oligodeoxyribonucleotide N3' P5' phosphoramidates, 2'-O-alkyl-substituted RNA, double- and single-stranded DNA, as well as double- and single-stranded RNA, and hybrids thereof including for example hybrids between DNA and RNA or between PNAs and DNA or RNA, and also include known types of modifications, for example, labels, alkylation, "caps," substitution of one or more of the nucleotides with an analog, internucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalkylphosphoramidates, aminoalkylphosphotriesters), those containing pendant moieties, such as, for example, proteins (including enzymes (e.g. nucleases), toxins, antibodies, signal peptides, poly-L-lysine, etc.), those with intercalators (e.g., acridine, psoralen, etc.), those containing chelates (of, e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide.

Where the polynucleotides are to be used to express encoded proteins, nucleotides that can perform that function or which can be modified (e.g., reverse transcribed) to perform that function are used. Where the polynucleotides are to be used in a scheme that requires that a complementary strand be formed to a given polynucleotide, nucleotides are used which permit such formation.

It will be appreciated that, as used herein, the terms "nucleoside" and "nucleotide" will include those moieties which contain not only the known purine and pyrimidine bases, but also other heterocyclic bases which have been modified. Such modifications include methylated purines or pyrimidines, acylated purines or pyrimidines, or other heterocycles. Modified nucleosides or nucleotides can also include modifications on the sugar moiety, e.g., where one or more of the hydroxyl groups are replaced with halogen, aliphatic groups, or is functionalized as ethers, amines, or the like.

Standard A-T and G-C base pairs form under conditions which allow the formation of hydrogen bonds between the N3-H and C4-oxy of thymidine and the NI and C6-NH2, respectively, of adenosine and between the C2-oxy, N3 and C4-NH2, of cytidine and the C2-$NH_2$, N'—H and C6-oxy, respectively, of guanosine. Thus, for example, guanosine (2-amino-6-oxy-9-beta-D-ribofuranosyl-purine) may be modified to form isoguanosine (2-oxy-6-amino-9-beta-D-ribofuranosyl-purine). Such modification results in a nucleoside base which will no longer effectively form a standard base pair with cytosine. However, modification of cytosine (1-beta-D-ribofuranosyl-2-oxy-4-amino-pyrimidine) to form isocytosine (1-beta-D-ribofuranosyl-2-amino-4-oxy-pyrimidine-) results in a modified nucleotide which will not effectively base pair with guanosine but will form a base pair with isoguanosine (U.S. Pat. No. 5,681,702 to Collins et al., hereby incorporated by reference in its entirety). Isocytosine is available from Sigma Chemical Co. (St. Louis, Mo.); isocytidine may be prepared by the method described by Switzer et al. (1993) Biochemistry 32:10489-10496 and references cited therein; 2'-deoxy-5-methyl-isocytidine may be prepared by the method of Tor et al., 1993, J. Am. Chem. Soc. 115:4461-4467 and references cited therein; and isoguanine nucleotides may be prepared using the method described by Switzer et al., 1993, supra, and Mantsch et al., 1993, Biochem. 14:5593-5601, or by the method described in U.S. Pat. No. 5,780,610 to Collins et al., each of which is hereby incorporated by reference in its entirety. Other nonnatural base pairs may be synthesized by the method described in Piccirilli et al., 1990, Nature 343:33-37, hereby incorporated by reference in it entirety, for the synthesis of 2,6-diaminopyrimidine and its complement (1-methylpyrazolo-[4,3]pyrimidine-5,7-(4H, 6H)-dione. Other such modified nucleotidic units which form unique base pairs are known, such as those described in Leach et al., 1992, J. Am. Chem. Soc. 114:3675-3683 and Switzer et al., supra.

The phrase "DNA sequence" refers to a contiguous nucleic acid sequence. The sequence can be either single stranded or double stranded, DNA or RNA, but double stranded DNA sequences are preferable. The sequence can be an oligonucleotide of 6 to 20 nucleotides in length to a full length genomic sequence of thousands or hundreds of thousands of base pairs. DNA sequences are written from 5' to 3' unless otherwise indicated.

The term "protein" refers to contiguous "amino acids" or amino acid "residues." Typically, proteins have a function. However, for purposes of this disclosure, proteins also encompass polypeptides and smaller contiguous amino acid sequences that do not have a functional activity. The functional proteins of this disclosure include, but are not limited to, esterases, dehydrogenases, hydrolases, oxidoreductases, transferases, lyases, ligases, receptors, receptor ligands, cytokines, antibodies, immunomodulatory molecules, signaling molecules, fluorescent proteins and proteins with insecticidal or biocidal activities. Useful general classes of enzymes include, but are not limited to, proteases, cellulases, lipases, hemicellulases, laccases, amylases, glucoamylases, esterases, lactases, polygalacturonases, galactosidases, ligninases, oxidases, peroxidases, glucose isomerases, nitrilases, hydroxylases, polymerases and depolymerases. In addition to enzymes, the encoded proteins which can be used in this disclosure include, but are not limited to, transcription factors, antibodies, receptors, growth factors (any of the PDGFs, EGFs, FGFs, SCF, HGF, TGFs, TNFs, insulin, IGFs, LIFs, oncostatins, and CSFs), immunomodulators, peptide hormones, cytokines, integrins, interleukins, adhesion molecules, thrombomodulatory molecules, protease inhibitors, angiostatins, defensins, cluster of differentiation antigens, interferons, chemokines, antigens including those from infectious viruses and organisms, oncogene products, thrombopoietin, erythropoietin, tissue plasminogen activator, and any other biologically active protein which is desired for use in a clinical, diagnostic or veterinary setting. All of these proteins are well defined in the literature and are so defined herein. Also included are deletion mutants of such proteins, individual domains of such proteins, fusion proteins made from such proteins, and mixtures of such proteins; particularly useful are those which have increased half-lives and/or increased activity.

"Polypeptide" and "protein" are used interchangeably herein and include a molecular chain of amino acids linked through peptide bonds. The terms do not refer to a specific length of the product. Thus, "peptides," "oligopeptides," and "proteins" are included within the definition of polypeptide. The terms include polypeptides containing in co- and/or post-translational modifications of the polypeptide made in vivo or in vitro, for example, glycosylations, acetylations, phosphorylations, PEGylations and sulphations. In addition, protein fragments, analogs (including amino acids not encoded by the genetic code, e.g. homocysteine, ornithine, p-acetylphenylalanine, D-amino acids, and creatine), natural or artificial mutants or variants or combinations thereof, fusion proteins, derivatized residues (e.g. alkylation of amine groups, acetylations or esterifications of carboxyl groups) and the like are included within the meaning of polypeptide.

"Amino acids" or "amino acid residues" may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The term "expression system" refers to any in vivo or in vitro biological system that is used to produce one or more protein encoded by a polynucleotide.

The term "translation" refers to the process by which a polypeptide is synthesized by a ribosome 'reading' the sequence of a polynucleotide.

In some embodiments, the term "disrupt" means to reduce or diminish the expression of a gene in a host cell organism.

In some embodiments, the term "disrupt" means to reduce or diminish a function of a protein encoded by a gene in a host cell organism. This function may be, for example, an enzymatic activity of the protein, a specific enzymatic activity of the protein, a protein-protein interaction that the protein undergoes in a host cell organism, or a protein-nucleic acid interaction that the protein undergoes in a host cell organism.

In some embodiments, the term "disrupt" means to eliminate the expression of a gene in a host cell organism.

In some embodiments, the term "disrupt" means to eliminate the function of a protein encoded by a gene in a host cell organism. This function may be, for example, an enzymatic activity of the protein, a specific enzymatic activity of the protein, a protein-protein interaction that the protein undergoes in a host cell organism, or a protein-nucleic acid interaction that the protein undergoes in a host cell organism.

In some embodiments, the term "disrupt" means to cause a protein encoded by a gene in a host cell organism to have a modified activity spectrum (e.g., reduced enzymatic activity) relative to wild-type activity spectrum of the protein.

In some embodiments, disruption is caused by mutating a gene in a host cell organism that encodes a protein. For example, a point mutation, an insertion mutation, a deletion mutation, or any combination of such mutations, can be used to disrupt the gene. In some embodiments, this mutation causes the protein encoded by the gene to express poorly or not at all in the host cell organism. In some embodiments, this mutation causes the gene to no longer be present in the host cell organism. In some embodiments, this mutation causes the gene to no longer encode a functional protein in the host cell organism. The mutation to the gene may be in the portion of the gene that encodes a protein product (exon), it may be in any of the regulatory sequences (e.g., promoter, enhancer, etc.) that regulate the expression of the gene, or it may arise in an intron.

In some embodiments, the disruption (e.g., mutation) of a gene causes the protein encoded by the gene to have a mutation that diminishes a function of the protein relative to the function of the wild type counterpart of the mutated protein.

As used, herein, the wild type counterpart of a mutated protein is the unmutated protein, occurring in wild type host cell organism, which corresponds to the mutated protein. For example, if the mutated protein is a protein encoded by mutated *Candida tropicalis* POX 5, the wild type counterpart of the mutated protein is the gene product from naturally occurring *Candida tropicalis* POX 5 that is not mutated.

As used herein, the wild type counterpart of a mutated gene is the unmutated gene occurring in wild type host cell organism, which corresponds to the mutated gene. For example, if the mutated gene is *Candida tropicalis* POX 5 containing a point mutation, the wild type counterpart is *Candida tropicalis* POX 5 without the point mutation.

In some embodiments, a gene is deemed to be disrupted when the gene is not capable of expressing protein in the host cell organism.

In some embodiments, a gene is deemed to be disrupted when the disrupted gene expresses protein in a first host cell organism that contains the disrupted gene in amounts that are 20% or less than the amounts of protein expressed by the wild type counterpart of the gene in a second host cell organism that does not contain the disrupted gene, when the first host cell organism and the second host cell organism are under the same environmental conditions (e.g., same temperature, same media, etc.).

In some embodiments, a gene is deemed to be disrupted when the disrupted gene expresses protein in a first host cell organism that contains the disrupted gene in amounts that are 30% or less than the amounts of protein expressed by the wild type counterpart of the gene in a second host cell organism that does not contain the disrupted gene, when the first host cell organism and the second host cell organism are under the same environmental conditions (e.g., same temperature, same media, etc.).

In some embodiments, a gene is deemed to be disrupted when the disrupted gene expresses protein in a first host cell organism that contains the disrupted gene in amounts that are 40% or less than the amounts of protein expressed by the wild type counterpart of the gene in a second host cell organism that does not contain the disrupted gene, when the first host cell organism and the second host cell organism are under the same environmental conditions (e.g., same temperature, same media, etc.).

In some embodiments, a gene is deemed to be disrupted when the disrupted gene expresses protein in a first host cell organism that contains the disrupted gene in amounts that are 50% or less than the amounts of protein expressed by the wild type counterpart of the gene in a second host cell organism that does not contain the disrupted gene, when the first host cell organism and the second host cell organism are under the same environmental conditions (e.g., same temperature, same media, etc.).

In some embodiments, a gene is deemed to be disrupted when the disrupted gene expresses protein in a first host cell organism that contains the disrupted gene in amounts that are 60% or less than the amounts of protein expressed by the wild type counterpart of the gene in a second host cell organism that does not contain the disrupted gene, when the first host cell organism and the second host cell organism are under the same environmental conditions (e.g., same temperature, same media, etc.).

In some embodiments, a gene is deemed to be disrupted when the disrupted gene expresses protein in a first host cell organism that contains the disrupted gene in amounts that are 70% or less than the amounts of protein expressed by the wild type counterpart of the gene in a second host cell organism that does not contain the disrupted gene, when the first host cell organism and the second host cell organism are under the same environmental conditions (e.g., same temperature, same media, etc.).

In some embodiments, a gene is deemed to be disrupted when the abundance of mRNA transcripts that encode the disrupted gene in a first host cell organism that has the disrupted gene are 20% or less than the abundance of mRNA transcripts that encode the gene in second wild type host cell organism that does not contain the disrupted gene when the first host cell organism and the second host cell organism are under the same environmental conditions (e.g., temperature, media, etc.).

In some embodiments, a gene is deemed to be disrupted when the abundance of mRNA transcripts that encode the disrupted gene in a first host cell organism that has the disrupted gene are 30% or less than the abundance of mRNA transcripts that encode the gene in second wild type host cell organism that does not contain the disrupted gene when the first host cell organism and the second host cell organism are under the same environmental conditions (e.g., temperature, media, etc.).

In some embodiments, a gene is deemed to be disrupted when the abundance of mRNA transcripts that encode the disrupted gene in a first host cell organism that has the disrupted gene are 40% or less than the abundance of mRNA transcripts that encode the gene in second wild type host cell organism that does not contain the disrupted gene when the first host cell organism and the second host cell organism are under the same environmental conditions (e.g., temperature, media, etc.).

In some embodiments, a gene is deemed to be disrupted when the abundance of mRNA transcripts that encode the disrupted gene in a first host cell organism that has the disrupted gene are 50% or less than the abundance of mRNA transcripts that encode the gene in second wild type host cell organism that does not contain the disrupted gene when the first host cell organism and the second host cell organism are under the same environmental conditions (e.g., temperature, media, etc.).

In some embodiments, a gene is deemed to be disrupted when the abundance of mRNA transcripts that encode the disrupted gene in a first host cell organism that has the disrupted gene are 60% or less than the abundance of mRNA transcripts that encode the gene in second wild type host cell organism that does not contain the disrupted gene when the first host cell organism and the second host cell organism are under the same environmental conditions (e.g., temperature, media, etc.).

In some embodiments, a gene is deemed to be disrupted when the abundance of mRNA transcripts that encode the disrupted gene in a first host cell organism that has the disrupted gene are 70% or less than the abundance of mRNA transcripts that encode the gene in second wild type host cell organism that does not contain the disrupted gene when the first host cell organism and the second host cell organism are under the same environmental conditions (e.g., temperature, media, etc.).

In some embodiments, a protein is deemed to be disrupted when the protein has an enzymatic activity that is 20% or less than the activity of the wild type counterpart of the protein when the disrupted protein and the wild type counterpart of the protein are under the same conditions (e.g., temperature, concentration, pH, concentration of substrate, salt concentration, etc.).

In some embodiments, a protein is deemed to be disrupted when the protein has an enzymatic activity that is 30% or less than the activity of the wild type counterpart of the protein when the disrupted protein and the wild type counterpart of the protein are under the same conditions (e.g., temperature, concentration, pH, concentration of substrate, salt concentration, etc.).

In some embodiments, a protein is deemed to be disrupted when the protein has an enzymatic activity that is 40% or less than the activity of the wild type counterpart of the protein when the disrupted protein and the wild type counterpart of the protein are under the same conditions (e.g., temperature, concentration, pH, concentration of substrate, salt concentration, etc.).

In some embodiments, a protein is deemed to be disrupted when the protein has an enzymatic activity that is 50% or less than the activity of the wild type counterpart of the protein when the disrupted protein and the wild type counterpart of the protein are under the same conditions (e.g., temperature, concentration, pH, concentration of substrate, salt concentration, etc.).

In some embodiments, a protein is deemed to be disrupted when the protein has an enzymatic activity that is 60% or less than the activity of the wild type counterpart of the protein when the disrupted protein and the wild type counterpart of the protein are under the same conditions (e.g., temperature, concentration, pH, concentration of substrate, salt concentration, etc.).

In some embodiments, a protein is deemed to be disrupted when the protein has an enzymatic activity that is 70% or less than the activity of the wild type counterpart of the protein when the disrupted protein and the wild type counterpart of the protein are under the same conditions (e.g., temperature, concentration, pH, concentration of substrate, salt concentration, etc.).

In some embodiments enzymatic activity is defined as moles of substrate converted per unit time=rate×reaction volume. Enzymatic activity is a measure of the quantity of active enzyme present and is thus dependent on conditions, which are to be specified. The SI unit for enzyme activity is the katal, 1 katal=1 mol s-1.

In some embodiments enzymatic activity is expressed as an enzyme unit (EU)=1 30 μmol/min, where 1 U corresponds to 16.67 nanokatals. See Nomenclature Committee of the International Union of Biochemistry (NC-IUB) (1979), "Units of Enzyme Activity," Eur. J. Biochem. 97: 319-320, which is hereby incorporated by reference herein.

In some embodiments, a protein is deemed to be disrupted when a sample of the disrupted protein "disrupted sample" having a purity of 50% weight per weight (w/w) or weight per volume (w/v) or greater, a purity of 55% (w/w or w/v) or greater, a purity of 60% (w/w or w/v) or greater, a purity of 65% (w/w or w/v) or greater, a purity of 70% (w/w or w/v) or greater, a purity of 75% (w/w or w/v) or greater, a purity of 80% (w/w or w/v) or greater, a purity of 85% (w/w or w/v) or greater, a purity of 90% (w/w or w/v) or greater, a purity of 95% (w/w or w/v) or greater, a purity of 99% (w/w or w/v) or greater in the disrupted sample has a specific enzymatic activity that is 20% or less than the specific enzymatic activity of a sample of the wild type counterpart of the protein "wild type sample" in which the purity of the wild type counterpart of the protein in the wild type sample is the same as or greater than the purity of the disrupted protein in the disrupted protein sample, wherein disrupted protein sample and the sample wild type sample are under the same conditions (e.g., temperature, concentration, pH, concentration of substrate, salt concentration, etc.).

In some embodiments, a protein is deemed to be disrupted when a sample of the disrupted protein "disrupted sample" having a purity of 50% (w/w or w/v) or greater, a purity of 55% (w/w or w/v) or greater, a purity of 60% (w/w or w/v) or greater, a purity of 65% (w/w or w/v) or greater, a purity of 70% (w/w or w/v) or greater, a purity of 75% (w/w or w/v) or greater, a purity of 80% (w/w or w/v) or greater, a purity of 85% (w/w or w/v) or greater, a purity of 90% (w/w or w/v) or greater, a purity of 95% (w/w or w/v) or greater, a purity of 99% (w/w or w/v) or greater in the disrupted sample has a specific enzymatic activity that is 30% or less than the specific enzymatic activity of a sample of the wild type counterpart of the protein "wild type sample" in which the purity of the wild type counterpart of the protein in the wild type sample is the same as or greater than the purity of the disrupted protein in the disrupted protein sample, wherein disrupted protein sample and the sample wild type sample are under the same conditions (e.g., temperature, concentration, pH, concentration of substrate, salt concentration, etc.).

In some embodiments, a protein is deemed to be disrupted when a sample of the disrupted protein "disrupted sample" having a purity of 50% (w/w or w/v) or greater, a purity of 55% (w/w or w/v) or greater, a purity of 60% (w/w or w/v) or greater, a purity of 65% (w/w or w/v) or greater, a purity of 70% (w/w or w/v) or greater, a purity of 75% (w/w or w/v) or greater, a purity of 80% (w/w or w/v) or greater, a purity of 85% (w/w or w/v) or greater, a purity of 90% (w/w or w/v) or greater, a purity of 95% (w/w or w/v) or greater, a purity of 99% (w/w or w/v) or greater in the disrupted sample has a specific enzymatic activity that is 40% or less than the specific enzymatic activity of a sample of the wild type counterpart of the protein "wild type sample" in which the purity of the wild type counterpart of the protein in the wild type sample is the same as or greater than the purity of the disrupted protein in the disrupted protein sample, wherein disrupted protein sample and the sample wild type sample are under the same conditions (e.g., temperature, concentration, pH, concentration of substrate, salt concentration, etc.).

In some embodiments, a protein is deemed to be disrupted when a sample of the disrupted protein "disrupted sample" having a purity of 50% (w/w or w/v) or greater, a purity of 55% (w/w or w/v) or greater, a purity of 60% (w/w or w/v) or greater, a purity of 65% (w/w or w/v) or greater, a purity of 70% (w/w or w/v) or greater, a purity of 75% (w/w or w/v) or greater, a purity of 80% (w/w or w/v) or greater, a purity of 85% (w/w or w/v) or greater, a purity of 90% (w/w or w/v) or greater, a purity of 95% (w/w or w/v) or greater, a purity of 99% (w/w or w/v) or greater in the disrupted sample has a specific enzymatic activity that is 50% or less than the specific enzymatic activity of a sample of the wild type counterpart of the protein "wild type sample" in which the purity of the wild type counterpart of the protein in the wild type sample is the same as or greater than the purity of the disrupted protein in the disrupted protein sample, wherein disrupted protein sample and the sample wild type sample are under the same conditions (e.g., temperature, concentration, pH, concentration of substrate, salt concentration, etc.).

In some embodiments, a protein is deemed to be disrupted when a sample of the disrupted protein "disrupted sample" having a purity of 50% (w/w or w/v) or greater, a purity of 55% (w/w or w/v) or greater, a purity of 60% (w/w or w/v) or greater, a purity of 65% (w/w or w/v) or greater, a purity of 70% (w/w or w/v) or greater, a purity of 75% (w/w or w/v) or greater, a purity of 80% (w/w or w/v) or greater, a purity of 85% (w/w or w/v) or greater, a purity of 90% (w/w or w/v) or greater, a purity of 95% (w/w or w/v) or greater, a purity of 99% (w/w or w/v) or greater in the disrupted sample has a specific enzymatic activity that is 60% or less than the specific enzymatic activity of a sample of the wild type counterpart of the protein "wild type sample" in which the purity of the wild type counterpart of the protein in the wild type sample is the same as or greater than the purity of the disrupted protein in the disrupted protein sample, wherein disrupted protein sample and the sample wild type sample are under the same conditions (e.g., temperature, concentration, pH, concentration of substrate, salt concentration, etc.).

In some embodiments, a protein is deemed to be disrupted when a sample of the disrupted protein "disrupted sample" having a purity of 50% (w/w or w/v) or greater, a purity of 55% (w/w or w/v) or greater, a purity of 60% (w/w or w/v) or greater, a purity of 65% (w/w or w/v) or greater, a purity of 70% (w/w or w/v) or greater, a purity of 75% (w/w or w/v) or greater, a purity of 80% (w/w or w/v) or greater, a purity of 85% (w/w or w/v) or greater, a purity of 90% (w/w or w/v) or greater, a purity of 95% (w/w or w/v) or greater, a purity of 99% (w/w or w/v) or greater in the disrupted sample has a specific enzymatic activity that is 70% or less than the specific enzymatic activity of a sample of the wild type counterpart of the protein "wild type sample" in which the purity of the wild type counterpart of the protein in the wild type sample is the same as or greater than the purity of the disrupted protein in the disrupted protein sample, wherein disrupted protein sample and the sample wild type sample are under the same conditions (e.g., temperature, concentration, pH, concentration of substrate, salt concentration, etc.).

In some embodiments, the enzymatic activity or enzymatic specific activity is measured by an assay that measures the consumption of substrate or the production of product over time such as those disclosed in Schnell et al., 2006, Comptes Rendus Biologies 329, 51-61, which is hereby incorporated by reference herein.

In some embodiments, the enzymatic activity or enzymatic specific activity is measured by an initial rate experiment. In such an assay, the protein (enzyme) is mixed with a large excess of the substrate, the enzyme-substrate intermediate builds up in a fast initial transient. Then the reaction achieves a steady-state kinetics in which enzyme substrate intermediates remains approximately constant over time and the reaction rate changes relatively slowly. Rates are measured for a short period after the attainment of the quasi-steady state, typically by monitoring the accumulation of product with time. Because the measurements are carried out for a very short period and because of the large excess of substrate, the approximation free substrate is approximately equal to the initial substrate can be made. The initial rate experiment is relatively free from complications such as back-reaction and enzyme degradation.

In some embodiments, the enzymatic activity or enzymatic specific activity is measured by progress curve experiments. In such experiments, the kinetic parameters are determined from expressions for the species concentrations as a function of time. The concentration of the substrate or product is recorded in time after the initial fast transient and for a sufficiently long period to allow the reaction to approach equilibrium.

In some embodiments, the enzymatic activity or enzymatic specific activity is measured by transient kinetics experiments. In such experiments, reaction behaviour is tracked during the initial fast transient as the intermediate reaches the steady-state kinetics period.

In some embodiments, the enzymatic activity or enzymatic specific activity is measured by relaxation experiments. In these experiments, an equilibrium mixture of enzyme, substrate and product is perturbed, for instance by a temperature, pressure or pH jump, and the return to equilibrium is monitored. The analysis of these experiments requires consideration of the fully reversible reaction.

In some embodiments, the enzymatic activity or enzymatic specific activity is measured by continuous assays, where the assay gives a continuous reading of activity, or discontinuous assays, where samples are taken, the reaction stopped and then the concentration of substrates/products determined.

In some embodiments, the enzymatic activity or enzymatic specific activity is measured by a fluorometric assay (e.g., Bergmeyer, 1974, "Methods of Enzymatic Analysis", Vol. 4, Academic Press, New York, N.Y., 2066-2072), a calorimetric assay (e.g., Todd and Gomez, 2001, Anal Biochem. 296, 179-187), a chemiluminescent assay, a light scattering assay, a radiometric assay, or a chromatographic assay (e.g., Churchwella et al., 2005, Journal of Chromatography B 825, 134-143).

In some embodiments, a protein is deemed to be disrupted when the protein has a function whose performance is 20% or less than the function of the wild type counterpart of the protein when the disrupted protein and the wild type counterpart of the protein are under the same conditions (e.g., temperature, concentration, pH, concentration of substrate, salt concentration, etc.).

In some embodiments, a protein is deemed to be disrupted when the protein has a function whose performance is 30% or less than the function of the wild type counterpart of the protein when the disrupted protein and the wild type counterpart of the protein are under the same conditions (e.g., temperature, concentration, pH, concentration of substrate, salt concentration, etc.).

In some embodiments, a protein is deemed to be disrupted when the protein has a function whose performance is 40% or less than the function of the wild type counterpart of the protein when the disrupted protein and the wild type counterpart of the protein are under the same conditions (e.g., temperature, concentration, pH, concentration of substrate, salt concentration, etc.).

In some embodiments, a protein is deemed to be disrupted when the protein has a function whose performance is 50% or less than the function of the wild type counterpart of the protein when the disrupted protein and the wild type counterpart of the protein are under the same conditions (e.g., temperature, concentration, pH, concentration of substrate, salt concentration, etc.).

In some embodiments, a protein is deemed to be disrupted when the protein has a function whose performance is 60% or less than the function of the wild type counterpart of the protein when the disrupted protein and the wild type counterpart of the protein are under the same conditions (e.g., temperature, concentration, pH, concentration of substrate, salt concentration, etc.).

In some embodiments, a protein is deemed to be disrupted when the protein has a function whose performance is 70% or less than the function of the wild type counterpart of the protein when the disrupted protein and the wild type counterpart of the protein are under the same conditions (e.g., temperature, concentration, pH, concentration of substrate, salt concentration, etc.).

In some embodiments, a protein is disrupted by a genetic modification. In some embodiments, a protein is disrupted by exposure of a host cell to a chemical (e.g., an inhibitor that substantially reduces or eliminates the activity of the enzyme). In some embodiments, this compound satisfies the Lipinski's Rule of Five: 30 (i) not more than five hydrogen bond donors (e.g., OH and NH groups), (ii) not more than ten hydrogen bond acceptors (e.g. N and O), (iii) a molecular weight under 500 Daltons, and (iv) a LogP under 5. The "Rule of Five" is so called because three of the four criteria involve the number five. See, Lipinski, 1997, Adv. Drug Del. Rev. 23, 3, which is hereby incorporated herein by reference in its entirety.

In some embodiments, the invention relates to nucleic acids hybridized using conditions of low stringency (low stringency conditions). By way of example and not limitation, hybridization using such conditions of low stringency are as follows (see also Shilo and Weinberg, 1981, Proc. Natl. Acad. Sci. U.S.A. 78:6789-6792): filters containing DNA are pretreated for 6 hours at 40° C. in a solution containing 35% formamide, 5×SSC, 50 mM Tris-HCl (pH 7.5), 5 mM EDTA, 0.1% PVP, 0.1% Ficoll, 1% BSA, and 500 mg/ml denatured salmon sperm DNA. Hybridizations are carried out in the same solution with the following modifications: 0.02% PVP, 0.02% Ficoll, 0.2% BSA, 100 mg g/ml salmon sperm DNA, 10% (wt/vol) dextran sulfate, and 5-20×106 cpm 32P-labeled probe. Filters are incubated in hybridization mixture for 18-20 hours at 40° C., and then washed for 1.5 hour at 55° C. in a solution containing 2×SSC, 25 mM Tris-HCl (pH 7.4), 5 mM EDTA, and 0.1% SDS. The wash solution is replaced with fresh solution and incubated an additional 1.5 hour at 60° C. Filters are blotted dry and exposed for autoradiography. If necessary, filters are washed for a third time at 65-68° C. and reexposed to film. Other conditions of low stringency that may be used are well known in the art (e.g., as employed for cross-species hybridizations).

In some embodiments, the invention relates to nucleic acids under conditions of moderate stringency (moderately stringent conditions). As used herein, conditions of moderate stringency (moderately stringent conditions), are as known to those having ordinary skill in the art. Such conditions are also defined by Sambrook et al., Molecular Cloning: A Laboratory Manual, 2nd Ed. Vol. 1, pp. 1.101-104, Cold Spring Harbor Laboratory Press, 1989, which is hereby incorporated by reference herein in its entirety. They include, for example, use of a prewashing solution for the nitrocellulose filters 5×SSC, 0.5% SDS, 1.0 mM EDTA (pH 8.0), hybridization conditions of 50 percent formamide, 6×SSC at 42° C. (or other similar hybridization solution, or Stark's solution, in 50% formamide at 42° C.), and washing conditions of about 60° C., 0.5×SSC, 0.1% SDS. See also, Ausubel et al., eds., in the Current Protocols in Molecular Biology series of laboratory technique manuals, © 1987-1997, Current Protocols, © 1994-1997, John Wiley and Sons, Inc., hereby incorporated by reference herein in its entirety. The skilled artisan will recognize that the temperature, salt concentration, and chaotrope composition of hybridization and wash solutions can be adjusted as necessary according to factors such as the length and nucleotide base composition of the probe. Other conditions of moderate stringency that may be used are well known in the art.

In some embodiments, the invention relates to nucleic acids under conditions of high stringency (high stringent conditions). As used herein conditions of high stringency (high stringent conditions) are as known to those having ordinary skill in the art. By way of example and not limitation, procedures using such conditions of high stringency are as follows. Prehybridization of filters containing DNA is carried out for 8 hours to overnight at 65 C in buffer composed of 6×SSC, 50 mM Tris-HCl (pH 7.5), 1 mM EDTA, 0.02% PVP, 0.02% Ficoll, 0.02% BSA, and 500 mg/ml denatured salmon sperm DNA. Filters are hybridized for 48 hours at 65 C in prehybridization mixture containing 100 mg/ml denatured salmon sperm DNA and 5-20×106 cpm of 32P-labeled probe. Washing of filters is done at 37 C for one hour in a solution containing 2×SSC, 0.01% PVP, 0.01% Ficoll, and 0.01% BSA. This is followed by a wash in 0.1×SSC at 50 C for 45 minutes before autoradiography. Other conditions of high stringency that may be used are well known in the art.

As used herein, computation of percent identity takes full weight of any insertions in two sequences for which percent identity is computed. To compute percent identity between two sequences, they are aligned and any necessary insertions in either sequence being compared are then made in accordance with sequence alignment algorithms known in the art. Then, the percent identity is computed, where each insertion in either sequence necessary to make the optimal alignment between the two sequences is counted as a mismatch. Unless explicitly indicated otherwise, the percent identity of two sequences is the percent identity across the entire length of each of the sequences being compared, with gaps insertions processed as specified in this paragraph.

5.2. Enzymes to Derive and Utilize Sugar from Plant Cell Walls and Plant Starches Many biofuel production pathways start from sugars which are expensive and compete, directly or indirectly, with food crops. Commercially advantageous production pathways are those that begin with cheaper raw materials such as agricultural by-products, or agricultural products that require minimal processing for example cell wall material.

In addition to naturally occurring enzymes, modified enzymes may be added into the host genome. For example enzymes may be altered by incorporating systematically varied sets of amino acid changes, with the resulting changes in phenotypes measured and used to identify sequence changes conferring improved function (see for example Liao et al., 2007, BMC Biotechnol 7: 16; Ehren et al., 2008, Protein Eng Des Sel 21:699-707 and Heinzelman et al., 2009, Proc Natl Acad Sci USA 106: 5610-5615).

5.2.1. Enzymes for Cellulose, Hemicellulose, and Lignocellulose Degradation

Organisms capable of generating enzymes for the breakdown of cellulose, hemicellulose, and pectin include, *Trichoderma viride, Fusarium oxysporium, Piptoporus betulinus, Penicillium echinulatum, Penicillium purpurogenum, Penicillium rubrum, Aspergillus niger, Aspergillus fumigatus, Aspergillus phoenicus, Sporotrichum thermophile, Scytalidium thermophillum, Clostridium straminisolvens, Thermonospora curvata, Rhodospirillum rubrum, Cellulomonas fimi, Clostridium stercorarium, Bacillus polymyxa, Bacillus coagulans, Pyrococcu furiosus, Acidothermus cellulolyticus, Saccharophagus degradans, Neurospora crass, Humicola fuscoatra, Chaectomium globosum, Thielavia terrestris*-255, *Mycelieopthra fergussi*-246C, *Aspergillus wentii, Aspergillus ornatus, Pleurotus florida, Pleurotus cornucopiae, Tramates versicolor, Bacteroides thetaiotaomicron*, and *Nectria catalinensis*; see Kumar et al., 2008, J Ind Microbiol Biotechnol: 35, 377-91.

5.2.1.1. Cellulose

Cellulose is a homopolymeric compound composed of β-D-glucopyranose units, linked by a β-(1→4)-glycosidic bond and represents the most abundant polysaccharide in plant cell walls.

*Trichoderma reesei* is one of the prototypical cellulose metabolizing fungi. It encodes genes for 3 enzyme classes required for the degradation of cellulose to glucose. These are Exoglucanases or cellobiohydrolases (genes CBH1 and CBH2), Endoglucanases (genes EG1, EG2, EG3, EG5) and β-glucosidase (gene BGL1). Genes for these 3 classes of enzymes could be expressed and secreted from a modified *C. tropicalis* strain to allow it to generate glucose from cellulose.

*Clostridium thermocellum* is a prototypical cellulose degrading bacterium. It encodes numerous genes that form the cellulosome, a complex of enzymes used in the degradation of cellulose. Enzymes participate in the formation of the cellulosome include scaffoldin (cipA), cellulase (celJ), cellobiohydrolase (cbhA, celK, cello), xylanase (xynY, xynZ, xynA, xynU, xynC, xynD, XynB, XynV), endoglucanase (celH, celE, celS, celF, celN, celQ, celD, celB, celT, celG, celA), mannanase (manA), chitinase (chiA), lichenase (licB) and a protein with unknown function CseP (cseP).

Encoding all or a subset of the genes required to replicate the *C. thermocellum* cellulosome, component enzymes or engineered derivatives would be of utility in a *Candida* strain configured for cellulose degradation. There is emerging evidence that effective hydrolysis of cellulose requires a multicomponent system like the cellulosome that interacts with the substrate and the surface of the cell. Cellulosomes are nanomachines consisting cellulase catalytic modules, carbohydrate binding domains that lock into the substrate, and dockerins plus cohesions that serve to connect the catalytic and carbohydrate binding domains to the surface of the bacterial cell that is expressing the cellulosome.

5.2.1.2. Hemicellulose

Hemicellulose is the second most abundant component of plant cell walls. Hemicelluloses are heterogeneous polymers built up by many different sugar monomers. In contrast, cellulose contains only anhydrous glucose. For instance, besides glucose, sugar monomers in hemicellulose can include xylose, mannose, galactose, rhamnose, and arabinose. Hemicelluloses contain most of the D-pentose sugars, and occasionally small amounts of L-sugars as well. Xylose is always the sugar monomer present in the largest amount, but mannuronic acid and galacturonic acid also tend to be present.

Hemicellulose degrading enzymes include the xylan degrading enzymes (endo-β-xylanase, α-glucuronidase, α-arabinofuranosidase, and β-xylosidase) and glucomannan degrading enzymes (β-mannanase and β-mannosidase). Xylan is the predominant component of hemicellulose from hardwood and agricultural plants, like grasses and stray. Glucomannan is the dominant component of hemicellulose from hardwood.

Cellulose does not typically exist in nature by itself and so other enzymes are needed for effective biomass utilization. Xylanases hydrolyze the β-1,4-xylan linkage of hemicellulose to produce the pentose xylose. There are a large number of distinct xylanase protein families. Some fungi secrete xylanase isozymes: *Trichoderma viride* makes 13 and *Aspergillus niger* produces 15. Xylanases will be an increasing important component of hemicellulose utilization as an added enzyme or part of an integrated bioprocessing system produced in situ by a suitable organism. Xylanases would be of utility in a *Candida* strain configured for cellulose degradation.

5.2.1.3. Pectin

Pectins are the third main structural polysaccharide of plant cell walls. Pectins are abundant in sugar beet pulp and fruits, e.g., citrus and apples, where it can form up to ½ the polymeric content of cell walls. The pectin backbone consists of homo-galacturonic acid regions and neutral sugar side chains from L-rhamnose, arabinose, galactose, and xylose. L-rhamnose residues in the backbone carry sidechains containing arabinose and galactose. Pectin degrading enzymes include pectin lyase, endo-polygalacturonase, α-arabinofuranosidase, α-galactosidase, polymethylgalacturonase, pectin depolymerase, pectinase, exopolygalacturanosidase hydrolase, α-L-Rhamnosidase, α-L-Arabinofuranosidase, polymethylgalacturonate lyase (pectin lyase), polygalacturonate lyase (pectate lyase), exopolygalacturonate lyase (pectate disaccharide-lyase). Pectinases would be of utility in a *Candida* strain configured for cellulose degradation 5.2.2. Biological Delignification The white rot fungi are a diverse group of Basidiomycetes that are capable of completely degrading all the major components of plant cell walls, including cellulose, hemicellulose and lignin. *Phanerochaete chrysosporium* is a prototypical example that has recently been the focus of a genome sequencing and anotization project. See review of genome project and genes used in delignification (Kersten et al., 2007, Fungal Genet Biol: 44, 77-87.).

Lignocellulosic biomass refers to plant biomass that is composed of cellulose, hemicellulose, and lignin. The carbohydrate polymers (cellulose and hemicelluloses) are tightly bound to the lignin, by hydrogen and covalent bonds. Biomass comes in many different types, which may be grouped into four main categories: (1) wood residues (including sawmill and paper mill discards), (2) municipal paper waste, (3) agricultural residues (including corn stover and sugarcane bagasse), and (4) dedicated energy crops (which are mostly composed of fast growing tall, woody grasses). Fermentation of lignocellulosic biomass to ethanol is an attractive route to energy feedstocks that supplements the depleting stores of fossil fuels. Biomass is a carbon-neutral source of energy, since it comes from dead plants, which means that the combustion of ethanol produced from lignocelluloses will produce no net carbon dioxide in the earth's atmosphere. Also, biomass is readily available, and the fermentation of lignocelluloses provides an attractive way to dispose of many industrial and agricultural waste products. Finally, lignocellulosic biomass is a very renewable resource. Many of the dedicated energy crops can provide high-energy biomass, which may be harvested multiple times each year.

One barrier to the production of biofuels from biomass is that the sugars necessary for fermentation are trapped inside the lignocellulose. Lignocellulose has evolved to resist degradation and to confer hydrolytic stability and structural robustness to the cell walls of the plants. This robustness or "recalcitrance" is attributable to the crosslinking between the polysaccharides (cellulose and hemicellulose) and the lignin via ester and ether linkages. Ester linkages arise between oxidized sugars, the uronic acids, and the phenols and phenylpropanols functionalities of the lignin. To extract the fermentable sugars, one must first disconnect the celluloses from the lignin, and then acid-hydrolyze the newly freed celluloses to break them down into simple monosaccharides. Another challenge to biomass fermentation is the high percentage of pentoses in the hemicellulose, such as xylose, or wood sugar. Unlike hexoses, like glucose, pentoses are difficult to ferment. The problems presented by the lignin and hemicellulose fractions are the foci of much contemporary research.

Hundreds of sequences from *P. chrysosporium* are predicted to encode extracellular enzymes including many oxidative enzymes potentially involved in lignocellulose degradation, including peroxidases, copper radical oxidases, FAD-dependent oxidases, and multicopper oxidases. The oxidases and peroxidases are responsible for generating reactive and nonspecific free radicals that affect lignin degradation. Enzymes that accelerate the rate of lignocellulose degradation would be of utility in a *Candida* strain configured for cellulose degradation.

Large and complex families of cytochrome P450s, peroxidases, glycoside hydrolases, proteases, copper radical oxidases and multicopper oxidases are observed in the *P. chrysosporium* genome. Structurally related genes may encode proteins with subtle differences in functions, and such diversity may provide flexibility needed to change environmental conditions (pH, temperature, ionic strength), substrate composition and accessibility, and wood species. Alternatively, some of the genetic multiplicity may merely reflect redundancy.

Lignin peroxidases (LiP) and manganese peroxidases (MnP) have been the most intensively studied extracellular enzymes of *P. chrysosporium*. Also, implicated in lignocellulose degradation are, copper radical oxidases (e.g., glyoxal oxidase, GLX), flavin and cytochrome enzymes such as, cellobiose dehydrogenase (CDH), glucose oxidases (glucose 1-oxidase and glucose 2-oxidase), aryl alcohol oxidases, veratryl alcohol oxidase, multicopper oxidases (mcol).

Proteases produced by *P. chrysosporium* may be involved in activation of cellulase activity. *P. chrysosporium* apparently does not code for laccases, which are used by other organisms for lignocellulose degradation.

Other lignocellulose degrading organisms include *Pleurotus erygii* (has a versatile peroxidase that exhibits both LiP and MnP activities), *Cyathus* sp., *Streptomyces viridosporus* T7A (the lignin peroxidase, LiP, has been studied in some detail), *Phelebia tremellosus, Pleurotus florida, Peurotus cornucopiae, Pleurotus ostreatus, Trametes versicolor, Irpex lacteus, Ganoderma lucidum, Ganoderma applanatum, Coriolus versicolor, Aspergillus* 2BNL1, *Aspergillus* 1AAL1, *Lentinus edodes* UEC 2019, *Ceriporiopsis subvermispora, Panus conchatus.*

5.2.3. Enzymes Needed for Utilization of Starch

Enzymes for saccharification include α-amylases, β-amylases, γ-amylases, glucoamylase, maltogenase and pullanase.

5.3. Potential Feedstocks Used Directly or Following Enzymatic, Physical, Chemical, and or Mechanical Pretreatment Almost anything derived from the Kingdom Plantae, and more specifically anything containing, lignocellulose, cellulose, hemicellulose, pectin, and/or starch can be used as a feedstock for the production of biofuels.

The heterogeneous structure of the lignin polymer renders it highly difficult to degrade. Lignin degradation occurs quite slowly in nature via the action of wood rot fungi that produce ligninases. These fungi and some bacteria recycle the carbon locked in woody plants taking years to digest a large tree. A major strategy for increasing availability of sugar polymers is to genetically decrease the lignin content of plants. Alfalfa lines downregulated in several steps of lignin biosynthesis were tested for sugar release during chemical saccharification with promising results. Plant with the lowest lignin compensated by making more carbohydrate. Moreover, the carbohydrate was more readily released with decreasing lignin. Sugars present were xylose, arabinose, glucose, and galactose that were representative of hemicellulosic and pectic cell wall polymers (Chen et al., 2007, Nat Biotechnol: 25, 759-61.).

5.3.1. Physical, Chemical, and/or Mechanical Lignocellulose Pre-treatments

Lignocellulosic substrates used by an engineered *C. tropicalis* strain may include one or more of the following pretreatments: mechanical pretreatment (milling), thermal pretreatment (steam pretreatment, steam explosion, and/or liquid hot water pretreatment), alkaline pretreatment, oxidative pretreatment, thermal pretreatment in combination with acid pretreatment, thermal pretreatment in combination with alkaline pretreatment, thermal pretreatment in combination with oxidative pretreatment, thermal pretreatment in combination with alkaline oxidative pretreatment, ammonia and carbon dioxide pretreatment, enzymatic pretreatment, and/or pretreatment with an engineered organism (Hendriks et al., 2009, Bioresour Technol: 100, 10-8.).

5.4. Sugars Derived from Plant Cell Walls that May Require Engineering of *C. Tropicalis*

Plant biomass hydrolysates contain carbon sources that may not be readily utilized by yeast unless appropriate enzymes are added via metabolic engineering (van Maris et al., 2006, Antonie Van Leeuwenhoek: 90, 391-418.). For example, *S. cerevisiae* readily ferments glucose, mannose, and fructose via the Embden-Meyerhof pathway of glycolysis, while galactose is fermented via the Leloir pathway. Construction of yeast strains that efficiently convert other potentially fermentable substrates in plant biomass will require metabolic engineering. The most abundant of these compounds is xylose. Other fermentable substrates include L-arabinose, galacturonic acid, and rhamnose.

5.4.1. Xylose Fermentation

Xylose-fermenting yeasts link xylose metabolism to the pentose-phosphate pathway. These yeasts use two oxidoreductases, xylose reductase (XR) and xylitol dehydrogenase (XDH), to convert xylose to xylulose 5-phosphate, which enters the pentose phosphate pathway.

Although strains of *S. cerevisiae* that express both xylose reductase (XR) and xylitol dehydrogenase (XDH) have been constructed, anaerobic fermentation was accompanied by considerable xylitol production. For every one NADPH used by XR, one NADH needs to be reoxidized, and the only way to do it be the engineered yeasts is to produce xylitol, although ethanol vs. xylitol production can be impacted both positively and negatively by starting strain, source of heterologous enzymes, and culture conditions. Ideally, the XR and XDH can be engineered to be linked to the same coenzyme system eliminating the production of excess NADH in the process of ethanol production.

One of the most successful examples of engineering *S. cerevisiae* for ethanol production from xylose uses the fungal xylose isomerase (XylA) from obligately anaerobic fungi *Piromyces* sp.E2. The introduction of the XylA gene was sufficient to enable the resulting strain to grow slowly with xylose as sole carbon source under aerobic conditions. Via an extensive selection procedure a new strain was derived (Kuyper et al., 2005, FEMS Yeast Res: 5, 399-409) which was capable of anaerobic growth on xylose producing mainly ethanol, CO2, glycerol, biomass, and notably little xylitol. The ethanol production rate was considered still too low for industrial applications. To obtain a higher specific rate of ethanol production, a strain was constructed that in addition to the XylA gene, overexpressed all genes involved in the conversion of xylose into the intermediates of glycolysis, including xylulokinase, ribulose 5-phosphate isomerase, ribulose 5-phosphate epimerase, transketolase, and transaldolase. In addition the gene GRE3, encoding aldose reductase, was deleted to further minimize xylitol production. The resulting strain could be cultivated under anaerobic conditions without further selection or mutagenesis and at the time had the highest reported specific ethanol production rate.

*Candida tropicalis* has been shown to be able to ferment xylose to ethanol (Zhang et al., 2008, Sheng Wu Gong Cheng Xue Bao: 24, 950-6.) *Pichia stipitis* is another yeast that is able to ferment xylose to alcohol and being studied (Agbogbo et al., 2008, Appl Biochem Biotechnol: 145, 53-8).

5.4.2. L-Arabinose Fermentation

Although D-xylose is the most abundant pentose in hemicellulosic substrates, L-arabinose is present in significant amounts, thus the importance of converting arabinose to ethanol.

*Saccharomyces* cannot ferment or assimilate L-arabinose. Although many types of yeast are capable of assimilating L-arabinose aerobically, most are unable to ferment it to ethanol. Some *Candida* species are able to make arabinose fermentation to ethanol, but production rates are low.

L-arabinose fermentation may be-rare among yeasts due to a redox imbalance in the fungal L-arabinose pathway, therefore an alternative approach to using the fungal enzymes is to construct L-arabinose fermenting yeast by overexpression of the bacterial L-arabinose pathway. In the bacterial pathway no redox reactions are involved in the initial steps of L-arabinose metabolism. Instead the enzymes, L-arabinose isomerase, L-ribulokinase, and L-ribulose-5-phosphate 4-epimerase are involved in converting L-arabinose to L-ribulose-5-phosphate and D-xyulose-5-phosphate, respectively. These enzymes are encoded by the araA, araB, and araD genes respectively.

A first attempt to express the *E. coli* genes in *S. cerevisiae* was only partly successful, with the strain generating only L-arabinitol. One of the most promising examples of *S. cerevisiae* engineering for L-arabinose fermentation is described in (Becker et al., 2003, Appl Environ Microbiol: 69, 4144-50.). In this work the bacterial L-arabinose operon consisted of *E. coli* araB and araD and *Bacillus subtilis* araA, along with overexpression of the yeast galactose permease gene (GAL2). Gal1p is known to transport L-arabinose. Although overexpression of these enzymes did not result in immediate growth on L-arabinose as the sole carbon source, the growth rate of the transformants increased progressively after 4-5 days incubation. Eventually an L-arabinose-utilizing strain was selected after several sequential transfers in L-arabinose medium. In addition to being able to grow aerobically on L-arabinose, the evolved strain produced ethanol from L-arabinose at 60% the theoretical yield under oxygen-limited conditions. An enhanced transaldolase (TAL1) activity was reported to enhance L-arabinose fermentation and overexpression of GAL2 was found not to be essential for growth on L-arabinose, suggesting that other yeast sugar transporters can also transport L-arabinose. A similar approach would be feasible in *Candida*, re-coding the genes to be better expressed in *Candida*, and to remove those codons that are non-canonical in *Candida*.

5.4.3. Galacturonic Acid Fermentation

Reduction of galacturonic acid to the same level of a hexose requires the input of two electron pairs, for instance via two NADH-dependent reduction steps. Galacturonic acid is a major component of pectin and therefore occurs in all plant biomass hydrolysates. Pectin-rich residues from citrus fruit, apples, sugar cane and sugar beets contain especially large amounts of D-galacturonic acid. If D-galacturonic acid can be converted to ethanol, this would increase the relevance of these abundantly available feedstocks.

Several yeasts, e.g., *Candida* and *Pichia*, can grow on D-galacturonic acid, and therefore potential sources for transport enzymes and a heterologous pathway if needed.

The ability to utilize D-galacturonic acid is widespread among bacteria, which all seem to use the same metabolic pathway. In the bacterial pathway, D-galacturonic acid is converted to pyruvate and glyceraldehydes-3-phosphate via a five-step pathway. Overall this results in the conversion of D-galacturonic acid, NADH, and ATP into pyruvate, glyceraldehydes-3-phosphate and water. Glyceraldehyde-3-phosphate can be converted to equimolar amounts of ethanol and CO2 via standard glycolytic reactions yielding 2 ATP. However, conversion of pyruvate to ethanol requires oxidation of a second NADH.

During anaerobic growth and fermentation on sugars (hexoses, but also xylose by engineered xylose-fermenting strains) of *S. cerevisiae*, a significant fraction of the carbon is channeled into glycerol to compensate for oxidative, NADH-generating reactions in biosynthesis.

In theory, introduction of the prokaryotic galacturonic acid fermentation route into yeast can create an alternative redox sink for the excess NADH formed in biosynthesis. This would have two advantages. Firstly, the NADH derived from biosynthetic processes can be used to increase ethanol yield on galacturonic acid to 2 mol ethanol per mol of galacturonic acid, as the pyruvate formed can now be converted to ethanol. Secondly, since the sugar requirements production for glycerol are reduced, the ethanol yield on sugars will increase.

Bacterial D-galacturonate catabolism uses the following enzymes: D-galacturonate isomerase, altronate oxidoreductase, altronate dehydratase, 2-dehydro-3-deoxygluconokinase, 2-keto-3-deoxy-6-phosphogluconate aldolase, glyceraldehydes-3-phosphate. Although a large number of yeasts and molds use galacturonic acid as carbon and energy for growth, knowledge of the underlying metabolic process is limited. At present, the prokaryotic pathway offers the most promising approach for engineering *Candida* for galacturonic acid metabolism.

5.4.4. L-Rhamnose Fermentation

The deoxyhexose L-rhamnose is named after the plant it was first isolated from: the buckthorn (*Rhamnus*). In contrast with most natural sugars, L-rhamnose is much more common than D-rhamnose. It occurs as part of the rhamnogalacturonan of pectin and hemicellulose. Being a 6-deoxy sugar, L-rhamnose is more reduced than the rapidly fermentable sugars glucose and fructose.

*S. cerevisiae* cannot grow on L-rhamnose. The metabolic engineering of *S. cerevisiae* for the production of ethanol will have to address two key aspects: the enhancement of rhamnose transport across the plasma membrane and the introduction of a rhamnose-metabolizing pathway.

Two possible strategies to engineer uptake follow. Firstly, after introduction of an ATP-yielding pathway for L-rhamnose catabolism (see below), selection for growth on L-rhamnose can be used to investigate whether or not mutations in hexose transporters enable uptake of L-rhamnose.

Although the rhamnose transporters from bacteria (e.g., *E. coli*) are well characterized, functional expression of bacterial transporters in the yeast plasma membrane may be challenging. *Pichia stipidis* is able to use L-rhamnose. Using information generated by the *P. stipidis* genome project, it might be possible to identify a rhamnose transporter if such a gene can be shown to be induced by rhamnose (as proposed for galacturonic acid above).

After uptake the next requirement for successful rhamnose fermentation is conversion into intermediates of central metabolism.

Two pathways for rhamnose utilization have been reported in microorganisms.

The first catabolic pathway involves phosphorylated intermediates and is used, for example, by *E. coli*. In this pathway, L-rhamnose is converted to L-rhamnulose by L-rhamnose isomerase. After the subsequent phosphorylation to L-rhamnulose by rhamnulokinase, L-rhamnulose-1-phosphate is split into dihydroxy-acetone-phosphate (DHAP) and L-lactaldehyde by rhamnulose-1-phosphate aldolase. DHAP can be normally processed by glycolysis, yielding 1 mol ethanol per mol L-rhamnose. In *E. coli*, further metabolism of L-lactaldehyde depends on the redox state of the cells. L-lactaldehyde can be oxidized to lactate by lactaldehyde dehydrogenase, reduced to 1,2-propanediol by lactaldehyde reductase, or processed via a redox-neutral mix of these two reactions. Introduction of this pathway into *S. cerevisiae*, L-rhamnulose is expected to be converted to equimolar amounts of ethanol, lactaldehyde and CO2 with generation of 1 ATP. In summary, this strategy would require the introduction of a transporter and three heterologous enzymes into *S. cerevisiae.*

A second route for rhamnose degradation, which does not involve phosphorylated intermediates was first described for the fungus *Aureobasidium pullulans* and is referred to as direct oxidative catabolism of rhamnose. A similar pathway occurs in the yeasts *P. stipitis* and *Debaryomyces polymorphus*. This pathway is initiated by the oxidation of L-rhamnose by NAD+-dependent L-rhamnose dehydrogenase, yielding either L-rhamnono-1,4-lactone or the unstable rhamnono-1,5-lactone. The 1,4 lactone is hydrolyzed to L-rhamnonate by L-rhamnono-1,4-lactonase. The unstable 1,5-lactone has been reported to spontaneously hydrolyze to L-rhamnonate. L-Rhamnonate is subsequently dehydrated to 2-keto-3-deoxy-L-rhamnonate by L-rhamnonate dehydratase. The product of this reaction is then cleaved into pyruvate and L-lactaldehyde by an aldolase. In *P. stipitis* the thus formed L-lactaldehyde is converted to lactate and NADH by lactaldehyde dehydrogenase. Introduction of this fungal pathway into *S. cerevisiae* should enable the conversion of L-rhamnose to equimolar amounts of ethanol, lactaldehyde and CO2 without a net generation of ATP. This conversion would require the introduction of a transporter and four heterologous enzymes (including 1,4-lactonase).

5.4.5. Inhibitor Tolerance

The harsh conditions that prevail during the chemical and physical pretreatment of lignocellulose result in the release of many substances that inhibit growth and productivity of microorganisms such as *S. cerevisiae*. The number and identity of the toxic compounds varies with the nature of the raw material and pretreatment conditions.

There are two approaches to limit the impact of the inhibitors on the fermentation process: (i) introduction of additional chemical, physical, or biological process steps for removal or inactivation of inhibitors (ii) improvement of *S. cerevisiae* to the inhibitors.

5.5. Fermentation Products from Biomass 5.5.1. Butanol

Metabolic engineering of *Escherichia coli* for butanol production by inserting genes from the butanol production bacteria *Clostridium acetobutylicum* into *E. coli* has been described (Inui et al., 2008, Appl Microbiol Biotechnol: 77, 1305-16).

A similar strategy can be envisioned for an engineered *C. tropicalis* strain configured to derive sugars from biomass. Enzymes (and genes) from *Clostridium acetobutylicum* required for butanol production from Acetyl-CoA include: Acetyl-CoA acetyltransferase (thiL), β-hydroxybutyryl-CoA dehydrogenase (hbd), 3-hydroxybutyryl-CoA dehydratase (crt), butyryl-CoA dehydrogenase (bcd, etfA, etfB), butyrlaldehyde dehydrogenase (adhe1, adhe), butanol dehydrogenase (adhe1, adhe), butyrlaldehyde dehydrogenase (bdhA), butanol dehydrogenase (bdhA), butyrlaldehyde dehydrogenase (bdhB), butanol dehydrogenase (bdhB).

n-Butanol is a commercially important alcohol that is considered by some to be a strong Candidate for widespread use as a motor fuel. n-Butanol is currently produced via chemical synthesis almost exclusively. The dominant synthetic process in industry, the acetaldehyde method, relies on propylene derived from petroleum [1]. The U.S. market for butanol is 2.9 billion pounds per year [2]. Currently, the primary use of n-butanol is as a solvent, however, several companies including British Petroleum and DuPont are developing methods to utilize bacteria to produce n-butanol on a large scale for fuel [3]. Microorganisms capable of producing n-butanol by fermentation are Clostridia *acetobutylicum, C. beijerinckii*, and *C. tetanomorphum.* n-Butanol has several characteristics that make it a viable alternative fuel option. It has an energy density that is similar to gasoline. Additionally, it could power a combustion engine with minimal or no modifications. In either a blended or neat form, n-butanol could be easily integrated into our current infrastructure.

Enzymes for butanol production include Pyruvate dehydrogenase complex, acetyl-CoA acetyltransferase, 3-hydroxybutyryl-CoA dehydrogenase, crotonase, butyryl-CoA dehydrogenase, aldehyde and/or alcohol dehydrogenase. (Steen et al., 2008, Microb Cell Fact: 7, 36; Atsumi et al., 2008, Metab Eng: 10, 305-11.)

5.5.2. Branched Chain Alcohols

In the quest to find a substitute for petroleum based fuels, several low energy molecules have been suggested due to the ease of production. However, a molecule with similar energy density to current fuels would be preferred as a biofuel. Branched higher alcohols have a higher energy density than some of the alcohols proposed as alternative fuels. Other various properties of these alcohols also display more desirable features. For example, a lower miscibility with water and lower vapor pressure are benefits of higher alcohols. A unique approach to alcohol synthesis taken by Atsumi et al. Atsumi et al., 2008, Nature: 451, 86-9, employs synthetic biology to engineer non-fermentative pathways based on amino acid biosynthesis. These pathways produce alcohols that are not natural fermentation products. Some of the features of these molecules include branching and addition of aromatic cyclic hydrocarbon structures.

An engineered *C. tropicalis* capable of generating 2-methyl-1-butanol from L-threonine would use either the endogenous or exogenously added threonine biosynthetic enzymes, L-threonine ammonia lyase, endogenous or exogenously added isoleucine biosynthetic enzymes, 2-keto-acid decarboxylase, and an alcohol dehydrogenase.

3-methyl-1-butanol pathway from pyruvate would require valine biosynthesis enzymes, leucine biosynthesis enzymes, 2-keto-acid decarboxylase, alcohol dehydrogenase.

2-phenylethanol pathway from pyruvate would require Phenylalanine biosynthesis enzymes, 2-keto acid decarboxylase, alcohol dehydrogenase.

5.5.3. Isobutanol Pathway from Pyruvate

Isobutanol has a higher carbon content than ethanol, therefore making its energy properties closer to gasoline. Currently, isobutanol is used as a precursor for commodity chemicals including isobutyl acetate. Atsumi et al, 2008, Nature: 451, 86-9, synthesized isobutanol via synthetic biology. The origin of the enzymes required to synthesize isobutanol were from a variety of microorganisms including *Lactococcus lactis* and *Saccharomyces cerevisiae*. In addition to expressing foreign enzymes, the host, *E. coli*, was modified to direct metabolism toward isobutanol production. The interesting feature of this pathway to synthesize isobutanol is that it employs amino acid biosynthesis to generate the essential precursor. This allows the microbe to produce the alcohol in the presence of oxygen. In fact, semi-aerobic conditions increased yields. This approach has been applied to generate several other alcohols, such as 2-phenylethanol and 2-methyl-1-butanol. The pathways for these interesting alcohols have not yet been optimized.

Synthesis would require valine biosynthesis enzymes, 2-keto-acid decarboxylase, alcohol dehydrogenase.

5.5.4. Isopropanol Pathway from Pyruvate

Isopropanol is commonly employed as an industrial cleaner and solvent. Additionally, it is sold as "rubbing alcohol" for use as a disinfectant. As a significant component in dry gas, a fuel additive, it solubilizes water in gasoline, thereby removing the threat of frozen supply lines. Proposed biofuel applications include partial replacement of gasoline and in production of fatty acid esters. A benefit of substituting isopropanol for methanol in fatty acid esters is a higher tolerance for cold temperatures. The fatty acid isopropyl ester would remain liquid in cooler climates. The biosynthesis genes for isopropanol originally found in Clostridia *acetobutylicum* were engineered into an *E. coli* strain for optimal industrial usage (Hanai et al., 2007, Appl Environ Microbiol: 73, 7814-8).

Synthesis would require pyruvate dehydrogenase complex, acetyl-CoA acetyltransferase, acetoacetyltransferase, secondary alcohol dehydrogenase.

5.5.5. Methanol Pathway from Methane

Methanol can be synthesized chemically or biochemically from methane gas. Over 30 million tons per year of methanol are produced worldwide [1]. Currently, chemical synthesis is the method of choice. Methanol is widely used as a solvent, in antifreeze, and as an intermediate in synthesis of more complex chemicals. Methanol is used as a fuel in Indy race cars and it has been blended into gasoline for civilian automobiles. Microorganisms capable of methanol production include *Methylobacterium* sp., *Methylococcus capsulatus*, and *Methylosinus trichosporium*.

Enzymes required: methane monooxygenase.

5.5.6. Other Possible End Products Requiring Metabolic Engineering

Esters: Fatty acid ethyl ester, Fatty acid methyl ester
Ethers: Dimethyl ether, Dimethylfuran, Methyl-t-butyl ether
Hydrocarbons: Alkanes, Alkenes, Isoprenoids 5.5.7. Over-Production of Fatty Acids Because many of the strains described here are no longer able to utilize many fatty acids as carbon and energy sources due to the knockouts in both β-oxidation (pox4a/pox4b pox5a/pox5b) and ω-oxidation pathways (P450 (cytochrome P450), fao (fatty alcohol oxidase), and adh (alcohol dehydrogenase) gene), the strain is an ideal Candidate for metabolic engineering for manipulation of the fatty acid biosynthetic pathways for overproduction of fatty acids.

Fatty acids (and/or lipids) so produced could either be used for production of biofuels such as biodiesel or by restoring a P450 or P450s for endogenous production of ω-hydroxy fatty acids. Methods for over-production of endogenous fatty acids may be similar to those used by Lu X et al., 2008, Metab Eng: 10, 333-9.

Steps include:

1. Knocking out the *E. coli* fadD gene, which encodes an acyl-CoA synthetase, to block fatty acid degradation. This may be accomplished by knocking out acyl-coA synthetases and acyl-coA oxidases of the *Candida tropicalis* (e.g., POX4 and POX4 genes are already absent).

2. Heterologous expression of acyl-ACP thioesterases to increase the abundance of shorter chain fatty acids, e.g., U31813 from *Cinnamomum camphorum* (improved fuel quality).

3. Increasing the supply of malonyl-CoA by over-expressing acetyl-coA carboxylase.

4. Releasing feedback inhibition caused by long-chain fatty acids by overexpression of an endogenous or exogenous acyl-ACP thioesterase. Acyl-ACP thioesterases release free fatty acids from acyl-ACPs.

Mechanisms for membrane proliferation (more membrane=more lipid?):

Expression/overexpression of P450s including fatty acid, alkane, and alkene metabolizing P450s lead to membrane proliferation in Yeasts. May be possible to express an enzymatically inactive P450 that elicits proliferation via membrane anchor. Expression of secreted enzymes, such as invertase (SUC2) can lead to membrane genesis in yeasts.

Growth with compounds that lead to membrane proliferation.

Altering genetics of peroxisome proliferation.

Enzymes that are Candidates for manipulating either by modulating or eliminating expression, or substituting homologues or engineered enzymes, e.g. that eliminate feedback or end product inhibition.

5.6. Production of Long-Chain Ω-Hydroxy Fatty Acids

Whole-cell biocatalysts currently used to oxidize long chain fatty acids include *Candida tropicalis, Candida cloa-*

*cae*, *Cryptococcus neoforman* and *Corynebacterium* sp. One preferred microorganisms is *Candida tropicalis* ATCC20962 in which the β-oxidation pathway is blocked by disrupting POX 4 and POX 5 genes which respectively encode the acyl-coenzyme A oxidases PXP-4 (SEQ ID NO: 134) and PXP-5 (SEQ ID NO: 135). This prevents metabolism of the fatty acid by the yeast (compare FIGS. 2 and 3). The fatty acids or alkynes used have 14 to 22 carbon atoms, can be natural materials obtained from plants or synthesized from natural fatty acids, such as lauric acid (C12:0), myristic acid (C14:0), palmitic acid (C16:0), stearic acid (C18:0), oleic acid (C18:1), linoleic acid (C18:2), α-linolenic acid (ω3, C18:3) ricinoleic acid (12-hydroxy-9-cis-octadecenoic acid, 12-OH—C18:1), erucic acid (C22:1), epoxy stearic acid. Examples of other substrates that can be used in biotransformations to produce α,ω-dicarboxylic acid and ω-hydroxyacid compounds are 7-tetradecyne and 8-hexadecyne. Disclosed herein, naturally derived fatty acids, chemically or enzymatically modified fatty acids, n-alkane, n-alkene, n-alkyne and/or fatty alcohols that have a carbon chain length from 12 to 22 are used as carbon sources for the yeast-catalyzed biotransformation. For example, *Candida tropicalis* ATCC20962 can be used as a catalyst under aerobic conditions in liquid medium to produce ω-hydroxy fatty acids and α,ω-dicarboxylic acids. *Candida tropicalis* ATCC20962 is initially cultivated in liquid medium containing inorganic salts, nitrogen source and carbon source. The carbon source for initial cultivations can be saccharide such as sucrose, glucose, sorbitol, etc., and other carbohydrates such as glycerol, acetate and ethanol. Then, the substrate such as naturally derived fatty acids, chemically or enzymatically modified fatty acids, n-alkane, n-alkene, n-alkyne and fatty alcohol for oxidation of terminal methyl or hydroxyl moieties is added into the culture. The pH is adjusted to 7.5-8.0 and fermentations are conducted under aerobic conditions with agitation in a shaker incubator, fermentor or other suitable bioreactor.

For example, the fermentation process may be divided into two phases: a growth phase and a transformation phase in which ω-oxidation of the substrate is performed. The seeds inoculated from fresh agar plate or glycerol stock are firstly cultivated in a pre-culture medium for 16-20 hours, at 30° C. and pH 6.5 in a shaker. Subsequently, this culture is used to inoculate the conversion medium with co-substrates. The growth phase of the culture is performed for 10-12 hours to generate high cell density cultures at pH 6.5 and 30° C. The transformation phase is begun with addition of the fatty acid or other substrate for the bio-oxidation. The medium pH is adjusted to 7.5-8.0 by addition of a base solution. Co-substrates are fed during the transformation phase to provide energy for cell growth. By use of this method, the terminal methyl group of fatty acids, synthetically derived substrates, n-alkanes, n-alkenes, n-alkynes and/or fatty alcohols that have a carbon chain length from 12 to 22 are converted to a hydroxyl or carboxyl group.

5.7. Genetic Modifications of *Candida Tropicalis*

Yeasts of the genus *Candida* including *Candida tropicalis* contains two pathways for the metabolism of fatty acids: ω-oxidation and β-oxidation. These pathways are shown schematically in FIG. 2, together with some classes of enzymes capable of catalyzing the chemical conversions in each pathway. In order for *Candida* to be used to transform fatty acids into useful compounds—such as diacids and hydroxyl fatty acids, or high energy compounds, or other chemicals it is advantageous to eliminate metabolic pathways that can divert either the substrates or products of the desired pathway. For example it may be desirable to prevent *Candida* from metabolizing fatty acids through the β-oxidation pathway, so that more fatty acids are available for conversion to α,ω-diacids and ω-hydroxy fatty acids by the ω-oxidation pathway. This can be accomplished by deleting the acyl coenzyme A oxidase genes, as shown in FIG. 2 (Picataggio et al., 1992, Biotechnology (NY): 10, 894-8.; Picataggio et al., 1991, Mol Cell Biol: 11, 4333-9.).

*Candida tropicalis* strains lacking both alleles of each of two acyl coenzyme A oxidase isozymes, encoded by the pox4 and pox5 genes, are efficient biocatalysts for the production of α,ω-diacids (Picataggio et al., 1992, Biotechnology (NY): 10, 894-8; Picataggio et al., 1991, Mol Cell Biol: 11, 4333-4339). However for the production of ω-hydroxy fatty acids, additional enzymes must be eliminated to prevent the oxidation of the ω-hydroxyl group to a carboxyl group.

To prevent the oxidation of hydroxyl groups to carboxyl groups, in some embodiments it is particularly advantageous to eliminate or inactivate one or more genes encoding a cytochrome P450.

To prevent the oxidation of hydroxyl groups to carboxyl groups, in some embodiments it is particularly advantageous to eliminate or inactivate one or more genes encoding a fatty alcohol dehydrogenase.

To prevent the oxidation of hydroxyl groups to carboxyl groups, in some embodiments it is particularly advantageous to eliminate or inactivate one or more genes encoding an alcohol dehydrogenase.

In one embodiment yeast genes can be inactivated by deleting regions from the yeast genome that encode a part of the yeast gene that encodes the protein product (the open reading frame) so that the full-length protein can no longer be made by the cell. In another embodiment yeast genes can be inactivated by inserting additional DNA sequences into the part of the yeast gene that encodes the protein product so that the protein that is made by the cell contains changes that prevent it from functioning correctly. In another embodiment yeast genes are inactivated by inserting or deleting sequences from control regions of the gene, so that the expression of the gene is no longer correctly controlled; for example additions or deletions to the promoter can be used to prevent transcription of the gene, additions or deletions to the polyadenylation signal can be used to affect the stability of the mRNA, additions or deletions to introns or intron splicing signals can be used to prevent correct splicing or nuclear export of the processed mRNA.

For the production of oxidized compounds in yeast—including ω-hydroxy fatty acids and high energy compounds, it may also be advantageous to add certain new genes into the yeast cell. For example to facilitate the production of ω-hydroxy fatty acids from fatty acids with different chain lengths or degrees or positions of unsaturation, the enzymes that are naturally present in the yeast are often inadequate; they may oxidise the fatty acid to the ω-hydroxy fatty acid too slowly, they may only oxidise a subset of the fatty acids in a mixture to their corresponding ω-hydroxy fatty acids, they may oxidise the fatty acid in the wrong position or they may oxidise the ω-hydroxy fatty acid itself to a diacid. Advantageous enzymes could thus be those that oxidise a compound to the corresponding hydroxylated compound more rapidly, those that oxidise a fatty acid to its corresponding ω-hydroxy fatty acid more rapidly, those that accept as substrates a wider range of substrates and those that do not over-oxidise target compounds including ω-hydroxy fatty acids to diacids.

To achieve novel phenotypes in *Candida* species, including the ability to perform biotransformations such as novel chemical conversions, or increased rates of conversion of one or more substrates to one or more products, or increased specificity of conversion of one or more substrates to one or more products, or increased tolerance of a compound by the yeast, or increased uptake of a compound by the yeast, it may be advantageous to incorporate a gene encoding a polypeptide into the genome of the yeast.

Preferred sites of integration include positions within the genome where the gene would be under control of a promoter that transcribes high levels of an endogenous protein, or under control of a promoter that leads to regulated transcription for example in response to changes in the concentrations of one or more compound in the cellular or extracellular environment. Examples of preferred sites of integration include sites in the genome that are under control of the promoter for an isocitrate lyase gene, sites in the genome that are under control of the promoter for a cytochrome P450 gene, sites in the genome that are under control of the promoter for a fatty alcohol oxidase gene and sites in the genome that are under control of the promoter for an alcohol dehydrogenase gene to obtain high levels of expression of a polypetidepolypeptide or expression of a polypeptide under specific circumstances.

To achieve such novel phenotypes in *Candida* species, it may be advantageous to modify the activity of a polypeptide by altering its sequence, and to test the effect of the polypeptide with altered sequence within the yeast. Polypeptides of particular interest for conferring the ability to synthesize novel hydroxyfatty acids include cytochrome P450s and their reductases, glycosyl transferases and desaturases. A preferred method for testing the effect of sequence changes in a polypeptide within yeast is to introduce a plurality of genes of known sequence, each encoding a unique modified polypeptide, into the same genomic location in a plurality of strains.

Some embodiments described herein make use of a selective marker. A selective marker can be a gene that produces a selective advantage for the cells under certain conditions such as a gene encoding a product that confers resistance to an antibiotic or other compound that normally inhibits the growth of the host cell.

A selective marker can be a reporter, such as, for example, any nucleic acid sequence encoding a detectable gene product. The gene product may be an untranslated RNA product such as mRNA or antisense RNA. Such untranslated RNA may be detected by techniques known in the art, such as PCR, Northern or Southern blots. The selective marker may encode a polypeptide, such as a protein or peptide. A polypeptide may be detected immunologically or by means of its biological activity. The selective marker may be any known in the art. The selective marker need not be a natural gene. Useful selective markers may be the same as certain natural genes, but may differ from them either in terms of non-coding sequences (for example one or more naturally occurring introns may be absent) or in terms of coding sequences. One example of such a detectable gene product is one that causes the yeast to adopt a unique characteristic color associated with the detectable gene product. For example, if the targeting construct contains a selective marker that is a gene that directs the cell to synthesize a fluorescent protein, then all of the colonies that contain the fluorescent protein are carrying the targeting construct and are therefore likely to be integrants. Thus the cells that will be selected for further analysis are those that contain the fluorescent protein.

The selective marker may encode a protein that allows the yeast cell to be selected by, for example, a nutritional requirement. For example, the selective marker may be the ura4 gene that encodes orotidine-5'-phosphate decarboxylase. The ura4 gene encodes an enzyme involved in the biosynthesis of uracil and offers both positive and negative selection. Only cells expressing ura4 are able to grow in the absence of uracil, where the appropriate yeast strain is used. Cells expressing ura4 die in the presence of 5-fluoro-orotic acid (FOA) as the ura4 gene product converts FOA into a toxic product. Cells not expressing ura4 can be maintained by adding uracil to the medium. The sensitivity of the selection process can be adjusted by using medium containing 6-azauracil, a competitive inhibitor of the ura4 gene product. The his3 gene, which encodes imidazoleglycerol-phosphate dehydratase, is also suitable for use as a selective marker that allows nutritional selection. Only cells expressing his3 are able to grow in the absence of histidine, where the appropriate yeast strain is used.

The selective marker may encode for a protein that allows the yeast to be used in a chromogenic assay. For example, the selective marker may be the lacZ gene from *Escherichia coli*. This encodes the β-galactosidase enzyme which catalyses the hydrolysis of β-galactoside sugars such as lactose. The enzymatic activity of the enzyme may be assayed with various specialized substrates, for example X-gal (5-bromo-4-chloro-3-indoyl-β-D-galactoside) or o-nitrophenyl-β-D-galactopyranoside, which allow selective marker enzyme activity to be assayed using a spectrophotometer, fluorometer or a luminometer.

In some embodiments, the selective marker comprises a gene that encodes green fluorescent protein (GFP), which is known in the art.

In some embodiments, the selective marker encodes a protein that is capable of inducing the cell, or an extract of a cell, to produce light. For example, the selective marker encodes luciferase in some embodiments. The use of luciferase is known in the art. They are usually derived from firefly (*Photinous pyralis*) or sea pansy (*Renilla reniformis*). The luciferase enzyme catalyses a reaction using D-luciferin and ATP in the presence of oxygen and $Mg^{2+}$ resulting in light emission. The luciferase reaction is quantitated using a luminometer that measures light output. The assay may also include coenzyme A in the reaction that provides a longer, sustained light reaction with greater sensitivity. An alternative form of enzyme that allows the production of light and which can serve as a selective marker is aequorin, which is known in the art.

In some embodiments the selective marker encodes β-lactamase. This selective marker has certain advantages over, for example, lacZ. There is no background activity in mammalian cells or yeast cells, it is compact (29 kDa), it functions as a monomer (in comparison with lacZ which is a tetramer), and has good enzyme activity. This may use CCF2/AM, a FRET-based membrane permeable, intracellularly trapped fluorescent substrate. CCF2/AM has a 7-hydroxycoumarin linked to a fluorescein by a cephalosporin core. In the intact molecules, excitation of the coumarin results in efficient FRET to the fluorescein, resulting in green fluorescent cleavage of the CCF2 by β-lactamase results in spatial separation of the two dyes, disrupting FRET and causing cells to change from green to blue when viewed using a fluorescent microscope. The retention of the cleaved product allows the blue colour to develop over time, giving a low detection limit of, for example, 50 enzyme molecules per cell. This results in the selective maker being able to be assayed with high sensitivity. It also allows the ability to confirm results by visual inspection of the cells or the samples.

In some embodiments, the selective marker comprises any of the aforementioned genes under the control of a promoter. In some embodiments, the selective marker comprises any of the aforementioned genes under the control of a promoter as well as one or more additional regulatory elements, such as upstream activating sequences (UAS), termination sequences and/or secretory sequences known in the art. The secretory sequences may be used to ensure that the product of the reporter gene is secreted out of the yeast cell.

5.7.1. Methods for Deletion of Sequences from the *Candida* Genome

Many yeasts recombine DNA in regions of sequence homology. A linear DNA molecule that is introduced into a yeast cell can recombine homologously with the chromosomal DNA if its ends share sufficient sequence identity with chromosomal sequences. Since the sequences of the ends of the DNA molecule are the primary determinant of where in the yeast chromosome the homologous recombination event occurs, it is possible to construct a DNA molecule that encodes one or more functional genes, and to target that molecule to integrate at a specific location in the yeast chromosome. In this way, yeast genes in the chromosome or mitochondria may be disrupted, by interrupting the gene sequence with other sequences.

In one embodiment, a DNA construct comprises two sequences with homology to two sequences in the target yeast genome ("targeting sequences"), separated by a selective marker, as shown in FIG. 11. The two target sequences within the yeast genome are preferably located on the same molecule of DNA (e.g. the same nuclear or mitochondrial chromosome), and are preferably less than 1,000,000 base pairs apart, more preferably they are less than 100,000 base pairs apart, and more preferably they are less than 10,000 base pairs apart. Cells containing a genomic integration of the targeting construct can be identified using the selective marker.

A schematic representation of one form of a DNA molecule for yeast genomic integration (a "genomic targeting construct") is shown in FIG. 4. In this embodiment the genomic targeting construct has two targeting sequences that are homologous to the sequences of two regions of the target yeast genome. In some embodiments these sequences are each at least 100 base pairs in length, or between 100 and 300 base pairs in length. The targeting sequences are preferably 100% identical to sequences in the host genome or between 95% and 100% identical to sequences in the host genome. Between these targeting sequences are two sites recognized by a site-specific recombinase such as the natural or modified versions of cre or flp or PhiC31 recombinases or serine recombinases such as those from bacteriophage R4 or bacteriophage TP901-1. Between the two site specific recombinase recognition sites are functional sequence elements which may include sequences that encode a site-specific recombinase that recognizes the recombinase sites and which may also encode a selective marker as illustrated in FIG. 4. In one embodiment this DNA construct incorporates the "SAT1 flipper", a DNA construct for inserting and deleting sequences into the chromosome of *Candida* (Reuss et al., 2004, Gene: 341, 119-27). In the "SAT1 flipper" the recombinase is the flp recombinase from *Saccharomyces cerevisiae* (Vetter et al., 1983, Proc Natl Acad Sci USA: 80, 7284-8) (FLP) and the flanking sequences recognized by the recombinase are recognition sites for the flp recombinase (FRT). The selective marker is the gene encoding resistance to the Nourseothricin resistance marker from transposon Tn1825 (Tietze et al., 1988, J Basic Microbiol: 28, 129-36). The entire construct can then be targeted to the *Candida* chromosome by adding flanking sequences with homology to a gene in the *Candida* chromosome. The DNA sequence of the SAT1-flipper is SEQ ID NO: 1.

Yeast preferentially recombines linear DNA. It is therefore advantageous to prepare the targeting construct as a linear molecule prior to transforming it into the yeast target. In some embodiments it is desirable to prepare and propagate the targeting construct as plasmid DNA in a bacterial host such as *E. coli*. For propagation in a bacterial host it is generally preferred that plasmid DNA be circular. It is thus sometimes necessary to convert the targeting construct from a circular molecule to a linear molecule. Furthermore for propagation of the targeting construct in a bacterial host, additional sequence elements may be necessary, so a targeting construct may, in addition to the elements shown in FIGS. 4 and 7, comprise an origin of replication and a bacterial selectable marker. It may therefore be advantageous to place restriction sites in the targeting construct to cleave between the elements of the targeting construct shown in FIGS. 4 and 7 and the elements not shown but required for propagation in a bacterial host. Cleavage with restriction enzymes that recognize these sites will linearize the DNA and leave the targeting sequences at the ends of the molecule, favoring homologous recombination with the target host genome. One of ordinary skill in the art will recognize that there are alternative ways to obtain linear DNA, for example by amplifying the desired segment of DNA by PCR. It is also possible to prepare the DNA directly and transform it into the target yeast strain without propagating as a plasmid in a bacterial host.

Introduction of the linearized targeting construct into a yeast host cell such as a *Candida* host cell is followed by homologous recombination catalyzed by host cell enzymes. This event is represented schematically in FIG. 5. Homologous recombination occurs between each of the two targeting sequences in the genomic targeting construct and the homologous sites in the yeast genome. The result is an integration of the targeting construct into the genomic DNA. Cells containing a genomic integration of the targeting construct can be identified using the selective marker.

Cells containing a genomic integration of the targeting construct can optionally be tested to ensure that the integration has occurred at the desired site within the genome. In one embodiment, such testing is performed by amplification of a section of the genomic DNA by the polymerase chain reaction. Integration of the targeting construct into the yeast genome will replace genomic sequences with targeting construct sequences. This replacement may be detected by a difference in size of amplicon using oligonucleotide primers that anneal to sequences outside the targeted sequence. This is illustrated in FIG. 10. One of ordinary skill in the art will readily appreciate that there are many alternative ways to design oligonucleotides to produce diagnostic amplicons using the polymerase chain reaction. For example one oligonucleotide that anneals inside the targeted region and one oligonucleotide that anneals outside but close to the targeted region can be used to produce an amplicon from the natural genomic sequence but will not produce an amplicon if the targeting construct has eliminated the targeted genomic sequence. Conversely one oligonucleotide that anneals inside the targeting construct and one oligonucleotide that anneals outside but close to the targeted region outside will not produce an amplicon from the natural genomic sequence but will produce an amplicon if the targeting construct has integrated at the targeted genomic location. In general oligonucleotide pairs for producing diagnostic amplicons should be oriented with their 3' ends towards each other and the sites in the genome where the two oligonucleotides anneal should be separated by between 100 and 10,000 bases, more preferably by between 150 and 5,000 bases and more preferably by between 200 and 2,000 bases. In some instances it may not be possible to distinguish between two possible genotypes based on the size of the amplicons produced by PCR from genomic DNA. In these cases an additional test is possible, for example digestion of the amplicon with one or more restriction enzymes and analysis of the sizes may enable the two possible genotypes to be distinguished, or sequencing of the amplicon may enable the two possible genotypes to be distinguished.

The same selectable marker may be used for the disruption of more than one genomic target. This can be achieved by removing the selectable marker from the yeast genome after each disruption. In one embodiment, this is achieved when the selectable marker separates two sites that are recognized by a recombinase. When the recombinase is present and active, it effects a recombination reaction between the two sites, excising the sequences between them. In the targeting construct shown in FIG. 6 this is done by induction of the gene encoding the recombinase present in the targeting construct. Expression of the recombinase causes a recombination event between the two recombinase recognition sites of the targeting construct, as shown schematically in FIG. 6. The result is that the sequences between the two recombinase sites are excised from the genome. In other embodiments it is possible to integrate a recombinase into a second site in the host genome instead of having it present in the targeting construct.

Cells from which a genomic integration of the targeting construct has been excised can optionally be tested to ensure that the excision has occurred by testing cells from individual colonies to determine whether they still carry the selective marker. In some embodiments, such testing is performed by amplification of a section of the genomic DNA by the polymerase chain reaction. Excision of part of the targeting construct from the yeast genome may be detected by a difference in size of amplicon using oligonucleotide primers that anneal to sequences outside the targeted sequence. This is illustrated in FIG. 10. One of ordinary skill in the art will readily appreciate that there are many alternative ways to design oligonucleotides to produce diagnostic amplicons using the polymerase chain reaction. For example one oligonucleotide that anneals inside the targeting construct (example.g. within the selective marker) and one oligonucleotide that anneals outside but close to the targeted region can be used to produce an amplicon from the integrated targeting construct but will not produce an amplicon if the targeting construct has been excised. In general oligonucleotide pairs for producing diagnostic amplicons should be oriented with their 3' ends towards each other and the sites in the genome where the two oligonucleotides anneal should be separated by between 100 and 10,000 bases, more preferably by between 150 and 5,000 bases and more preferably by between 200 and 2,000 bases. In some instances it may not be possible to distinguish between two possible genotypes based on the size of the amplicons produced by PCR from genomic DNA. In these cases an additional test is possible, for example digestion of the amplicon with one or more restriction enzymes and analysis of the sizes may enable the two possible genotypes to be distinguished, or sequencing of the amplicon may enable the two possible genotypes to be distinguished.

In some embodiments it may be advantageous to delete sequences whose deletion will result in the inactivation of a cytochrome P450; in some embodiments it may be advantageous to delete sequences whose deletion will result in the inactivation of a fatty alcohol oxidase; in some embodiments it may be advantageous to delete sequences whose deletion will result in the inactivation of an alcohol dehydrogenase.

5.7.2. Methods for Addition of Sequences to the *Candida* Genome

In some embodiments, new DNA sequences can be inserted into the yeast genome at a specific location using variations of the targeting construct. Because many yeasts recombine DNA in regions of sequence homology, a linear DNA molecule that is introduced into a yeast cell can recombine homologously with the chromosomal DNA if its ends share sufficient sequence identity with chromosomal sequences. It is thus possible to insert a DNA sequence into the yeast genome at a specific location by flanking that sequence with sequences homologous to sequences within the yeast genome that surround the desired genomic insertion site. Such replacements are quite rare, generally occurring less than 1 time in 1,000 yeast cells, so it is often advantageous to use a selective marker to indicate when new DNA sequences have been incorporated into the yeast genome. A selective marker can be used in conjunction with a sequence to be integrated into the yeast genome by modifying the strategy described for deleting sequences form the yeast genome.

If a targeting construct comprises additional sequences between one of the targeting sequences and the proximal recombinase site, those sequences will be retained in the genome following integration and excision of the targeting construct. An example of such a construct is shown in FIG. 7, with the additional sequences indicated as "insertion sequences." Integration of the targeting construct for insertion into the yeast genome is shown schematically in FIG. 8. Homologous recombination occurs between each of the two targeting sequences in the genomic targeting construct and the homologous sites in the yeast genome. The result is an integration of the targeting construct into the genomic DNA. Cells containing a genomic integration of the targeting construct can be identified using the selective marker.

Cells containing a genomic integration of the targeting construct can optionally be tested to ensure that the integration has occurred at the desired site within the genome. In one embodiment, such testing may be performed by amplification of a section of the genomic DNA by the polymerase chain reaction, for example as illustrated in FIG. 10. One of ordinary skill in the art will readily appreciate that there are many alternative ways to design oligonucleotides to produce diagnostic amplicons using the polymerase chain reaction.

The selectable marker and other sequences from the targeting construct can be removed from the yeast genome using a recombinase-based strategy: the recombinase effects a recombination reaction between the two recombinase sites, excising the sequences between them. In the targeting construct shown in FIG. 7 this is done by induction of the gene encoding the recombinase present in the targeting construct. Expression of the recombinase causes a recombination event between the two recombinase recognition sites of the targeting construct, as shown schematically in FIG. 9. The result is that the sequences between the two recombinase sites are excised from the genome, leaving the insertion sequences integrated into the yeast genome.

Cells to which a genomic integration has been introduced can optionally be tested to ensure that the addition has occurred correctly by polymerase chain reaction amplification of DNA from the yeast genome. These amplicons may then be tested to measure their size (for example by agarose gel electrophoresis), or their sequence may be determined to ensure that precisely the desired changes have been effected.

In some embodiments, it may be advantageous to insert sequences into a site in the genome that is known to be transcriptionally active. For example inserting a sequence encoding a polypeptide into a genomic site where transcription is regulated by a promoter that expresses high levels of mRNA can produce high levels of mRNA encoding the polypeptide. In some embodiments this can be done by replacing a polypeptide encoding sequence in the genome with a sequence encoding a different polypeptide, for example using the genomic targeting constructs of the form shown in FIG. 7.

In some embodiments, the insertion of a sequence encoding a polypeptide into a genomic site where transcription is regulated by a promoter that expresses high levels of mRNA is accomplished by adding a polypeptide encoding sequence into the genome at a position where a part of the genomic sequence is duplicated so that the gene that was originally present in the genome remains. In some embodiments this can be effected using a DNA construct comprising a promoter sequence found in the yeast genome positioned such that transcription initiated by the promoter produces RNA that can subsequently encode the polypeptide. Such a construct also comprises a selectable marker that will function in the yeast and optionally a selectable marker that will function in a bacterial host. These may optionally be the same selectable marker. An example of such a construct is shown in FIG. 21. Integration of this construct into the yeast genome is shown schematically in FIG. 22.

In some embodiments, a sequence encoding a polypeptide is inserted under control of the promoter for an isocitrate lyase gene or the promoter for a cytochrome P450 gene including the promoter of CYP52A12 or the promoter of CYP52A13 or the promoter of CYP52A14 or the promoter of CYP52A17 or the promoter of CYP52A18 or the promoter for a fatty alcohol oxidase gene including the promoter of FAO1 or the promoter of FAO1B or the promoter of FAO2A or the promoter of FAO2B, or the promoter for an alcohol dehydrogenase gene including the promoter of ADH-A4 or the promoter of ADH-A4B or the promoter of ADH-B4 or the promoter of ADH-B4B or the promoter of ADH-A10 or the promoter of ADH-B11 or the promoter of ADH-A10B or the promoter of ADH-B11B to obtain high levels of expression of a polypeptide.

In addition to naturally occurring enzymes, modified enzymes may be added into the host genome. For example enzymes may be altered by incorporating systematically varied sets of amino acid changes, with the resulting changes in phenotypes measured and used to identify sequence changes conferring improved function. See, for example, United States Patent Publications Nos. 20060136184 and 20080050357; Liao et al., 2007, BMC Biotechnol 7, 16; Ehren et al., 2008, Protein Eng Des Sel 21, 699-707 and Heinzelman et al., 2009, Proc Natl Acad Sci USA 106, 5610-5615. Using these methods, modified versions of enzymes may be obtained that confer on the host cell an improved ability to utilize one or more substrate or an improved ability to perform one or more chemical conversion. A gene that has been modified by these methods may be made more useful in the genome of the host by amplification, that is by genetic manipulations causing the presence of more than one copy of the gene within the host cell genome and frequently resulting in higher activity of the gene.

5.7.3. Other Microorganisms of Interest for the Production of Oxidized Fatty Acids Homology-based recombination occurs in the Saccharomycetacaeae Family (which is in the Saccharomycotina Subphylum); Saccharomycetacaeae include the Genera *Ascobotryozyma, Candida, Citeromyces, Debaryomyces, Dekkera* (*Brettanomyces*), *Eremothecium, Issatchenkia, Kazachstania, Kluyveromyces, Kodamaea, Kregervanrija, Kuraishia, Lachancea, Lodderomyces, Nakaseomyces, Pachysolen, Pichia* (*Hansenula*), *Saccharomyces, Saturnispora, Tetrapisispora, Torulaspora, Vanderwaltozyma, Williopsis, Zygosaccharomyces*. The deletion and insertion methods described here are therefore likely to work in these Genera.

Within the Subphylum Saccharomycotina is a monophyletic clade containing organisms that translate CTG as serine instead of leucine (Fitzpatrick et al., A fungal phylogeny based on 42 complete genomes derived from supertree and combined gene analysis *BMC Evolutionary Biology* 2006, 6:99) including the species *Candida lusitaniae, Candida guilliermondii* and *Debaryomyces hansenii*, and the second group containing *Candida albicans, Candida dubliniensis, Candida tropicalis, Candida parapsilosis* and *Lodderomyces elongisporus*. Of particular interest are modifications of the activities of cytochrome P450s, fatty alcohol oxidases and alcohol dehydrogenases to modulate the host's production of oxidized molecules by yeasts in this clade. Yeast species of particular interest and industrial relevance within this clade include—*Candida aaseri, Candida abiesophila, Candida africana, Candida aglyptinia, Candida agrestis, Candida akabanensis, Candida alai, Candida albicans, Candida alimentaria, Candida amapae, Candida ambrosiae, Candida amphixiae, Candida anatomiae, Candida ancudensis, Candida anglica, Candida anneliseae, Candida antarctica, Candida antillancae, Candida anutae, Candida apicola, Candida apis, Candida arabinofermentans, Candida arcana, Candida ascalaphidarum, Candida asparagi, Candida atakaporum, Candida atbi, Candida athensensis, Candida atlantica, Candida atmosphaerica, Candida auringiensis, Candida auris, Candida aurita, Candida austromarina, Candida azyma, Candida azymoides, Candida barrocoloradensis, Candida batistae, Candida beechii, Candida bentonensis, Candida bertae, Candida berthetii, Candida bituminiphila, Candida blankii, Candida blattae, Candida blattariae, Candida bohiensis, Candida boidinii, Candida bokatorum, Candida boleticola, Candida bolitotheri, Candida bombi, Candida bombiphila, Candida bondarzewiae, Candida bracarensis, Candida bribrorum, Candida bromeliacearum, Candida buenavistaensis, Candida buinensis, Candida butyri, Candida californica, Candida canberraensis, Candida cariosilignicola, Candida carpophila, Candida caryicola, Candida caseinolytica, Candida castrensis, Candida catenulata, Candida cellae, Candida cellulolytica, Candida cerambycidarum, Candida chauliodes, Candida chickasaworum, Candida chilensis, Candida choctaworum, Candida chodatii, Candida chrysomelidarum, Candida cidri, Candida cloacae, Candida coipomoensis, Candida conglobata, Candida corydali, Candida cylindracea, Candida davenportii, Candida davisiana, Candida deformans, Candida dendrica, Candida dendronema, Candida derodonti, Candida diddensiae, Candida digboiensis, Candida diospyri, Candida diversa, Candida dosseyi, Candida drimydis, Candida drosophilae, Candida dubliniensis, Candida easanensis, Candida edaphicus, Candida edax, Candida elateridarum, Candida emberorum, Candida endomychidarum, Candida entomophila, Candida ergastensis, Candida ernobii, Candida etchellsii, Candida ethanolica, Candida famata, Candida fennica, Candida fermenticarens, Candida flocculosa, Candida floricola, Candida floris, Candida flosculorum, Candida fluviatilis, Candida fragi, Candida freyschussii, Candida friedrichii, Candida frijolesensis, Candida fructus, Candida fukazawae, Candida fungicola, Candida galacta, Candida galis, Candida galli, Candida gatunensis, Candida gelsemii, Candida geochares, Candida germanica, Candida ghanaensis, Candida gigantensis, Candida glaebosa, Candida glucosophila, Candida glycerinogenes, Candida gorgasii, Candida gotoi, Candida gropengiesseri, Candida guaymorum, Candida haemulonii, Candida halonitratophila, Candida halophila, Candida hasegawae, Candida hawaiiana, Candida heliconiae, Candida hispaniensis, Candida homilentoma, Candida humicola, Candida humilis, Candida hungarica, Candida*

*hyderabadensis, Candida incommunis, Candida inconspicua, Candida insectalens, Candida insectamans, Candida insectorum, Candida intermedia, Candida ipomoeae, Candida ishiwadae, Candida jaroonii, Candida jeffriesii, Candida kanchanaburiensis, Candida karawaiewii, Candida kashinagacola, Candida kazuoi, Candida khmerensis, Candida kipukae, Candida kofuensis, Candida krabiensis, Candida kruisii, Candida kunorum, Candida labiduridarum, Candida lactis-condensi, Candida lassenensis, Candida laureliae, Candida leandrae, Candida lessepsii, Candida lignicola, Candida litsaeae, Candida litseae, Candida llanquihuensis, Candida lycoperdinae, Candida lyxosophila, Candida magnifica, Candida magnoliae, Candida maltosa, Candida mannitofaciens, Candida maris, Candida maritima, Candida maxii, Candida melibiosica, Candida membranifaciens, Candida mesenterica, Candida metapsilosis, Candida methanolophaga, Candida methanolovescens, Candida methanosorbosa, Candida methylica, Candida michaelii, Candida mogii, Candida montana, Candida multigemmis, Candida mycetangii, Candida naeodendra, Candida nakhonratchasimensis, Candida nanaspora, Candida natalensis, Candida neerlandica, Candida nemodendra, Candida nitrativorans, Candida nitratophila, Candida nivariensis, Candida nodaensis, Candida norvegica, Candida novakii, Candida odintsovae, Candida oleophila, Candida ontarioensis, Candida ooitensis, Candida orba, Candida oregonensis, Candida orthopsilosis, Candida ortonii, Candida ovalis, Candida pallodes, Candida palmioleophila, Candida paludigena, Candida panamensis, Candida panamericana, Candida parapsilosis, Candida pararugosa, Candida pattaniensis, Candida peltata, Candida peoriaensis, Candida petrohuensis, Candida phangngensis, Candida picachoensis, Candida piceae, Candida picinguabensis, Candida pignaliae, Candida pimensis, Candida pini, Candida plutei, Candida pomicola, Candida ponderosae, Candida populi, Candida powellii, Candida prunicola, Candida pseudoglaebosa, Candida pseudohaemulonii, Candida pseudointermedia, Candida pseudolambica, Candida pseudorhagii, Candida pseudovanderkliftii, Candida psychrophila, Candida pyralidae, Candida qinlingensis, Candida quercitrusa, Candida quercuum, Candida railenensis, Candida ralunensis, Candida rancensis, Candida restingae, Candida rhagii, Candida riodocensis, Candida rugopelliculosa, Candida rugosa, Candida sagamina, Candida saitoana, Candida sake, Candida salmanticensis, Candida santamariae, Candida santjacobensis, Candida saopaulonensis, Candida savonica, Candida schatavii, Candida sequanensis, Candida sergipensis, Candida shehatae, Candida silvae, Candida silvanorum, Candida silvatica, Candida silvicola, Candida silvicultrix, Candida sinolaborantium, Candida sithepensis, Candida smithsonii, Candida sojae, Candida solani, Candida songkhlaensis, Candida sonorensis, Candida sophiae-reginae, Candida sorbophila, Candida sorbosivorans, Candida sorboxylosa, Candida spandovensis, Candida steatolytica, Candida stellata, Candida stellimalicola, Candida stri, Candida subhashii, Candida succiphila, Candida suecica, Candida suzukii, Candida takamatsuzukensis, Candida taliae, Candida tammaniensis, Candida tanzawaensis, Candida tartarivorans, Candida temnochilae, Candida tenuis, Candida tepae, Candida terraborum, Candida tetrigidarum, Candida thaimueangensis, Candida thermophila, Candida tilneyi, Candida tolerans, Candida torresii, Candida tritomae, Candida tropicalis, Candida trypodendroni, Candida tsuchiyae, Candida tumulicola, Candida ubatubensis, Candida ulmi, Candida vaccinii, Candida valdiviana, Candida vanderkliftii, Candida vanderwaltii, Candida vartiovaarae, Candida versatilis, Candida vini, Candida viswanathii, Candida wickerhamii, Candida wounanorum, Candida wyomingensis, Candida xylopsoci, Candida yuchorum, Candida zemplinina, Candida zeylanoides*

5.7.4. Engineering of Additional Enzymes into *Candida* to Further Diversify Structures of Products Formed.

Different fatty acids are hydroxylated at different rates by different cytochrome P450s. To achieve efficient hydroxylation of a desired fatty acid feedstock, one strategy is to express P450 enzymes within *Candida* that are active for ω-hydroxylation of a wide range of highly abundant fatty acid feedstocks. Of particular interest are P450 enzymes that catalyze ω-hydroxylation of lauric acid (C12:0), myristic acid (C14:0), palmitic acid (C16:0), stearic acid (C18:0), oleic acid (C18:1), linoleic acid (C18:2), and α-linolenic acid (ω3, C18:3). Examples of P450 enzymes with known ω-hydroxylation activity on different fatty acids that may be cloned into *Candida* are the following: CYP94A1 from *Vicia sativa* (Tijet et al., 1988, Biochemistry Journal 332, 583-589); CYP 94A5 from *Nicotiana tabacum* (Le Bouquin et al., 2001, Eur J Biochem 268, 3083-3090); CYP78A1 from *Zea mays* (Larkin, 1994, Plant Mol Biol 25, 343-353); CYP 86A1 (Benveniste et al., 1998, Biochem Biophys Res Commun 243, 688-693) and CYP86A8 (Wellesen et al., 2001, Proc Natl Acad Sci USA 98, 9694-9699) from *Arabidopsis thaliana*; CYP 92B1 from *Petunia hybrida* (Petkova-Andonova et al., 2002, Biosci Biotechnol Biochem 66, 1819-1828); CYP102A1 (BM-3) mutant F87 from *Bacillus megaterium* (Oliver et al., 1997, Biochemistry 36, 1567-1572); and CYP 4 family from mammal and insect (Hardwick, 2008, Biochem Pharmacol 75, 2263-2275).

A second strategy to obtain efficient hydroxylation (or further oxidation of the hydroxy group to an aldehyde or dicarboxylic acid) of a modified fatty acid is to perform the hydroxylation first and then to expose the hydroxylated fatty acid or aldehyde or dicarboxylic acid to an additional enzyme.

For example incorporating one or more desaturase enzymes into engineered *Candida* would allow the introduction of double bonds into ω-hydroxyl fatty acids or aldehydes or dicarboxylic acids at desired positions. Examples of desaturases with known specificity that may be cloned into *Candida* are the following: $\Delta^4$ desaturase from rat liver microsomes (Savile et al., 2001, J Am Chem Soc 123, 4382-4385), $\Delta^5$ desaturase from *Bacillus subtilis* (Fauconnot and Buist, 2001, Bioorg Med Chem Lett 11, 2879-2881), $\Delta^6$ desaturase from *Tetrahymena thermophila* (Fauconnot and Buist, 2001, J Org Chem 66, 1210-1215), $\Delta^9$ desaturase from *Saccharomyces cerevisiae* (Buist and Behrouzian, 1996, J Am Chem Soc 118, 6295-6296); $\Delta^{11}$ desaturase from *Spodoptera littoralis* (Pinilla et al., 1999, Biochemistry 38, 15272-15277), $\Delta^{12}$ desaturase from *Arabidopsis thaliana* (Buist and Behrouzian, 1998, J Am Chem Soc 120, 871-876); $\Delta^{15}$ desaturase from *Caenorhabditis elegans* (Meesapyodsuk et al., 2000, Biochemistry 39, 11948-11954). Many other desaturases are known in the literature that can also be expressed in engineered *Candida* strains including *Candida tropicalis* strains to introduce unsaturation at specific sites of fatty acid substrates prior to ω-hydroxylation or to catalyze carbon-carbon double bond formation after ω-hydroxylation of fatty acids.

Expression in engineered *Candida* strains of P450 enzymes that are known in the literature to introduce additional internal hydroxylation at specific sites of fatty acids or ω-hydroxyfatty acids can be used to produce internally oxidized fatty acids or ω-hydroxyfatty acids or aldehydes or dicarboxylic acids. Examples of P450 enzymes with known in-chain hydroxylation activity on different fatty acids that may be cloned into *Candida* are the following: CYP81B1 from *Helianthus tuberosus* with ω-1 to ω-5 hydroxylation (Cabello-Hurtado et al, 1998, J Biol Chem 273, 7260-7267); CYP790C1 from *Helianthus tuberosus* with ω-1 and ω-2 hydroxylation (Kandel et al., 2005, J Biol Chem 280, 35881-35889); CYP726A1 from *Euphorbia lagscae* with epoxidation on fatty acid unsaturation (Cahoon et al., 2002, Plant Physiol 128, 615-624); CYP152B1 from *Sphingomonas paucimobilis* with α-hydroxylation (Matsunaga et al., 2000, Biomed Life Sci 35, 365-371); CYP2E1 and 4A1 from human liver with ω-1 hydroxylation (Adas et al., 1999, J Lip Res 40, 1990-1997); $P450_{BS\beta}$ from *Bacillus substilis* with α- and β-hydroxylation (Lee et al., 2003, J Biol Chem 278, 9761-9767); and CYP102A1 (BM-3) from *Bacillus megaterium* with ω-1, ω-2 and ω-3 hydroxylation (Shirane et al., 1993, Biochemistry 32, 13732-13741).

In addition to naturally occurring enzymes, modified enzymes may be added into the host genome. For example enzymes may be altered by incorporating systematically varied sets of amino acid changes, with the resulting changes in phenotypes measured and used to identify sequence changes conferring improved function. See, for example, United States Patent Publications Nos. 20060136184 and 20080050357; Liao et al., 2007, BMC Biotechnol 7, 16; Ehren et al., 2008, Protein Eng Des Sel 21, 699-707 and Heinzelman et al., 2009, Proc Natl Acad Sci USA 106, 5610-5615. Using these methods, modified versions of cytochrome P450s may be obtained with improved ability to oxidise fatty acids of different lengths (for example C6, C7, C8, C9, C10, C11, C12, C13, C14, C15, C16, C17, C18, C19, C20, C21, C22, C23, C24) or different degrees of saturation (for example fatty acids with one carbon-carbon double bond, fatty acids with two carbon-carbon double bonds and fatty acids with three carbon-carbon double bonds) or with unsaturated fatty acids where the unsaturated bond is at different positions relative to the carboxyl group and the ω-position, to hydroxy fatty acids or to dicarboxylic fatty acids. Further, using these methods modified versions of fatty alcohol oxidases or alcohol dehydrogenases may be obtained with improved ability to oxidise hydroxy-fatty acids of different lengths (for example C6, C7, C8, C9, C10, C11, C12, C13, C14, C15, C16, C17, C18, C19, C20, C21, C22, C23, C24) or different degrees of saturation (for example fatty acids with one carbon-carbon double bond, fatty acids with two carbon-carbon double bonds and fatty acids with three carbon-carbon double bonds) or with unsaturated fatty acids where the unsaturated bond is at different positions relative to the carboxyl group and the ω-position. A gene that has been modified by these methods may be made more useful in the genome of the host by amplification, that is by genetic manipulations causing the presence of more than one copy of the gene within the host cell genome and frequently resulting in higher activity of the gene. Expression of one or more additional enzymes may also be used to functionalize the oxidized fatty acid, either the hydroxyl group or more highly oxidized groups such as aldehydes or carboxylic acids

6. BIOTRANSFORMATION EXAMPLES

The following examples are set forth so as to provide those of ordinary skill in the art with a complete description of how to practice, make and use exemplary embodiments of the disclosed methods, and are not intended to limit the scope of what is regarded as the invention.

6.1. General Biotransformation Procedure in Shake-Flask

*C. tropicalis* ATCC20962 from fresh agar plate or glycerol stock was precultured in 30 ml YPD medium consisting of (g $l^{-1}$): yeast extract, 10; peptone, 10; glucose, 20 and shaken at 250 rpm, 30° for 20 hours in 500 ml flask. After 16 hours of cultivation at 250 rpm, 30° C., preculture was inoculated at 10% (v/v) to 30 ml conversion medium consisting of (g $l^{-1}$): peptone, 3; yeast extract, 6; yeast nitrogen base, 6.7; acetic acid, 3; $K_2HPO_4$, 7.2; $KH_2PO_4$ 9.3; glucose/glycerol, 20 in 500 ml flask and shaked at 250 rpm. The initial concentration of substrate was about 10-20 g $l^{-1}$. pH was adjusted to 7.5 by addition of 2 mol l-1 NaOH solution after 12 hour culture. During biotransformation, concentrated co-substrate (glucose/glycerol/sodium acetate/ethanol) was fed (1-2.5% per day) and pH was maintained at 7.5~8.0 by addition of NaOH solution. Samples were taken on a daily basis to determine levels of product by LC-MS.

6.2. General Biotransformation Procedure in Fermentor

Fermentation was carried out in 3-l Bioflo3000 fermentor (New Brunswick Scientific Co., USA) in fed-batch culture. The conversion medium mentioned above was used except for addition of 0.05% antifoam 204 (Sigma) and 0.5% substrate. The seed culture from fresh agar plate or glycerol stock was prepared in 50 ml of conversion medium for 20 hours at 30° C., 250 rpm prior to inoculation into the fermentor vessel. Following inoculation, the culture was maintained at pH 6.3 and grown at 30°, 900 rpm with aeration rate of 1.5 vvm. After 12 hour fermentations (growth phase), biotransformation phase was started with feeding of substrate (2 ml $l^{-1}$). Concentrated glucose (500 g $l^{-1}$) as co-substrate was fed continuously at the rate of 1.2 g l-1 h-1. During the biotransformation phase, pH was maintained at 7.6 automatically by addition of 4 mol $l^{-1}$ NaOH solution. Antifoam (Antifoam 204) was also added to the fermentor as necessary. Samples were taken on a daily basis to determine levels of product by LC-MS.

6.3. General Extraction and Purification Procedure of Biotransformation Products The fermentation broth was acidified to pH 1.0 with HCl and extracted twice with diethyl ether. To avoid the epoxy ring-opening during acidification, the fermentation broth with products containing epoxy groups was slowly acidified to pH 3.0 with 5 N HCl. Solvent was evaporated under vacuum with a rotary evaporator. The residual obtained was separated by silica gel column chromatography using silica gel 60. The fractions containing impurities, un-reacted mono fatty acids and products were gradually eluted with a mixture of n-hexane/diethyl ether that their ratio ranges from 90:30 to 10:90. The fractions containing same compound were collected together and the solvents were evaporated under vacuum with a rotary evaporator.

7. GENETIC MODIFICATION EXAMPLES

The following examples are set forth so as to provide those of ordinary skill in the art with a description of how to practice, make and use various disclosed exemplary embodiments, and are not intended to limit the scope of what is regarded as the invention.

The strains shown in Table 2 and further described in this section were constructed by the synthesis and cloning of DNA and its subsequent transformation into the appropriate *C. tropicalis* strain. Table 2 summarizes the DNA sequences synthesized and used in these examples. Table 3 summarizes the *C. tropicalis* strains constructed in these examples. Section 7.1 describes the methods used for transformation of *Candida tropicalis*.

TABLE 2

| NAME | SEQ ID NO: | GI No. | SOURCE/ CONSTRUCTION | APPLICATION |
|---|---|---|---|---|
| SAT1 Flipper | 1 | 50059745 | Joachim Morschhauser | Source of the SAT1 Flipper |
| CYP52A17 | 2 | 29469874 | | Used to design CYP52A17_Δ |
| CYP52A17_Δ | 3 | Not applicable | Gene synthesis | Used to construct CYP52A17::SAT1 |
| CYP52A17::SAT1 | 4 | Not applicable | Subcloning of SAT1 flipper into CYP52A17_Δ | Used to delete CYP52A17 |
| CYP52A13 | 5 | 29469864 | | Used to design CYP52A13_Δ |
| CYP52A13_Δ | 6 | Not applicable | Gene synthesis | Used to construct CYP52A13::SAT1 |
| CYP52A13::SAT1 | 7 | Not applicable | Subcloning of SAT1 flipper into CYP52A13_Δ | Used to delete CYP52A13 |
| CYP52A18 | 8 | 29469876 | | Used to design CYP52A18_Δ |
| CYP52A18_Δ | 9 | Not applicable | Gene synthesis | Used to construct CYP52A18::SAT1 |
| CYP52A18::SAT1 | 11 | Not applicable | Subcloning of SAT1 flipper into CYP52A18_Δ | Used to delete CYP52A18 |
| CYP52A14 | 13 | 29469866 | | Used to design CYP52A14_Δ_Gene#1179 1179 |
| CYP52A14_Δ | 14 | Not applicable | Gene synthesis | Used to construct CYP52A14::SAT1 |
| CYP52A14::SAT1 | 15 | Not applicable | Subcloning of SAT1 flipper into CYP52A14_Δ | Used to delete CYP52A14 |
| FAO1 | 16 | 44194456 | | Used to design FAO1_Δ |
| FAO1_Δ | 17 | Not applicable | Gene synthesis | Used to construct FAO1::SAT1 |
| FAO1::SAT1 | 18 | Not applicable | Subcloning of SAT1 flipper into FAO1_Δ | Used to delete FAO1 |
| FAO1B | 19 | Not applicable | | Used to design FAO1B_Δ |
| FAO1B_Δ | 20 | Not applicable | Assembly PCR. Product not cloned. | Used to construct FAO1B::SAT1 |
| FAO1B::SAT1 | 21 | Not applicable | Ligation of SAT1 flipper to assembly PCR product of FAO1B_Δ | Used to delete FAO1B |
| FAO2A | 22 | 44194479 | | Used to design FAO2A_Δ |
| FAO2A_Δ | 23 | Not applicable | Gene synthesis | Used to construct FAO2A::SAT1 |
| FAO2A::SAT1 | 24 | Not applicable | Subcloning of SAT1 flipper into FAO2A_Δ | Used to delete FAO2A |
| FAO2B | 25 | 44194514 | | Used to design FAO2B_Δ |
| FAO2B_Δ | 26 | Not applicable | Gene synthesis | Used to construct FAO2B::SAT1 |
| FAO2B::SAT1 | 27 | Not applicable | Subcloning of SAT1 flipper into FAO2B_Δ | Used to delete FAO2B |
| CYP52A12 | 28 | 29469862 | | Used to design CYP52A12_Δ |
| CYP52A12_Δ | 29 | Not applicable | Gene synthesis | Used to construct CYP52A12::SAT1 |
| CYP52A12::SAT1 | 30 | Not applicable | Subcloning of SAT1 flipper into CYP52A12_Δ | Used to delete CYP52A12 |
| CYP52A12B | | Not applicable | | Used to design CYP52A12B_Δ |
| CYP52A12B_Δ | 31 | Not applicable | Gene synthesis | Used to construct CYP52A12B::SAT1 |
| CYP52A12B::SAT1 | 32 | Not applicable | Subcloning of SAT1 flipper into CYP52A12B_Δ | Used to delete CYP52A12B |
| ADH-A4 | 39 | Not applicable | | Used to design ADH-A4_Δ |
| ADH-A4_Δ | 44 | Not applicable | Gene synthesis | Used to construct ADH-A4::SAT1 |
| ADH-A4::SAT1 | 45 | Not applicable | Subcloning of SAT1 flipper into ADH-A4_Δ | Used to delete ADH-A4 |
| ADH-A4B | | Not applicable | | Used to design ADH-A4B_Δ |
| ADH-A4B_Δ | 46 | Not applicable | Gene synthesis | Used to construct ADH-A4B::SAT1 |
| ADH-A4B::SAT1 | 47 | Not applicable | Subcloning of SAT1 flipper into ADH-A4B_Δ | Used to delete ADH-A4B |
| ADH-B4 | 42 | Not applicable | | Used to design ADH-B4_Δ |

TABLE 2-continued

| NAME | SEQ ID NO: | GI No. | SOURCE/ CONSTRUCTION | APPLICATION |
|---|---|---|---|---|
| ADH-B4_Δ | 48 | Not applicable | Gene synthesis | Used to construct ADH-B4::SAT1 |
| ADH-B4::SAT1 | 49 | Not applicable | Subcloning of SAT1 flipper into ADH-B4_Δ | Used to delete ADH-B4 |
| ADH-B4B | | Not applicable | | Used to design ADH-B4B_Δ |
| ADH-B4B_Δ | 50 | Not applicable | Gene synthesis | Used to construct ADH-B4B::SAT1 |
| ADH-B4B::SAT1 | 51 | Not applicable | Subcloning of SAT1 flipper into ADH-B4B_Δ | Used to delete ADH-B4B |
| ADH-A10 | 40 | Not applicable | | Used to design ADH-A10_Δ |
| ADH-A10_Δ | 52 | Not applicable | Gene synthesis | Used to construct ADH-A10::SAT1 |
| ADH-A10::SAT1 | 53 | Not applicable | Subcloning of SAT1 flipper into ADH-A10_Δ | Used to delete ADH-A10 |
| ADH-B11 | 43 | Not applicable | | Used to design ADH-B11_Δ |
| ADH-B11_Δ | 54 | Not applicable | Gene synthesis | Used to construct ADH-B11::SAT1 |
| ADH-B11::SAT1 | 55 | Not applicable | Subcloning of SAT1 flipper into ADH-B11_Δ | Used to delete ADH-B11 |
| ADH-A10B | 56 | Not applicable | | Used to design ADH-A10B_Δ |
| ADH-A10B_Δ | 57 | Not applicable | Gene synthesis | Used to construct ADH-A10B::SAT1 |
| ADH-A10B::SAT1 | 58 | Not applicable | Subcloning of SAT1 flipper into ADH-A10B_Δ | Used to delete ADH-A10B |
| ADH-B11B | 59 | Not applicable | | Used to design ADH-B11B_Δ |
| ADH-B11B_Δ | 60 | Not applicable | Gene synthesis | Used to construct ADH-B11B::SAT1 |
| ADH-B11B::SAT1 | 61 | Not applicable | Subcloning of SAT1 flipper into ADH-B11B_Δ | Used to delete ADH-B11B |
| ICL promoter | 62 | Not applicable | Gene synthesis | Used as a component of genomic integration and expression constructs (e.g. SEQ ID NO: 70, SEQ ID NO: 71, SEQ ID NO: 74, etc.) |
| ICL terminator | 63 | Not applicable | Gene synthesis | Used as a component of genomic integration and expression constructs (e.g. SEQ ID NO: 70, SEQ ID NO: 71, SEQ ID NO: 74, etc.) |
| TEF1 promoter | 64 | Not applicable | Gene synthesis | Used as a component of genomic integration and expression constructs (e.g. SEQ ID NO: 70, SEQ ID NO: 71, SEQ ID NO: 74, etc.) |
| EM7 promoter | 65 | Not applicable | Gene synthesis | Used as a component of genomic integration and expression constructs (e.g. SEQ ID NO: 70, SEQ ID NO: 71, SEQ ID NO: 74, etc.) |
| ZeoR | 66 | Not applicable | Gene synthesis of gene optimized for *Candida* | Used as a component of genomic integration and expression constructs (e.g. SEQ ID NO: 70, SEQ ID NO: 71, SEQ ID NO: 74, etc.) |
| CYC1 transcription terminator | 67 | Not applicable | Gene synthesis | Used as a component of genomic integration and expression constructs (e.g. SEQ ID NO: 70, SEQ ID NO: 71, SEQ ID NO: 74, etc.) |
| pUC origin of replication | 68 | Not applicable | Gene synthesis | Used as a component of genomic integration and expression constructs (e.g. SEQ ID NO: 70, SEQ ID |

TABLE 2-continued

| NAME | SEQ ID NO: | GI No. | SOURCE/ CONSTRUCTION | APPLICATION |
|---|---|---|---|---|
| | | | | NO: 71, SEQ ID NO: 74, etc.) |
| CYP52A17 | 69 | Not applicable | Gene synthesis | Cloned into genomic integration and expression constructs to express (e.g. SEQ ID No: 70) |
| pXICL::CYP52A17 | 70 | Not applicable | CYP52A17 cloned into genomic integration vector | Used to express CYP52A17 in *Candida tropicalis* under control of the isocitrate lyase promoter |
| CYP52A13 | 71 | Not applicable | Gene synthesis | Cloned into genomic integration and expression constructs to express(e.g. SEQ ID NO: 71) |
| pXICL::CYP52A13 | 72 | Not applicable | CYP52A13 cloned into genomic integration vector | Used to express CYP52A13 in *Candida tropicalis* under control of the isocitrate lyase promoter |
| CYP52A12 | 73 | Not applicable | Gene synthesis | Cloned into genomic integration and expression constructs to express(e.g. SEQ ID NO: 74) |
| pXICL::CYP52A12 | 74 | Not applicable | CYP52A12 cloned into genomic integration vector | Used to express CYP52A12 in *Candida tropicalis* under control of the isocitrate lyase promoter |
| mCherry | 75 | Not applicable | Gene synthesis | Cloned into genomic integration and expression constructs to express mCherry (e.g. SEQ ID NO: 76) |
| pXICL::mCherry | 76 | Not applicable | mCherry cloned into genomic integration vector | Used to express mCherry in *Candida tropicalis* under control of the isocitrate lyase promoter |

TABLE 3

| Strain Name | Genotype | Description |
|---|---|---|
| DP1 | ura3A/ura3B pox5::ura3A/pox5::ura3A pox4A::ura3A/pox4B::URA3A | American Type Culture Collection (ATCC 20962) |
| DP65 | DP1 CYP52A17::SAT1 | Electroporation of DP1 with CYP52A17::SAT1 (SEQ ID NO: 4) and selection for nourseothricin resistance followed by PCR screens for targeting construct insertion into CYP52A17 |
| DP78 | DP1 ΔCYP52A17 | Growth of DP65 with maltose followed by agar plate screen for loss of nourseothricin resistance and PCR screen for excision of targeting construct from CYP52A17 |
| DP107 | DP1 ΔCYP52A17 CYP52A13::SAT1 | Electroporation of DP78 with CYP52A13::SAT1 (SEQ ID NO: 7) and selection for nourseothricin resistance followed by PCR screens for targeting construct insertion into CYP52A13 |
| DP113 | DP1 ΔCYP52A17 ΔCYP52A13 | Growth of DP107 with maltose followed by agar plate screen for loss of nourseothricin resistance and PCR screen for excision of targeting construct from CYP52A13 |
| DP140 | DP1 ΔCYP52A17/CYP52A18::SAT1 ΔCYP52A13 | Electroporation of DP113 with CYP52A18::SAT1 (SEQ ID NO: 11) and selection for nourseothricin resistance followed by PCR screens for targeting construct insertion into CYP52A18 |
| DP142 | DP1 ΔCYP52A17/ΔCYP52A18 ΔCYP52A13 | Growth of DP140 with maltose followed by agar plate screen for loss of nourseothricin resistance and PCR screen for excision of targeting construct from CYP52A18 |

TABLE 3-continued

| Strain Name | Genotype | Description |
|---|---|---|
| DP170 | DP1 ΔCYP52A17/ΔCYP52A18 ΔCYP52A13/CYP52A14::SAT1 | Electroporation of DP142 with CYP52A14::SAT1(SEQ ID NO: 15) and selection for nourseothricin resistance followed by PCR screens for targeting construct insertion into CYP52A14 |
| DP174 | DP1 ΔCYP52A17/ΔCYP52A18 ΔCYP52A13/ΔCYP52A14 | Growth of DP170 with maltose followed by agar plate screen for loss of nourseothricin resistance and PCR screen for excision of targeting construct from CYP52A14 |
| DP182 | DP1 ΔCYP52A17/ΔCYP52A18 ΔCYP52A13/ΔCYP52A14 FAO1::SAT1 | Electroporation of DP174 with FAO1::SAT1(SEQ ID NO: 18) and selection for nourseothricin resistance followed by PCR screens for targeting construct insertion into FAO1 |
| DP186 | DP1 ΔCYP52A17/ΔCYP52A18 ΔCYP52A13/ΔCYP52A14 ΔFAO1 | Growth of DP182 with maltose followed by agar plate screen for loss of nourseothricin resistance and PCR screen for excision of targeting construct from FAO1 |
| DP197 | DP1 ΔCYP52A17/ΔCYP52A18 ΔCYP52A13/ΔCYP52A14 ΔFAO1 pXICL::mCherry | Electroporation of DP186 with pXICL::mCherry (SEQ ID NO: 76) and selection for zeocin resistance followed by PCR screens for targeting construct insertion into the isocitrate lyase gene |
| DP201 | DP1 ΔCYP52A17/ΔCYP52A18 ΔCYP52A13/ΔCYP52A14 ΔFAO1 pXICL::CYP52A17 | Electroporation of DP186 with pXICL::CYP52A17 (SEQ ID NO: 70) and selection for zeocin resistance followed by PCR screens for targeting construct insertion into the isocitrate lyase gene |
| DP238 | DP1 ΔCYP52A17/ΔCYP52A18 ΔCYP52A13/ΔCYP52A14 ΔFAO1/FAO1B::SAT1 | Electroporation of DP186 with FAO1B::SAT1(SEQ ID NO: 21) and selection for nourseothricin resistance followed by PCR screens for targeting construct insertion into FAO1B |
| DP240 | DP1 ΔCYP52A17/ΔCYP52A18 ΔCYP52A13/ΔCYP52A14 ΔFAO1/ΔFAO1B | Growth of DP238 with maltose followed by agar plate screen for loss of nourseothricin resistance and PCR screen for excision of targeting construct from FAO1B |
| DP255 | DP1 ΔCYP52A17/ΔCYP52A18 ΔCYP52A13/ΔCYP52A14 ΔFAO1/ΔFAO1B FAO2A::SAT1 | Electroporation of DP240 with FAO2A::SAT1(SEQ ID NO: 21) and selection for nourseothricin resistance followed by PCR screens for targeting construct insertion into FAO2A |
| DP256 | DP1 ΔCYP52A17/ΔCYP52A18 ΔCYP52A13/ΔCYP52A14 ΔFAO1/ΔFAO1B ΔFAO2A | Growth of DP255 with maltose followed by agar plate screen for loss of nourseothricin resistance and PCR screen for excision of targeting construct from FAO2A |
| DP258 DP259 | DP1 ΔCYP52A17/ΔCYP52A18 ΔCYP52A13/ΔCYP52A14 ΔFAO1/ΔFAO1B ΔFAO2A/FAO2B::SAT1 | Electroporation of DP256 with FAO2B::SAT1(SEQ ID NO: 27) and selection for nourseothricin resistance followed by PCR screens for targeting construct insertion into FAO2B |
| DP261 | DP1 ΔCYP52A17/ΔCYP52A18 ΔCYP52A13/ΔCYP52A14 ΔFAO1/ΔFAO1B ΔFAO2A/ΔFAO2B | Growth of DP259 with maltose followed by agar plate screen for loss of nourseothricin resistance and PCR screen for excision of targeting construct from FAO2B |
| DP268 | DP1 ΔCYP52A17/ΔCYP52A18 ΔCYP52A13/ΔCYP52A14 ΔFAO1/ΔFAO1B ΔFAO2A/ΔFAO2B CYP52A12::SAT1 | Electroporation of DP261 with CYP52A12::SAT1 (SEQ ID NO: 30) and selection for nourseothricin resistance followed by PCR screens for targeting construct insertion into CYP52A12 |
| DP272 | DP1 ΔCYP52A17/ΔCYP52A18 ΔCYP52A13/ΔCYP52A14 ΔFAO1/ΔFAO1B ΔFAO2A/ΔFAO2B ΔCYP52A12 | Growth of DP268 with maltose followed by agar plate screen for loss of nourseothricin resistance and PCR screen for excision of targeting construct from CYP52A12 |
| DP282 | DP1 ΔCYP52A17/ΔCYP52A18 ΔCYP52A13/ΔCYP52A14 ΔFAO1/ΔFAO1B ΔFAO2A/ΔFAO2B ΔCYP52A12/CYP52A12B::SAT1 | Electroporation of DP272 with CYP52A12B::SAT1 (SEQ ID NO: 32) and selection for nourseothricin resistance followed by PCR screens for targeting construct insertion into CYP52A12B |
| DP283 | DP1 ΔCYP52A17/ΔCYP52A18 | Growth of DP282 with maltose followed |

TABLE 3-continued

| Strain Name | Genotype | Description |
|---|---|---|
| DP284 | ΔCYP52A13/ΔCYP52A14 ΔFAO1/ΔFAO1B ΔFAO2A/ΔFAO2B ΔCYP52A12/ΔCYP52A12B | by agar plate screen for loss of nourseothricin resistance and PCR screen for excision of targeting construct from CYP52A12B |
| DP387 | DP1 ΔCYP52A17/ΔCYP52A18 ΔCYP52A13/ΔCYP52A14 ΔFAO1/ΔFAO1B ΔFAO2A/ΔFAO2B ΔCYP52A12/ΔCYP52A12B ADH-A4::SAT1 | Electroporation of DP283 with ADH-A4::SAT1(SEQ ID NO: 45) and selection for nourseothricin resistance followed by PCR screens for targeting construct insertion into ADH-A4 |
| DP388 | DP1 ΔCYP52A17/ΔCYP52A18 ΔCYP52A13/ΔCYP52A14 ΔFAO1/ΔFAO1B ΔFAO2A/ΔFAO2B ΔCYP52A12/ΔCYP52A12B ΔADH-A4 | Growth of DP387 with maltose followed by agar plate screen for loss of nourseothricin resistance and PCR screen for excision of targeting construct from ADH-A4 |
| DP389 | DP1 ΔCYP52A17/ΔCYP52A18 ΔCYP52A13/ΔCYP52A14 ΔFAO1/ΔFAO1B ΔFAO2A/ΔFAO2B ΔCYP52A12/ΔCYP52A12B ΔADH-A4/ADH-A4B::SAT1 | Electroporation of DP388 with ADH-A4B::SAT1 (SEQ ID NO: 47) and selection for nourseothricin resistance followed by PCR screens for targeting construct insertion into ADH-A4B |
| DP390 | DP1 ΔCYP52A17/ΔCYP52A18 ΔCYP52A13/ΔCYP52A14 ΔFAO1/ΔFAO1B ΔFAO2A/ΔFAO2B ΔCYP52A12/ΔCYP52A12B ΔADH-A4/ΔADH-A4B | Growth of DP389 with maltose followed by agar plate screen for loss of nourseothricin resistance and PCR screen for excision of targeting construct from ADH-A4B |
| DP397 | DP1 ΔCYP52A17/ΔCYP52A18 ΔCYP52A13/ΔCYP52A14 ΔFAO1/ΔFAO1B ΔFAO2A/ΔFAO2B ΔCYP52A12/ΔCYP52A12B ΔADH-A4/ΔADH-A4B ADH-B4::SAT1 | Electroporation of DP390 with ADH-B4::SAT1 (SEQ ID NO: 49) and selection for nourseothricin resistance followed by PCR screens for targeting construct insertion into ADH-B4 |
| DP398 | DP1 ΔCYP52A17/ΔCYP52A18 ΔCYP52A13/ΔCYP52A14 ΔFAO1/ΔFAO1B ΔFAO2A/ΔFAO2B ΔCYP52A12/ΔCYP52A12B ΔADH-A4/ΔADH-A4B ΔADH-B4 | Growth of DP397 with maltose followed by agar plate screen for loss of nourseothricin resistance and PCR screen for excision of targeting construct from ADH-B4 |
| DP409 | DP1 ΔCYP52A17/ΔCYP52A18 ΔCYP52A13/ΔCYP52A14 ΔFAO1/ΔFAO1B ΔFAO2A/ΔFAO2B ΔCYP52A12/ΔCYP52A12B ΔADH-A4/ΔADH-A4B ΔADH-B4/ADH-B4B::SAT1 | Electroporation of DP398 with ADH-B4B::SAT1 (SEQ ID NO: 49) and selection for nourseothricin resistance followed by PCR screens for targeting construct insertion into ADH-B4B |
| DP411 | DP1 ΔCYP52A17/ΔCYP52A18 ΔCYP52A13/ΔCYP52A14 ΔFAO1/ΔFAO1B ΔFAO2A/ΔFAO2B ΔCYP52A12/ΔCYP52A12B ΔADH-A4/ΔADH-A4B ΔADH-B4/ΔADH-B4B | Growth of DP409 with maltose followed by agar plate screen for loss of nourseothricin resistance and PCR screen for excision of targeting construct from ADH-B4B |
| DP415 | DP1 ΔCYP52A17/ΔCYP52A18 ΔCYP52A13/ΔCYP52A14 ΔFAO1/ΔFAO1B ΔFAO2A/ΔFAO2B ΔCYP52A12/ΔCYP52A12B ΔADH-A4/ΔADH-A4B ΔADH-B4/ΔADH-B4B ADH-A10::SAT1 | Electroporation of DP411 with ADH-A10::SAT1 (SEQ ID NO: 53) and selection for nourseothricin resistance followed by PCR screens for targeting construct insertion into ADH-A10 |
| DP416 | DP1 ΔCYP52A17/ΔCYP52A18 ΔCYP52A13/ΔCYP52A14 ΔFAO1/ΔFAO1B ΔFAO2A/ΔFAO2B ΔCYP52A12/ΔCYP52A12B ΔADH-A4/ΔADH-A4B ΔADH-B4/ΔADH-B4B ΔADH-A10 | Growth of DP415 with maltose followed by agar plate screen for loss of nourseothricin resistance and PCR screen for excision of targeting construct from ADH-A10 |
| DP417 | DP1 ΔCYP52A17/ΔCYP52A18 ΔCYP52A13/ΔCYP52A14 ΔFAO1/ΔFAO1B ΔFAO2A/ΔFAO2B ΔCYP52A12/ΔCYP52A12B ΔADH-A4/ΔADH-A4B ΔADH- | Electroporation of DP416 with ADH-B11::SAT1 (SEQ ID NO: 55) and selection for nourseothricin resistance followed by PCR screens for targeting construct insertion into ADH-B11 |

TABLE 3-continued

| Strain Name | Genotype | Description |
|---|---|---|
| | B4/ΔADH-B4B ΔADH-A10 ADH-B11::SAT1 | |
| DP421 | DP1 ΔCYP52A17/ΔCYP52A18 ΔCYP52A13/ΔCYP52A14 ΔFAO1/ΔFAO1B ΔFAO2A/ΔFAO2B ΔCYP52A12/ΔCYP52A12B ΔADH-A4/ΔADH-A4B ΔADH-B4/ΔADH-B4B ΔADH-A10 ΔADH-B11 | Growth of DP417 with maltose followed by agar plate screen for loss of nourseothricin resistance and PCR screen for excision of targeting construct from ADH-B11 |
| DP423 DP424 | DP1 ΔCYP52A17/ΔCYP52A18 ΔCYP52A13/ΔCYP52A14 ΔFAO1/ΔFAO1B ΔFAO2A/ΔFAO2B ΔCYP52A12/ΔCYP52A12B ΔADH-A4/ΔADH-A4B ΔADH-B4/ΔADH-B4B ΔADH-A10/ADH-A10B::SAT1 ΔADH-B11 | Electroporation of DP421 with ADH-A10B::SAT1 (SEQ ID No: 58) and selection for nourseothricin resistance followed by PCR screens for targeting construct insertion into ADH-A10B |
| DP427 DP428 | DP1 ΔCYP52A17/ΔCYP52A18 ΔCYP52A13/ΔCYP52A14 ΔFAO1/ΔFAO1B ΔFAO2A/ΔFAO2B ΔCYP52A12/ΔCYP52A12B ΔADH-A4/ΔADH-A4B ΔADH-B4/ΔADH-B4B ΔADH-A10 ΔADH-B11 pXICL::CYP52A17 | Electroporation of DP421 with pXICL::CYP52A17 (SEQ ID NO: 70) and selection for zeocin resistance followed by PCR screens for targeting construct insertion into the isocitrate lyase gene |
| DP431 | DP1 ΔCYP52A17/ΔCYP52A18 ΔCYP52A13/ΔCYP52A14 ΔFAO1/ΔFAO1B ΔFAO2A/ΔFAO2B ΔCYP52A12/ΔCYP52A12B ΔADH-A4/ΔADH-A4B ΔADH-B4/ΔADH-B4B ΔADH-A10/ΔADH-A10B ΔADH-B11 | Growth of DP424 with maltose followed by agar plate screen for loss of nourseothricin resistance and PCR screen for excision of targeting construct from ADH-A10B |
| DP433 DP434 | DP1 ΔCYP52A17/ΔCYP52A18 ΔCYP52A13/ΔCYP52A14 ΔFAO1/ΔFAO1B ΔFAO2A/ΔFAO2B ΔCYP52A12/ΔCYP52A12B ΔADH-A4/ΔADH-A4B ΔADH-B4/ΔADH-B4B ΔADH-A10/ΔADH-A10B ΔADH-B11/ADHB11B::SAT1 | Electroporation of DP431 with ADH-B11B::SAT1 (SEQ ID NO: 61) and selection for nourseothricin resistance followed by PCR screens for targeting construct insertion into ADH-B11B |
| DP436 DP437 | DP1 ΔCYP52A17/ΔCYP52A18 ΔCYP52A13/ΔCYP52A14 ΔFAO1/ΔFAO1B ΔFAO2A/ΔFAO2B ΔCYP52A12/ΔCYP52A12B ΔADH-A4/ΔADH-A4B ΔADH-B4/ΔADH-B4B ΔADH-A10/ΔADH-A10B ΔADH-B11/ΔADHB11B | Growth of DP433 with maltose followed by agar plate screen for loss of nourseothricin resistance and PCR screen for excision of targeting construct from ADH-B11B |
| DP522 DP523 | DP1 ΔCYP52A17/ΔCYP52A18 ΔCYP52A13/ΔCYP52A14 ΔFAO1/ΔFAO1B ΔFAO2A/ΔFAO2B ΔCYP52A12/ΔCYP52A12B ΔADH-A4/ΔADH-A4B ΔADH-B4/ΔADH-B4B ΔADH-A10 ΔADH-B11 pXICL::CYP52A13 | Electroporation of DP421 with pXICL::CYP52A13 (SEQ ID NO: 72) and selection for zeocin resistance followed by PCR screens for targeting construct insertion into the isocitrate lyase gene |
| DP526 DP527 | DP1 ΔCYP52A17/ΔCYP52A18 ΔCYP52A13/ΔCYP52A14 ΔFAO1/ΔFAO1B ΔFAO2A/ΔFAO2B ΔCYP52A12/ΔCYP52A12B ΔADH-A4/ΔADH-A4B ΔADH-B4/ΔADH-B4B ΔADH-A10 ΔADH-B11 pXICL::CYP52A12 | Electroporation of DP421 with pXICL::CYP52A12 (SEQ ID NO: 74) and selection for zeocin resistance followed by PCR screens for targeting construct insertion into the isocitrate lyase gene |

7.1. General Protocols for Transformation of *Candida*

The protocols described in this section have been performed using *Candida tropicalis*. However it is expected that they will work in the Saccharomycetacaeae Family in general and the *Candida* genus in particular without undue experimentation since the methods rely upon homologous recombination which is found throughout this Family.

7.1.1. Preparation of DNA Targeting Constructs Prior to Integration into *Candida tropicalis*

A linear segment of DNA of the form shown schematically in either FIG. 4 or FIG. 7 was prepared by digesting between 2.5 and 5 μg of the plasmid containing the targeting construct with flanking restriction enzymes, in the examples below the restriction enzyme BsmBI from New England Biolabs was used according to the manufacturer's instructions. The digest was purified using Qiagen's PCR purification kit, eluted in 75 μl of Qiagen's EB buffer (elution buffer) and transformed into *C. tropicalis* by electroporation.

7.1.2. Preparation of Electrocompetent *Candida tropicalis*

The desired *C. tropicalis* strain was densely streaked from a culture stored at −80° C. in growth media (YPD) containing 10% glycerol, onto 2-3 100 mm YPD Agar plates and incubated overnight at 30° C. The next morning 10 ml YPD broth was spread onto the surface of the YPD agar plates and the yeast cells were scraped from the plates with the aid of a sterile glass spreader. Cells (of the same strain) from the 2-3 plates were combined in a 50 ml conical tube, and the $A_{600}$ of a 1:20 dilution determined. Sufficient cells to prepare 50 ml of YPD containing yeast cells at an $A_{600}$ of 0.2 were placed in each of two 50 ml conical tubes and pelleted in a centrifuge for 5 min at 400×g. The cells in each tube were suspended in 10 ml of TE/Li mix (100 mM LiCl, 10 mM Tris-Cl, 1 mM EDTA, pH 7.4). Both tubes were incubated in a shaking incubator for 1 hour at 30° C. and 125 rpm, then 250 μl of 1M DTT was added to each 10 ml cell suspension and incubation continued for a further 30 min at 30° C. and 125 rpm.

The cells were then washed twice in water and once in sorbitol. Sterile, ice-cold purified water (40 ml) was added to each of the cell suspensions which were then centrifuged for 5 min at 400×g at 4° C. and the supernatant decanted off. The cells in each tube were resuspended in 50 ml of sterile, ice-cold purified water, centrifuged for 5 min at 400×g at 4° C., the supernatant decanted off supernatant. The cells in each tube were then resuspended in 25 ml of ice cold 1 M Sorbitol (prepared with purified water) and centrifuged for 5 min at 400×g. The supernatant was decanted from each tube and cells resuspended in the small residual volume of Sorbitol solution (the volume of each suspension was approximately 200 μl). The cell suspensions from both tubes were then pooled, this provided enough cells for 4-8 electroporations. In a 1.5 ml eppendorf tube on ice, 60 μl of cells were mixed with 60 μl (~2.5 μg) of BsmBI digested vector DNA containing the genomic targeting construct. A No DNA Control was prepared for every transformation by mixing cells with Qiagen EB (elution buffer) instead of DNA. The cell-DNA mixtures were mixed with a vortexer and transferred to an ice-cold Bio-Rad 0.2 cm electrode gap Gene Pulser cuvette. The cells were then electroporated at 1.8 kV using a Bio-Rad *E. coli* Pulser, 1 ml of 1M D-Sorbitol was added and the electroporated cells were transferred to a 14 ml culture tube and 1 ml of 2×YPD broth was added. Cells were then rolled on a Rollerdrum for 1 hour at 37° C. before spreading 100 ul on 100 mm diameter plates containing YPD Agar+200 μg/ml nourseothricin. Plates were incubated for 2-4 days at 30° C. Large colonies (8-16) were individually streaked onto a YPD Agar plate to purify. A single colony from each streak was patched to a YPD agar stock plate and incubated overnight at 30° C.

7.1.3. Genomic DNA Preparation and PCR Test for Integration of Genomic Targeting Constructs at the Desired Location in *Candida tropicalis*

Between 5 and 30 nourseothricin-resistant isolates were each inoculated into 2 ml of YP Broth and rolled overnight at 30° C. on a Rollerdrum. Genomic DNA from a 0.5 ml sample of each culture was isolated using Zymo Research's YeaStar genomic DNA isolation kit according to the manufacturer's instructions, eluting the DNA in 120 μl of TE, pH 8.0.

For PCR tests, 2.5 μl of the resulting gDNA was used in a 50 ul PCR amplification reaction. As a control for each analysis, genomic DNA was prepared from the parental strain that was transformed with the targeting construct. Oligonucleotide primers for PCR analysis were chosen to lie within the targeting construct and/or in the genomic sequence surrounding the desired integration location, as shown for example in FIG. 10. The size of amplicons was used to determine which strain(s) possessed the desired genomic structure. PCR primer sequences and diagnostic amplicon sizes are described for many of the targeting constructs in Section 7. PCR reaction mixes were prepared containing 5 μl of 10×NEB Standard Taq Buffer, 2.5 μl of dNTP mix (6 mM of each of dATP, dCTP, dGTP, dTTP), 2.5 μl of oligonucleotide primer 1 (10 mM), 2.5 μl of oligonucleotide primer 2 (10 mM), 1 μl of NEB Taq DNA polymerase (5 U of enzyme), 2.5 μl of *Candida* gDNA and water to 50 μl. PCR reactions were subjected to the following temperatures for the times indicated to amplify the target DNA:

Step 1: 1.5 min @ 95° C.

Step 2: 30 sec @ 95° C.

Step 3: 30 sec @ 48° C. (or ~5° C. lower than the calculated Tm for the primers as appropriate)

Step 4: 1 min @ 72° C. (or 1 minute per 1 kb for predicted amplicon size)

Step 5: Go to step 2 a further 29 times

Step 6: 2 min @ 72° C.

Step 7: Hold @ 4° C.

Step 8: End

The amplicon sizes were determined by running 5-10 μl of the completed PCR reaction on a 1% Agarose-TBE gel.

7.1.4. Selection and Screen for Isolates Having Excised Targeting Constructs from the Genome of *Candida tropicalis*

Strains carrying a genomic targeting construct to be excised were inoculated from a YPD agar stock plate into 2 ml YP (YPD without dextrose) broth+2% maltose in a 14 ml culture tube. The culture tubes were rolled for ~48 hours at 30° C. on a rollerdrum. Growth with maltose induced production of Flp recombinase in the host strain from the integrated targeting construct. The Flp recombinase then acted at Frt sites located near the ends of the targeting construct (between the targeting sequences) to excise the sequences between the Frt sites, including the genes encoding Flp recombinase and conferring nourseothricin resistance. The culture was then diluted in serial 10-fold dilutions from 10-fold to 10,000-fold. Aliquots (100 μl) of 100, 1,000 and 10,000-fold dilutions were spread onto YPD agar plates.

Putative excisants were identified by replica-plating colonies on the YPD agar plates from the dilution series (the most useful plates for this purpose were those with 50-500 colonies) to a YPD agar+200 ug/ml nourseothricin plates and then to a YPD agar plate. Putative excisants were identified as colonies that grow on YPD agar, but not YPD agar+200 ug/ml nourseothricin following overnight incubation at room temperature. Putative excisants were streaked for single colonies to a YPD agar plate and incubated overnight at 30 C. A single isolate of each of the putative excisants is patched to a YPD agar stock plate and incubated overnight at 30° C.

Putative excisants were inoculated from the stock plate to 2 ml of YPD broth in a 14 ml culture tube and rolled overnight at 30° C. on a Rollerdrum. Genomic DNA was prepared from 0.5 ml of the overnight culture using the YeaStar Genomic DNA Isolation Kit from Zymo Research and eluted in 120 ul of TE, pH 8.0. Excision of the targeting construct was tested by PCR as described in 7.1.3.

7.2. Deletion of Cytochrome P450 Genes from *Candida*

The CYP52A type P450s are responsible for oxidation of a variety of compounds in several *Candida* species, including ω-hydroxylation of fatty acids (Craft et al., 2003, Appl Environ Microbiol: 69, 5983-91; Eschenfeldt et al., 2003, Appl Environ Microbiol: 69, 5992-9; Ohkuma et al., 1991, DNA Cell Biol: 10, 271-82; Zimmer et al., 1995, DNA Cell Biol: 14, 619-28; and Zimmer et al., 1996, Biochem Biophys Res Commun: 224, 784-9.) They have also been implicated in the further oxidation of these compounds. See Eschenfeldt et al., 2003, "Transformation of fatty acids catalyzed by cytochrome P450 monooxygenase enzymes of *Candida tropicalis*." Appl. Environ. Microbiol. 69: 5992-5999, which is hereby incorporated by reference herein. In some embodiments it is desirable to engineer one or more CYP52A type P450s in a strain of *Candida* in order to modify the activity or specificity of the P450 enzyme. In some such embodiments it is advantageous to eliminate the activities of one or more CYP52A type P450 enzymes endogenous to the strain. Reasons to delete endogenous P450 enzymes include more accurate determination of the activity and specificity of a P450 enzyme that is being engineered and elimination of P450 enzymes whose activities may interfere with synthesis of the desired product. Strains lacking one or more of their natural CYP52A P450s are within the scope of the disclosed technology. For example in order to obtain a strain of *Candida* species of yeast including *Candida tropicalis* for the production of oxidized compounds including ω-hydroxy fatty acids, one method is to reduce or eliminate CYP52A type P450s and other enzyme activities within the cell—that oxidise ω-hydroxy fatty acids to α,ω-diacids. It is then possible to re-introduce one CYP52A type P450 or other enzyme that performs the desired reaction, and to engineer it so that its activity is increased towards desired substrates and reduced towards undesired substrates. In one embodiment its activity for ω-hydroxylation of fatty acids is increased relative to its oxidation of ω-hydroxy fatty acids to α,ω-diacids, thereby favoring the production of ω-hydroxy fatty acids over α,ω-diacids.

7.2.1. Deletion of CYP52A17

The sequence of a gene encoding a cytochrome P450 in *Candida tropicalis*, CYP52A17 is given as SEQ ID NO: 2. This sequence was used to design a "pre-targeting" construct comprising two targeting sequences from the 5' and 3' end of the structural gene. The targeting sequences were separated by a sequence, given as SEQ ID NO: 12, comprising a NotI restriction site, a 20 base pair stuffer fragment and an XhoI restriction site. The targeting sequences were flanked by two BsmBI restriction sites, so that the final targeting construct can be linearized prior to transformation into *Candida tropicalis*. The sequence of the CYP52A17 pre-targeting construct is given as SEQ ID NO: 3. Not shown in SEQ ID NO: 3 but also present in the pre-targeting construct were a selective marker conferring resistance to kanamycin and a bacterial origin of replication, so that the pre-targeting construct can be grown and propagated in *E coli*. The sequence was synthesized using standard DNA synthesis techniques well known in the art.

A targeting construct for deletion of CYP52A17 from the *Candida tropicalis* genome was prepared by digesting the SAT-1 flipper (SEQ ID NO: 1) with restriction enzymes NotI and XhoI, and ligating it into the CYP52A17 pre-targeting construct (SEQ ID NO: 3) from which the 20 bp stuffer had been removed by digestion with restriction enzymes NotI and XhoI. The sequence of the resulting targeting construct for deletion of CYP52A17 is given as SEQ ID NO: 4. This sequence is a specific example of the construct shown generically in FIG. 4: it has nearly 300 base pairs of the genomic sequence of CYP52A17 at each end to serve as a targeting sequence; between the targeting sequences are two frt sites that are recognized by the flp recombinase; between the two frt sites are sequences encoding the flp recombinase and a protein conferring resistance to the antibiotic nourseothricin. Not shown in SEQ ID NO: 4 but also present in the targeting construct were a selective marker conferring resistance to kanamycin and a bacterial origin of replication, so that the targeting construct can be grown and propagated in *E coli*. The targeting sequences shown in SEQ ID NO: 4 also include a BsmBI restriction site at each end of the construct, so that the final targeting construct can be linearized and optionally separated from the bacterial antibiotic resistance marker and origin of replication prior to transformation into *Candida tropicalis*.

*Candida tropicalis* strain DP65 was prepared by integration of the construct shown as SEQ ID NO: 4 into the genome of strain DP1 (Table 3) at the site of the genomic sequence of the gene for CYP52A17. *Candida tropicalis* strain DP78 was prepared by excision of the targeting construct from the genome of strain DP65, thereby deleting the gene encoding CYP52A17. Integration and deletion of targeting sequence SEQ ID NO: 4, and analysis of integrants and excisants were performed as described in Section 7.1. Sequences of oligonucleotide primers for analysis of strains were:

```
17-IN-L3:
TGGCGGAAGTGCATGTGACACAACG       (SEQ ID NO: 77)

17-IN-R2:
GTGGTTGGTTTGTCTGAGTGGAGAG       (SEQ ID NO: 78)

SAT1-R:
TGGTACTGGTTCTCGGGAGCACAGG       (SEQ ID NO: 79)

SAT1-F:
CGCTAGACAAATTCTTCCAAAAATTTTAGA  (SEQ ID NO: 80)
```

For strain DP65 (integration of SEQ ID NO: 4), PCR with primers 17-IN-L3 and SAT1-R produces a 959 base pair amplicon; PCR with primers SAT1-F and 17-IN-R2 produces a 922 base pair amplicon. PCR with primers 17-IN-L3 and 17-IN-R2 from a strain carrying a wild type copy of CYP52A17 produces a 2,372 base pair amplicon. For strain DP78, with a deleted copy of CYP52A17, PCR with primers 17-IN-L3 and 17-IN-R2 produces a 1,478 base pair amplicon.

Deletion of a portion of the coding sequence of the gene for CYP52A17 will disrupt the function of the protein encoded by this gene in the *Candida* host cell.

7.2.2. Deletion of CYP52A13

The sequence of a gene encoding a cytochrome P450 in *Candida tropicalis*, CYP52A13 is given as SEQ ID NO: 5. This sequence was used to design a "pre-targeting" construct comprising two targeting sequences from the 5' and 3' end of the structural gene. The targeting sequences were separated by a sequence, given as SEQ ID NO: 12, comprising a NotI restriction site, a 20 base pair stuffer fragment and an XhoI restriction site. The targeting sequences were flanked by two BsmBI restriction sites, so that the final targeting construct can be linearized prior to transformation into *Candida tropicalis*. The sequence of the CYP52A13 pre-targeting construct is given as SEQ ID NO: 6. Not shown in SEQ ID NO: 6 but also present in the pre-targeting construct were a selective marker conferring resistance to kanamycin and a bacterial origin of replication, so that the pre-targeting construct can be grown and propagated in *E coli*. The sequence was synthesized using standard DNA synthesis techniques well known in the art.

A targeting construct for deletion of CYP52A13 from the *Candida tropicalis* genome was prepared by digesting the SAT-1 flipper (SEQ ID NO: 1) with restriction enzymes NotI and XhoI, and ligating it into the CYP52A13 pre-targeting construct (SEQ ID NO: 6) from which the 20 bp stuffer had been removed by digestion with restriction enzymes NotI and XhoI. The sequence of the resulting targeting construct for deletion of CYP52A13 is given as SEQ ID NO: 7. This sequence is a specific example of the construct shown generically in FIG. 4: it has nearly 300 base pair of the genomic sequence of CYP52A13 at each end to serve as a targeting sequence; between the targeting sequences are two frt sites that are recognized by the flp recombinase; between the two frt sites are sequences encoding the flp recombinase and a protein conferring resistance to the antibiotic nourseothricin. Not shown in SEQ ID NO: 7 but also present in the targeting construct were a selective marker conferring resistance to kanamycin and a bacterial origin of replication, so that the targeting construct can be grown and propagated in *E coli*. The targeting sequences shown in SEQ ID NO: 7 also include a BsmBI restriction site at each end of the construct, so that the final targeting construct can be linearized and optionally separated from the bacterial antibiotic resistance marker and origin of replication prior to transformation into *Candida tropicalis*.

*Candida tropicalis* strain DP107 was prepared by integration of the construct shown as SEQ ID NO: 7 into the genome of strain DP65 (Table 3) at the site of the genomic sequence of the gene for CYP52A13. *Candida tropicalis* strain DP113 was prepared by excision of the targeting construct from the genome of strain DP107, thereby deleting the gene encoding CYP52A13. Integration and deletion of targeting sequence SEQ ID NO: 7, and analysis of integrants and excisants were performed as described in Section 7.1.

Sequences of oligonucleotide primers for analysis of strains were:

```
13-IN-L2:
CATGTGGCCGCTGAATGTGGGGGCA          (SEQ ID NO: 81)

13-IN-R2:
GCCATTTTGTTTTTTTTACCCCTCTAACA      (SEQ ID NO: 82)

SAT1-R:                            (SEQ ID NO: 79)

SAT1-F:                            (SEQ ID NO: 80)
```

For strain DP107 (integration of SEQ ID NO: 7), PCR with primers 13-IN-L2 and SAT1-R produces an 874 base pair amplicon; PCR with primers SAT1-F and 13-IN-R2 produces an 879 base pair amplicon. PCR with primers 13-IN-L2 and 13-IN-R2 from a strain with wild type CYP52A13 produces a 2,259 base pair amplicon. For strain DP113 with a deleted version of CYP52A13 PCR with primers 13-IN-L2 and 13-IN-R2 produces a 1,350 base pair amplicon.

Deletion of a portion of the coding sequence of the gene for CYP52A13 will disrupt the function of the protein encoded by this gene in the *Candida* host cell.

7.2.3. Deletion of CYP52A18

The sequence of a gene encoding a cytochrome P450 in *Candida tropicalis*, CYP52A18 is given as SEQ ID NO: 8. This sequence was used to design a "pre-targeting" construct comprising two targeting sequences from the 5' and 3' end of the structural gene. The targeting sequences were separated by a sequence, given as SEQ ID NO: 12, comprising a NotI restriction site, a 20 base pair stuffer fragment and an XhoI restriction site. The targeting sequences were flanked by two BsmBI restriction sites, so that the final targeting construct can be linearized prior to transformation into *Candida tropicalis*. The sequence of the CYP52A18 pre-targeting construct is given as SEQ ID NO: 9. The CYP52A18 pre-targeting construct also contains a polylinker sequence (SEQ ID NO: 10) between the 5' targeting sequence and the NotI site. This polylinker sequence was placed to allow the insertion of sequences into the targeting construct to allow it to function as an insertion targeting construct of the form shown schematically in FIG. 7. Not shown in SEQ ID NO: 9 but also present in the pre-targeting construct were a selective marker conferring resistance to kanamycin and a bacterial origin of replication, so that the pre-targeting construct can be grown and propagated in *E coli*. The sequence was synthesized using standard DNA synthesis techniques well known in the art. A targeting construct for deletion of CYP52A18 from the *Candida tropicalis* genome was prepared by digesting the SAT-1 flipper (SEQ ID NO: 1) with restriction enzymes NotI and XhoI, and ligating it into the CYP52A18 pre-targeting construct (SEQ ID NO: 9) from which the 20 base pair stuffer had been removed by digestion with restriction enzymes NotI and XhoI. The sequence of the resulting targeting construct for deletion of CYP52A18 is given as SEQ ID NO: 11. This sequence is a specific example of the construct shown generically in FIG. 4: it has nearly 300 base pairs of the genomic sequence of CYP52A18 at each end to serve as a targeting sequence; between the targeting sequences are two frt sites that are recognized by the flp recombinase; between the two frt sites are sequences encoding the flp recombinase and a protein conferring resistance to the antibiotic nourseothricin. Not shown in SEQ ID NO: 11 but also present in the targeting construct were a selective marker conferring resistance to kanamycin and a bacterial origin of replication, so that the targeting construct can be grown and propagated in *E coli*. The targeting sequences shown in SEQ ID NO: 11 also include a BsmBI restriction site at each end of the construct, so that the final targeting construct can be linearized and optionally separated from the bacterial antibiotic resistance marker and origin of replication prior to transformation into *Candida tropicalis*.

*Candida tropicalis* strain DP140 was prepared by integration of the construct shown as SEQ ID NO: 11 into the genome of strain DP113 (Table 3) at the site of the genomic sequence of the gene for CYP52A18. *Candida tropicalis* strain DP142 was prepared by excision of the targeting construct from the genome of strain DP140, thereby deleting the gene encoding CYP52A18. Integration and deletion of targeting sequence SEQ ID NO: 11, and analysis of integrants and excisants were performed as described in Section 7.1.

Oligonucleotide primers for analysis of strains were:

```
18-IN-L2:
GGAAGTGCATGTGACACAATACCCT          (SEQ ID NO: 83)

18-IN-R2:
GGTGGTTTGTCTGAGTGAGAACGTTTAATT     (SEQ ID NO: 84)

SAT1-R:
TGGTACTGGTTCTCGGGAGCACAGG          (SEQ ID NO: 79)

SAT1-F:
GCTAGACAAATTCTTCCAAAAATTTTAGA      (SEQ ID NO: 80)
```

For strain DP140 (integration of SEQ ID NO: 11), PCR with primers 18-IN-L2 and SAT1-R produces a 676 base pair amplicon; PCR with primers SAT1-F and 18-IN-R2 produces a 605 base pair amplicon. PCR from a strain with a wild type version of CYP52A18 with primers 18-IN-L2 and 18-IN-R2 produces a 2,328 base pair amplicon. For strain DP142 with a deleted version of CYP52A18, PCR with primers 18-IN-L2 and 18-IN-R2 produces an 878 base pair amplicon.

Deletion of a portion of the coding sequence of the gene for CYP52A18 will disrupt the function of the protein encoded by this gene in the *Candida* host cell.

7.2.4. Deletion of CYP52A14

The sequence of a gene encoding a cytochrome P450 in *Candida tropicalis*, CYP52A14 is given as SEQ ID NO: 13. This sequence was used to design a "pre-targeting" construct comprising two targeting sequences from the 5' and 3' end of the structural gene. The targeting sequences were separated by a sequence, given as SEQ ID NO: 12, comprising a NotI restriction site, a 20 base pair stuffer fragment and an XhoI restriction site. The targeting sequences were flanked by two BsmBI restriction sites, so that the final targeting construct can be linearized prior to transformation into *Candida tropicalis*. The sequence of the CYP52A14 pre-targeting construct is given as SEQ ID NO: 14. The CYP52A14 pre-targeting construct also contains a polylinker sequence (SEQ ID NO: 10) between the 5' targeting sequence and the NotI site. This polylinker sequence was placed to allow the insertion of sequences into the targeting construct to allow it to function as an insertion targeting construct of the form shown schematically in FIG. 7. Not shown in SEQ ID NO: 14 but also present in the pre-targeting construct were a selective marker conferring resistance to kanamycin and a bacterial origin of replication, so that the pre-targeting construct can be grown and propagated in *E coli*. The sequence was synthesized using standard DNA synthesis techniques well known in the art.

A targeting construct for deletion of CYP52A14 from the *Candida tropicalis* genome was prepared by digesting the SAT-1 flipper (SEQ ID NO: 1) with restriction enzymes NotI and XhoI, and ligating it into the CYP52A14 pre-targeting construct (SEQ ID NO: 14) from which the 20 bp stuffer had been removed by digestion with restriction enzymes NotI and XhoI. The sequence of the resulting targeting construct for deletion of CYP52A14 is given as SEQ ID NO: 15. This sequence is a specific example of the construct shown generically in FIG. 4: it has nearly 300 base pairs of the genomic sequence of CYP52A14 at each end to serve as a targeting sequence; between the targeting sequences are two frt sites that are recognized by the flp recombinase; between the two frt sites are sequences encoding the flp recombinase and a protein conferring resistance to the antibiotic nourseothricin. Not shown in SEQ ID NO: 15 but also present in the targeting construct were a selective marker conferring resistance to kanamycin and a bacterial origin of replication, so that the targeting construct can be grown and propagated in *E coli*. The targeting sequences shown in SEQ ID NO: 15 also include a BsmBI restriction site at each end of the construct, so that the final targeting construct can be linearized and optionally separated from the bacterial antibiotic resistance marker and origin of replication prior to transformation into *Candida tropicalis*.

*Candida tropicalis* strain DP170 was prepared by integration of the construct shown as SEQ ID NO: 15 into the genome of strain DP142 (Table 3) at the site of the genomic sequence of the gene for CYP52A14. *Candida tropicalis* strain DP174 was prepared by excision of the targeting construct from the genome of strain DP170, thereby deleting the gene encoding CYP52A14. Integration and deletion of targeting sequence SEQ ID NO: 15, and analysis of integrants and excisants were performed as described in Section 7.1.

Oligonucleotide primers for analysis of strains were:

```
14-IN-L2:
GACGTAGCCGATGAATGTGGGGTGC          (SEQ ID NO: 85)
```

-continued

```
14-IN-R2:
TGCCATTTATTTTTATTACCCCTCTAAAT    (SEQ ID NO: 86)

SAT1-R:                          (SEQ ID NO: 79)

SAT1-F:                          (SEQ ID NO: 80)
```

For strain DP170 (integration of SEQ ID NO: 15), PCR with primers 14-IN-L2 and SAT1-R produces a 664 base pair amplicon; PCR with primers SAT1-F and 14-IN-R2 produces a 609 base pair amplicon. For a strain with a wild type version of CYP52A14, PCR with primers 14-IN-L2 and 14-IN-R2 produces a 2,234 base pair amplicon. For strain DP174 with a deleted version of CYP52A14, PCR with primers 14-IN-L2 and 14-IN-R2 produces an 870 base pair amplicon.

Deletion of a portion of the coding sequence of the gene for CYP52A14 will disrupt the function of the protein encoded by this gene in the *Candida* host cell.

7.3. Deletion of Fatty Alcohol Oxidase Genes from *Candida*

At least one enzyme capable of oxidizing ω-hydroxy fatty acids is present in *Candida tropicalis* in addition to the cytochrome P450 genes encoding CYP52A13, CYP52A14, CYP52A17 and CYP52A18. Oxidation of energy rich molecules reduces their energy content. For the production of incompletely oxidized compounds—including ω-hydroxy fatty acids, it is advantageous to reduce or eliminate the further oxidation of incompletely oxidized compounds—such as ω-hydroxy fatty acids. Under one aspect, this can be achieved by deleting the genes encoding the oxidizing enzymes from the *Candida* genome Candidate genes for this activity include fatty alcohol oxidase and dehydrogenases as shown in FIG. 14. One class of enzymes known to oxidize incompletely oxidised compounds including hydroxy fatty acids are the fatty alcohol oxidases.

7.3.1. Deletion of FAO1

The sequence of a gene encoding a fatty alcohol oxidase in *Candida tropicalis*, FAO1 is given as SEQ ID NO: 16. This sequence was used to design a "pre-targeting" construct comprising two targeting sequences from the 5' and 3' end of the structural gene. The targeting sequences were separated by a sequence, given as SEQ ID NO: 12, comprising a NotI restriction site, a 20 base pair stuffer fragment and an XhoI restriction site. The targeting sequences were flanked by two BsmBI restriction sites, so that the final targeting construct can be linearized prior to transformation into *Candida tropicalis*. The sequence of the FAO1 pre-targeting construct is given as SEQ ID NO: 17. The FAO1 pre-targeting construct also contains a polylinker sequence (SEQ ID NO: 10) between the 5' targeting sequence and the NotI site. This polylinker sequence was placed to allow the insertion of sequences into the targeting construct to allow it to function as an insertion targeting construct of the form shown schematically in FIG. 7. Not shown in SEQ ID NO: 17 but also present in the pre-targeting construct were a selective marker conferring resistance to kanamycin and a bacterial origin of replication, so that the pre-targeting construct can be grown and propagated in *E coli*. The sequence was synthesized using standard DNA synthesis techniques well known in the art.

A targeting construct for deletion of FAO1 from the *Candida tropicalis* genome was prepared by digesting the SAT-1 flipper (SEQ ID NO: 1) with restriction enzymes NotI and XhoI, and ligating it into the FAO1 pre-targeting construct (SEQ ID NO: 17) from which the 20 base pair stuffer had been removed by digestion with restriction enzymes NotI and XhoI. The sequence of the resulting targeting construct for deletion of FAO1 is given as SEQ ID NO: 18. This sequence is a specific example of the construct shown generically in FIG. 4: it has nearly 300 base pairs of the genomic sequence of FAO1 at the 5' end and 220 base pairs of the genomic sequence of FAO1 at the 3' end to serve as a targeting sequence; between the targeting sequences are two frt sites that are recognized by the flp recombinase; between the two frt sites are sequences encoding the flp recombinase and a protein conferring resistance to the antibiotic nourseothricin. Not shown in SEQ ID NO: 18 but also present in the targeting construct were a selective marker conferring resistance to kanamycin and a bacterial origin of replication, so that the targeting construct can be grown and propagated in *E coli*. The targeting sequences shown in SEQ ID NO: 18 also include a BsmBI restriction site at each end of the construct, so that the final targeting construct can be linearized and optionally separated from the bacterial antibiotic resistance marker and origin of replication prior to transformation into *Candida tropicalis*.

*Candida tropicalis* strain DP182 was prepared by integration of the construct shown as SEQ ID NO: 18 into the genome of strain DP174 (Table 3) at the site of the genomic sequence of the gene for FAO1. *Candida tropicalis* strain DP186 was prepared by excision of the targeting construct from the genome of strain DP182, thereby deleting the gene encoding FAO1. Integration and deletion of targeting sequence SEQ ID NO: 18, and analysis of integrants and excisants were performed as described in Section 7.1.

Sequences of oligonucleotide primers for analysis of strains were:

```
FAO1-IN-L:
ATTGGCGTCGTGGCATTGGCGGCTC          (SEQ ID NO: 87)

FAO1-IN-R:
TGGGCGGAATCAAGTGGCTT               (SEQ ID NO: 88)

SAT1-R:
TGGTACTGGTTCTCGGGAGCACAGG          (SEQ ID NO: 79)

SAT1-F:
CGCTAGACAAATTCTTCCAAAAATTTTAGA     (SEQ ID NO: 80)
```

For strain DP182 (integration of SEQ ID NO: 18), PCR with primers FAO1-IN-L and SAT1-R produces a 624 base pair amplicon; PCR with primers SAT1-F and FAO1-IN-R produces a 478 base pair amplicon. For a strain with a wild type copy of FAO1, PCR with primers FAO1-IN-L and FAO1-IN-R produces a 2,709 base pair amplicon. For strain DP186 with a deleted copy of FAO1, PCR with primers FAO1-IN-L and FAO1-IN-R produces a 699 base pair amplicon.

Deletion of a portion of the coding sequence of the gene for FAO1A will disrupt the function of the protein encoded by this gene in the *Candida* host cell.

7.3.2. Deletion of FAO1B

No sequence had been reported for a second allele for FAO1 (FAO1B) at the time of this work. To identify the allele (BAO1B) we used PCR amplification primers and sequencing primers designed to anneal to the known sequenced allele of FAO1. The primers used were:

```
FAO1_F1;  CGTCGACACCCTTATGTTAT    (SEQ ID NO: 89)

FAO1_F2;  CGTTGACTCCTATCAAGGACA   (SEQ ID NO: 90)
```

-continued

```
FAO1_R1;  GGTCTTCTCTTCCTGGATAATG  (SEQ ID NO: 91)

FAO1_F3;  CCAGCAGTTGTTTGTTCTTG    (SEQ ID NO: 92)

FAO1_R2;  AATCCTGTGCTTTGTCGTAGGC  (SEQ ID NO: 93)

FAO1_F4;  TCCTTAACAAGAAGGGCATCG   (SEQ ID NO: 94)

FAO1_R3;  TTCTTGAATCCGGAGTTGAC    (SEQ ID NO: 95)

FAO1_F5;  TCTTAGTCGTGATACCACCA    (SEQ ID NO: 96)

FAO1_R4;  CTAAGGATTCTCTTGGCACC    (SEQ ID NO: 97)

FAO1_R5;  GTGACCATAGGATTAGCACC    (SEQ ID NO: 98)
```

Genomic DNA was prepared from strains DP1 (which has FAO1) and DP186 (which is deleted for FAO1) as described in section 7.1.3. The FAO genes were amplified from genomic DNA by PCR using oligonucleotide primers FAO1_F1 and FAO1_R5. Genomic DNA from both strains yielded an amplicon of approximately 2 kilobases. Both amplicons were directly sequenced using the ten oligonucleotide primers listed above. The amplicon from DP1 gave sequence where there were occasionally two bases that appeared to be equally represented. The amplicon from DP186 had no such ambiguous bases but its sequence was slightly different (~95% identical) from the reported sequence of FAO1. We concluded that the sequence corresponded to a second allele of FAO1, which we refer to as FAO1B. The sequence of FAO1B is given as SEQ ID NO: 19.

This sequence was used to design a "pre-targeting" construct comprising two targeting sequences from the 5' and 3' end of the structural gene. The targeting sequences were separated by a sequence, given as SEQ ID NO: 12, comprising a NotI restriction site, a 20 bp stuffer fragment and an XhoI restriction site. The targeting sequences were flanked by two BsmBI restriction sites, so that the final targeting construct can be linearized prior to transformation into *Candida tropicalis*. The sequence of the FAO pre-targeting construct is given as SEQ ID NO: 20.

A targeting construct for deletion of FAO1 from the *Candida tropicalis* genome was prepared by digesting the SAT-1 flipper (SEQ ID NO: 1) with restriction enzymes NotI and XhoI, and ligating it into the FAO pre-targeting construct (SEQ ID NO: 20) that had also been digested with restriction enzymes NotI and XhoI. the FAO1B pre-targeting construct (SEQ ID NO: 20) was not cloned or propagated in a bacterial host, so digestion with restriction enzymes NotI and XhoI produced two fragments which were then ligated with the digested SAT-1 flipper to produce a targeting construct for deletion of FAO1B, given as SEQ ID NO: 21. This sequence is a specific example of the construct shown generically in FIG. 4: it has nearly 300 base pairs of the genomic sequence of FAO1B at the 5' end and 220 base pairs of the genomic sequence of FAO1B at the 3' end to serve as a targeting sequence; between the targeting sequences are two frt sites that are recognized by the flp recombinase; between the two frt sites are sequences encoding the flp recombinase and a protein conferring resistance to the antibiotic nourseothricin.

*Candida tropicalis* strain DP238 was prepared by integration of the construct shown as SEQ ID NO: 21 into the genome of strain DP186 (Table 3) at the site of the genomic sequence of the gene for FAO1B. *Candida tropicalis* strain DP240 was prepared by excision of the targeting construct from the genome of strain DP238, thereby deleting the gene encoding FAO1B. Integration and deletion of targeting sequence SEQ ID NO: 21, and analysis of integrants and excisants were performed as described in Section 7.1. Sequences of oligonucleotide primers for analysis of strains were, FAO1_F1 (SEQ ID NO: 89), FAO1_R5 (SEQ ID NO: 98), SAT1-R (SEQ ID NO: 79), SAT1-F (SEQ ID NO: 80).

For strain DP182 (integration of SEQ ID NO: 18), PCR with primers FAO1_F1 and SAT1-R produces a 558 base pair amplicon; PCR with primers SAT1-F and FAO1_R5 produces a 557 base pair amplicon. For a strain with a wild type copy of FAO1B, PCR with primers FAO1_F1 and FAO1_R5 produces a 2,007 base pair amplicon. For strain DP186, with a deleted copy of FAO1B, PCR with primers FAO1_F1 and FAO1_R5 produces a 711 base pair amplicon.

Deletion of a portion of the coding sequence of the gene for FAO1B will disrupt the function of the protein encoded by this gene in the *Candida* host cell.

7.3.3. Deletion of FAO2A

The sequence of a gene encoding a fatty alcohol oxidase in *Candida tropicalis*, FAO2A is given as SEQ ID NO: 22. This sequence was used to design a "pre-targeting" construct comprising two targeting sequences from the 5' and 3' end of the structural gene. The targeting sequences were separated by a sequence, given as SEQ ID NO: 12, comprising a NotI restriction site, a 20 bp stuffer fragment and an XhoI restriction site. The targeting sequences were flanked by two BsmBI restriction sites, so that the final targeting construct can be linearized prior to transformation into *Candida tropicalis*. The sequence of the FAO2A pre-targeting construct is given as SEQ ID NO: 23. Not shown in SEQ ID NO: 23 but also present in the pre-targeting construct were a selective marker conferring resistance to kanamycin and a bacterial origin of replication, so that the pre-targeting construct can be grown and propagated in *E coli*. The sequence was synthesized using standard DNA synthesis techniques well known in the art.

A targeting construct for deletion of FAO2A from the *Candida tropicalis* genome was prepared by digesting the SAT-1 flipper (SEQ ID NO: 1) with restriction enzymes NotI and XhoI, and ligating it into the FAO2A pre-targeting construct (SEQ ID NO: 23) from which the 20 bp stuffer had been removed by digestion with restriction enzymes NotI and XhoI. The sequence of the resulting targeting construct for deletion of FAO2A is given as SEQ ID NO: 24. This sequence is a specific example of the construct shown generically in FIG. 4: it has nearly 300 base pair of the genomic sequence of FAO2A at the 5' and 3' ends of the structural gene to serve as a targeting sequence; between the targeting sequences are two frt sites that are recognized by the flp recombinase; between the two frt sites are sequences encoding the flp recombinase and a protein conferring resistance to the antibiotic nourseothricin. Not shown in SEQ ID NO: 24 but also present in the targeting construct were a selective marker conferring resistance to kanamycin and a bacterial origin of replication, so that the targeting construct can be grown and propagated in *E coli*. The targeting sequences shown in SEQ ID NO: 24 also include a BsmBI restriction site at each end of the construct, so that the final targeting construct can be linearized and optionally separated from the bacterial antibiotic resistance marker and origin of replication prior to transformation into *Candida tropicalis.*

*Candida tropicalis* strain DP255 was prepared by integration of the construct shown as SEQ ID NO: 24 into the genome of strain DP240 (Table 3) at the site of the genomic sequence of the gene for FAO2A. *Candida tropicalis* strain DP256 was prepared by excision of the targeting construct from the genome of strain DP255, thereby deleting most of the coding portion of the gene encoding FAO2A. Integration and deletion of targeting sequence SEQ ID NO: 24, and analysis of integrants and excisants were performed as described in Section 7.1. Sequences of oligonucleotide primers for analysis of strains were:

```
FAO2A-IN-L:
CTTTTCTGATTCTTGATTTTCCCTTTTCAT    (SEQ ID NO: 99)

FAO2A-IN-R:
ATACATCTAGTATATAAGTGTCGTATTTCC    (SEQ ID NO: 100)

SAT1-R:                           (SEQ ID NO: 79)

SAT1-F:                           (SEQ ID NO: 80)
```

For strain DP255 (integration of SEQ ID NO: 24), PCR with primers FAO2A-IN-L and SAT1-R produces a 581 base pair amplicon; PCR with primers SAT1-F and FAO2A-IN-R produces a 569 base pair amplicon. For a strain with a wild type copy of FAO2A, PCR with primers FAO2A-IN-L and FAO2A-IN-R produces a 2,199 base pair amplicon. For strain DP186 with a deleted copy of FAO2A, PCR with primers FAO2A-IN-L and FAO2A-IN-R produces a 747 base pair amplicon.

Deletion of a portion of the coding sequence of the gene for FAO2A will disrupt the function of the protein encoded by this gene in the *Candida* host cell.

7.3.4. Deletion of FAO2B

The sequence of a gene encoding a fatty alcohol oxidase in *Candida tropicalis*, FAO2B is given as SEQ ID NO: 25. This sequence was used to design a "pre-targeting" construct comprising two targeting sequences from the 5' and 3' end of the structural gene. The targeting sequences were separated by a sequence, given as SEQ ID NO: 12, comprising a NotI restriction site, a 20 base pair stuffer fragment and an XhoI restriction site. The targeting sequences were flanked by two BsmBI restriction sites, so that the final targeting construct can be linearized prior to transformation into *Candida tropicalis*. The sequence of the FAO2B pre-targeting construct is given as SEQ ID NO: 26. Not shown in SEQ ID NO: 26 but also present in the pre-targeting construct were a selective marker conferring resistance to kanamycin and a bacterial origin of replication, so that the pre-targeting construct can be grown and propagated in *E coli*. The sequence was synthesized using standard DNA synthesis techniques well known in the art.

A targeting construct for deletion of FAO2B from the *Candida tropicalis* genome was prepared by digesting the SAT-1 flipper (SEQ ID NO: 1) with restriction enzymes NotI and XhoI, and ligating it into the FAO2B pre-targeting construct (SEQ ID NO: 26) from which the 20 base pair stuffer had been removed by digestion with restriction enzymes NotI and XhoI. The sequence of the resulting targeting construct for deletion of FAO2B is given as SEQ ID NO: 27. This sequence is a specific example of the construct shown generically in FIG. 4: it has nearly 300 base pairs of the genomic sequence of FAO2B at the 5' and 3' ends of the structural gene to serve as a targeting sequence; between the targeting sequences are two frt sites that are recognized by the flp recombinase; between the two frt sites are sequences encoding the flp recombinase and a protein conferring resistance to the antibiotic nourseothricin. Not shown in SEQ ID NO: 27 but also present in the targeting construct were a selective marker conferring resistance to kanamycin and a bacterial origin of replication, so that the targeting construct can be grown and propagated in *E coli*. The targeting sequences shown in SEQ ID NO: 27 also includes a BsmBI restriction site at each end of the construct, so that the final targeting construct can be linearized and optionally separated from the bacterial antibiotic resistance marker and origin of replication prior to transformation into *Candida tropicalis.*

*Candida tropicalis* strain DP259 was prepared by integration of the construct shown as SEQ ID NO: 27 into the genome of strain DP256 (Table 3) at the site of the genomic sequence of the gene for FAO2BA. *Candida tropicalis* strain DP261 was prepared by excision of the targeting construct from the genome of strain DP259, thereby deleting most of the coding region of the gene encoding FAO2B. Integration and deletion of targeting sequence SEQ ID NO: 27, and analysis of integrants and excisants were performed as described in Section 7.1.

Sequences of oligonucleotide primers for analysis of strains were:

```
FAO2B-IN-L:
TGCTTTTCTGATTCTTGATCATCCCCTTAG    (SEQ ID NO: 101)

FAO2B-IN-R:
ATACATCTAGTATATAAGTGTCGTATTTCT    (SEQ ID NO: 102)

SAT1-R:                           (SEQ ID NO: 79)

SAT1-F:                           (SEQ ID NO: 80)
```

For strain DP259 (integration of SEQ ID NO: 27), PCR with primers FAO2B-IN-L and SAT1-R produces a 551 base pair amplicon; PCR with primers SAT1-F and FAO2B-IN-R produces a 571 base pair amplicon. For a strain with a wild type copy of FAO2B, PCR with primers FAO2B-IN-L and FAO2B-IN-R produces a 2,198 base pair amplicon. For strain DP186 with a deleted copy of FAO2B, PCR with primers FAO2B-IN-L and FAO2B-IN-R produces a 719 base pair amplicon.

Deletion of a portion of the coding sequence of the gene for FAO2B will disrupt the function of the protein encoded by this gene in the *Candida* host cell.

7.4. Deletion of More Cytochrome P450 Genes from *Candida*

At least one enzyme capable of oxidizing ω-hydroxy fatty acids is present in *Candida tropicalis* in addition to the cytochrome P450 genes encoding CYP52A13, CYP52A14, CYP52A17 and CYP52A18 and fatty alcohol oxidase genes FAO1, FAO1B, FAO2A and FAO2B. Oxidation of energy rich molecules reduces their energy content. For the production of incompletely oxidized compounds—including ω-hydroxy fatty acids, it is advantageous to reduce or eliminate the further oxidation of incompletely oxidized compounds ω-hydroxy fatty acids. Under one aspect, this can be achieved by deleting the genes encoding the oxidizing enzymes from the *Candida* genome. One class of enzymes known to oxidize incompletely oxidised compounds are the cytochrome P450s.

The CYP52A type P450s are responsible for ω-hydroxylation of fatty acids in several *Candida* species (Craft et al., 2003, Appl Environ Microbiol: 69, 5983-91; Eschenfeldt et al., 2003, Appl Environ Microbiol: 69, 5992-9; Ohkuma et al., 1991, DNA Cell Biol: 10, 271-82; Zimmer et al., 1995, DNA Cell Biol: 14, 619-28; Zimmer et al., 1996, Biochem Biophys Res Commun: 224, 784-9.) They have also been implicated in the further oxidation of these ω-hydroxy fatty acids to α,ω-diacids. See Eschenfeldt, et al., 2003, Appli. Environ. Microbiol. 69: 5992-5999, which is hereby incorporated by reference herein. Another CYP52A type P450 whose expression is induced by fatty acids is CYP52A12.

7.4.1. Deletion of CYP52A12

The sequence of a gene encoding a cytochrome P450 in *Candida tropicalis*, CYP52A12 is given as SEQ ID NO: 28. This sequence was used to design a "pre-targeting" construct comprising two targeting sequences from the 5' and 3' end of the structural gene. The targeting sequences were separated by a sequence, given as SEQ ID NO: 12, comprising a NotI restriction site, a 20 base pair stuffer fragment and a XhoI restriction site. The targeting sequences were flanked by two BsmBI restriction sites, so that the final targeting construct can be linearized prior to transformation into *Candida tropicalis*. The sequence of the CYP52A12 pre-targeting construct is given as SEQ ID NO: 29. Not shown in SEQ ID NO: 29 but also present in the pre-targeting construct were a selective marker conferring resistance to kanamycin and a bacterial origin of replication, so that the pre-targeting construct can be grown and propagated in *E coli*. The sequence was synthesized using standard DNA synthesis techniques well known in the art.

A targeting construct for deletion of CYP52A12 from the *Candida tropicalis* genome was prepared by digesting the SAT-1 flipper (SEQ ID NO: 1) with restriction enzymes NotI and XhoI, and ligating it into the CYP52A12 pre-targeting construct (SEQ ID NO: 29) from which the 20 base pair stuffer had been removed by digestion with restriction enzymes NotI and XhoI. The sequence of the resulting targeting construct for deletion of CYP52A12 is given as SEQ ID NO: 30. This sequence is a specific example of the construct shown generically in FIG. 4: it has nearly 300 base pairs of the genomic sequence of CYP52A12 at each end to serve as a targeting sequence; between the targeting sequences are two frt sites that are recognized by the flp recombinase; between the two frt sites are sequences encoding the flp recombinase and a protein conferring resistance to the antibiotic nourseothricin. Not shown in SEQ ID NO: 30 but also present in the targeting construct were a selective marker conferring resistance to kanamycin and a bacterial origin of replication, so that the targeting construct can be grown and propagated in *E coli*. The targeting sequences shown in SEQ ID NO: 30 also include a BsmBI restriction site at each end of the construct, so that the final targeting construct can be linearized and optionally separated from the bacterial antibiotic resistance marker and origin of replication prior to transformation into *Candida tropicalis*.

*Candida tropicalis* strain DP268 was prepared by integration of the construct shown as SEQ ID NO: 30 into the genome of strain DP261 (Table 3) at the site of the genomic sequence of the gene for CYP52A12. *Candida tropicalis* strain DP272 was prepared by excision of the targeting construct from the genome of strain DP268, thereby deleting the gene encoding CYP52A12. Integration and deletion of targeting sequence SEQ ID NO: 30, and analysis of integrants and excisants were performed as described in Section 7.1.

Sequences of oligonucleotide primers for analysis of strains were:

```
12-IN-L:
CGCCAGTCTTTCCTGATTGGGCAAG    (SEQ ID NO: 103)

12-IN-R2:
GGACGTTGTCGAGTAGAGGGATGTG    (SEQ ID NO: 104)

SAT1-R:                      (SEQ ID NO: 79)

SAT1-F:                      (SEQ ID NO: 80)
```

For strain DP268 (integration of SEQ ID NO: 30), PCR with primers 12-IN-L and SAT1-R produces a 596 base pair amplicon; PCR with primers SAT1-F and 12-IN-R2 produces a 650 base pair amplicon. For a strain with a wild type copy of CYP52A12, PCR with primers 12-IN-L and 12-IN-R2 produces a 2,348 base pair amplicon. For strain DP272 with a deleted copy of CYP52A12, PCR with primers 12-IN-L and 12-IN-R2 produces a 843 base pair amplicon.

Deletion of a portion of the coding sequence of the gene for CYP52A12 will disrupt the function of the protein encoded by this gene in the *Candida* host cell.

7.4.2. Deletion of CYP52A12B

No sequence had been reported for a second allele for CYP52A12 at the time of this work. We reasoned that in a diploid organisms a second allele existed (CYP52A17 and CYP52A18 are an allelic pair and CYP52A13 and CYP52A14 are an allelic pair). To delete the second allele we synthesized a deletion construct based on the CYP52A12 sequence (SEQ ID NO: 28), but designed it so that the targeting sequences were homologous to regions of the CYP52A12 gene that are missing because they have been deleted in strain DP272. First we constructed a "pre-targeting" construct comprising two targeting sequences from near the 5' and 3' ends of the structural gene, but internal to the two sequences used in the design of the targeting construct for the deletion of CYP52A12. The targeting sequences were separated by a sequence, given as SEQ ID NO: 12, comprising a NotI restriction site, a 20 base pair stuffer fragment and a XhoI restriction site. The targeting sequences were flanked by two BsmBI restriction sites, so that the final targeting construct can be linearized prior to transformation into *Candida tropicalis*. The sequence of the CYP52A12B pre-targeting construct is given as SEQ ID NO: 31. Not shown in SEQ ID NO: 31 but also present in the pre-targeting construct were a selective marker conferring resistance to kanamycin and a bacterial origin of replication, so that the pre-targeting construct can be grown and propagated in *E coli*. The sequence was synthesized using standard DNA synthesis techniques well known in the art.

A targeting construct for deletion of CYP52A12B from the *Candida tropicalis* genome was prepared by digesting the SAT-1 flipper (SEQ ID NO: 1) with restriction enzymes NotI and XhoI, and ligating it into the CYP52A12B pre-targeting construct (SEQ ID NO: 31) from which the 20 base pair stuffer had been removed by digestion with restriction enzymes NotI and XhoI. The sequence of the resulting targeting construct for deletion of CYP52A12B is given as SEQ ID NO: 32. This sequence is a specific example of the construct shown generically in FIG. 4: it has nearly 300 base pairs of the genomic sequence of CYP52A12 at each end to serve as a targeting sequence; between the targeting sequences are two frt sites that are recognized by the flp recombinase; between the two frt sites are sequences encoding the flp recombinase and a protein conferring resistance to the antibiotic nourseothricin. Not shown in SEQ ID NO: 32 but also present in the targeting construct were a selective marker conferring resistance to kanamycin and a bacterial origin of replication, so that the targeting construct can be grown and propagated in *E coli*. The targeting sequences shown in SEQ ID NO: 32 also include a BsmBI restriction site at each end of the construct, so that the final targeting construct can be linearized and optionally separated from the bacterial antibiotic resistance marker and origin of replication prior to transformation into *Candida tropicalis*.

*Candida tropicalis* strain DP282 was prepared by integration of the construct shown as SEQ ID NO: 32 into the genome of strain DP272 (Table 3) at the site of the genomic sequence of the gene for CYP52A12B. *Candida tropicalis* strain DP284 was prepared by excision of the targeting construct from the genome of strain DP282, thereby deleting a portion of the coding region of the gene encoding CYP52A12B. Integration and deletion of targeting sequence SEQ ID NO: 32, and analysis of integrants and excisants were performed as described in Section 7.1.

Sequences of oligonucleotide primers for analysis of strains were:

```
12-F1:     CTGTACTTCCGTACTTGACC  (SEQ ID NO: 105)
12-R1:     GAGACCTGGATCAGATGAGA  (SEQ ID NO: 106)
SAT1-R:                          (SEQ ID NO: 79)
SAT1-F:                          (SEQ ID NO: 80)
```

Oligonucleotides 12-F1 and 12-R1 are designed to anneal to a part of the genome that is missing in strains with deletions in CYP52A12. In such strains they will thus only be able to anneal to and amplify from the second allele CYP52A12B. For strain DP282 (integration of SEQ ID NO: 32), PCR with primers 12-F1 and SAT1-R produces a 978 base pair amplicon; PCR with primers SAT1-F and 12-R1 produces a 947 base pair amplicon. PCR from a strain with a wild type copy of CYP52A12B with primers 12-F1 and 12-R1 produces a 1,478 base pair amplicon. For strain DP272 with a deleted copy of CYP52A12B, PCR with primers 12-F1 and 12-R1 produces a 505 base pair amplicon.

Deletion of a portion of the coding sequence of the gene for CYP52A12B will disrupt the function of the protein encoded by this gene in the *Candida* host cell.

7.5. Deletion of Alcohol Dehydrogenase Genes from *Candida*

At least one enzyme capable of oxidizing ω-hydroxy fatty acids is present in *Candida tropicalis* in addition to the cytochrome P450 genes encoding CYP52A13, CYP52A14, CYP52A17, CYP52A18, CYP52A12, CYP52A12B and the fatty alcohol oxidase genes FAO1, FAO1B, FAO2A and FAO2B. Oxidation of energy rich molecules reduces their energy content. For the production of incompletely oxidized compounds including ω-hydroxy fatty acids, it is advantageous to reduce or eliminate the further oxidation of incompletely oxidized compounds, including for example ω-hydroxy fatty acids. Under one aspect, this can be achieved by deleting the genes encoding the oxidizing enzymes from the *Candida* genome. One class of enzymes known to oxidize alcohols is alcohol dehydrogenases.

7.5.1. Identification of *Candida tropicalis* Alcohol Dehydrogenases

The sequences of four alcohol dehydrogenase genes were obtained from the *Candida* Genome Database in the Department of Genetics at the School of Medicine, Stanford University, Palo Alto, Calif. The sequences of these genes are given as SEQ ID NO: 33, SEQ ID NO: 34, SEQ ID NO: 35 and SEQ ID NO: 36. These sequences were aligned and two degenerate oligonucleotide primers were designed, whose sequences are given as SEQ ID NO: 37 and SEQ ID NO: 38. These two primers were used to PCR amplify from genomic DNA from *Candida tropicalis* strain DP1. The resulting amplicon of ~1,000 base pairs was cloned and 96 independent transformants were picked, plasmid prepared and sequenced using two primers with annealing sites located in the vector reading into the cloning site and two primers designed to anneal to highly conserved sequences within the *Candida albicans* alcohol dehydrogenase sequences:

```
ADH-F:    GTTTACAAAGCCTTAAAGACT   (SEQ ID NO: 107)
ADH-R:    TTGAACGGCCAAAGAACCTAA.  (SEQ ID NO: 108)
```

Five different sequences were obtained by sequencing the 96 independent clones, called Ct_ADH-A4, Ct_ADH-A10, Ct_ADH-B2, Ct_ADH-B4 and Ct_ADH-B11. These sequences are provided as SEQ ID NO: 39, SEQ ID NO: 40, SEQ ID NO: 41, SEQ ID NO: 42 and SEQ ID NO: 43 respectively. In silico translation of Ct_ADH-B2 (SEQ ID NO: 41) yielded an amino acid sequence with multiple in-frame stop codons, so it is almost certainly a pseudogene and does not encode a functional protein. The other four sequences all encode protein sequences without stop codons.

Amino acid sequences of the partial genes are predicted and provided: SEQ ID NO:155 (ADH-A4), SEQ ID NO:154 (ADH-B4), SEQ ID NO:152 (ADH-A10), SEQ ID NO:153 (ADH-A10B) and SEQ ID NO:151 (ADH-B11).

In some embodiments an alcohol dehydrogenase gene is identified in the genome of a yeast of the genus *Candida* by comparison with the nucleotide sequence of an alcohol dehydrogenase from *Candida tropicalis* and is identified as an alcohol dehydrogenase if (i) it comprises an open reading frame encoding a polypeptide at least 275 amino acids long or at least 300 amino acids long and (ii) the gene is at least 65% identical, at least 70% identical, at least 75% identical, at least 80% identical, at least 85% identical, at least 90% identical, at least 95% identical, or at least 98% identical for a stretch of at least 80, at least 85, at least 90, at least 95, at least 100, at least 105, at least 110, at least 115, or at least 120 contiguous nucleotides of the coding sequence of a *Candida tropicalis* gene selected from the group consisting of ADH-A4 (SEQ ID NO: 39), ADH-B4 (SEQ ID NO: 42), ADH-A10 (SEQ ID NO: 40), ADH-A10B (SEQ ID NO: 56), and ADH-B11 (SEQ ID NO: 43).

The sequence relationships of these protein sequences are shown in a phylogenetic tree in FIG. 17. Ct_ADH-A4 (encoded by SEQ ID NO: 39) is most homologous to *Candida albicans* ADH1A and Ct_ADH-B4 (encoded by SEQ ID NO: 42) is most homologous to *Candida albicans* ADH2A.

An alignment, using ClustalW, of the amino acid sequences of alcohol dehydrogenase proteins predicted from the sequences of genes from *Candida albicans* and *Candida tropicalis* is shown in FIG. 3. The genes from *Candida tropicalis* were isolated as partial genes by PCR with degenerate primers, so the nucleic acid sequences obtained for the genes represent only a partial sequence of the gene, and the predicted amino acid sequences of the encoded proteins represent only a partial sequence of the protein. A consensus is indicated underneath the aligned amino acid sequences of FIG. 3, with a * indicating that all 4 *Candida albicans* alcohol dehydrogenase sequences and all 4 *Candida tropicalis* alcohol dehydrogenase sequences are completely identical at those residues. BLAST searching of protein sequences in Genbank with highly conserved peptide regions within the alcohol dehydrogenases yields results that identify uniquely yeast alcohol dehydrogenases.

In some embodiments an alcohol dehydrogenase gene is identified in the genome of a yeast of the genus *Candida* by comparison of the amino acid sequence of its predicted translation product with the predicted polypeptide sequence of an alcohol dehydrogenase from *Candida tropicalis* and is identified as an alcohol dehydrogenase if it comprises a first peptide sequence VKYSGVCH (SEQ ID NO: 156) or VKYSGVCHxxxxxWKGDW (SEQ ID NO: 162) or VKYSGVCHxxxxxWKGDWxxxxKLPxVGGHEGAGVVV (SEQ ID NO: 163) or VGGHEGAGVVV (SEQ ID NO: 157).

In some embodiments an alcohol dehydrogenase gene is identified in the genome of a yeast of the genus *Candida* by comparison of the amino acid sequence of its predicted translation product with the predicted polypeptide sequence of an alcohol dehydrogenase from *Candida tropicalis* and is identified as an alcohol dehydrogenase if it comprises a second peptide sequence QYATADAVQAA (SEQ ID NO: 158) or SGYxHDGxFxQYATADAVQAA (SEQ ID NO: 164) or GAEPNCxxADxSGYxHDGxFxQYATADAVQAA (SEQ ID NO: 165). In some embodiments an alcohol dehydrogenase gene is identified in the genome of a yeast of the genus *Candida* by comparison of the amino acid sequence of its predicted translation product with the predicted polypeptide sequence of an alcohol dehydrogenase from *Candida tropicalis* and is identified as an alcohol dehydrogenase if it comprises a third peptide sequence CAGVTVYKALK (SEQ ID NO: 159) or APIxCAGVTVYKALK (SEQ ID NO: 166).

In some embodiments an alcohol dehydrogenase gene is identified in the genome of a yeast of the genus *Candida* by comparison of the amino acid sequence of its predicted translation product with the predicted polypeptide sequence of an alcohol dehydrogenase from *Candida tropicalis* and is identified as an alcohol dehydrogenase if it comprises a fourth peptide sequence GQWVAISGA (SEQ ID NO: 160) or GQWVAISGAxGGLGSL (SEQ ID NO: 167) or GQWVAISGAxGGLGSLxVQYA (SEQ ID NO: 168) or GQWVAISGAxGGLGSLxVQYAxAMG (SEQ ID NO: 169) or GQWVAISGAxGGLGSLxVQYAxAMGxRVxAIDGG (SEQ ID NO: 170).

The four coding sequences were sufficiently dissimilar to reach the conclusion that they were not allelic pairs, but rather represented four different genes, each of which probably had its own allelic partner in the genome. Each of the coding sequences was thus used to design two targeting constructs, similarly to the strategy described for CYP52A12B in Section 7.4.2. The construct for the first allele of each ADH gene used ~200 base pairs at the 5' end and ~200 base pairs at the 3' end as targeting sequences (5'-ADH Out and 3'-ADH Out in FIG. 18). The construct for the second allele used two sections of ~200 base pairs between the first two targeting sequences (5'-ADH In and 3'-ADH in FIG. 18). These sequences will be eliminated by the first targeting construct from the first allele of the gene and will thus serve as a targeting sequence for the second allele of the gene. As described below, this strategy succeeded with two ADH allelic pairs: those for ADH-A4 and ADH-B4. However at the first attempt it was not successful for deletion of the second allele of ADH-A10 or ADH-B11, so the second allele of these genes were isolated, sequenced and those sequences were used to delete the second alleles of ADH-A10 or ADH-B11.

Deletion of a portion of the sequence of an alcohol dehydrogenase gene will disrupt the function of that alcohol dehydrogenase enzyme in the *Candida* host cell.

In some embodiments, disruption of an alcohol dehydrogenase in a first host cell organism is measured by incubating the first host cell organism in a mixture comprising a substrate possessing a hydroxyl group and measuring the rate of conversion of the substrate to a more oxidized product such as an aldehyde or a carboxyl group. The rate of conversion of the substrate by the first host cell organism is compared with the rate of conversion produced by a second host cell organism that does not contain the disrupted gene but contains a wild type counterpart of the gene, when the first host cell organism and the second host cell organism are under the same environmental conditions (e.g., same temperature, same media, etc.). The rate of formation of the product can be measured using colorimetric assays, or chromatographic assays, or mass spectroscopy assays. In some embodiments the alcohol dehydrogenase is disrupted if the rate of conversion is at least 5% lower, at least 10% lower, at least 15% lower, at least 20% lower, at least 25% lower in the first host cell organism than the second host cell organism.

In some embodiments, disruption of an alcohol dehydrogenase in a first host cell organism is measured by incubating said first host cell organism in a mixture comprising a substrate possessing a hydroxyl group and measuring the rate of conversion of the substrate to a more oxidized product such as an aldehyde or a carboxyl group. The amount of the substrate converted to product by the first host cell organism in a specified time is compared with the amount of substrate converted to product by a second host cell organism that does not contain the disrupted gene but contains a wild type counterpart of the gene, when the first host cell organism and the second host cell organism are under the same environmental conditions (e.g., same temperature, same media, etc.). The amount of product can be measured using colorimetric assays, or chromatographic assays, or mass spectroscopy assays. In some embodiments the alcohol dehydrogenase is disrupted if the amount of product is at least 5% lower, at least 10% lower, at least 15% lower, at least 20% lower, at least 25% lower, or at least 30% lower in the first host cell organism than the second host cell organism.

7.5.2. Deletion of ADH-A4

Sequence SEQ ID NO: 39 was used to design a "pre-targeting" construct comprising two targeting sequences from the 5' and 3' end of the ADH-A4 structural gene. The targeting sequences were separated by a sequence, given as SEQ ID NO: 12, comprising a NotI restriction site, a 20 base pair stuffer fragment and an XhoI restriction site. The targeting sequences were flanked by two BsmBI restriction sites, so that the final targeting construct can be linearized prior to transformation into *Candida tropicalis*. The sequence of the ADH-A4 pre-targeting construct is given as SEQ ID NO: 44. Not shown in SEQ ID NO: 44 but also present in the pre-targeting construct were a selective marker conferring resistance to kanamycin and a bacterial origin of replication, so that the pre-targeting construct can be grown and propagated in *E coli*. The sequence was synthesized using standard DNA synthesis techniques well known in the art.

A targeting construct for deletion of ADH-A4 from the *Candida tropicalis* genome was prepared by digesting the SAT-1 flipper (SEQ ID NO: 1) with restriction enzymes NotI and XhoI, and ligating it into the ADH-A4 pre-targeting construct (SEQ ID NO: 44) from which the 20 bp stuffer had been removed by digestion with restriction enzymes NotI and XhoI. The sequence of the resulting targeting construct for deletion of ADH-A4 is given as SEQ ID NO: 45. This sequence is a specific example of the construct shown generically in FIG. 4: it has nearly 200 base pairs of the genomic sequence of ADH-A4 at each end to serve as a targeting sequence; between the targeting sequences are two frt sites that are recognized by the flp recombinase; between the two frt sites are sequences encoding the flp recombinase and a protein conferring resistance to the antibiotic nourseothricin. Not shown in SEQ ID NO: 44 but also present in the targeting construct were a selective marker conferring resistance to kanamycin and a bacterial origin of replication, so that the targeting construct can be grown and propagated in *E coli*. The targeting sequences shown in SEQ ID NO: 44 also include a BsmBI restriction site at each end of the construct, so that the final targeting construct can be linearized and optionally separated from the bacterial antibiotic resistance marker and origin of replication prior to transformation into *Candida tropicalis.*

*Candida tropicalis* strain DP387 was prepared by integration of the construct shown as SEQ ID NO: 45 into the genome of strain DP283 (Table 3) at the site of the genomic sequence of the gene for ADH-A4. *Candida tropicalis* strain DP388 was prepared by excision of the targeting construct from the genome of strain DP387, thereby deleting the gene encoding ADH-A4. Integration and deletion of targeting sequence SEQ ID NO: 45, and analysis of integrants and excisants were performed as described in Section 7.1.

Sequences of oligonucleotide primers for analysis of strains were:

```
A4-OUT-F:
GAATTAGAATACAAAGATATCCCAGTG      (SEQ ID NO: 109)

A4-OUT-R:
CATCAACTTGAAGACCTGTGGCAAT        (SEQ ID NO: 110)

SAT1-R:                          (SEQ ID NO: 79)

SAT1-F:                          (SEQ ID NO: 80)
```

For strain DP387 (integration of SEQ ID NO: 45), PCR with primers A4-OUT-F and SAT1-R produces a 464 base pair amplicon; PCR with primers SAT1-F and A4-OUT-R produces a 464 base pair amplicon. PCR from a strain with a wild type copy of ADH-A4 with primers A4-OUT-F and A4-OUT-R produces a 948 base pair amplicon. For strain DP388 with a deleted copy of ADH-A4, PCR with primers A4-OUT-F and A4-OUT-R produces a 525 base pair amplicon.

7.5.3. Deletion of ADH-A4B

No sequence was identified for a second allele for ADH-A4 in the initial set of 96 sequences but we reasoned that in a diploid organism, a second allele existed. To delete the second allele (ADH-A4B) we synthesized a deletion construct based on the ADH-A4 sequence (SEQ ID NO: 39), but designed it so that the targeting sequences were homologous to regions of the ADH-A4 gene that are missing because they have been deleted in strain DP388. First we constructed a "pre-targeting" construct comprising two targeting sequences internal to the two sequences used in the design of the targeting construct for the deletion of ADH-A4. The targeting sequences were separated by a sequence, given as SEQ ID NO: 12, comprising a NotI restriction site, a 20 base pair stuffer fragment and an XhoI restriction site. The targeting sequences were flanked by two BsmBI restriction sites, so that the final targeting construct can be linearized prior to transformation into *Candida tropicalis*. The sequence of the ADH-A4B pre-targeting construct is given as SEQ ID NO: 46. Not shown in SEQ ID NO: 46 but also present in the pre-targeting construct were a selective marker conferring resistance to kanamycin and a bacterial origin of replication, so that the pre-targeting construct can be grown and propagated in *E coli*. The sequence was synthesized using standard DNA synthesis techniques well known in the art.

A targeting construct for deletion of ADH-A4B from the *Candida tropicalis* genome was prepared by digesting the SAT-1 flipper (SEQ ID NO: 1) with restriction enzymes NotI and XhoI, and ligating it into the ADH-A4B pre-targeting construct (SEQ ID NO: 46) from which the 20 base pair stuffer had been removed by digestion with restriction enzymes NotI and XhoI. The sequence of the resulting targeting construct for deletion of ADH-A4B is given as SEQ ID NO: 47. This sequence is a specific example of the construct shown generically in FIG. 4: it has nearly 200 base pairs of the genomic sequence of ADH-A4B at each end to serve as a targeting sequence; between the targeting sequences are two frt sites that are recognized by the flp recombinase; between the two frt sites are sequences encoding the flp recombinase and a protein conferring resistance to the antibiotic nourseothricin. Not shown in SEQ ID NO: 47 but also present in the targeting construct were a selective marker conferring resistance to kanamycin and a bacterial origin of replication, so that the targeting construct can be grown and propagated in *E coli*. The targeting sequences shown in SEQ ID NO: 47 also include a BsmBI restriction site at each end of the construct, so that the final targeting construct can be linearized and optionally separated from the bacterial antibiotic resistance marker and origin of replication prior to transformation into *Candida tropicalis*.

*Candida tropicalis* strain DP389 was prepared by integration of the construct shown as SEQ ID NO: 47 into the genome of strain DP388 (Table 3) at the site of the genomic sequence of the gene for ADH-A4B. *Candida tropicalis* strain DP390 was prepared by excision of the targeting construct from the genome of strain DP389, thereby deleting a portion of the coding region of the gene encoding ADH-A4B. Integration and deletion of targeting sequence SEQ ID NO: 47, and analysis of integrants and excisants were performed as described in Section 7.1.

Sequences of oligonucleotide primers for analysis of strains were:

```
A4-IN-F:
GAACGGTTCCTGTATGTCCTGTGAGTT     (SEQ ID NO: 111)

A4-IN-R:
CGGATTGGTCAATGGCTTTTTCGGAA      (SEQ ID NO: 112)

SAT1-R:                         (SEQ ID NO: 79)

SAT1-F:                         (SEQ ID NO: 80)
```

Oligonucleotides A4-IN-F and A4-IN-R are designed to anneal to a part of the genome that is missing in strains with deletions in ADH-A4. In such strains they will thus only be able to anneal to and amplify from the second allele ADH-A4B. For strain DP389 (integration of SEQ ID NO: 47), PCR with primers A4-IN-F and SAT1-R produces a 462 base pair amplicon; PCR with primers SAT1-F and A4-IN-R produces a 462 base pair amplicon. PCR from a strain with a wild-type copy of ADH-A4B with primers A4-IN-F and A4-IN-R produces a 488 base pair amplicon. For strain DP390 with a deleted copy of ADH-A4B, PCR with primers A4-IN-F and A4-IN-R produces a 521 base pair amplicon. The amplicons with primers A4-IN-F and A4-IN-R could not distinguish between a strain carrying a wild-type or a deleted copy of ADH-A4B, but digestion of the amplicon with either NotI or XhoI will cleave the amplicon derived from the deleted copy of the gene but not from the wild type, thereby distinguishing between them.

7.5.4. Deletion of ADH-B4

Sequence SEQ ID NO: 42 was used to design a "pre-targeting" construct comprising two targeting sequences from the 5' and 3' end of the ADH-B4 structural gene. The targeting sequences were separated by a sequence, given as SEQ ID NO: 12, comprising a NotI restriction site, a 20 bp stuffer fragment and an XhoI restriction site. The targeting sequences were flanked by two BsmBI restriction sites, so that the final targeting construct can be linearized prior to transformation into *Candida tropicalis*. The sequence of the ADH-B4 pre-targeting construct is given as SEQ ID NO: 48. Not shown in SEQ ID NO: 48 but also present in the pre-targeting construct were a selective marker conferring resistance to kanamycin and a bacterial origin of replication, so that the pre-targeting construct can be grown and propagated in *E coli*. The sequence was synthesized using standard DNA synthesis techniques well known in the art.

A targeting construct for deletion of ADH-B4 from the *Candida tropicalis* genome was prepared by digesting the SAT-1 flipper (SEQ ID NO: 1) with restriction enzymes NotI and XhoI, and ligating it into the ADH-B4 pre-targeting construct (SEQ ID NO: 48) from which the 20 bp stuffer had been removed by digestion with restriction enzymes NotI and XhoI. The sequence of the resulting targeting construct for deletion of ADH-B4 is given as SEQ ID NO: 49. This sequence is a specific example of the construct shown generically in FIG. 4: it has nearly 200 bp of the genomic sequence of ADH-B4 at each end to serve as a targeting sequence; between the targeting sequences are two frt sites that are recognized by the flp recombinase; between the two frt sites are sequences encoding the flp recombinase and a protein conferring resistance to the antibiotic nourseothricin. Not shown in SEQ ID NO: 49 but also present in the targeting construct were a selective marker conferring resistance to kanamycin and a bacterial origin of replication, so that the targeting construct can be grown and propagated in *E coli*. The targeting sequences shown in SEQ ID NO: 49 also include a BsmBI restriction site at each end of the construct, so that the final targeting construct can be linearized and optionally separated from the bacterial antibiotic resistance marker and origin of replication prior to transformation into *Candida tropicalis*.

*Candida tropicalis* strain DP397 was prepared by integration of the construct shown as SEQ ID NO: 49 into the genome of strain DP390 (Table 3) at the site of the genomic sequence of the gene for ADH-B4. *Candida tropicalis* strain DP398 was prepared by excision of the targeting construct from the genome of strain DP397, thereby deleting the gene encoding ADH-B4. Integration and deletion of targeting sequence SEQ ID NO: 49, and analysis of integrants and excisants were performed as described in Section 7.1.

Sequences of oligonucleotide primers for analysis of strains were:

```
B4-OUT-F:
AAATTAGAATACAAGGACATCCCAGTT     (SEQ ID NO: 113)

B4-OUT-R:
CATCAACTTGTAGACTTCTGGCAAT       (SEQ ID NO: 114)

SAT1-R:                         (SEQ ID NO: 79)

SAT1-F:                         (SEQ ID NO: 80)
```

For strain DP397 (integration of SEQ ID NO: 49), PCR with primers B4-OUT-F and SAT1-R produces a 464 bp amplicon; PCR with primers SAT1-F and B4-OUT-R produces a 464 base pair amplicon. PCR from a strain with a wild type copy of ADH-B4 with primers B4-OUT-F and B4-OUT-R produces a 948 base pair amplicon. For strain DP398 with a deleted copy of ADH-B4, PCR with primers B4-OUT-F and B4-OUT-R produces a 525 base pair amplicon.

7.5.5. Deletion of ADH-B4B

No sequence was identified for a second allele for ADH-B4 in the initial set of 96 sequences but we reasoned that in a diploid organism a second allele existed. To delete the second allele (ADH-B4B) we synthesized a deletion construct based on the ADH-B4 sequence (SEQ ID NO: 42), but designed it so that the targeting sequences were homologous to regions of the ADH-B4 gene that are missing because they have been deleted in strain DP398. First we constructed a "pre-targeting" construct comprising two targeting sequences internal to the two sequences used in the design of the targeting construct for the deletion of ADH-B4. The targeting sequences were separated by a sequence, given as SEQ ID NO: 12, comprising a NotI restriction site, a 20 base pair stuffer fragment and an XhoI restriction site. The targeting sequences were flanked by two BsmBI restriction sites, so that the final targeting construct can be linearized prior to transformation into *Candida tropicalis*. The sequence of the ADH-B4B pre-targeting construct is given as SEQ ID NO: 50. Not shown in SEQ ID NO: 50 but also present in the pre-targeting construct were a selective marker conferring resistance to kanamycin and a bacterial origin of replication, so that the pre-targeting construct can be grown and propagated in *E coli*. The sequence was synthesized using standard DNA synthesis techniques well known in the art.

A targeting construct for deletion of ADH-B4B from the *Candida tropicalis* genome was prepared by digesting the SAT-1 flipper (SEQ ID NO: 1) with restriction enzymes NotI and XhoI, and ligating it into the ADH-B4B pre-targeting construct (SEQ ID NO: 50) from which the 20 base pair stuffer had been removed by digestion with restriction enzymes NotI and XhoI. The sequence of the resulting targeting construct for deletion of ADH-B4B is given as SEQ ID NO: 51. This sequence is a specific example of the construct shown generically in FIG. 4: it has nearly 200 bp of the genomic sequence of ADH-B4B at each end to serve as a targeting sequence; between the targeting sequences are two frt sites that are recognized by the flp recombinase; between the two frt sites are sequences encoding the flp recombinase and a protein conferring resistance to the antibiotic nourseothricin. Not shown in SEQ ID NO: 51 but also present in the targeting construct were a selective marker conferring resistance to kanamycin and a bacterial origin of replication, so that the targeting construct can be grown and propagated in *E coli*. The targeting sequences shown in SEQ ID NO: 51 also include a BsmBI restriction site at each end of the construct, so that the final targeting construct can be linearized and optionally separated from the bacterial antibiotic resistance marker and origin of replication prior to transformation into *Candida tropicalis.*

*Candida tropicalis* strain DP409 was prepared by integration of the construct shown as SEQ ID NO: 51 into the genome of strain DP398 (Table 3) at the site of the genomic sequence of the gene for ADH-B4B. *Candida tropicalis* strain DP411 was prepared by excision of the targeting construct from the genome of strain DP409, thereby deleting a portion of the coding region of the gene encoding ADH-B4B. Integration and deletion of targeting sequence SEQ ID NO: 51, and analysis of integrants and excisants were performed as described in Section 7.1.

Sequences of oligonucleotide primers for analysis of strains were:

```
B4-IN-F:
GAACGGTTCCTGTATGAACTGTGAGTA      (SEQ ID NO: 115)

B4-IN-R:
CAGATTGGTTGATGGCCTTTTCGGAG       (SEQ ID NO: 116)

SAT1-R:                          (SEQ ID NO: 79)

SAT1-F:                          (SEQ ID NO: 80)
```

Oligonucleotides B4-IN-F and B4-IN-R are designed to anneal to a part of the genome that is missing in strains with deletions in ADH-B4. In such strains they will thus only be able to anneal to and amplify from the second allele ADH-B4B. For strain DP409 (integration of SEQ ID NO: 51), PCR with primers B4-IN-F and SAT1-R produces a 462 base pair amplicon; PCR with primers SAT1-F and B4-IN-R produces a 462 base pair amplicon. PCR from a strain with a wild-type copy of ADH-B4B with primers B4-IN-F and B4-IN-R produces a 488 base pair amplicon. For strain DP411 with a deleted copy of ADH-B4B, PCR with primers B4-IN-F and B4-IN-R produces a 521 base pair amplicon. The amplicons with primers B4-IN-F and B4-IN-R could not distinguish between a strain carrying a wild-type or a deleted copy of ADH-B4B, but digestion of the amplicon with either NotI or XhoI will cleave the amplicon derived from the deleted copy of the gene but not from the wild type, thereby distinguishing between them.

7.5.6. Deletion of ADH-A10

Sequence SEQ ID NO: 40 was used to design a "pre-targeting" construct comprising two targeting sequences from the 5' and 3' end of the ADH-A10 structural gene. The targeting sequences were separated by a sequence, given as SEQ ID NO: 12, comprising a NotI restriction site, a 20 bp stuffer fragment and an XhoI restriction site. The targeting sequences were flanked by two BsmBI restriction sites, so that the final targeting construct can be linearized prior to transformation into *Candida tropicalis*. The sequence of the ADH-A10 pre-targeting construct is given as SEQ ID NO: 52. Not shown in SEQ ID NO: 52 but also present in the pre-targeting construct were a selective marker conferring resistance to kanamycin and a bacterial origin of replication, so that the pre-targeting construct can be grown and propagated in *E coli*. The sequence was synthesized using standard DNA synthesis techniques well known in the art.

A targeting construct for deletion of ADH-A10 from the *Candida tropicalis* genome was prepared by digesting the SAT-1 flipper (SEQ ID NO: 1) with restriction enzymes NotI and XhoI, and ligating it into the ADH-A10 pre-targeting construct (SEQ ID NO: 52) from which the 20 base pair stuffer had been removed by digestion with restriction enzymes NotI and XhoI. The sequence of the resulting targeting construct for deletion of ADH-A10 is given as SEQ ID NO: 53. This sequence is a specific example of the construct shown generically in FIG. 4: it has nearly 200 bp of the genomic sequence of ADH-A10 at each end to serve as a targeting sequence; between the targeting sequences are two frt sites that are recognized by the flp recombinase; between the two frt sites are sequences encoding the flp recombinase and a protein conferring resistance to the antibiotic nourseothricin. Not shown in SEQ ID NO: 53 but also present in the targeting construct were a selective marker conferring resistance to kanamycin and a bacterial origin of replication, so that the targeting construct can be grown and propagated in *E coli*. The targeting sequences shown in SEQ ID NO: 53 also include a BsmBI restriction site at each end of the construct, so that the final targeting construct can be linearized and optionally separated from the bacterial antibiotic resistance marker and origin of replication prior to transformation into *Candida tropicalis.*

*Candida tropicalis* strain DP415 was prepared by integration of the construct shown as SEQ ID NO: 53 into the genome of strain DP411 (Table 3) at the site of the genomic sequence of the gene for ADH-A10. *Candida tropicalis* strain DP416 was prepared by excision of the targeting construct from the genome of strain DP415, thereby deleting the gene encoding ADH-A10. Integration and deletion of targeting sequence SEQ ID NO: 53, and analysis of integrants and excisants were performed as described in Section 7.1.

Sequences of oligonucleotide primers for analysis of strains were:

```
A10-OUT-F:
AAGTTAGAATACAAAGACGTGCCGGTC      (SEQ ID NO: 117)

A10-OUT-R:
CATCAAGTCAAAAATCTCTGGCACT        (SEQ ID NO: 118)

SAT1-R:                          (SEQ ID NO: 147)

SAT1-F:                          (SEQ ID NO: 80)
```

For strain DP415 (integration of SEQ ID NO: 49), PCR with primers A10-OUT-F and SAT1-R produces a 464 base pair amplicon; PCR with primers SAT1-F and A10-OUT-R produces a 464 base pair amplicon. PCR from a strain with a wild type copy of ADH-A10 with primers A10-OUT-F and A10-OUT-R produces a 948 base pair amplicon. For strain DP416 with a deleted copy of ADH-A10, PCR with primers A10-OUT-F and A10-OUT-R produces a 525 base pair amplicon.

7.5.7. Deletion of ADH-B11

Sequence SEQ ID NO: 43 was used to design a "pre-targeting" construct comprising two targeting sequences from the 5' and 3' end of the ADH-B11 structural gene. The targeting sequences were separated by a sequence, given as SEQ ID NO: 12, comprising a NotI restriction site, a 20 base pair stuffer fragment and an XhoI restriction site. The targeting sequences were flanked by two BsmBI restriction sites, so that the final targeting construct can be linearized prior to transformation into *Candida tropicalis*. The sequence of the ADH-B11 pre-targeting construct is given as SEQ ID NO: 54. Not shown in SEQ ID NO: 54 but also present in the pre-targeting construct were a selective marker conferring resistance to kanamycin and a bacterial origin of replication, so that the pre-targeting construct can be grown and propagated in *E coli*. The sequence was synthesized using standard DNA synthesis techniques well known in the art.

A targeting construct for deletion of ADH-B11 from the *Candida tropicalis* genome was prepared by digesting the SAT-1 flipper (SEQ ID NO: 1) with restriction enzymes NotI and XhoI, and ligating it into the ADH-B11 pre-targeting construct (SEQ ID NO: 54) from which the 20 base pair stuffer had been removed by digestion with restriction enzymes NotI and XhoI. The sequence of the resulting targeting construct for deletion of ADH-B11 is given as SEQ ID NO: 55. This sequence is a specific example of the construct shown generically in FIG. 4: it has nearly 200 base pair of the genomic sequence of ADH-B11 at each end to serve as a targeting sequence; between the targeting sequences are two frt sites that are recognized by the flp recombinase; between the two frt sites are sequences encoding the flp recombinase and a protein conferring resistance to the antibiotic nourseothricin. Not shown in SEQ ID NO: 55 but also present in the targeting construct were a selective marker conferring resistance to kanamycin and a bacterial origin of replication, so that the targeting construct can be grown and propagated in *E coli*. The targeting sequences shown in SEQ ID NO: 53 also include a BsmBI restriction site at each end of the construct, so that the final targeting construct can be linearized and optionally separated from the bacterial antibiotic resistance marker and origin of replication prior to transformation into *Candida tropicalis*.

*Candida tropicalis* strain DP417 was prepared by integration of the construct shown as SEQ ID NO: 55 into the genome of strain DP416 (Table 3) at the site of the genomic sequence of the gene for ADH-B11. *Candida tropicalis* strain DP421 was prepared by excision of the targeting construct from the genome of strain DP417, thereby deleting the gene encoding ADH-B11. Integration and deletion of targeting sequence SEQ ID NO: 55, and analysis of integrants and excisants were performed as described in Section 7.1.

Sequences of oligonucleotide primers for analysis of strains were:

```
B11-OUT-F:
CCATTGCAATACACCGATATCCCAGTT      (SEQ ID NO: 119)

B11-OUT-R:
CAACAATTTGAAAATCTCTGGCAAT        (SEQ ID NO: 120)

SAT1-R:                          (SEQ ID NO: 79)

SAT1-F:                          (SEQ ID NO: 80)
```

For strain DP417 (integration of SEQ ID NO: 49), PCR with primers B11-OUT-F and SAT1-R produces a 464 base pair amplicon; PCR with primers SAT1-F and B11-OUT-R produces a 464 base pair amplicon. PCR from a strain with a wild type copy of ADH-B11 with primers B11-OUT-F and B11-OUT-R produces a 948 base pair amplicon. For strain DP421 with a deleted copy of ADH-B11, PCR with primers B11-OUT-F and B11-OUT-R produces a 525 base pair amplicon.

7.5.8. Deletion of ADH-A10B

No sequence was identified for a second allele for ADH-A10 in the initial set of 96 sequences but we reasoned that in a diploid organism a second allele existed. At our first attempt we were unable to delete the second allele (ADH-A10B) using the strategy described for ADH-A4B and ADH-B4B. We used the primers A 10-IN-F and A10-IN-R to amplify an ~500 base pair amplicon from genomic DNA from strain DP415 which has the SAT1-flipper inserted into the first ADH-A10 allele, preventing it from amplifying with these primers. The amplicon was cloned and sequenced, the sequence is given as SEQ ID NO: 56.

```
A10-IN-F:
GAATGGTTCGTGTATGAACTGTGAGTT      (SEQ ID NO: 121)

A10-IN-R:
CCGACTGGTTGATTGCCTTTTCGGAC       (SEQ ID NO: 122)
```

We constructed a "pre-targeting" construct comprising two targeting sequences based on SEQ ID NO: 56. A single mutation was introduced into the sequence obtained as SEQ ID NO: 56: a G at position 433 was mutated to a C to destroy an unwanted BsmBI site. The targeting sequences were separated by a sequence, given as SEQ ID NO: 12, comprising a NotI restriction site, a 20 base pair stuffer fragment and an XhoI restriction site. The targeting sequences were flanked by two BsmBI restriction sites, so that the final targeting construct can be linearized prior to transformation into *Candida tropicalis*. The sequence of the ADH-A10B pre-targeting construct is given as SEQ ID NO: 57. Not shown in SEQ ID NO: 57 but also present in the pre-targeting construct were a selective marker conferring resistance to kanamycin and a bacterial origin of replication, so that the pre-targeting construct can be grown and propagated in *E coli*. The sequence was synthesized using standard DNA synthesis techniques well known in the art.

A targeting construct for deletion of ADH-A10B from the *Candida tropicalis* genome was prepared by digesting the SAT-1 flipper (SEQ ID NO: 1) with restriction enzymes NotI and XhoI, and ligating it into the ADH-A10B pre-targeting construct (SEQ ID NO: 57) from which the 20 bp stuffer had been removed by digestion with restriction enzymes NotI and XhoI. The sequence of the resulting targeting construct for deletion of ADH-A10B is given as SEQ ID NO: 58. This sequence is a specific example of the construct shown generically in FIG. 4: it has nearly 200 base pairs of the genomic sequence of ADH-A10B at each end to serve as a targeting sequence; between the targeting sequences are two frt sites that are recognized by the flp recombinase; between the two frt sites are sequences encoding the flp recombinase and a protein conferring resistance to the antibiotic nourseothricin. Not shown in SEQ ID NO: 58 but also present in the targeting construct were a selective marker conferring resistance to kanamycin and a bacterial origin of replication, so that the targeting construct can be grown and propagated in *E coli*. The targeting sequences shown in SEQ ID NO: 58 also include a BsmBI restriction site at each end of the construct, so that the final targeting construct can be linearized and optionally separated from the bacterial antibiotic resistance marker and origin of replication prior to transformation into *Candida tropicalis*.

*Candida tropicalis* strain DP424 was prepared by integration of the construct shown as SEQ ID NO: 58 into the genome of strain DP421 (Table 3) at the site of the genomic sequence of the gene for ADH-A10B. *Candida tropicalis* strain DP431 was prepared by excision of the targeting construct from the genome of strain DP424, thereby deleting a portion of the coding region of the gene encoding ADH-A10B. Integration and deletion of targeting sequence SEQ ID NO: 58, and analysis of integrants and excisants were performed as described in Section 7.1. Sequences of oligonucleotide primers for analysis of strains were A10-IN-F (SEQ ID NO: 121), A10-IN-R (SEQ ID NO: 122), SAT1-R (SEQ ID NO: 79), and SAT1-F (SEQ ID NO: 80).

Oligonucleotides A10-IN-F and A10-IN-R are designed to anneal to a part of the genome that is missing in strains with deletions in ADH-A10. In such strains they will thus only be able to anneal to and amplify from the second allele ADH-A10B. For strain DP424 (integration of SEQ ID NO: 58), PCR with primers A10-IN-F and SAT1-R produces a 462 base pair amplicon; PCR with primers SAT1-F and A10-IN-R produces a 462 base pair amplicon. PCR from a strain with a wild-type copy of ADH-A10B with primers A10-IN-F and A10-IN-R produces a 488 base pair amplicon. For strain DP431 with a deleted copy of ADH-A10B, PCR with primers A10-IN-F and A10-IN-R produces a 521 base pair amplicon. The amplicons with primers A10-IN-F and A10-IN-R could not distinguish between a strain carrying a wild-type or a deleted copy of ADH-A10B, but digestion of the amplicon with either NotI or XhoI will cleave the amplicon derived from the deleted copy of the gene but not from the wild type, thereby distinguishing between them.

7.5.9. Deletion of ADH-B11B

No sequence was identified for a second allele for ADH-B11 in the initial set of 96 sequences but we reasoned that in a diploid organism a second allele existed. At our first attempt we were unable to delete the second allele (ADH-B11B) using the strategy described for ADH-A4B and ADH-B4B. We used the primers B11-OUT-F and B11-OUT-R to amplify an ~950 base pair amplicon from genomic DNA from strain DP417 which has the SAT1-flipper inserted into the first ADH-B11 allele, preventing it from amplifying with these primers. The amplicon was cloned and sequenced, the sequence is given as SEQ ID NO: 59.

```
B11-OUT-F
GAATGGTTCGTGTATGAACTGTGAGTT     (SEQ ID NO: 121)

B11-OUT-R
CCGACTGGTTGATTGCCTTTTCGGAC      (SEQ ID NO: 122)
```

We constructed a "pre-targeting" construct comprising two targeting sequences based on SEQ ID NO: 59. The targeting sequences were separated by a sequence, given as SEQ ID NO: 12, comprising a NotI restriction site, a 20 base pair stuffer fragment and an XhoI restriction site. The targeting sequences were flanked by two BsmBI restriction sites, so that the final targeting construct can be linearized prior to transformation into *Candida tropicalis*. The sequence of the ADH-B11B pre-targeting construct is given as SEQ ID NO: 60. Not shown in SEQ ID NO: 60 but also present in the pre-targeting construct were a selective marker conferring resistance to kanamycin and a bacterial origin of replication, so that the pre-targeting construct can be grown and propagated in *E coli*. The sequence was synthesized using standard DNA synthesis techniques well known in the art.

A targeting construct for deletion of ADH-B11B from the *Candida tropicalis* genome was prepared by digesting the SAT-1 flipper (SEQ ID NO: 1) with restriction enzymes NotI and XhoI, and ligating it into the ADH-B11B pre-targeting construct (SEQ ID NO: 60) from which the 20 base pair stuffer had been removed by digestion with restriction enzymes NotI and XhoI. The sequence of the resulting targeting construct for deletion of ADH-B11B is given as SEQ ID NO: 61. This sequence is a specific example of the construct shown generically in FIG. 4: it has nearly 200 base pair of the genomic sequence of ADH-B11B at each end to serve as a targeting sequence; between the targeting sequences are two frt sites that are recognized by the flp recombinase; between the two frt sites are sequences encoding the flp recombinase and a protein conferring resistance to the antibiotic nourseothricin. Not shown in SEQ ID NO: 61 but also present in the targeting construct were a selective marker conferring resistance to kanamycin and a bacterial origin of replication, so that the targeting construct can be grown and propagated in *E coli*. The targeting sequences shown in SEQ ID NO: 61 also include a BsmBI restriction site at each end of the construct, so that the final targeting construct can be linearized and optionally separated from the bacterial antibiotic resistance marker and origin of replication prior to transformation into *Candida tropicalis*.

*Candida tropicalis* strain DP433 was prepared by integration of the construct shown as SEQ ID NO: 61 into the genome of strain DP431 (Table 3) at the site of the genomic sequence of the gene for ADH-B11B. *Candida tropicalis* strain DP437 was prepared by excision of the targeting construct from the genome of strain DP433, thereby deleting a portion of the coding region of the gene encoding ADH-B11B. Integration and deletion of targeting sequence SEQ ID NO: 61, and analysis of integrants and excisants were performed as described in Section 7.1.

Sequences of oligonucleotide primers for analysis of strains were:

```
B11-OUT-F:                      (SEQ ID NO: 119)

B11-IN-R:
CAGACTGGTTGATGGCTTTTTCAGAA      (SEQ ID NO: 123)

SAT1-R:                         (SEQ ID NO: 79)

SAT1-F:                         (SEQ ID NO: 80)
```

For strain DP433 (integration of SEQ ID NO: 61), PCR with primers B11-OUT-F and SAT1-R produces a 692 base pair amplicon. PCR from a strain with a wild-type copy of ADH-B11B with primers B11-OUT-F and B11-IN-R produces a 718 base pair amplicon. For strain DP437 with a deleted copy of ADH-B11B, PCR with primers B11-OUT-F and B11-IN-R produces a 751 base pair amplicon. The amplicons with primers B11-OUT-F and B11-IN-R could not distinguish between a strain carrying a wild-type or a deleted copy of ADH-B11B, but digestion of the amplicon with either NotI or XhoI will cleave the amplicon derived from the deleted copy of the gene but not from the wild type, thereby distinguishing between them.

7.6. Insertion of P450 Genes into the Genome of *Candida*

To achieve novel phenotypes in yeasts of the genus *Candida* (e.g., *Candida tropicalis*), including biotransformations of compounds by *Candida tropicalis*, including chemical conversions not previously obtained, or increased rates of conversion of one or more substrates to one or more products, or increased specificity of conversion of one or more substrates to one or more products, or increased tolerance of a compound by the yeast, or increased uptake of a compound by the yeast, it may be advantageous to incorporate a gene encoding a polypeptide into the genome of the yeast. Expression of the polypeptide in the yeast then allows the phenotype of the yeast to be modified.

In some embodiments of the invention it may be advantageous to integrate a gene encoding a polypeptide into a strain of *Candida tropicalis* in which one or more of the alcohol dehydrogenase genes ADH-A4, ADH-A4B, ADH-B4, ADH-B4B, ADH-A10, ADH-A10B, ADH-B1B and ADH-B11 have been disrupted. In some embodiments of the invention it may be advantageous to integrate a gene encoding a polypeptide into a yeast strain of the genus *Candida* in which one or more alcohol dehydrogenase genes have been disrupted, and wherein the disrupted alcohol dehydrogenase gene shares at least 95% nucleotide identity, or at least 90% nucleotide identity, or at least 85% nucleotide identity for a stretch of at least 100 contiguous nucleotides within the coding region, or at least 80% identical for a stretch of at least 100 contiguous nucleotides of the coding sequence or at least 75% identical for a stretch of at least 100 contiguous nucleotides of the coding sequence, or at least 70% identical for a stretch of at least 100 contiguous nucleotides of the coding sequence, or at least 65% identical for a stretch of at least 100 contiguous nucleotides of the coding sequence, or at least 60% identical for a stretch of at least 100 contiguous nucleotides of the coding sequence with one of the *Candida tropicalis* genes ADH-A4 (SEQ ID NO: 39), ADH-B4 (SEQ ID NO: 42), ADH-A10 (SEQ ID NO: 40), ADH-A10B (SEQ ID NO: 56), ADH-B11 (SEQ ID NO: 43).

In some embodiments it may be advantageous to integrate a gene encoding a polypeptide into a yeast strain of the genus *Candida* in which (i) one or more alcohol dehydrogenase genes have been disrupted and (ii) the disrupted alcohol dehydrogenase comprises a first peptide. In some embodiments said first peptide has the sequence VKYSGVCH (SEQ ID NO: 156). In some embodiments said first peptide has the sequence VKYSGVCHxxxxxWKGDW (SEQ ID NO: 162). In some embodiments the first peptide has the sequence VKYSGVCHxxxxxWKGDWxxxxKLPxVG-GHEGAGVVV (SEQ ID NO: 163).

In some embodiments the disrupted alcohol dehydrogenase sequence, predicted from translation of the gene that encodes it, comprises a second peptide. In some embodiments said second peptide has the sequence QYATA-DAVQAA (SEQ ID NO: 158). In some embodiments said second peptide has the sequence SGYxHDGxFxQYATA-DAVQAA (SEQ ID NO: 164). In some embodiments said second peptide has the sequence GAEPNCxxADxSGYx-HDGxFxQYATADAVQAA (SEQ ID NO: 165). In some embodiments the disrupted alcohol dehydrogenase sequence, predicted from translation of the gene that encodes it, comprises a third peptide. In some embodiments said third peptide has the sequence CAGVTVYKALK (SEQ ID NO: 159). In some embodiments said third peptide has the sequence APIx-CAGVTVYKALK (SEQ ID NO: 166).

In some embodiments the first genetic modification class comprises disruption of at least one alcohol dehydrogenase whose amino acid sequence, predicted from translation of the gene that encodes it, comprises a fourth peptide. In some embodiments said fourth peptide has the sequence GQWVAISGA (SEQ ID NO: 160). In some embodiments said fourth peptide has the sequence GQWVAISGAxG-GLGSL (SEQ ID NO: 167). In some embodiments said fourth peptide has the sequence GQWVAISGAxGGLGSLx-VQYA (SEQ ID NO: 168). In some embodiments said fourth peptide has the sequence GQWVAISGAxGGLGSLx-VQYAxAMG (SEQ ID NO: 169). In some embodiments said fourth peptide has the sequence GQWVAISGAxGGLGSLx-VQYAxAMGxRVxAIDGG. (SEQ ID NO: 170). In some embodiments the disrupted alcohol dehydrogenase sequence, predicted from translation of the gene that encodes it, comprises a fifth peptide. In some embodiments said fifth peptide has the sequence VGGHEGAGVVV (SEQ ID NO: 157).

Cytochrome P450s are of particular utility in the hydroxylation of a variety of substrates including fatty acids. Different cytochrome P450s are known to have different substrate and regiospecificities and different specific activities. It is therefore useful in some embodiments of the invention to incorporate a gene encoding a cytochrome P450 into the genome of the yeast. The exact P450 to be used will depend upon the substrate and the position on the substrate to be hydroxylated. A list of P450 enzymes that may be of utility in the hydroxylation of substrates when expressed within a yeast cell are given in Table 4.

TABLE 4

| First Database Accession Number | Second Database Accession Number | Name | Species |
|---|---|---|---|
| gi 29469875 | gb AAO73958.1 | CYP52A17 | *Candida tropicalis* |
| gi 29469877 | gb AAO73959.1 | CYP52A18 | *Candida tropicalis* |
| gi 231889 | sp P30610.1 | CP52H_CANTR (Cytochrome P450 52A8) | |
| gi 3913326 | sp Q12586.1 | CP52I_CANMA (Cytochrome P450 52A9) | |
| gi 29469881 | gb AAO73961.1 | CYP52A20 | *Candida tropicalis* |
| gi 29469879 | gb AAO73960.1 | CYP52A19 | *Candida tropicalis* |
| gi 3913329 | sp Q12589.1 | CP52K_CANMA (Cytochrome P450 52A11) | |

TABLE 4-continued

| First Database Accession Number | Second Database Accession Number | Name | Species |
|---|---|---|---|
| gi 3913328 | sp Q12588.1 | CP52J_CANMA (Cytochrome P450 52A10) | |
| gi 68492087 | ref XP_710174.1 | P450 drug resistance protein | *Candida albicans* |
| gi 3395458 | emb CAA75058.1 | alk8 | *Candida albicans* |
| gi 68474594 | ref XP_718670.1 | CaO19.7513 | *Candida albicans* |
| gi 29469865 | gb AAO73953.1 | CYP52A13 | *Candida tropicalis* |
| gi 149239010 | ref XP_001525381.1 | cytochrome P450 52A11 | *Lodderomyces elongisporus* |
| gi 29469867 | gb AAO73954.1 | CYP52A14 | *Candida tropicalis* |
| gi 7548332 | gb AAA34353.2 | cytochrome P-450-alk2 | *Candida tropicalis* |
| gi 732622 | emb CAA39366.1 | n-alkane inducible cytochrome P-450 | *Candida maltosa* |
| gi 231886 | sp P30607.1 | CP52B_CANTR (Cytochrome P450 52A2) | |
| gi 68474592 | ref XP_718669.1 | CaO19.7512 | *Candida albicans* |
| gi 150864612 | ref XP_001383506.2 | n-alkane inducible cytochrome P-450 | *Pichia stipitis* |
| gi 231888 | sp P30609.1 | CP52G_CANTR (Cytochrome P450 52A7) | |
| gi 298217 | gb AAB24479.1 | cytochrome P450 monoxygenase alk4, P450 alk4 = CYP52A7 gene product {alkane-inducible} | *Candida tropicalis* |
| gi 149246109 | ref XP_001527524.1 | cytochrome P450 52A2 | *Lodderomyces elongisporus* |
| gi 29469869 | gb AAO73955.1 | CYP52A15 | *Candida tropicalis* |
| gi 190319368 | gb AAD22536.2 | AF103948_1 cytochrome P450 alkane hydroxylase | *Debaryomyces hansenii* |
| gi 146419207 | ref XP_001485567.1 | cytochrome P450 52A12 | *Pichia guilliermondii* |
| gi 29469863 | gb AAO73952.1 | CYP52A12 | *Candida tropicalis* |
| gi 50423067 | ref XP_460112.1 | DEHA0E19635g | *Debaryomyces hansenii* |
| gi 29469871 | gb AAO73956.1 | CYP52A16 | *Candida tropicalis* |
| gi 199432969 | emb CAG88381.2 | DEHA2E18612p | *Debaryomyces hansenii* |
| gi 170892 | gb AAA34354.1 | cytochrome P-450-alk1 | *Candida tropicalis* |
| gi 50423065 | ref XP_460111.1 | DEHA0E19613g | *Debaryomyces hansenii* |
| gi 1169075 | sp P10615.3 | CP52A_CANTR (Cytochrome P450 52A1) | |
| gi 226487 | prf 1515252A | cytochrome P450alk1 | |
| gi 732623 | emb CAA39367.1 | n-alkane inducible cytochrome P-450 | *Candida maltosa* |
| gi 146413358 | ref XP_001482650.1 | PGUG_05670 | *Pichia guilliermondii* |
| gi 117182 | sp P16141.3 | CP52D_CANMA (Cytochrome P450 52A4) | |
| gi 2608 | emb CAA36197.1 | unnamed protein product | *Candida maltosa* |
| gi 231887 | sp P30608.1 | CP52F_CANTR (Cytochrome P450 52A6) | |
| gi 199432970 | emb CAG88382.2 | DEHA2E18634p | *Debaryomyces hansenii* |
| gi 190349008 | gb EDK41572.2 | PGUG_05670 | *Pichia guilliermondii* |
| gi 150864699 | ref XP_001383636.2 | Cytochrome P450 52A12 (Alkane hydroxylase 1) (Alkane-inducible p450alk 1) (DH-ALK2) | *Pichia stipitis* |
| gi 117181 | sp P16496.3 | CP52C_CANMA (Cytochrome P450 52A3) | |
| gi 199432968 | emb CAG88380.2 | DEHA2E18590p | *Debaryomyces hansenii* |
| gi 50423063 | ref XP_460110.1 | DEHA0E19591g | *Debaryomyces hansenii* |
| gi 553118 | gb AAA34320.1 | alkane hydroxylating cytochrome P-450 | |
| gi 117183 | sp P24458.1 | CP52E_CANMA (Cytochrome P450 52A5) | |
| gi 68475852 | ref XP_717999.1 | potential alkane hydroxylating monooxygenase P450 | *Candida albicans* |
| gi 18203639 | sp Q9Y758.1 | CP52M_DEBHA (Cytochrome P450 52A13) | |
| gi 146412241 | ref XP_001482092.1 | cytochrome P450 52A13 | *Pichia guilliermondii* |
| gi 126134585 | ref XP_001383817.1 | Cytochrome P450 52A13 (Alkane hydroxylase 2) (Alkane-inducible p450alk2) (DH-ALK2) | *Pichia stipitis* |
| gi 50418551 | ref XP_457792.1 | DEHA0C02981g | *Debaryomyces hansenii* |
| gi 149236533 | ref XP_001524144.1 | cytochrome P450 52A5 | *Lodderomyces elongisporus* |
| gi 150864746 | ref XP_001383710.2 | Cytochrome P450 52A6 (CYPLIIA6) (Alkane-inducible P450-ALK3) | *Pichia stipitis* |

TABLE 4-continued

| First Database Accession Number | Second Database Accession Number | Name | Species |
|---|---|---|---|
| gi 149239404 | ref XP_001525578.1 | cytochrome P450 52A3 | *Lodderomyces elongisporus* |
| gi 50417817 | ref XP_457727.1 | DEHA0C01177g | *Debaryomyces hansenii* |
| gi 199430432 | emb CAG85755.2 | DEHA2C01100p | *Debaryomyces hansenii* |
| gi 149239402 | ref XP_001525577.1 | cytochrome P450 52A8 | *Lodderomyces elongisporus* |
| gi 29469873 | gb AAO73957.1 | CYP52D2 | *Candida tropicalis* |
| gi 150866745 | ref XP_001386440.2 | Cytochrome P450 52A3 (CYPLIIA3) (Alkane-inducible P450-ALK1-A) (P450-CM1) (CYP52A3-A) (Cytochrome P-450ALK) | *Pichia stipitis* |
| gi 190347603 | gb EDK39907.2 | PGUG_04005 | *Pichia guilliermondii* |
| gi 146414612 | ref XP_001483276.1 | PGUG_04005 | *Pichia guilliermondii* |
| gi 3913325 | sp Q12585.1 | CP52T_CANMA (Cytochrome P450 52D1) | |
| gi 50553995 | ref XP_504406.1 | YALI0E25982p | *Yarrowia lipolytica* |
| gi 3298289 | dbj BAA31433.1 | ALK1 | *Yarrowia lipolytica* |
| gi 50554897 | ref XP_504857.1 | YALI0F01320p | *Yarrowia lipolytica* |
| gi 50545727 | ref XP_500402.1 | YALI0B01848p | *Yarrowia lipolytica* |
| gi 50546066 | ref XP_500560.1 | YALI0B06248p | *Yarrowia lipolytica* |
| gi 50547357 | ref XP_501148.1 | YALI0B20702p | *Yarrowia lipolytica* |
| gi 50546771 | ref XP_500855.1 | YALI0B13816p | *Yarrowia lipolytica* |
| gi 50546773 | ref XP_500856.1 | YALI0B13838p | *Yarrowia lipolytica* |
| gi 70982077 | ref XP_746567.1 | cytochrome P450 alkane hydroxylase | *Aspergillus fumigatus* |
| gi 119487140 | ref XP_001262425.1 | cytochrome P450 alkane hydroxylase | *Neosartorya fischeri* |
| gi 50545119 | ref XP_500097.1 | YALI0A15488p | *Yarrowia lipolytica* |
| gi 115387741 | ref XP_001211376.1 | cytochrome P450 52A12 | *Aspergillus terreus* |
| gi 145248800 | ref XP_001400739.1 | An14g01110 | *Aspergillus niger* |
| gi 121714465 | ref XP_001274843.1 | cytochrome P450 alkane hydroxylase | *Aspergillus clavatus* |
| gi 50545471 | ref XP_500273.1 | YALI0A20130p | *Yarrowia lipolytica* |
| gi 212541280 | ref XP_002150795.1 | cytochrome P450 alkane hydroxylase | *Penicillium marneffei* |
| gi 169783066 | ref XP_001825995.1 | | *Aspergillus oryzae* |
| gi 67541935 | ref XP_664735.1 | AN7131.2 | *Aspergillus nidulans* |
| gi 218716670 | gb EED16091.1 | cytochrome P450 alkane hydroxylase | *Talaromyces stipitatus* |
| gi 211584648 | emb CAP74173.1 | Pc14g00320 | *Penicillium chrysogenum* |
| gi 68475719 | ref XP_718066.1 | potential alkane hydroxylating monooxygenase P450 fragment | *Candida albicans* |
| gi 231890 | sp P30611.1 | CP52N_CANTR (Cytochrome P450 52B1) | |
| gi 50553800 | ref XP_504311.1 | YALI0E23474p | *Yarrowia lipolytica* |
| gi 115391153 | ref XP_001213081.1 | ATEG_03903 | *Aspergillus terreus* |
| gi 1169076 | sp P43083.1 | CP52V_CANAP (Cytochrome P450 52E1) | |
| gi 212537573 | ref XP_002148942.1 | cytochrome P450 family protein | *Penicillium marneffei* |
| gi 119480837 | ref XP_001260447.1 | cytochrome P450 family protein | *Neosartorya fischeri* |
| gi 159129370 | gb EDP54484.1 | cytochrome P450 family protein | *Aspergillus fumigatus* |
| gi 71001214 | ref XP_755288.1 | cytochrome P450 family protein | *Aspergillus fumigatus* |
| gi 50548557 | ref XP_501748.1 | YALI0C12122p | *Yarrowia lipolytica* |
| gi 211592844 | emb CAP99212.1 | Pc22g19240 | *Penicillium chrysogenum* |
| gi 231891 | sp P30612.1 | CP52P_CANTR (Cytochrome P450 52C1) | |
| gi 3913327 | sp Q12587.1 | CP52Q_CANMA (Cytochrome P450 52C2) | |
| gi 50548395 | ref XP_501667.1 | YALI0C10054p | *Yarrowia lipolytica* |
| gi 145248373 | ref XP_001396435.1 | An13g03000 | *Aspergillus niger* |
| gi 169783674 | ref XP_001826299.1 | | *Aspergillus oryzae* |
| gi 169774249 | ref XP_001821592.1 | | *Aspergillus oryzae* |
| gi 212536398 | ref XP_002148355.1 | cytochrome P450 alkane hydroxylase | *Penicillium marneffei* |
| gi 211590140 | emb CAP96310.1 | Pc21g14130 | *Penicillium chrysogenum* |

TABLE 4-continued

| First Database Accession Number | Second Database Accession Number | Name | Species |
|---|---|---|---|
| gi 189200681 | ref XP_001936677.1 | cytochrome P450 52A12 | *Pyrenophora tritici-repentis* |
| gi 121698992 | ref XP_001267871.1 | cytochrome P450 family protein | *Aspergillus clavatus* |
| gi 154310961 | ref XP_001554811.1 | BC1G_06459 | *Botryotinia fuckeliana* |
| gi 119497443 | ref XP_001265480.1 | cytochrome P450 alkane hydroxylase | *Neosartorya fischeri* |
| gi 67539774 | ref XP_663661.1 | AN6057.2 | *Aspergillus nidulans* |
| gi 3913324 | sp Q12573.1 | CP52W_CANAP (Cytochrome P450 52E2) | |
| gi 159130401 | gb EDP55514.1 | cytochrome P450 alkane hydroxylase | *Aspergillus fumigatus* |
| gi 70990140 | ref XP_749919.1 | cytochrome P450 alkane hydroxylase | *Aspergillus fumigatus* |
| gi 212543867 | ref XP_002152088.1 | N-alkane-inducible cytochrome P450 | *Penicillium marneffei* ATCC 18224 |
| gi 189204508 | ref XP_001938589.1 | cytochrome P450 52A12 | *Pyrenophora tritici-repentis* |
| gi 67904794 | ref XP_682653.1 | AN9384.2 | *Aspergillus nidulans* |
| gi 115401146 | ref XP_001216161.1 | ATEG_07540 | *Aspergillus terreus* |
| gi 169765686 | ref XP_001817314.1 | | *Aspergillus oryzae* |
| gi 156034334 | ref XP_001585586.1 | SS1G_13470 | *Sclerotinia sclerotiorum* |
| gi 115389132 | ref XP_001212071.1 | ATEG_02893 | *Aspergillus terreus* |
| gi 149249004 | ref XP_001528842.1 | LELG_05768 | *Lodderomyces elongisporus* |
| gi 119490743 | ref XP_001263094.1 | n-alkane-inducible cytochrome P450 | *Neosartorya fischeri* |
| gi 169598696 | ref XP_001792771.1 | SNOG_02153 | *Phaeosphaeria nodorum* |
| gi 145233653 | ref XP_001400199.1 | An02g10700 | *Aspergillus niger* |
| gi 121703415 | ref XP_001269972.1 | cytochrome P450 alkane hydroxylase | *Aspergillus clavatus* |
| gi 145244813 | ref XP_001394678.1 | An11g07010 | *Aspergillus niger* |
| gi 115400535 | ref XP_001215856.1 | ATEG_06678 | *Aspergillus terreus* |
| gi 156054264 | ref XP_001593058.1 | SS1G_05980 | *Sclerotinia sclerotiorum* |
| gi 145235009 | ref XP_001390153.1 | An03g02570 | *Aspergillus niger* |
| gi 121714697 | ref XP_001274959.1 | n-alkane-inducible cytochrome P450 | *Aspergillus clavatus* |
| gi 115383936 | ref XP_001208515.1 | ATEG_01150 | *Aspergillus terreus* |
| gi 119188703 | ref XP_001244958.1 | CIMG_04399 | *Coccidioides immitis* |
| gi 154303347 | ref XP_001552081.1 | BC1G_09422 | *Botryotinia fuckeliana* |
| gi 68469246 | ref XP_721410.1 | potential n-alkane inducible cytochrome P-450 | *Candida albicans* |
| gi 211588353 | emb CAP86458.1 | Pc20g11290 | *Penicillium chrysogenum* |
| gi 218719422 | gb EED18842.1 | cytochrome P450 | *Talaromyces stipitatus* |
| gi 189196472 | ref XP_001934574.1 | cytochrome P450 52A11 | *Pyrenophora tritici-repentis* |
| gi 145228377 | ref XP_001388497.1 | An01g00510 | *Aspergillus niger* |
| gi 145243810 | ref XP_001394417.1 | An11g04220 | *Aspergillus niger* |
| gi 119467390 | ref XP_001257501.1 | n-alkane-inducible cytochrome P450 | *Neosartorya fischeri* |
| gi 218713692 | gb EED13116.1 | cytochrome P450 alkane hydroxylase | *Talaromyces stipitatus* |
| gi 156040904 | ref XP_001587438.1 | SS1G_11430 | *Sclerotinia sclerotiorum* |
| gi 211588608 | emb CAP86724.1 | Pc20g13950 | *Penicillium chrysogenum* |
| gi 189210960 | ref XP_001941811.1 | cytochrome P450 52A11 | *Pyrenophora tritici-repentis* |
| gi 154300280 | ref XP_001550556.1 | BC1G_11329 | *Botryotinia fuckeliana* |
| gi 39965179 | ref XP_365075.1 | MGG_09920 | *Magnaporthe grisea* |
| gi 70984521 | ref XP_747767.1 | cytochrome P450 alkane hydroxylase | *Aspergillus fumigatus* |
| gi 164424932 | ref XP_958030.2 | NCU09115 | *Neurospora crassa* |
| gi 169785321 | ref XP_001827121.1 | | *Aspergillus oryzae* |
| gi 171687345 | ref XP_001908613.1 | | *Podospora anserina* |
| gi 495225 | dbj BAA05145.1 | n-alkane-inducible cytochrome P-450 | *Candida maltosa* |
| gi 169778468 | ref XP_001823699.1 | | *Aspergillus oryzae* |
| gi 685237 | emb CAA35593.1 | cytochrome P-450-alk2 | *Candida tropicalis* |
| gi 115398792 | ref XP_001214985.1 | ATEG_05807 | *Aspergillus terreus* |
| gi 156045685 | ref XP_001589398.1 | SS1G_10037 | *Sclerotinia sclerotiorum* |
| gi 116181964 | ref XP_001220831.1 | CHGG_01610 | *Chaetomium globosum* |
| gi 212539338 | ref XP_002149824.1 | N-alkane-inducible cytochrome P450 | *Penicillium marneffei* |
| gi 55823915 | gb AAV66104.1 | cytochrome P450 | *Fusarium heterosporum* |

TABLE 4-continued

| First Database Accession Number | Second Database Accession Number | Name | Species |
|---|---|---|---|
| gi 169786131 | ref XP_001827526.1 | | *Aspergillus oryzae* |
| gi 67526919 | ref XP_661521.1 | AN3917.2 | *Aspergillus nidulans* |
| gi 57157397 | dbj BAD83681.1 | cytochrome P-450 | *Alternaria solani* |
| gi 39954838 | ref XP_364111.1 | MGG_08956 | *Magnaporthe grisea* |
| gi 46108804 | ref XP_381460.1 | FG01284.1 | *Gibberella zeae* |
| gi 167962420 | dbj BAG09241.1 | n-alkane inducible cytochrome P-450 | *Candida maltosa* |
| gi 119469615 | ref XP_001257962.1 | cytochrome P450 alkane hydroxylase | *Neosartorya fischeri* |
| gi 70991773 | ref XP_750735.1 | cytochrome P450 alkane hydroxylase | *Aspergillus fumigatus* |
| gi 171679185 | ref XP_001904540.1 | unnamed protein product | *Podospora anserina* |
| gi 119488606 | ref XP_001262753.1 | n-alkane-inducible cytochrome P450 | *Neosartorya fischeri* |
| gi 218722969 | gb EED22387.1 | cytochrome P450 | *Talaromyces stipitatus* |
| gi 145243244 | ref XP_001394159.1 | An11g01550 | *Aspergillus niger* |
| gi 212533853 | ref XP_002147083.1 | N-alkane-inducible cytochrome P450 | *Penicillium marneffei* |
| gi 218720976 | gb EED20395.1 | cytochrome P450 alkane hydroxylase | *Talaromyces stipitatus* |
| gi 145604320 | ref XP_362943.2 | MGG_08494 | *Magnaporthe grisea* |
| gi 154319876 | ref XP_001559255.1 | BC1G_02419 | *Botryotinia fuckeliana* |
| gi 154272319 | ref XP_001537012.1 | HCAG_08121 | *Ajellomyces capsulatus* |
| gi 39976331 | ref XP_369556.1 | MGG_05908 | *Magnaporthe grisea* |
| gi 116200125 | ref XP_001225874.1 | CHGG_08218 | *Chaetomium globosum* |
| gi 218722681 | gb EED22099.1 | cytochrome P450 alkane hydroxylase | *Talaromyces stipitatus* |
| gi 145606889 | ref XP_361347.2 | MGG_03821 | *Magnaporthe grisea* |
| gi 211592275 | emb CAP98620.1 | Pc22g13320 | *Penicillium chrysogenum* |
| gi 171688034 | ref XP_001908957.1 | unnamed protein product | *Podospora anserina* |
| gi 211587061 | emb CAP94723.1 | Pc18g04990 | *Penicillium chrysogenum* |
| gi 169612986 | ref XP_001799910.1 | SNOG_09621 | *Phaeosphaeria nodorum* |
| gi 212539354 | ref XP_002149832.1 | N-alkane-inducible cytochrome P450 | *Penicillium marneffei* |
| gi 212533239 | ref XP_002146776.1 | cytochrome P450 alkane hydroxylase | *Penicillium marneffei* |
| gi 41079162 | gb AAR99474.1 | alkane monooxygenase P-450 | *Graphium* sp. |
| gi 159122944 | gb EDP48064.1 | cytochrome P450 alkane hydroxylase | *Aspergillus fumigatus* |
| gi 67537376 | ref XP_662462.1 | AN4858.2 | *Aspergillus nidulans* |
| gi 39954738 | ref XP_364102.1 | MGG_08947 | *Magnaporthe grisea* |
| gi 39968921 | ref XP_365851.1 | MGG_10071 | *Magnaporthe grisea* |
| gi 70983886 | ref XP_747469.1 | cytochrome P450 alkane hydroxylase | *Aspergillus fumigatus* |
| gi 171691438 | ref XP_001910644.1 | unnamed protein product | *Podospora anserina* |
| gi 119193452 | ref XP_001247332.1 | CIMG_01103 | *Coccidioides immitis* |
| gi 10303293 | emb CAC10088.1 | related to n-alkane-inducible cytochrome P450 | *Neurospora crassa* |
| gi 169626152 | ref XP_001806478.1 | SNOG_16355 | *Phaeosphaeria nodorum* |
| gi 119191908 | ref XP_001246560.1 | CIMG_00331 | *Coccidioides immitis* |
| gi 154296077 | ref XP_001548471.1 | BC1G_12768 | *Botryotinia fuckeliana* |
| gi 164429645 | ref XP_964653.2 | NCU02031 | *Neurospora crassa* |
| gi 12311700 | emb CAC24473.1 | | *Candida albicans* |
| gi 154305169 | ref XP_001552987.1 | BC1G_08879 | *Botryotinia fuckeliana* |
| gi 39978177 | ref XP_370476.1 | MGG_06973 | *Magnaporthe grisea* |
| gi 70982576 | ref XP_746816.1 | cytochrome P450 alkane hydroxylase | *Aspergillus fumigatus* |
| gi 154319145 | ref XP_001558890.1 | BC1G_02524 | *Botryotinia fuckeliana* |
| gi 46127885 | ref XP_388496.1 | FG08320.1 | *Gibberella zeae* |
| gi 32330665 | gb AAP79879.1 | cytochrome P450 monooxygenase pc-3 | *Phanerochaete chrysosporium* |
| gi 116193605 | ref XP_001222615.1 | CHGG_06520 | *Chaetomium globosum* |
| gi 145241598 | ref XP_001393445.1 | An09g01270 | *Aspergillus niger* |
| gi 149210127 | ref XP_001522438.1 | MGCH7_ch7g545 | *Magnaporthe grisea* |
| gi 121699244 | ref XP_001267956.1 | cytochrome P450 alkane hydroxylase | *Aspergillus clavatus* |
| gi 156032429 | ref XP_001585052.1 | SS1G_13912 | *Sclerotinia sclerotiorum* |
| gi 159122551 | gb EDP47672.1 | cytochrome P450 alkane hydroxylase | *Aspergillus fumigatus* |
| gi 145613078 | ref XP_001412594.1 | MGG_12496 | *Magnaporthe grisea* |

TABLE 4-continued

| First Database Accession Number | Second Database Accession Number | Name | Species |
|---|---|---|---|
| gi 212531571 | ref XP_002145942.1 | N-alkane-inducible cytochrome P450 | *Penicillium marneffei* |
| gi 145252862 | ref XP_001397944.1 | An16g06420 | *Aspergillus niger* |
| gi 169855683 | ref XP_001834508.1 | CC1G_02244 | *Coprinopsis cinerea okayama* |
| gi 212530338 | ref XP_002145326.1 | N-alkane-inducible cytochrome P450 | *Penicillium marneffei* |
| gi 61657996 | gb AAX49400.1 | cytochrome P450 monooxygenase pc-2 | *Phanerochaete chrysosporium* |
| gi 170110164 | ref XP_001886288.1 | CYP63 cytochrome P450 monooxygenase-like protein | *Laccaria bicolor* |
| gi 146323950 | ref XP_748328.2 | cytochrome P450 oxidoreductase/alkane hydroxylase | *Aspergillus fumigatus* |
| gi 156042346 | ref XP_001587730.1 | SS1G_10970 | *Sclerotinia sclerotiorum* |
| gi 189196282 | ref XP_001934479.1 | cytochrome P450 71A23 | *Pyrenophora tritici-repentis* |
| gi 18369901 | gb AAL67906.1 | cytochrome P450 monooxygenase pc-2 | *Phanerochaete chrysosporium* |
| gi 218714942 | gb EED14365.1 | cytochrome P450 | *Talaromyces stipitatus* |
| gi 170106497 | ref XP_001884460.1 | cytochrome P450 | *Laccaria bicolor* |
| gi 169865534 | ref XP_001839366.1 | CC1G_08233 | *Coprinopsis cinerea okayama* |
| gi 169855669 | ref XP_001834501.1 | CC1G_02237 | *Coprinopsis cinerea okayama* |
| gi 189197495 | ref XP_001935085.1 | cytochrome P450 52A1 | *Pyrenophora tritici-repentis* |
| gi 218713646 | gb EED13070.1 | cytochrome P450 | *Talaromyces stipitatus* |
| gi 170106217 | ref XP_001884320.1 | cytochrome P450 | *Laccaria bicolor* |
| gi 116197088 | ref XP_001224356.1 | CHGG_05142 | *Chaetomium globosum* |
| gi 18369899 | gb AAL67905.1 | cytochrome P450 monooxygenase pc-1 | *Phanerochaete chrysosporium* |
| gi 154312290 | ref XP_001555473.1 | BC1G_06178 | *Botryotinia fuckeliana* |
| gi 156064223 | ref XP_001598033.1 | SS1G_00119 | *Sclerotinia sclerotiorum* |
| gi 156039263 | ref XP_001586739.1 | SS1G_11768 | *Sclerotinia sclerotiorum* |
| gi 170105206 | ref XP_001883816.1 | | *Laccaria bicolor* |
| gi 169613228 | ref XP_001800031.1 | SNOG_09744 | *Phaeosphaeria nodorum* |
| gi 169863123 | ref XP_001838184.1 | CC1G_12233 | *Coprinopsis cinerea okayama* |
| gi 67902848 | ref XP_681680.1 | AN8411.2 | *Aspergillus nidulans* |
| gi 158392452 | emb CAO91865.1 | monooxygenase | *Penicillium expansum* |
| gi 169857173 | ref XP_001835239.1 | CC1G_07782 | *Coprinopsis cinerea okayama* |
| gi 169781220 | ref XP_001825073.1 | | *Aspergillus oryzae* |
| gi 67540302 | ref XP_663925.1 | AN6321.2 | *Aspergillus nidulans* |
| gi 145234553 | ref XP_001389925.1 | An03g00180 | *Aspergillus niger* |
| gi 170106275 | ref XP_001884349.1 | | *Laccaria bicolor* |
| gi 145610012 | ref XP_366716.2 | MGG_02792 | *Magnaporthe grisea* |
| gi 119473653 | ref XP_001258702.1 | cytochrome P450 monooxygenase | *Neosartorya fischeri* |
| gi 118026355 | emb CAL69S94.1 | | *Cordyceps bassiana* |
| gi 154309945 | ref XP_001554305.1 | BC1G_06893 | *Botryotinia fuckeliana* |
| gi 211593324 | emb CAP99706.1 | Pc22g24180 | *Penicillium chrysogenum* |
| gi 170111410 | ref XP_001886909.1 | cytochrome P450 monooxygenase CYP63 | *Laccaria bicolor* |
| gi 169864610 | ref XP_001838912.1 | CC1G_05465 | *Coprinopsis cinerea okayama* |
| gi 145240007 | ref XP_001392650.1 | An08g05330 | *Aspergillus niger* |
| gi 115433302 | ref XP_001216788.1 | | *Aspergillus terreus* |
| gi 121701751 | ref XP_001269140.1 | Cytochrome P450 oxidoreductase | *Aspergillus clavatus* |
| gi 154289956 | ref XP_001545581.1 | BC1G_15919 | *Botryotinia fuckeliana* |
| gi 212527006 | ref XP_002143660.1 | cytochrome P450 alkane hydroxylase | *Penicillium marneffei* |
| gi 156054506 | ref XP_001593179.1 | SS1G_06101 | *Sclerotinia sclerotiorum* |
| gi 167962125 | dbj BAG09240.1 | n-alkane inducible cytochrome P-450 | *Candida maltosa* |
| gi 169610561 | ref XP_001798699.1 | SNOG_08385 | *Phaeosphaeria nodorum* |
| gi 154322320 | ref XP_001560475.1 | BC1G_01307 | *Botryotinia fuckeliana* |
| gi 171986596 | gb ACB59278.1 | cytochrome P450 monooxygenase | *Pseudozyma flocculosa* |
| gi 169850022 | ref XP_001831709.1 | CC1G_12229 | *Coprinopsis cinerea okayama* |

TABLE 4-continued

| First Database Accession Number | Second Database Accession Number | Name | Species |
|---|---|---|---|
| gi 84514171 | gb ABC59094.1 | cytochrome P450 monooxygenase CYP704G9 | *Medicago truncatula* |
| gi 157349259 | emb CAO24405.1 | | *Vitis vinifera* |
| gi 154322983 | ref XP_001560806.1 | BC1G_00834 | *Botryotinia fuckeliana* |
| gi 71726950 | gb AAZ39646.1 | cytochrome P450 monooxygenase | *Petunia × hybrida* |
| gi 2160323 | dbj BAA05146.1 | n-alkane-inducible cytochrome P-450 | *Candida maltosa* |
| gi 218717320 | gb EED16741.1 | cytochrome P450 | *Talaromyces stipitatus* |
| gi 118485860 | gb ABK94777.1 | | *Populus trichocarpa* |
| gi 71024781 | ref XP_762620.1 | UM06473.1 | *Ustilago maydis* |
| gi 58265104 | ref XP_569708.1 | | *Cryptococcus neoformans* var. *neoformans* |
| gi 169596949 | ref XP_001791898.1 | SNOG_01251 | *Phaeosphaeria nodorum* |
| gi 157355912 | emb CAO49769.1 | | *Vitis vinifera* |
| gi 134109309 | ref XP_776769.1 | CNBC2600 | *Cryptococcus neoformans* var. *neoformans* |
| gi 157349262 | emb CAO24408.1 | | *Vitis vinifera* |
| gi 147765747 | emb CAN60189.1 | | *Vitis vinifera* |
| gi 169864676 | ref XP_001838945.1 | CC1G_05498 | *Coprinopsis cinerea okayama* |
| gi 157352095 | emb CAO43102.1 | | *Vitis vinifera* |
| gi 147791153 | emb CAN63571.1 | | *Vitis vinifera* |
| gi 84514173 | gb ABC59095.1 | cytochrome P450 monooxygenase CYP704G7 | *Medicago truncatula* |
| gi 71024761 | ref XP_762610.1 | UM06463.1 | *Ustilago maydis* |
| gi 157355911 | emb CAO49768.1 | | *Vitis vinifera* |
| gi 115451645 | ref NP_001049423.1 | Os03g0223100 | *Oryza sativa* |
| gi 22748335 | gb AAN05337.1 | cytochrome P450 | *Oryza sativa* |
| gi 168059245 | ref XP_001781614.1 | | *Physcomitrella patens* subsp. *patens* |
| gi 15225499 | ref NP_182075.1 | CYP704A2 (cytochrome P450, family 704, subfamily A, polypeptide 2) oxygen binding | *Arabidopsis thaliana* |
| gi 75319885 | sp Q50EK3.1 | C04C1_PINTA (Cytochrome P450 704C1) | |
| gi 167521978 | ref XP_001745327.1 | | *Monosiga brevicollis* |
| gi 21536522 | gb AAM60854.1 | cytochrome P450-like protein | *Arabidopsis thaliana* |
| gi 15242759 | ref NP_201150.1 | CYP94B1 (cytochrome P450, family 94, subfamily B, polypeptide 1) oxygen binding | *Arabidopsis thaliana* |
| gi 168031659 | ref XP_001768338.1 | | *Physcomitrella patens* subsp. *patens* |
| gi 157339131 | emb CAO42482.1 | | *Vitis vinifera* |
| gi 30682301 | ref NP_196442.2 | cytochrome P450 family protein | *Arabidopsis thaliana* |
| gi 8346562 | emb CAB93726.1 | cytochrome P450-like protein | *Arabidopsis thaliana* |
| gi 2344895 | gb AAC31835.1 | cytochrome P450 | *Arabidopsis thaliana* |
| gi 30689861 | ref NP_850427.1 | CYP704A1 (cytochrome P450, family 704, subfamily A, polypeptide 1) oxygen binding | *Arabidopsis thaliana* |
| gi 15221776 | ref NP_173862.1 | CYP86C1 (cytochrome P450, family 86, subfamily C, polypeptide 1) oxygen binding | *Arabidopsis thaliana* |
| gi 147793015 | emb CAN77648.1 | | *Vitis vinifera* |
| gi 157356646 | emb CAO62841.1 | | *Vitis vinifera* |
| gi 147844260 | emb CAN80040.1 | | *Vitis vinifera* |
| gi 215466577 | gb EEB96517.1 | MPER_04337 | *Moniliophthora perniciosa* |
| gi 15222515 | ref NP_176558.1 | CYP86A7 (cytochrome P450, family 86, subfamily A, polypeptide 7) oxygen binding | *Arabidopsis thaliana* |
| gi 194697724 | gb ACF82946.1 | | *Zea mays* |
| gi 168021353 | ref XP_001763206.1 | | *Physcomitrella patens* subsp. *patens* |

TABLE 4-continued

| First Database Accession Number | Second Database Accession Number | Name | Species |
|---|---|---|---|
| gi 115483036 | ref NP_001065111.1 | Os10g0525000 | *Oryza sativa* (*japonica* cultivar-group) |
| gi 157338660 | emb CAO42011.1 | | *Vitis vinifera* |
| gi 147836212 | emb CAN75428.1 | | *Vitis vinifera* |
| gi 5042165 | emb CAB44684.1 | cytochrome P450-like protein | *Arabidopsis thaliana* |
| gi 79326551 | ref NP_001031814.1 | CYP96A10 (cytochrome P450, family 96, subfamily A, polypeptide 10) heme binding/iron ion binding/ monooxygenase | *Arabidopsis thaliana* |
| gi 26452145 | dbj BAC43161.1 | cytochrome P450 | *Arabidopsis thaliana* |
| gi 110289450 | gb AAP54707.2 | Cytochrome P450 family protein, expressed | *Oryza sativa* |
| gi 21593258 | gb AAM65207.1 | cytochrome P450 | *Arabidopsis thaliana* |
| gi 115483034 | ref NP_001065110.1 | Os10g0524700 | *Oryza sativa* |
| gi 118486379 | gb ABK95030.1 | | *Populus trichocarpa* |
| gi 10442763 | gb AAG17470.1 | AF123610_9 cytochrome P450 | *Triticum aestivum* |
| gi 125532704 | gb EAY79269.1 | OsI_34384 | *Oryza sativa* |
| gi 15237250 | ref NP_197710.1 | CYP86B1 (cytochrome P450, family 86, subfamily B, polypeptide 1) oxygen binding | *Arabidopsis thaliana* |
| gi 125549414 | gb EAY95236.1 | OsI_17053 | *Oryza sativa* |
| gi 110289453 | gb AAP54710.2 | Cytochrome P450 family protein | *Oryza sativa* |
| gi 20146744 | gb AAM12480.1 | AC074232_7 cytochrome P450-like protein | *Oryza sativa* |
| gi 218184911 | gb EEC67338.1 | OsI_34388 | *Oryza sativa Indica* Group |
| gi 125549325 | gb EAY95147.1 | OsI_16965 | *Oryza sativa Indica* Group |
| gi 198472816 | ref XP_002133118.1 | GA29000 | *Drosophila pseudoobscura pseudoobscura* |
| gi 195574346 | ref XP_002105150.1 | GD21336 | *Drosophila simulans* |
| gi 168024173 | ref XP_001764611.1 | | *Physcomitrella patens* subsp. *patens* |
| gi 115440549 | ref NP_001044554.1 | Os01g0804400 | *Oryza sativa* (*japonica* cultivar-group) |
| gi 15223657 | ref NP_176086.1 | CYP96A15/MAH1 (MID-CHAIN ALKANE HYDROXYLASE 1) oxygen binding | *Arabidopsis thaliana* |
| gi 125540131 | gb EAY86526.1 | OsI_07906 | *Oryza sativa* |
| gi 115460030 | ref NP_001053615.1 | Os04g0573900 | *Oryza sativa* (*japonica* cultivar-group) |
| gi 157349258 | emb CAO24404.1 | | *Vitis vinifera* |
| gi 157346575 | emb CAO16644.1 | | *Vitis vinifera* |
| gi 147835182 | emb CAN76753.1 | | *Vitis vinifera* |
| gi 195613956 | gb ACG28808.1 | | *Zea mays* |
| gi 194753285 | ref XP_001958947.1 | GF12635 | *Drosophila ananassae* |
| gi 156546811 | ref XP_001606040.1 | | *Nasonia vitripennis* |
| gi 125583181 | gb EAZ24112.1 | OsJ_007595 | *Oryza sativa* (*japonica* cultivar-group) |
| gi 15229477 | ref NP_189243.1 | CYP86C2 (cytochrome P450, family 86, subfamily C, polypeptide 2) oxygen binding | *Arabidopsis thaliana* |
| gi 940446 | emb CAA62082.1 | cytochrome p450 | *Arabidopsis thaliana* |
| gi 115447789 | ref NP_001047674.1 | Os02g0666500 | *Oryza sativa* (*japonica* cultivar-group) |
| gi 15227788 | ref NP_179899.1 | CYP96A1 (cytochrome P450, family 96, subfamily A, polypeptide 1) oxygen binding | *Arabidopsis thaliana* |
| gi 195503768 | ref XP_002098791.1 | GE23738 | *Drosophila yakuba* |
| gi 147804860 | emb CAN66874.1 | | *Vitis vinifera* |
| gi 84514169 | gb ABC59093.1 | cytochrome P450 monooxygenase CYP94C9 | *Medicago truncatula* |
| gi 19698839 | gb AAL91155.1 | cytochrome P450 | *Arabidopsis thaliana* |
| gi 15237768 | ref NP_200694.1 | CYP86A1 (cytochrome P450, family 86, subfamily A, polypeptide 1) oxygen binding | *Arabidopsis thaliana* |

TABLE 4-continued

| First Database Accession Number | Second Database Accession Number | Name | Species |
|---|---|---|---|
| gi 157353969 | emb CAO46510.1 | | *Vitis vinifera* |
| gi 169865676 | ref XP_001839436.1 | CC1G_06649 | *Coprinopsis cinerea okayama* |
| gi 85001697 | gb ABC68403.1 | cytochrome P450 monooxygenase CYP86A24 | *Glycine max* |
| gi 115466172 | ref NP_001056685.1 | Os06g0129900 | *Oryza sativa* |
| gi 195637782 | gb ACG38359.1 | cytochrome P450 86A2 | *Zea mays* |
| gi 194704220 | gb ACF86194.1 | | *Zea mays* |
| gi 71006408 | ref XP_757870.1 | UM01723.1 | *Ustilago maydis* 521 |
| gi 195161677 | ref XP_002021689.1 | GL26642 | *Drosophila persimilis* |
| gi 115459886 | ref NP_001053543.1 | Os04g0560100 | *Oryza sativa* |
| gi 194704096 | gb ACF86132.1 | | *Zea mays* |
| gi 147773635 | emb CAN67559.1 | | *Vitis vinifera* |
| gi 125575195 | gb EAZ16479.1 | OsJ_030688 | *Oryza sativa* |
| gi 115482616 | ref NP_001064901.1 | Os10g0486100 | *Oryza sativa* |
| gi 71726942 | gb AAZ39642.1 | cytochrome P450 fatty acid omega-hydroxylase | *Petunia* x *hybrida* |
| gi 195626182 | gb ACG34921.1 | cytochrome P450 86A1 | *Zea mays* |
| gi 194907382 | ref XP_001981543.1 | GG11553 | *Drosophila erecta* |
| gi 71006688 | ref XP_758010.1 | UM01863.1 | *Ustilago maydis* |
| gi 157346247 | emb CAO15944.1 | | *Vitis vinifera* |
| gi 116830948 | gb ABK28430.1 | | *Arabidopsis thaliana* |
| gi 13641298 | gb AAK31592.1 | cytochrome P450 | *Brassica rapa* subsp. *pekinensis* |
| gi 2258321 | gb AAB63277.1 | cytochrome P450 | *Phanerochaete chrysosporium* |
| gi 15218671 | ref NP_174713.1 | CYP94D1 (cytochrome P450, family 94, subfamily D, polypeptide 1) oxygen binding | *Arabidopsis thaliana* |
| gi 195623910 | gb ACG33785.1 | cytochrome P450 86A1 | *Zea mays* |
| gi 157337152 | emb CAO21498.1 | | *Vitis vinifera* |

In some embodiments of the invention it is advantageous to integrate one or more genes encoding a P450 enzyme—into a yeast strain, a species of the genus *Candida* or a strain of *Candida tropicalis* in which genes or pathways that cause further oxidation of the substrate have been disrupted. In some embodiments, a strain of yeast in which one or more cytochrome P450s or one or more alcohol oxidase or one or more alcohol dehydrogenase have been disrupted will oxidize hydroxyl groups to aldehydes or acids more slowly than strains of yeast in which these genes have not been disrupted.

In some embodiments of the invention it may be advantageous to integrate a cytochrome P450 into a strain of *Candida tropicalis* in which fatty alcohol oxidase genes FAO1, FAO1B, FAO2 and FAO2B have been disrupted. In some embodiments of the invention it may be advantageous to integrate a cytochrome P450 into a strain of *Candida tropicalis* in which at least one of the fatty alcohol oxidase genes FAO1, FAO1B, FAO2 and FAO2B have been disrupted. In some embodiments of the invention it may be advantageous to integrate a cytochrome P450 into a strain of *Candida tropicalis* in which alcohol dehydrogenase genes ADH-A4, ADH-A4B, ADH-B4, ADH-B4B, ADH-A10 and ADH-B11 have been disrupted. In some embodiments of the invention it may be advantageous to integrate a cytochrome P450 into a strain of *Candida tropicalis* in which one or more of the alcohol dehydrogenase genes ADH-A4, ADH-A4B, ADH-B4, ADH-B4B, ADH-A10, ADH-A10B, ADH-B1B and ADH-B11 have been disrupted. In some embodiments of the invention it may be advantageous to integrate a gene encoding a cytochrome P450 into a yeast species of the genus *Candida* in which one or more alcohol dehydrogenase genes have been disrupted, and wherein the disrupted alcohol dehydrogenase gene shares at least 95% nucleotide identity, or at least 90% nucleotide identity, or at least 85% nucleotide identity for a stretch of at least 100 contiguous nucleotides, or at least 80% identical for a stretch of at least 100 contiguous nucleotides of the coding sequence, or at least 75% identical for a stretch of at least 100 contiguous nucleotides of the coding sequence, or at least 70% identical for a stretch of at least 100 contiguous nucleotides of the coding sequence, or at least 65% identical for a stretch of at least 100 contiguous nucleotides of the coding sequence, or at least 60% identical for a stretch of at least 100 contiguous nucleotides of the coding sequence within the coding region with one of the *Candida tropicalis* genes ADH-A4 (SEQ ID NO: 39), ADH-B4 (SEQ ID NO: 42), ADH-A10 (SEQ ID NO: 40), ADH-A10B (SEQ ID NO: 56), ADH-B11 (SEQ ID NO: 43).

In some embodiments it may be advantageous to integrate a gene encoding a cytochrome P450 into a yeast strain of the genus *Candida* in which (i) one or more alcohol dehydrogenase genes have been disrupted and (ii) the disrupted alcohol dehydrogenase comprises a first peptide. In some embodiments the first peptide has the sequence VKYSGVCH (SEQ ID NO: 156). In some embodiments the first peptide has the sequence VKYSGVCHxxxxxWKGDW (SEQ ID NO: 162). In some embodiments the first peptide has the sequence KYSGVCHxxxxxWKGDWxxxxKLPxVGGHEGAGVVV (SEQ ID NO: 163). In some embodiments the disrupted alcohol dehydrogenase sequence, predicted from translation of the gene that encodes it, comprises a second peptide. In some embodiments the second peptide has the sequence QYATADAVQAA (SEQ ID NO: 158). In some embodiments the second peptide has the sequence SGYxHDGxFxQYATADAVQAA (SEQ ID NO: 164). In some embodiments the second peptide has the sequence GAEPNCxxADxSGYxHDGxFxQYATADAVQAA (SEQ ID NO: 165).

In some embodiments the disrupted alcohol dehydrogenase sequence, predicted from translation of the gene that encodes it, comprises a third peptide. In some embodiments the third peptide has the sequence CAGVTVYKALK (SEQ ID NO: 159). In some embodiments the third peptide has the sequence APIxCAGVTVYKALK (SEQ ID NO: 166).

In some embodiments the first genetic modification class comprises disruption of at least one alcohol dehydrogenase whose amino acid sequence, predicted from translation of the gene that encodes it, comprises a fourth peptide. In some embodiments the fourth peptide has the sequence GQWVAISGA (SEQ ID NO: 160). In some embodiments the fourth peptide has the sequence GQWVAISGAxGGLGSL (SEQ ID NO: 167). In some embodiments the fourth peptide has the sequence GQWVAISGAxGGLGSLxVQYA (SEQ ID NO: 168). In some embodiments the fourth peptide has the sequence GQWVAISGAxGGLGSLxVQYAxAMG (SEQ ID NO: 169). In some embodiments the fourth peptide has the sequence GQWVAISGAxGGLGSLxVQYAxAMGxRVxAIDGG (SEQ ID NO: 170).

In some embodiments the disrupted alcohol dehydrogenase sequence, predicted from translation of the gene that encodes it, comprises a fifth peptide. In some embodiments said fifth peptide has the sequence VGGHEGAGVVV (SEQ ID NO: 157).

In some embodiments of the invention it may be advantageous to integrate a cytochrome P450 into a strain of *Candida tropicalis* in which cytochrome P450 genes CYP52A17, CYP52A18, CYP52A13, CYP52A14, CYP52A12 and CYP52A12B have been disrupted. In some embodiments it may be advantageous to integrate a cytochrome P450 into a strain of *Candida tropicalis* in which one or more of the cytochrome P450 genes CYP52A17, CYP52A18, CYP52A13, CYP52A14, CYP52A12 and CYP52A12B have been disrupted. In some embodiments it may be advantageous to integrate a cytochrome P450 into a strain of *Candida tropicalis* in which fatty alcohol oxidase genes FAO1, FAO1B, FAO2 and FAO2B, alcohol dehydrogenase genes ADH-A4, ADH-A4B, ADH-B4, ADH-B4B, ADH-A10 and ADH-B11 and cytochrome P450 genes CYP52A17, CYP52A18, CYP52A13, CYP52A14, CYP52A12 and CYP52A12B have been disrupted, for example strain DP421, in which the β-oxidation pathway has also been disrupted.

In some embodiments, a cytochrome P450 is integrated into a strain of *Candida tropicalis* in which endogenous cytochrome P450s have been disrupted.

In some embodiments, a cytochrome P450 is integrated into a strain of *Candida* in which endogenous cytochrome P450s have been disrupted.

In some embodiments, a cytochrome P450 is integrated into a strain of yeast of a species of the genus *Candida* in which endogenous cytochrome P450s have been disrupted.

In some embodiments, one or more genes, two or more genes, or three or more genes listed in Table 4 are integrated into a yeast strain, a species of *Candida*, or a strain of *Candida tropicalis* in which genes or pathways that cause further oxidation of a fatty acid substrate (e.g., a α-carboxyl-ω-hydroxy fatty acid having a carbon chain length in the range from C6 to C22, an α,ω-dicarboxylic fatty acid having a carbon chain length in the range from C6 to C22, or mixtures thereof) have been disrupted. In some embodiments, this strain of yeast is one in which one or more disrupted cytochrome P450s, or one or more disrupted alcohol oxidases, or one or more disrupted alcohol dehydrogenases present in the strain of yeast will oxidize hydroxyl groups to aldehydes or acids more slowly than strains of yeast in which these genes have not been disrupted. In some embodiments, this strain of yeast is one in which one or more disrupted cytochrome P450s, one or more disrupted alcohol oxidases, and one or more disrupted alcohol dehydrogenases will oxidize hydroxyl groups to aldehydes or acids more slowly than strains of yeast in which these genes have not been disrupted.

In some embodiments, one or more genes, two or more genes, or three or more genes listed in Table 4 are integrated into a strain of *Candida tropicalis* in which fatty alcohol oxidase genes FAO1, FAO1B, FAO2 and FAO2B have been disrupted.

In some embodiments, one or more genes, two or more genes, or three or more genes listed in Table 4 are integrated into a strain of *Candida tropicalis* in which endogenous alcohol dehydrogenase genes ADH-A4, ADH-A4B, ADH-B4, ADH-B4B, ADH-A10 and ADH-B11 have been disrupted.

In some embodiments, one or more genes, two or more genes, or three or more genes listed in Table 4 are integrated into a strain of *Candida tropicalis* in which endogenous cytochrome P450 genes CYP52A17, CYP52A18, CYP52A13, CYP52A14, CYP52A12 and CYP52A12B have been disrupted.

In some embodiments, one or more genes, two or more genes, or three or more genes listed in Table 4 are integrated into a strain of *Candida tropicalis* in which fatty alcohol oxidase genes FAO1, FAO1B, FAO2 and FAO2B, alcohol dehydrogenase genes ADH-A4, ADH-A4B, ADH-B4, ADH-B4B, ADH-A10 and ADH-B11 and cytochrome P450 genes CYP52A17, CYP52A18, CYP52A13, CYP52A14, CYP52A12 and CYP52A12B have been disrupted, for example strain DP421, in which the β-oxidation pathway has also been disrupted.

In some embodiments, one or more genes, two or more genes, or three or more genes listed in Table 4 are integrated into a strain of *Candida tropicalis* in which endogenous cytochrome P450s have been disrupted.

In some embodiments, one or more genes, two or more genes, or three or more genes listed in Table 4 are integrated into a strain of *Candida* in which endogenous cytochrome P450s have been disrupted.

In some embodiments, a gene having at least 40 percent sequence identity, at least 45 percent sequence identity, at least 50 percent sequence identity, at least 55 percent sequence identity, at least 60 percent sequence identity, at least 65 percent sequence identity, at least 70 percent sequence identity, at least 75 percent sequence identity, at least 80 percent sequence identity, at least 85 percent sequence identity, at least 90 percent sequence identity, or at least 95 percent sequence identity to a gene listed in Table 4 is integrated into a yeast strain, a species of *Candida*, or a strain of *Candida tropicalis* in which genes or pathways that cause further oxidation of a fatty acid substrate (e.g., a α-carboxyl-ω-hydroxy fatty acid having a carbon chain length in the range from C6 to C22, an α,ω-dicarboxylic fatty acid having a carbon chain length in the range from C6 to C22, or mixtures thereof) have been disrupted. In some embodiments, this strain of yeast is one in which one or more disrupted cytochrome P450s, or one or more disrupted alcohol oxidases, or one or more disrupted alcohol dehydrogenases present in the strain of yeast will oxidize hydroxyl groups to aldehydes or acids more slowly than strains of yeast in which these genes have not been disrupted. In some embodiments, this strain of yeast is one in which one or more disrupted cytochrome P450s, one or more disrupted alcohol oxidases, and one or more disrupted alcohol dehydrogenases will oxidize hydroxyl groups to aldehydes or acids more slowly than strains of yeast in which these genes have not been disrupted.

In some embodiments, a gene having at least 40 percent sequence identity, at least 45 percent sequence identity, at least 50 percent sequence identity, at least 55 percent sequence identity, at least 60 percent sequence identity, at least 65 percent sequence identity, at least 70 percent sequence identity, at least 75 percent sequence identity, at least 80 percent sequence identity, at least 85 percent sequence identity, at least 90 percent sequence identity, or at least 95 percent sequence identity to a gene listed in Table 4 is integrated into a strain of *Candida tropicalis* in which fatty alcohol oxidase genes FAO1, FAO1B, FAO2 and FAO2B have been disrupted.

In some embodiments, a gene having at least 40 percent sequence identity, at least 45 percent sequence identity, at least 50 percent sequence identity, at least 55 percent sequence identity, at least 60 percent sequence identity, at least 65 percent sequence identity, at least 70 percent sequence identity, at least 75 percent sequence identity, at least 80 percent sequence identity, at least 85 percent sequence identity, at least 90 percent sequence identity, or at least 95 percent sequence identity to a gene listed in Table 4 is integrated into a strain of *Candida tropicalis* in which endogenous alcohol dehydrogenase genes ADH-A4, ADH-A4B, ADH-B4, ADH-B4B, ADH-A10 and ADH-B11 have been disrupted.

In some embodiments, a gene having at least 40 percent sequence identity, at least 45 percent sequence identity, at least 50 percent sequence identity, at least 55 percent sequence identity, at least 60 percent sequence identity, at least 65 percent sequence identity, at least 70 percent sequence identity, at least 75 percent sequence identity, at least 80 percent sequence identity, at least 85 percent sequence identity, at least 90 percent sequence identity, or at least 95 percent sequence identity to a gene listed in Table 4 is integrated into a strain of yeast species of the genus *Candida* in which one or more alcohol dehydrogenase genes have been disrupted, and wherein at least one disrupted alcohol dehydrogenase gene shares at least 95% nucleotide identity, or at least 90% nucleotide identity, or at least 85% nucleotide identity for a stretch of at least 100 contiguous nucleotides within the coding region, or at least 80% identical for a stretch of at least 100 contiguous nucleotides of the coding sequence, or at least 75% identical for a stretch of at least 100 contiguous nucleotides of the coding sequence, or at least 70% identical for a stretch of at least 100 contiguous nucleotides of the coding sequence, or at least 65% identical for a stretch of at least 100 contiguous nucleotides of the coding sequence, or at least 60% identical for a stretch of at least 100 contiguous nucleotides of the coding sequence with one of the *Candida tropicalis* genes ADH-A4 (SEQ ID NO: 39), ADH-B4 (SEQ ID NO: 42), ADH-A10 (SEQ ID NO: 40), ADH-A10B (SEQ ID NO: 56), ADH-B11 (SEQ ID NO: 43).

In some embodiments, a gene listed in Table 4 is integrated into a strain of yeast of the genus *Candida* in which (i) one or more alcohol dehydrogenase genes has been disrupted and (ii) at least one disrupted alcohol dehydrogenase gene comprises a first peptide. In some embodiments the first peptide has the sequence VKYSGVCH (SEQ ID NO: 156). In some embodiments the first peptide has the sequence VKYSGVCHxxxxxWKGDW (SEQ ID NO: 162). In some embodiments the first peptide has the sequence VKYSGVCHxxxxxWKGDWxxxxKLPxVGGHEGAGVVV (SEQ ID NO: 163). In some embodiments the disrupted alcohol dehydrogenase sequence, predicted from translation of the gene that encodes it, comprises a second peptide. In some embodiments the second peptide has the sequence QYATADAVQAA (SEQ ID NO: 158). In some embodiments the second peptide has the sequence SGYxHDGxFxQYATADAVQAA (SEQ ID NO: 164). In some embodiments the second peptide has the sequence GAEPNCxxADxSGYxHDGxFxQYATADAVQAA (SEQ ID NO: 165).

In some embodiments the disrupted alcohol dehydrogenase sequence, predicted from translation of the gene that encodes it, comprises a third peptide. In some embodiments the third peptide has the sequence CAGVTVYKALK (SEQ ID NO: 159). In some embodiments the third peptide has the sequence APIxCAGVTVYKALK (SEQ ID NO: 166).

In some embodiments the fourth peptide has the sequence GQWVAISGA (SEQ ID NO: 160). In some embodiments the fourth peptide has the sequence GQWVAISGAxGGLGSL (SEQ ID NO: 167). In some embodiments the fourth peptide has the sequence GQWVAISGAxGGLGSLxVQYA (SEQ ID NO: 168). In some embodiments, the fourth peptide has the sequence GQWVAISGAxGGLGSLxVQYAxAMG (SEQ ID NO: 169). In some embodiments the fourth peptide has the sequence GQWVAISGAxGGLGSLxVQYAxAMGxRVxAIDGG (SEQ ID NO: 170).

In some embodiments the disrupted alcohol dehydrogenase sequence, predicted from translation of the gene that encodes it, comprises a fifth peptide. In some embodiments the fifth peptide has the sequence VGGHEGAGVVV (SEQ ID NO: 157).

In some embodiments, a gene having at least 40 percent sequence identity, at least 45 percent sequence identity, at least 50 percent sequence identity, at least 55 percent sequence identity, at least 60 percent sequence identity, at least 65 percent sequence identity, at least 70 percent sequence identity, at least 75 percent sequence identity, at least 80 percent sequence identity, at least 85 percent sequence identity, at least 90 percent sequence identity, or at least 95 percent sequence identity to a gene listed in Table 4 is integrated into a strain of yeast species of the genus *Candida* in which one or more alcohol dehydrogenase genes have been disrupted and wherein at least one disrupted alcohol dehydrogenase gene comprises a first peptide. In some embodiments the first peptide has the sequence VKYSGVCH (SEQ ID NO: 156). In some embodiments the first peptide has the sequence VKYSGVCHxxxxxWKGDW (SEQ ID NO: 162). In some embodiments the first peptide has the sequence VKYSGVCHxxxxxWKGDWxxxxKLPxVGGHEGAGVVV (SEQ ID NO: 163). In some embodiments the disrupted alcohol dehydrogenase sequence, predicted from translation of the gene that encodes it, comprises a second peptide. In some embodiments the second peptide has the sequence QYATADAVQAA (SEQ ID NO: 158). In some embodiments the second peptide has the sequence SGYxHDGxFxQYATADAVQAA (SEQ ID NO: 164). In some embodiments the second peptide has the sequence GAEPNCxxADxSGYxHDGxFxQYATADAVQAA (SEQ ID NO: 165).

In some embodiments, the disrupted alcohol dehydrogenase sequence, predicted from translation of the gene that encodes it, comprises a third peptide. In some embodiments the third peptide has the sequence CAGVTVYKALK (SEQ ID NO: 159). In some embodiments the third peptide has the sequence APIxCAGVTVYKALK (SEQ ID NO: 166).

In some embodiments the first genetic modification class comprises disruption of at least one alcohol dehydrogenase whose amino acid sequence, predicted from translation of the gene that encodes it, comprises a fourth peptide. In some embodiments the fourth peptide has the sequence GQWVAISGA (SEQ ID NO: 160). In some embodiments the fourth peptide has the sequence GQWVAISGAxGGLGSL (SEQ ID NO: 167). In some embodiments the fourth peptide has the sequence GQWVAISGAxGGLGSLxVQYA (SEQ ID NO: 168). In some embodiments, the fourth peptide has the sequence GQWVAISGAxGGLGSLxVQYAxAMG (SEQ ID NO: 169). In some embodiments the fourth peptide has the sequence GQWVAISGAxGGLGSLxVQYAxAM-GxRVxAIDGG (SEQ ID NO: 170).

In some embodiments the disrupted alcohol dehydrogenase sequence, predicted from translation of the gene that encodes it, comprises a fifth peptide. In some embodiments said fifth peptide has the sequence VGGHEGAGVVV (SEQ ID NO: 157).

In some embodiments, a gene having at least 40 percent sequence identity, at least 45 percent sequence identity, at least 50 percent sequence identity, at least 55 percent sequence identity, at least 60 percent sequence identity, at least 65 percent sequence identity, at least 70 percent sequence identity, at least 75 percent sequence identity, at least 80 percent sequence identity, at least 85 percent sequence identity, at least 90 percent sequence identity, or at least 95 percent sequence identity to a gene listed in Table 4 is integrated into a strain of *Candida tropicalis* in which endogenous cytochrome P450 genes CYP52A17, CYP52A18, CYP52A13, CYP52A14, CYP52A12 and CYP52A12B have been disrupted.

In some embodiments, a gene having at least 40 percent sequence identity, at least 45 percent sequence identity, at least 50 percent sequence identity, at least 55 percent sequence identity, at least 60 percent sequence identity, at least 65 percent sequence identity, at least 70 percent sequence identity, at least 75 percent sequence identity, at least 80 percent sequence identity, at least 85 percent sequence identity, at least 90 percent sequence identity, or at least 95 percent sequence identity to a gene listed in Table 4 is integrated into a strain of *Candida tropicalis* in which fatty alcohol oxidase genes FAO1, FAO1B, FAO2 and FAO2B, alcohol dehydrogenase genes ADH-A4, ADH-A4B, ADH-B4, ADH-B4B, ADH-A10 and ADH-B11 and cytochrome P450 genes CYP52A17, CYP52A18, CYP52A13, CYP52A14, CYP52A12 and CYP52A12B have been disrupted, for example strain DP421, in which the β-oxidation pathway has also been disrupted.

In some embodiments, a gene having at least 40 percent sequence identity, at least 45 percent sequence identity, at least 50 percent sequence identity, at least 55 percent sequence identity, at least 60 percent sequence identity, at least 65 percent sequence identity, at least 70 percent sequence identity, at least 75 percent sequence identity, at least 80 percent sequence identity, at least 85 percent sequence identity, at least 90 percent sequence identity, or at least 95 percent sequence identity to a gene listed in Table 4 is integrated into a strain of *Candida tropicalis* in which endogenous cytochrome P450s have been disrupted.

In some embodiments, a gene having at least 40 percent sequence identity, at least 45 percent sequence identity, at least 50 percent sequence identity, at least 55 percent sequence identity, at least 60 percent sequence identity, at least 65 percent sequence identity, at least 70 percent sequence identity, at least 75 percent sequence identity, at least 80 percent sequence identity, at least 85 percent sequence identity, at least 90 percent sequence identity, or at least 95 percent sequence identity to a gene listed in Table 4 is integrated into a strain of *Candida* in which endogenous cytochrome P450s have been disrupted.

In some embodiments, a gene having at least 40 percent sequence identity, at least 45 percent sequence identity, at least 50 percent sequence identity, at least 55 percent sequence identity, at least 60 percent sequence identity, at least 65 percent sequence identity, at least 70 percent sequence identity, at least 75 percent sequence identity, at least 80 percent sequence identity, at least 85 percent sequence identity, at least 90 percent sequence identity, or at least 95 percent sequence identity to a gene listed in Table 4 is integrated into a yeast strain, a species of *Candida*, or a strain of *Candida tropicalis* in which genes or pathways that cause further oxidation of a fatty acid substrate (e.g., a α-carboxyl-ω-hydroxy fatty acid having a carbon chain length in the range from C6 to C22, an α,ω-dicarboxylic fatty acid having a carbon chain length in the range from C6 to C22, or mixtures thereof) have been disrupted. In some embodiments, this strain of yeast is one in which one or more disrupted cytochrome P450s, or one or more disrupted alcohol oxidases, or one or more disrupted alcohol dehydrogenases present in the strain of yeast will oxidize hydroxyl groups to aldehydes or acids more slowly than strains of yeast in which these genes have not been disrupted. In some embodiments, this strain of yeast is one in which one or more disrupted cytochrome P450s, one or more disrupted alcohol oxidases, and one or more disrupted alcohol dehydrogenases will oxidize hydroxyl groups to aldehydes or acids more slowly than strains of yeast in which these genes have not been disrupted.

In some embodiments, a gene having at least 40 percent sequence identity, at least 45 percent sequence identity, at least 50 percent sequence identity, at least 55 percent sequence identity, at least 60 percent sequence identity, at least 65 percent sequence identity, at least 70 percent sequence identity, at least 75 percent sequence identity, at least 80 percent sequence identity, at least 85 percent sequence identity, at least 90 percent sequence identity, or at least 95 percent sequence identity to a gene listed in Table 4 is integrated into a strain of *Candida tropicalis* in which fatty alcohol oxidase genes FAO1, FAO1B, FAO2 and FAO2B have been disrupted.

In some embodiments, a gene having at least 40 percent sequence identity, at least 45 percent sequence identity, at least 50 percent sequence identity, at least 55 percent sequence identity, at least 60 percent sequence identity, at least 65 percent sequence identity, at least 70 percent sequence identity, at least 75 percent sequence identity, at least 80 percent sequence identity, at least 85 percent sequence identity, at least 90 percent sequence identity, or at least 95 percent sequence identity to a gene listed in Table 4 is integrated into a strain of *Candida tropicalis* in which endogenous alcohol dehydrogenase genes ADH-A4, ADH-A4B, ADH-B4, ADH-B4B, ADH-A10 and ADH-B11 have been disrupted.

In some embodiments, a gene having at least 40 percent sequence identity, at least 45 percent sequence identity, at least 50 percent sequence identity, at least 55 percent sequence identity, at least 60 percent sequence identity, at least 65 percent sequence identity, at least 70 percent sequence identity, at least 75 percent sequence identity, at least 80 percent sequence identity, at least 85 percent sequence identity, at least 90 percent sequence identity, or at least 95 percent sequence identity to a gene listed in Table 4 is integrated into a strain of *Candida tropicalis* in which endogenous cytochrome P450 genes CYP52A17, CYP52A18, CYP52A13, CYP52A14, CYP52A12 and CYP52A12B have been disrupted.

In some embodiments, a gene having at least 40 percent sequence identity, at least 45 percent sequence identity, at least 50 percent sequence identity, at least 55 percent sequence identity, at least 60 percent sequence identity, at least 65 percent sequence identity, at least 70 percent sequence identity, at least 75 percent sequence identity, at least 80 percent sequence identity, at least 85 percent sequence identity, at least 90 percent sequence identity, or at least 95 percent sequence identity to a gene listed in Table 4 is integrated into a strain of *Candida tropicalis* in which fatty alcohol oxidase genes FAO1, FAO1B, FAO2 and FAO2B, alcohol dehydrogenase genes ADH-A4, ADH-A4B, ADH-B4, ADH-B4B, ADH-A10 and ADH-B11 and cytochrome P450 genes CYP52A17, CYP52A18, CYP52A13, CYP52A14, CYP52A12 and CYP52A12B have been disrupted, for example strain DP421, in which the β-oxidation pathway has also been disrupted.

In some embodiments, a gene having at least 40 percent sequence identity, at least 45 percent sequence identity, at least 50 percent sequence identity, at least 55 percent sequence identity, at least 60 percent sequence identity, at least 65 percent sequence identity, at least 70 percent sequence identity, at least 75 percent sequence identity, at least 80 percent sequence identity, at least 85 percent sequence identity, at least 90 percent sequence identity, or at least 95 percent sequence identity to a gene listed in Table 4 is integrated into a strain of *Candida tropicalis* in which endogenous cytochrome P450s have been disrupted.

In some embodiments, a gene having at least 40 percent sequence identity, at least 45 percent sequence identity, at least 50 percent sequence identity, at least 55 percent sequence identity, at least 60 percent sequence identity, at least 65 percent sequence identity, at least 70 percent sequence identity, at least 75 percent sequence identity, at least 80 percent sequence identity, at least 85 percent sequence identity, at least 90 percent sequence identity, or at least 95 percent sequence identity to a gene listed in Table 4 is integrated into a strain of *Candida* in which endogenous cytochrome P450s have been disrupted.

To achieve novel phenotypes of *Candida*, it may be advantageous to modify the activity of a polypeptide by altering its sequence and to test the effect of the polypeptide with altered sequence within the yeast. A preferred method for testing the effect of sequence changes in a polypeptide within yeast is to introduce a plurality of genes of known sequence, each encoding a unique modified polypeptide, into the same genomic location in a plurality of strains.

The isocitrate lyase promoter from *Candida tropicalis* has been shown to be an inducible promoter in both *Saccharomyces cerevisiae* and *E. coli* (Atomi et al., 1995, Arch Microbiol: 163, 322-8; Umemura et al., 1995, Appl Microbiol Biotechnol: 43, 489-92.) When expressed in *S. cerevisiae*, the isocitrate lyase gene was found to be inducible by acetate, glycerol, lactate, ethanol, or oleate. Ethanol is interesting from the perspective that is a relatively cheap inducer and oleate for the fact that it is a potential substrate for the system for converting fatty acids to omega hydroxy fatty acids. Inducible expression of the *Candida tropicalis* ICL gene was found to be high in *S. cerevisiae* (as much as 30% of soluble protein), indicating that it may serve as a strong inducible promoter in *C. tropicalis*.

To insert genes under control of the isocitrate lyase promoter a genomic insertion construct of the form shown in FIG. 21 was synthesized. The sequence used for the sequence of promoter 1 was that of the *Candida tropicalis* isocitrate lyase promoter, given as SEQ ID NO: 62. This promoter has a BsiWI site that can be used to linearize the construct for subsequent insertion into the *Candida tropicalis* genome. The sequence used for transcription terminator 1 was that of the *Candida tropicalis* isocitrate lyase terminator, given as SEQ ID NO: 63. The sequence used for Promoter 2 was the TEF1 promoter, given as SEQ ID NO: 64. The sequence used for the bacterial promoter was the EM7 promoter, given as SEQ ID NO: 65. The sequence used for the selectable marker was the zeocin resistance gene, a version optimized for expression in *Candida tropicalis* is given as SEQ ID NO: 66. The sequence use for Transcription terminator 2 was the CYC1 transcription terminator, given as SEQ ID NO: 67. The sequence used as the bacterial origin of replication was the pUC origin, given as SEQ ID NO: 68. A genomic integration vector with these components is represented graphically as FIG. 23.

7.6.1. Insertion of CYP52A17 Under Control of the Isocitrate Lyase Promoter

A construct for expressing *Candida tropicalis* cytochrome P450 CYP52A17 under the control of the isocitrate lyase promoter was made by cloning the sequence of a gene encoding *Candida tropicalis* cytochrome P450 CYP52A17 (given as SEQ ID NO: 69) into a vector of the form shown in FIG. 23. The sequence of the complete vector is given as SEQ ID NO: 70.

The vector was prepared as described in Section 7.1.1, except that the construct was linearized with BsiWI instead of BsmBI. *Candida tropicalis* strains were transformed with the construct as described in Section 7.1.2, except that 100 μg/ml of zeocin was used instead of 200 μg/ml nourseothricin as the selective antibiotic. Genomic DNA was prepared and tested for the presence of the integrated DNA as described in Section 7.1.3.

*Candida tropicalis* strain DP201 was prepared by integration of the construct shown as SEQ ID NO: 70 into the genome of strain DP186 (Table 3) at the site of the genomic sequence of the gene for isocitrate lyase. DP428 was prepared by integration of the construct shown as SEQ ID NO: 70 into the genome of strain DP421 (Table 3) at the site of the genomic sequence of the gene for isocitrate lyase. Sequences of oligonucleotide primers for analysis of strains were:

```
                                    (SEQ ID NO: 124)
ICL-IN-F1:
GGATCCGTCTGAAGAAATCAAGAACC

                                    (SEQ ID NO: 125)
1758R2:
TGGTGTAGGCCAATAATTGCTTAATGATATACAAAACTGGCACCACAA

                                    (SEQ ID NO: 126)
1758F2:
GAGCAATTGTTGGAATATTGGTACGTTGTGGTGCCAGTTTTGTATATCA

                                    (SEQ ID NO: 127)
1758R34:
GAACTTAACAATAGCACCGTCTTGCAAACACATGGTCAAGTTAGTTAA
```

For strains DP201 and DP428 (integrants of SEQ ID NO: 70), PCR with primers ICL-IN-F1 and 1758R2 produces a 1609 base pair amplicon indicating that the construct has been integrated in the ICL promoter region; PCR with primers 1758F2 and 1758R34 produces a 1543 base pair amplicon indicating that CYP52A17 has been integrated. Neither primer pair produces an amplicon from the parental strains DP186 or DP421.

7.6.2. Insertion of CYP52A13 Under Control of the Isocitrate Lyase Promoter

A construct for expressing *Candida tropicalis* cytochrome P450 CYP52A13 under the control of the isocitrate lyase promoter was made by cloning the sequence of a gene encoding *Candida tropicalis* cytochrome P450 CYP52A13 (given as SEQ ID NO: 71) into a vector of the form shown in FIG. 23. The sequence of the complete vector is given as SEQ ID NO: 72.

The vector was prepared as described in Section 7.1.1, except that the construct was linearized with BsiWI instead of BsmBI. *Candida tropicalis* strains were transformed with the construct as described in Section 7.1.2, except that 100 μg/ml of zeocin was used instead of 200 μg/ml nourseothricin as the selective antibiotic. Genomic DNA was prepared and tested for the presence of the integrated DNA as described in Section 7.1.3.

*Candida tropicalis* strain DP522 was prepared by integration of the construct shown as SEQ ID NO: 72 into the genome of strain DP421 (Table 3) at the site of the genomic sequence of the gene for isocitrate lyase. Sequences of oligonucleotide primers for analysis of strains were:

```
                                    (SEQ ID NO: 124)
ICL-IN-F1:

                                    (SEQ ID NO: 128)
4082R2:
CGATTAAGGCCAATGGAACAATGACGTACCACTTAGTAAA
GTAGGTA

                                    (SEQ ID NO: 129)
4082F2:
CATGACTGTTCACGACATTATTGCTACCTACTTTACTAAGTGG
TACGTC

                                    (SEQ ID NO: 130)
4082R34:
ACATTTCAATATTAGCACCGTCAAATAATGACATGGTCAAAT
GGGACA
```

For strain DP522 (integration of SEQ ID NO: 72), PCR with primers ICL-IN-F1 and 4082R2 produces a 1600 base pair amplicon indicating that the construct has been integrated in the ICL promoter region; PCR with primers 4082F2 and 4082R34 produces a 1565 base pair amplicon indicating that CYP52A13 has been integrated. Neither primer pair produces an amplicon from the parental strain DP421.

7.6.3. Insertion of CYP52A12 Under Control of the Isocitrate Lyase Promoter

A construct for expressing *Candida tropicalis* cytochrome P450 CYP52A12 under the control of the isocitrate lyase promoter was made by cloning the sequence of a gene encoding *Candida tropicalis* cytochrome P450 CYP52A12 (given as SEQ ID NO: 73) into a vector of the form shown in FIG. 23. The sequence of the complete vector is given as SEQ ID NO: 74.

The vector was prepared as described in Section 7.1.1, except that the construct was linearized with BsiWI instead of BsmBI. *Candida tropicalis* strains were transformed with the construct as described in Section 7.1.2, except that 100 μg/ml of zeocin was used instead of 200 μg/ml nourseothricin as the selective antibiotic. Genomic DNA was prepared and tested for the presence of the integrated DNA as described in Section 7.1.3.

*Candida tropicalis* strain DP526 was prepared by integration of the construct shown as SEQ ID NO: 74 into the genome of strain DP421 (Table 3) at the site of the genomic sequence of the gene for isocitrate lyase. Sequences of oligonucleotide primers for analysis of strains were:

```
ICL-IN-F1:                          (SEQ ID NO: 124)

CYP52A12-R2:
ATCAATAATTTCCTGGGTTGCCAT            (SEQ ID NO: 131)

CYP52A12-F1:
ATGGCAACCCAGGAAATTATTGAT            (SEQ ID NO: 132)

CYP52A12-R1:
CTACATCTTGACAAAAACACCATCATT         (SEQ ID NO: 133)
```

For strain DP526 (integration of SEQ ID NO: 74), PCR with primers ICL-IN-F1 and 4082R2 produces a 1554 base pair amplicon indicating that the construct has been integrated in the ICL promoter region; PCR with primers 4082F2 and 4082R34 produces a 1572 base pair amplicon indicating that CYP52A12 has been integrated. Neither primer pair produces an amplicon from the parental strain DP421.

7.7. Deletion of POX Genes from *Candida Tropicalis*

Picataggio et al., 1991, Mol Cell Biol: 11, 4333-9, describe a system for the sequential disruption of the *Candida tropicalis* chromosomal POX4 and POX5 genes, encoding distinct isozymes of the acyl coenzyme A (acyl-CoA) oxidase, which catalyze the first reaction in the β-oxidation pathway of fatty acids. An alternative method is to use the SAT-1 flipper.

7.7.1. Deletion of POX4 Alleles

The sequence of a gene encoding an acyl-coenzyme A oxidase II (PXP-4) of *Candida tropicalis*, POX4, is given as SEQ ID NO: 136. This sequence was used to design two "pre-targeting" constructs. The first pre-targeting construct is comprised of two targeting sequences from the 5' and 3' end of the structural gene. The targeting sequences are separated by a sequence, given as SEQ ID NO: 12, comprising a NotI restriction site, a 20 bp stuffer fragment and an XhoI restriction site. The targeting sequences are flanked by BsmBI restriction sites, so that the final targeting construct can be linearized prior to transformation into *Candida tropicalis*. The sequence of the first POX4 pre-targeting construct is given as SEQ ID NO: 137. Not shown in SEQ ID NO: 137 but also present in the pre-targeting construct were a selective marker conferring resistance to kanamycin and a bacterial origin of replication, so that the pre-targeting construct can be grown and propagated in *E. coli*. The first pre-targeting sequence can be synthesized using standard DNA synthesis techniques well known in the art.

The second pre-targeting construct is comprised of two targeting sequences from the 5' and 3' end of the structural gene that lie internal to the 5' and 3' targeting sequences of the first pre-targeting construct. The targeting sequences are separated by a sequence, given as SEQ ID NO: 12, comprising a NotI restriction site, a 20 bp stuffer fragment and an XhoI restriction site. The targeting sequences are flanked by BsmBI restriction sites, so that the final targeting construct can be linearized prior to transformation into *Candida tropicalis*. The sequence of the second POX4 pre-targeting construct is given as SEQ ID NO: 138. Not shown in SEQ ID NO: 138 but also present in the pre-targeting construct are a selective marker conferring resistance to kanamycin and a bacterial origin of replication, so that the pre-targeting construct can be grown and propagated in *E. coli*. The second pre-targeting sequence can synthesized using standard DNA synthesis techniques well known in the art.

Targeting sequences for deletion of the two POX4 alleles from the *Candida tropicalis* genome can be prepared by digesting the SAT-1 flipper (SEQ ID NO: 1) with restriction enzymes NotI and XhoI, and ligating into the POX4 pre-targeting constructs (SEQ ID NO: 137 or SEQ ID NO: 138) from which the 20 bp stuffer has been removed by digestion with restriction enzymes NotI and XhoI. The sequence of the resulting first targeting construct for the deletion of the first allele of POX4 is given as SEQ ID NO: 139. The sequence of the resulting second targeting construct for the deletion of the second allele of POX4 is given is SEQ ID NO: 140. Because the POX4 targeting sequences of the second targeting construct lie internal to the targeting sequences of the first targeting construct, use of the first targeting construct to delete the first POX4 allele assures that use of the second targeting construct is specific for the second POX4 allele since the targeting sequences of the second targeting construct no longer exist in the first deleted allele.

Analysis of integrants and excisants can be performed as described in Section 7.1. Sequences of oligonucleotide primers for the analysis of strains are:

```
                                          (SEQ ID NO: 141)
POX4-IN-L:    ATGACTTTTACAAAGAAAAACGTTAGTGTATCACAAG

                                          (SEQ ID NO: 142)
POX4-IN-R:    TTACTTGGACAAGATAGCAGCGGTTTC

                                          (SEQ ID NO: 79)
SAT1-R:       TGGTACTGGTTCTCGGGAGCACAGG

                                          (SEQ ID NO: 80)
SAT1-F:       CGCTAGACAAATTCTTCCAAAAATTTTAGA
```

7.7.2. Deletion of POX5 Alleles

The sequence of a gene encoding an acyl-coenzyme A oxidase I (PXP-5) of *Candida tropicalis*, POX5, is given as SEQ ID NO: 143. This sequence was used to design two "pre-targeting" constructs. The first pre-targeting construct is comprised of two targeting sequences from the 5' and 3' end of the structural gene. The targeting sequences were separated by a sequence, given as SEQ ID NO: 12, comprising a NotI restriction site, a 20 bp stuffer fragment and an XhoI restriction site. The targeting sequences are flanked by BsmBI restriction sites, so that the final targeting construct can be linearized prior to transformation into *Candida tropicalis*. The sequence of the first POX5 pre-targeting construct is given as SEQ ID NO: 144. Not shown in SEQ ID NO: 144 but also present in the pre-targeting construct were a selective marker conferring resistance to kanamycin and a bacterial origin of replication, so that the pre-targeting construct can be grown and propagated in *E. coli*. The first pre-targeting sequence can be synthesized using standard DNA synthesis techniques well known in the art.

The second pre-targeting construct is comprised of two targeting sequences from the 5' and 3' end of the structural gene that lie internal to the 5' and 3' targeting sequences of the first pre-targeting construct. The 5' targeting sequence of the second pre-targeting construct is modified at position 248 (C248T) and 294 (G294A) to remove unwanted XhoI and BsmBI sites, respectively. The targeting sequences were separated by a sequence, given as SEQ ID NO: 12, comprising a NotI restriction site, a 20 bp stuffer fragment and an XhoI restriction site. The targeting sequences are flanked by BsmBI restriction sites, so that the final targeting construct can be linearized prior to transformation into *Candida tropicalis*. The sequence of the second POX5 pre-targeting construct is given as SEQ ID NO: 145. Not shown in SEQ ID NO: 145 but also present in the pre-targeting construct were a selective marker conferring resistance to kanamycin and a bacterial origin of replication, so that the pre-targeting construct can be grown and propagated in *E. coli*. The second pre-targeting sequence can be synthesized using standard DNA synthesis techniques well known in the art.

Targeting sequences for deletion of the two POX5 alleles from the *Candida tropicalis* genome were prepared by digesting the SAT-1 flipper (SEQ ID NO: 1) with restriction enzymes NotI and XhoI, and ligating into both of the POX5 pre-targeting constructs (SEQ ID NO 144 or 145) from which the 20 bp stuffer had been removed by digestion with restriction enzymes NotI and XhoI. The sequence of the resulting first targeting construct for the deletion of the first allele of POX5 is given as SEQ ID NO: 146. The sequence of the resulting second targeting construct for the deletion of the second allele of POX5 is given is SEQ ID NO: 147. Because the POX5 targeting sequences of the second targeting construct lie internal to the targeting sequences of the first targeting construct, use of the first targeting construct to delete the first POX5 allele assures that use of the second targeting construct is specific for the second POX5 allele since the targeting sequences of the second targeting construct no longer exist in the first deleted allele.

Analysis of integrants and excisants can be performed as described in section 7.1. Sequences of oligonucleotide primers for the analysis of strains are:

```
POX5-IN-L:
ATGCCTACCGAACTTCAAAAAGAAAGAGAA    (SEQ ID NO: 148)

POX5-IN-R:
TTAACTGGACAAGATTTCAGCAGCTTCTTC    (SEQ ID NO: 149)

SAT1-R:
TGGTACTGGTTCTCGGGAGCACAGG         (SEQ ID NO: 79)

SAT1-F:
CGCTAGACAAATTCTTCCAAAAATTTTAGA    (SEQ ID NO: 80)
```

7.8. Insertion of Genes into the Genome of *Candida*

To achieve novel phenotypes in yeasts of the genus *Candida* (e.g., *Candida tropicalis*), including biotransformations of compounds by *Candida tropicalis*, including chemical conversions not previously obtained, or increased rates of conversion of one or more substrates to one or more products, or increased specificity of conversion of one or more substrates to one or more products, or increased tolerance of a compound by the yeast, or increased uptake of a compound by the yeast, it may be advantageous to incorporate a gene encoding a polypeptide into the genome of the yeast. Expression of the polypeptide in the yeast then allows the phenotype of the yeast to be modified.

To achieve novel phenotypes of *Candida*, it may be advantageous to modify the activity of a polypeptide by altering its sequence and to test the effect of the polypeptide with altered sequence within the yeast. A preferred method for testing the effect of sequence changes in a polypeptide within yeast is to introduce a plurality of genes of known sequence, each encoding a unique modified polypeptide, into the same genomic location in a plurality of strains.

The isocitrate lyase promoter from *Candida tropicalis* has been shown to be an inducible promoter in both *Saccharomyces cerevisiae* and *E. coli* as described in Atomi H. et al, 1995 Arch Microbiol. 163:322-8; Umemura K. et al, 1995 Appl Microbiol Biotechnol. 43:489-92; Kanai T. et al, 1996 Appl Microbiol Biotechnol. 44:759-65. The paper by Atomi H. et al, 1995 Arch Microbiol. 163:322-8, identified the sequence between bases −394 and −379 of the promoter as a promoter that regulates the isocitrate lyase promoter in the yeast *Saccharomyces cerevisiae*. The DNA sequence of an isocitrate lyase promoter from *Candida tropicalis* from base −394 to −1 is given as SEQ ID NO 161. Inducible expression of the *Candida tropicalis* ICL gene was found to be high in *S. cerevisiae* (as much as 30% of soluble protein), indicating that it may serve as a strong inducible promoter in *C. tropicalis*. The sequence of an isocitrate lyase promoter that has been used to drive expression of a protein in the yeast *Saccharomyces cerevisiae* is given as SEQ ID NO: 171. To insert genes under control of the isocitrate lyase promoter a genomic insertion construct of the form shown in FIG. 21 was synthesized. A genomic integration vector with these components is represented graphically as FIG. 23.

In some embodiments, a construct for integration of a gene to be expressed into the genome of a yeast of the genus *Candida* comprises an isocitrate lyase promoter, in some embodiments a construct for integration of a gene to be expressed into the genome of a yeast of the genus *Candida* comprises the sequence shown as SEQ ID NO: 62, in some embodiments a construct for integration of a gene to be expressed into the genome of a yeast of the genus *Candida* comprises the sequence shown as SEQ ID 161, in some embodiments a construct for integration of a gene to be expressed into the genome of a yeast of the genus *Candida* comprises a sequence that is 70%, 75%, 80%, 85%, 90%, or 95% identical to the sequence shown as SEQ ID 161. In some embodiments a construct for integration of a gene to be expressed into the genome of a yeast of the genus *Candida* comprises a sequence of sufficient length and identity to the isocitrate lyase promoter to ensure integration at that locus; in some embodiments said construct comprises at least 100 contiguous base pairs or at least 200 contiguous base pairs or at least 300 contiguous base pairs or at least 400 contiguous base pairs or at least 500 contiguous base pairs of the sequence shown as SEQ ID NO: 62 or to the sequence shown as SEQ ID NO: 171; in some embodiments the construct comprises at least 100 contiguous base pairs or at least 200 contiguous base pairs or at least 300 contiguous base pairs or at least 400 contiguous base pairs or at least 500 contiguous base pairs that are at least 65%, at least 70%, at least 75%, at least 80%, at least 85%, at least 90%, at least 95%, or at least 98% identical to the sequence shown as SEQ ID NO: 62 or to the sequence shown as SEQ ID NO: 171.

Genes may also be inserted into the genome of yeasts of the genus *Candida* under control of other promoters by constructing analogous constructs to the one shown schematically in FIG. 21. Of particular utility may be the promoters for alcohol dehydrogenase genes, which are known to be highly expressed in other yeasts such as *Saccharomyces cerevisiae*. A construct for integrating into an alcohol dehydrogenase gene locus could also have an advantage in embodiments in which it is desirable to disrupt the alcohol dehydrogenase gene itself. In these cases it would be unnecessary to know the full sequence of the promoter: replacing all or a part of the coding sequence of the gene to be disrupted with the coding sequence of the gene to be inserted would be sufficient.

In some embodiments a construct for integration of a gene into the *Candida* genome with the aim of expressing a protein from that gene comprises a promoter from an alcohol dehydrogenase gene or a promoter from a cytochrome P450 gene, or a promoter for a fatty alcohol oxidase gene.

In some embodiments of the invention a gene encoding a polypeptide is integrated under control of an isocitrate lyase promoter, an alcohol dehydrogenase promoter, a fatty alcohol oxidase promoter or a cytochrome P450 promoter into a strain of *Candida tropicalis* in which one or more of the alcohol dehydrogenase genes ADH-A4, ADH-A4B, ADH-B4, ADH-B4B, ADH-A10, ADH-A10B, ADH-B1B and ADH-B11 have been disrupted. In some embodiments of the invention a gene encoding a polypeptide is integrated under control of an isocitrate lyase promoter, an alcohol dehydrogenase promoter, a fatty alcohol oxidase promoter or a cytochrome P450 promoter into a yeast strain of the genus *Candida* in which one or more alcohol dehydrogenase genes have been disrupted, and wherein the disrupted alcohol dehydrogenase gene shares at least 95% nucleotide identity, or at least 90% nucleotide identity, or at least 85% nucleotide identity for a stretch of at least 100 contiguous nucleotides within the coding region, or at least 80% identical for a stretch of at least 100 contiguous nucleotides of the coding sequence or at least 75% identical for a stretch of at least 100 contiguous nucleotides of the coding sequence, or at least 70% identical for a stretch of at least 100 contiguous nucleotides of the coding sequence, or at least 65% identical for a stretch of at least 100 contiguous nucleotides of the coding sequence, or at least 60% identical for a stretch of at least 100 contiguous nucleotides of the coding sequence with one of the *Candida tropicalis* genes ADH-A4 (SEQ ID NO: 39), ADH-B4 (SEQ ID NO: 42), ADH-A10 (SEQ ID NO: 40), ADH-A10B (SEQ ID NO: 56), ADH-B11 (SEQ ID NO: 43). In some embodiments of the invention a gene encoding a polypeptide is integrated under control of an isocitrate lyase promoter, an alcohol dehydrogenase promoter, a fatty alcohol oxidase promoter or a cytochrome P450 promoter into a yeast strain of the genus *Candida* in which one or more alcohol dehydrogenase genes have been disrupted, and wherein the disrupted alcohol dehydrogenase comprises a first peptide. In some embodiments the first peptide has the sequence VKYSGVCH (SEQ ID NO: 156). In some embodiments, the first peptide has the sequence VKYSGVCHxxxxxWKGDW (SEQ ID NO: 162). In some embodiments the first peptide has the sequence VKYSGVCHxxxxxWKGDWxxxxKLPxVGGHEGAGVVV (SEQ ID NO: 163).

In some embodiments the disrupted alcohol dehydrogenase sequence, predicted from translation of the gene that encodes it, comprises a second peptide. In some embodiments the second peptide has the sequence QYATADAVQAA (SEQ ID NO: 158). In some embodiments the second peptide has the sequence SGYxHDGxFxQYATADAVQAA (SEQ ID NO: 164). In some embodiments the second peptide has the sequence GAEPNCxxADxSGYxHDGxFxQYATADAVQAA (SEQ ID NO: 165).

In some embodiments the disrupted alcohol dehydrogenase sequence, predicted from translation of the gene that encodes it, comprises a third peptide. In some embodiments the third peptide has the sequence CAGVTVYKALK (SEQ ID NO: 159). In some embodiments the third peptide has the sequence APIxCAGVTVYKALK (SEQ ID NO: 166).

In some embodiments the first genetic modification class comprises disruption of at least one alcohol dehydrogenase whose amino acid sequence, predicted from translation of the gene that encodes it, comprises a fourth peptide. In some embodiments the fourth peptide has the sequence GQWVAISGA (SEQ ID NO: 160). In some embodiments the fourth peptide has the sequence GQWVAISGAxGGLGSL (SEQ ID NO: 167). In some embodiments the fourth peptide has the sequence GQWVAISGAxGGLGSLxVQYA (SEQ ID NO: 168). In some embodiments, the fourth peptide has the sequence GQWVAISGAxGGLGSLxVQYAxAMG (SEQ ID NO: 169). In some embodiments the fourth peptide has the sequence GQWVAISGAxGGLGSLxVQYAxAMGxRVxAIDGG (SEQ ID NO: 170).

In some embodiments the first genetic modification class comprises disruption of at least one alcohol dehydrogenase whose amino acid sequence, predicted from translation of the gene that encodes it, comprises a fifth peptide. In some embodiments the fifth peptide has the sequence VGGHEGAGVVV (SEQ ID NO: 157).

Insertion of the gene encoding mCherry under control of the isocitrate lyase promoter A construct for expressing mCherry (Shaner N C, Campbell R E, Steinbach P A, Giepmans B N, Palmer A E, Tsien R Y. (2004) Nat Biotechnol. 22:1567-72) under the control of the *C. tropicalis* isocitrate lyase promoter (given as SEQ ID NO: 62) was made by cloning the sequence of a gene encoding mCherry (given as SEQ ID NO: 75) into a vector of the form shown in FIG. 23 with the mCherry open reading frame in the position indicated by the element labeled "Gene for expression". The sequence of the complete vector is given as SEQ ID NO: 76.

The vector was prepared as described in Section 7.1.1, except that the construct was linearized with BsiWI instead of BsmBI. *Candida tropicalis* strain DP186 (Table 3) was transformed with the construct or a no DNA control as described in Section 7.1.2, except that 200, 400 or 600 μg/ml of zeocin were used instead of 200 μg/ml nourseothricin as the selective antibiotic. Following ~48 hours at 30° C. and an additional 24 hours at room temperature, 10 large red colonies were observed amongst a virtually confluent background of small white colonies on YPD agar plates with 200 ug/ml zeocin. Likewise, following 48 hours at 30° C. and an additional 48 hours at room temperature, large red colonies were observed on the 400 and 600 ug/ml zeocin YPD agar plates amongst a background of smaller white colonies. No red colonies were observed on plates transformed with the no DNA control. A total of 8 large, red colonies were isolated and selected for further characterization (see FIG. 27). Genomic DNA was prepared from the isolates and tested for the presence of the integrated mCherry DNA at the isocitrate lyase promoter as described in Section 7.1.3. All 8 tested positive for mCherry integration at the isocitrate lyase promoter demonstrating that expression of genes other than isocitrate lyase can be driven in *C. tropicalis* using this promoter One of the eight isolates, *Candida tropicalis* strain DP197 (Table 3), was prepared by integration of the construct shown as SEQ ID NO: 75 into the genome of strain DP186 (Table 3) at the site of the genomic sequence of the gene for isocitrate lyase.

```
                                    (SEQ ID NO: 124)
ICL-IN-F1:
GGATCCGTCTGAAGAAATCAAGAACC

                                    (SEQ ID NO: 150)
1759R33:
ACCTTAAAACGCATAAATTCCTTGATGATTGCCATGTTGTCTTCTTCA
```

For strain DP197 (integrant of SEQ ID NO: 75), PCR with primers ICL-IN-F1 and 1759R33 produces a 1592 base pair amplicon indicating that the construct has been integrated in the ICL promoter region. The primer pair does not produces an amplicon from the parental strain DP186.

8. CONVERSION OF FATTY ACIDS USING MODIFIED STRAINS OF *CANDIDA TROPICALIS*

8.1. Analytical Methods 8.1.1. GC-MS for Identification of Fatty Acids, Omega-Hydroxy Fatty Acids and Diacids Gas chromatography/mass spectrometry (GC/MS) analysis was performed at 70 eV with ThermoFinnigan TraceGC Ultra gas chromatograph coupled with Trace DSQ mass spectrometer. Products were esterified with $BF_3$ in methanol (10%, w/w) at 70° C. for 20 min, and further silylation of the methyl esters with HMDS/TMCS/Pyridine at 70° C. for 10 min when needed. The experiments were carried out with injector, ion source and interface temperature of 200° C., 250° C. and 280° C., respectively. Samples in hexane (1 μl) were injected in PTV split mode and run on a capillary column (Varian CP8944 VF-5MS, 0.25 mm×0.25 um×30 m). The oven temperature was programmed at 120° C. for one minute increasing to 260° C. at the rate of 20° C./minute, and then to 280° C. at the rate of 4.0° C./minute.

8.1.2. LC-MS for Measurement of Fatty Acids, Omega-Hydroxy Fatty Acids and Diacids The concentration of omega-hydroxy fatty acids and diacids during biotransformation was measured by liquid chromatography/mass spectrometry (LC/MS) with purified products as standards. The solvent delivery system was a Waters Alliance 2795 Separation Module (Milford, Mass., USA) coupled with a Waters 2996 photodiode array detector and Waters ZQ detector with an electron spray ionization mode. The separation was carried on a reversed-phase column with a dimension of 150×4.6 mm and particle size of 5 μm. The mobile phase used for separation contained 10% $H_2O$, 5% acetonitrile, 5% Formic acid solution (1% in water) and 80% methanol.

8.1.3. NMR for Characterization of Omega-Hydroxyfatty Acids and Diacids

Proton ($^1H$) and $^{13}C$-NMR spectra were recorded on a Bruker DPX300 NMR spectrometer at 300 MHz. The chemical shifts (ppm) for $^1H$-NMR were referenced relative to tetramethylsilane (TMS, 0.00 ppm) as the internal reference.

8.2. Oxidation of Fatty Acids by *Candida Tropicalis* Strains Lacking Four CYP52A P450S We compared the *Candida tropicalis* strain lacking CYP52A13, CYP52A14, CYP52A17 and CYP52A18 (DP174) constructed in Section 7.2 with the starting strain (DP1) for their abilities to oxidize fatty acids. To engineer P450s for optimal oxidation of fatty acids or other substrates it is advantageous to eliminate the endogenous P450s whose activities may mask the activities of the enzymes being engineered. We tested *Candida tropicalis* strains DP1 and DP174 (genotypes given in Table 3) to determine whether the deletion of the four CYP52 P450S had affected the ability of the yeast to oxidize fatty acids.

Cultures of the yeast strains were grown at 30° C. and 250 rpm for 16 hours in a 500 ml flask containing 30 ml of media F (media F is peptone 3 g/l, yeast extract 6 g/l, yeast nitrogen base 6.7 g/l, sodium acetate 3 g/l, $K_2HPO_4$ 7.2 g/l, $KH_2PO_4$ 9.3 g/l) plus 30 g/l glucose. After 16 hours 0.5 ml of culture was added to 4.5 ml fresh media F plus 60 g/l glucose in a 125 ml flask, and grown at 30° C. and 250 rpm for 12 hours. Substrates were added and shaking was continued at 30° C. and 250 rpm. We then tested the conversion of C14 fatty acid substrates as shown in FIG. 13. FIG. 13 parts A and B show that the starting strain DP1 converts methyl myristate to ω-hydroxy myristate and to the C14 diacid produced by oxidation of the ω-hydroxy myristate over a 48 hour time course, while the quadruple P450 deletion strain DP174 can effect almost no detectable conversion. FIG. 13 parts C and D show that the starting strain DP1 converts methyl myristate and sodium myristate to ω-hydroxy myristate and to the C14 diacid produced by oxidation of the ω-hydroxy myristate after 48 hours, while the quadruple P450 deletion strain DP174 effects almost no detectable conversion of these substrates.

These results confirm that at least one of the four *Candida tropicalis* cytochrome P450 genes encoding CYP52A13, CYP52A14, CYP52A17 and CYP52A18 is required for hydroxylation of fatty acids, consistent with the schematic representation of *Candida tropicalis* fatty acid metabolism pathways shown in FIG. 12. Further it shows that strain DP174 is an appropriate strain to use for testing of engineered cytochrome P450s, since it has essentially no ability to oxidize fatty acids without an added P450.

8.3. Oxidation of Ω-Hydroxy Fatty Acids by *Candida Tropicalis* Strains Lacking Four CYP52A P450S We compared the *Candida tropicalis* strain lacking CYP52A13, CYP52A14, CYP52A17 and CYP52A18 (DP174) constructed in Section 7.2 with the starting strain (DP1) for their abilities to oxidize ω-hydroxy fatty acids. To engineer a strain for the production of ω-hydroxy fatty acids it is desirable to eliminate enzymes from the cell that can oxidize ω-hydroxy fatty acids. It is possible to determine whether other enzymes involved in oxidation of ω-hydroxy fatty acids are present in the strain by feeding it ω-hydroxy fatty acids in the media. If there are enzymes present that can oxidize ω-hydroxy fatty acids, then the strain will convert ω-hydroxy fatty acids fed in the media to α,ω-dicarboxylic acids.

Cultures of the yeast strains were grown at 30° C. and 250 rpm for 16 hours in a 500 ml flask containing 30 ml of media F (media F is peptone 3 g/l, yeast extract 6 g/l, yeast nitrogen base 6.7 g/l, sodium acetate 3 g/l, $K_2HPO_4$ 7.2 g/l, $KH_2PO_4$ 9.3 g/l) plus 20 g/l glycerol. After 16 hours 0.5 ml of culture was added to 4.5 ml fresh media F plus 20 g/l glycerol in a 125 ml flask, and grown at 30° C. and 280 rpm for 12 hours. We then tested the conversion of C12 and C16 ω-hydroxy fatty acid substrates by adding these substrates to independent flasks at final concentrations of 5 g/l and the pH was adjusted to between 7.5 and 8 and shaking was continued at 30° C. and 250 rpm. Samples were taken at the times indicated, cell culture was acidified to pH~1.0 by addition of 6 N HCl, products were extracted from the cell culture by diethyl ether and the concentrations of ω-hydroxy fatty acids and α,ω-diacids in the media were measured by LC-MS (liquid chromatography mass spectroscopy). The results are shown in Table 5.

TABLE 5

Oxidation of ω-hydroxy fatty acids by *Candida tropicalis*

| Ω-HYDROXY FATTY ACID SUBSTRATE CHAIN LENGTH | REACTION TIME | DIACID PRODUCED BY DP1 (G/L) | DIACID PRODUCED BY DP174 (G/L) |
|---|---|---|---|
| C12 | 60 hours | 5.6 | 5.2 |
| C16 | 60 hours | 1.4 | 0.8 |
| C12 | 24 hours | 5.4 | 5 |
| C12 | 48 hours | 6 | 6.7 |
| C12 | 72 hours | 6.2 | 6.5 |
| C16 | 24 hours | 2.3 | 0.9 |
| C16 | 48 hours | 2.4 | 1.7 |
| C16 | 72 hours | 2.8 | 1.8 |

These results show that at least one enzyme capable of oxidizing ω-hydroxy fatty acids is present in *Candida tropicalis* in addition to the cytochrome P450 genes encoding CYP52A13, CYP52A14, CYP52A17 and CYP52A18.

8.4. Oxidation of Ω-Hydroxy Fatty Acids by *Candida Tropicalis* Strains Lacking Four CYP52A P450S and Four Fatty Alcohol Oxidases We compared the *Candida tropicalis* strain lacking CYP52A13, CYP52A14, CYP52A17, CYP52A18 and FAO1 (DP186) constructed in Section 7.3 with the *Candida tropicalis* strain lacking CYP52A13, CYP52A14, CYP52A17, CYP52A18, FAO1, FAO1B, FAO2A and FAO2B (DP258 and DP259) for their abilities to oxidize ω-hydroxy fatty acids. To engineer a strain for the production of ω-hydroxy fatty acids it is desirable to eliminate enzymes from the cell that can oxidize ω-hydroxy fatty acids. It is possible to determine whether other enzymes involved in oxidation of ω-hydroxy fatty acids are present in the strain by feeding it ω-hydroxy fatty acids in the media. If there are enzymes present that can oxidize ω-hydroxy fatty acids, then the strain will convert ω-hydroxy fatty acids fed in the media to α,ω-dicarboxylic acids.

Cultures of the yeast strains were grown at 30° C. and 250 rpm for 16 hours in a 500 ml flask containing 30 ml of media F (media F is peptone 3 g/l, yeast extract 6 g/l, yeast nitrogen base 6.7 g/l, sodium acetate 3 g/l, $K_2HPO_4$ 7.2 g/l, $KH_2PO_4$ 9.3 g/l) plus 20 g/l glycerol. After 16 hours 0.5 ml of culture was added to 4.5 ml fresh media F plus 20 g/l glycerol in a 125 ml flask, and grown at 30° C. and 250 rpm for 12 hours. We then tested the conversion of C12 and C16 ω-hydroxy fatty acid substrates by adding these substrates to independent flasks at final concentrations of 5 g/l and the pH was adjusted to between 7.5 and 8 and shaking was continued at 30° C. and 250 rpm. Samples were taken after 24 hours, cell culture was acidified to pH~1.0 by addition of 6 N HCl, products were extracted from the cell culture by diethyl ether and the concentrations of ω-hydroxy fatty acids and α,ω-diacids in the media were measured by LC-MS (liquid chromatography mass spectroscopy). As shown in FIG. 15 most of the hydroxy fatty acids are converted to diacid after 24 hours. These results show that at least one enzyme capable of oxidizing ω-hydroxy fatty acids is present in *Candida tropicalis* in addition to the cytochrome P450 genes encoding CYP52A13, CYP52A14, CYP52A17, CYP52A18, FAO1, FAO1B, FAO2A and FAO2B.

8.5. Oxidation of Ω-Hydroxy Fatty Acids by *Candida Tropicalis* Strains Lacking Six CYP52A P450S and Four Fatty Alcohol Oxidases We compared the *Candida tropicalis* strain lacking CYP52A13, CYP52A14, CYP52A17, CYP52A18 and FAO1 (DP186) constructed in Section 7.2 with the *Candida tropicalis* strain lacking CYP52A13, CYP52A14, CYP52A17, CYP52A18, FAO1, FAO1B, FAO2A, FAO2B, CYP52A12 and CYP52A12B (DP283 and DP284) for their abilities to oxidize ω-hydroxy fatty acids. To engineer a strain for the production of ω-hydroxy fatty acids it is desirable to eliminate enzymes from the cell that can oxidize ω-hydroxy fatty acids. It is possible to determine whether other enzymes involved in oxidation of ω-hydroxy fatty acids are present in the strain by feeding it ω-hydroxy fatty acids in the media. If there are enzymes present that can oxidize ω-hydroxy fatty acids, then the strain will convert ω-hydroxy fatty acids fed in the media to α,ω-dicarboxylic acids.

Cultures of the yeast strains were grown at 30° C. and 250 rpm for 16 hours in a 500 ml flask containing 30 ml of media F (media F is peptone 3 g/l, yeast extract 6 g/l, yeast nitrogen base 6.7 g/l, sodium acetate 3 g/l, $K_2HPO_4$ 7.2 g/l, $KH_2PO_4$ 9.3 g/l) plus 20 g/l glycerol. After 16 hours 0.5 ml of culture was added to 4.5 ml fresh media F plus 20 g/l glycerol in a 125 ml flask, and grown at 30° C. and 250 rpm for 12 hours. We then tested the conversion of C12 and C16 ω-hydroxy fatty acid substrates by adding these substrates to independent flasks at final concentrations of 5 g/l and the pH was adjusted to between 7.5 and 8 and shaking was continued at 30° C. and 250 rpm. Samples were taken after 24 hours, cell culture was acidified to pH~1.0 by addition of 6 N HCl, products were extracted from the cell culture by diethyl ether and the concentrations of ω-hydroxy fatty acids and α,ω-diacids in the media were measured by LC-MS (liquid chromatography mass spectroscopy). As shown in FIG. 16 most of the C12 hydroxy fatty acids and a substantial fraction of the C16 hydroxy fatty acids are converted to diacid after 24 hours. These results show that at least one enzyme capable of oxidizing ω-hydroxy fatty acids is present in *Candida tropicalis* in addition to the cytochrome P450 genes encoding CYP52A13, CYP52A14, CYP52A17, CYP52A18, CYP52A12, CYP52A12B, FAO1, FAO1B, FAO2A and FAO2B.

8.6. Oxidation of Ω-Hydroxy Fatty Acids by *Candida Tropicalis* Strains Lacking Six CYP52A P450S, Four Fatty Alcohol Oxidases and Five Alcohol Dehydrogenases We compared the *Candida tropicalis* strain DP1 with the *Candida tropicalis* strain lacking CYP52A13, CYP52A14, CYP52A17, CYP52A18, FAO1, FAO1B, FAO2A, FAO2B, CYP52A12 and CYP52A12B (DP283) and the *Candida tropicalis* strain lacking CYP52A13, CYP52A14, CYP52A17, CYP52A18, FAO1, FAO1B, FAO2A, FAO2B, CYP52A12, CYP52A12B, ADH-A4, ADH-A4B, ADH-B4, ADH-B4B and ADH-A10 (DP415) for their abilities to oxidize ω-hydroxy fatty acids. To engineer a strain for the production of ω-hydroxy fatty acids it is desirable to eliminate enzymes from the cell that can oxidize ω-hydroxy fatty acids. It is possible to determine whether other enzymes involved in oxidation of ω-hydroxy fatty acids are present in the strain by feeding it ω-hydroxy fatty acids in the media. If there are enzymes present that can oxidize ω-hydroxy fatty acids, then the strain will convert ω-hydroxy fatty acids fed in the media to α,ω-dicarboxylic acids.

Cultures of the yeast strains were grown at 30° C. and 250 rpm for 18 hours in a 500 ml flask containing 30 ml of media F (media F is peptone 3 g/l, yeast extract 6 g/l, yeast nitrogen base 6.7 g/l, sodium acetate 3 g/l, $K_2HPO_4$ 7.2 g/l, $KH_2PO_4$ 9.3 g/l) plus 20 g/l glycerol. After 18 hours the preculture was diluted in fresh media to $A_{600}$=1.0. This culture was shaken until the $A_{600}$ reached between 5.0 and 6.0. Biocatalytic conversion was initiated by adding 5 ml culture to a 125 ml flask together with 50 mg of ω-hydroxy lauric acid, and pH adjusted to ~7.5 with 2M NaOH. Samples were taken at the times indicated, cell culture was acidified to pH~1.0 by addition of 6 N HCl, products were extracted from the cell culture by diethyl ether and the concentrations of α,ω-diacids in the media were measured by LC-MS (liquid chromatography mass spectroscopy). As shown in FIG. 19 Part A, the cell growth was almost identical for the 3 strains. Strain DP415 produced much less α,ω-dicarboxy laurate than the other two strains, however, as shown in FIG. 19 part B.

These results show that a significant reduction in the ability of *Candida tropicalis* to oxidize ω-hydroxy fatty acids can be reduced by deleting genes encoding CYP52A13, CYP52A14, CYP52A17, CYP52A18, FAO1, FAO1B, FAO2A, FAO2B, CYP52A12, CYP52A12B, ADH-A4, ADH-A4B, ADH-B4, ADH-B4B and ADH-A10.

8.7. Oxidation of Ω-Hydroxy Fatty Acids by *Candida Tropicalis* Strains Lacking Six CYP52A P450S, Four Fatty Alcohol Oxidases and Eight Alcohol Dehydrogenases We compared the *Candida tropicalis* strain DP1 with the *Candida tropicalis* strain lacking CYP52A13, CYP52A14, CYP52A17, CYP52A18, FAO1, FAO1B, FAO2A, FAO2B, CYP52A12, CYP52A12B, ADH-A4 and ADH-A4B (DP390), the *Candida tropicalis* strain lacking CYP52A13, CYP52A14, CYP52A17, CYP52A18, FAO1, FAO1B, FAO2A, FAO2B, CYP52A12, CYP52A12B, ADH-A4, ADH-A4B, ADH-B4, ADH-B4B and ADH-A10 (DP415), the *Candida tropicalis* strain lacking CYP52A13, CYP52A14, CYP52A17, CYP52A18, FAO1, FAO1B, FAO2A, FAO2B, CYP52A12, CYP52A12B, ADH-A4, ADH-A4B, ADH-B4, ADH-B4B, ADH-A10 and ADH-B11 (DP417 and DP421), the *Candida tropicalis* strain lacking CYP52A13, CYP52A14, CYP52A17, CYP52A18, FAO1, FAO1B, FAO2A, FAO2B, CYP52A12, CYP52A12B, ADH-A4, ADH-A4B, ADH-B4, ADH-B4B, ADH-A10, ADH-A10B and ADH-B11 (DP423), the *Candida tropicalis* strain lacking CYP52A13, CYP52A14, CYP52A17, CYP52A18, FAO1, FAO1B, FAO2A, FAO2B, CYP52A12, CYP52A12B, ADH-A4, ADH-A4B, ADH-B4, ADH-B4B, ADH-A10, ADH-A10B, ADH-B11 and ADH-B11B (DP434 and DP436) for their abilities to oxidize ω-hydroxy fatty acids. To engineer a strain for the production of ω-hydroxy fatty acids it is desirable to eliminate enzymes from the cell that can oxidize ω-hydroxy fatty acids. It is possible to determine whether other enzymes involved in oxidation of ω-hydroxy fatty acids are present in the strain by feeding it ω-hydroxy fatty acids in the media. If there are enzymes present that can oxidize ω-hydroxy fatty acids, then the strain will convert ω-hydroxy fatty acids fed in the media to α,ω-dicarboxylic acids.

Cultures of the yeast strains were grown at 30° C. and 250 rpm for 18 hours in a 500 ml flask containing 30 ml of media F (media F is peptone 3 g/l, yeast extract 6 g/l, yeast nitrogen base 6.7 g/l, sodium acetate 3 g/l, $K_2HPO_4$ 7.2 g/l, $KH_2PO_4$ 9.3 g/l) plus 20 g/l glycerol. After 18 hours the preculture was diluted in fresh media to $A_{600}$=1.0. This culture was shaken until the $A_{600}$ reached between 5.0 and 6.0. Biocatalytic conversion was initiated by adding 5 ml culture to a 125 ml flask together with 50 mg of ω-hydroxy lauric acid, and pH adjusted to ~7.5 with 2M NaOH. Samples were taken at the times indicated, cell culture was acidified to pH~1.0 by addition of 6 N HCl, products were extracted from the cell culture by diethyl ether and the concentrations of α,ω-diacids in the media were measured by LC-MS (liquid chromatography mass spectroscopy). As shown in FIG. 20, a significant reduction in the ability of *Candida tropicalis* to oxidize ω-hydroxy fatty acids can be obtained by deleting genes encoding alcohol dehydrogenases in strains lacking some cytochrome P450s and fatty alcohol oxidases.

8.8. Oxidation of Methyl Myristate by *Candida Tropicalis* Strains Lacking Six CYP52A P450S, Four Fatty Alcohol Oxidases and Six Alcohol Dehydrogenases with a Single CYP52A P450 Added Back Under Control of the ICL Promoter We compared the *Candida tropicalis* strain DP1 with the *Candida tropicalis* strain lacking CYP52A13, CYP52A14, CYP52A17, CYP52A18 and FAO1 and with CYP52A17 added back under control of the isocitrate lyase promoter (DP201) and with the *Candida tropicalis* strain lacking CYP52A13, CYP52A14, CYP52A17, CYP52A18, FAO1, FAO1B, FAO2A, FAO2B, CYP52A12, CYP52A12B, ADH-A4, ADH-A4B, ADH-B4, ADH-B4B, ADH-A10 and ADH-B11 and with CYP52A17 added back under control of the isocitrate lyase promoter (DP428) for their abilities to oxidize methyl myristate.

Cultures of the yeast strains were grown at 30° C. and 250 rpm for 18 hours in a 500 ml flask containing 30 ml of media F (media F is peptone 3 g/l, yeast extract 6 g/l, yeast nitrogen base 6.7 g/l, sodium acetate 3 g/l, $K_2HPO_4$ 7.2 g/l, $KH_2PO_4$ 9.3 g/l) plus 20 g/l glucose plus 5 g/l ethanol. After 18 hours 3 ml of preculture was added to 27 ml fresh media F plus 20 g/l glucose plus 5 g/l ethanol in a 500 ml flask, and grown at 30° C. and 250 rpm for 20 hours before addition of substrate. Biocatalytic conversion was initiated by adding 40 g/l of methyl myristate, the pH was adjusted to ~7.8 with 2M NaOH. The culture was pH controlled by adding 2 mol/l NaOH every 12 hours, glycerol was fed as cosubstrate by adding 500 g/l glycerol and ethanol was fed as a inducer by adding 50% ethanol every 12 hours. Samples were taken at the times indicated, cell culture was acidified to pH~1.0 by addition of 6 N HCl, products were extracted from the cell culture by diethyl ether and the concentrations of ω-hydroxy myristate and α,ω-dicarboxymyristate were measured by LC-MS (liquid chromatography mass spectroscopy).

As shown in FIG. 24, strains DP1 and DP201 both produce significant levels of tetradecanedioic acid (the α,ω-diacid) and negligible levels of ω-hydroxy myristic acid. In contrast, under these conditions strain DP428 produces approximately five-fold less tetradecanedioic acid, while converting nearly 70% of the methyl myristate to ω-hydroxy myristic acid after 60 hours. This shows that elimination of one or more of the genes FAO1B, FAO2A, FAO2B, CYP52A12, CYP52A12B, ADH-A4, ADH-A4B, ADH-B4, ADH-B4B, ADH-A10 and ADH-B11 prevents the over-oxidation of the fatty acid myristic acid by *Candida tropicalis*, and that the presence of CYP52A17 under control of the isocitrate lyase promoter in this strain background produces a strain that can convert methyl myristate to ω-hydroxy myristic acid, but that does not over-oxidize the product to tetradecanedioic acid.

8.9. Oxidation of Methyl Myristate by an Engineered *Candida Tropicalis* Strain in a Fermentor We compared the production of ω-hydroxy myristic acid and α,ω-tetradecanoic acid by a *Candida tropicalis* strain lacking CYP52A13, CYP52A14, CYP52A17, CYP52A18, FAO1, FAO1B, FAO2A, FAO2B, CYP52A12, CYP52A12B, ADH-A4, ADH-A4B, ADH-B4, ADH-B4B, ADH-A10 and ADH-B11 and with CYP52A17 added back under control of the isocitrate lyase promoter (DP428).

*C. tropicalis* DP428 was taken from a glycerol stock or fresh agar plate and inoculated into 500 ml shake flask containing 30 mL of YPD medium (20 g/l glucose, 20 g/l peptone and 10 g/l yeast extract) and shaken at 30° C., 250 rpm for 20 h. Cells were collected by centrifugation and re-suspended in FM3 medium for inoculation. (FM3 medium is 30 g/l glucose, 7 g/l ammonium sulfate, 5.1 g/l potassium phosphate, monobasic, 0.5 g/l magnesium sulfate, 0.1 g/l calcium chloride, 0.06 g/l citric acid, 0.023 g/l ferric chloride, 0.0002 g/l biotin and 1 ml/l of a trace elements solution. The trace elements solution contains 0.9 g/l boric acid, 0.07 g/l cupric sulfate, 0.18 g/l potassium iodide, 0.36 g/l ferric chloride, 0.72 g/l manganese sulfate, 0.36 g/l sodium molybdate, 0.72 g/l zinc sulfate.) Conversion was performed by inoculating 15 ml of preculture into 135 ml FM3 medium, methyl myristate was added to 20 g/l and the temperature was kept at 30° C. The pH was maintained at 6.0 by automatic addition of 6 M NaOH or 2 M $H_2SO_4$ solution. Dissolved oxygen was kept at 70% by agitation and $O_2$-cascade control mode. After 6 hours growth, ethanol was fed into the cell culture to 5 g/l. During the conversion phase, 80% glycerol was fed as co-substrate by dissolved oxygen-stat control mode (the high limit of dissolved oxygen was 75% and low limit of dissolved oxygen was 70%, which means glycerol feeding was initiated when dissolved oxygen is higher than 75% and stopped when dissolved oxygen was lower than 70%). Every 12 hours, ethanol was added into cell culture to 2 g/l, and methyl myristate was added to 40 g/l until the total methyl myristate added was 140 g/l (i.e. the initial 20 g/l plus 3 subsequent 40 g/l additions). Formation of products was measured at the indicated intervals by taking samples and acidifying to pH~1.0 by addition of 6 N HCl; products were extracted from the cell culture by diethyl ether and the concentrations of ω-hydroxy myristate and α,ω-dicarboxymyristate were measured by LC-MS (liquid chromatography mass spectroscopy), as shown in FIG. 26. Under these conditions the strain produced a final concentration of 91.5 g/l ω-hydroxy myristic acid, with a productivity of 1.63 g/l/hr and a w/w ratio of ω-hydroxy myristic acid:tetradecanedioic acid of 20.3:1. This shows that elimination of one or more of the genes FAO1B, FAO2A, FAO2B, CYP52A12, CYP52A12B, ADH-A4, ADH-A4B, ADH-B4, ADH-B4B, ADH-A10 and ADH-B11 prevents the over-oxidation of the fatty acid myristic acid by *Candida tropicalis*, and that the presence of CYP52A17 under control of the isocitrate lyase promoter in this strain background produces a strain that can convert methyl myristate to ω-hydroxy myristic acid, but that does not over-oxidize the product to tetradecanedioic acid.

8.10. Oxidation of Methyl Myristate, Oleic Acid and Linoleic Acid by Engineered *Candida Tropicalis* Strains We compared the fatty acid oxidizing activities of two *Candida tropicalis* strains which lack CYP52A13, CYP52A14, CYP52A17, CYP52A18, FAO1, FAO1B, FAO2A, FAO2B, CYP52A12, CYP52A12B, ADH-A4, ADH-A4B, ADH-B4, ADH-B4B, ADH-A10 and ADH-B11, one of which has CYP52A17 added back under control of the isocitrate lyase promoter (DP428) and one of which has CYP52A13 added back under control of the isocitrate lyase promoter (DP522).

Cultures of the yeast strains were grown at 30° C. in a DASGIP parallel fermentor containing 200 ml of media F (media F is peptone 3 g/l, yeast extract 6 g/l, yeast nitrogen base 6.7 g/l, sodium acetate 3 g/l, $K_2HPO_4$ 7.2 g/l, $KH_2PO_4$ 9.3 g/l) plus 30 g/l glucose. The pH was maintained at 6.0 by automatic addition of 6 M NaOH or 2 M $H_2SO_4$ solution. Dissolved oxygen was kept at 70% by agitation and $O_2$-cascade control mode. After 6 hour growth, ethanol was fed into the cell culture to 5 g/l. After 12 h growth, biocatalytic conversion was initiated by adding methyl myristate acid to 60 g/l or oleic acid to 60 g/l or linoleic acid to 30 g/l. During the conversion phase, 80% glycerol was fed as co-substrate for conversion of methyl myristate and 500 g/l glucose was fed as co-substrate for conversion of oleic acid and linoleic acid by dissolved oxygen-stat control mode (the high limit of dissolved oxygen was 75% and low limit of dissolved oxygen was 70%, which means glycerol feeding was initiated when dissolved oxygen is higher than 75% and stopped when dissolved oxygen was lower than 70%). Every 12 hour, ethanol was added into cell culture to 2 g/l. Samples were taken at various times, cell culture was acidified to pH~1.0 by addition of 6 N HCl, products were extracted from the cell culture by diethyl ether and the concentrations of ω-hydroxy fatty acids and α,ω-diacids in the media were measured by LC-MS (liquid chromatography mass spectroscopy). As shown in FIG. 25, strains DP428 and DP522 were both able to produce ω-hydroxy fatty acids from these substrates, as well as some α,ω-diacids. FIG. 25 also shows that the different P450s had different preferences for the fatty acid substrates, and different propensities to oxidize the ω-hydroxy group.

9. DEPOSIT OF MICROORGANISMS

A living cultures of strain DP421 has been deposited with American Type Culture Collection, 12301 Parklawn Drive, Rockville, Md. 20852, on May 4, 2009, under the Budapest Treaty on the International Recognition of the Deposit of Microorganisms for the purposes of patent procedure.

10. EQUIVALENTS

Those skilled in the art will recognize, or be able to ascertain using no more than routine experimentation, many equivalents to the specific embodiments of the invention described herein. Such equivalents are intended to be encompassed by the following claims.

All publications, patents, patent applications, and databases mentioned in this specification are herein incorporated by reference into the specification to the same extent as if each individual publication, patent, patent application or database was specifically and individually indicated to be incorporated herein by reference.

11. EXEMPLARY EMBODIMENTS

The following are nonlimiting exemplary embodiments in accordance with the disclosed application:

Embodiment 1. A substantially pure *Candida* host cell for the biotransformation of a substrate to a product, wherein the *Candida* host cell is characterized by a first genetic modification class that comprises one or more genetic modifications that collectively or individually disrupt an alcohol dehydrogenase gene in the substantially pure *Candida* host cell.

Embodiment 2. The substantially pure *Candida* host cell of embodiment 1, wherein the substantially pure *Candida* host cell is genetically modified *Candida glabrata, Candida zeylenoides, Candida lipolytica, Candida guillermondii, Candida aaseri, Candida abiesophila, Candida africana, Candida aglyptinia, Candida agrestis, Candida akabanensis, Candida alai, Candida albicans, Candida alimentaria, Candida amapae, Candida ambrosiae, Candida amphixiae, Candida anatomiae, Candida ancudensis, Candida anglica, Candida anneliseae, Candida antarctica, Candida antillancae, Candida anutae, Candida apicola, Candida apis, Candida arabinofermentans, Candida arcana, Candida ascalaphidarum, Candida asparagi, Candida atakaporum, Candida atbi, Candida athensensis, Candida atlantica, Candida atmosphaerica, Candida auringiensis, Candida auris, Candida aurita, Candida austromarina, Candida azyma, Candida azymoides, Candida barrocoloradensis, Candida batistae, Candida beechii, Candida bentonensis, Candida bertae, Candida berthetii, Candida bituminiphila, Candida blankii, Candida blattae, Candida blattariae, Candida bohiensis, Candida boidinii, Candida bokatorum, Candida boleticola, Candida bolitotheri, Candida bombi, Candida bombiphila, Candida bondarzewiae, Candida bracarensis, Candida bribrorum, Candida bromeliacearum, Candida buenavistaensis, Candida buinensis, Candida butyri, Candida californica, Candida canberraensis, Candida cariosilignicola, Candida carpophila, Candida caryicola, Candida caseinolytica, Candida castrensis, Candida catenulata, Candida cellae, Candida cellulolytica, Candida cerambycidarum, Candida chauliodes, Candida chickasaworum, Candida chilensis, Candida choctaworum, Candida chodatii, Candida chrysomelidarum, Candida cidri, Candida cloacae, Candida coipomoensis, Candida conglobata, Candida corydali, Candida cylindracea, Candida davenportii, Candida davisiana, Candida deformans, Candida dendrica, Candida dendronema, Candida derodonti, Candida diddensiae, Candida digboiensis, Candida diospyri, Candida diversa, Candida dosseyi, Candida drimydis, Candida drosophilae, Candida dubliniensis, Candida easanensis, Candida edaphicus, Candida edax, Candida elateridarum, Candida emberorum, Candida endomychidarum, Candida entomophila, Candida ergastensis, Candida ernobii, Candida etchellsii, Candida ethanolica, Candida famata, Candida fennica, Candida fermenticarens, Candida flocculosa, Candida floricola, Candida floris, Candida flosculorum, Candida fluviatilis, Candida fragi, Candida freyschussii, Candida friedrichii, Candida frijolesensis, Candida fructus, Candida fukazawae, Candida fungicola, Candida galacta, Candida galis, Candida galli, Candida gatunensis, Candida gelsemii, Candida geochares, Candida germanica, Candida ghanaensis, Candida gigantensis, Candida glaebosa, Candida glucosophila, Candida glycerinogenes, Candida gorgasii, Candida gotoi, Candida gropengiesseri, Candida guaymorum, Candida haemulonii, Candida halonitratophila, Candida halophila, Candida hasegawae, Candida hawaiiana, Candida heliconiae, Candida hispaniensis, Candida homilentoma, Candida humicola, Candida humilis, Candida hungarica, Candida hyderabadensis, Candida incommunis, Candida inconspicua, Candida insectalens, Candida insectamans, Candida insectorum, Candida intermedia, Candida ipomoeae, Candida ishiwadae, Candida jaroonii, Candida jeffriesii, Candida kanchanaburiensis, Candida karawaiewii, Candida kashinagacola, Candida kazuoi, Candida khmerensis, Candida kipukae, Candida kofuensis, Candida krabiensis, Candida kruisii, Candida kunorum, Candida labiduridarum, Candida lactis-condensi, Candida lassenensis, Candida laureliae, Candida leandrae, Candida lessepsii, Candida lignicola, Candida litsaeae, Candida litseae, Candida llanquihuensis, Candida lycoperdinae, Candida lyxosophila, Candida magnifica, Candida magnoliae, Candida maltosa, Candida mannitofaciens, Candida maris, Candida maritima, Candida maxii, Candida melibiosica, Candida membranifaciens, Candida mesenterica, Candida metapsilosis, Candida methanolophaga, Candida methanolovescens, Candida methanosorbosa, Candida methylica, Candida michaelii, Candida mogii, Candida montana, Candida multigemmis, Candida mycetangii, Candida naeodendra, Candida nakhonratchasimensis, Candida nanaspora, Candida natalensis, Candida neerlandica, Candida nemodendra, Candida nitrativorans, Candida nitratophila, Candida nivariensis, Candida nodaensis, Candida norvegica, Candida novakii, Candida odintsovae, Candida oleophila, Candida ontarioensis, Candida ooitensis, Candida orba, Candida oregonensis, Candida orthopsilosis, Candida ortonii, Candida ovalis, Candida pallodes, Candida palmioleophila, Candida paludigena, Candida panamensis, Candida panamericana, Candida parapsilosis, Candida pararugosa, Candida pattaniensis, Candida peltata, Candida peoriaensis, Candida petrohuensis, Candida phangngensis, Candida picachoensis, Candida piceae, Candida picinguabensis, Candida pignaliae, Candida pimensis, Candida pini, Candida plutei, Candida pomicola, Candida ponderosae, Candida populi, Candida powellii, Candida prunicola, Candida pseudoglaebosa, Candida pseudohaemulonii, Candida pseudointermedia, Candida pseudolambica, Candida pseudorhagii, Candida pseudovanderkliftii, Candida psychrophila, Candida pyralidae, Candida qinlingensis, Candida quercitrusa, Candida quercuum, Candida railenensis, Candida ralunensis, Candida rancensis, Candida restingae,*

*Candida rhagii, Candida riodocensis, Candida rugopelliculosa, Candida rugosa, Candida sagamina, Candida saitoana, Candida sake, Candida salmanticensis, Candida santamariae, Candida santjacobensis, Candida saopaulonensis, Candida savonica, Candida schatavii, Candida sequanensis, Candida sergipensis, Candida shehatae, Candida silvae, Candida silvanorum, Candida silvatica, Candida silvicola, Candida silvicultrix, Candida sinolaborantium, Candida sithepensis, Candida smithsonii, Candida sojae, Candida solani, Candida songkhlaensis, Candida sonorensis, Candida sophiae-reginae, Candida sorbophila, Candida sorbosivorans, Candida sorboxylosa, Candida spandovensis, Candida steatolytica, Candida stellata, Candida stellimalicola, Candida stri, Candida subhashii, Candida succiphila, Candida suecica, Candida suzukii, Candida takamatsuzukensis, Candida taliae, Candida tammaniensis, Candida tanzawaensis, Candida tartarivorans, Candida temnochilae, Candida tenuis, Candida tepae, Candida terraborum, Candida tetrigidarum, Candida thaimueangensis, Candida thermophila, Candida tilneyi, Candida tolerans, Candida torresii, Candida tritomae, Candida tropicalis, Candida trypodendroni, Candida tsuchiyae, Candida tumulicola, Candida ubatubensis, Candida ulmi, Candida vaccinii, Candida valdiviana, Candida vanderkliftii, Candida vanderwaltii, Candida vartiovaarae, Candida versatilis, Candida vini, Candida viswanathii, Candida wickerhamii, Candida wounanorum, Candida wyomingensis, Candida xylopsoci, Candida yuchorum, Candida zemplinina*, or *Candida zeylanoides*.

Embodiment 3. The substantially pure *Candida* host cell of embodiment 2, wherein the substantially pure *Candida* host cell is genetically modified *Candida tropicalis*.

Embodiment 4. The substantially pure *Candida* host cell of embodiment 3, wherein the substantially pure *Candida* host cell is selected from the group consisting of DP428, DP522 and DP 527.

Embodiment 5. The substantially pure *Candida* host cell of embodiment 1, wherein the substantially pure *Candida* host cell is genetically modified *Candida tropicalis* and wherein the alcohol dehydrogenase gene is selected from the group consisting of ADH-A4, ADH-A4B, ADH-B4, ADH-B4B, ADH-A10, ADH-A10B, ADH-B11, and ADH-B11B.

Embodiment 6. The substantially pure *Candida* host cell of embodiment 1, wherein the alcohol dehydrogenase gene comprises a nucleic acid sequence that binds under conditions of high stringency to SEQ ID NO: 39, SEQ ID NO: 40, SEQ ID NO: 42, SEQ ID NO: 43, or SEQ ID NO: 56.

Embodiment 7. The substantially pure *Candida* host cell of embodiment 1, wherein the alcohol dehydrogenase gene comprises a nucleic acid sequence that binds under conditions of moderate stringency to SEQ ID NO: 39, SEQ ID NO: 40, SEQ ID NO: 42, SEQ ID NO: 43, or SEQ ID NO: 56.

Embodiment 8. The substantially pure *Candida* host cell of embodiment 1, wherein the alcohol dehydrogenase gene comprises a nucleic acid sequence that binds under conditions of low stringency to SEQ ID NO: 39, SEQ ID NO: 40, SEQ ID NO: 42, SEQ ID NO: 43, or SEQ ID NO: 56.

Embodiment 9. The substantially pure *Candida* host cell of embodiment 1, wherein the alcohol dehydrogenase gene encodes an amino acid sequence that has at least 90 percent sequence identity to a stretch of at least 100 contiguous residues of any one of SEQ ID NO: 151, SEQ ID NO: 152, SEQ ID NO: 153, SEQ ID NO: 154, or SEQ ID NO:155.

Embodiment 10. The substantially pure *Candida* host cell of embodiment 9, wherein the alcohol dehydrogenase gene comprises a nucleic acid sequence that binds under conditions of high stringency to a first sequence selected from the group consisting of SEQ ID NO: 39, SEQ ID NO: 40, SEQ ID NO: 42, SEQ ID NO: 43, and SEQ ID NO: 56.

Embodiment 11. The substantially pure *Candida* host cell of embodiment 9, wherein the alcohol dehydrogenase gene comprises a nucleic acid sequence that binds under conditions of moderate stringency to a first sequence selected from the group consisting of SEQ ID NO: 39, SEQ ID NO: 40, SEQ ID NO: 42, SEQ ID NO: 43, and SEQ ID NO: 56.

Embodiment 12. The substantially pure *Candida* host cell of embodiment 9, wherein the alcohol dehydrogenase gene comprises a nucleic acid sequence that binds under conditions of low stringency to a first sequence selected from the group consisting of SEQ ID NO: 39, SEQ ID NO: 40, SEQ ID NO: 42, SEQ ID NO: 43, and SEQ ID NO: 56.

Embodiment 13. The substantially pure *Candida* host cell of embodiment 1, wherein the alcohol dehydrogenase gene encodes an amino acid sequence that has 100 percent sequence identity to a stretch of at least 100 contiguous residues of any one of SEQ ID NO: 151, SEQ ID NO: 152, SEQ ID NO: 153, SEQ ID NO: 154, or SEQ ID NO:155.

Embodiment 14. The substantially pure *Candida* host cell of embodiment 13, wherein the alcohol dehydrogenase gene comprises a nucleic acid sequence that binds under conditions of high stringency to a first sequence selected from the group consisting of SEQ ID NO: 39, SEQ ID NO: 40, SEQ ID NO: 42, SEQ ID NO: 43, and SEQ ID NO: 56.

Embodiment 15. The substantially pure *Candida* host cell of embodiment 13, wherein the alcohol dehydrogenase gene comprises a nucleic acid sequence that binds under conditions of moderate stringency to a first sequence selected from the group consisting of SEQ ID NO: 39, SEQ ID NO: 40, SEQ ID NO: 42, SEQ ID NO: 43, and SEQ ID NO: 56.

Embodiment 16. The substantially pure *Candida* host cell of embodiment 13, wherein the alcohol dehydrogenase gene comprises a nucleic acid sequence that binds under conditions of low stringency to a first sequence selected from the group consisting of SEQ ID NO: 39, SEQ ID NO: 40, SEQ ID NO: 42, SEQ ID NO: 43, and SEQ ID NO: 56.

Embodiment 17. The substantially pure *Candida* host cell of embodiment 1, wherein the alcohol dehydrogenase gene encodes an amino acid sequence that comprises at least one peptide selected from the group consisting of SEQ ID NO: 156, SEQ ID NO: 157, SEQ ID NO: 158, SEQ ID NO: 159, and SEQ ID NO: 160.

Embodiment 18. The substantially pure *Candida* host cell of embodiment 1, wherein the alcohol dehydrogenase gene encodes an amino acid sequence that comprises at least two peptides selected from the group consisting of SEQ ID NO: 156, SEQ ID NO: 157, SEQ ID NO: 158, SEQ ID NO: 159, and SEQ ID NO: 160.

Embodiment 19. The substantially pure *Candida* host cell of embodiment 1, wherein the alcohol dehydrogenase gene encodes an amino acid sequence that comprises at least three peptides selected from the group consisting of SEQ ID NO: 156, SEQ ID NO: 157, SEQ ID NO: 158, SEQ ID NO: 159, and SEQ ID NO: 160.

Embodiment 20. The substantially pure *Candida* host cell of embodiment 1, wherein the alcohol dehydrogenase gene encodes an amino acid sequence that comprises at least four peptides selected from the group consisting of SEQ ID NO: 156, SEQ ID NO: 157, SEQ ID NO: 158, SEQ ID NO: 159, and SEQ ID NO: 160.

Embodiment 21. The substantially pure *Candida* host cell of embodiment 1, wherein the one or more genetic modifications in the first genetic modification class cause the alcohol dehydrogenase to have decreased function relative to the function of the wild-type counterpart, be nonfunctional, or have a modified activity spectrum relative to an activity spectrum of the wild-type counterpart.

Embodiment 22. The substantially pure *Candida* host cell of embodiment 1 that further comprises a second genetic modification class, wherein the second genetic modification class comprises an insertion of a first gene into the *Candida* host cell genome; wherein the first gene encodes a protein that is not identical to a naturally occurring protein in the substantially pure *Candida* host cell, or a protein that is identical to a naturally occurring protein in the substantially pure *Candida* host cell, but expression of the gene is controlled by a promoter that is different from the promoter that controls the expression of the naturally occurring protein.

Embodiment 23. The substantially pure *Candida* host cell of embodiment 22, wherein the first gene encodes a desaturase, a lipase, a fatty alcohol oxidase, an alcohol dehydrogenase, a glycosyl transferase, a cytochrome P450, a cellulose, an exoglucanase, a cellobiohydrolase, an endoglucanase, a β-glucosidase, an α-amylase, a β-amylase, a γ-amylases, a glucoamylase, a maltogenase, a pullanase, an endo-β-xylanase, an α-glucuronidase, an α-arabinofuranosidase, a β-xylosidase, a β-mannanase, a β-mannosidase, a pectin lyase, an endo-polygalacturonase, an α-arabinofuranosidase, an α-galactosidase, a polymethylgalacturonase, a pectin depolymerase, a pectinase, an exopolygalacturanosidase hydrolase, an α-L-Rhamnosidase, an α-L-Arabinofuranosidase, a polymethylgalacturonate lyase, a polygalacturonate lyase, an exopolygalacturonate lyase, a peroxidase, a copper radical oxidase, an FAD-dependent oxidase, a multicopper oxidase, a lignin peroxidase or a manganese peroxidase that is not identical to a naturally occurring protein in the substantially pure *Candida* host cell; or identical to a naturally occurring protein in the substantially pure *Candida* host cell, but expression of the gene is controlled by a promoter that is different from the promoter that controls the expression of the naturally occurring protein.

Embodiment 24. The substantially pure *Candida* host cell of embodiment 22, wherein the first gene encodes a cytochrome P450 that is not identical to a naturally occurring cytochrome P450 in the substantially pure *Candida* host cell.

Embodiment 25. The substantially pure *Candida* host cell of embodiment 22, wherein the first gene is a gene listed in Table 4 other than a gene that naturally occurs in the substantially pure *Candida* host cell.

Embodiment 26. The substantially pure *Candida* host cell of embodiment 22, wherein the first gene has at least 40 percent sequence identity to a gene listed in Table 4, and wherein the first gene does not naturally occur in the substantially pure *Candida* host cell.

Embodiment 27. The substantially pure *Candida* host cell of embodiment 22, wherein the first gene has at least 60 percent sequence identity to a gene listed in Table 4, and wherein the first gene does not naturally occur in the substantially pure *Candida* host cell.

Embodiment 28. The substantially pure *Candida* host cell of embodiment 22, wherein the first gene has at least 80 percent sequence identity to a gene listed in Table 4, and wherein the first gene does not naturally occur in the substantially pure *Candida* host cell.

Embodiment 29. The substantially pure *Candida* host cell of embodiment 22, wherein the first gene has at least 95 percent sequence identity to a gene listed in Table 4, and wherein the first gene does not naturally occur in the substantially pure *Candida* host cell.

Embodiment 30. The substantially pure *Candida* host cell of embodiment 22, wherein the first gene is encoded by a nucleic acid that binds under conditions of high stringency to a nucleic acid that encodes a gene listed in Table 4, and wherein the first gene does not naturally occur in the substantially pure *Candida* host cell.

Embodiment 31. The substantially pure *Candida* host cell of embodiment 22, wherein the first gene is encoded by a nucleic acid that binds under conditions of moderate stringency to a nucleic acid that encodes a gene listed in Table 4, and wherein the first gene does not naturally occur in the substantially pure *Candida* host cell.

Embodiment 32. The substantially pure *Candida* host cell of embodiment 22, wherein the first gene is encoded by a nucleic acid that binds under conditions of low stringency to a nucleic acid that encodes a gene listed in Table 4, and wherein the first gene does not naturally occur in the substantially pure *Candida* host cell.

Embodiment 33. The substantially pure *Candida* host cell of embodiment 22, wherein the promoter is an isocitrate lyase promoter, a cytochrome P450 promoter, a fatty alcohol oxidase promoter or an alcohol dehydrogenase promoter in the *Candida* host cell genome.

Embodiment 34. The substantially pure *Candida* host cell of embodiment 33, wherein the promoter is an isocitrate lyase promoter.

Embodiment 35. The substantially pure *Candida* host cell of embodiment 1 that further comprises a third genetic modification class, wherein the third genetic modification class comprises one or more genetic modifications in the *Candida* host cell genome that collectively or individually disrupt the β-oxidation pathway; or a gene selected from the group consisting of a CYP52A type cytochrome P450 and a fatty alcohol oxidase.

Embodiment 36. A method of using a genetically modified *Candida* cell for the biotransformation of a substrate to a product, wherein the genetically modified *Candida* cell is characterized by a first genetic modification class that comprises one or more genetic modifications that collectively or individually disrupt an alcohol dehydrogenase gene; and the method comprises fermenting the genetically modified *Candida* cell in a culture medium comprising a nitrogen source and a carbon source.

Embodiment 37. The method of embodiment 36, wherein the culture medium further comprises the substrate.

Embodiment 38. The method of embodiment 36, wherein the genetically modified *Candida* cell is genetically modified *Candida glabrata, Candida zeylenoides, Candida lipolytica, Candida guillermondii, Candida aaseri, Candida abiesophila, Candida africana, Candida aglyptinia, Candida agrestis, Candida akabanensis, Candida alai, Candida albicans, Candida alimentaria, Candida amapae, Candida ambrosiae, Candida amphixiae, Candida anatomiae, Candida ancudensis, Candida anglica, Candida anneliseae, Candida antarctica, Candida antillancae, Candida anutae, Candida apicola, Candida apis, Candida arabinofermentans, Candida arcana, Candida ascalaphidarum, Candida asparagi, Candida atakaporum, Candida atbi, Candida athensensis, Candida atlantica, Candida atmosphaerica, Candida auringiensis, Candida auris, Candida aurita, Candida austromarina, Candida azyma, Candida azymoides, Candida barrocoloradensis, Candida batistae, Candida beechii, Candida bentonensis, Candida bertae, Candida berthetii, Candida bituminiphila, Candida blankii, Candida blattae, Candida blattariae, Candida bohiensis, Candida boidinii, Candida bokatorum, Candida boleticola, Candida bolitotheri, Candida bombi, Candida bombiphila, Candida bondarzewiae,*

*Candida bracarensis, Candida bribrorum, Candida bromeliacearum, Candida buenavistaensis, Candida buinensis, Candida butyri, Candida californica, Candida canberraensis, Candida cariosilignicola, Candida carpophila, Candida caryicola, Candida caseinolytica, Candida castrensis, Candida catenulata, Candida cellae, Candida cellulolytica, Candida cerambycidarum, Candida chauliodes, Candida chickasaworum, Candida chilensis, Candida choctaworum, Candida chodatii, Candida chrysomelidarum, Candida cidri, Candida cloacae, Candida coipomoensis, Candida conglobata, Candida corydali, Candida cylindracea, Candida davenportii, Candida davisiana, Candida deformans, Candida dendrica, Candida dendronema, Candida derodonti, Candida diddensiae, Candida digboiensis, Candida diospyri, Candida diversa, Candida dosseyi, Candida drimydis, Candida drosophilae, Candida dubliniensis, Candida easanensis, Candida edaphicus, Candida edax, Candida elateridarum, Candida emberorum, Candida endomychidarum, Candida entomophila, Candida ergastensis, Candida ernobii, Candida etchellsii, Candida ethanolica, Candida famata, Candida fennica, Candida fermenticarens, Candida flocculosa, Candida floricola, Candida floris, Candida flosculorum, Candida fluviatilis, Candida fragi, Candida freyschussii, Candida friedrichii, Candida frijolesensis, Candida fructus, Candida fukazawae, Candida fungicola, Candida galacta, Candida galis, Candida galli, Candida gatunensis, Candida gelsemii, Candida geochares, Candida germanica, Candida ghanaensis, Candida gigantensis, Candida glaebosa, Candida glucosophila, Candida glycerinogenes, Candida gorgasii, Candida gotoi, Candida gropengiesseri, Candida guaymorum, Candida haemulonii, Candida halonitratophila, Candida halophila, Candida hasegawae, Candida hawaiiana, Candida heliconiae, Candida hispaniensis, Candida homilentoma, Candida humicola, Candida humilis, Candida hungarica, Candida hyderabadensis, Candida incommunis, Candida inconspicua, Candida insectalens, Candida insectamans, Candida insectorum, Candida intermedia, Candida ipomoeae, Candida ishiwadae, Candida jaroonii, Candida jeffriesii, Candida kanchanaburiensis, Candida karawaiewii, Candida kashinagacola, Candida kazuoi, Candida khmerensis, Candida kipukae, Candida kofuensis, Candida krabiensis, Candida kruisii, Candida kunorum, Candida labiduridarum, Candida lactis-condensi, Candida lassenensis, Candida laureliae, Candida leandrae, Candida lessepsii, Candida lignicola, Candida litsaeae, Candida litseae, Candida llanquihuensis, Candida lycoperdinae, Candida lyxosophila, Candida magnifica, Candida magnoliae, Candida maltosa, Candida mannitofaciens, Candida maris, Candida maritima, Candida maxii, Candida melibiosica, Candida membranifaciens, Candida mesenterica, Candida metapsilosis, Candida methanolophaga, Candida methanolovescens, Candida methanosorbosa, Candida methylica, Candida michaelii, Candida mogii, Candida montana, Candida multigemmis, Candida mycetangii, Candida naeodendra, Candida nakhonratchasimensis, Candida nanaspora, Candida natalensis, Candida neerlandica, Candida nemodendra, Candida nitrativorans, Candida nitratophila, Candida nivariensis, Candida nodaensis, Candida norvegica, Candida novakii, Candida odintsovae, Candida oleophila, Candida ontarioensis, Candida ooitensis, Candida orba, Candida oregonensis, Candida orthopsilosis, Candida ortonii, Candida ovalis, Candida pallodes, Candida palmioleophila, Candida paludigena, Candida panamensis, Candida panamericana, Candida parapsilosis, Candida pararugosa, Candida pattaniensis, Candida peltata, Candida peoriaensis, Candida petrohuensis, Candida phangngensis, Candida picachoensis, Candida piceae, Candida picinguabensis, Candida pignaliae, Candida pimensis, Candida pini, Candida plutei, Candida pomicola, Candida ponderosae, Candida populi, Candida powellii, Candida prunicola, Candida pseudoglaebosa, Candida pseudohaemulonii, Candida pseudointermedia, Candida pseudolambica, Candida pseudorhagii, Candida pseudovanderkliftii, Candida psychrophila, Candida pyralidae, Candida qinlingensis, Candida quercitrusa, Candida quercuum, Candida railenensis, Candida ralunensis, Candida rancensis, Candida restingae, Candida rhagii, Candida riodocensis, Candida rugopelliculosa, Candida rugosa, Candida sagamina, Candida saitoana, Candida sake, Candida salmanticensis, Candida santamariae, Candida santjacobensis, Candida saopaulonensis, Candida savonica, Candida schatavii, Candida sequanensis, Candida sergipensis, Candida shehatae, Candida silvae, Candida silvanorum, Candida silvatica, Candida silvicola, Candida silvicultrix, Candida sinolaborantium, Candida sithepensis, Candida smithsonii, Candida sojae, Candida solani, Candida songkhlaensis, Candida sonorensis, Candida sophiae-reginae, Candida sorbophila, Candida sorbosivorans, Candida sorboxylosa, Candida spandovensis, Candida steatolytica, Candida stellata, Candida stellimalicola, Candida stri, Candida subhashii, Candida succiphila, Candida suecica, Candida suzukii, Candida takamatsuzukensis, Candida taliae, Candida tammaniensis, Candida tanzawaensis, Candida tartarivorans, Candida temnochilae, Candida tenuis, Candida tepae, Candida terraborum, Candida tetrigidarum, Candida thaimueangensis, Candida thermophila, Candida tilneyi, Candida tolerans, Candida torresii, Candida tritomae, Candida tropicalis, Candida trypodendroni, Candida tsuchiyae, Candida tumulicola, Candida ubatubensis, Candida ulmi, Candida vaccinii, Candida valdiviana, Candida vanderkliftii, Candida vanderwaltii, Candida vartiovaarae, Candida versatilis, Candida vini, Candida viswanathii, Candida wickerhamii, Candida wounanorum, Candida wyomingensis, Candida xylopsoci, Candida yuchorum, Candida zemplinina*, or *Candida zeylanoides.*

Embodiment 39. The method of embodiment 36, wherein the genetically modified *Candida* cell is genetically modified *Candida tropicalis.*

Embodiment 40. The method of embodiment 36, wherein the genetically modified *Candida* cell is genetically modified *Candida tropicalis* and wherein the alcohol dehydrogenase is selected from the group consisting of ADH-A4, ADH-A4B, ADH-B4, ADH-B4B, ADH-A10, ADH-A10B, ADH-B11, and ADH-B11B.

Embodiment 41. The method of embodiment 36, wherein the alcohol dehydrogenase gene comprises a nucleic acid sequence that binds under conditions of high stringency to SEQ ID NO: 39, SEQ ID NO: 40, SEQ ID NO: 42, SEQ ID NO: 43, or SEQ ID NO: 56.

Embodiment 42. The method of embodiment 36, wherein the alcohol dehydrogenase gene comprises a nucleic acid sequence that binds under conditions of moderate stringency to SEQ ID NO: 39, SEQ ID NO: 40, SEQ ID NO: 42, SEQ ID NO: 43, or SEQ ID NO: 56.

Embodiment 43. The method of embodiment 36, wherein the alcohol dehydrogenase gene comprises a nucleic acid sequence that binds under conditions of low stringency to SEQ ID NO: 39, SEQ ID NO: 40, SEQ ID NO: 42, SEQ ID NO: 43, or SEQ ID NO: 56.

Embodiment 44. The method of embodiment 36, wherein the alcohol dehydrogenase gene encodes an amino acid sequence that has at least 90 percent sequence identity to a stretch of at least 100 contiguous residues of any one of SEQ ID NO: 151, SEQ ID NO: 152, SEQ ID NO: 153, SEQ ID NO: 154, or SEQ ID NO:155.

Embodiment 45. The method of embodiment 44, wherein the alcohol dehydrogenase gene comprises a nucleic acid sequence that binds under conditions of high stringency to a first sequence selected from the group consisting of SEQ ID NO: 39, SEQ ID NO: 40, SEQ ID NO: 42, SEQ ID NO: 43, and SEQ ID NO: 56.

Embodiment 46. The method of embodiment 44, wherein the alcohol dehydrogenase gene comprises a nucleic acid sequence that binds under conditions of moderate stringency to a first sequence selected from the group consisting of SEQ ID NO: 39, SEQ ID NO: 40, SEQ ID NO: 42, SEQ ID NO: 43, and SEQ ID NO: 56.

Embodiment 47. The method of embodiment 44, wherein the alcohol dehydrogenase gene comprises a nucleic acid sequence that binds under conditions of low stringency to a first sequence selected from the group consisting of SEQ ID NO: 39, SEQ ID NO: 40, SEQ ID NO: 42, SEQ ID NO: 43, and SEQ ID NO: 56.

Embodiment 48. The method of embodiment 36, wherein the alcohol dehydrogenase gene encodes an amino acid sequence that has 100 percent sequence identity to a stretch of at least 100 contiguous residues of any one of SEQ ID NO: 151, SEQ ID NO: 152, SEQ ID NO: 153, SEQ ID NO: 154, or SEQ ID NO:155.

Embodiment 49. The method of embodiment 48, wherein the alcohol dehydrogenase gene comprises a nucleic acid sequence that binds under conditions of high stringency to a first sequence selected from the group consisting of SEQ ID NO: 39, SEQ ID NO: 40, SEQ ID NO: 42, SEQ ID NO: 43, and SEQ ID NO: 56.

Embodiment 50. The method of embodiment 48, wherein the alcohol dehydrogenase gene comprises a nucleic acid sequence that binds under conditions of moderate stringency to a first sequence selected from the group consisting of SEQ ID NO: 39, SEQ ID NO: 40, SEQ ID NO: 42, SEQ ID NO: 43, and SEQ ID NO: 56.

Embodiment 51. The method of embodiment 48, wherein the alcohol dehydrogenase gene comprises a nucleic acid sequence that binds under conditions of low stringency to a first sequence selected from the group consisting of SEQ ID NO: 39, SEQ ID NO: 40, SEQ ID NO: 42, SEQ ID NO: 43, and SEQ ID NO: 56.

Embodiment 52. The method of embodiment 36, wherein the alcohol dehydrogenase gene encodes an amino acid sequence that comprises at least one peptide selected from the group consisting of SEQ ID NO: 156, SEQ ID NO: 157, SEQ ID NO: 158, SEQ ID NO: 159, and SEQ ID NO: 160.

Embodiment 53. The method of embodiment 36, wherein the alcohol dehydrogenase gene encodes an amino acid sequence that comprises at least two peptides selected from the group consisting of SEQ ID NO: 156, SEQ ID NO: 157, SEQ ID NO: 158, SEQ ID NO: 159, and SEQ ID NO: 160.

Embodiment 54. The method of embodiment 36, wherein the alcohol dehydrogenase gene encodes an amino acid sequence that comprises at least three peptides selected from the group consisting of SEQ ID NO: 156, SEQ ID NO: 157, SEQ ID NO: 158, SEQ ID NO: 159, and SEQ ID NO: 160.

Embodiment 55. The method of embodiment 36, wherein the alcohol dehydrogenase gene encodes an amino acid sequence that comprises at least four peptides selected from the group consisting of SEQ ID NO: 156, SEQ ID NO: 157, SEQ ID NO: 158, SEQ ID NO: 159, and SEQ ID NO: 160.

Embodiment 56. The method of embodiment 36, wherein the one or more genetic modifications in the first genetic modification class cause the alcohol dehydrogenase to have decreased function relative to the function of the wild-type counterpart, be nonfunctional, or have a modified activity spectrum relative to an activity spectrum of the wild-type counterpart.

Embodiment 57. The method of embodiment 36, wherein the genetically modified *Candida* cell further comprises a second genetic modification class, wherein the second genetic modification class comprises an insertion of a first gene into the *Candida* host cell genome; wherein the first gene encodes a protein that is not identical to a naturally occurring protein in the *Candida* host cell, or a protein that is identical to a naturally occurring protein in the *Candida* host cell, but expression of the gene is controlled by a promoter that is different from the promoter that controls the expression of the naturally occurring protein.

Embodiment 58. The method of embodiment 57, wherein the first gene encodes a desaturase, a lipase, a fatty alcohol oxidase, an alcohol dehydrogenase, a glycosyl transferase, a cytochrome P450, a cellulose, an exoglucanase, a cellobiohydrolase, an endoglucanase, a β-glucosidase, an α-amylase, a β-amylase, a γ-amylases, a glucoamylase, a maltogenase, a pullanase, an endo-β-xylanase, an α-glucuronidase, an α-arabinofuranosidase, a β-xylosidase, a β-mannanase, a β-mannosidase, a pectin lyase, an endo-polygalacturonase, an α-arabinofuranosidase, an α-galactosidase, a polymethylgalacturonase, a pectin depolymerase, a pectinase, an exopolygalacturanosidase hydrolase, an α-L-Rhamnosidase, an α-L-Arabinofuranosidase, a polymethylgalacturonate lyase, a polygalacturonate lyase, an exopolygalacturonate lyase, a peroxidase, a copper radical oxidase, an FAD-dependent oxidase, a multicopper oxidase, a lignin peroxidase or a manganese peroxidase that is not identical to a naturally occurring protein in the *Candida* host cell or is identical to a naturally occurring protein in the *Candida* host cell, but expression of the gene is controlled by a promoter that is different from the promoter that controls the expression of the naturally occurring protein.

Embodiment 59. The method of embodiment 57, wherein the first gene encodes a cytochrome P450 that is not identical to a naturally occurring cytochrome P450 in the *Candida* host cell.

Embodiment 60. The method of embodiment 57, wherein the first gene is a gene listed in Table 4 other than a gene that naturally occurs in the *Candida* host cell.

Embodiment 61. The method of embodiment 57, wherein the first gene has at least 40 percent sequence identity to a gene listed in Table 4, and wherein the first gene does not naturally occur in the *Candida* host cell.

Embodiment 62. The method of embodiment 57, wherein the first gene has at least 60 percent sequence identity to a gene listed in Table 4, and wherein the first gene does not naturally occur in the *Candida* host cell.

Embodiment 63. The method of embodiment 57, wherein the first gene has at least 80 percent sequence identity to a gene listed in Table 4, and wherein the first gene does not naturally occur in the *Candida* host cell.

Embodiment 64. The method of embodiment 57, wherein the first gene has at least 95 percent sequence identity to a gene listed in Table 4, and wherein the first gene does not naturally occur in the *Candida* host cell.

Embodiment 65. The method of embodiment 57, wherein the first gene is encoded by a nucleic acid that binds under conditions of high stringency to a nucleic acid that encodes a gene listed in Table 4, and wherein the first gene does not naturally occur in the *Candida* host cell.

Embodiment 66. The method of embodiment 57, wherein the first gene is encoded by a nucleic acid that binds under conditions of moderate stringency to a nucleic acid that encodes a gene listed in Table 4, and wherein the first gene does not naturally occur in the *Candida* host cell.

Embodiment 67. The method of embodiment 57, wherein the first gene is encoded by a nucleic acid that binds under conditions of low stringency to a nucleic acid that encodes a gene listed in Table 4, and wherein the first gene does not naturally occur in the *Candida* host cell.

Embodiment 68. The method of embodiment 57, wherein the promoter is an isocitrate lyase promoter, a cytochrome P450 promoter, a fatty alcohol oxidase promoter or an alcohol dehydrogenase promoter in the *Candida* host cell genome.

Embodiment 69. The method of embodiment 57, wherein the promoter is an isocitrate lyase promoter.

Embodiment 70. The method of embodiment 36, wherein the genetically modified *Candida* cell further comprises a third genetic modification class, wherein the third genetic modification class comprises one or more genetic modifications in the *Candida* host cell genome that collectively or individually disrupt

- the β-oxidation pathway; or
- a gene selected from the group consisting of a CYP52A type cytochrome P450 and a fatty alcohol oxidase.

Embodiment 71. A method for the biotransformation of a substrate to a product in a *Candida* host cell, the method comprising:

- making one or more first genetic modifications in a first genetic modification class to the *Candida* host cell, wherein the first genetic modification class comprises one or more genetic modifications that collectively or individually disrupt an alcohol dehydrogenase gene; and
- transforming the substrate to the product by fermenting the *Candida* host cell in a culture medium comprising a nitrogen source and a carbon source.

Embodiment 72. The method of embodiment 71, wherein the *Candida* host cell is genetically modified *Candida glabrata, Candida zeylenoides, Candida lipolytica, Candida guillermondii, Candida aaseri, Candida abiesophila, Candida africana, Candida aglyptinia, Candida agrestis, Candida akabanensis, Candida alai, Candida albicans, Candida alimentaria, Candida amapae, Candida ambrosiae, Candida amphixiae, Candida anatomiae, Candida ancudensis, Candida anglica, Candida anneliseae, Candida antarctica, Candida antillancae, Candida anutae, Candida apicola, Candida apis, Candida arabinofermentans, Candida arcana, Candida ascalaphidarum, Candida asparagi, Candida atakaporum, Candida atbi, Candida athensensis, Candida atlantica, Candida atmosphaerica, Candida auringiensis, Candida auris, Candida aurita, Candida austromarina, Candida azyma, Candida azymoides, Candida barrocoloradensis, Candida batistae, Candida beechii, Candida bentonensis, Candida bertae, Candida berthetii, Candida bituminiphila, Candida blankii, Candida blattae, Candida blattariae, Candida bohiensis, Candida boidinii, Candida bokatorum, Candida boleticola, Candida bolitotheri, Candida bombi, Candida bombiphila, Candida bondarzewiae, Candida bracarensis, Candida bribrorum, Candida bromeliacearum, Candida buenavistaensis, Candida buinensis, Candida butyri, Candida californica, Candida canberraensis, Candida cariosilignicola, Candida carpophila, Candida caryicola, Candida caseinolytica, Candida castrensis, Candida catenulata, Candida cellae, Candida cellulolytica, Candida cerambycidarum, Candida chauliodes, Candida chickasaworum, Candida chilensis, Candida choctaworum, Candida chodatii, Candida chrysomelidarum, Candida cidri, Candida cloacae, Candida coipomoensis, Candida conglobata, Candida corydali, Candida cylindracea, Candida davenportii, Candida davisiana, Candida deformans, Candida dendrica, Candida dendronema, Candida derodonti, Candida diddensiae, Candida digboiensis, Candida diospyri, Candida diversa, Candida dosseyi, Candida drimydis, Candida drosophilae, Candida dubliniensis, Candida easanensis, Candida edaphicus, Candida edax, Candida elateridarum, Candida emberorum, Candida endomychidarum, Candida entomophila, Candida ergastensis, Candida ernobii, Candida etchellsii, Candida ethanolica, Candida famata, Candida fennica, Candida fermenticarens, Candida flocculosa, Candida floricola, Candida floris, Candida flosculorum, Candida fluviatilis, Candida fragi, Candida freyschussii, Candida friedrichii, Candida frijolesensis, Candida fructus, Candida fukazawae, Candida fungicola, Candida galacta, Candida galis, Candida galli, Candida gatunensis, Candida gelsemii, Candida geochares, Candida germanica, Candida ghanaensis, Candida gigantensis, Candida glaebosa, Candida glucosophila, Candida glycerinogenes, Candida gorgasii, Candida gotoi, Candida gropengiesseri, Candida guaymorum, Candida haemulonii, Candida halonitratophila, Candida halophila, Candida hasegawae, Candida hawaiiana, Candida heliconiae, Candida hispaniensis, Candida homilentoma, Candida humicola, Candida humilis, Candida hungarica, Candida hyderabadensis, Candida incommunis, Candida inconspicua, Candida insectalens, Candida insectamans, Candida insectorum, Candida intermedia, Candida ipomoeae, Candida ishiwadae, Candida jaroonii, Candida jeffriesii, Candida kanchanaburiensis, Candida karawaiewii, Candida kashinagacola, Candida kazuoi, Candida khmerensis, Candida kipukae, Candida kofuensis, Candida krabiensis, Candida kruisii, Candida kunorum, Candida labiduridarum, Candida lactis-condensi, Candida lassenensis, Candida laureliae, Candida leandrae, Candida lessepsii, Candida lignicola, Candida litsaeae, Candida litseae, Candida llanquihuensis, Candida lycoperdinae, Candida lyxosophila, Candida magnifica, Candida magnoliae, Candida maltosa, Candida mannitofaciens, Candida maris, Candida maritima, Candida maxii, Candida melibiosica, Candida membranifaciens, Candida mesenterica, Candida metapsilosis, Candida methanolophaga, Candida methanolovescens, Candida methanosorbosa, Candida methylica, Candida michaelii, Candida mogii, Candida montana, Candida multigemmis, Candida mycetangii, Candida naeodendra, Candida nakhonratchasimensis, Candida nanaspora, Candida natalensis, Candida neerlandica, Candida nemodendra, Candida nitrativorans, Candida nitratophila, Candida nivariensis, Candida nodaensis, Candida norvegica, Candida novakii, Candida odintsovae, Candida oleophila, Candida ontarioensis, Candida ooitensis, Candida orba, Candida oregonensis, Candida orthopsilosis, Candida ortonii, Candida ovalis, Candida pallodes, Candida palmioleophila, Candida paludigena, Candida panamensis, Candida panamericana, Candida parapsilosis, Candida pararugosa, Candida pattaniensis, Candida peltata, Candida peoriaensis, Candida petrohuensis, Candida phangngensis, Candida picachoensis, Candida piceae, Candida picinguabensis, Candida pignaliae, Candida pimensis, Candida pini, Candida plutei, Candida pomicola, Candida ponderosae, Candida populi, Candida powellii, Candida prunicola, Candida pseudoglaebosa, Candida pseudohaemulonii, Candida pseudointermedia, Candida pseudolambica, Candida pseudorhagii, Candida pseudovanderkliftii, Candida psychrophila, Candida pyralidae, Candida qinlingensis, Candida quercitrusa, Candida quercuum, Candida railenensis, Candida ralunensis, Candida rancensis, Candida restingae, Candida rhagii, Candida riodocensis, Candida rugopelliculosa, Candida rugosa, Candida sagamina, Candida saitoana, Candida sake, Can-*

*dida salmanticensis, Candida santamariae, Candida santjacobensis, Candida saopaulonensis, Candida savonica, Candida schatavii, Candida sequanensis, Candida sergipensis, Candida shehatae, Candida silvae, Candida silvanorum, Candida silvatica, Candida silvicola, Candida silvicultrix, Candida sinolaborantium, Candida sithepensis, Candida smithsonii, Candida sojae, Candida solani, Candida songkhlaensis, Candida sonorensis, Candida sophiae-reginae, Candida sorbophila, Candida sorbosivorans, Candida sorboxylosa, Candida spandovensis, Candida steatolytica, Candida stellata, Candida stellimalicola, Candida stri, Candida subhashii, Candida succiphila, Candida suecica, Candida suzukii, Candida takamatsuzukensis, Candida taliae, Candida tammaniensis, Candida tanzawaensis, Candida tartarivorans, Candida temnochilae, Candida tenuis, Candida tepae, Candida terraborum, Candida tetrigidarum, Candida thaimueangensis, Candida thermophila, Candida tilneyi, Candida tolerans, Candida torresii, Candida tritomae, Candida tropicalis, Candida trypodendroni, Candida tsuchiyae, Candida tumulicola, Candida ubatubensis, Candida ulmi, Candida vaccinii, Candida valdiviana, Candida vanderkliftii, Candida vanderwaltii, Candida vartiovaarae, Candida versatilis, Candida vini, Candida viswanathii, Candida wickerhamii, Candida wounanorum, Candida wyomingensis, Candida xylopsoci, Candida yuchorum, Candida zemplinina*, or *Candida zeylanoides.*

Embodiment 73. The method of embodiment 71, wherein the *Candida* host cell is genetically modified *Candida tropicalis.*

Embodiment 74. The method of embodiment 71, wherein the *Candida* host cell is selected from the group consisting of DP428, DP522 and DP 527.

Embodiment 75. The method of embodiment 71, wherein the *Candida* host cell is genetically modified *Candida tropicalis* and wherein the alcohol dehydrogenase gene is selected from the group consisting of ADH-A4, ADH-A4B, ADH-B4, ADH-B4B, ADH-A10, ADH-A10B, ADH-B11, and ADH-B11B.

Embodiment 76. The method of embodiment 71, wherein the alcohol dehydrogenase gene comprises a nucleic acid sequence that binds under conditions of high stringency to SEQ ID NO: 39, SEQ ID NO: 40, SEQ ID NO: 42, SEQ ID NO: 43, or SEQ ID NO: 56.

Embodiment 77. The method of embodiment 71, wherein the alcohol dehydrogenase gene comprises a nucleic acid sequence that binds under conditions of moderate stringency to SEQ ID NO: 39, SEQ ID NO: 40, SEQ ID NO: 42, SEQ ID NO: 43, or SEQ ID NO: 56.

Embodiment 78. The method of embodiment 71, wherein the alcohol dehydrogenase gene comprises a nucleic acid sequence that binds under conditions of low stringency to SEQ ID NO: 39, SEQ ID NO: 40, SEQ ID NO: 42, SEQ ID NO: 43, or SEQ ID NO: 56.

Embodiment 79. The method of embodiment 71, wherein the alcohol dehydrogenase gene encodes an amino acid sequence that has at least 90 percent sequence identity to a stretch of at least 100 contiguous residues of any one of SEQ ID NO: 151, SEQ ID NO: 152, SEQ ID NO: 153, SEQ ID NO: 154, or SEQ ID NO:155.

Embodiment 80. The method of embodiment 79, wherein the alcohol dehydrogenase gene comprises a nucleic acid sequence that binds under conditions of high stringency to a first sequence selected from the group consisting of SEQ ID NO: 39, SEQ ID NO: 40, SEQ ID NO: 42, SEQ ID NO: 43, and SEQ ID NO: 56.

Embodiment 81. The method of embodiment 79, wherein the alcohol dehydrogenase gene comprises a nucleic acid sequence that binds under conditions of moderate stringency to a first sequence selected from the group consisting of SEQ ID NO: 39, SEQ ID NO: 40, SEQ ID NO: 42, SEQ ID NO: 43, and SEQ ID NO: 56.

Embodiment 82. The method of embodiment 79, wherein the alcohol dehydrogenase gene comprises a nucleic acid sequence that binds under conditions of low stringency to a first sequence selected from the group consisting of SEQ ID NO: 39, SEQ ID NO: 40, SEQ ID NO: 42, SEQ ID NO: 43, and SEQ ID NO: 56.

Embodiment 83. The method of embodiment 71, wherein the alcohol dehydrogenase gene encodes an amino acid sequence that has 100 percent sequence identity to a stretch of at least 100 contiguous residues of any one of SEQ ID NO: 151, SEQ ID NO: 152, SEQ ID NO: 153, SEQ ID NO: 154, or SEQ ID NO:155.

Embodiment 84. The method of embodiment 83, wherein the alcohol dehydrogenase gene comprises a nucleic acid sequence that binds under conditions of high stringency to a first sequence selected from the group consisting of SEQ ID NO: 39, SEQ ID NO: 40, SEQ ID NO: 42, SEQ ID NO: 43, and SEQ ID NO: 56.

Embodiment 85. The method of embodiment 83, wherein the alcohol dehydrogenase gene comprises a nucleic acid sequence that binds under conditions of moderate stringency to a first sequence selected from the group consisting of SEQ ID NO: 39, SEQ ID NO: 40, SEQ ID NO: 42, SEQ ID NO: 43, and SEQ ID NO: 56.

Embodiment 86. The method of embodiment 83, wherein the alcohol dehydrogenase gene comprises a nucleic acid sequence that binds under conditions of low stringency to a first sequence selected from the group consisting of SEQ ID NO: 39, SEQ ID NO: 40, SEQ ID NO: 42, SEQ ID NO: 43, and SEQ ID NO: 56.

Embodiment 87. The method of embodiment 71, wherein the alcohol dehydrogenase gene encodes an amino acid sequence that comprises at least one peptide selected from the group consisting of SEQ ID NO: 156, SEQ ID NO: 157, SEQ ID NO: 158, SEQ ID NO: 159, and SEQ ID NO: 160.

Embodiment 88. The method of embodiment 71, wherein the alcohol dehydrogenase gene encodes an amino acid sequence that comprises at least two peptides selected from the group consisting of SEQ ID NO: 156, SEQ ID NO: 157, SEQ ID NO: 158, SEQ ID NO: 159, and SEQ ID NO: 160.

Embodiment 89. The method of embodiment 71, wherein the alcohol dehydrogenase gene encodes an amino acid sequence that comprises at least three peptides selected from the group consisting of SEQ ID NO: 156, SEQ ID NO: 157, SEQ ID NO: 158, SEQ ID NO: 159, and SEQ ID NO: 160.

Embodiment 90. The method of embodiment 71, wherein the alcohol dehydrogenase gene encodes an amino acid sequence that comprises at least four peptides selected from the group consisting of SEQ ID NO: 156, SEQ ID NO: 157, SEQ ID NO: 158, SEQ ID NO: 159, and SEQ ID NO: 160.

Embodiment 91. The method of embodiment 71, wherein the one or more genetic modifications in the first genetic modification class cause the alcohol dehydrogenase to have decreased function relative to the function of the wild-type counterpart, be nonfunctional, or have a modified activity spectrum relative to an activity spectrum of the wild-type counterpart.

Embodiment 92. The method of embodiment 71 that further comprises a second genetic modification class, wherein the second genetic modification class comprises an insertion of a first gene into the *Candida* host cell genome; wherein the first gene encodes

- a protein that is not identical to a naturally occurring protein in the *Candida* host cell, or a protein that is identical to a naturally occurring protein in the *Candida* host cell, but expression of the gene is controlled by a promoter that is different from the promoter that controls the expression of the naturally occurring protein.

Embodiment 93. The method of embodiment 92, wherein the first gene encodes a desaturase, a lipase, a fatty alcohol oxidase, an alcohol dehydrogenase, a glycosyl transferase, a cytochrome P450, a cellulose, an exoglucanase, a cellobiohydrolase, an endoglucanase, a β-glucosidase, an α-amylase, a β-amylase, a γ-amylases, a glucoamylase, a maltogenase, a pullanase, an endo-β-xylanase, an α-glucuronidase, an α-arabinofuranosidase, a β-xylosidase, a β-mannanase, a β-mannosidase, a pectin lyase, an endo-polygalacturonase, an α-arabinofuranosidase, an α-galactosidase, a polymethylgalacturonase, a pectin depolymerase, a pectinase, an exopolygalacturanosidase hydrolase, an α-L-Rhamnosidase, an α-L-Arabinofuranosidase, a polymethylgalacturonate lyase, a polygalacturonate lyase, an exopolygalacturonate lyase, a peroxidase, a copper radical oxidase, an FAD-dependent oxidase, a multicopper oxidase, a lignin peroxidase or a manganese peroxidase that is not identical to a naturally occurring protein in the *Candida* host cell; or identical to a naturally occurring protein in the *Candida* host cell, but expression of the gene is controlled by a promoter that is different from the promoter that controls the expression of the naturally occurring protein.

Embodiment 94. The method of embodiment 92, wherein the first gene encodes a cytochrome P450 that is not identical to a naturally occurring cytochrome P450 in the *Candida* host cell.

Embodiment 95. The method of embodiment 92, wherein the first gene is a gene listed in Table 4 other than a gene that naturally occurs in the *Candida* host cell.

Embodiment 96. The method of embodiment 92, wherein the first gene has at least 40 percent sequence identity to a gene listed in Table 4, and wherein the first gene does not naturally occur in the *Candida* host cell.

Embodiment 97. The method of embodiment 92, wherein the first gene has at least 60 percent sequence identity to a gene listed in Table 4, and wherein the first gene does not naturally occur in the *Candida* host cell.

Embodiment 98. The method of embodiment 92, wherein the first gene has at least 80 percent sequence identity to a gene listed in Table 4, and wherein the first gene does not naturally occur in the *Candida* host cell.

Embodiment 99. The method of embodiment 92, wherein the first gene has at least 95 percent sequence identity to a gene listed in Table 4, and wherein the first gene does not naturally occur in the *Candida* host cell.

Embodiment 100. The method of embodiment 92, wherein the first gene is encoded by a nucleic acid that binds under conditions of high stringency to a nucleic acid that encodes a gene listed in Table 4, and wherein the first gene does not naturally occur in the *Candida* host cell.

Embodiment 101. The method of embodiment 92, wherein the first gene is encoded by a nucleic acid that binds under conditions of moderate stringency to a nucleic acid that encodes a gene listed in Table 4, and wherein the first gene does not naturally occur in the *Candida* host cell.

Embodiment 102. The method of embodiment 92, wherein the first gene is encoded by a nucleic acid that binds under conditions of low stringency to a nucleic acid that encodes a gene listed in Table 4, and wherein the first gene does not naturally occur in the *Candida* host cell.

Embodiment 103. The method of embodiment 71, wherein the culture medium further comprises the substrate.

Embodiment 104. The method of embodiment 71, wherein the method further comprises making one or more second genetic modifications in a second genetic modification class to the *Candida* host cell, wherein the second genetic modification class comprises one or more genetic modifications that collectively or individually disrupt the β-oxidation pathway; or a gene selected from the group consisting of a CYP52A type cytochrome P450 and a fatty alcohol oxidase.

Embodiment 105. A method for producing a genetically modified *Candida* host cell for the biotransformation of a substrate to a product, the method comprising making one or more genetic modifications that disrupt an alcohol dehydrogenase gene in a *Candida* host cell.

Embodiment 106. The method of embodiment 105, wherein the *Candida* host cell is *Candida glabrata, Candida zeylenoides, Candida lipolytica, Candida guillermondii, Candida aaseri, Candida abiesophila, Candida africana, Candida aglyptinia, Candida agrestis, Candida akabanensis, Candida alai, Candida albicans, Candida alimentaria, Candida amapae, Candida ambrosiae, Candida amphixiae, Candida anatomiae, Candida ancudensis, Candida anglica, Candida anneliseae, Candida antarctica, Candida antillancae, Candida anutae, Candida apicola, Candida apis, Candida arabinofermentans, Candida arcana, Candida ascalaphidarum, Candida asparagi, Candida atakaporum, Candida atbi, Candida athensensis, Candida atlantica, Candida atmosphaerica, Candida auringiensis, Candida auris, Candida aurita, Candida austromarina, Candida azyma, Candida azymoides, Candida barrocoloradensis, Candida batistae, Candida beechii, Candida bentonensis, Candida bertae, Candida berthetii, Candida bituminiphila, Candida blankii, Candida blattae, Candida blattariae, Candida bohiensis, Candida boidinii, Candida bokatorum, Candida boleticola, Candida bolitotheri, Candida bombi, Candida bombiphila, Candida bondarzewiae, Candida bracarensis, Candida bribrorum, Candida bromeliacearum, Candida buenavistaensis, Candida buinensis, Candida butyri, Candida californica, Candida canberraensis, Candida cariosilignicola, Candida carpophila, Candida caryicola, Candida caseinolytica, Candida castrensis, Candida catenulata, Candida cellae, Candida cellulolytica, Candida cerambycidarum, Candida chauliodes, Candida chickasaworum, Candida chilensis, Candida choctaworum, Candida chodatii, Candida chrysomelidarum, Candida cidri, Candida cloacae, Candida coipomoensis, Candida conglobata, Candida corydali, Candida cylindracea, Candida davenportii, Candida davisiana, Candida deformans, Candida dendrica, Candida dendronema, Candida derodonti, Candida diddensiae, Candida digboiensis, Candida diospyri, Candida diversa, Candida dosseyi, Candida drimydis, Candida drosophilae, Candida dubliniensis, Candida easanensis, Candida edaphicus, Candida edax, Candida elateridarum, Candida emberorum, Candida endomychidarum, Candida entomophila, Candida ergastensis, Candida ernobii, Candida etchellsii, Candida ethanolica, Candida famata, Candida fennica, Candida fermenticarens, Candida flocculosa, Candida floricola, Candida floris, Candida flosculorum, Candida fluviatilis, Candida fragi, Candida freyschussii, Candida friedrichii, Candida frijolesensis, Candida fructus, Candida fukazawae, Candida fungicola, Candida galacta, Candida galis, Candida galli, Candida gatunensis, Candida gelsemii, Candida geochares, Candida germanica, Candida ghanaensis, Candida gigantensis, Candida glaebosa, Candida glucosophila, Candida glycerinogenes, Candida gorgasii, Candida gotoi, Candida gropeng-*

*iesseri, Candida guaymorum, Candida haemulonii, Candida halonitratophila, Candida halophila, Candida hasegawae, Candida hawaiiana, Candida heliconiae, Candida hispaniensis, Candida homilentoma, Candida humicola, Candida humilis, Candida hungarica, Candida hyderabadensis, Candida incommunis, Candida inconspicua, Candida insectalens, Candida insectamans, Candida insectorum, Candida intermedia, Candida ipomoeae, Candida ishiwadae, Candida jaroonii, Candida jeffriesii, Candida kanchanaburiensis, Candida karawaiewii, Candida kashinagacola, Candida kazuoi, Candida khmerensis, Candida kipukae, Candida kofuensis, Candida krabiensis, Candida kruisii, Candida kunorum, Candida labiduridarum, Candida lactis-condensi, Candida lassenensis, Candida laureliae, Candida leandrae, Candida lessepsii, Candida lignicola, Candida litsaeae, Candida litseae, Candida llanquihuensis, Candida lycoperdinae, Candida lyxosophila, Candida magnifica, Candida magnoliae, Candida maltosa, Candida mannitofaciens, Candida maris, Candida maritima, Candida maxii, Candida melibiosica, Candida membranifaciens, Candida mesenterica, Candida metapsilosis, Candida methanolophaga, Candida methanolovescens, Candida methanosorbosa, Candida methylica, Candida michaelii, Candida mogii, Candida montana, Candida multigemmis, Candida mycetangii, Candida naeodendra, Candida nakhonratchasimensis, Candida nanaspora, Candida natalensis, Candida neerlandica, Candida nemodendra, Candida nitrativorans, Candida nitratophila, Candida nivariensis, Candida nodaensis, Candida norvegica, Candida novakii, Candida odintsovae, Candida oleophila, Candida ontarioensis, Candida ooitensis, Candida orba, Candida oregonensis, Candida orthopsilosis, Candida ortonii, Candida ovalis, Candida pallodes, Candida palmioleophila, Candida paludigena, Candida panamensis, Candida panamericana, Candida parapsilosis, Candida pararugosa, Candida pattaniensis, Candida peltata, Candida peoriaensis, Candida petrohuensis, Candida phangngensis, Candida picachoensis, Candida piceae, Candida picinguabensis, Candida pignaliae, Candida pimensis, Candida pini, Candida plutei, Candida pomicola, Candida ponderosae, Candida populi, Candida powellii, Candida prunicola, Candida pseudoglaebosa, Candida pseudohaemulonii, Candida pseudointermedia, Candida pseudolambica, Candida pseudorhagii, Candida pseudovanderkliftii, Candida psychrophila, Candida pyralidae, Candida qinlingensis, Candida quercitrusa, Candida quercuum, Candida railenensis, Candida ralunensis, Candida rancensis, Candida restingae, Candida rhagii, Candida riodocensis, Candida rugopelliculosa, Candida rugosa, Candida sagamina, Candida saitoana, Candida sake, Candida salmanticensis, Candida santamariae, Candida santjacobensis, Candida saopaulonensis, Candida savonica, Candida schatavii, Candida sequanensis, Candida sergipensis, Candida shehatae, Candida silvae, Candida silvanorum, Candida silvatica, Candida silvicola, Candida silvicultrix, Candida sinolaborantium, Candida sithepensis, Candida smithsonii, Candida sojae, Candida solani, Candida songkhlaensis, Candida sonorensis, Candida sophiae-reginae, Candida sorbophila, Candida sorbosivorans, Candida sorboxylosa, Candida spandovensis, Candida steatolytica, Candida stellata, Candida stellimalicola, Candida stri, Candida subhashii, Candida succiphila, Candida suecica, Candida suzukii, Candida takamatsuzukensis, Candida taliae, Candida tammaniensis, Candida tanzawaensis, Candida tartarivorans, Candida temnochilae, Candida tenuis, Candida tepae, Candida terraborum, Candida tetrigidarum, Candida thaimueangensis, Candida thermophila, Candida tilneyi, Candida tolerans, Candida torresii, Candida tritomae, Candida tropicalis, Candida trypodendroni, Candida tsuchiyae, Candida tumulicola, Candida ubatubensis, Candida ulmi, Candida vaccinii, Candida valdiviana, Candida vanderkliftii, Candida vanderwaltii, Candida vartiovaarae, Candida versatilis, Candida vini, Candida viswanathii, Candida wickerhamii, Candida wounanorum, Candida wyomingensis, Candida xylopsoci, Candida yuchorum, Candida zemplinina*, or *Candida zeylanoides.*

Embodiment 107. The method of embodiment 105, wherein the *Candida* host cell is *Candida tropicalis.*

Embodiment 108. The method of embodiment 105, wherein the *Candida* host cell is selected from the group consisting of DP428, DP522 and DP 527.

Embodiment 109. The method of embodiment 105, wherein the *Candida* host cell is genetically modified *Candida tropicalis* and wherein the alcohol dehydrogenase gene is selected from the group consisting of ADH-A4, ADH-A4B, ADH-B4, ADH-B4B, ADH-A10, ADH-A10B, ADH-B11, and ADH-B11B.

Embodiment 110. The method of embodiment 105, wherein the alcohol dehydrogenase gene comprises a nucleic acid sequence that binds under conditions of high stringency to SEQ ID NO: 39, SEQ ID NO: 40, SEQ ID NO: 42, SEQ ID NO: 43, or SEQ ID NO: 56.

Embodiment 111. The method of embodiment 105, wherein the alcohol dehydrogenase gene comprises a nucleic acid sequence that binds under conditions of moderate stringency to SEQ ID NO: 39, SEQ ID NO: 40, SEQ ID NO: 42, SEQ ID NO: 43, or SEQ ID NO: 56.

Embodiment 112. The method of embodiment 105, wherein the alcohol dehydrogenase gene comprises a nucleic acid sequence that binds under conditions of low stringency to SEQ ID NO: 39, SEQ ID NO: 40, SEQ ID NO: 42, SEQ ID NO: 43, or SEQ ID NO: 56.

Embodiment 113. The method of embodiment 105, wherein the alcohol dehydrogenase gene encodes an amino acid sequence that has at least 90 percent sequence identity to a stretch of at least 100 contiguous residues of any one of SEQ ID NO: 151, SEQ ID NO: 152, SEQ ID NO: 153, SEQ ID NO: 154, or SEQ ID NO:155.

Embodiment 114. The method of embodiment 113, wherein the alcohol dehydrogenase gene comprises a nucleic acid sequence that binds under conditions of high stringency to a first sequence selected from the group consisting of SEQ ID NO: 39, SEQ ID NO: 40, SEQ ID NO: 42, SEQ ID NO: 43, and SEQ ID NO: 56.

Embodiment 115. The method of embodiment 113, wherein the alcohol dehydrogenase gene comprises a nucleic acid sequence that binds under conditions of moderate stringency to a first sequence selected from the group consisting of SEQ ID NO: 39, SEQ ID NO: 40, SEQ ID NO: 42, SEQ ID NO: 43, and SEQ ID NO: 56.

Embodiment 116. The method of embodiment 113, wherein the alcohol dehydrogenase gene comprises a nucleic acid sequence that binds under conditions of low stringency to a first sequence selected from the group consisting of SEQ ID NO: 39, SEQ ID NO: 40, SEQ ID NO: 42, SEQ ID NO: 43, and SEQ ID NO: 56.

Embodiment 117. The method of embodiment 105, wherein the alcohol dehydrogenase gene encodes an amino acid sequence that has 100 percent sequence identity to a stretch of at least 100 contiguous residues of any one of SEQ ID NO: 151, SEQ ID NO: 152, SEQ ID NO: 153, SEQ ID NO: 154, or SEQ ID NO:155.

Embodiment 118. The method of embodiment 117, wherein the alcohol dehydrogenase gene comprises a nucleic acid sequence that binds under conditions of high stringency to a first sequence selected from the group consisting of SEQ ID NO: 39, SEQ ID NO: 40, SEQ ID NO: 42, SEQ ID NO: 43, and SEQ ID NO: 56.

Embodiment 119. The method of embodiment 117, wherein the alcohol dehydrogenase gene comprises a nucleic acid sequence that binds under conditions of moderate stringency to a first sequence selected from the group consisting of SEQ ID NO: 39, SEQ ID NO: 40, SEQ ID NO: 42, SEQ ID NO: 43, and SEQ ID NO: 56.

Embodiment 120

The method of embodiment 117, wherein the alcohol dehydrogenase gene comprises a nucleic acid sequence that binds under conditions of low stringency to a first sequence selected from the group consisting of SEQ ID NO: 39, SEQ ID NO: 40, SEQ ID NO: 42, SEQ ID NO: 43, and SEQ ID NO: 56.

Embodiment 121. The method of embodiment 105, wherein the alcohol dehydrogenase gene encodes an amino acid sequence that comprises at least one peptide selected from the group consisting of SEQ ID NO: 156, SEQ ID NO: 157, SEQ ID NO: 158, SEQ ID NO: 159, and SEQ ID NO: 160.

Embodiment 122. The method of embodiment 105, wherein the alcohol dehydrogenase gene encodes an amino acid sequence that comprises at least two peptides selected from the group consisting of SEQ ID NO: 156, SEQ ID NO: 157, SEQ ID NO: 158, SEQ ID NO: 159, and SEQ ID NO: 160.

Embodiment 123. The method of embodiment 105, wherein the alcohol dehydrogenase gene encodes an amino acid sequence that comprises at least three peptides selected from the group consisting of SEQ ID NO: 156, SEQ ID NO: 157, SEQ ID NO: 158, SEQ ID NO: 159, and SEQ ID NO: 160.

Embodiment 124. The method of embodiment 105, wherein the alcohol dehydrogenase gene encodes an amino acid sequence that comprises at least four peptides selected from the group consisting of SEQ ID NO: 156, SEQ ID NO: 157, SEQ ID NO: 158, SEQ ID NO: 159, and SEQ ID NO: 160.

Embodiment 125. The method of embodiment 105, wherein the one or more genetic modifications cause an alcohol dehydrogenase to have decreased function relative to the function of the wild-type counterpart, be nonfunctional, or have a modified activity spectrum relative to an activity spectrum of the wild-type counterpart.

Embodiment 126. The method of embodiment 105 that further comprises a second genetic modification class, wherein the second genetic modification class comprises an insertion of a first gene into the *Candida* host cell genome; wherein the first gene encodes

- a protein that is not identical to a naturally occurring protein in the *Candida* host cell, or
- a protein that is identical to a naturally occurring protein in the *Candida* host cell, but expression of the gene is controlled by a promoter that is different from the promoter that controls the expression of the naturally occurring protein.

Embodiment 127. The method of embodiment 126, wherein the first gene encodes a desaturase, a lipase, a fatty alcohol oxidase, an alcohol dehydrogenase, a glycosyl transferase, a cytochrome P450, a cellulose, an exoglucanase, a cellobiohydrolase, an endoglucanase, a β-glucosidase, an α-amylase, a β-amylase, a γ-amylases, a glucoamylase, a maltogenase, a pullanase, an endo-β-xylanase, an α-glucuronidase, an α-arabinofuranosidase, a β-xylosidase, a β-mannanase, a β-mannosidase, a pectin lyase, an endo-polygalacturonase, an α-arabinofuranosidase, an α-galactosidase, a polymethylgalacturonase, a pectin depolymerase, a pectinase, an exopolygalacturanosidase hydrolase, an α-L-Rhamnosidase, an α-L-Arabinofuranosidase, a polymethylgalacturonate lyase, a polygalacturonate lyase, an exopolygalacturonate lyase, a peroxidase, a copper radical oxidase, an FAD-dependent oxidase, a multicopper oxidase, a lignin peroxidase or a manganese peroxidase that is

- not identical to a naturally occurring protein in the *Candida* host cell; or
- identical to a naturally occurring protein in the *Candida* host cell, but expression of the gene is controlled by a promoter that is different from the promoter that controls the expression of the naturally occurring protein.

Embodiment 128. The method of embodiment 126, wherein the first gene encodes a cytochrome P450 that is not identical to a naturally occurring cytochrome P450 in the *Candida* host cell.

Embodiment 129. The method of embodiment 126, wherein the first gene is a gene listed in Table 4 other than a gene that naturally occurs in the *Candida* host cell.

Embodiment 130. The method of embodiment 126, wherein the first gene has at least 40 percent sequence identity to a gene listed in Table 4, and wherein the first gene does not naturally occur in the *Candida* host cell.

Embodiment 131. The method of embodiment 126, wherein the first gene has at least 60 percent sequence identity to a gene listed in Table 4, and wherein the first gene does not naturally occur in the *Candida* host cell.

Embodiment 132. The method of embodiment 126, wherein the first gene has at least 80 percent sequence identity to a gene listed in Table 4, and wherein the first gene does not naturally occur in the *Candida* host cell.

Embodiment 133. The method of embodiment 126, wherein the first gene has at least 95 percent sequence identity to a gene listed in Table 4, and wherein the first gene does not naturally occur in the *Candida* host cell.

Embodiment 134. The method of embodiment 126, wherein the first gene is encoded by a nucleic acid that binds under conditions of high stringency to a nucleic acid that encodes a gene listed in Table 4, and wherein the first gene does not naturally occur in the *Candida* host cell.

Embodiment 135. The method of embodiment 126, wherein the first gene is encoded by a nucleic acid that binds under conditions of moderate stringency to a nucleic acid that encodes a gene listed in Table 4, and wherein the first gene does not naturally occur in the *Candida* host cell.

Embodiment 136. The method of embodiment 126, wherein the first gene is encoded by a nucleic acid that binds under conditions of low stringency to a nucleic acid that encodes a gene listed in Table 4, and wherein the first gene does not naturally occur in the *Candida* host cell.

Embodiment 137. The method of embodiment 105, wherein the method further comprises making one or more second genetic modifications in a second genetic modification class to the *Candida* host cell, wherein the second genetic modification class comprises one or more genetic modifications that collectively or individually disrupt

- the β-oxidation pathway; or
- a gene selected from the group consisting of a CYP52A type cytochrome P450 and a fatty alcohol oxidase.

Embodiment 138. A genetically modified *Candida* cell for the biotransformation of a substrate to a product, wherein the genetically modified *Candida* cell is characterized by an insertion of a first gene into the *Candida* host cell genome, wherein the expression of the first gene is controlled by an isocitrate lyase promoter.

Embodiment 139. The genetically modified *Candida* cell of embodiment 138, wherein the isocitrate lyase promoter is encoded by a nucleic acid sequence that binds under conditions of high stringency to SEQ ID NO: 161.

Embodiment 140. The genetically modified *Candida* cell of embodiment 138, wherein the isocitrate lyase promoter is encoded by a nucleic acid sequence that binds under conditions of moderate stringency to SEQ ID NO: 161.

Embodiment 141. The genetically modified *Candida* cell of embodiment 138, wherein the isocitrate lyase promoter is encoded by a nucleic acid sequence that binds under conditions of low stringency to SEQ ID NO: 161.

Embodiment 142. The genetically modified *Candida* cell of embodiment 138, wherein the isocitrate lyase promoter is encoded by a nucleic acid sequence that binds under conditions of high stringency to SEQ ID NO: 171.

Embodiment 143. The genetically modified *Candida* cell of embodiment 138, wherein the isocitrate lyase promoter is encoded by a nucleic acid sequence that binds under conditions of moderate stringency to SEQ ID NO: 171.

Embodiment 144. The genetically modified *Candida* cell of embodiment 138, wherein the isocitrate lyase promoter is encoded by a nucleic acid sequence that binds under conditions of low stringency to SEQ ID NO: 171.

Embodiment 145. The genetically modified *Candida* cell of embodiment 138, wherein the isocitrate lyase promoter comprises a sequence that has at least 60 percent sequence identity to SEQ ID NO: 161.

Embodiment 146. The genetically modified *Candida* cell of embodiment 138, wherein the isocitrate lyase promoter comprises a sequence that has at least 80 percent sequence identity to SEQ ID NO: 161.

Embodiment 147. The genetically modified *Candida* cell of embodiment 138, wherein the isocitrate lyase promoter comprises a sequence that has at least 95 percent sequence identity to SEQ ID NO: 161.

Embodiment 148. The genetically modified *Candida* cell of embodiment 138, wherein the isocitrate lyase promoter comprises a sequence that is identical to SEQ ID NO: 161.

Embodiment 149. The genetically modified *Candida* cell of embodiment 138, wherein the first gene encodes a desaturase, a lipase, a fatty alcohol oxidase, an alcohol dehydrogenase, a glycosyl transferase, a cytochrome P450, a cellulose, an exoglucanase, a cellobiohydrolase, an endoglucanase, a β-glucosidase, an α-amylase, a β-amylase, a γ-amylases, a glucoamylase, a maltogenase, a pullanase, an endo-β-xylanase, an α-glucuronidase, an α-arabinofuranosidase, a β-xylosidase, a β-mannanase, a β-mannosidase, a pectin lyase, an endo-polygalacturonase, an α-arabinofuranosidase, an α-galactosidase, a polymethylgalacturonase, a pectin depolymerase, a pectinase, an exopolygalacturanosidase hydrolase, an α-L-Rhamnosidase, an α-L-Arabinofuranosidase, a polymethylgalacturonate lyase, a polygalacturonate lyase, an exopolygalacturonate lyase, a peroxidase, a copper radical oxidase, an FAD-dependent oxidase, a multicopper oxidase, a lignin peroxidase or a manganese peroxidase.

Embodiment 150. The genetically modified *Candida* cell of embodiment 138, wherein the first gene encodes a cytochrome P450 that is not identical to a naturally occurring cytochrome P450 in the *Candida* host cell.

Embodiment 151. The genetically modified *Candida* cell of embodiment 138, wherein the first gene is a gene listed in Table 4 other than a gene that naturally occurs in the *Candida* host cell.

Embodiment 152. The genetically modified *Candida* cell of embodiment 138, wherein the first gene has at least 40 percent sequence identity to a gene listed in Table 4, and wherein the first gene does not naturally occur in the *Candida* host cell.

Embodiment 153. The genetically modified *Candida* cell of embodiment 138, wherein the first gene has at least 60 percent sequence identity to a gene listed in Table 4, and wherein the first gene does not naturally occur in the *Candida* host cell.

Embodiment 154. The genetically modified *Candida* cell of embodiment 138, wherein the first gene has at least 80 percent sequence identity to a gene listed in Table 4, and wherein the first gene does not naturally occur in the *Candida* host cell.

Embodiment 155. The genetically modified *Candida* cell of embodiment 138, wherein the first gene has at least 95 percent sequence identity to a gene listed in Table 4, and wherein the first gene does not naturally occur in the *Candida* host cell.

Embodiment 156. The genetically modified *Candida* cell of embodiment 138, wherein the genetically modified *Candida* cell is genetically modified *Candida glabrata, Candida zeylenoides, Candida lipolytica, Candida guillermondii, Candida aaseri, Candida abiesophila, Candida africana, Candida aglyptinia, Candida agrestis, Candida akabanensis, Candida alai, Candida albicans, Candida alimentaria, Candida amapae, Candida ambrosiae, Candida amphixiae, Candida anatomiae, Candida ancudensis, Candida anglica, Candida anneliseae, Candida antarctica, Candida antillancae, Candida anutae, Candida apicola, Candida apis, Candida arabinofermentans, Candida arcana, Candida ascalaphidarum, Candida asparagi, Candida atakaporum, Candida atbi, Candida athensensis, Candida atlantica, Candida atmosphaerica, Candida auringiensis, Candida auris, Candida aurita, Candida austromarina, Candida azyma, Candida azymoides, Candida barrocoloradensis, Candida batistae, Candida beechii, Candida bentonensis, Candida bertae, Candida berthetii, Candida bituminiphila, Candida blankii, Candida blattae, Candida blattariae, Candida bohiensis, Candida boidinii, Candida bokatorum, Candida boleticola, Candida bolitotheri, Candida bombi, Candida bombiphila, Candida bondarzewiae, Candida bracarensis, Candida bribrorum, Candida bromeliacearum, Candida buenavistaensis, Candida buinensis, Candida butyri, Candida californica, Candida canberraensis, Candida cariosilignicola, Candida carpophila, Candida caryicola, Candida caseinolytica, Candida castrensis, Candida catenulata, Candida cellae, Candida cellulolytica, Candida cerambycidarum, Candida chauliodes, Candida chickasaworum, Candida chilensis, Candida choctaworum, Candida chodatii, Candida chrysomelidarum, Candida cidri, Candida cloacae, Candida coipomoensis, Candida conglobata, Candida corydali, Candida cylindracea, Candida davenportii, Candida davisiana, Candida deformans, Candida dendrica, Candida dendronema, Candida derodonti, Candida diddensiae, Candida digboiensis, Candida diospyri, Candida diversa, Candida dosseyi, Candida drimydis, Candida drosophilae, Candida dubliniensis, Candida easanensis, Candida edaphicus, Candida edax, Candida elateridarum, Candida emberorum, Candida endomychidarum, Candida entomophila, Candida ergastensis, Candida ernobii, Candida etchellsii, Candida ethanolica, Candida famata, Candida fennica, Candida fermenticarens, Candida flocculosa, Candida floricola, Candida floris, Candida flosculorum, Candida fluviatilis, Candida fragi, Candida freyschussii, Candida friedrichii, Candida frijolesensis, Candida fructus, Candida fukazawae, Candida fungicola, Candida galacta, Candida galis, Candida galli, Candida gatunensis, Candida gelsemii, Candida geochares, Candida germanica, Candida ghanaensis, Candida gigantensis, Candida glaebosa, Candida glucosophila, Candida glycerinogenes, Candida gorgasii, Candida gotoi, Candida gropengiesseri, Candida guaymorum, Candida haemulonii, Candida halonitratophila, Candida halophila, Candida hasegawae, Candida hawaiiana, Candida heliconiae, Candida hispaniensis, Candida homilentoma, Candida humicola, Candida humilis, Candida hungarica, Candida hyderabadensis, Can-*

*dida incommunis, Candida inconspicua, Candida insectalens, Candida insectamans, Candida insectorum, Candida intermedia, Candida ipomoeae, Candida ishiwadae, Candida jaroonii, Candida jeffriesii, Candida kanchanaburiensis, Candida karawaiewii, Candida kashinagacola, Candida kazuoi, Candida khmerensis, Candida kipukae, Candida kofuensis, Candida krabiensis, Candida kruisii, Candida kunorum, Candida labiduridarum, Candida lactis-condensi, Candida lassenensis, Candida laureliae, Candida leandrae, Candida lessepsii, Candida lignicola, Candida litsaeae, Candida litseae, Candida llanquihuensis, Candida lycoperdinae, Candida lyxosophila, Candida magnifica, Candida magnoliae, Candida maltosa, Candida mannitofaciens, Candida maris, Candida maritima, Candida maxii, Candida melibiosica, Candida membranifaciens, Candida mesenterica, Candida metapsilosis, Candida methanolophaga, Candida methanolovescens, Candida methanosorbosa, Candida methylica, Candida michaelii, Candida mogii, Candida montana, Candida multigemmis, Candida mycetangii, Candida naeodendra, Candida nakhonratchasimensis, Candida nanaspora, Candida natalensis, Candida neerlandica, Candida nemodendra, Candida nitrativorans, Candida nitratophila, Candida nivariensis, Candida nodaensis, Candida norvegica, Candida novakii, Candida odintsovae, Candida oleophila, Candida ontarioensis, Candida ooitensis, Candida orba, Candida oregonensis, Candida orthopsilosis, Candida ortonii, Candida ovalis, Candida pallodes, Candida palmioleophila, Candida paludigena, Candida panamensis, Candida panamericana, Candida parapsilosis, Candida pararugosa, Candida pattaniensis, Candida peltata, Candida peoriaensis, Candida petrohuensis, Candida phangngensis, Candida picachoensis, Candida piceae, Candida picinguabensis, Candida pignaliae, Candida pimensis, Candida pini, Candida plutei, Candida pomicola, Candida ponderosae, Candida populi, Candida powellii, Candida prunicola, Candida pseudoglaebosa, Candida pseudohaemulonii, Candida pseudointermedia, Candida pseudolambica, Candida pseudorhagii, Candida pseudovanderkliftii, Candida psychrophila, Candida pyralidae, Candida qinlingensis, Candida quercitrusa, Candida quercuum, Candida railenensis, Candida ralunensis, Candida rancensis, Candida restingae, Candida rhagii, Candida riodocensis, Candida rugopelliculosa, Candida rugosa, Candida sagamina, Candida saitoana, Candida sake, Candida salmanticensis, Candida santamariae, Candida santjacobensis, Candida saopaulonensis, Candida savonica, Candida schatavii, Candida sequanensis, Candida sergipensis, Candida shehatae, Candida silvae, Candida silvanorum, Candida silvatica, Candida silvicola, Candida silvicultrix, Candida sinolaborantium, Candida sithepensis, Candida smithsonii, Candida sojae, Candida solani, Candida songkhlaensis, Candida sonorensis, Candida sophiae-reginae, Candida sorbophila, Candida sorbosivorans, Candida sorboxylosa, Candida spandovensis, Candida steatolytica, Candida stellata, Candida stellimalicola, Candida stri, Candida subhashii, Candida succiphila, Candida suecica, Candida suzukii, Candida takamatsuzukensis, Candida taliae, Candida tammaniensis, Candida tanzawaensis, Candida tartarivorans, Candida temnochilae, Candida tenuis, Candida tepae, Candida terraborum, Candida tetrigidarum, Candida thaimueangensis, Candida thermophila, Candida tilneyi, Candida tolerans, Candida torresii, Candida tritomae, Candida tropicalis, Candida trypodendroni, Candida tsuchiyae, Candida tumulicola, Candida ubatubensis, Candida ulmi, Candida vaccinii, Candida valdiviana, Candida vanderkliftii, Candida vanderwaltii, Candida vartiovaarae, Candida versatilis, Candida vini, Candida viswanathii, Candida wickerhamii, Candida wounanorum, Candida wyomingensis, Candida xylopsoci, Candida yuchorum, Candida zemplinina*, or *Candida zeylanoides*.

Embodiment 157. The genetically modified *Candida* cell of embodiment 138, wherein the genetically modified *Candida* cell is genetically modified *Candida tropicalis*.

Embodiment 158. The genetically modified *Candida* cell of embodiment 138, wherein the genetically modified *Candida* cell is selected from the group consisting of DP428, DP522 and DP 527.

Embodiment 159. The genetically modified *Candida* cell of embodiment 138, wherein the genetically modified *Candida* cell further comprises one or more genetic modifications that collectively or individually disrupt an alcohol dehydrogenase gene.

Embodiment 160. The genetically modified *Candida* cell of embodiment 159, wherein the genetically modified *Candida* cell is genetically modified *Candida tropicalis* and wherein the alcohol dehydrogenase gene is selected from the group consisting of ADH-A4, ADH-A4B, ADH-B4, ADH-B4B, ADH-A10, ADH-A10B, ADH-B11, and ADH-B11B.

Embodiment 161. The genetically modified *Candida* cell of embodiment 159, wherein the alcohol dehydrogenase gene comprises a nucleic acid sequence that binds under conditions of high stringency to SEQ ID NO: 39, SEQ ID NO: 40, SEQ ID NO: 42, SEQ ID NO: 43, or SEQ ID NO: 56.

Embodiment 162. The genetically modified *Candida* cell of embodiment 159, wherein the alcohol dehydrogenase gene comprises a nucleic acid sequence that binds under conditions of moderate stringency to SEQ ID NO: 39, SEQ ID NO: 40, SEQ ID NO: 42, SEQ ID NO: 43, or SEQ ID NO: 56.

Embodiment 163. The genetically modified *Candida* cell of embodiment 159, wherein the alcohol dehydrogenase gene comprises a nucleic acid sequence that binds under conditions of low stringency to SEQ ID NO: 39, SEQ ID NO: 40, SEQ ID NO: 42, SEQ ID NO: 43, or SEQ ID NO: 56.

Embodiment 164. The genetically modified *Candida* cell of embodiment 159, wherein the alcohol dehydrogenase gene encodes an amino acid sequence that has at least 90 percent sequence identity to a stretch of at least 100 contiguous residues of any one of SEQ ID NO: 151, SEQ ID NO: 152, SEQ ID NO: 153, SEQ ID NO: 154, or SEQ ID NO:155.

Embodiment 165. The genetically modified *Candida* cell of embodiment 164, wherein the alcohol dehydrogenase gene comprises a nucleic acid sequence that binds under conditions of high stringency to a first sequence selected from the group consisting of SEQ ID NO: 39, SEQ ID NO: 40, SEQ ID NO: 42, SEQ ID NO: 43, and SEQ ID NO: 56.

Embodiment 166. The genetically modified *Candida* cell of embodiment 164, wherein the alcohol dehydrogenase gene comprises a nucleic acid sequence that binds under conditions of moderate stringency to a first sequence selected from the group consisting of SEQ ID NO: 39, SEQ ID NO: 40, SEQ ID NO: 42, SEQ ID NO: 43, and SEQ ID NO: 56.

Embodiment 167. The genetically modified *Candida* cell of embodiment 164, wherein the alcohol dehydrogenase gene comprises a nucleic acid sequence that binds under conditions of low stringency to a first sequence selected from the group consisting of SEQ ID NO: 39, SEQ ID NO: 40, SEQ ID NO: 42, SEQ ID NO: 43, and SEQ ID NO: 56.

Embodiment 168. The genetically modified *Candida* cell of embodiment 159, wherein the alcohol dehydrogenase gene encodes an amino acid sequence that has 100 percent sequence identity to a stretch of at least 100 contiguous residues of any one of SEQ ID NO: 151, SEQ ID NO: 152, SEQ ID NO: 153, SEQ ID NO: 154, or SEQ ID NO:155.

Embodiment 169. The genetically modified *Candida* cell of embodiment 168, wherein the alcohol dehydrogenase gene comprises a nucleic acid sequence that binds under conditions of high stringency to a first sequence selected from the group consisting of SEQ ID NO: 39, SEQ ID NO: 40, SEQ ID NO: 42, SEQ ID NO: 43, and SEQ ID NO: 56.

Embodiment 170. The genetically modified *Candida* cell of embodiment 168, wherein the alcohol dehydrogenase gene comprises a nucleic acid sequence that binds under conditions of moderate stringency to a first sequence selected from the group consisting of SEQ ID NO: 39, SEQ ID NO: 40, SEQ ID NO: 42, SEQ ID NO: 43, and SEQ ID NO: 56.

Embodiment 171. The genetically modified *Candida* cell of embodiment 168, wherein the alcohol dehydrogenase gene comprises a nucleic acid sequence that binds under conditions of low stringency to a first sequence selected from the group consisting of SEQ ID NO: 39, SEQ ID NO: 40, SEQ ID NO: 42, SEQ ID NO: 43, and SEQ ID NO: 56.

Embodiment 172. The genetically modified *Candida* cell of embodiment 159, wherein the alcohol dehydrogenase gene encodes an amino acid sequence that comprises at least one peptide selected from the group consisting of SEQ ID NO: 156, SEQ ID NO: 157, SEQ ID NO: 158, SEQ ID NO: 159, and SEQ ID NO: 160.

Embodiment 173. The genetically modified *Candida* cell of embodiment 159, wherein the alcohol dehydrogenase gene encodes an amino acid sequence that comprises at least two peptides selected from the group consisting of SEQ ID NO: 156, SEQ ID NO: 157, SEQ ID NO: 158, SEQ ID NO: 159, and SEQ ID NO: 160.

Embodiment 174. The genetically modified *Candida* cell of embodiment 159, wherein the alcohol dehydrogenase gene encodes an amino acid sequence that comprises at least three peptides selected from the group consisting of SEQ ID NO: 156, SEQ ID NO: 157, SEQ ID NO: 158, SEQ ID NO: 159, and SEQ ID NO: 160.

Embodiment 175. The genetically modified *Candida* cell of embodiment 159, wherein the alcohol dehydrogenase gene encodes an amino acid sequence that comprises at least four peptides selected from the group consisting of SEQ ID NO: 156, SEQ ID NO: 157, SEQ ID NO: 158, SEQ ID NO: 159, and SEQ ID NO: 160.

Embodiment 176. The genetically modified *Candida* cell of embodiment 159, wherein the one or more genetic modifications cause an alcohol dehydrogenase to have decreased function relative to the function of the wild-type counterpart, be nonfunctional, or have a modified activity spectrum relative to an activity spectrum of the wild-type counterpart.

Embodiment 177. A method for the biotransformation of a substrate to a product in a *Candida* host cell, the method comprising inserting a first gene into the *Candida* host cell genome, wherein the expression of the first gene is controlled by an isocitrate lyase promoter; and transforming the substrate to the product by fermenting the *Candida* host cell in a culture medium comprising a nitrogen source and a carbon source.

Embodiment 178. The method of embodiment 177, wherein the culture medium further comprises the substrate.

Embodiment 179. The method of embodiment 177, wherein the isocitrate lyase promoter comprises a sequence that has at least 90 percent sequence identity to SEQ ID NO: 161.

Embodiment 180. The method of embodiment 177, wherein inserting the first gene into the host *Candida* cell genome comprises cloning said first gene into a vector, wherein the vector comprises a stretch of at least 100 contiguous nucleotides of any one of SEQ ID NO: 171, SEQ ID NO: 161 or SEQ ID NO: 62.

Embodiment 181. The method of embodiment 177, wherein inserting the first gene into the host *Candida* cell genome comprises cloning said first gene into a vector, wherein the vector comprises SEQ ID NO: 161.

Embodiment 182. The method of embodiment 177, wherein inserting the first gene into the host *Candida* cell genome comprises cloning said first gene into a vector, wherein the vector comprises a sequence that is at least 95% identical to SEQ ID NO: 161.

Embodiment 183. A vector for an insertion of a first gene into a host *Candida* cell genome, wherein the first gene is under the control of an isocitrate lyase promoter in the host *Candida* cell genome; wherein the vector comprises a stretch of at least 100 contiguous nucleotides of any one of SEQ ID NO: 171, SEQ ID NO: 161 or SEQ ID NO: 62.

Embodiment 184. The substantially pure *Candida* host cell of embodiment 1, wherein said one or more genetic modifications comprise an insertion of one or more nucleic acids into the alcohol dehydrogenase gene.

Embodiment 185. The substantially pure *Candida* host cell of embodiment 1, wherein said one or more genetic modifications comprise a deletion of one or more nucleic acids from the alcohol dehydrogenase gene.

What is claimed:

1. A method of using a substantially pure *Candida* host cell for the oxidation of a fatty acid into a corresponding α-carboxyl-ω-hydroxyl fatty acid, wherein the substantially pure *Candida* host cell is characterized by:

a first genetic modification class that comprises one or more genetic modifications that collectively or individually disrupt an alcohol dehydrogenase gene, and a second genetic modification class, wherein the second genetic modification class comprises an insertion of a first gene into the *Candida* cell genome; wherein the first gene encodes a first protein that is not identical to a naturally occurring protein in the substantially pure *Candida* cell, wherein the first protein oxidizes the fatty acid to the corresponding α-carboxyl-ω-hydroxyl fatty acid, or a second protein that is identical to a naturally occurring protein in the substantially pure *Candida* cell wherein, when the first gene encodes the second protein, expression of the first gene is controlled by a promoter that is different from a promoter that controls the expression of the naturally occurring first gene, and wherein the second protein oxidizes the fatty acid to the corresponding α-carboxyl-ω-hydroxyl fatty acid, wherein the method comprises:

fermenting the substantially pure *Candida* host cell in a culture medium comprising a nitrogen source and a carbon source, thereby oxidizing the fatty acid to the corresponding α-carboxyl-ω-hydroxyl fatty acid.

2. The method of claim 1, wherein the culture medium further comprises the fatty acid.

3. The method of claim 1, wherein the substantially pure *Candida* cell is genetically modified *Candida glabrata, Candida zeylenoides, Candida lipolytica, Candida guillermondii, Candida aaseri, Candida abiesophila, Candida africana, Candida aglyptinia, Candida agrestis, Candida akabanensis, Candida alai, Candida albicans, Candida alimentaria, Candida amapae, Candida ambrosiae, Candida amphixiae, Candida anatomiae, Candida ancudensis, Candida anglica, Candida anneliseae, Candida antarctica, Candida antillancae, Candida anutae, Candida apicola, Candida apis, Candida arabinofermentans, Candida arcana, Candida ascalaphidarum, Candida asparagi, Candida atakaporum, Candida atbi, Candida athensensis, Candida atlantica, Candida atmosphaerica, Candida auringiensis, Candida auris, Candida aurita, Candida austromarina, Candida azyma, Candida azymoides, Candida barrocoloradensis, Candida batistae, Candida beechii, Candida bentonensis, Candida bertae, Candida berthetii, Candida bituminiphila, Candida blankii, Candida blattae, Candida blattariae, Candida bohiensis, Candida boidinii, Candida bokatorum, Candida boleticola, Candida bolitotheri, Candida bambi, Candida bombiphila, Candida bondarzewiae, Candida bracarensis, Candida bribrorum, Candida bromeliacearum, Candida buenavistaensis, Candida buinensis, Candida butyri, Candida californica, Candida canberraensis, Candida cariosilignicola, Candida carpophila, Candida caryicola, Candida caseinolytica, Candida castrensis, Candida catenulata, Candida cellae, Candida cellulolytica, Candida cerambycidarum, Candida chauliodes, Candida chickasaworum, Candida chilensis, Candida choctaworum, Candida chodatii, Candida chrysomelidarum, Candida cidri, Candida cloacae, Candida coipomoensis, Candida conglobata, Candida corydali, Candida cylindracea, Candida davenportii, Candida davisiana, Candida deformans, Candida dendrica, Candida dendronema, Candida derodonti, Candida diddensiae, Candida digboiensis, Candida diospyri, Candida diversa, Candida dosseyi, Candida drimydis, Candida drosophilae, Candida dubliniensis, Candida easanensis, Candida edaphicus, Candida edax, Candida elateridarum, Candida emberorum, Candida endomychidarum, Candida entomophila, Candida ergastensis, Candida ernobii, Candida etchellsii, Candida ethanolica, Candida famata, Candida fennica, Candida fermenticarens, Candida flocculosa, Candida floricola, Candida floris, Candida flosculorum, Candida fluviatilis, Candida fragi, Candida freyschussii, Candida friedrichii, Candida frijolesensis, Candida fructus, Candida fukazawae, Candida fungicola, Candida galacta, Candida galis, Candida galli, Candida gatunensis, Candida gelsemii, Candida geochares, Candida germanica, Candida ghanaensis, Candida gigantensis, Candida glaebosa, Candida glucosophila, Candida glycerinogenes, Candida gorgasii, Candida gotoi, Candida gropengiesseri, Candida guaymorum, Candida haemulonii, Candida halonitratophila, Candida halophila, Candida hasegawae, Candida hawaiiana, Candida heliconiae, Candida hispaniensis, Candida homilentoma, Candida humicola, Candida humilis, Candida hungarica, Candida hyderabadensis, Candida incommunis, Candida inconspicua, Candida insectaens, Candida insectamans, Candida insectorum, Candida intermedia, Candida ipomoeae, Candida ishiwadae, Candidajaroonii, Candidajeffriesii, Candida kanchanaburiensis, Candida karawaiewii, Candida kashinagacola, Candida kazuoi, Candida khmerensis, Candida kipukae, Candida kofuensis, Candida krabiensis, Candida kruisii, Candida kunorum, Candida labiduridarum, Candida lactis-condensi, Candida lassenensis, Candida laureliae, Candida leandrae, Candida lessepsii, Candida lignicola, Candida litsaeae, Candida litseae, Candida llanquihuensis, Candida lycoperdinae, Candida lyxosophila, Candida magnifica, Candida magnoliae, Candida maltosa, Candida mannitofaciens, Candida maris, Candida maritima, Candida maxii, Candida melibiosica, Candida membranifaciens, Candida mesenterica, Candida metapsilosis, Candida methanolophaga, Candida methanolovescens, Candida methanosorbosa, Candida methylica, Candida michaelli, Candida mogii, Candida montana, Candida multigemmis, Candida mycetangii, Candida naeodendra, Candida nakhonratchasimensis, Candida nanaspora,*

*Candida natalensis, Candida neerlandica, Candida nemodendra, Candida nitrativorans, Candida nitratophila, Candida nivariensis, Candida nodaensis, Candida norvegica, Candida novakii, Candida odintsovae, Candida oleophila, Candida ontarioensis, Candida ooitensis, Candida orba, Candida oregonensis, Candida orthopsilosis, Candida ortonii, Candida ovalis, Candida pallodes, Candida palmioleophila, Candida paludigena, Candida panamensis, Candida panamericana, Candida parapsilosis, Candida pararugosa, Candida pattaniensis, Candida peltata, Candida peoriaensis, Candida petrohuensis, Candida phangngensis, Candida picachoensis, Candida piceae, Candida picinguabensis, Candida pignaliae, Candida pimensis, Candida pini, Candida plutei, Candida pomicola, Candida ponderosae, Candida populi, Candida powellii, Candida prunicola, Candida pseudoglaebosa, Candida pseudohaemulonii, Candida pseudointermedia, Candida pseudolambica, Candida pseudorhagii, Candida pseudovanderkliftii, Candida psychrophila, Candida pyralidae, Candida qinlingensis, Candida quercitrusa, Candida quercuum, Candida railenensis, Candida ralunensis, Candida rancensis, Candida restingae, Candida rhagii, Candida riodocensis, Candida rugopelliculosa, Candida rugosa, Candida sagamina, Candida saitoana, Candida sake, Candida salmanticensis, Candida santamariae, Candida santjacobensis, Candida saopaulonensis, Candida savonica, Candida schatavii, Candida sequanensis, Candida sergipensis, Candida shehatae, Candida silvae, Candida silvanorum, Candida silvatica, Candida silvicola, Candida silvicultrix, Candida sinolaborantium, Candida sithepensis, Candida smithsonii, Candida sojae, Candida solani, Candida songkhlaensis, Candida sonorensis, Candida sophiae-reginae, Candida sorbophila, Candida sorbosivorans, Candida sorboxylosa, Candida spandovensis, Candida steatolytica, Candida stellata, Candida stellimalicola, Candida stri, Candida subhashii, Candida succiphila, Candida suecica, Candida suzukii, Candida takamatsuzukensis, Candida taliae, Candida tammaniensis, Candida tanzawaensis, Candida tartarivorans, Candida temnochilae, Candida tenuis, Candida tepae, Candida terraborum, Candida tetrigidarum, Candida thaimueangensis, Candida thermophila, Candida tilneyi, Candida tolerans, Candida torresii, Candida tritomae, Candida tropicalis, Candida trypodendroni, Candida tsuchiyae, Candida tumulicola, Candida ubatubensis, Candida ulmi, Candida vaccinii, Candida valdiviana, Candida vanderkliftii, Candida vanderwaltii, Candida vartiovaarae, Candida versatilis, Candida vini, Candida viswanathii, Candida wickerhamii, Candida wounanorum, Candida wyomingensis, Candida xylopsoci, Candida yuchorum, Candida zemplinina*, or *Candida zeylanoides*.

4. The method of claim 1, wherein the alcohol dehydrogenase gene encodes an amino acid sequence that comprises at least one peptide selected from the group consisting of SEQ ID NO: 156, SEQ ID NO: 157, SEQ ID NO: 158, SEQ ID NO: 159, and SEQ ID NO: 160.

5. The method of claim 1, wherein the alcohol dehydrogenase gene encodes an amino acid sequence that comprises at least three peptides selected from the group consisting of SEQ ID NO: 156, SEQ ID NO: 157, SEQ ID NO: 158, SEQ ID NO: 159, and SEQ ID NO: 160.

6. The method of claim 1, wherein the one or more genetic modifications in the first genetic modification class cause the alcohol dehydrogenase to be nonfunctional.

7. The method of claim 1, wherein the first gene encodes a cytochrome P450 that is not identical to a naturally occurring cytochrome P450 in the substantially pure *Candida* host cell.

8. The method of claim 1, wherein the first gene encodes the second protein and the promoter is an isocitrate lyase promoter, a cytochrome P450 promoter, a fatty alcohol oxidase promoter or an alcohol dehydrogenase promoter in the *Candida* host cell genome.

9. The method of claim 1, wherein the first gene encodes the second protein and the promoter is an isocitrate lyase promoter.

10. The method of claim 1, wherein the first gene encodes the second protein and the promoter is an isocitrate lyase promoter that comprises a sequence that has at least 95 percent sequence identity to SEQ ID NO: 161.

11. The method of claim 1, wherein the insertion of the first gene into the host *Candida* cell genome comprises cloning said first gene into a vector, wherein the vector comprises a stretch of at least 100 contiguous nucleotides of SEQ ID NO: 171.

12. The method of claim 1, wherein the substantially pure *Candida* cell is characterized by:

a third genetic modification class that comprises one or more genetic modifications that collectively or individually disrupt a fatty alcohol oxidase.

13. The method of claim 1, wherein the substantially pure *Candida* cell is genetically modified *Candida tropicalis*.

14. A method of using a substantially pure *Candida* host cell for the oxidation of a substrate to a corresponding hydroxylated compound, wherein the substantially pure *Candida* host cell is characterized by:

a first genetic modification class that comprises one or more genetic modifications that collectively or individually disrupt an alcohol dehydrogenase gene, and a second genetic modification class, wherein the second genetic modification class comprises an insertion of a first gene into the *Candida* cell genome;

wherein the first gene encodes a cytochrome P450 that is not identical to a naturally occurring cytochrome P450 in the Candida host cell, and wherein the method comprises fermenting the substantially pure *Candida* host cell in a culture medium comprising a nitrogen source and a carbon source, thereby oxidizing the substrate to the corresponding hydroxylated compound.

15. The method of claim 1, wherein the substantially pure *Candida* cell is genetically modified *Candida glabrata, Candida zeylenoides, Candida lipolytica, Candida guillermondii, Candida aaseri, Candida abiesophila, Candida africana, Candida aglyptinia, Candida agrestis, Candida akabanensis, Candida alai, Candida albicans, Candida alimentaria, Candida amapae, Candida ambrosiae, Candida amphixiae, Candida anatomiae, Candida ancudensis, Candida anglica, Candida anneliseae, Candida antarctica, Candida antillancae, Candida anutae, Candida apicola, Candida apis, Candida arabinofermentans, Candida arcana, Candida ascalaphidarum, Candida asparagi, Candida atakaporum, Candida atbi, Candida athensensis, Candida atlantica, Candida atmosphaerica, Candida auringiensis, Candida auris, Candida aurita, Candida austromarina, Candida azyma, Candida azymoides, Candida barrocoloradensis, Candida batistae, Candida beechii, Candida bentonensis, Candida bertae, Candida berthetii, Candida bituminiphila, Candida blankii, Candida blattae, Candida blattariae, Candida bohiensis, Candida boidinii, Candida bokatorum, Candida boleticola, Candida bolitotheri, Candida bambi, Candida bombiphila, Candida bondarzewiae, Candida bracarensis, Candida bribrorum, Candida bromeliacearum, Candida buenavistaensis, Candida buinensis, Candida butyri, Candida californica, Candida canberraensis, Candida cariosilignicola, Candida carpophila, Candida caryicola, Candida caseinolytica, Candida castrensis, Candida catenulata, Candida cellae, Can-*

*dida cellulolytica, Candida cerambycidarum, Candida chauliodes, Candida chickasaworum, Candida chilensis, Candida choctaworum, Candida chodatii, Candida chrysomelidarum, Candida cidri, Candida cloacae, Candida coipomoensis, Candida conglobata, Candida corydali, Candida cylindracea, Candida davenportii, Candida davisiana, Candida deformans, Candida dendrica, Candida dendronema, Candida derodonti, Candida diddensiae, Candida digboiensis, Candida diospyri, Candida diversa, Candida dosseyi, Candida drimydis, Candida drosophilae, Candida dubliniensis, Candida easanensis, Candida edaphicus, Candida edax, Candida elateridarum, Candida emberorum, Candida endomychidarum, Candida entomophila, Candida ergastensis, Candida ernobii, Candida etchellsii, Candida ethanolica, Candida famata, Candida fennica, Candida fermenticarens, Candida flocculosa, Candida floricola, Candida floris, Candida flosculorum, Candida fluviatilis, Candida fragi, Candida freyschussii, Candida friedrichii, Candida frijolesensis, Candida fructus, Candida fukazawae, Candida fungicola, Candida galacta, Candida galis, Candida galli, Candida gatunensis, Candida gelsemii, Candida geochares, Candida germanica, Candida ghanaensis, Candida gigantensis, Candida glaebosa, Candida glucosophila, Candida glycerinogenes, Candida gorgasii, Candida gotoi, Candida gropengiesseri, Candida guaymorum, Candida haemulonii, Candida halonitratophila, Candida halophila, Candida hasegawae, Candida hawaiiana, Candida heliconiae, Candida hispaniensis, Candida homilentoma, Candida humicola, Candida humilis, Candida hungarica, Candida hyderabadensis, Candida incommunis, Candida inconspicua, Candida insectaens, Candida insectamans, Candida insectorum, Candida intermedia, Candida ipomoeae, Candida ishiwadae, Candidajaroonii, Candidajeffriesii, Candida kanchanaburiensis, Candida karawaiewii, Candida kashinagacola, Candida kazuoi, Candida khmerensis, Candida kipukae, Candida kofuensis, Candida krabiensis, Candida kruisii, Candida kunorum, Candida labiduridarum, Candida lactis-condensi, Candida lassenensis, Candida laureliae, Candida leandrae, Candida lessepsii, Candida lignicola, Candida litsaeae, Candida litseae, Candida llanquihuensis, Candida lycoperdinae, Candida lyxosophila, Candida magnifica, Candida magnoliae, Candida maltosa, Candida mannitofaciens, Candida maris, Candida maritima, Candida maxii, Candida melibiosica, Candida membranifaciens, Candida mesenterica, Candida metapsilosis, Candida methanolophaga, Candida methanolovescens, Candida methanosorbosa, Candida methylica, Candida michaelii, Candida mogii, Candida montana, Candida multigemmis, Candida mycetangii, Candida naeodendra, Candida nakhonratchasimensis, Candida nanaspora, Candida natalensis, Candida neerlandica, Candida nemodendra, Candida nitrativorans, Candida nitratophila, Candida nivariensis, Candida nodaensis, Candida norvegica, Candida novakii, Candida odintsovae, Candida oleophila, Candida ontarioensis, Candida ooitensis, Candida orba, Candida oregonensis, Candida orthopsilosis, Candida ortonii, Candida ovalis, Candida pallodes, Candida palmioleophila, Candida paludigena, Candida panamensis, Candida panamericana, Candida parapsilosis, Candida pararugosa, Candida pattaniensis, Candida peltata, Candida peoriaensis, Candida petrohuensis, Candida phangngensis, Candida picachoensis, Candida piceae, Candida picinguabensis, Candida pignaliae, Candida pimensis, Candida pini, Candida plutei, Candida pomicola, Candida ponderosae, Candida populi, Candida powellii, Candida prunicola, Candida pseudoglaebosa, Candida pseudohaemulonii, Candida pseudointermedia, Candida pseudolambica, Candida pseudorhagii, Candida pseudovanderkliftii, Candida psychrophila, Candida pyralidae, Candida qinlingensis, Candida quercitrusa, Candida quercuum, Candida railenensis, Candida ralunensis, Candida rancensis, Candida restingae, Candida rhagii, Candida riodocensis, Candida rugopelliculosa, Candida rugosa, Candida sagamina, Candida saitoana, Candida sake, Candida salmanticensis, Candida santamariae, Candida santjacobensis, Candida saopaulonensis, Candida savonica, Candida schatavii, Candida sequanensis, Candida sergipensis, Candida shehatae, Candida silvae, Candida silvanorum, Candida silvatica, Candida silvicola, Candida silvicultrix, Candida sinolaborantium, Candida sithepensis, Candida smithsonii, Candida sojae, Candida solani, Candida songkhlaensis, Candida sonorensis, Candida sophiae-reginae, Candida sorbophila, Candida sorbosivorans, Candida sorboxylosa, Candida spandovensis, Candida steatolytica, Candida stellata, Candida stellimalicola, Candida stri, Candida subhashii, Candida succiphila, Candida suecica, Candida suzukii, Candida takamatsuzukensis, Candida taliae, Candida tammaniensis, Candida tanzawaensis, Candida tartarivorans, Candida temnochilae, Candida tenuis, Candida tepae, Candida terraborum, Candida tetrigidarum, Candida thaimueangensis, Candida thermophila, Candida tilneyi, Candida tolerans, Candida torresii, Candida tritomae, Candida tropicalis, Candida trypodendroni, Candida tsuchiyae, Candida tumulicola, Candida ubatubensis, Candida ulmi, Candida vaccinii, Candida valdiviana, Candida vanderkliftii, Candida vanderwaltii, Candida vartiovaarae, Candida versatilis, Candida vini, Candida viswanathii, Candida wickerhamii, Candida wounanorum, Candida wyomingensis, Candida xylopsoci, Candida yuchorum, Candida zemplinina*, or *Candida zeylanoides.*

16. The method of claim 14, wherein the alcohol dehydrogenase gene encodes an amino acid sequence that comprises at least one peptide selected from the group consisting of SEQ ID NO: 156, SEQ ID NO: 157, SEQ ID NO: 158, SEQ ID NO: 159, and SEQ ID NO: 160.

17. The method of claim 14, wherein the alcohol dehydrogenase gene encodes an amino acid sequence that comprises at least three peptides selected from the group consisting of SEQ ID NO: 156, SEQ ID NO: 157, SEQ ID NO: 158, SEQ ID NO: 159, and SEQ ID NO: 160.

18. The method of claim 14, wherein the one or more genetic modifications in the first genetic modification class cause the alcohol dehydrogenase to be nonfunctional.

19. The method of claim 14, wherein the insertion of the first gene into the *Candida* host cell genome comprises cloning said first gene into a vector, wherein the vector comprises a stretch of at least 100 contiguous nucleotides of SEQ ID NO: 171.

20. The method of claim 14, wherein the substantially pure *Candida* host cell is characterized by a third genetic modification class that comprises one or more genetic modifications that collectively or individually disrupt a fatty alcohol oxidase.

21. The method of claim 14, wherein the substantially pure *Candida* host cell is genetically modified *Candida tropicalis*.

22. The method of claim 1, wherein the first gene is expressed under the control of a promoter comprising an isocitrate lyase promoter, an alcohol dehydrogenase promoter, a cytochrome P450 promoter, or a fatty alcohol oxidase promoter.

23. The method of claim 14, wherein the first gene is expressed under the control of a promoter comprising an isocitrate lyase promoter, an alcohol dehydrogenase promoter, a cytochrome P450 promoter, or a fatty alcohol oxidase promoter.

* * * * *

SEQUENCE LISTING

```
<160> NUMBER OF SEQ ID NOS: 175

<210> SEQ ID NO 1
<211> LENGTH: 4186
<212> TYPE: DNA
<213> ORGANISM: Artificial Sequence
<220> FEATURE:
<223> OTHER INFORMATION: Contains flp recominase from Saccharomyces
      cerevisiae with flanking regions as well as the gene encoding
      resistance to the Nourseothricin resistance marker from transposon
      Tn1825

<400> SEQUENCE: 1

ctcgaggaag ttcctatact ttctagagaa taggaacttc ggatccaata atgattggtt     60

tgatattttt gtctagtacc atctgtacca ttacacttaa attatcttta tatctgtcta    120

actcgactgt ctggatttca ttgatgtagt cgtatgcatc gttagttcca aaaaatattg    180
```

-continued

```
tcatcaattt gatattggtt tccgactcta aaatttttgg aagaatttgt ctagcgtgct    240
ctgagttgta gccactgaaa ccacggttaa taacatccaa ttttcggata tacacattct    300
gtaatgctgg atgaaagcca tactgggtac aactaaactg ggtgatggag tcaccgaaca    360
acacaaattt accgtattcc atgattgcta tggttgagaa ttttttttt ttcttgtccc    420
acgccatttt tcaaattatg cagttgagaa tgttagtttt tgtgtacacc ccgttcgctg    480
aatatttcgg aataattcaa agattgggga gtgggggagg cgatagacga agacacggta    540
taaaaatggg caaaattttc cccaactttt tgcagtggtt taactaataa tcgtcgacat    600
gccacaattt gatatattat gtaaaacacc acctaaggtg cttgttcgtc agtttgtgga    660
aaggtttgaa agaccttcag gtgagaaaat agcattatgt gctgctgaac taacctattt    720
atgttggatg attacacata acggaacagc aatcaagaga gccacattca tgagctataa    780
tactatcata agcaattcgt tgagtttcga tattgtcaat aaatcactcc agtttaaata    840
caagacgcaa aaagcaacaa ttttggaagc ctcattaaag aaattgattc ctgcttggga    900
atttacaatt attccttact atggacaaaa acatcaatct gatatcactg atattgtaag    960
tagtttgcaa ttacagttcg aatcatcgga agaagcagat aagggaaata gccacagtaa   1020
aaaaatgctt aaagcacttc taagtgaggg tgaaagcatc tgggagatca ctgagaaaat   1080
actaaattcg tttgagtata cttcgagatt tacaaaaaca aaaactttat accaattcct   1140
cttcctagct actttcatca attgtggaag attcagcgat attaagaacg ttgatccgaa   1200
atcatttaaa ttagtccaaa ataagtattt gggagtaata atccagtgtt tagtgacaga   1260
gacaaagaca agcgttagta ggcacatata cttctttagc gcaaggggta ggatcgatcc   1320
acttgtatat ttggatgaat tttgaggaa ttctgaacca gtcctaaaac gagtaaatag    1380
gaccggcaat tcttcaagca ataaacagga ataccaatta ttaaaagata acttagtcag   1440
atcgtacaat aaagctttga agaaaaatgc gccttattca atctttgcta taaaaaatgg   1500
cccaaaatct cacattggaa gacatttgat gacctcattt ctttcaatga agggcctaac   1560
ggagttgact aatgttgtgg gaaattggag cgataagcgt gcttctgccg tggccaggac   1620
aacgtatact catcagataa cagcaatacc tgatcactac ttcgcactag tttctcggta   1680
ctatgcatat gatccaatat caaaggaaat gatagcattg aaggatgaga ctaatccaat   1740
tgaggagtgg cagcatatag aacagctaaa gggtagtgct gaaggaagca tacgataccc   1800
cgcatggaat gggataatat cacaggaggt actagactac ctttcatcct acataaatag   1860
acgcatataa gagtgaaatt ctggaaatct ggaaatctgg ttttgtattc ttgttattct   1920
tctttttgtt attacatata taacttgtta ctttttaaa aaaatctttg tatattttat    1980
aaatatataa aactaaattt aagaaaaaga gaaaaatgtt ttatttgaga gattgaaatt   2040
ttacttgaat ttagcttagc ttttataaag tattattatg taaaaaaaca aaacaaatat   2100
acattaaaaa gttaagacta taaaatagcc acccaaggca tttctatatc ttgttgttgt   2160
tgttttcatc ttctgtatca gaggaactta ttttattatt ttcgtcacgg gtattttctc   2220
ttgtttgatg attcatccca ttcattccat cataaaatgt cgagcgtcaa aactagagaa   2280
taataaagaa aacgatcttt tcaaaaagaa aaaacctttt agttttcctt tgttgttgtt   2340
gtgggtgtgt gctatttata ttatatagtt tactcataat accataaaat attcggtttg   2400
attaggttat tttaataagc taatttgttt ctaatcgtgt aatttatgct gtgtatatta   2460
agtagtgtgt gcactgccca aaaatgtttg ttgtttatag tcggttaaag agaaaaaaga   2520
aaaaaagatc catacacaca cgttaattag ttgttcaacg taatacactc atattttgtt   2580
```

```
cttatttgct ttcggtcgct gttctcacca agatttattg ccaacgaaac aattttttt    2640

tatatatttt cagattttc ttttttcct ttcctttcct tttctaattt tcactcctgg     2700

ttttctttct ttcttagaaa cattatctcg atattaatat taaaaaaata taatcattca   2760

aaatggacgg tggtatgttt tagtttagct tcaattctaa ttgattgatt aatcagttga   2820

ttggtttcaa tatgacaaat gggtagggtg ggaaaacttc attttcaatt cagatcaaac   2880

tttttgttg tcgacataat atttctcgtt tgggatgtta ctgtcacatt aataatacac    2940

acacatcagc ttataatttt gaaagtaatt tatcagatat gttgtgacga tcaatggaaa   3000

tggctaactt caatgtatct gttcttcccc tttttcaaag ttcacgtttt ttgattgatt   3060

gattgatctg tcggcagtgg tttcaaaacc attcggtgag taatcctatc aatcaatgtt   3120

acgacaaaag gctcaatatt caaaattgca atgttttatg ttttcctacg tgtacttgtg   3180

caaggcaatt gattcaacat tgcttttggt gtttgacgag tttctagttt ggacttgtgt   3240

tgttatctgg gctatacaga tttcccggct cactatgaat tttttttttc gacgctcagt   3300

gcacacaact ataaacaaca caaacacaaa cacagcaaga aaaaaaaaaa acgaacattg   3360

aattgaaacc aagccaactg aaaaattcct tatttaaatg actgtcatac taacccattt   3420

ttatagaaga agttgctgct ttagttatcg ataacggttc tcatatgaaa atttcggtga   3480

tccctgagca ggtggcggaa acattggatg ctgagaacca tttcattgtt cgtgaagtgt   3540

tcgatgtgca cctatccgac caaggctttg aactatctac cagaagtgtg agcccctacc   3600

ggaaggatta catctcggat gatgactctg atgaagactc tgcttgctat ggcgcattca   3660

tcgaccaaga gcttgtcggg aagattgaac tcaactcaac atggaacgat ctagcctcta   3720

tcgaacacat tgttgtgtcg cacacgcacc gaggcaaagg agtcgcgcac agtctcatcg   3780

aatttgcgaa aaagtgggca ctaagcagac agctccttgg catacgatta gagacacaaa   3840

cgaacaatgt acctgcctgc aatttgtacg caaaatgtgg ctttactctc ggcggcattg   3900

acctcttcac gtataaaact agacctcaag tctcgaacga aacagcgatg tactggtact   3960

ggttctcggg agcacaggat gacgcctaac atatgtgaag tgtgaagggg gagatttca    4020

ctttattaga tttgtatata tgtataataa ataaataaat aagttaaata aataattaga   4080

taagggtggt aattattact atttacaatc aaaggtggtc ctgcaggaag ttcctatact   4140

ttctagagaa taggaacttc agatccacta gttctagagc ggccgc                  4186
```

<210> SEQ ID NO 2
<211> LENGTH: 3826
<212> TYPE: DNA
<213> ORGANISM: Candida tropicalis

<400> SEQUENCE: 2

```
tggagtcgcc agacttgctc acttttgact cccttcgaaa ctcaaagtac gttcaggcgg     60

tgctcaacga aacgctccgt atctacccgg gggtaccacg aaacatgaag acagctacgt    120

gcaacacgac gttgccacgc ggaggaggca aagacggcaa ggaacctatc ttggtgcaga    180

agggacagtc cgttgggttg attactattg ccacgcagac ggacccagag tattttgggg    240

ccgacgctgg tgagtttaag ccggagagat ggtttgattc aagcatgaag aacttggggt    300

gtaaatactt gccgttcaat gctgggccac ggacttgctt ggggcagcag tacactttga    360

ttgaagcgag ctacttgcta gtccggttgg cccagaccta ccgggcaata gatttgcagc    420

caggatcggc gtacccacca agaaagaagt cgttgatcaa catgagtgct gccgacgggg    480

tgtttgtaaa gctttataag gatgtaacgg tagatggata gttgtgtagg aggagcggag    540
```

```
ataaattaga tttgattttg tgtaaggttt tggatgtcaa cctactccgc acttcatgca    600
gtgtgtgtga cacaagggtg tactacgtgt gcgtgtgcgc caagagacag cccaaggggg    660
tggtagtgtg tgttggcgga agtgcatgtg acacaacgcg tgggttctgg ccaatggtgg    720
actaagtgca ggtaagcagc gacctgaaac attcctcaac gcttaagaca ctggtggtag    780
agatgcggac caggctattc ttgtcgtgct acccggcgca tggaaaatca actgcgggaa    840
gaataaattt atccgtagaa tccacagagc ggataaattt gcccacctcc atcatcaacc    900
acgccgccac taactacatc actcccctat ttctctctc tctctttgtc ttactccgct     960
cccgtttcct tagccacaga tacacaccca ctgcaaacag cagcaacaat tataaagata   1020
cgccaggccc accttctttc tttttcttca cttttttgac tgcaactttc tacaatccac   1080
cacagccacc accacagccg ctatgattga acaactccta gaatattggt atgtcgttgt   1140
gccagtgttg tacatcatca aacaactcct tgcatacaca aagactcgcg tcttgatgaa   1200
aaagttgggt gctgctccag tcacaaacaa gttgtacgac aacgctttcg gtatcgtcaa   1260
tggatggaag gctctccagt tcaagaaaga gggcagggct caagagtaca acgattacaa   1320
gtttgaccac tccaagaacc caagcgtggg cacctacgtc agtattcttt tcggcaccag   1380
gatcgtcgtg accaaagatc cagagaatat caaagctatt ttggcaaccc agtttggtga   1440
tttttctttg ggcaagaggc acactctttt taagcctttg ttaggtgatg ggatcttcac   1500
attggacggc gaaggctgga agcacagcag agccatgttg agaccacagt ttgccagaga   1560
acaagttgct catgtgacgt cgttggaacc acacttccag ttgttgaaga agcatattct   1620
taagcacaag ggtgaatact ttgatatcca ggaattgttc tttagattta ccgttgattc   1680
ggccacggag ttcttatttg gtgagtccgt gcactcctta aaggacgaat ctattggtat   1740
caaccaagac gatatagatt ttgctggtag aaaggacttt gctgagtcgt tcaacaaagc   1800
ccaggaatac ttggctatta gaaccttggt gcagacgttc tactggttgg tcaacaacaa   1860
ggagtttaga gactgtacca agctggtgca caagttcacc aactactatg ttcagaaagc   1920
tttggatgct agcccagaag agcttgaaaa gcaaagtggg tatgtgttct tgtacgagct   1980
tgtcaagcag acaagagacc ccaatgtgtt gcgtgaccag tctttgaaca tcttgttggc   2040
cggaagagac accactgctg ggttgttgtc gtttgctgtc tttgagttgg ccagacaccc   2100
agagatctgg gccaagttga gagaggaaat tgaacaacag tttggtcttg gagaagactc   2160
tcgtgttgaa gagattacct ttgagagctt gaagagatgt gagtacttga aagcgttcct   2220
taatgaaacc ttgcgtattt acccaagtgt cccaagaaac ttcagaatcg ccaccaagaa   2280
cacgacattg ccaaggggcg gtggttcaga cggtacctcg ccaatcttga tccaaaaggg   2340
agaagctgtg tcgtatggta tcaactctac tcatttggac cctgtctatt acggccctga   2400
tgctgctgag ttcagaccag agagatggtt tgagccatca accaaaaagc tcggctgggc   2460
ttacttgcca ttcaacggtg gtccaagaat ctgtttgggt cagcagtttg ccttgacgga   2520
agctggctat gtgttggtta gattggtgca agagttctcc cacgttaggc tggacccaga   2580
cgaggtgtac ccgccaaaga ggttgaccaa cttgaccatg tgtttgcagg atggtgctat   2640
tgtcaagttt gactagcggc gtggtgaatg cgtttgattt tgtagtttct gtttgcagta   2700
atgagataac tattcagata aggcgagtgg atgtacgttt tgtaagagtt tccttacaac   2760
cttggtgggg tgtgtgaggt tgaggttgca tcttggggag attacacctt ttgcagctct   2820
ccgtatacac ttgtactctt tgtaacctct atcaatcatg tggggggggg ggttcattgt   2880
ttggccatgg tggtgcatgt taaatccgcc aactacccaa tctcacatga aactcaagca   2940
```

```
cactaaaaaa aaaaaagatg ttgggggaaa actttggttt cccttcttag taattaaaca   3000

ctctcactct cactctcact ctctccactc agacaaacca accacctggg ctgcagacaa   3060

ccagaaaaaa aaagaacaaa atccagatag aaaaacaaag ggctggacaa ccataaataa   3120

acaatctagg gtctactcca tcttccactg tttcttcttc ttcagactta gctaacaaac   3180

aactcacttc accatggatt acgcaggcat cacgcgtggc tccatcagag gcgaggcctt   3240

gaagaaactc gcagaattga ccatccagaa ccagccatcc agcttgaaag aaatcaacac   3300

cggcatccag aaggacgact ttgccaagtt gttgtctgcc accccgaaaa tccccaccaa   3360

gcacaagttg aacggcaacc acgaattgtc tgaggtcgcc attgccaaaa aggagtacga   3420

ggtgttgatt gccttgagcg acgccacaaa agacccaatc aaagtgacct cccagatcaa   3480

gatcttgatt gacaagttca aggtgtactt gtttgagttg cctgaccaga agttctccta   3540

ctccatcgtg tccaactccg tcaacatcgc cccctggacc ttgctcgggg agaagttgac   3600

cacgggcttg atcaacttgg ccttccagaa caacaagcag cacttggacg aggtcattga   3660

catcttcaac gagttcatcg acaagttctt tggcaacacg gagccgcaat tgaccaactt   3720

cttgaccttg tgcggtgtgt tggacgggtt gattgaccat gccaacttct tgagcgtgtc   3780

ctcgcggacc ttcaagatct tcttgaactt ggactcgtat gtggac                  3826
```

<210> SEQ ID NO 3
<211> LENGTH: 640
<212> TYPE: DNA
<213> ORGANISM: Artificial Sequence
<220> FEATURE:
<223> OTHER INFORMATION: Comprises two sequences from the 5' and 3' ends of the CYP52A17 cytochrome P450 from Candida tropicalis (i) separated by a sequence comprising a NotI restriction site and a 20 bp stuffer fragment and an XhoI restriciton site and (ii) flanked by XhoI

<400> SEQUENCE: 3

```
cgtctcatga ttgaacaact cctagaatat tggtatgtcg ttgtgccagt gttgtacatc     60

atcaaacaac tccttgcata cacaaagact cgcgtcttga tgaaaaagtt gggtgctgct    120

ccagtcacaa acaagttgta cgacaacgct ttcggtatcg tcaatggatg gaaggctctc    180

cagttcaaga aagagggcag ggctcaagag tacaacgatt acaagtttga ccactccaag    240

aacccaagcg tgggcaccta cgtcagtatt cttttcggca ccaggatcgt cgtgaccaaa    300

gatgcggccg ctagatcttg cgaagctcca tctcgagatc aactctactc atttggaccc    360

tgtctattac ggccctgatg ctgctgagtt cagaccagag agatggtttg agccatcaac    420

caaaaagctc ggctgggctt acttgccatt caacggtggt ccaagaatct gtttgggtca    480

gcagtttgcc ttgacggaag ctggctatgt gttggttaga ttggtgcaag agttctccca    540

cgttaggctg gacccagacg aggtgtaccc gccaaagagg ttgaccaact tgaccatgtg    600

tttgcaggat ggtgctattg tcaagtttga ctaggagacg                          640
```

<210> SEQ ID NO 4
<211> LENGTH: 4792
<212> TYPE: DNA
<213> ORGANISM: Artificial Sequence
<220> FEATURE:
<223> OTHER INFORMATION: Targeting construct for deletion of Candida tropicalis CYP52A17

<400> SEQUENCE: 4

```
cgtctcatga ttgaacaact cctagaatat tggtatgtcg ttgtgccagt gttgtacatc     60

atcaaacaac tccttgcata cacaaagact cgcgtcttga tgaaaaagtt gggtgctgct    120
```

```
ccagtcacaa acaagttgta cgacaacgct ttcggtatcg tcaatggatg gaaggctctc    180
cagttcaaga aagagggcag ggctcaagag tacaacgatt acaagtttga ccactccaag    240
aacccaagcg tgggcaccta cgtcagtatt cttttcggca ccaggatcgt cgtgaccaaa    300
gatgcggccg ctctagaact agtggatctg aagttcctat tctctagaaa gtataggaac    360
ttcctgcagg accacctttg attgtaaata gtaataatta ccacccttat ctaattattt    420
atttaactta tttatttatt tattatacat atatacaaat ctaataaagt gaaaatctcc    480
cccttcacac ttcacatatg ttaggcgtca tcctgtgctc ccgagaacca gtaccagtac    540
atcgctgttt cgttcgagac ttgaggtcta gttttatacg tgaagaggtc aatgccgccg    600
agagtaaagc cacattttgc gtacaaattg caggcaggta cattgttcgt ttgtgtctct    660
aatcgtatgc caaggagctg tctgcttagt gcccactttt tcgcaaattc gatgagactg    720
tgcgcgactc ctttgcctcg gtgcgtgtgc gacacaacaa tgtgttcgat agaggctaga    780
tcgttccatg ttgagttgag ttcaatcttc ccgacaagct cttggtcgat gaatgcgcca    840
tagcaagcag agtcttcatc agagtcatca tccgagatgt aatccttccg gtaggggctc    900
acacttctgg tagatagttc aaagccttgg tcggataggt gcacatcgaa cacttcacga    960
acaatgaaat ggttctcagc atccaatgtt tccgccacct gctcagggat caccgaaatt   1020
ttcatatgag aaccgttatc gataactaaa gcagcaactt cttctataaa aatgggttag   1080
tatgacagtc atttaaataa ggaatttttc agttggcttg gtttcaattc aatgttcgtt   1140
ttttttttt cttgctgtgt ttgtgtttgt gttgtttata gttgtgtgca ctgagcgtcg   1200
aaaaaaaaaa ttcatagtga gccgggaaat ctgtatagcc cagataacaa cacaagtcca   1260
aactagaaac tcgtcaaaca ccaaaagcaa tgttgaatca attgccttgc acaagtacac   1320
gtaggaaaac ataaaacatt gcaattttga atattgagcc ttttgtcgta acattgattg   1380
ataggattac tcaccgaatg gttttgaaac cactgccgac agatcaatca atcaatcaaa   1440
aaacgtgaac tttgaaaaag gggaagaaca gatacattga agttagccat ttccattgat   1500
cgtcacaaca tatctgataa attactttca aaattataag ctgatgtgtg tgtattatta   1560
atgtgacagt aacatcccaa acgagaaata ttatgtcgac aacaaaaaag tttgatctga   1620
attgaaaatg aagttttccc accctaccca tttgtcatat tgaaaccaat caactgatta   1680
atcaatcaat tagaattgaa gctaaactaa aacataccac cgtccatttt gaatgattat   1740
attttttaa tattaatatc gagataatgt ttctaagaaa gaaagaaaac caggagtgaa   1800
aattagaaaa ggaaaggaaa ggaaaaaaag aaaaatctga aaatatataa aaaaaaattg   1860
tttcgttggc aataaatctt ggtgagaaca gcgaccgaaa gcaaataaga acaaaatatg   1920
agtgtattac gttgaacaac taattaacgt gtgtgtatgg atcttttttt cttttttctc   1980
tttaaccgac tataaacaac aaacattttt gggcagtgca cacactactt aatatacaca   2040
gcataaatta cacgattaga aacaaattag cttattaaaa taacctaatc aaaccgaata   2100
ttttatggta ttatgagtaa actatataat ataaatagca cacacccaca acaacaacaa   2160
aggaaaacta aaaggttttt tctttttgaa aagatcgttt tctttattat tctctagttt   2220
tgacgctcga cattttatga tggaatgaat gggatgaatc atcaaacaag agaaaatacc   2280
cgtgacgaaa ataataaaat aagttcctct gatacagaag atgaaaacaa caacaacaag   2340
atatagaaat gccttgggtg gctattttat agtcttaact ttttaatgta tatttgtttt   2400
gttttttac ataataatac tttataaaag ctaagctaaa ttcaagtaaa atttcaatct   2460
ctcaaataaa acatttttct ctttttctta aatttagttt tatatattta taaaatatac   2520
```

```
aaagattttt ttaaaaaagt aacaagttat atatgtaata acaaaaagaa gaataacaag   2580
aatacaaaac cagatttcca gatttccaga atttcactct tatatgcgtc tatttatgta   2640
ggatgaaagg tagtctagta cctcctgtga tattatccca ttccatgcgg ggtatcgtat   2700
gcttccttca gcactaccct ttagctgttc tatatgctgc cactcctcaa ttggattagt   2760
ctcatccttc aatgctatca tttcctttga tattggatca tatgcatagt accgagaaac   2820
tagtgcgaag tagtgatcag gtattgctgt tatctgatga gtatacgttg tcctggccac   2880
ggcagaagca cgcttatcgc tccaatttcc cacaacatta gtcaactccg ttaggccctt   2940
cattgaaaga aatgaggtca tcaaatgtct tccaatgtga gattttgggc cattttttat   3000
agcaaagatt gaataaggcg catttttctt caaagcttta ttgtacgatc tgactaagtt   3060
atcttttaat aattggtatt cctgtttatt gcttgaagaa ttgccggtcc tatttactcg   3120
ttttaggact ggttcagaat tcctcaaaaa ttcatccaaa tatacaagtg gatcgatcct   3180
accccttgcg ctaaagaagt atatgtgcct actaacgctt gtctttgtct ctgtcactaa   3240
acactggatt attactccca aatacttatt ttggactaat ttaaatgatt tcggatcaac   3300
gttcttaata tcgctgaatc ttccacaatt gatgaaagta gctaggaaga ggaattggta   3360
taaagttttt gtttttgtaa atctcgaagt atactcaaac gaatttagta ttttctcagt   3420
gatctcccag atgctttcac cctcacttag aagtgcttta agcatttttt tactgtggct   3480
atttccctta tctgcttctt ccgatgattc gaactgtaat tgcaaactac ttacaatatc   3540
agtgatatca gattgatgtt tttgtccata gtaaggaata attgtaaatt cccaagcagg   3600
aatcaatttc tttaatgagg cttccaaaat tgttgctttt tgcgtcttgt atttaaactg   3660
gagtgattta ttgacaatat cgaaactcaa cgaattgctt atgatagtat tatagctcat   3720
gaatgtggct ctcttgattg ctgttccgtt atgtgtaatc atccaacata aataggttag   3780
ttcagcagca cataatgcta ttttctcacc tgaaggtctt tcaaaccttt ccacaaactg   3840
acgaacaagc accttaggtg gtgttttaca taatatatca aattgtggca tgtcgacgat   3900
tattagttaa accactgcaa aaagttgggg aaaattttgc ccatttttat accgtgtctt   3960
cgtctatcgc ctcccccact ccccaatctt tgaattattc cgaaatattc agcgaacggg   4020
gtgtacacaa aaactaacat tctcaactgc ataatttgaa aaatggcgtg ggacaagaaa   4080
aaaaaaaaat tctcaaccat agcaatcatg gaatacggta aatttgtgtt gttcggtgac   4140
tccatcaccc agtttagttg tacccagtat ggctttcatc cagcattaca gaatgtgtat   4200
atccgaaaat tggatgttat taaccgtggt ttcagtggct acaactcaga gcacgctaga   4260
caaattcttc caaaaatttt agagtcggaa accaatatca aattgatgac aatatttttt   4320
ggaactaacg atgcatacga ctacatcaat gaaatccaga cagtcgagtt agacagatat   4380
aaagataatt taagtgtaat ggtacagatg gtactagaca aaaatatcaa accaatcatt   4440
attggatccg aagttcctat tctctagaaa gtataggaac ttcctcgaga tcaactctac   4500
tcatttggac cctgtctatt acggccctga tgctgctgag ttcagaccag agagatggtt   4560
tgagccatca accaaaaagc tcggctgggc ttacttgcca ttcaacggtg gtccaagaat   4620
ctgtttgggt cagcagtttg ccttgacgga agctggctat gtgttggtta gattggtgca   4680
agagttctcc cacgttaggc tggacccaga cgaggtgtac ccgccaaaga ggttgaccaa   4740
cttgaccatg tgtttgcagg atggtgctat tgtcaagttt gactaggaga cg            4792
```

<210> SEQ ID NO 5
<211> LENGTH: 3948

<212> TYPE: DNA
<213> ORGANISM: Candida tropicalis

<400> SEQUENCE: 5

```
gacctgtgac gcttccggtg tcttgccacc agtctccaag ttgaccgacg cccaagtcat     60
gtaccacttt atttccggtt acacttccaa gatggctggt actgaagaag gtgtcacgga    120
accacaagct actttctccg cttgtttcgg tcaaccattc ttggtgttgc acccaatgaa    180
gtacgctcaa caattgtctg acaagatctc gcaacacaag gctaacgcct ggttgttgaa    240
caccggttgg gttggttctt ctgctgctag aggtggtaag agatgctcat tgaagtacac    300
cagagccatt ttggacgcta tccactctgg tgaattgtcc aaggttgaat acgaaacttt    360
cccagtcttc aacttgaatg tcccaacctc ctgtccaggt gtcccaagtg aaatcttgaa    420
cccaaccaag gcctggaccg gaaggtgttg actccttcaa caaggaaatc aagtctttgg    480
ctggtaagtt tgctgaaaac ttcaagacct atgctgacca agctaccgct gaagtgagag    540
ctgcaggtcc agaagcttaa agatatttat tcattattta gtttgcctat ttatttctca    600
ttacccatca tcattcaaca ctatatataa agttacttcg gatatcattg taatcgtgcg    660
tgtcgcaatt ggatgatttg gaactgcgct tgaaacggat tcatgcacga agcggagata    720
aaagattacg taatttatct cctgagacaa ttttagccgt gttcacacgc ccttctttgt    780
tctgagcgaa ggataaataa ttagacttcc acagctcatt ctaatttccg tcacgcgaat    840
attgaagggg ggtacatgtg gccgctgaat gtgggggcag taaacgcagt ctctcctctc    900
ccaggaatag tgcaacggag gaaggataac ggatagaaag cggaatgcga ggaaaatttt    960
gaacgcgcaa gaaaagcaat atccgggcta ccaggttttg agccagggaa cacactccta   1020
tttctgctca atgactgaac atagaaaaaa caccaagacg caatgaaacg cacatggaca   1080
tttagacctc cccacatgtg atagtttgtc ttaacagaaa agtataataa gaacccatgc   1140
cgtccctttt ctttcgccgc ttcaactttt ttttttttat cttacacaca tcacgaccat   1200
gactgtacac gatattatcg ccacatactt caccaaatgg tacgtgatag taccactcgc   1260
tttgattgct tatagagtcc tcgactactt ctatggcaga tacttgatgt acaagcttgg   1320
tgctaaacca tttttccaga aacagacaga cggctgtttc ggattcaaag ctccgcttga   1380
attgttgaag aagaagagcg acggtaccct catagacttc acactccagc gtatccacga   1440
tctcgatcgt cccgatatcc caactttcac attcccggtc ttttccatca accttgtcaa   1500
taccottgag ccggagaaca tcaaggccat cttggccact cagttcaacg atttctcctt   1560
gggtaccaga cactcgcact ttgctccttt gttgggtgat ggtatcttta cgttggatgg   1620
cgccggctgg aagcacagca gatctatgtt gagaccacag tttgccagag aacagatttc   1680
ccacgtcaag ttgttggagc cacacgttca ggtgttcttc aaacacgtca gaaaggcaca   1740
gggcaagact tttgacatcc aggaattgtt tttcagattg accgtcgact ccgccaccga   1800
gtttttgttt ggtgaatccg ttgagtcctt gagagatgaa tctatcggca tgtccatcaa   1860
tgcgcttgac tttgacggca aggctggctt tgctgatgct tttaactatt cgcagaatta   1920
tttggcttcg agagcggtta tgcaacaatt gtactgggtg ttgaacggga aaaagtttaa   1980
ggagtgcaac gctaaagtgc acaagtttgc tgactactac gtcaacaagg ctttggactt   2040
gacgcctgaa caattggaaa agcaggatgg ttatgtgttt ttgtacgaat tggtcaagca   2100
aaccagagac aagcaagtgt tgagagacca attgttgaac atcatggttg ctggtagaga   2160
caccaccgcc ggtttgttgt cgtttgtttt ctttgaattg gccagaaacc cagaagttac   2220
caacaagttg agagaagaaa ttgaggacaa gtttggactc ggtgagaatg ctagtgttga   2280
```

```
agacatttcc tttgagtcgt tgaagtcctg tgaatacttg aaggctgttc tcaacgaaac   2340

cttgagattg tacccatccg tgccacagaa tttcagagtt gccaccaaga acactaccct   2400

cccaagaggt ggtggtaagg acgggttgtc tcctgttttg gtgagaaagg gtcagaccgt   2460

tatttacggt gtctacgcag cccacagaaa cccagctgtt tacggtaagg acgctcttga   2520

gtttagacca gagagatggt ttgagccaga gacaaagaag cttggctggg ccttcctccc   2580

attcaacggt ggtccaagaa tctgtttggg acagcagttt gccttgacag aagcttcgta   2640

tgtcactgtc aggttgctcc aggagtttgc acacttgtct atggacccag acaccgaata   2700

tccacctaag aaaatgtcgc atttgaccat gtcgcttttc gacggtgcca atattgagat   2760

gtattagagg gtcatgtgtt attttgattg tttagtttgt aattactgat taggttaatt   2820

catggattgt tatttattga taggggtttg cgcgtgttgc attcacttgg gatcgttcca   2880

ggttgatgtt tccttccatc ctgtcgagtc aaaaggagtt ttgttttgta actccggacg   2940

atgttttaaa tagaaggtcg atctccatgt gattgttttg actgttactg tgattatgta   3000

atctgcggac gttatacaag catgtgattg tggttttgca gccttttgca cgacaaatga   3060

tcgtcagacg attacgtaat ctttgttaga ggggtaaaaa aaaacaaaat ggcagccaga   3120

atttcaaaca ttctgcaaac aatgcaaaaa atgggaaact ccaacagaca aaaaaaaaaa   3180

ctccgcagca ctccgaaccc acagaacaat ggggcgccag aattattgac tattgtgact   3240

tttttacgct aacgctcatt gcagtgtagt gcgtcttaca cggggtattg ctttctacaa   3300

tgcaagggca cagttgaagg tttgcaccta acgttgcccc gtgtcaactc aatttgacga   3360

gtaacttcct aagctcgaat tatgcagctc gtgcgtcaac ctatgtgcag gaaagaaaaa   3420

atccaaaaaa atcgaaaatg cgactttcga ttttgaataa accaaaaaga aaaatgtcgc   3480

actttttttct cgctctcgct ctctcgaccc aaatcacaac aaatcctcgc gcgcagtatt   3540

tcgacgaaac cacaacaaat aaaaaaaaca aattctacac cacttctttt tcttcaccag   3600

tcaacaaaaa acaacaaatt atacaccatt tcaacgattt ttgctcttat aaatgctata   3660

taatggttta attcaactca ggtatgttta ttttactgtt ttcagctcaa gtatgttcaa   3720

atactaacta cttttgatgt ttgtcgcttt tctagaatca aaacaacgcc cacaacacgc   3780

cgagcttgtc gaatagacgg tttgtttact cattagatgg tcccagatta cttttcaagc   3840

caaagtctct cgagttttgt ttgctgtttc cccaattcct aactatgaag ggtttttata   3900

aggtccaaag accccaaggc atagtttttt tggttccttc ttgtcgtg                 3948
```

<210> SEQ ID NO 6
<211> LENGTH: 640
<212> TYPE: DNA
<213> ORGANISM: Artificial Sequence
<220> FEATURE:
<223> OTHER INFORMATION: Pre-targeting construct for Candida tropicalis CYP52A13

<400> SEQUENCE: 6

```
cgtctcatga ctgtacacga tattatcgcc acatacttca ccaaatggta cgtgatagta     60

ccactcgctt tgattgctta tagagtcctc gactacttct atggcagata cttgatgtac    120

aagcttggtg ctaaaccatt tttccagaaa cagacagacg gctgtttcgg attcaaagct    180

ccgcttgaat tgttgaagaa gaagagcgac ggtaccctca tagacttcac actccagcgt    240

atccacgatc tcgatcgtcc cgatatccca actttcacat tcccggtctt ttccatcaac    300

cttgcggccg ctagatcttg cgaagctcca tctcgaggtc tacgcagccc acagaaaccc    360
```

agctgtttac ggtaaggacg ctcttgagtt tagaccagag agatggtttg agccagagac 420
aaagaagctt ggctgggcct tcctcccatt caacggtggt ccaagaatct gtttgggaca 480
gcagtttgcc ttgacagaag cttcgtatgt cactgtcagg ttgctccagg agtttgcaca 540
cttgtctatg gacccagaca ccgaatatcc acctaagaaa atgtcgcatt tgaccatgtc 600
gcttttcgac ggtgccaata ttgagatgta ttaggagacg 640

<210> SEQ ID NO 7
<211> LENGTH: 4792
<212> TYPE: DNA
<213> ORGANISM: Artificial Sequence
<220> FEATURE:
<223> OTHER INFORMATION: Targeting construct for deletion of Candida tropicalis CYP52A13

<400> SEQUENCE: 7
cgtctcatga ctgtacacga tattatcgcc acatacttca ccaaatggta cgtgatagta 60
ccactcgctt tgattgctta tagagtcctc gactacttct atggcagata cttgatgtac 120
aagcttggtg ctaaaccatt tttccagaaa cagacagacg gctgtttcgg attcaaagct 180
ccgcttgaat tgttgaagaa gaagagcgac ggtaccctca tagacttcac actccagcgt 240
atccacgatc tcgatcgtcc cgatatccca actttcacat tcccggtctt ttccatcaac 300
cttgcggccg ctctagaact agtggatctg aagttcctat tctctagaaa gtataggaac 360
ttcctgcagg accacctttg attgtaaata gtaataatta ccacccttat ctaattattt 420
atttaactta tttatttatt tattatacat atatacaaat ctaataaagt gaaaatctcc 480
cccttcacac ttcacatatg ttaggcgtca tcctgtgctc ccgagaacca gtaccagtac 540
atcgctgttt cgttcgagac ttgaggtcta gttttatacg tgaagaggtc aatgccgccg 600
agagtaaagc cacattttgc gtacaaattg caggcaggta cattgttcgt ttgtgtctct 660
aatcgtatgc caaggagctg tctgcttagt gcccactttt tcgcaaattc gatgagactg 720
tgcgcgactc ctttgcctcg gtgcgtgtgc gacacaacaa tgtgttcgat agaggctaga 780
tcgttccatg ttgagttgag ttcaatcttc ccgacaagct cttggtcgat gaatgcgcca 840
tagcaagcag agtcttcatc agagtcatca tccgagatgt aatccttccg gtaggggctc 900
acacttctgg tagatagttc aaagccttgg tcggataggt gcacatcgaa cacttcacga 960
acaatgaaat ggttctcagc atccaatgtt tccgccacct gctcagggat caccgaaatt 1020
ttcatatgag aaccgttatc gataactaaa gcagcaactt cttctataaa aatgggttag 1080
tatgacagtc atttaaataa ggaatttttc agttggcttg gtttcaattc aatgttcgtt 1140
tttttttttt cttgctgtgt ttgtgtttgt gttgtttata gttgtgtgca ctgagcgtcg 1200
aaaaaaaaaa ttcatagtga gccgggaaat ctgtatagcc cagataacaa cacaagtcca 1260
aactagaaac tcgtcaaaca ccaaaagcaa tgttgaatca attgccttgc acaagtacac 1320
gtaggaaaac ataaaacatt gcaattttga atattgagcc ttttgtcgta acattgattg 1380
ataggattac tcaccgaatg gttttgaaac cactgccgac agatcaatca atcaatcaaa 1440
aaacgtgaac tttgaaaaag gggaagaaca gatacattga agttagccat ttccattgat 1500
cgtcacaaca tatctgataa attactttca aaattataag ctgatgtgtg tgtattatta 1560
atgtgacagt aacatcccaa acgagaaata ttatgtcgac aacaaaaaag tttgatctga 1620
attgaaaatg aagttttccc accctaccca tttgtcatat tgaaaccaat caactgatta 1680
atcaatcaat tagaattgaa gctaaactaa aacataccac cgtccatttt gaatgattat 1740 attttttttaa tattaatatc gagataatgt ttctaagaaa gaaagaaaac caggagtgaa 1800

-continued

```
aattagaaaa ggaaaggaaa ggaaaaaaag aaaaatctga aaatatataa aaaaaaattg   1860
tttcgttggc aataaatctt ggtgagaaca gcgaccgaaa gcaaataaga acaaaatatg   1920
agtgtattac gttgaacaac taattaacgt gtgtgtatgg atcttttttt cttttttctc   1980
tttaaccgac tataaacaac aaacattttt gggcagtgca cacactactt aatatacaca   2040
gcataaatta cacgattaga aacaaattag cttattaaaa taacctaatc aaaccgaata   2100
ttttatggta ttatgagtaa actatataat ataaatagca cacacccaca acaacaacaa   2160
aggaaaacta aaaggttttt tctttttgaa aagatcgttt tctttattat tctctagttt   2220
tgacgctcga cattttatga tggaatgaat gggatgaatc atcaaacaag agaaaatacc   2280
cgtgacgaaa ataataaaat aagttcctct gatacagaag atgaaaacaa caacaacaag   2340
atatagaaat gccttgggtg gctattttat agtcttaact ttttaatgta tatttgtttt   2400
gtttttttac ataataatac tttataaaag ctaagctaaa ttcaagtaaa atttcaatct   2460
ctcaaataaa acattttttct ctttttctta aatttagttt tatatattta taaaatatac   2520
aaagattttt ttaaaaaagt aacaagttat atatgtaata acaaaaagaa gaataacaag   2580
aatacaaaac cagatttcca gatttccaga atttcactct tatatgcgtc tatttatgta   2640
ggatgaaagg tagtctagta cctcctgtga tattatccca ttccatgcgg ggtatcgtat   2700
gcttccttca gcactaccct ttagctgttc tatatgctgc cactcctcaa ttggattagt   2760
ctcatccttc aatgctatca tttcctttga tattggatca tatgcatagt accgagaaac   2820
tagtgcgaag tagtgatcag gtattgctgt tatctgatga gtatacgttg tcctggccac   2880
ggcagaagca cgcttatcgc tccaatttcc cacaacatta gtcaactccg ttaggccctt   2940
cattgaaaga aatgaggtca tcaaatgtct tccaatgtga gattttgggc catttttttat   3000
agcaaagatt gaataaggcg cattttttctt caaagcttta ttgtacgatc tgactaagtt   3060
atcttttaat aattggtatt cctgtttatt gcttgaagaa ttgccggtcc tatttactcg   3120
ttttaggact ggttcagaat tcctcaaaaa ttcatccaaa tatacaagtg gatcgatcct   3180
accccttgcg ctaaagaagt atatgtgcct actaacgctt gtctttgtct ctgtcactaa   3240
acactggatt attactccca aatacttatt ttggactaat ttaaatgatt tcggatcaac   3300
gttcttaata tcgctgaatc ttccacaatt gatgaaagta gctaggaaga ggaattggta   3360
taaagttttt gtttttgtaa atctcgaagt atactcaaac gaatttagta ttttctcagt   3420
gatctcccag atgctttcac cctcacttag aagtgcttta agcatttttt tactgtggct   3480
atttccctta tctgcttctt ccgatgattc gaactgtaat tgcaaactac ttacaatatc   3540
agtgatatca gattgatgtt tttgtccata gtaaggaata attgtaaatt cccaagcagg   3600
aatcaatttc tttaatgagg cttccaaaat tgttgctttt tgcgtcttgt atttaaactg   3660
gagtgattta ttgacaatat cgaaactcaa cgaattgctt atgatagtat tatagctcat   3720
gaatgtggct ctcttgattg ctgttccgtt atgtgtaatc atccaacata aataggttag   3780
ttcagcagca cataatgcta ttttctcacc tgaaggtctt tcaaaccttt ccacaaactg   3840
acgaacaagc accttaggtg gtgttttaca taatatatca aattgtggca tgtcgacgat   3900
tattagttaa accactgcaa aaagttgggg aaaattttgc ccattttttat accgtgtctt   3960
cgtctatcgc ctccccccact ccccaatctt tgaattattc cgaaatattc agcgaacggg   4020
gtgtacacaa aaactaacat tctcaactgc ataatttgaa aaatggcgtg ggacaagaaa   4080
aaaaaaaaat tctcaaccat agcaatcatg gaatacggta aatttgtgtt gttcggtgac   4140
tccatcaccc agtttagttg tacccagtat ggctttcatc cagcattaca gaatgtgtat   4200
```

```
atccgaaaat tggatgttat taaccgtggt ttcagtggct acaactcaga gcacgctaga   4260
caaattcttc caaaaatttt agagtcggaa accaatatca aattgatgac aatatttttt   4320
ggaactaacg atgcatacga ctacatcaat gaaatccaga cagtcgagtt agacagatat   4380
aaagataatt taagtgtaat ggtacagatg gtactagaca aaaatatcaa accaatcatt   4440
attggatccg aagttcctat tctctagaaa gtataggaac ttcctcgagg tctacgcagc   4500
ccacagaaac ccagctgttt acggtaagga cgctcttgag tttagaccag agagatggtt   4560
tgagccagag acaaagaagc ttggctgggc cttcctccca ttcaacggtg gtccaagaat   4620
ctgtttggga cagcagtttg ccttgacaga agcttcgtat gtcactgtca ggttgctcca   4680
ggagtttgca cacttgtcta tggacccaga caccgaatat ccacctaaga aaatgtcgca   4740
tttgaccatg tcgcttttcg acggtgccaa tattgagatg tattaggaga cg             4792
```

<210> SEQ ID NO 8
<211> LENGTH: 3910
<212> TYPE: DNA
<213> ORGANISM: Candida tropicalis

<400> SEQUENCE: 8

```
ttacaatcat ggagctcgct aggaacccag atgtctggga gaagctccgc gaagaggtca     60
acacgaactt tggcatggag tcgccagact tgctcacttt tgactctctt agaagctcaa    120
agtacgttca ggcggtgctc aacgaaacgc ttcgtatcta cccgggggtg ccacgaaaca    180
tgaagacagc tacgtgcaac acgacgttgc cgcgtggagg aggcaaagac ggtaaggaac    240
ctattttggt gcagaagggc cagtccgttg ggttgattac tattgccacg cagacggacc    300
cagagtattt tggggcagat gctggtgagt tcaaaccgga gagatggttt gattcaagca    360
tgaagaactt ggggtgtaag tacttgccgt tcaatgctgg gccccggact tgtttggggc    420
agcagtacac tttgattgaa gcgagctatt tgctagtcag gttggcgcag acctaccggg    480
taatcgattt gctgccaggg tcggcgtacc caccaagaaa gaagtcgttg atcaatatga    540
gtgctgccga tggggtggtt gtaaagtttc acaaggatct agatggatat gtaaggtgtg    600
taggaggagc ggagataaat tagatttgat tttgtgtaag gtttagcacg tcaagctact    660
ccgcactttg tgtgtaggga gcacatactc cgtctgcgcc tgtgccaaga gacggcccag    720
gggtagtgtg tggtggtgga agtgcatgtg acacaatacc ctggttctgg ccaattgggg    780
atttagtgta ggtaagctgc gacctgaaac actcctcaac gcttgagaca ctggtgggta    840
gagatgcggg ccaggaggct attcttgtcg tgctacccgt gcacggaaaa tcgattgagg    900
gaagaacaaa tttatccgtg aaatccacag agcggataaa tttgtcacat tgctgcgttg    960
cccacccaca gcattctctt ttctctctct ttgtcttact ccgctcctgt ttccttatcc   1020
agaaatacac accaactcat ataaagatac gctagcccag ctgtctttct ttttcttcac   1080
ttttttggt gtgttgcttt tttggctgct actttctaca accaccacca ccaccaccac   1140
catgattgaa caaatcctag aatattggta tattgttgtg cctgtgttgt acatcatcaa   1200
acaactcatt gcctacagca agactcgcgt cttgatgaaa cagttgggtg ctgctccaat   1260
cacaaaccag ttgtacgaca acgttttcgg tatcgtcaac ggatggaagg ctctccagtt   1320
caagaaagag ggcagagctc aagagtacaa cgatcacaag tttgacagct ccaagaaccc   1380
aagcgtcggc acctatgtca gtattctttt tggcaccaag attgtcgtga ccaaggatcc   1440
agagaatatc aaagctattt tggcaaccca gtttggcgat ttttctttgg gcaagagaca   1500
cgctcttttt aaacctttgt taggtgatgg gatcttcacc ttggacggcg aaggctggaa   1560
```

```
gcatagcaga tccatgttaa gaccacagtt tgccagagaa caagttgctc atgtgacgtc   1620

gttggaacca cacttccagt tgttgaagaa gcatatcctt aaacacaagg gtgagtactt   1680

tgatatccag gaattgttct ttagatttac tgtcgactcg gccacggagt tcttatttgg   1740

tgagtccgtg cactccttaa aggacgaaac tatcggtatc aaccaagacg atatagattt   1800

tgctggtaga aaggactttg ctgagtcgtt caacaaagcc caggagtatt tgtctattag   1860

aattttggtg cagaccttct actggttgat caacaacaag gagtttagag actgtaccaa   1920

gctggtgcac aagtttacca actactatgt tcagaaagct ttggatgcta ccccagagga   1980

acttgaaaag caaggcgggt atgtgttctt gtatgagctt gtcaagcaga cgagagaccc   2040

caaggtgttg cgtgaccagt ctttgaacat cttgttggca ggaagagaca ccactgctgg   2100

gttgttgtcc tttgctgtgt ttgagttggc cagaaaccca cacatctggg ccaagttgag   2160

agaggaaatt gaacagcagt ttggtcttgg agaagactct cgtgttgaag agattacctt   2220

tgagagcttg aagagatgtg agtacttgaa agcgttcctt aacgaaacct tgcgtgttta   2280

cccaagtgtc ccaagaaact tcagaatcgc caccaagaat acaacattgc caaggggtgg   2340

tggtccagac ggtacccagc caatcttgat ccaaaaggga gaaggtgtgt cgtatggtat   2400

caactctacc cacttagatc ctgtctatta tggccctgat gctgctgagt tcagaccaga   2460

gagatggttt gagccatcaa ccagaaagct cggctgggct tacttgccat tcaacggtgg   2520

gccacgaatc tgtttgggtc agcagtttgc cttgaccgaa gctggttacg ttttggtcag   2580

attggtgcaa gagttctccc acattaggct ggacccagat gaagtgtatc caccaaagag   2640

gttgaccaac ttgaccatgt gtttgcagga tggtgctatt gtcaagtttg actagtacgt   2700

atgagtgcgt ttgattttgt agtttctgtt tgcagtaatg agataactat tcagataagg   2760

cgggtggatg tacgttttgt aagagtttcc ttacaaccct ggtgggtgtg tgaggttgca   2820

tcttagggag agatagcacc ttttgcagct ctccgtatac agttttactc tttgtaacct   2880

atgccaatca tgtggggatt cattgtttgc ccatggtggt gcatgcaaaa tccccccaac   2940

tacccaatct cacatgaaac tcaagcacac tagaaaaaaa agatgttgcg tgggttcttt   3000

tgatgttggg gaaaactttc gtttcctttc tcagtaatta aacgttctca ctcagacaaa   3060

ccacctgggc tgcagacaac cagaaaaaac aaaatccaga tagaagaaga aagggctgga   3120

caaccataaa taaacaacct agggtccact ccatctttca cttcttcttc ttcagactta   3180

tctaacaaac gactcacttc accatggatt acgcaggtat cacgcgtggg tccatcagag   3240

gcgaagcctt gaagaaactc gccgagttga ccatccagaa ccagccatcc agcttgaaag   3300

aaatcaacac cggcatccag aaggacgact ttgccaagtt gttgtcttcc accccgaaaa   3360

tccacaccaa gcacaagttg aatggcaacc acgaattgtc cgaagtcgcc attgccaaaa   3420

aggagtacga ggtgttgatt gccttgagcg acgccacgaa agaaccaatc aaagtcacct   3480

cccagatcaa gatcttgatt gacaagttca aggtgtactt gtttgagttg cccgaccaga   3540

agttctccta ctccatcgtg tccaactccg ttaacattgc cccctggacc ttgctcggtg   3600

agaagttgac cacgggcttg atcaacttgg cgttccagaa caacaagcag cacttggacg   3660

aagtcatcga catcttcaac gagttcatcg acaagttctt tggcaacaca gagccgcaat   3720

tgaccaactt cttgaccttg tccggtgtgt tggacgggtt gattgaccat gccaacttct   3780

tgagcgtgtc ctccaggacc ttcaagatct tcttgaactt ggactcgttt gtggacaact   3840

cggacttctt gaacgacgtg gagaactact ccgacttttt gtacgacgag ccgaacgagt   3900

accagaactt                                                          3910
```

<210> SEQ ID NO 9
<211> LENGTH: 687
<212> TYPE: DNA
<213> ORGANISM: Artificial Sequence
<220> FEATURE:
<223> OTHER INFORMATION: Pre-targeting construct for Candida tropicalis CYP52A18

<400> SEQUENCE: 9

```
cgtctcagag atgcgggcca ggaggctatt cttgtcgtgc tacccgtgca cggaaaatcg     60

attgagggaa gaacaaattt atccgtgaaa tccacagagc ggataaattt gtcacattgc    120

tgcgttgccc acccacagca ttctcttttc tctctctttg tcttactccg ctcctgtttc    180

cttatccaga aatacacacc aactcatata aagatacgct agcccagctg tctttctttt    240

tcttcacttt ttttggtgtg ttgctttttt ggctgctact ttctacaacc accaccacca    300

ccaccaccat ggggcaatca gtgagtctcg caggtaccgc ggagctcgcg gccgctagat    360

cttgcgaagc tccatctcga gtcgtatgag tgcgtttgat tttgtagttt ctgtttgcag    420

taatgagata actattcaga taaggcgggt ggatgtacgt tttgtaagag tttccttaca    480

accctggtgg gtgtgtgagg ttgcatctta gggagagata gcaccttttg cagctctccg    540

tatacagttt tactctttgt aacctatgcc aatcatgtgg ggattcattg tttgcccaag    600

gtggtgcatg caaaatcccc ccaactaccc aatctcacat gaaactcaag cacactagaa    660

aaaaaagatg ttgcgtgggt tgagacg                                        687
```

<210> SEQ ID NO 10
<211> LENGTH: 41
<212> TYPE: DNA
<213> ORGANISM: Artificial Sequence
<220> FEATURE:
<223> OTHER INFORMATION: polylinker sequence

<400> SEQUENCE: 10

```
ccatggggca atcagtgagt ctcgcaggta ccgcggagct c                        41
```

<210> SEQ ID NO 11
<211> LENGTH: 4839
<212> TYPE: DNA
<213> ORGANISM: Artificial Sequence
<220> FEATURE:
<223> OTHER INFORMATION: Targeting construct for deletion of Candida tropicalis CYP52A18

<400> SEQUENCE: 11

```
cgtctcagag atgcgggcca ggaggctatt cttgtcgtgc tacccgtgca cggaaaatcg     60

attgagggaa gaacaaattt atccgtgaaa tccacagagc ggataaattt gtcacattgc    120

tgcgttgccc acccacagca ttctcttttc tctctctttg tcttactccg ctcctgtttc    180

cttatccaga aatacacacc aactcatata aagatacgct agcccagctg tctttctttt    240

tcttcacttt ttttggtgtg ttgctttttt ggctgctact ttctacaacc accaccacca    300

ccaccaccat ggggcaatca gtgagtctcg caggtaccgc ggagctcgcg gccgctctag    360

aactagtgga tctgaagttc ctattctcta gaaagtatag gaacttcctg caggaccacc    420

tttgattgta aatagtaata attaccaccc ttatctaatt atttatttaa cttatttatt    480

tatttattat acatatatac aaatctaata aagtgaaaat ctcccccttc acacttcaca    540

tatgttaggc gtcatcctgt gctcccgaga accagtacca gtacatcgct gtttcgttcg    600

agacttgagg tctagtttta tacgtgaaga ggtcaatgcc gccgagagta aagccacatt    660
```

```
ttgcgtacaa attgcaggca ggtacattgt tcgtttgtgt ctctaatcgt atgccaagga    720
gctgtctgct tagtgcccac tttttcgcaa attcgatgag actgtgcgcg actcctttgc    780
ctcggtgcgt gtgcgacaca acaatgtgtt cgatagaggc tagatcgttc catgttgagt    840
tgagttcaat cttcccgaca agctcttggt cgatgaatgc gccatagcaa gcagagtctt    900
catcagagtc atcatccgag atgtaatcct tccggtaggg gctcacactt ctggtagata    960
gttcaaagcc ttggtcggat aggtgcacat cgaacacttc acgaacaatg aaatggttct   1020
cagcatccaa tgtttccgcc acctgctcag ggatcaccga aattttcata tgagaaccgt   1080
tatcgataac taaagcagca acttcttcta taaaaatggg ttagtatgac agtcatttaa   1140
ataaggaatt tttcagttgg cttggtttca attcaatgtt cgtttttttt ttttcttgct   1200
gtgtttgtgt ttgtgttgtt tatagttgtg tgcactgagc gtcgaaaaaa aaaattcata   1260
gtgagccggg aaatctgtat agcccagata acaacacaag tccaaactag aaactcgtca   1320
aacaccaaaa gcaatgttga atcaattgcc ttgcacaagt acacgtagga aaacataaaa   1380
cattgcaatt ttgaatattg agccttttgt cgtaacattg attgatagga ttactcaccg   1440
aatggttttg aaaccactgc cgacagatca atcaatcaat caaaaaacgt gaactttgaa   1500
aaaggggaag aacagataca ttgaagttag ccatttccat tgatcgtcac aacatatctg   1560
ataaattact ttcaaaatta taagctgatg tgtgtgtatt attaatgtga cagtaacatc   1620
ccaaacgaga aatattatgt cgacaacaaa aaagtttgat ctgaattgaa aatgaagttt   1680
tcccacccta cccatttgtc atattgaaac caatcaactg attaatcaat caattagaat   1740
tgaagctaaa ctaaaacata ccaccgtcca ttttgaatga ttatattttt ttaatattaa   1800
tatcgagata atgtttctaa gaaagaaaga aaaccaggag tgaaaattag aaaaggaaag   1860
gaaaggaaaa aaagaaaaat ctgaaaatat ataaaaaaaa attgtttcgt tggcaataaa   1920
tcttggtgag aacagcgacc gaaagcaaat aagaacaaaa tatgagtgta ttacgttgaa   1980
caactaatta acgtgtgtgt atggatcttt ttttcttttt tctctttaac cgactataaa   2040
caacaaacat ttttgggcag tgcacacact acttaatata cacagcataa attacacgat   2100
tagaaacaaa ttagcttatt aaaataacct aatcaaaccg aatattttat ggtattatga   2160
gtaaactata taatataaat agcacacacc cacaacaaca acaaaggaaa actaaaaggt   2220
tttttctttt tgaaaagatc gttttcttta ttattctcta gttttgacgc tcgacatttt   2280
atgatggaat gaatgggatg aatcatcaaa caagagaaaa tacccgtgac gaaaataata   2340
aaataagttc ctctgataca gaagatgaaa acaacaacaa caagatatag aaatgccttg   2400
ggtggctatt ttatagtctt aactttttaa tgtatatttg ttttgttttt ttacataata   2460
atactttata aaagctaagc taaattcaag taaaatttca atctctcaaa taaaacattt   2520
ttctcttttt cttaaattta gttttatata tttataaaat atacaaagat ttttttaaaa   2580
aagtaacaag ttatatatgt aataacaaaa agaagaataa caagaataca aaaccagatt   2640
tccagatttc cagaatttca ctcttatatg cgtctattta tgtaggatga aaggtagtct   2700
agtacctcct gtgatattat cccattccat gcggggtatc gtatgcttcc ttcagcacta   2760
ccctttagct gttctatatg ctgccactcc tcaattggat tagtctcatc cttcaatgct   2820
atcatttcct ttgatattgg atcatatgca tagtaccgag aaactagtgc gaagtagtga   2880
tcaggtattg ctgttatctg atgagtatac gttgtcctgg ccacggcaga agcacgctta   2940
tcgctccaat ttcccacaac attagtcaac tccgttaggc ccttcattga aagaaatgag   3000
gtcatcaaat gtcttccaat gtgagatttt gggccatttt ttatagcaaa gattgaataa   3060
```

```
ggcgcatttt tcttcaaagc tttattgtac gatctgacta agttatcttt taataattgg   3120

tattcctgtt tattgcttga agaattgccg gtcctattta ctcgttttag gactggttca   3180

gaattcctca aaaattcatc caaatataca agtggatcga tcctacccct tgcgctaaag   3240

aagtatatgt gcctactaac gcttgtcttt gtctctgtca ctaaacactg gattattact   3300

cccaaatact tattttggac taatttaaat gatttcggat caacgttctt aatatcgctg   3360

aatcttccac aattgatgaa agtagctagg aagaggaatt ggtataaagt tttgtttttt   3420

gtaaatctcg aagtatactc aaacgaattt agtattttct cagtgatctc ccagatgctt   3480

tcaccctcac ttagaagtgc tttaagcatt tttttactgt ggctatttcc cttatctgct   3540

tcttccgatg attcgaactg taattgcaaa ctacttacaa tatcagtgat atcagattga   3600

tgtttttgtc catagtaagg aataattgta aattcccaag caggaatcaa tttctttaat   3660

gaggcttcca aaattgttgc tttttgcgtc ttgtatttaa actggagtga tttattgaca   3720

atatcgaaac tcaacgaatt gcttatgata gtattatagc tcatgaatgt ggctctcttg   3780

attgctgttc cgttatgtgt aatcatccaa cataaatagg ttagttcagc agcacataat   3840

gctattttct cacctgaagg tctttcaaac ctttccacaa actgacgaac aagcacctta   3900

ggtggtgttt tacataatat atcaaattgt ggcatgtcga cgattattag ttaaaccact   3960

gcaaaaagtt ggggaaaatt ttgcccattt ttataccgtg tcttcgtcta tcgcctcccc   4020

cactccccaa tctttgaatt attccgaaat attcagcgaa cggggtgtac acaaaaacta   4080

acattctcaa ctgcataatt tgaaaaatgg cgtgggacaa gaaaaaaaaa aaattctcaa   4140

ccatagcaat catggaatac ggtaaatttg tgttgttcgg tgactccatc acccagttta   4200

gttgtaccca gtatggcttt catccagcat tacagaatgt gtatatccga aaattggatg   4260

ttattaaccg tggtttcagt ggctacaact cagagcacgc tagacaaatt cttccaaaaa   4320

ttttagagtc ggaaaccaat atcaaattga tgacaatatt ttttggaact aacgatgcat   4380

acgactacat caatgaaatc cagacagtcg agttagacag atataaagat aatttaagtg   4440

taatggtaca gatggtacta gacaaaaata tcaaaccaat cattattgga tccgaagttc   4500

ctattctcta gaaagtatag gaacttcctc gagtcgtatg agtgcgtttg attttgtagt   4560

ttctgtttgc agtaatgaga taactattca gataaggcgg gtggatgtac gttttgtaag   4620

agtttcctta caaccctggt gggtgtgtga ggttgcatct tagggagaga tagcaccttt   4680

tgcagctctc cgtatacagt tttactcttt gtaacctatg ccaatcatgt ggggattcat   4740

tgtttgccca aggtggtgca tgcaaaatcc ccccaactac ccaatctcac atgaaactca   4800

agcacactag aaaaaaaaga tgttgcgtgg gttgagacg                          4839
```

<210> SEQ ID NO 12
<211> LENGTH: 34
<212> TYPE: DNA
<213> ORGANISM: Artificial Sequence
<220> FEATURE:
<223> OTHER INFORMATION: NotI-XhoI and 20 base pair stuffer

<400> SEQUENCE: 12

```
gcggccgcta gatcttgcga agctccatct cgag                                 34
```

<210> SEQ ID NO 13
<211> LENGTH: 3755
<212> TYPE: DNA
<213> ORGANISM: Candida tropicalis

<400> SEQUENCE: 13

```
gctcaacaat tgtctgacaa gatctcgcaa cacaaggcta acgcctggtt gttgaacact     60
ggttgggttg gttcttctgc tgctagaggt ggtaagagat gttcattgaa gtacaccaga    120
gccattttgg acgctatcca ctctggtgaa ttgtccaagg ttgaatacga gactttccca    180
gtcttcaact tgaatgtccc aacctcctgc ccaggtgtcc caagtgaaat cttgaaccca    240
accaaggcct ggaccgaagg tgttgactcc ttcaacaagg aaatcaagtc tttggctggt    300
aagtttgctg aaaacttcaa gacctatgct gaccaagcta ccgctgaagt tagagctgca    360
ggtccagaag cttaaagata tttattcact atttagtttg cctatttatt tctcatcacc    420
catcatcatt caacaatata tataaagtta tttcggaact catatatcat tgtaatcgtg    480
cgtgttgcaa ttgggtaatt tgaaactgta gttggaacgg attcatgcac gatgcggaga    540
taacacgaga ttatctccta agacaatttt ggcctcattc acacgccctt cttctgagct    600
aaggataaat aattagactt cacaagttca ttaaaatatc cgtcacgcga aaactgcaac    660
aataaggaag gggggggtag acgtagccga tgaatgtggg gtgccagtaa acgcagtctc    720
tctctccccc cccccccccc cccccctcagg aatagtacaa cgggggaagg ataacggata    780
gcaagtggaa tgcgaggaaa attttgaatg cgcaaggaaa gcaatatccg ggctatcagg    840
ttttgagcca ggggacacac tcctcttctg cacaaaaact taacgtagac aaaaaaaaaa    900
aactccacca agacacaatg aatcgcacat ggacatttag acctccccac atgtgaaagc    960
ttctctggcg aaagcaaaaa aagtataata aggacccatg ccttccctct tcctgggccg   1020
tttcaacttt ttctttttct ttgtctatca acacacacac acctcacgac catgactgca   1080
caggatatta tcgccacata catcaccaaa tggtacgtga tagtaccact cgctttgatt   1140
gcttataggg tcctcgacta cttttacggc agatacttga tgtacaagct tggtgctaaa   1200
ccgtttttcc agaaacaaac agacggttat ttcggattca aagctccact tgaattgtta   1260
aaaaagaaga gtgacggtac cctcatagac ttcactctcg agcgtatcca agcgctcaat   1320
cgtccagata tcccaacttt tacattccca atcttttcca tcaaccttat cagcaccctt   1380
gagccggaga acatcaaggc tatcttggcc acccagttca acgatttctc cttgggcacc   1440
agacactcgc actttgctcc tttgttgggc gatggtatct ttaccttgga cggtgccggc   1500
tggaagcaca gcagatctat gttgagacca cagtttgcca gagaacagat ttcccacgtc   1560
aagttgttgg agccacacat gcaggtgttc ttcaagcacg tcagaaaggc acagggcaag   1620
acttttgaca tccaagaatt gtttttcaga ttgaccgtcg actccgccac tgagtttttg   1680
tttggtgaat ccgttgagtc cttgagagat gaatctattg ggatgtccat caatgcactt   1740
gactttgacg gcaaggctgg ctttgctgat gcttttaact actcgcagaa ctatttggct   1800
tcgagagcgg ttatgcaaca attgtactgg gtgttgaacg ggaaaaagtt taaggagtgc   1860
aacgctaaag tgcacaagtt tgctgactat tacgtcagca aggctttgga cttgacacct   1920
gaacaattgg aaaagcagga tggttatgtg ttcttgtacg agttggtcaa gcaaaccaga   1980
gacaggcaag tgttgagaga ccagttgttg aacatcatgg ttgccggtag agacaccacc   2040
gccggtttgt tgtcgtttgt ttctctttgaa ttggccagaa acccagaggt gaccaacaag   2100
ttgagagaag aaatcgagga caagtttggt cttggtgaga atgctcgtgt tgaagacatt   2160
tcctttgagt cgttgaagtc atgtgaatac ttgaaggctg ttctcaacga aactttgaga   2220
ttgtacccat ccgtgccaca gaatttcaga gttgccacca aaaacactac ccttccaagg   2280
ggaggtggta aggacgggtt atctcctgtt ttggtcagaa agggtcaaac cgttatgtac   2340
ggtgtctacg ctgcccacag aaacccagct gtctacggta aggacgccct tgagtttaga   2400
```

```
ccagagaggt ggtttgagcc agagacaaag aagcttggct gggccttcct tccattcaac   2460

ggtggtccaa gaatttgctt gggacagcag tttgccttga cagaagcttc gtatgtcact   2520

gtcagattgc tccaagagtt tggacacttg tctatggacc ccaacaccga atatccacct   2580

aggaaaatgt cgcatttgac catgtccctt ttcgacggtg ccaacattga gatgtattag   2640

aggatcatgt gttatttttg attggtttag tctgtttgta gctattgatt aggttaattc   2700

acggattgtt atttattgat agggggtgcg tgtgtgtgtg tgtgttgcat tcacatggga   2760

tcgttccagg ttgttgtttc cttccatcct gttgagtcaa aaggagtttt gttttgtaac   2820

tccggacgat gtcttagata gaaggtcgat ctccatgtga ttgtttgact gctactctga   2880

ttatgtaatc tgtaaagcct agacgttatg caagcatgtg attgtggttt ttgcaacctg   2940

tttgcacgac aaatgatcga cagtcgatta cgtaatccat attatttaga ggggtaataa   3000

aaaataaatg gcagccagaa tttcaaacat tttgcaaaca atgcaaaaga tgagaaactc   3060

caacagaaaa aataaaaaaa ctccgcagca ctccgaacca acaaaacaat ggggggcgcc   3120

agaattattg actattgtga cttttttta tttttccgt taactttcat tgcagtgaag   3180

tgtgttacac ggggtggtga tggtgttggt ttctacaatg caagggcaca gttgaaggtt   3240

tccacataac gttgcaccat atcaactcaa tttatcctca ttcatgtgat aaaagaagag   3300

ccaaaaggta attggcagac cccccaaggg gaacacggag tagaaagcaa tggaaacacg   3360

cccatgacag tgccatttag cccacaacac atctagtatt cttttttttt tttgtgcgca   3420

ggtgcacacc tggactttag ttattgcccc ataaagttaa caatctcacc tttggctctc   3480

ccagtgtctc cgcctccaga tgctcgtttt acaccctcga gctaacgaca acacaacacc   3540

catgagggga atgggcaaag ttaaacactt ttggtttcaa tgattcctat ttgctactct   3600

cttgttttgt gttttgattt gcaccatgtg aaataaacga caattatata taccttttcg   3660

tctgtcctcc aatgtctctt tttgctgcca ttttgctttt tgctttttgc ttttgcactc   3720

tctcccactc ccacaatcag tgcagcaaca cacaa                              3755
```

<210> SEQ ID NO 14
<211> LENGTH: 687
<212> TYPE: DNA
<213> ORGANISM: Artificial Sequence
<220> FEATURE:
<223> OTHER INFORMATION: Pre-targeting construct for Candida tropicalis CYP52A14

<400> SEQUENCE: 14

```
cgtctcgata acggatagca agtggaatgc gaggaaaatt ttgaatgcgc aaggaaagca     60

atatccgggc tatcaggttt tgagccaggg gacacactcc tcttctgcac aaaaacttaa    120

cgtagacaaa aaaaaaaaac tccaccaaga cacaatgaat cgcacatgga catttagacc    180

tccccacatg tgaaagcttc tctggcgaaa gcaaaaaaag tataataagg acccatgcct    240

tccctcttcc tgggccgttt caactttttc tttttctttg tctatcaaca cacacacacc    300

tcacgaccat ggggcaatca gtgagtctcg caggtaccgc ggagctcgcg gccgctagat    360

cttgcgaagc tccatctcga gaggatcatg tgttattttt gattggttta gtctgtttgt    420

agctattgat taggttaatt cacggattgt tatttattga tagggggtgc gtgtgtgtgt    480

gtgtgttgca ttcacatggg atcgttccag gttgttgttt ccttccatcc tgttgagtca    540

aaaggagttt tgttttgtaa ctccggacga tgtcttagat agaaggtcga tctccatgtg    600

attgtttgac tgctactctg attatgtaat ctgtaaagcc tagacgttat gcaagcatgt    660
```

```
gattgtggtt tttgcaacct ggagacg                                  687


<210> SEQ ID NO 15
<211> LENGTH: 4839
<212> TYPE: DNA
<213> ORGANISM: Artificial Sequence
<220> FEATURE:
<223> OTHER INFORMATION: Targeting construct for deletion of Candida
      tropicalis CYP52A14

<400> SEQUENCE: 15

cgtctcgata acggatagca agtggaatgc gaggaaaatt ttgaatgcgc aaggaaagca     60

atatccgggc tatcaggttt tgagccaggg gacacactcc tcttctgcac aaaaacttaa    120

cgtagacaaa aaaaaaaaac tccaccaaga cacaatgaat cgcacatgga catttagacc    180

tccccacatg tgaaagcttc tctggcgaaa gcaaaaaaag tataataagg acccatgcct    240

tccctcttcc tgggccgttt caactttttc tttttctttg tctatcaaca cacacacacc    300

tcacgaccat ggggcaatca gtgagtctcg caggtaccgc ggagctcgcg gccgctctag    360

aactagtgga tctgaagttc ctattctcta gaaagtatag gaacttcctg caggaccacc    420

tttgattgta aatagtaata attaccaccc ttatctaatt atttatttaa cttatttatt    480

tatttattat acatatatac aaatctaata aagtgaaaat ctcccccttc acacttcaca    540

tatgttaggc gtcatcctgt gctcccgaga accagtacca gtacatcgct gtttcgttcg    600

agacttgagg tctagtttta tacgtgaaga ggtcaatgcc gccgagagta aagccacatt    660

ttgcgtacaa attgcaggca ggtacattgt tcgtttgtgt ctctaatcgt atgccaagga    720

gctgtctgct tagtgcccac tttttcgcaa attcgatgag actgtgcgcg actcctttgc    780

ctcggtgcgt gtgcgacaca acaatgtgtt cgatagaggc tagatcgttc catgttgagt    840

tgagttcaat cttcccgaca agctcttggt cgatgaatgc gccatagcaa gcagagtctt    900

catcagagtc atcatccgag atgtaatcct tccggtaggg gctcacactt ctggtagata    960

gttcaaagcc ttggtcggat aggtgcacat cgaacacttc acgaacaatg aaatggttct   1020

cagcatccaa tgtttccgcc acctgctcag ggatcaccga aattttcata tgagaaccgt   1080

tatcgataac taaagcagca acttcttcta taaaaatggg ttagtatgac agtcatttaa   1140

ataaggaatt tttcagttgg cttggtttca attcaatgtt cgtttttttt ttttcttgct   1200

gtgtttgtgt ttgtgttgtt tatagttgtg tgcactgagc gtcgaaaaaa aaaattcata   1260

gtgagccggg aaatctgtat agcccagata acaacacaag tccaaactag aaactcgtca   1320

aacaccaaaa gcaatgttga atcaattgcc ttgcacaagt acacgtagga aaacataaaa   1380

cattgcaatt ttgaatattg agccttttgt cgtaacattg attgatagga ttactcaccg   1440

aatggttttg aaaccactgc cgacagatca atcaatcaat caaaaaacgt gaactttgaa   1500

aaaggggaag aacagataca ttgaagttag ccatttccat tgatcgtcac aacatatctg   1560

ataaattact ttcaaaatta taagctgatg tgtgtgtatt attaatgtga cagtaacatc   1620

ccaaacgaga aatattatgt cgacaacaaa aaagtttgat ctgaattgaa aatgaagttt   1680

tcccacccta cccatttgtc atattgaaac caatcaactg attaatcaat caattagaat   1740

tgaagctaaa ctaaaacata ccaccgtcca ttttgaatga ttatattttt ttaatattaa   1800

tatcgagata atgtttctaa gaaagaaaga aaaccaggag tgaaaattag aaaaggaaag   1860

gaaaggaaaa aaagaaaaat ctgaaaatat ataaaaaaaa attgtttcgt tggcaataaa   1920

tcttggtgag aacagcgacc gaaagcaaat aagaacaaaa tatgagtgta ttacgttgaa   1980

caactaatta acgtgtgtgt atggatcttt ttttcttttt tctctttaac cgactataaa   2040
```

-continued

```
caacaaacat ttttgggcag tgcacacact acttaatata cacagcataa attacacgat   2100
tagaaacaaa ttagcttatt aaaataacct aatcaaaccg aatattttat ggtattatga   2160
gtaaactata taatataaat agcacacacc cacaacaaca acaaaggaaa actaaaaggt   2220
tttttctttt tgaaaagatc gttttcttta ttattctcta gttttgacgc tcgacatttt   2280
atgatggaat gaatgggatg aatcatcaaa caagagaaaa tacccgtgac gaaaataata   2340
aaataagttc ctctgataca gaagatgaaa acaacaacaa caagatatag aaatgccttg   2400
ggtggctatt ttatagtctt aactttttaa tgtatatttg ttttgttttt ttacataata   2460
atactttata aaagctaagc taaattcaag taaaatttca atctctcaaa taaaacattt   2520
ttctcttttt cttaaattta gttttatata tttataaaat atacaaagat tttttttaaaa   2580
aagtaacaag ttatatatgt aataacaaaa agaagaataa caagaataca aaaccagatt   2640
tccagatttc cagaatttca ctcttatatg cgtctattta tgtaggatga aaggtagtct   2700
agtacctcct gtgatattat cccattccat gcggggtatc gtatgcttcc ttcagcacta   2760
ccctttagct gttctatatg ctgccactcc tcaattggat tagtctcatc cttcaatgct   2820
atcatttcct ttgatattgg atcatatgca tagtaccgag aaactagtgc gaagtagtga   2880
tcaggtattg ctgttatctg atgagtatac gttgtcctgg ccacggcaga agcacgctta   2940
tcgctccaat ttcccacaac attagtcaac tccgttaggc ccttcattga aagaaatgag   3000
gtcatcaaat gtcttccaat gtgagatttt gggccatttt ttatagcaaa gattgaataa   3060
ggcgcatttt tcttcaaagc tttattgtac gatctgacta agttatcttt taataattgg   3120
tattcctgtt tattgcttga agaattgccg gtcctattta ctcgttttag gactggttca   3180
gaattcctca aaaattcatc caaatataca agtggatcga tcctacccct tgcgctaaag   3240
aagtatatgt gcctactaac gcttgtcttt gtctctgtca ctaaacactg gattattact   3300
cccaaatact tattttggac taatttaaat gatttcggat caacgttctt aatatcgctg   3360
aatcttccac aattgatgaa agtagctagg aagaggaatt ggtataaagt tttgttttt   3420
gtaaatctcg aagtatactc aaacgaattt agtattttct cagtgatctc ccagatgctt   3480
tcaccctcac ttagaagtgc tttaagcatt tttttactgt ggctatttcc cttatctgct   3540
tcttccgatg attcgaactg taattgcaaa ctacttacaa tatcagtgat atcagattga   3600
tgtttttgtc catagtaagg aataattgta aattcccaag caggaatcaa tttctttaat   3660
gaggcttcca aaattgttgc tttttgcgtc ttgtatttaa actggagtga tttattgaca   3720
atatcgaaac tcaacgaatt gcttatgata gtattatagc tcatgaatgt ggctctcttg   3780
attgctgttc cgttatgtgt aatcatccaa cataaatagg ttagttcagc agcacataat   3840
gctattttct cacctgaagg tctttcaaac ctttccacaa actgacgaac aagcacctta   3900
ggtggtgttt tacataatat atcaaattgt ggcatgtcga cgattattag ttaaaccact   3960
gcaaaaagtt ggggaaaatt ttgcccattt ttataccgtg tcttcgtcta tcgcctcccc   4020
cactccccaa tctttgaatt attccgaaat attcagcgaa cggggtgtac acaaaaacta   4080
acattctcaa ctgcataatt tgaaaaatgg cgtgggacaa gaaaaaaaaa aaattctcaa   4140
ccatagcaat catggaatac ggtaaatttg tgttgttcgg tgactccatc acccagttta   4200
gttgtaccca gtatggcttt catccagcat tacagaatgt gtatatccga aaattggatg   4260
ttattaaccg tggtttcagt ggctacaact cagagcacgc tagacaaatt cttccaaaaa   4320
ttttagagtc ggaaaccaat atcaaattga tgacaatatt ttttggaact aacgatgcat   4380
acgactacat caatgaaatc cagacagtcg agttagacag atataaagat aatttaagtg   4440
```

```
taatggtaca gatggtacta gacaaaaata tcaaaccaat cattattgga tccgaagttc   4500
ctattctcta gaaagtatag gaacttcctc gagaggatca tgtgttattt ttgattggtt   4560
tagtctgttt gtagctattg attaggttaa ttcacggatt gttatttatt gatagggggt   4620
gcgtgtgtgt gtgtgtgttg cattcacatg ggatcgttcc aggttgttgt ttccttccat   4680
cctgttgagt caaaaggagt tttgttttgt aactccggac gatgtcttag atagaaggtc   4740
gatctccatg tgattgtttg actgctactc tgattatgta atctgtaaag cctagacgtt   4800
atgcaagcat gtgattgtgg tttttgcaac ctggagacg                          4839
```

<210> SEQ ID NO 16
<211> LENGTH: 4296
<212> TYPE: DNA
<213> ORGANISM: Candida tropicalis

<400> SEQUENCE: 16

```
tgcatactcg gagcatatcg ccatcgtcca tatcgttggc actccatcca ctgagtcagc     60
caagaagcaa ttgttgttgc accacacctt aggtaatggt gactttactg ttttccacaa    120
gatctcgtca ttcatcagtg ccactactgc tgggttgacc gacccagaca ccgccgctga    180
tgaaattgat agagtgattg agtcagccta catcaaccag cgtccaacgt acttgggatt    240
cccttccaac atggttgacg ttcaagtgcc agtcagcaag ttggacaagc cattgaactt    300
aaccccacct gcaaacaatc caaagatcca gtctgaggtc ttgagcgaca ttattgcctt    360
gattgaaacc gccaaggatc cagttatcat cattgatgct tgttgtggaa ggcacaatgc    420
taccccagag gcacagaagt tgattgagtt gacaaagttc aagtttgctg tcaccccaat    480
ggctaaaggg tctaaggaca ttgatgaaag tgatccgaag ttcattggtt gctacgttgg    540
tgacttgtct tatccaagag tcaaagagtt ggttgaaagc tcggacttgg tcttgtcctt    600
gggtgctgtc ttgtctgatt tcaacactgg ttcgttctca tactctttgg acaatgccaa    660
ggttgttgaa ttccactccg actacactca aatcaagagc gctcagtacc caggtatcag    720
aatgaaggaa ttgttgggca agttggttga ggagccagaa ttggtcaaga cgtgttccaa    780
gatcccagca aagaagttgg tcactgacaa ctttgaacca ttggtcttgc caccggacca    840
caagctcacc caatcctggt tgtggagtaa cttgggtaat tggttgaaag aaggtgatgt    900
gattgttacc gaaaccggta cttccaattt cggtattgtc cagaccaaat tcccaaagaa    960
tgctgtcggt atctcgcaag tcttgtgggg ttccattggc tactcggtcg gttctgccgc   1020
tggtgccgtt atcgccgccg aggagcttga tcccagccgt agagtcatct tgtttgttgg   1080
tgacggttct ttgcagttga ccgtgcagga aatctccacc atggccagac acaagaacaa   1140
catctacatc tttgtcttga acaacaacgg tttcaccatt gaaagattga ttcacggtcc   1200
agaagctggt tacaacagta ttcaagaatg ggagaacgct gagttattga agactttcaa   1260
ggctaccaac tacgagagtt tcaccgtcaa gactgtcggc gaacttgaca aggtgttcaa   1320
ggatgaaaag tttgccgtca acgacaagat tagattggtt gagatcatgt tagacacttt   1380
cgatgctcca gagaacttgg ttaagcaagc tgagagatct gccaacacca acaagtagag   1440
tttgtctatg ttttccgttt gccttttctt tctagtacga gacgttattg aacgaagttt   1500
ttatatatct agatctaata catattccat gtctgttcat ttttgacgga gtttcataag   1560
gtggcagttt ctaatcaaag gtccgtcatt ggcgtcgtgg cattggcggc tcgcatcaac   1620
tcgtatgtca atattttctg ttaactccgc cagacatacg atcaaaacct acaagcaaaa   1680
aaattccaca tgctttgttt gagatctcca caaacaacaa cggggtaaga aaatcatggg   1740
```

```
gcgattaatc atgccatctt tgtaaatttc tttgtttcaa catcaccctc tttagtcaaa   1800
ccttcacagg actgtctgct ctactttgcc acccagttca tatataaatt accaacttcc   1860
accgagcacc accaacacct caccccactc tctccccccc cctttttttt ccagcttaga   1920
cacacacttc aaactcgaca tggctccatt tttgcccgac caggtcgact acaaacacgt   1980
cgacaccctt atgttattat gtgacgggat catccacgaa accaccgtgg acgaaatcaa   2040
agacgtcatt gcccctgact tccccgccga caaatacgag gagtacgtca ggacattcac   2100
caaaccctcc gaaaccccag ggttcaggga aaccgtctac aacaccgtca acgcaaacac   2160
catggatgca atccaccagt tcattatctt gaccaatgtt ttgggatcaa gggtcttggc   2220
accagctttg accaactcgt tgactcctat caaggacatg agcttggaag accgtgaaaa   2280
gttgttagcc tcgtggcgtg actcccctat tgctgctaaa aggaagttgt tcaggttggt   2340
ttctacgctt accttggtca cgttcacgag attggccaat gagttgcatt tgaaagccat   2400
tcattatcca ggaagagaag accgtgaaaa ggcttatgaa acccaggaga ttgacccttt   2460
taagtaccag tttttggaaa aaccgaagtt ttacggcgct gagttgtact tgccagatat   2520
tgatgtgatc attattggat ctggggccgg tgctggtgtc gtggcccaca ctttgaccaa   2580
cgacggcttc aagagtttgg ttttggaaaa gggcagatac tttagcaact ccgagttgaa   2640
ctttgatgac aaggacgggg ttcaagaatt ataccaaagt ggaggtactt tgaccaccgt   2700
caaccagcag ttgtttgttc ttgctggttc cacttttggt ggtggtacca ctgtcaattg   2760
gtcggcctgt cttaaaacgc cattcaaggt gcgtaaggaa tggtatgatg agtttggcgt   2820
tgactttgct gccgatgaag cctacgacaa agcacaggat tatgtttggc agcaaatggg   2880
agcttctacc gaaggcatca cccactcttt ggctaacgag attattattg aaggtggcaa   2940
gaaattaggt tacaaggcca aggtattaga ccaaaacagc ggtggtcatc ctcatcacag   3000
atgcggtttc tgttatttgg gttgtaagca cggtatcaag cagggctctg ttaataactg   3060
gtttagagac gcagctgccc acggttctca gttcatgcaa caggttagag ttttgcaaat   3120
ccttaacaag aagggcatcg cttatggtat cttgtgtgag gatgttgtaa ccggtgccaa   3180
gttcaccatt actggcccca aaaagtttgt tgttgccgcc ggcgccttaa acactccatc   3240
tgtgttggtc aactccggat tcaagaacaa gaacatcggt aagaacttaa ctttgcatcc   3300
agtttctgtc gtgtttggtg attttggcaa agacgttcaa gcagatcact tccacaactc   3360
catcatgact gctctttgtt cagaagccgc tgatttagac ggcaagggtc atggatgcag   3420
aattgaaacc atcttgaacg ctccattcat ccaggcttca ttcttaccat ggagaggtag   3480
taacgaggct agacgagact tgttgcgtta caacaacatg gtggccatgt tacttcttag   3540
tcgtgatacc accagtggtt ccgtttcgtc ccatccaact aaacctgaag cattagttgt   3600
cgagtacgac gtgaacaagt ttgacagaaa ctccatcttg caggcattgt tggtcactgc   3660
tgacttgttg tacattcaag gtgccaagag aatccttagt ccccaaccat gggtgccaat   3720
ttttgaatcc gacaagccaa aggataagag atcaatcaag gacgaggact atgtcgaatg   3780
gagagccaag gttgccaaga ttccttttga cacctacggc tcgccttatg gttcggcgca   3840
tcaaatgtct tcttgtcgta tgtcaggtaa gggtcctaaa tacggtgctg ttgataccga   3900
tggtagattg tttgaatgtt cgaatgttta tgttgctgac gctagtcttt tgccaactgc   3960
tagcggtgct aatcctatgg tcaccaccat gactcttgca agacatgttg cgttaggttt   4020
ggcagactcc ttgaagacca aggccaagtt gtagttctgt atacgtatct tataatttag   4080
atttcctttt attgacggta aacattcagg ataggtacta cccttgctgc aaaagcccag   4140
```

cacgccccaa tcgcgatgac ttgagcgaag caaacacgca cacaaaaggg gtacacaaaa 4200
aataacgaga tgcccttgaa gcacacaccc aaacacgatg gaacacaaga tggccctaga 4260
aagtacaaaa aaagtaaagc cacttgattc cgccca 4296

<210> SEQ ID NO 17
<211> LENGTH: 609
<212> TYPE: DNA
<213> ORGANISM: Artificial Sequence
<220> FEATURE:
<223> OTHER INFORMATION: Pre-targeting construct for Candida tropicalis FAO1

<400> SEQUENCE: 17
cgtctcctgt taactccgcc agacatacga tcaaaaccta caagcaaaaa aattccacat 60
gctttgtttg agatctccac aaacaacaac ggggtaagaa aatcatgggg cgattaatca 120
tgccatcttt gtaaatttct ttgtttcaac atcaccctct ttagtcaaac cttcacagga 180
ctgtctgctc tactttgcca cccagttcat atataaatta ccaacttcca ccgagcacca 240
ccaacacctc accccactct ctcccccccc cttttttttc cagcttagac acacacttca 300
aactcgccat ggggcaatca gtgagtctcg caggtaccgc ggagctcgcg gccgctagat 360
cttgcgaagc tccatctcga gttctgtata cgtatcttat aatttagatt tccttttatt 420
gacggtaaac attcaggata ggtactaccc ttgctgcaaa agcccagcac gccccaatcg 480
cgatgacttg agcgaagcaa acacgcacac aaaaggggta cacaaaaaat aacgagatgc 540
ccttgaagca cacacccaaa cacgatggaa cacaagatgg ccctagaaag tacaaaaaaa 600
gtagagacg 609

<210> SEQ ID NO 18
<211> LENGTH: 4761
<212> TYPE: DNA
<213> ORGANISM: Artificial Sequence
<220> FEATURE:
<223> OTHER INFORMATION: Targeting construct for deletion of Candida tropicalis FAO1

<400> SEQUENCE: 18
cgtctcctgt taactccgcc agacatacga tcaaaaccta caagcaaaaa aattccacat 60
gctttgtttg agatctccac aaacaacaac ggggtaagaa aatcatgggg cgattaatca 120
tgccatcttt gtaaatttct ttgtttcaac atcaccctct ttagtcaaac cttcacagga 180
ctgtctgctc tactttgcca cccagttcat atataaatta ccaacttcca ccgagcacca 240
ccaacacctc accccactct ctcccccccc cttttttttc cagcttagac acacacttca 300
aactcgccat ggggcaatca gtgagtctcg caggtaccgc ggagctcgcg gccgctctag 360
aactagtgga tctgaagttc ctattctcta gaaagtatag gaacttcctg caggaccacc 420
tttgattgta aatagtaata attaccaccc ttatctaatt atttatttaa cttatttatt 480
tatttattat acatatatac aaatctaata aagtgaaaat ctcccccttc acacttcaca 540
tatgttaggc gtcatcctgt gctcccgaga accagtacca gtacatcgct gtttcgttcg 600
agacttgagg tctagtttta tacgtgaaga ggtcaatgcc gccgagagta aagccacatt 660
ttgcgtacaa attgcaggca ggtacattgt tcgtttgtgt ctctaatcgt atgccaagga 720
gctgtctgct tagtgcccac tttttcgcaa attcgatgag actgtgcgcg actcctttgc 780
ctcggtgcgt gtgcgacaca acaatgtgtt cgatagaggc tagatcgttc catgttgagt 840
tgagttcaat cttcccgaca agctcttggt cgatgaatgc gccatagcaa gcagagtctt 900

```
catcagagtc atcatccgag atgtaatcct tccggtaggg gctcacactt ctggtagata    960
gttcaaagcc ttggtcggat aggtgcacat cgaacacttc acgaacaatg aaatggttct   1020
cagcatccaa tgtttccgcc acctgctcag ggatcaccga aattttcata tgagaaccgt   1080
tatcgataac taaagcagca acttcttcta taaaaatggg ttagtatgac agtcatttaa   1140
ataaggaatt tttcagttgg cttggtttca attcaatgtt cgtttttttt ttttcttgct   1200
gtgtttgtgt ttgtgttgtt tatagttgtg tgcactgagc gtcgaaaaaa aaaattcata   1260
gtgagccggg aaatctgtat agcccagata acaacacaag tccaaactag aaactcgtca   1320
aacaccaaaa gcaatgttga atcaattgcc ttgcacaagt acacgtagga aaacataaaa   1380
cattgcaatt ttgaatattg agccttttgt cgtaacattg attgatagga ttactcaccg   1440
aatggttttg aaaccactgc cgacagatca atcaatcaat caaaaaacgt gaactttgaa   1500
aaaggggaag aacagataca ttgaagttag ccatttccat tgatcgtcac aacatatctg   1560
ataaattact ttcaaaatta taagctgatg tgtgtgtatt attaatgtga cagtaacatc   1620
ccaaacgaga aatattatgt cgacaacaaa aaagtttgat ctgaattgaa aatgaagttt   1680
tcccacccta cccatttgtc atattgaaac caatcaactg attaatcaat caattagaat   1740
tgaagctaaa ctaaaacata ccaccgtcca ttttgaatga ttatattttt ttaatattaa   1800
tatcgagata atgtttctaa gaaagaaaga aaaccaggag tgaaaattag aaaaggaaag   1860
gaaaggaaaa aaagaaaaat ctgaaaatat ataaaaaaaa attgtttcgt tggcaataaa   1920
tcttggtgag aacagcgacc gaaagcaaat aagaacaaaa tatgagtgta ttacgttgaa   1980
caactaatta acgtgtgtgt atggatcttt ttttcttttt tctctttaac cgactataaa   2040
caacaaacat ttttgggcag tgcacacact acttaatata cacagcataa attacacgat   2100
tagaaacaaa ttagcttatt aaaataacct aatcaaaccg aatattttat ggtattatga   2160
gtaaactata taatataaat agcacacacc cacaacaaca acaaaggaaa actaaaaggt   2220
tttttctttt tgaaaagatc gttttcttta ttattctcta gttttgacgc tcgacatttt   2280
atgatggaat gaatgggatg aatcatcaaa caagagaaaa tacccgtgac gaaaataata   2340
aaataagttc ctctgataca gaagatgaaa acaacaacaa caagatatag aaatgccttg   2400
ggtggctatt ttatagtctt aactttttaa tgtatatttg ttttgttttt ttacataata   2460
atactttata aaagctaagc taaattcaag taaaatttca atctctcaaa taaaacattt   2520
ttctcttttt cttaaattta gttttatata tttataaaat atacaaagat ttttttaaaa   2580
aagtaacaag ttatatatgt aataacaaaa agaagaataa caagaataca aaaccagatt   2640
tccagatttc cagaatttca ctcttatatg cgtctattta tgtaggatga aaggtagtct   2700
agtacctcct gtgatattat cccattccat gcggggtatc gtatgcttcc ttcagcacta   2760
ccctttagct gttctatatg ctgccactcc tcaattggat tagtctcatc cttcaatgct   2820
atcatttcct ttgatattgg atcatatgca tagtaccgag aaactagtgc gaagtagtga   2880
tcaggtattg ctgttatctg atgagtatac gttgtcctgg ccacggcaga agcacgctta   2940
tcgctccaat ttcccacaac attagtcaac tccgttaggc ccttcattga aagaaatgag   3000
gtcatcaaat gtcttccaat gtgagatttt gggccatttt ttatagcaaa gattgaataa   3060
ggcgcatttt tcttcaaagc tttattgtac gatctgacta agttatcttt taataattgg   3120
tattcctgtt tattgcttga agaattgccg gtcctattta ctcgttttag gactggttca   3180
gaattcctca aaaattcatc caaatataca agtggatcga tcctacccct tgcgctaaag   3240
aagtatatgt gcctactaac gcttgtcttt gtctctgtca ctaaacactg gattattact   3300
```

```
cccaaatact tattttggac taatttaaat gatttcggat caacgttctt aatatcgctg   3360

aatcttccac aattgatgaa agtagctagg aagaggaatt ggtataaagt ttttgttttt   3420

gtaaatctcg aagtatactc aaacgaattt agtattttct cagtgatctc ccagatgctt   3480

tcaccctcac ttagaagtgc tttaagcatt tttttactgt ggctatttcc cttatctgct   3540

tcttccgatg attcgaactg taattgcaaa ctacttacaa tatcagtgat atcagattga   3600

tgtttttgtc catagtaagg aataattgta aattcccaag caggaatcaa tttctttaat   3660

gaggcttcca aaattgttgc tttttgcgtc ttgtatttaa actggagtga tttattgaca   3720

atatcgaaac tcaacgaatt gcttatgata gtattatagc tcatgaatgt ggctctcttg   3780

attgctgttc cgttatgtgt aatcatccaa cataaatagg ttagttcagc agcacataat   3840

gctattttct cacctgaagg tctttcaaac ctttccacaa actgacgaac aagcacctta   3900

ggtggtgttt tacataatat atcaaattgt ggcatgtcga cgattattag ttaaaccact   3960

gcaaaaagtt ggggaaaatt ttgcccattt ttataccgtg tcttcgtcta tcgcctcccc   4020

cactccccaa tctttgaatt attccgaaat attcagcgaa cggggtgtac acaaaaacta   4080

acattctcaa ctgcataatt tgaaaaatgg cgtgggacaa gaaaaaaaaa aaattctcaa   4140

ccatagcaat catggaatac ggtaaatttg tgttgttcgg tgactccatc acccagttta   4200

gttgtaccca gtatggcttt catccagcat tacagaatgt gtatatccga aaattggatg   4260

ttattaaccg tggtttcagt ggctacaact cagagcacgc tagacaaatt cttccaaaaa   4320

ttttagagtc ggaaaccaat atcaaattga tgacaatatt ttttggaact aacgatgcat   4380

acgactacat caatgaaatc cagacagtcg agttagacag atataaagat aatttaagtg   4440

taatggtaca gatggtacta gacaaaaata tcaaaccaat cattattgga tccgaagttc   4500

ctattctcta gaaagtatag gaacttcctc gagttctgta tacgtatctt ataatttaga   4560

tttcctttta ttgacggtaa acattcagga taggtactac ccttgctgca aaagcccagc   4620

acgccccaat cgcgatgact tgagcgaagc aaacacgcac acaaaagggg tacacaaaaa   4680

ataacgagat gcccttgaag cacacaccca aacacgatgg aacacaagat ggccctagaa   4740

agtacaaaaa aagtagagac g                                             4761
```

<210> SEQ ID NO 19
<211> LENGTH: 1992
<212> TYPE: DNA
<213> ORGANISM: Candida tropicalis

<400> SEQUENCE: 19

```
cttatgttat tatgtgacgg gatcatccac gaaaccaccg tcgaccaaat caaagacgtt     60

attgctcctg acttccctgc tgacaagtac gaagagtacg tcaggacatt caccaaaccc    120

tccgaaaccc cagggttcag ggaaaccgtc tacaacacag tcaacgcaaa caccacggac    180

gcaatccacc agttcattat cttgaccaat gttttggcat ccagggtctt ggctccagct    240

ttgaccaact cgttgacgcc tatcaaggac atgagcttgg aagaccgtga aaaattgttg    300

gcctcgtggc gcgactcccc aatcgctgcc aaaaggaaat tgttcaggtt ggtttccacg    360

cttaccttgg ttactttcac gagattggcc aatgagttgc atttgaaagc cattcactat    420

ccaggaagag aagaccgtga aaaggcttat gaaacccagg agattgaccc tttcaagtac    480

cagtttatgg aaaagccaaa gtttgacggc gctgagttgt acttgccaga tattgatgtt    540

atcattattg gatctggtgc cggtgctggt gttgtggccc acactttggc caacgatggc    600

ttcaagagtt tggttttgga aaagggcaaa tactttagca actccgagtt gaactttgat    660
```

```
gacaaggacg gcgttcaaga attataccaa agtggaggta ctttgactac agtcaaccaa    720

cagttgtttg ttcttgctgg ttccactttt ggtggcggta ccactgtcaa ttggtcagcc    780

tgtcttaaga cgccattcaa ggtgcgtaag gaatggtatg atgagtttgg tgttgacttt    840

gctgctgatg aagcatacga taaagcgcag gattatgttt ggcagcaaat gggagcttct    900

accgaaggca tcacccactc tttggctaac gagattatta ttgaaggtgg taagaaatta    960

ggttacaagg ccaaggtatt agaccaaaac agcggtggtc atcctcagca cagatgcggt   1020

ttctgttatt tgggctgtaa gcacggtatc aagcagggtt ctgttaataa ctggtttaga   1080

gacgcagctg cccacggttc ccagttcatg caacaggtta gagttttgca aatacttaac   1140

aagaagggga tcgcttacgg tatcttgtgt gaggatgttg taaccggcgc caagttcacc   1200

attactggcc ccaaaaagtt tgttgttgct gccggtgctt tgaacactcc atctgtgttg   1260

gtcaactccg gcttcaagaa caagaacatc ggtaagaact taactttgca cccagtttct   1320

gtcgtgtttg gtgattttgg caaagacgtt caagcagacc acttccacaa ctccatcatg   1380

actgcccttt gttcagaagc cgctgattta gacggcaagg gccatggatg cagaattgaa   1440

accatcttga acgctccatt catccaggct tcattcttac catggagagg tagtaacgag   1500

gctagacgag acttgttgcg ttacaacaac atggtggcga tgttgctcct tagtcgtgac   1560

accaccagtg gttccgtttc tgctcatcca accaaacctg aagctttggt tgtcgagtac   1620

gacgtgaaca agtttgacag aaactcgatc ttgcaggcat tgttggtcac tgctgacttg   1680

ttgtatatcc aaggtgccaa gagaatcctt agtccacagg catgggtgcc aatttttgaa   1740

tccgacaagc caaaggataa gagatcaatc aaggacgagg actatgtcga atggagagcc   1800

aaggttgcca agattccttt cgacacctac ggctcacctt atggttcggc acatcaaatg   1860

tcttcttgcc gtatgtcagg taagggtcct aaatacggtg ctgttgacac cgatggtaga   1920

ttgtttgaat gttcgaatgt ttatgttgcc gatgcaagtc ttttgccaac tgcaagcggt   1980

gctaatccta tg                                                       1992
```

```
<210> SEQ ID NO 20
<211> LENGTH: 603
<212> TYPE: DNA
<213> ORGANISM: Artificial Sequence
<220> FEATURE:
<223> OTHER INFORMATION: Pre-targeting construct for Candida tropicalis
      FAO1

<400> SEQUENCE: 20

cgaaaccacc gtcgaccaaa tcaaagacgt tattgctcct gacttccctg ctgacaagta     60

cgaagagtac gtcaggacat tcaccaaacc ctccgaaacc ccagggttca gggaaaccgt    120

ctacaacaca gtcaacgcaa acaccacgga cgcaatccac cagttcatta tcttgaccaa    180

tgttttggca tccagggtct tggctccagc tttgaccaac tcgttgacgc ctatcaagga    240

catgagcttg gaagaccgtg aaaaattgtt ggcctcgtgg cgcgactagg cggccgctag    300

atcttgcgaa gctccatctc gagttgttgt atatccaagg tgccaagaga atccttagtc    360

cacaggcatg ggtgccaatt tttgaatccg acaagccaaa ggataagaga tcaatcaagg    420

acgaggacta tgtcgaatgg agagccaagg ttgccaagat tcctttcgac acctacggct    480

caccttatgg ttcggcacat caaatgtctt cttgccgtat gtcaggtaag ggtcctaaat    540

acggtgctgt tgacaccgat ggtagattgt ttgaatgttc gaatgtttat gttgccgatg    600

caa                                                                  603
```

```
<210> SEQ ID NO 21
<211> LENGTH: 4755
<212> TYPE: DNA
<213> ORGANISM: Artificial Sequence
<220> FEATURE:
<223> OTHER INFORMATION: Targeting construct for deletion of Candida
      tropicalis FAO1

<400> SEQUENCE: 21

cgaaaccacc gtcgaccaaa tcaaagacgt tattgctcct gacttccctg ctgacaagta     60

cgaagagtac gtcaggacat tcaccaaacc ctccgaaacc ccagggttca gggaaaccgt    120

ctacaacaca gtcaacgcaa acaccacgga cgcaatccac cagttcatta tcttgaccaa    180

tgttttggca tccagggtct tggctccagc tttgaccaac tcgttgacgc ctatcaagga    240

catgagcttg gaagaccgtg aaaaattgtt ggcctcgtgg cgcgactagg cggccgctct    300

agaactagtg gatctgaagt tcctattctc tagaaagtat aggaacttcc tgcaggacca    360

cctttgattg taaatagtaa taattaccac ccttatctaa ttatttattt aacttattta    420

tttatttatt atacatatat acaaatctaa taaagtgaaa atctcccct tcacacttca     480

catatgttag gcgtcatcct gtgctcccga gaaccagtac cagtacatcg ctgtttcgtt    540

cgagacttga ggtctagttt tatacgtgaa gaggtcaatg ccgccgagag taaagccaca    600

ttttgcgtac aaattgcagg caggtacatt gttcgtttgt gtctctaatc gtatgccaag    660

gagctgtctg cttagtgccc actttttcgc aaattcgatg agactgtgcg cgactccttt    720

gcctcggtgc gtgtgcgaca caacaatgtg ttcgatagag gctagatcgt tccatgttga    780

gttgagttca atcttcccga caagctcttg gtcgatgaat gcgccatagc aagcagagtc    840

ttcatcagag tcatcatccg agatgtaatc cttccggtag ggctcacac ttctggtaga     900

tagttcaaag ccttggtcgg ataggtgcac atcgaacact tcacgaacaa tgaaatggtt    960

ctcagcatcc aatgtttccg ccacctgctc agggatcacc gaaattttca tatgagaacc   1020

gttatcgata actaaagcag caacttcttc tataaaaatg ggttagtatg acagtcattt   1080

aaataaggaa tttttcagtt ggcttggttt caattcaatg ttcgtttttt tttttcttg    1140

ctgtgtttgt gtttgtgttg tttatagttg tgtgcactga gcgtcgaaaa aaaaaattca   1200

tagtgagccg ggaaatctgt atagcccaga taacaacaca agtccaaact agaaactcgt   1260

caaacaccaa aagcaatgtt gaatcaattg ccttgcacaa gtacacgtag gaaaacataa   1320

aacattgcaa ttttgaatat tgagcctttt gtcgtaacat tgattgatag gattactcac   1380

cgaatggttt tgaaaccact gccgacagat caatcaatca atcaaaaaac gtgaactttg   1440

aaaaagggga agaacagata cattgaagtt agccatttcc attgatcgtc acaacatatc   1500

tgataaatta ctttcaaaat tataagctga tgtgtgtgta ttattaatgt gacagtaaca   1560

tcccaaacga gaaatattat gtcgacaaca aaaaagtttg atctgaattg aaaatgaagt   1620

tttcccaccc tacccatttg tcatattgaa accaatcaac tgattaatca atcaattaga   1680

attgaagcta aactaaaaca taccaccgtc cattttgaat gattatattt ttttaatatt   1740

aatatcgaga taatgtttct aagaaagaaa gaaaaccagg agtgaaaatt agaaaaggaa   1800

aggaaaggaa aaaaagaaaa atctgaaaat atataaaaaa aaattgtttc gttggcaata   1860

aatcttggtg agaacagcga ccgaaagcaa ataagaacaa aatatgagtg tattacgttg   1920

aacaactaat taacgtgtgt gtatggatct tttttcttt tttctcttta accgactata    1980

aacaacaaac atttttgggc agtgcacaca ctacttaata tacacagcat aaattacacg   2040

attagaaaca aattagctta ttaaaataac ctaatcaaac cgaatatttt atggtattat   2100
```

```
gagtaaacta tataatataa atagcacaca cccacaacaa caacaaagga aaactaaaag   2160
gttttttctt tttgaaaaga tcgttttctt tattattctc tagttttgac gctcgacatt   2220
ttatgatgga atgaatggga tgaatcatca aacaagagaa aatacccgtg acgaaaataa   2280
taaaataagt tcctctgata cagaagatga aaacaacaac aacaagatat agaaatgcct   2340
tgggtggcta ttttatagtc ttaacttttt aatgtatatt tgttttgttt ttttacataa   2400
taatacttta taaaagctaa gctaaattca agtaaaattt caatctctca aataaaacat   2460
ttttctcttt ttcttaaatt tagttttata tatttataaa atatacaaag atttttttaa   2520
aaaagtaaca agttatatat gtaataacaa aaagaagaat aacaagaata caaaaccaga   2580
tttccagatt tccagaattt cactcttata tgcgtctatt tatgtaggat gaaaggtagt   2640
ctagtacctc ctgtgatatt atcccattcc atgcggggta tcgtatgctt ccttcagcac   2700
taccctttag ctgttctata tgctgccact cctcaattgg attagtctca tccttcaatg   2760
ctatcatttc ctttgatatt ggatcatatg catagtaccg agaaactagt gcgaagtagt   2820
gatcaggtat tgctgttatc tgatgagtat acgttgtcct ggccacggca gaagcacgct   2880
tatcgctcca atttcccaca acattagtca actccgttag gcccttcatt gaaagaaatg   2940
aggtcatcaa atgtcttcca atgtgagatt ttgggccatt ttttatagca aagattgaat   3000
aaggcgcatt tttcttcaaa gctttattgt acgatctgac taagttatct tttaataatt   3060
ggtattcctg tttattgctt gaagaattgc cggtcctatt tactcgtttt aggactggtt   3120
cagaattcct caaaaattca tccaaatata caagtggatc gatcctaccc cttgcgctaa   3180
agaagtatat gtgcctacta acgcttgtct ttgtctctgt cactaaacac tggattatta   3240
ctcccaaata cttattttgg actaatttaa atgatttcgg atcaacgttc ttaatatcgc   3300
tgaatcttcc acaattgatg aaagtagcta ggaagaggaa ttggtataaa gtttttgttt   3360
ttgtaaatct cgaagtatac tcaaacgaat ttagtatttt ctcagtgatc tcccagatgc   3420
tttcaccctc acttagaagt gctttaagca ttttttttact gtggctattt cccttatctg   3480
cttcttccga tgattcgaac tgtaattgca aactacttac aatatcagtg atatcagatt   3540
gatgtttttg tccatagtaa ggaataattg taaattccca agcaggaatc aatttcttta   3600
atgaggcttc caaaattgtt gctttttgcg tcttgtattt aaactggagt gatttattga   3660
caatatcgaa actcaacgaa ttgcttatga tagtattata gctcatgaat gtggctctct   3720
tgattgctgt tccgttatgt gtaatcatcc aacataaata ggttagttca gcagcacata   3780
atgctatttt ctcacctgaa ggtctttcaa acctttccac aaactgacga acaagcacct   3840
taggtggtgt tttacataat atatcaaatt gtggcatgtc gacgattatt agttaaacca   3900
ctgcaaaaag ttggggaaaa ttttgcccat ttttataccg tgtcttcgtc tatcgcctcc   3960
cccactcccc aatctttgaa ttattccgaa atattcagcg aacggggtgt acacaaaaac   4020
taacattctc aactgcataa tttgaaaaat ggcgtgggac aagaaaaaaa aaaaattctc   4080
aaccatagca atcatggaat acggtaaatt tgtgttgttc ggtgactcca tcacccagtt   4140
tagttgtacc cagtatggct ttcatccagc attacagaat gtgtatatcc gaaaattgga   4200
tgttattaac cgtggtttca gtggctacaa ctcagagcac gctagacaaa ttcttccaaa   4260
aattttagag tcggaaacca atatcaaatt gatgacaata ttttttggaa ctaacgatgc   4320
atacgactac atcaatgaaa tccagacagt cgagttagac agatataaag ataatttaag   4380
tgtaatggta cagatggtac tagacaaaaa tatcaaacca atcattattg gatccgaagt   4440
tcctattctc tagaaagtat aggaacttcc tcgagttgtt gtatatccaa ggtgccaaga   4500
```

```
gaatccttag tccacaggca tgggtgccaa tttttgaatc cgacaagcca aaggataaga   4560

gatcaatcaa ggacgaggac tatgtcgaat ggagagccaa ggttgccaag attcctttcg   4620

acacctacgg ctcaccttat ggttcggcac atcaaatgtc ttcttgccgt atgtcaggta   4680

agggtcctaa atacggtgct gttgacaccg atggtagatt gtttgaatgt tcgaatgttt   4740

atgttgccga tgcaa                                                    4755
```

<210> SEQ ID NO 22
<211> LENGTH: 4158
<212> TYPE: DNA
<213> ORGANISM: Candida tropicalis

<400> SEQUENCE: 22

```
tctcaccaag tacgagaacg agcttgttga tagagcttag acttgtcttt tgtatttgta     60

atctgacgtt gaccgtttga gtttttcctg tgatatcacg taaatctggc aaccagcttt    120

ctattttttt tgcaacactt tttctcttca ccactctcag aaccaatgcc accgaagaag    180

ggtctcaacc aggaggaaaa gctctcgtca atcctcgcct ggttccaaag cagccactgc    240

ttctatacgc tcaaagaggt tgaacagaag gctagcaaag cgtgcaagat ctcgtctatg    300

cagatcaagg acttggttgc aaccttagtc aacgaaggtt tagtggaaca ggaaaaatgt    360

gggaccacca acttgtactg gtcgttcccg tactcggaac acaaacgcaa gctacagaga    420

tacgagcagc taagacaatc cgttgccaaa cttcaagcga ataaaggcaa gttggcggaa    480

gagttgcgaa acgcgtgtgg tgagcgtgac atggacagca ataggctaaa ccggatgcaa    540

cagtgcgatc agcttgttca cgaggcggca cgcctccagg aggaactaaa actgtcgagg    600

cagagagata ccattgacga gttggttcag gccattgact tcttcaacga gctgatagag    660

accgtcctca gctacatcag ccatcagtcg gggaccagcg tgtcggtatt gaaaacggag    720

tttgagatac ccgcagaact agaagaggct ccccagataa acaatgccgg agttagtgcg    780

taaatcgagc atgcatacgt tggagagaaa tagagaaaca gatttccggt gaaacgctac    840

aacacagacg aggaatacag aatggaacat gacggaaata taatatccga ggaaagacga    900

aagtacgaca tggaactccg ttactgcaac atcgatcgtg ctagatacga catagaacaa    960

tgttgctatt acatggaaag ctgttgctac aatccagaat acggttgtac tcaagggaga   1020

tgaggctggg agccgagtgg tacataaata ggcatatagg accgtcactt ggtctaggat   1080

cgtgtagagg gtggaagagg taggcaagat ccattctaat ctactgagtg acggctaata   1140

tacgatcagc gttctcaggc gagcacagtc attcctcatt tctgtacata cgttgcccct   1200

ttatgttttt tttcacagga tgctcacgcc caacatttcc ccccacattt tattacccac   1260

attgagccgt caaatgcatt ttttttatcc gtcgcttgct aagacaaaat tccacatgct   1320

ttgtctcaga gtatataaac aacggggcaa aaaaacatgg ggttaatagc ttattcgtgg   1380

attgatattt ttatatttta gttcgcccct ttcgccacca agctcaattg gactatttgt   1440

cagtggtgta taagctagag attactagac tgcttttctg attcttgatt ttcccttttc   1500

attagttcca gtacctagag atgaatacct tcttgccaga cgtgctcgaa tacaaacacg   1560

tcgacaccct tttgttattg tgtgacggga tcatccacga aaccacagtc gatcagatca   1620

aggacgccat tgctcccgac ttccctgagg accagtacga ggagtatctc aagaccttca   1680

ccaagccatc tgagacccct gggttcagag aagccgtcta cgacacgatc aacgccaccc   1740

caaccgatgc cgtgcacatg tgtattgtct tgaccaccgc attggactcc agaatcttgg   1800

cccccacgtt gaccaactcg ttgacgccta tcaaggatat gaccttgaag gagcgtgaac   1860
```

```
aattgttggc ctcttggcgt gattccccga ttgcggcaaa gagaagattg ttcagattga   1920
tttcctcgct taccttgacg acgtttacga gattggccag cgaattgcac ttgaaagcca   1980
tccactaccc tggcagagac ttgcgtgaaa aggcgtatga aacccaggtg gttgaccctt   2040
tcaggtacct gtttatggag aaaccaaagt ttgacggcgc cgaattgtac ttgccagata   2100
tcgacgtcat catcattgga tcaggcgccg gtgctggtgt catggcccac actctcgcca   2160
acgacgggtt caagaccttg gttttggaaa agggaaagta tttcagcaac tccgagttga   2220
actttaatga cgctgatggc gtgaaagagt tgtaccaagg taaaggtgct ttggccacca   2280
ccaatcagca gatgtttatt cttgccggtt ccactttggg cggtggtacc actgtcaact   2340
ggtctgcttg ccttaaaaca ccatttaaag tgcgtaagga gtggtacgac gagtttggtc   2400
ttgaatttgc tgccgatgaa gcctacgaca aagcgcagga ttatgtttgg aaacaaatgg   2460
gtgcttcaac agatggaatc actcactcct tggccaacga agttgtggtt gaaggaggta   2520
agaagttggg ctacaagagc aaggaaattg agcagaacaa cggtggccac cctgaccacc   2580
catgtggttt ctgttacttg ggctgtaagt acggtattaa acagggttct gtgaataact   2640
ggtttagaga cgcagctgcc cacgggtcca agttcatgca acaagtcaga gttgtgcaaa   2700
tcctcaacaa gaatggcgtc gcttatggta tcttgtgtga ggatgtcgaa accggagtca   2760
ggttcactat tagtggcccc aaaaagtttg ttgtttctgc tggttctttg aacacgccaa   2820
ctgtgttgac caactccgga ttcaagaaca agcacattgg taagaacttg acgttgcacc   2880
cagtttccac cgtgtttggt gactttggca gagacgtgca agccgaccat ttccacaaat   2940
ctattatgac ttcgctttgt tacgaggttg ctgacttgga cggcaagggc cacggatgca   3000
gaatcgaaac catcttgaac gctccattca tccaagcttc tttgttgcca tggagaggaa   3060
gtgacgaggt cagaagagac ttgttgcgtt acaacaacat ggtggccatg ttgcttatca   3120
cgcgtgatac caccagtggt tcagtttctg ctgacccaaa gaagcccgac gctttgattg   3180
tcgactatga gattaacaag tttgacaaga atgccatctt gcaagctttc ttgatcactt   3240
ccgacatgtt gtacattgaa ggtgccaaga gaatcctcag tccacagcca tgggtgccaa   3300
tctttgagtc gaacaagcca aaggagcaaa gaacgatcaa ggacaaggac tatgttgagt   3360
ggagagccaa ggctgctaag atacctttcg acacctacgg ttctgcatat gggtccgcac   3420
atcaaatgtc cacctgtcgt atgtccggaa agggtcctaa atacggtgct gttgatactg   3480
atggtagatt gtttgaatgt tcgaatgtct atgttgctga tgctagtgtt ttgcctactg   3540
ccagcggtgc caacccaatg atatccacca tgacctttgc tagacagatt gcgttaggtt   3600
tggctgactc cttgaagacc aaacccaagt tgtagagaga cggaaatacg acacttatat   3660
actagatgta tcttacaatt tatattctcg atgatggctt ttactatctc ctatgttaca   3720
ctataatgac atcaccacaa cctctactac tgtctccagt atcctccttg ctgttgaccg   3780
tacccaccag cctgttgatt gaaccctgtg aactgtggtt gctgttgagc gtaccccacg   3840
ttagtgaact gcggttgttg ggcaaactgc tgtacgggct gttgctgctg ctgctgttgt   3900
tgttgttgtt gttgtcccgt gggctggttg tacaacgaca tgatgttctg cttgtttgtc   3960
tgttgggcaa ccaactgtgg gttattcatc tgcatcaact gctgctggtg ttgagggttg   4020
tttggatcca agtactcttg cccgttggcg tcgatataag aaatctgccc cgtgactggg   4080
tcagtgtact ggtatatctg tggcatgcca ccagcttgtg caggcatgcc ggttgccaat   4140
ggcacctgtg cttgcgtc                                                 4158
```

<210> SEQ ID NO 23
<211> LENGTH: 643
<212> TYPE: DNA
<213> ORGANISM: Artificial Sequence
<220> FEATURE:
<223> OTHER INFORMATION: Pre-targeting construct for Candida tropicalis FAO2A

<400> SEQUENCE: 23

```
cgtctcatga ataccttctt gccagacgtg ctcgaataca aacacgtcga caccctttttg     60
ttattgtgtg acgggatcat ccacgaaacc acagtcgatc agatcaagga cgccattgct    120
cccgacttcc ctgaggacca gtacgaggag tatctcaaga ccttcaccaa gccatctgag    180
acccctgggt tcagagaagc cgtctacgac acgatcaacg ccaccccaac cgatgccgtg    240
cacatgtgta ttgtcttgac caccgcattg gactccagaa tcttggcccc cacgttgacc    300
aactaggcgg ccgctagatc ttgcgaagct ccatctcgag aaggacaagg actatgttga    360
gtggagagcc aaggctgcta agataccttt cgacacctac ggttctgcat atgggtccgc    420
acatcaaatg tccacctgtc gtatgtccgg aaagggtcct aaatacggtg ctgttgatac    480
tgatggtaga ttgtttgaat gttcgaatgt ctatgttgct gatgctagtg ttttgcctac    540
tgccagcggt gccaacccaa tgatatccac catgaccttt gctagacaga ttgcgttagg    600
tttggctgac tccttgaaga ccaaacccaa gttgtaggag acg                      643
```

<210> SEQ ID NO 24
<211> LENGTH: 4795
<212> TYPE: DNA
<213> ORGANISM: Artificial Sequence
<220> FEATURE:
<223> OTHER INFORMATION: Targeting construct for deletion of Candida tropicalis FAO2A

<400> SEQUENCE: 24

```
cgtctcatga ataccttctt gccagacgtg ctcgaataca aacacgtcga caccctttttg     60
ttattgtgtg acgggatcat ccacgaaacc acagtcgatc agatcaagga cgccattgct    120
cccgacttcc ctgaggacca gtacgaggag tatctcaaga ccttcaccaa gccatctgag    180
acccctgggt tcagagaagc cgtctacgac acgatcaacg ccaccccaac cgatgccgtg    240
cacatgtgta ttgtcttgac caccgcattg gactccagaa tcttggcccc cacgttgacc    300
aactaggcgg ccgctctaga actagtggat ctgaagttcc tattctctag aaagtatagg    360
aacttcctgc aggaccacct ttgattgtaa atagtaataa ttaccaccct tatctaatta    420
tttatttaac ttatttattt atttattata catatataca aatctaataa agtgaaaatc    480
tccccccttca cacttcacat atgttaggcg tcatcctgtg ctcccgagaa ccagtaccag    540
tacatcgctg tttcgttcga gacttgaggt ctagttttat acgtgaagag gtcaatgccg    600
ccgagagtaa agccacattt tgcgtacaaa ttgcaggcag gtacattgtt cgtttgtgtc    660
tctaatcgta tgccaaggag ctgtctgctt agtgcccact tttcgcaaa ttcgatgaga    720
ctgtgcgcga ctcctttgcc tcggtgcgtg tgcgacacaa caatgtgttc gatagaggct    780
agatcgttcc atgttgagtt gagttcaatc ttcccgacaa gctcttggtc gatgaatgcg    840
ccatagcaag cagagtcttc atcagagtca tcatccgaga tgtaatcctt ccggtagggg    900
ctcacacttc tggtagatag ttcaaagcct tggtcggata ggtgcacatc gaacacttca    960
cgaacaatga aatggttctc agcatccaat gtttccgcca cctgctcagg gatcaccgaa   1020
attttcatat gagaaccgtt atcgataact aaagcagcaa cttcttctat aaaaatgggt   1080
tagtatgaca gtcatttaaa taaggaattt ttcagttggc ttggtttcaa ttcaatgttc   1140
```

```
gttttttttt tttcttgctg tgtttgtgtt tgtgttgttt atagttgtgt gcactgagcg   1200
tcgaaaaaaa aaattcatag tgagccggga aatctgtata gcccagataa caacacaagt   1260
ccaaactaga aactcgtcaa acaccaaaag caatgttgaa tcaattgcct tgcacaagta   1320
cacgtaggaa aacataaaac attgcaattt tgaatattga gccttttgtc gtaacattga   1380
ttgataggat tactcaccga atggttttga aaccactgcc gacagatcaa tcaatcaatc   1440
aaaaaacgtg aactttgaaa aaggggaaga acagatacat tgaagttagc catttccatt   1500
gatcgtcaca acatatctga taaattactt tcaaaattat aagctgatgt gtgtgtatta   1560
ttaatgtgac agtaacatcc caaacgagaa atattatgtc gacaacaaaa aagtttgatc   1620
tgaattgaaa atgaagtttt cccaccctac ccatttgtca tattgaaacc aatcaactga   1680
ttaatcaatc aattagaatt gaagctaaac taaaacatac caccgtccat tttgaatgat   1740
tatatttttt taatattaat atcgagataa tgtttctaag aaagaaagaa aaccaggagt   1800
gaaaattaga aaaggaaagg aaaggaaaaa aagaaaaatc tgaaaatata taaaaaaaaa   1860
ttgtttcgtt ggcaataaat cttggtgaga acagcgaccg aaagcaaata agaacaaaat   1920
atgagtgtat tacgttgaac aactaattaa cgtgtgtgta tggatctttt tttctttttt   1980
ctctttaacc gactataaac aacaaacatt tttgggcagt gcacacacta cttaatatac   2040
acagcataaa ttacacgatt agaaacaaat tagcttatta aaataaccta atcaaaccga   2100
atattttatg gtattatgag taaactatat aatataaata gcacacaccc acaacaacaa   2160
caaaggaaaa ctaaaaggtt ttttcttttt gaaaagatcg ttttctttat tattctctag   2220
ttttgacgct cgacatttta tgatggaatg aatgggatga atcatcaaac aagagaaaat   2280
acccgtgacg aaaataataa aataagttcc tctgatacag aagatgaaaa caacaacaac   2340
aagatataga aatgccttgg gtggctattt tatagtctta actttttaat gtatatttgt   2400
tttgtttttt tacataataa tactttataa aagctaagct aaattcaagt aaaatttcaa   2460
tctctcaaat aaaacatttt tctcttttc ttaaatttag ttttatatat ttataaaata   2520
tacaaagatt tttttaaaaa agtaacaagt tatatatgta ataacaaaaa gaagaataac   2580
aagaatacaa aaccagattt ccagatttcc agaatttcac tcttatatgc gtctatttat   2640
gtaggatgaa aggtagtcta gtacctcctg tgatattatc ccattccatg cggggtatcg   2700
tatgcttcct tcagcactac cctttagctg ttctatatgc tgccactcct caattggatt   2760
agtctcatcc ttcaatgcta tcatttcctt tgatattgga tcatatgcat agtaccgaga   2820
aactagtgcg aagtagtgat caggtattgc tgttatctga tgagtatacg ttgtcctggc   2880
cacggcagaa gcacgcttat cgctccaatt tcccacaaca ttagtcaact ccgttaggcc   2940
cttcattgaa agaaatgagg tcatcaaatg tcttccaatg tgagattttg ggccattttt   3000
tatagcaaag attgaataag gcgcattttt cttcaaagct ttattgtacg atctgactaa   3060
gttatctttt aataattggt attcctgttt attgcttgaa gaattgccgg tcctatttac   3120
tcgttttagg actggttcag aattcctcaa aaattcatcc aaatatacaa gtggatcgat   3180
cctacccctt gcgctaaaga agtatatgtg cctactaacg cttgtctttg tctctgtcac   3240
taaacactgg attattactc ccaaatactt attttggact aatttaaatg atttcggatc   3300
aacgttctta atatcgctga atcttccaca attgatgaaa gtagctagga agaggaattg   3360
gtataaagtt tttgtttttg taaatctcga agtatactca aacgaattta gtattttctc   3420
agtgatctcc cagatgcttt caccctcact tagaagtgct ttaagcattt ttttactgtg   3480
gctatttccc ttatctgctt cttccgatga ttcgaactgt aattgcaaac tacttacaat   3540
```

```
atcagtgata tcagattgat gtttttgtcc atagtaagga ataattgtaa attcccaagc   3600
aggaatcaat ttctttaatg aggcttccaa aattgttgct ttttgcgtct tgtatttaaa   3660
ctggagtgat ttattgacaa tatcgaaact caacgaattg cttatgatag tattatagct   3720
catgaatgtg gctctcttga ttgctgttcc gttatgtgta atcatccaac ataaataggt   3780
tagttcagca gcacataatg ctattttctc acctgaaggt ctttcaaacc tttccacaaa   3840
ctgacgaaca agcaccttag gtggtgtttt acataatata tcaaattgtg gcatgtcgac   3900
gattattagt taaaccactg caaaaagttg ggaaaaattt tgcccatttt tataccgtgt   3960
cttcgtctat cgcctccccc actccccaat ctttgaatta ttccgaaata ttcagcgaac   4020
ggggtgtaca caaaaactaa cattctcaac tgcataattt gaaaaatggc gtgggacaag   4080
aaaaaaaaaa aattctcaac catagcaatc atggaatacg gtaaatttgt gttgttcggt   4140
gactccatca cccagtttag ttgtacccag tatggctttc atccagcatt acagaatgtg   4200
tatatccgaa aattggatgt tattaaccgt ggtttcagtg gctacaactc agagcacgct   4260
agacaaattc ttccaaaaat tttagagtcg gaaaccaata tcaaattgat gacaatattt   4320
tttggaacta acgatgcata cgactacatc aatgaaatcc agacagtcga gttagacaga   4380
tataaagata atttaagtgt aatggtacag atggtactag acaaaaatat caaaccaatc   4440
attattggat ccgaagttcc tattctctag aaagtatagg aacttcctcg agaaggacaa   4500
ggactatgtt gagtggagag ccaaggctgc taagatacct ttcgacacct acggttctgc   4560
atatgggtcc gcacatcaaa tgtccacctg tcgtatgtcc ggaaagggtc ctaaatacgg   4620
tgctgttgat actgatggta gattgtttga atgttcgaat gtctatgttg ctgatgctag   4680
tgttttgcct actgccagcg gtgccaaccc aatgatatcc accatgacct ttgctagaca   4740
gattgcgtta ggtttggctg actccttgaa gaccaaaccc aagttgtagg agacg         4795
```

<210> SEQ ID NO 25
<211> LENGTH: 3753
<212> TYPE: DNA
<213> ORGANISM: Candida tropicalis

<400> SEQUENCE: 25

```
tgttgataga gcttagactt gtgttttgta tttgtaatct gacgttgatc gtttgatatt     60
ttcctgtgat atcacgtaaa ttcggcaacc aactttttac tttttgcaac actttctctt    120
caccactctc agaaccaatg ccaccgaaga agggtctcag ccaggaggaa aagctctcgg    180
cactcctcac ctggttccaa gccagtcatt gcttctacac actcaaggag gttgaacaga    240
aggcgagcaa agcgtgcaag atctcgtcta tgcagatcaa ggacttggtt gcaagcttag    300
tcaacgaagg tttggtagaa caggaaaagt gtgggaccac aaacttgtac tggtcgttcc    360
agtactcgga attcaaacgg aagctacaga gatacgggca gctaagacaa tcagccgcca    420
aacttcaagc ggataaaggc aagttggcgg aagagttgcg aaacgcatgt ggtgaacggg    480
acatggacaa caataggcaa gaccggatgc aacaatacga tcaccttgtt aacgaggcgg    540
cacgtctcca ggaggaacta aaactgtcaa ggcagataga taccattgac gagttagttc    600
aggccattga tttcttcaac gagctgatag agaccgtcct cagctacatc agccatcagt    660
cagggaccag cgtgtcgata ttgaaaacgg agtttgagat acccgcagaa ctagaagagg    720
ccccccagat aagcaatgcc ggagttagtg cgtaaatcga gcaggcatac attgcccctt    780
tgtatttttt cacaggatgc tcaccccacc acgcccaaca tttcccccca cattttatta    840
cccacattga gccgtcaaat gcattttttt atccgtcgct agctaaacca aaattccaca    900
```

```
tgcgttgcct cagagtatat aaacaacggg gcaaaaaaca tgggattaat agcttatttg    960
tggattgata tttttatatt ttagttcgcc ccttctacga ccaagctcaa ttggactatt   1020
tgtcagtggt gtataagcta gagattacta gactgctttt ctgattcttg atcatcccct   1080
tagttccagt gcctagagat gaataccttc ttgccagacg tgctcgaata caaacacgtc   1140
gataccctt tgttattatg tgacgggatc atccacgaaa ccacagtcga ccagatcagg    1200
gacgccattg ctcccgactt ccctgaagac cagtacgagg agtatctcaa gaccttcacc   1260
aagccatctg agacccctgg gttcagagaa gccgtctacg acacgatcaa cagcacccca   1320
accgaggctg tgcacatgtg tattgtattg accaccgcat tggactcgag aatcttggcc   1380
cccacgttga ccaactcgtt gacgcctatc aaggatatga ccttgaaaga gcgtgaacaa   1440
ttgttggctg cctggcgtga ttccccgatc gcggccaaga gaagattgtt cagattgatt   1500
tcctcactta ccttgacgac ctttacgaga ttggccagcg acttgcactt gagagccatc   1560
cactaccctg gcagagactt gcgtgaaaag gcatatgaaa cccaggtggt tgaccctttc   1620
aggtacctgt ttatggaaaa accaaagttt gacggcaccg agttgtactt gccagatatc   1680
gacgtcatca tcattggatc cggtgccggt gctggtgtca tggcccacac tttagccaac   1740
gacgggtaca agaccttggt tttggaaaag ggaaagtatt tcagcaactc cgagttgaac   1800
tttaatgatg ccgatggtat gaaagagttg taccaaggta aatgtgcgtt gaccaccacg   1860
aaccagcaga tgtttattct tgccggttcc actttgggcg gtggtaccac tgttaactgg   1920
tctgcttgtc ttaaaacacc atttaaagtg cgtaaggagt ggtacgacga gtttggtctt   1980
gaatttgctg ccgacgaagc ctacgacaaa gcacaagact atgtttggaa acaaatgggc   2040
gcttctaccg aaggaatcac tcactctttg gcgaacgcgg ttgtggttga aggaggtaag   2100
aagttgggtt acaagagcaa ggaaatcgag cagaacaatg gtggccatcc tgaccacccc   2160
tgtggtttct gttacttggg ctgtaagtac ggtattaagc agggttctgt gaataactgg   2220
tttagagacg cagctgccca cgggtccaag ttcatgcaac aagtcagagt tgtgcaaatc   2280
ctccacaata aaggcgtcgc ttatggcatc ttgtgtgagg atgtcgagac cggagtcaaa   2340
ttcactatca gtggccccaa aaagtttgtt gtttctgcag gttctttgaa cacgccaacg   2400
gtgttgacca actccggatt caagaacaaa cacatcggta agaacttgac gttgcaccca   2460
gtttcgaccg tgtttggtga ctttggcaga gacgtgcaag ccgaccattt ccacaaatct   2520
attatgactt cgctctgtta cgaagtcgct gacttggacg gcaagggcca cggatgcaga   2580
atcgagacca tcttgaacgc tccattcatc caagcttctt tgttgccatg gagaggaagc   2640
gacgaggtca gaagagactt gttgcgttac aacaacatgg tggccatgtt gcttatcacc   2700
cgtgacacca ccagtggttc agtttctgct gacccaaaga agcccgacgc tttgattgtc   2760
gactatgaca tcaacaagtt tgacaagaat gccatcttgc aagctttctt gatcacctcc   2820
gacatgttgt acatcgaagg tgccaagaga atcctcagtc cacaggcatg ggtgccaatc   2880
tttgagtcga acaagccaaa ggagcaaaga acaatcaagg acaaggacta tgtcgaatgg   2940
agagccaagg ctgccaagat acctttcgac acctacggtt ctgcctatgg gtccgcacat   3000
caaatgtcca cctgtcgtat gtccggaaag ggtcctaaat acggcgccgt tgataccgat   3060
ggtagattgt ttgaatgttc gaatgtctat gttgctgatg ctagtgtttt gcctactgcc   3120
agcggtgcca acccaatgat ctccaccatg acgtttgcta gacagattgc gttaggtttg   3180
gctgactctt tgaagaccaa acccaagttg tagagagaga cagaaatacg acacttatat   3240
actagatgta tcttacaatt tatattttcg atgatggctt ttactatctc ctatgttaca   3300
```

ctataatgac atcaccacat cttctactac tgtctccagt atcctccttg ctgttgaccg 3360
tatccaccag cctgttggtt gaaccccgtg aactgtggtt gctgttgagc gtaccccacg 3420
ttagtgaact gcggttgttg ggtaaactgc tgtacgggct gttgttgctg ttgctgttgt 3480
tgctgttgtt gctgttgttg ctgttgttgc tgttgttgtt gttgtcccgt tggctggttg 3540
tacaacgaca tgatgttctg cttgtttgtc tgctgggcaa ccaactgtgg gttattcatc 3600
tgcatcaact gctgctggtg ctgagggttg tttggatcca agtactcctg cccgttggcg 3660
tcgatataag aaatctgccc cgtgactggg tcagtgtact ggtatatctg tggcatgcca 3720
cccgcttgtg caggcatgcc ggttgccaat ggc 3753

<210> SEQ ID NO 26
<211> LENGTH: 616
<212> TYPE: DNA
<213> ORGANISM: Artificial Sequence
<220> FEATURE:
<223> OTHER INFORMATION: Pre-targeting construct for Candida tropicalis FAO2B

<400> SEQUENCE: 26
cgtctcatga ataccttctt gccagacgtg ctcgaataca aacacgtcga taccctttg 60 ttattatgtg acgggatcat ccacgaaacc acagtcgacc agatcaggga cgccattgct 120
cccgacttcc ctgaagacca gtacgaggag tatctcaaga ccttcaccaa gccatctgag 180
acccctgggt tcagagaagc cgtctacgac acgatcaaca gcaccccaac cgaggctgtg 240
cacatgtgta ttgtattgac caccgcattg gactcgtagg cggccgctag atcttgcgaa 300
gctccatctc gagaaggaca aggactatgt cgaatggaga gccaaggctg ccaagatacc 360
tttcgacacc tacggttctg cctatgggtc cgcacatcaa atgtccacct gtcgtatgtc 420
cggaaagggt cctaaatacg gcgccgttga taccgatggt agattgtttg aatgttcgaa 480
tgtctatgtt gctgatgcta gtgttttgcc tactgccagc ggtgccaacc caatgatctc 540
caccatgacg tttgctagac agattgcgtt aggtttggct gactctttga agaccaaacc 600
caagttgtag gagacg 616

<210> SEQ ID NO 27
<211> LENGTH: 4768
<212> TYPE: DNA
<213> ORGANISM: Artificial Sequence
<220> FEATURE:
<223> OTHER INFORMATION: Targeting construct for deletion of Candida tropicalis FAO2B

<400> SEQUENCE: 27
cgtctcatga ataccttctt gccagacgtg ctcgaataca aacacgtcga taccctttg 60 ttattatgtg acgggatcat ccacgaaacc acagtcgacc agatcaggga cgccattgct 120
cccgacttcc ctgaagacca gtacgaggag tatctcaaga ccttcaccaa gccatctgag 180
acccctgggt tcagagaagc cgtctacgac acgatcaaca gcaccccaac cgaggctgtg 240
cacatgtgta ttgtattgac caccgcattg gactcgtagg cggccgctct agaactagtg 300
gatctgaagt tcctattctc tagaaagtat aggaacttcc tgcaggacca cctttgattg 360
taaatagtaa taattaccac ccttatctaa ttatttattt aacttattta tttatttatt 420
atacatatat acaaatctaa taaagtgaaa atctccccct tcacacttca catatgttag 480
gcgtcatcct gtgctcccga gaaccagtac cagtacatcg ctgtttcgtt cgagacttga 540
ggtctagttt tatacgtgaa gaggtcaatg ccgccgagag taaagccaca ttttgcgtac 600

```
aaattgcagg caggtacatt gttcgtttgt gtctctaatc gtatgccaag gagctgtctg    660
cttagtgccc actttttcgc aaattcgatg agactgtgcg cgactccttt gcctcggtgc    720
gtgtgcgaca caacaatgtg ttcgatagag gctagatcgt tccatgttga gttgagttca    780
atcttcccga caagctcttg gtcgatgaat gcgccatagc aagcagagtc ttcatcagag    840
tcatcatccg agatgtaatc cttccggtag gggctcacac ttctggtaga tagttcaaag    900
ccttggtcgg ataggtgcac atcgaacact tcacgaacaa tgaaatggtt ctcagcatcc    960
aatgtttccg ccacctgctc agggatcacc gaaattttca tatgagaacc gttatcgata   1020
actaaagcag caacttcttc tataaaaatg ggttagtatg acagtcattt aaataaggaa   1080
tttttcagtt ggcttggttt caattcaatg ttcgtttttt ttttttcttg ctgtgtttgt   1140
gtttgtgttg tttatagttg tgtgcactga gcgtcgaaaa aaaaaattca tagtgagccg   1200
ggaaatctgt atagcccaga taacaacaca agtccaaact agaaactcgt caaacaccaa   1260
aagcaatgtt gaatcaattg ccttgcacaa gtacacgtag gaaaacataa aacattgcaa   1320
ttttgaatat tgagcctttt gtcgtaacat tgattgatag gattactcac cgaatggttt   1380
tgaaaccact gccgacagat caatcaatca atcaaaaaac gtgaactttg aaaaagggga   1440
agaacagata cattgaagtt agccatttcc attgatcgtc acaacatatc tgataaatta   1500
ctttcaaaat tataagctga tgtgtgtgta ttattaatgt gacagtaaca tcccaaacga   1560
gaaatattat gtcgacaaca aaaaagtttg atctgaattg aaaatgaagt tttcccaccc   1620
tacccatttg tcatattgaa accaatcaac tgattaatca atcaattaga attgaagcta   1680
aactaaaaca taccaccgtc cattttgaat gattatattt ttttaatatt aatatcgaga   1740
taatgtttct aagaaagaaa gaaaaccagg agtgaaaatt agaaaaggaa aggaaaggaa   1800
aaaaagaaaa atctgaaaat atataaaaaa aaattgtttc gttggcaata aatcttggtg   1860
agaacagcga ccgaaagcaa ataagaacaa aatatgagtg tattacgttg aacaactaat   1920
taacgtgtgt gtatggatct tttttttctt tttctcttta accgactata aacaacaaac   1980
atttttgggc agtgcacaca ctacttaata tacacagcat aaattacacg attagaaaca   2040
aattagctta ttaaaataac ctaatcaaac cgaatatttt atggtattat gagtaaacta   2100
tataatataa atagcacaca cccacaacaa caacaaagga aaactaaaag gtttttttctt   2160
tttgaaaaga tcgttttctt tattattctc tagttttgac gctcgacatt ttatgatgga   2220
atgaatggga tgaatcatca aacaagagaa aatacccgtg acgaaaataa taaaataagt   2280
tcctctgata cagaagatga aaacaacaac aacaagatat agaaatgcct tgggtggcta   2340
ttttatagtc ttaacttttt aatgtatatt tgttttgttt ttttacataa taatacttta   2400
taaaagctaa gctaaattca agtaaaattt caatctctca aataaaacat ttttctcttt   2460
ttcttaaatt tagttttata tatttataaa atatacaaag attttttttaa aaaagtaaca   2520
agttatatat gtaataacaa aaagaagaat aacaagaata caaaaccaga tttccagatt   2580
tccagaattt cactcttata tgcgtctatt tatgtaggat gaaaggtagt ctagtacctc   2640
ctgtgatatt atcccattcc atgcggggta tcgtatgctt ccttcagcac taccctttag   2700
ctgttctata tgctgccact cctcaattgg attagtctca tccttcaatg ctatcatttc   2760
ctttgatatt ggatcatatg catagtaccg agaaactagt gcgaagtagt gatcaggtat   2820
tgctgttatc tgatgagtat acgttgtcct ggccacggca gaagcacgct tatcgctcca   2880
atttcccaca acattagtca actccgttag gcccttcatt gaaagaaatg aggtcatcaa   2940
atgtcttcca atgtgagatt ttgggccatt ttttatagca aagattgaat aaggcgcatt   3000
```

```
tttcttcaaa gctttattgt acgatctgac taagttatct tttaataatt ggtattcctg   3060

tttattgctt gaagaattgc cggtcctatt tactcgtttt aggactggtt cagaattcct   3120

caaaaattca tccaaatata caagtggatc gatcctaccc cttgcgctaa agaagtatat   3180

gtgcctacta acgcttgtct ttgtctctgt cactaaacac tggattatta ctcccaaata   3240

cttattttgg actaatttaa atgatttcgg atcaacgttc ttaatatcgc tgaatcttcc   3300

acaattgatg aaagtagcta ggaagaggaa ttggtataaa gtttttgttt ttgtaaatct   3360

cgaagtatac tcaaacgaat ttagtatttt ctcagtgatc tcccagatgc tttcaccctc   3420

acttagaagt gctttaagca ttttttttact gtggctattt cccttatctg cttcttccga   3480

tgattcgaac tgtaattgca aactacttac aatatcagtg atatcagatt gatgtttttg   3540

tccatagtaa ggaataattg taaattccca agcaggaatc aatttcttta atgaggcttc   3600

caaaattgtt gctttttgcg tcttgtattt aaactggagt gatttattga caatatcgaa   3660

actcaacgaa ttgcttatga tagtattata gctcatgaat gtggctctct tgattgctgt   3720

tccgttatgt gtaatcatcc aacataaata ggttagttca gcagcacata atgctatttt   3780

ctcacctgaa ggtctttcaa acctttccac aaactgacga acaagcacct taggtggtgt   3840

tttacataat atatcaaatt gtggcatgtc gacgattatt agttaaacca ctgcaaaaag   3900

ttggggaaaa ttttgcccat ttttataccg tgtcttcgtc tatcgcctcc cccactcccc   3960

aatctttgaa ttattccgaa atattcagcg aacggggtgt acacaaaaac taacattctc   4020

aactgcataa tttgaaaaat ggcgtgggac aagaaaaaaa aaaaattctc aaccatagca   4080

atcatggaat acggtaaatt tgtgttgttc ggtgactcca tcacccagtt tagttgtacc   4140

cagtatggct ttcatccagc attacagaat gtgtatatcc gaaaattgga tgttattaac   4200

cgtggtttca gtggctacaa ctcagagcac gctagacaaa ttcttccaaa aattttagag   4260

tcggaaacca atatcaaatt gatgacaata ttttttggaa ctaacgatgc atacgactac   4320

atcaatgaaa tccagacagt cgagttagac agatataaag ataatttaag tgtaatggta   4380

cagatggtac tagacaaaaa tatcaaacca atcattattg gatccgaagt tcctattctc   4440

tagaaagtat aggaacttcc tcgagaagga caaggactat gtcgaatgga gagccaaggc   4500

tgccaagata cctttcgaca cctacggttc tgcctatggg tccgcacatc aaatgtccac   4560

ctgtcgtatg tccggaaagg gtcctaaata cggcgccgtt gataccgatg gtagattgtt   4620

tgaatgttcg aatgtctatg ttgctgatgc tagtgttttg cctactgcca gcggtgccaa   4680

cccaatgatc tccaccatga cgtttgctag acagattgcg ttaggtttgg ctgactcttt   4740

gaagaccaaa cccaagttgt aggagacg                                       4768
```

<210> SEQ ID NO 28
<211> LENGTH: 4115
<212> TYPE: DNA
<213> ORGANISM: Candida tropicalis

<400> SEQUENCE: 28

```
catatgcgct aatcttcttt ttctttttat cacaggagaa actatcccac ccccacttcg     60

aaacacaatg acaactcctg cgtaacttgc aaattcttgt ctgactaatt gaaaactccg    120

gacgagtcag acctccagtc aaacggacag acagacaaac acttggtgcg atgttcatac    180

ctacagacat gtcaacgggt gttagacgac ggtttcttgc aaagacaggt gttggcatct    240

cgtacgatgg caactgcagg aggtgtcgac ttctccttta ggcaatagaa aaagactaag    300

agaacagcgt ttttacaggt tgcattggtt aatgtagtat ttttttagtc ccagcattct    360
```

```
gtgggttgct ctgggtttct agaataggaa atcacaggag aatgcaaatt cagatggaag    420
aacaaagaga taaaaaacaa aaaaaaactg agttttgcac caatagaatg tttgatgata    480
tcatccactc gctaaacgaa tcatgtgggt gatcttctct ttagttttgg tctatcataa    540
aacacatgaa agtgaaatcc aaatacacta cactccgggt attgtccttc gttttacaga    600
tgtctcattg tcttactttt gaggtcatag gagttgcctg tgagagatca cagagattat    660
cacactcaca tttatcgtag tttcctatct catgctgtgt gtctctggtt ggttcatgag    720
tttggattgt tgtacattaa aggaatcgct ggaaagcaaa gctaactaaa ttttctttgt    780
cacaggtaca ctaacctgta aaacttcact gccacgccag tctttcctga ttgggcaagt    840
gcacaaacta caacctgcaa aacagcactc cgcttgtcac aggttgtctc ctctcaacca    900
acaaaaaaat aagattaaac tttctttgct catgcatcaa tcggagttat ctctgaaaga    960
gttgcctttg tgtaatgtgt gccaaactca aactgcaaaa ctaaccacag aatgatttcc   1020
ctcacaatta tataaactca cccacatttc cacagaccgt aatttcatgt ctcactttct   1080
cttttgctct tcttttactt agtcaggttt gataacttcc ttttttatta ccctatctta   1140
tttatttatt tattcattta taccaaccaa ccaaccatgg ccacacaaga aatcatcgat   1200
tctgtacttc cgtacttgac caaatggtac actgtgatta ctgcagcagt attagtcttc   1260
cttatctcca caaacatcaa gaactacgtc aaggcaaaga aattgaaatg tgtcgatcca   1320
ccatacttga aggatgccgg tctcactggt attctgtctt tgatcgccgc catcaaggcc   1380
aagaacgacg gtagattggc taactttgcc gatgaagttt tcgacgagta cccaaaccac   1440
accttctact tgtctgttgc cggtgctttg aagattgtca tgactgttga cccagaaaac   1500
atcaaggctg tcttggccac ccaattcact gacttctcct tgggtaccag acacgcccac   1560
tttgctcctt tgttgggtga cggtatcttc accttggacg gagaaggttg gaagcactcc   1620
agagctatgt tgagaccaca gtttgctaga gaccagattg gacacgttaa agccttggaa   1680
ccacacatcc aaatcatggc taagcagatc aagttgaacc agggaaagac tttcgatatc   1740
caagaattgt tctttagatt taccgtcgac accgctactg agttcttgtt tggtgaatcc   1800
gttcactcct tgtacgatga aaaattgggc atcccaactc caaacgaaat cccaggaaga   1860
gaaaactttg ccgctgcttt caacgtttcc caacactact tggccaccag aagttactcc   1920
cagacttttt actttttgac caaccctaag gaattcagag actgtaacgc caaggtccac   1980
cacttggcca agtactttgt caacaaggcc ttgaacttta ctcctgaaga actcgaagag   2040
aaatccaagt ccggttacgt tttcttgtac gaattggtta agcaaaccag agatccaaag   2100
gtcttgcaag atcaattgtt gaacattatg gttgccggaa gagacaccac tgccggtttg   2160
ttgtcctttg ctttgtttga attggctaga cacccagaga tgtggtccaa gttgagagaa   2220
gaaatcgaag ttaactttgg tgttggtgaa gactcccgcg ttgaagaaat taccttcgaa   2280
gccttgaaga gatgtgaata cttgaaggct atccttaacg aaaccttgcg tatgtaccca   2340
tctgttcctg tcaactttag aaccgccacc agagacacca ctttgccaag aggtggtggt   2400
gctaacggta ccgacccaat ctacattcct aaaggctcca ctgttgctta cgttgtctac   2460
aagacccacc gtttggaaga atactacggt aaggacgcta acgacttcag accagaaaga   2520
tggtttgaac catctactaa gaagttgggc tgggcttatg ttccattcaa cggtggtcca   2580
agagtctgct tgggtcaaca attcgccttg actgaagctt cttatgtgat cactagattg   2640
gcccagatgt ttgaaactgt ctcatctgat ccaggtctcg aataccctcc accaaagtgt   2700
attcacttga ccatgagtca caacgatggt gtctttgtca agatgtaaag tagtcgatgc   2760
```

```
tgggtattcg attacatgtg tataggaaga ttttggtttt ttattcgttc ttttttttaa   2820

tttttgttaa attagtttag agatttcatt aatacataga tgggtgctat ttccgaaact   2880

ttacttctat cccctgtatc ccttattatc cctctcagtc acatgattgc tgtaattgtc   2940

gtgcaggaca caaactccct aacggactta aaccataaac aagctcagaa ccataagccg   3000

acatcactcc ttcttctctc ttctccaacc aatagcatgg acagacccac cctcctatcc   3060

gaatcgaaga cccttattga ctccataccc acctggaagc ccctcaagcc acacacgtca   3120

tccagcccac ccatcaccac atccctctac tcgacaacgt ccaaagacgg cgagttctgg   3180

tgtgcccgga aatcagccat cccggccaca tacaagcagc cgttgattgc gtgcatactc   3240

ggcgagccca caatgggagc cacgcattcg gaccatgaag caaagtacat tcacgagatc   3300

acgggtgttt cagtgtcgca gattgagaag ttcgacgatg gatggaagta cgatctcgtt   3360

gcggattacg acttcggtgg gttgttatct aaacgaagat tctatgagac gcagcatgtg   3420

tttcggttcg aggattgtgc gtacgtcatg agtgtgcctt ttgatggacc caaggaggaa   3480

ggttacgtgg ttgggacgta cagatccatt gaaaggttga gctggggtaa agacggggac   3540

gtggagtgga ccatggcgac gacgtcggat cctggtgggt ttatcccgca atggataact   3600

cgattgagca tccctggagc aatcgcaaaa gatgtgccta gtgtattaaa ctacatacag   3660

aaataaaaac gtgtcttgat tcattggttt ggttcttgtt gggttccgag ccaatatttc   3720

acatcatctc ctaaattctc caagaatccc aacgtagcgt agtccagcac gccctctgag   3780

atcttattta atatcgactt ctcaaccacc ggtggaatcc cgttcagacc attgttacct   3840

gtagtgtgtt tgctcttgtt cttgatgaca atgatgtatt tgtcacgata cctgaaataa   3900

taaaacatcc agtcattgag cttattactc gtgaacttat gaaagaactc attcaagccg   3960

ttcccaaaaa acccagaatt gaagatcttg ctcaactggt catgcaagta gtagatcgcc   4020

atgatctgat actttaccaa gctatcctct ccaagttctc ccacgtacgg caagtacggc   4080

aacgagctct ggaagctttg ttgtttgggg tcata                              4115
```

```
<210> SEQ ID NO 29
<211> LENGTH: 649
<212> TYPE: DNA
<213> ORGANISM: Artificial Sequence
<220> FEATURE:
<223> OTHER INFORMATION: Pre-targeting construct for Candida tropicalis
      CYP52A12

<400> SEQUENCE: 29
```

```
cgtctctcac aggttgtctc ctctcaacca acaaaaaaat aagattaaac tttctttgct     60

catgcatcaa tcggagttat ctctgaaaga gttgcctttg tgtaatgtgt gccaaactca    120

aactgcaaaa ctaaccacag aatgatttcc ctcacaatta tataaactca cccacatttc    180

cacagaccgt aatttcatgt ctcactttct cttttgctct tcttttactt agtcaggttt    240

gataacttcc ttttttatta ccctatctta tttatttatt tattcattta taccaaccaa    300

ccaacctagg cggccgctag atcttgcgaa gctccatctc gagagtagtc gatgctgggt    360

attcgattac atgtgtatag gaagattttg gtttttttatt cgttcttttt tttaattttt    420

gttaaattag tttagagatt tcattaatac atagatgggt gctatttccg aaactttact    480

tctatcccct gtatccctta ttatccctct cagtcacatg attgctgtaa ttgtcgtgca    540

ggacacaaac tccctaacgg acttaaacca taaacaagct cagaaccata agccgacatc    600

actccttctt ctctcttctc caaccaatag catggacaga cccgagacg                649
```

<210> SEQ ID NO 30
<211> LENGTH: 4801
<212> TYPE: DNA
<213> ORGANISM: Artificial Sequence
<220> FEATURE:
<223> OTHER INFORMATION: Targeting construct for deletion of Candida tropicalis CYP52A12

<400> SEQUENCE: 30

```
cgtctctcac aggttgtctc ctctcaacca acaaaaaaat aagattaaac tttctttgct     60
catgcatcaa tcggagttat ctctgaaaga gttgcctttg tgtaatgtgt gccaaactca    120
aactgcaaaa ctaaccacag aatgatttcc ctcacaatta tataaactca cccacatttc    180
cacagaccgt aatttcatgt ctcactttct cttttgctct tcttttactt agtcaggttt    240
gataacttcc ttttttatta ccctatctta tttatttatt tattcattta taccaaccaa    300
ccaacctagg cggccgctct agaactagtg gatctgaagt tcctattctc tagaaagtat    360
aggaacttcc tgcaggacca cctttgattg taaatagtaa taattaccac ccttatctaa    420
ttatttattt aacttattta tttatttatt atacatatat acaaatctaa taaagtgaaa    480
atctccccct tcacacttca catatgttag gcgtcatcct gtgctcccga gaaccagtac    540
cagtacatcg ctgtttcgtt cgagacttga ggtctagttt tatacgtgaa gaggtcaatg    600
ccgccgagag taaagccaca ttttgcgtac aaattgcagg caggtacatt gttcgtttgt    660
gtctctaatc gtatgccaag gagctgtctg cttagtgccc actttttcgc aaattcgatg    720
agactgtgcg cgactccttt gcctcggtgc gtgtgcgaca caacaatgtg ttcgatagag    780
gctagatcgt tccatgttga gttgagttca atcttcccga caagctcttg gtcgatgaat    840
gcgccatagc aagcagagtc ttcatcagag tcatcatccg agatgtaatc cttccggtag    900
gggctcacac ttctggtaga tagttcaaag ccttggtcgg ataggtgcac atcgaacact    960
tcacgaacaa tgaaatggtt ctcagcatcc aatgtttccg ccacctgctc agggatcacc   1020
gaaattttca tatgagaacc gttatcgata actaaagcag caacttcttc tataaaaatg   1080
ggttagtatg acagtcattt aaataaggaa tttttcagtt ggcttggttt caattcaatg   1140
ttcgtttttt tttttcttg ctgtgtttgt gtttgtgttg tttatagttg tgtgcactga    1200
gcgtcgaaaa aaaaaattca tagtgagccg ggaaatctgt atagcccaga taacaacaca   1260
agtccaaact agaaactcgt caaacaccaa aagcaatgtt gaatcaattg ccttgcacaa   1320
gtacacgtag gaaaacataa aacattgcaa ttttgaatat tgagcctttt gtcgtaacat   1380
tgattgatag gattactcac cgaatggttt tgaaaccact gccgacagat caatcaatca   1440
atcaaaaaac gtgaactttg aaaaagggga agaacagata cattgaagtt agccatttcc   1500
attgatcgtc acaacatatc tgataaatta ctttcaaaat tataagctga tgtgtgtgta   1560
ttattaatgt gacagtaaca tcccaaacga gaaatattat gtcgacaaca aaaaagtttg   1620
atctgaattg aaaatgaagt tttcccaccc tacccatttg tcatattgaa accaatcaac   1680
tgattaatca atcaattaga attgaagcta aactaaaaca taccaccgtc cattttgaat   1740
gattatattt ttttaatatt aatatcgaga taatgtttct aagaaagaaa gaaaaccagg   1800
agtgaaaatt agaaaaggaa aggaaaggaa aaaaagaaaa atctgaaaat atataaaaaa   1860
aaattgtttc gttggcaata aatcttggtg agaacagcga ccgaaagcaa ataagaacaa   1920
aatatgagtg tattacgttg aacaactaat taacgtgtgt gtatggatct tttttttcttt   1980
tttctcttta accgactata aacaacaaac atttttgggc agtgcacaca ctacttaata   2040
tacacagcat aaattacacg attagaaaca aattagctta ttaaaataac ctaatcaaac   2100
```

```
cgaatatttt atggtattat gagtaaacta tataatataa atagcacaca cccacaacaa   2160
caacaaagga aaactaaaag gtttttttctt tttgaaaaga tcgttttctt tattattctc   2220
tagttttgac gctcgacatt ttatgatgga atgaatggga tgaatcatca aacaagagaa   2280
aatacccgtg acgaaaataa taaaataagt tcctctgata cagaagatga aaacaacaac   2340
aacaagatat agaaatgcct tgggtggcta ttttatagtc ttaacttttt aatgtatatt   2400
tgttttgttt ttttacataa taatacttta taaaagctaa gctaaattca agtaaaattt   2460
caatctctca aataaaacat ttttctcttt ttcttaaatt tagttttata tatttataaa   2520
atatacaaag atttttttaa aaaagtaaca agttatatat gtaataacaa aaagaagaat   2580
aacaagaata caaaaccaga tttccagatt tccagaattt cactcttata tgcgtctatt   2640
tatgtaggat gaaaggtagt ctagtacctc ctgtgatatt atcccattcc atgcggggta   2700
tcgtatgctt ccttcagcac taccctttag ctgttctata tgctgccact cctcaattgg   2760
attagtctca tccttcaatg ctatcatttc ctttgatatt ggatcatatg catagtaccg   2820
agaaactagt gcgaagtagt gatcaggtat tgctgttatc tgatgagtat acgttgtcct   2880
ggccacggca gaagcacgct tatcgctcca atttcccaca acattagtca actccgttag   2940
gcccttcatt gaaagaaatg aggtcatcaa atgtcttcca atgtgagatt ttgggccatt   3000
ttttatagca aagattgaat aaggcgcatt tttcttcaaa gctttattgt acgatctgac   3060
taagttatct tttaataatt ggtattcctg tttattgctt gaagaattgc cggtcctatt   3120
tactcgtttt aggactggtt cagaattcct caaaaattca tccaaatata caagtggatc   3180
gatcctaccc cttgcgctaa agaagtatat gtgcctacta acgcttgtct ttgtctctgt   3240
cactaaacac tggattatta ctcccaaata cttattttgg actaatttaa atgatttcgg   3300
atcaacgttc ttaatatcgc tgaatcttcc acaattgatg aaagtagcta ggaagaggaa   3360
ttggtataaa gtttttgttt ttgtaaatct cgaagtatac tcaaacgaat ttagtatttt   3420
ctcagtgatc tcccagatgc tttcaccctc acttagaagt gctttaagca ttttttttact   3480
gtggctattt cccttatctg cttcttccga tgattcgaac tgtaattgca aactacttac   3540
aatatcagtg atatcagatt gatgtttttg tccatagtaa ggaataattg taaattccca   3600
agcaggaatc aatttcttta atgaggcttc caaaattgtt gctttttgcg tcttgtattt   3660
aaactggagt gatttattga caatatcgaa actcaacgaa ttgcttatga tagtattata   3720
gctcatgaat gtggctctct tgattgctgt tccgttatgt gtaatcatcc aacataaata   3780
ggttagttca gcagcacata atgctatttt ctcacctgaa ggtctttcaa acctttccac   3840
aaactgacga acaagcacct taggtggtgt tttacataat atatcaaatt gtggcatgtc   3900
gacgattatt agttaaacca ctgcaaaaag ttggggaaaa ttttgcccat ttttataccg   3960
tgtcttcgtc tatcgcctcc cccactcccc aatctttgaa ttattccgaa atattcagcg   4020
aacggggtgt acacaaaaac taacattctc aactgcataa tttgaaaaat ggcgtgggac   4080
aagaaaaaaa aaaaattctc aaccatagca atcatggaat acggtaaatt tgtgttgttc   4140
ggtgactcca tcacccagtt tagttgtacc cagtatggct ttcatccagc attacagaat   4200
gtgtatatcc gaaaattgga tgttattaac cgtggtttca gtggctacaa ctcagagcac   4260
gctagacaaa ttcttccaaa aattttagag tcggaaacca atatcaaatt gatgacaata   4320
ttttttggaa ctaacgatgc atacgactac atcaatgaaa tccagacagt cgagttagac   4380
agatataaag ataatttaag tgtaatggta cagatggtac tagacaaaaa tatcaaacca   4440
atcattattg gatccgaagt tcctattctc tagaaagtat aggaacttcc tcgagagtag   4500
```

```
tcgatgctgg gtattcgatt acatgtgtat aggaagattt tggtttttta ttcgttcttt   4560

tttttaattt ttgttaaatt agtttagaga tttcattaat acatagatgg gtgctatttc   4620

cgaaacttta cttctatccc ctgtatccct tattatccct ctcagtcaca tgattgctgt   4680

aattgtcgtg caggacacaa actccctaac ggacttaaac cataaacaag ctcagaacca   4740

taagccgaca tcactccttc ttctctcttc tccaaccaat agcatggaca gacccgagac   4800

g                                                                   4801
```

<210> SEQ ID NO 31
<211> LENGTH: 643
<212> TYPE: DNA
<213> ORGANISM: Artificial Sequence
<220> FEATURE:
<223> OTHER INFORMATION: Pre-targeting construct for Candida tropicalis CYP52A12B

<400> SEQUENCE: 31

```
cgtctcatgg ccacacaaga aatcatcgat tctgtacttc cgtacttgac caaatggtac     60

actgtgatta ctgcagcagt attagtcttc cttatctcca caaacatcaa gaactacgtc    120

aaggcaaaga aattgaaatg tgtcgatcca ccatacttga aggatgccgg tctcactggt    180

attctgtctt tgatcgccgc catcaaggcc aagaacgacg gtagattggc taactttgcc    240

gatgaagttt tcgacgagta cccaaaccac accttctact tgtctgttgc cggtgctttg    300

aagtaggcgg ccgctagatc ttgcgaagct ccatctcgag gttgtctaca agacccaccg    360

tttggaagaa tactacggta aggacgctaa cgacttcaga ccagaaagat ggtttgaacc    420

atctactaag aagttgggct gggcttatgt tccattcaac ggtggtccaa gagtctgctt    480

gggtcaacaa ttcgccttga ctgaagcttc ttatgtgatc actagattgg cccagatgtt    540

tgaaactgtc tcatctgatc caggtctcga ataccctcca ccaaagtgta ttcacttgac    600

catgagtcac aacgatggtg tctttgtcaa gatgtaagag acg                      643
```

<210> SEQ ID NO 32
<211> LENGTH: 4795
<212> TYPE: DNA
<213> ORGANISM: Artificial Sequence
<220> FEATURE:
<223> OTHER INFORMATION: Targeting construct for deletion of Candida tropicalis CYP52A12B

<400> SEQUENCE: 32

```
cgtctcatgg ccacacaaga aatcatcgat tctgtacttc cgtacttgac caaatggtac     60

actgtgatta ctgcagcagt attagtcttc cttatctcca caaacatcaa gaactacgtc    120

aaggcaaaga aattgaaatg tgtcgatcca ccatacttga aggatgccgg tctcactggt    180

attctgtctt tgatcgccgc catcaaggcc aagaacgacg gtagattggc taactttgcc    240

gatgaagttt tcgacgagta cccaaaccac accttctact tgtctgttgc cggtgctttg    300

aagtaggcgg ccgctctaga actagtggat ctgaagttcc tattctctag aaagtatagg    360

aacttcctgc aggaccacct ttgattgtaa atagtaataa ttaccaccct tatctaatta    420

tttatttaac ttatttattt atttattata catatataca aatctaataa agtgaaaatc    480

tcccccttca cacttcacat atgttaggcg tcatcctgtg ctcccgagaa ccagtaccag    540

tacatcgctg tttcgttcga gacttgaggt ctagttttat acgtgaagag gtcaatgccg    600

ccgagagtaa agccacattt tgcgtacaaa ttgcaggcag gtacattgtt cgtttgtgtc    660

tctaatcgta tgccaaggag ctgtctgctt agtgcccact tttcgcaaa ttcgatgaga     720
```

```
ctgtgcgcga ctcctttgcc tcggtgcgtg tgcgacacaa caatgtgttc gatagaggct    780
agatcgttcc atgttgagtt gagttcaatc ttcccgacaa gctcttggtc gatgaatgcg    840
ccatagcaag cagagtcttc atcagagtca tcatccgaga tgtaatcctt ccggtagggg    900
ctcacacttc tggtagatag ttcaaagcct tggtcggata ggtgcacatc gaacacttca    960
cgaacaatga aatggttctc agcatccaat gtttccgcca cctgctcagg gatcaccgaa   1020
attttcatat gagaaccgtt atcgataact aaagcagcaa cttcttctat aaaaatgggt   1080
tagtatgaca gtcatttaaa taaggaattt ttcagttggc ttggtttcaa ttcaatgttc   1140
gttttttttt tttcttgctg tgtttgtgtt tgtgttgttt atagttgtgt gcactgagcg   1200
tcgaaaaaaa aaattcatag tgagccggga aatctgtata gcccagataa caacacaagt   1260
ccaaactaga aactcgtcaa acaccaaaag caatgttgaa tcaattgcct tgcacaagta   1320
cacgtaggaa aacataaaac attgcaattt tgaatattga gccttttgtc gtaacattga   1380
ttgataggat tactcaccga atggttttga aaccactgcc gacagatcaa tcaatcaatc   1440
aaaaaacgtg aactttgaaa aaggggaaga acagatacat tgaagttagc catttccatt   1500
gatcgtcaca acatatctga taaattactt tcaaaattat aagctgatgt gtgtgtatta   1560
ttaatgtgac agtaacatcc caaacgagaa atattatgtc gacaacaaaa aagtttgatc   1620
tgaattgaaa atgaagtttt cccaccctac ccatttgtca tattgaaacc aatcaactga   1680
ttaatcaatc aattagaatt gaagctaaac taaaacatac caccgtccat tttgaatgat   1740
tatatttttt taatattaat atcgagataa tgtttctaag aaagaaagaa aaccaggagt   1800
gaaaattaga aaaggaaagg aaaggaaaaa aagaaaaatc tgaaaatata taaaaaaaaa   1860
ttgtttcgtt ggcaataaat cttggtgaga acagcgaccg aaagcaaata agaacaaaat   1920
atgagtgtat tacgttgaac aactaattaa cgtgtgtgta tggatctttt tttctttttt   1980
ctctttaacc gactataaac aacaaacatt tttgggcagt gcacacacta cttaatatac   2040
acagcataaa ttacacgatt agaaacaaat tagcttatta aaataaccta atcaaaccga   2100
atattttatg gtattatgag taaactatat aatataaata gcacacaccc acaacaacaa   2160
caaaggaaaa ctaaaaggtt ttttcttttt gaaaagatcg ttttctttat tattctctag   2220
ttttgacgct cgacatttta tgatggaatg aatgggatga atcatcaaac aagagaaaat   2280
acccgtgacg aaaataataa aataagttcc tctgatacag aagatgaaaa caacaacaac   2340
aagatataga aatgccttgg gtggctattt tatagtctta actttttaat gtatatttgt   2400
tttgtttttt tacataataa tactttataa aagctaagct aaattcaagt aaaatttcaa   2460
tctctcaaat aaaacatttt tctctttttc ttaaatttag ttttatatat ttataaaata   2520
tacaaagatt tttttaaaaa agtaacaagt tatatatgta ataacaaaaa gaagaataac   2580
aagaatacaa aaccagattt ccagatttcc agaatttcac tcttatatgc gtctatttat   2640
gtaggatgaa aggtagtcta gtacctcctg tgatattatc ccattccatg cggggtatcg   2700
tatgcttcct tcagcactac cctttagctg ttctatatgc tgccactcct caattggatt   2760
agtctcatcc ttcaatgcta tcatttcctt tgatattgga tcatatgcat agtaccgaga   2820
aactagtgcg aagtagtgat caggtattgc tgttatctga tgagtatacg ttgtcctggc   2880
cacggcagaa gcacgcttat cgctccaatt tcccacaaca ttagtcaact ccgttaggcc   2940
cttcattgaa agaaatgagg tcatcaaatg tcttccaatg tgagattttg ggccattttt   3000
tatagcaaag attgaataag gcgcattttt cttcaaagct ttattgtacg atctgactaa   3060
gttatctttt aataattggt attcctgttt attgcttgaa gaattgccgg tcctatttac   3120
```

tcgttttagg actggttcag aattcctcaa aaattcatcc aaatatacaa gtggatcgat 3180
cctacccctt gcgctaaaga agtatatgtg cctactaacg cttgtctttg tctctgtcac 3240
taaacactgg attattactc ccaaatactt attttggact aatttaaatg atttcggatc 3300
aacgttctta atatcgctga atcttccaca attgatgaaa gtagctagga agaggaattg 3360
gtataaagtt tttgtttttg taaatctcga agtatactca aacgaattta gtattttctc 3420
agtgatctcc cagatgcttt caccctcact tagaagtgct ttaagcattt ttttactgtg 3480
gctatttccc ttatctgctt cttccgatga ttcgaactgt aattgcaaac tacttacaat 3540
atcagtgata tcagattgat gtttttgtcc atagtaagga ataattgtaa attcccaagc 3600
aggaatcaat ttctttaatg aggcttccaa aattgttgct ttttgcgtct tgtatttaaa 3660
ctggagtgat ttattgacaa tatcgaaact caacgaattg cttatgatag tattatagct 3720
catgaatgtg gctctcttga ttgctgttcc gttatgtgta atcatccaac ataaataggt 3780
tagttcagca gcacataatg ctattttctc acctgaaggt ctttcaaacc tttccacaaa 3840
ctgacgaaca agcaccttag gtggtgtttt acataatata tcaaattgtg gcatgtcgac 3900
gattattagt taaaccactg caaaaagttg ggaaaaattt tgcccatttt tataccgtgt 3960
cttcgtctat cgcctccccc actccccaat ctttgaatta ttccgaaata ttcagcgaac 4020
ggggtgtaca caaaaactaa cattctcaac tgcataattt gaaaaatggc gtgggacaag 4080
aaaaaaaaaa aattctcaac catagcaatc atggaatacg gtaaatttgt gttgttcggt 4140
gactccatca cccagtttag ttgtacccag tatggctttc atccagcatt acagaatgtg 4200
tatatccgaa aattggatgt tattaaccgt ggtttcagtg gctacaactc agagcacgct 4260
agacaaattc ttccaaaaat tttagagtcg gaaaccaata tcaaattgat gacaatattt 4320
tttggaacta acgatgcata cgactacatc aatgaaatcc agacagtcga gttagacaga 4380
tataaagata atttaagtgt aatggtacag atggtactag acaaaaatat caaaccaatc 4440
attattggat ccgaagttcc tattctctag aaagtatagg aacttcctcg aggttgtcta 4500
caagacccac cgtttggaag aatactacgg taaggacgct aacgacttca gaccagaaag 4560
atggtttgaa ccatctacta agaagttggg ctgggcttat gttccattca acggtggtcc 4620
aagagtctgc ttgggtcaac aattcgcctt gactgaagct tcttatgtga tcactagatt 4680
ggcccagatg tttgaaactg tctcatctga tccaggtctc gaataccctc caccaaagtg 4740
tattcacttg accatgagtc acaacgatgg tgtctttgtc aagatgtaag agacg 4795

<210> SEQ ID NO 33
<211> LENGTH: 1305
<212> TYPE: DNA
<213> ORGANISM: Candida albicans

<400> SEQUENCE: 33
atgcaagcaa gcttattcag aattttcaga ggtgcgagtc tcaccactac cactgcagct 60
gcatctttta cagcaacagc aacagcaggt gccaccacgg caaagacatt gtctggatcc 120
actgtgctcc gaaaactgta taaaaggacc tattcatccc tggtcttatc ttctccagaa 180
ttattttttt ttcatcagtt taacaacaac aaacgttatt gtcatacaac aacaacaaca 240
aatacaaaaa caattatgtc tgaacaaatc ccaaaaactc aaaaagccgt tgtctttgat 300
accaatggtg gtcaattagt ctacaaggat tacccagttc caactccaaa gccaaatgaa 360
ttgttgattc acgtcaaata ctctggtgtc tgtcacactg atttacatgc ttggaaaggt 420
gactggccat tggctactaa attgccatta gttggtggtc acgaaggtgc cggtgtcgtt 480

```
gtcggtatgg gtgaaaacgt caaaggatgg aaaatcggtg actttgccgg tatcaaatgg    540

ttgaacggtt cttgtatgag ttgtgaattc tgtcaacaag gtgctgaacc aaactgtggt    600

gaagctgact tgtctggtta cactcacgat ggttcattcg aacaatacgc tactgctgat    660

gctgtccaag ccgctaaaat tccagctggt actgatttag ccaatgtcgc accaatctta    720

tgtgctggtg ttactgttta caaagcctta aagactgctg acttagcagc tggccaatgg    780

gttgctatct ccggtgctgg tggtggttta ggttctttgg ccgttcaata cgccagagcc    840

atgggtttga gagttgttgc tattgacggt ggtgacgaaa aaggtgaatt tgtcaaatca    900

ttgggtgctg aagcttacgt tgatttcacc aaagataaag atattgttga agctgttaag    960

aaggctactg atggtggtcc acacggtgct atcaatgtct ctgtttctga aaaagctatt   1020

gaccaatctg ttgaatatgt tagaccatta ggtaaagttg ttttggttgg tttaccagct   1080

cacgctaaag tcactgctcc agttttcgat gctgttgtca aatccattga aatcaaaggt   1140

tcttacgttg gtaacagaaa agatactgct gaagctattg acttcttctc cagaggttta   1200

atcaaatgcc caatcaagat tgtcggttta tctgacttgc cagaagtctt caaattgatg   1260

gaagaaggta aaatcttgag tagatacgta ttggacacca gttga                   1305
```

```
<210> SEQ ID NO 34
<211> LENGTH: 1308
<212> TYPE: DNA
<213> ORGANISM: Candida albicans

<400> SEQUENCE: 34

atggaagcaa ggtttttcag aattttcaag ggggggagtc tcaccactac cactgcagct     60

gcatctttta cagcaacagc aacagcaggt gccaccacgg caaagacatt gtctggatcc    120

actgtgctcc gaaaactgta taaaaggacc tattcatccc tggtcttatc ttctccagaa    180

ttattttttt ttcatcagtt taacaacaac aaacgttatt gtcatacaac aacaacaaca    240

aatacaaaaa caattatgtc tgaacaaatc ccaaaaactc aaaaagccgt tgtctttgat    300

accaatggtg gtcaattagt ctacaaggat tacccagttc caactccaaa gccaaatgaa    360

ttgttaatca acgtcaaata ctctggtgtc tgtcacactg atttacacgc ttggaaaggt    420

gactggccat tggctaccaa attgccatta gttggtggtc acgaaggtgc cggtgtcgtt    480

gtcggtatgg gtgaaaacgt caaaggatgg aaaatcggtg actttgccgg tatcaaatgg    540

ttgaacggtt cttgtatgag ctgtgaattc tgtcaacaag gtgctgaacc aaactgtggt    600

gaagctgact tgtctggtta cactcacgat ggttcattcg aacaatacgc tactgctgat    660

gctgtccaag ccgctaaaat tccagctggt actgatttag ccaatgtcgc accaatctta    720

tgtgctggtg ttactgttta caaagcctta aagactgctg acttagcagc tggccaatgg    780

gttgctatct ccggtgctgg tggtggttta ggttctttgg ccgttcaata cgccagagcc    840

atgggtttga gagttgttgc tattgacggt ggtgacgaaa aaggtgaatt tgttaaatca    900

ttgggtgctg aagcttacgt tgatttcacc aaagataaag atattgttga agctgtcaag    960

aaagctactg atggtggtcc acacggtgct atcaatgtct ctgtttctga aaaagccatt   1020

gaccaatctg ttgaatatgt tagaccatta ggtaaagttg ttttggttgg tttaccagct   1080

cacgctaaag tcactgctcc agttttcgat gctgttgtca aatccattga aatcaaaggt   1140

tcttacgttg gtaacagaaa agacactgct gaagctattg acttcttctc cagaggttta   1200

atcaaatgtc caatcaagat tgtcggttta tctgacttgc cagaagtctt caaattgatg   1260

gaagaaggta aaatcttggg tagatacgtc ttggacacca gtaaataa                1308
```

<210> SEQ ID NO 35
<211> LENGTH: 1047
<212> TYPE: DNA
<213> ORGANISM: Candida albicans

<400> SEQUENCE: 35

```
atgtctgtcc caactactca aaaagctgtt attttcgaaa ccaacggtgg taagttggaa      60

tacaaagata tcccagtccc aaaaccaaaa gcaaatgaat tgttaatcaa cgttaaatac     120

tctggtgtct gtcacactga tttacacgct tggaaaggtg actggccatt ggctactaaa     180

ttgccattgg ttggtggtca cgaaggtgct ggtgttgttg tcgccttggg tgaaaacgtt     240

aaaggctgga aagttggtga ttacgctggt gttaaatggt tgaacggctc ttgtttgaac     300

tgtgaatact gtcaatcagg tgctgaacca aactgtgctg aagctgattt atccggttac     360

acccacgatg gttctttcca acaatatgct actgctgacg ctgttcaagc tgccagaatc     420

ccagctggta ccgacttagc caatgttgca ccaatcttat gtgctggtgt caccgtctac     480

aaagctttaa agactgctga attagaagcc ggtcaatggg ttgctatttc cggtgccgct     540

ggtggtttag gttctttagc tgttcaatac gccaaggcca tgggttacag agttcttgcc     600

atcgatggtg gtgaagacaa gggtgaattc gtcaaatcct tgggtgctga aacctttatt     660

gattttacca aagaaaaaga cgttgtcgaa gctgtcaaga aggccaccaa tggtggtcca     720

catggtgtta tcaatgtctc tgtctcagaa agagccattg gtcaatccac tgaatatgtc     780

agaactttag gtaaagttgt tttggttggt ttgccagctg gtgctaaaat tagtacccca     840

gtctttgatg ctgttatcaa gaccattcaa attaaaggtt cttatgtcgg taacagaaaa     900

gatactgctg aagccgttga tttcttcaca agaggtttga tcaaatgtcc aatcaagatt     960

gttggcttat ccgaattacc agaagtttac aaattgatgg aagaaggtaa aatcttgggt    1020

agatatgtct tggacaacga caaataa                                        1047
```

<210> SEQ ID NO 36
<211> LENGTH: 1047
<212> TYPE: DNA
<213> ORGANISM: Candida albicans

<400> SEQUENCE: 36

```
atgtctgtcc caactactca aaaagctgtt attttcgaaa ccaacggtgg taagttggaa      60

tacaaagata tcccagtccc aaaaccaaaa gcaaatgaat tgttaatcaa cgtcaaatac     120

tctggtgtct gtcacactga tttacacgct tggaaaggtg actggccatt ggctactaaa     180

ttgccattgg ttggtggtca cgaaggtgct ggtgttgttg tcgccttggg tgaaaacgtt     240

aaaggctgga aagttggtga ttacgctggt gttaaatggt tgaacggttc ttgtttgaac     300

tgtgaatact gtcaatcagg tgctgaacca aactgtgctg aagctgattt atccggttac     360

acccacgatg gttctttcca acaatatgct actgctgacg ctgttcaagc tgccagaatc     420

ccagctggta ccgacttagc caatgttgca ccaatcttat gtgctggtgt caccgtctac     480

aaagctttaa agactgctga attagaagcc ggtcaatggg ttgctatttc cggtgccgct     540

ggtggtttag gttctttagc tgttcaatac gccaaggcca tgggttacag agttcttgcc     600

atcgatggtg gtgaagacaa gggtgaattc gtcaaatcct tgggtgctga aacctttatt     660

gattttacca aagaaaaaga cgttgtcgaa gctgtcaaga aggccaccaa tggtggtcca     720

catggtgtta tcaatgtctc tgtctcagaa agagccattg gtcaatccac tgaatatgtc     780

agaactttag gtaaagttgt tttggttggt ttgccagctg gtgctaaaat tagtacccca     840
```

```
gtctttgatg ctgttatcaa gaccattcaa attaaaggtt cttatgtcgg taacagaaaa    900

gatactgctg aagccgttga tttcttcaca agaggtttga tcaaatgtcc aatcaagatt    960

gttggcttat ccgaattacc agaagtttac aaattgatgg aagaaggtaa aatcttgggt   1020

agatatgtct tggacaacga caaataa                                       1047
```

<210> SEQ ID NO 37
<211> LENGTH: 35
<212> TYPE: DNA
<213> ORGANISM: Artificial Sequence
<220> FEATURE:
<223> OTHER INFORMATION: Degenerate 5' oligonucleotide for PCR amplification of Candida tropicalis alcohol dehydrogenase genes

<400> SEQUENCE: 37

```
actcaaaaag cygttrtytt ygawaccaay ggtgg                                35
```

<210> SEQ ID NO 38
<211> LENGTH: 36
<212> TYPE: DNA
<213> ORGANISM: Artificial Sequence
<220> FEATURE:
<223> OTHER INFORMATION: Degenerate 3' oligonucleotide for PCR amplification of Candida tropicalis alcohol dehydrogenase genes

<400> SEQUENCE: 38

```
gtccaakacr tatctacyca agattttacc ttcttc                               36
```

<210> SEQ ID NO 39
<211> LENGTH: 948
<212> TYPE: DNA
<213> ORGANISM: Candida tropicalis

<400> SEQUENCE: 39

```
gaattagaat acaaagatat cccagtgcca accccaaagg ccaacgaatt gctcatcaac     60

gtcaaatact cgggtgtctg ccacactgat ttgcacgcct ggaagggtga ctggccattg    120

gccaccaagt tgccattggt tggtggtcac gaaggtgctg gtgtcgttgt cggcatgggt    180

gaaaacgtca agggctggaa gattggtgac ttcgccggta tcaaatggtt gaacggttcc    240

tgtatgtcct gtgagttctg tcaacaaggt gctgaaccaa actgtggtga ggccgacttg    300

tctggttaca cccacgatgg ttctttcgaa caatacgcca ctgctgatgc tgttcaagcc    360

gccagaatcc cagctggtac tgatttggcc gaagttgccc caatcttgtg tgcgggtgtc    420

accgtctaca aagccttgaa gactgccgac ttggccgctg gtcaatgggt cgctatctcc    480

ggtgctggtg gtggtttggg ttccttggct gtccaatacg ccgtcgccat gggcttgaga    540

gtcgttgcca ttgacggtgg tgacgaaaag ggtgcctttg tcaagtcctt gggtgctgaa    600

gcctacattg atttcctcaa ggaaaaggac attgtctctg ctgtcaagaa ggccaccgat    660

ggaggtccac acggtgctat caatgtttcc gtttccgaaa aagccattga ccaatccgtc    720

gagtacgtta gaccattggg taaggttgtt ttggttggtt tgccagctgg ctccaaggtc    780

actgctggtg ttttcgaagc cgttgtcaag tccattgaaa tcaagggttc ctatgtcggt    840

aacagaaagg ataccgccga agccgttgac tttttctcca gaggcttgat caagtgtcca    900

atcaagattg ttggcttgag tgaattgcca caggtcttca agttgatg                 948
```

<210> SEQ ID NO 40
<211> LENGTH: 948
<212> TYPE: DNA
<213> ORGANISM: Candida tropicalis

<400> SEQUENCE: 40

```
aagttagaat acaaagacgt gccggtccct gtccctaaac ccaacgaatt gcttgtcaac      60
gtcaagtact cgggtgtgtg tcattctgac ttgcatgtct ggaaaggcga ctggcccatt     120
cctgccaagt tgcccttggt gggaggtcac gaaggtgctg gtgtcgttgt cggcatgggt     180
gacaacgtca agggctggaa ggtgggggac ttggctggta tcaagtggtt gaatggttcg     240
tgtatgaact gtgagttttg ccaacagggc gcagaaccta actgttcaag agccgacatg     300
tctgggtata cccacgatgg aactttccaa caatacgcca ctgctgatgc tgtccaagct     360
gccaagatcc cagaaggcgc cgacatggct agtatcgccc cgatcttgtg cgctggtgtg     420
accgtgtaca aggctttgaa gaacgccgac ttgttggctg gccaatgggt ggctatctct     480
ggtgctggtg gtggtttggg ctccttgggt gtgcagtacg ctaaagccat gggttacaga     540
gtgttggcta tcgacggtgg tgacgagaga ggagagtttg tcaagtcctt gggcgccgaa     600
gtgtacattg acttccttaa ggaacaggac atcgttagtg ctatcagaaa ggcaactggt     660
ggtggtccac acggtgttat taacgtgtca gtgtccgaaa aggcaatcaa ccagtcggtg     720
gagtacgtca gaactttggg gaaagtggtt ttagttagct tgccggcagg tggtaaactc     780
actgctcctc ttttcgagtc tgttgctaga tcaatccaga ttagaactac gtgtgttggc     840
aacagaaagg atactactga agctattgat ttctttgtta gagggttgat cgattgccca     900
attaaagtcg ctggtttaag tgaagtgcca gagatttttg acttgatg                  948
```

<210> SEQ ID NO 41
<211> LENGTH: 948
<212> TYPE: DNA
<213> ORGANISM: Candida tropicalis

<400> SEQUENCE: 41

```
ccattgcaat acatcgatat tccagtccca gtccctaagc caaacgattt gctcgtcaat      60
gtcaaatact ccggtctttg tcactcagat atacacctct ggaagggtga ctgattccca     120
gcatcaaaat tgccagttgt tggtggtcac gaaggtgcca gtgttgtcgt tgctattggt     180
gaaaacgtcc agggctggaa agtaggtgcc ttggcgggca taaagatgtt gaatggttcc     240
tgtatgaact gtgaattctg tcaacaaagt gcttaaccaa gctgtcccca tgctgatgtc     300
tcgggttact cccacgacgg cactttccaa cagtacgcta ccgctgatgc tgctcaagct     360
gctaaattcc cagctggttc tgatttagct agcatcgcac ctatatcctg tgccggtgtt     420
actgtttaca aagcattgaa gactgctggc ttgcatccgg gccaatgggt tgccatctcc     480
gatgctggtg gtggtttggg ttctttggcc gtgcaatacg ccaaggccat gggctacaga     540
gtggtggcca ttgactgcgg cggcgaaaat ggagtgtttg tcagatcgtt gggtactgaa     600
gctttcgttg attccaccaa ggaggccaat gtctctgagg ctatcatcaa ggctaccgac     660
ggtggtgtcc atggtgtcat caacgtttcc atttctgaaa aagccatcaa ccagtctgtt     720
gaaaatgtca gaactttggg tactgttgtc ttggttggtt tgccagctgg tgccaagctc     780
gaagcaccta tcttcaatgc cgttgccaaa tccatctaaa tcaaggattc ttacgtgggt     840
aaccgaagag acactgctga ggctgttgat ttcttcgcga aaggtttggt caagtgtcca     900
attaaggttg ttgagttgag tgaattgcca gagattttca aattgttg                  948
```

<210> SEQ ID NO 42
<211> LENGTH: 948
<212> TYPE: DNA
<213> ORGANISM: Candida tropicalis

<400> SEQUENCE: 42
aaattagaat acaaggacat cccagttcca aagccaaagc caaacgaatt gctcatcaac 60
gtcaagtact ccggtgtctg ccacactgat ttacacgcct ggaagggtga ctggccattg 120
gacaccaagt tgccattggt gggtggtcac gaaggtgctg gtgttgttgt tgccattggt 180
gacaatgtca agggatggaa ggtcggtgat ttggccggtg tcaagtggtt gaacggttcc 240
tgtatgaact gtgagtactg tcaacagggt gccgaaccaa actgtccaca ggctgacttg 300
tctggttaca cccacgacgg ttctttccag caatacgcca ctgcagatgc cgtgcaagcc 360
gctagaattc cagctggtac tgatttagcc aacgttgccc ccatcttgtg tgctggtgtc 420
actgtttaca aggccttgaa gaccgccgac ttgcagccag gtcaatgggt cgccatttcc 480
ggtgccgctg gtggtttggg ttctttggcc gttcaatacg ccaaggccat gggctacaga 540
gttgtcgcca tcgatggtgg tgccgacaag ggtgagttcg tcaagtcttt gggcgctgag 600
gtctttgttg atttcctcaa ggaaaaggac attgttggtg ctgtcaagaa ggcaaccgat 660
ggtggcccac acggtgccgt taacgtttcc atctccgaaa aggccatcaa ccaatctgtc 720
gactacgtta gaaccttggg taaggttgtc ttggtcggtt tgccagctgg ctccaaggtt 780
tctgctccag tctttgactc cgtcgtcaag tccatccaaa tcaagggttc ctatgtcggt 840
aacagaaagg acactgccga agctgttgac tttttctcca gaggcttgat caagtgtcca 900
atcaaggttg tcggtttgag tgaattgcca gaagtctaca agttgatg 948

<210> SEQ ID NO 43
<211> LENGTH: 948
<212> TYPE: DNA
<213> ORGANISM: Candida tropicalis

<400> SEQUENCE: 43
ccattgcaat acaccgatat cccagttcca gtccctaagc caaacgaatt gctcgtccac 60
gtcaaatact ccggtgtttg tcactcagat atacacgtct ggaagggtga ctggttccca 120
gcatcgaaat tgcccgttgt tggtggtcac gaaggtgccg gtgttgtcgt tgccattggt 180
gaaaacgtcc aaggctggaa agtaggtgac ttggcaggta taaagatgtt gaatggttcc 240
tgtatgaact gtgaatactg tcaacaaggt gctgaaccaa actgtcccca cgctgatgtc 300
tcgggttact cccacgacgg tactttccaa cagtacgcta ccgccgatgc tgttcaagct 360
gctaaattcc cagctggttc tgatttagct agcatcgcac ctatatcctg cgccggtgtt 420
actgtttaca aagcattgaa aactgcaggc ttgcagccag gtcaatgggt tgccatctct 480
ggtgcagctg gtggtttggg ttctttggct gtgcaatacg ccaaggccat gggtttgaga 540
gtcgtggcca ttgacggtgg tgacgaaaga ggagtgtttg tcaaatcgtt gggtgctgaa 600
gttttcgttg atttcaccaa agaggccaat gtctctgagg ctatcatcaa ggctaccgac 660
ggtggtgccc atggcgtcat caacgtttcc atttctgaaa aagccatcaa ccagtctgtt 720
gaatatgtta gaactttggg aactgttgtc ttggttggtt tgccagctgg tgcaaagctc 780
gaagctccta tcttcaatgc cgttgccaaa tccatccaaa tcaaaggttc ttacgtggga 840
aacagaagag acactgctga ggctgttgat ttcttcgcta gaggtttggt caaatgtcca 900
attaaggttg ttgggttgag tgaattgcca gagattttca aattgttg 948

<210> SEQ ID NO 44
<211> LENGTH: 445
<212> TYPE: DNA
<213> ORGANISM: Artificial Sequence
<220> FEATURE:
<223> OTHER INFORMATION: Pre-targeting construct for Candida tropicalis ADH-A4

<400> SEQUENCE: 44

```
cgtctcaccc caaaggccaa cgaattgctc atcaacgtca aatactcggg tgtctgccac     60

actgatttgc acgcctggaa gggtgactgg ccattggcca ccaagttgcc attggttggt    120

ggtcacgaag gtgctggtgt cgttgtcggc atgggtgaaa acgtcaaggg ctggaagatt    180

ggtgacttcg ccggtatcaa atggtaggcg gccgctagat cttgcgaagc tccatctcga    240

ggagtacgtt agaccattgg gtaaggttgt tttggttggt ttgccagctg gctccaaggt    300

cactgctggt gttttcgaag ccgttgtcaa gtccattgaa atcaagggtt cctatgtcgg    360

taacagaaag gataccgccg aagccgttga ctttttctcc agaggcttga tcaagtgtcc    420

aatcaagatt gttggcttgg agacg                                          445
```

<210> SEQ ID NO 45
<211> LENGTH: 4597
<212> TYPE: DNA
<213> ORGANISM: Artificial Sequence
<220> FEATURE:
<223> OTHER INFORMATION: Targeting construct for deletion of Candida tropicalis ADH-A4

<400> SEQUENCE: 45

```
cgtctcaccc caaaggccaa cgaattgctc atcaacgtca aatactcggg tgtctgccac     60

actgatttgc acgcctggaa gggtgactgg ccattggcca ccaagttgcc attggttggt    120

ggtcacgaag gtgctggtgt cgttgtcggc atgggtgaaa acgtcaaggg ctggaagatt    180

ggtgacttcg ccggtatcaa atggtaggcg gccgctctag aactagtgga tctgaagttc    240

ctattctcta gaaagtatag gaacttcctg caggaccacc tttgattgta aatagtaata    300

attaccaccc ttatctaatt atttatttaa cttatttatt tatttattat acatatatac    360

aaatctaata aagtgaaaat ctcccccttc acacttcaca tatgttaggc gtcatcctgt    420

gctcccgaga accagtacca gtacatcgct gtttcgttcg agacttgagg tctagtttta    480

tacgtgaaga ggtcaatgcc gccgagagta aagccacatt ttgcgtacaa attgcaggca    540

ggtacattgt tcgtttgtgt ctctaatcgt atgccaagga gctgtctgct tagtgcccac    600

tttttcgcaa attcgatgag actgtgcgcg actcctttgc ctcggtgcgt gtgcgacaca    660

acaatgtgtt cgatagaggc tagatcgttc catgttgagt tgagttcaat cttcccgaca    720

agctcttggt cgatgaatgc gccatagcaa gcagagtctt catcagagtc atcatccgag    780

atgtaatcct tccggtaggg gctcacactt ctggtagata gttcaaagcc ttggtcggat    840

aggtgcacat cgaacacttc acgaacaatg aaatggttct cagcatccaa tgtttccgcc    900

acctgctcag ggatcaccga aattttcata tgagaaccgt tatcgataac taaagcagca    960

acttcttcta taaaaatggg ttagtatgac agtcatttaa ataaggaatt tttcagttgg   1020

cttggtttca attcaatgtt cgtttttttt ttttcttgct gtgtttgtgt ttgtgttgtt   1080

tatagttgtg tgcactgagc gtcgaaaaaa aaaattcata gtgagccggg aaatctgtat   1140

agcccagata acaacacaag tccaaactag aaactcgtca aacaccaaaa gcaatgttga   1200

atcaattgcc ttgcacaagt acacgtagga aaacataaaa cattgcaatt ttgaatattg   1260

agccttttgt cgtaacattg attgatagga ttactcaccg aatggttttg aaaccactgc   1320

cgacagatca atcaatcaat caaaaaacgt gaactttgaa aaaggggaag aacagataca   1380

ttgaagttag ccatttccat tgatcgtcac aacatatctg ataaattact ttcaaaatta   1440
```

```
taagctgatg tgtgtgtatt attaatgtga cagtaacatc ccaaacgaga aatattatgt   1500
cgacaacaaa aaagtttgat ctgaattgaa aatgaagttt tcccacccta cccatttgtc   1560
atattgaaac caatcaactg attaatcaat caattagaat tgaagctaaa ctaaaacata   1620
ccaccgtcca ttttgaatga ttatattttt ttaatattaa tatcgagata atgtttctaa   1680
gaaagaaaga aaaccaggag tgaaaattag aaaaggaaag gaaaggaaaa aaagaaaaat   1740
ctgaaaatat ataaaaaaaa attgtttcgt tggcaataaa tcttggtgag aacagcgacc   1800
gaaagcaaat aagaacaaaa tatgagtgta ttacgttgaa caactaatta acgtgtgtgt   1860
atggatcttt ttttcttttt tctctttaac cgactataaa caacaaacat ttttgggcag   1920
tgcacacact acttaatata cacagcataa attacacgat tagaaacaaa ttagcttatt   1980
aaaataacct aatcaaaccg aatattttat ggtattatga gtaaactata taatataaat   2040
agcacacacc cacaacaaca acaaaggaaa actaaaaggt tttttctttt tgaaaagatc   2100
gttttcttta ttattctcta gttttgacgc tcgacatttt atgatggaat gaatgggatg   2160
aatcatcaaa caagagaaaa tacccgtgac gaaaataata aaataagttc ctctgataca   2220
gaagatgaaa acaacaacaa caagatatag aaatgccttg ggtggctatt ttatagtctt   2280
aactttttaa tgtatatttg ttttgttttt ttacataata atactttata aaagctaagc   2340
taaattcaag taaaatttca atctctcaaa taaaacattt ttctcttttt cttaaattta   2400
gttttatata tttataaaat atacaaagat ttttttaaaa aagtaacaag ttatatatgt   2460
aataacaaaa agaagaataa caagaataca aaaccagatt tccagatttc cagaatttca   2520
ctcttatatg cgtctattta tgtaggatga aaggtagtct agtacctcct gtgatattat   2580
cccattccat gcggggtatc gtatgcttcc ttcagcacta ccctttagct gttctatatg   2640
ctgccactcc tcaattggat tagtctcatc cttcaatgct atcatttcct ttgatattgg   2700
atcatatgca tagtaccgag aaactagtgc gaagtagtga tcaggtattg ctgttatctg   2760
atgagtatac gttgtcctgg ccacggcaga agcacgctta tcgctccaat ttcccacaac   2820
attagtcaac tccgttaggc ccttcattga aagaaatgag gtcatcaaat gtcttccaat   2880
gtgagatttt gggccatttt ttatagcaaa gattgaataa ggcgcatttt tcttcaaagc   2940
tttattgtac gatctgacta agttatcttt taataattgg tattcctgtt tattgcttga   3000
agaattgccg gtcctattta ctcgttttag gactggttca gaattcctca aaaattcatc   3060
caaatataca agtggatcga tcctacccct tgcgctaaag aagtatatgt gcctactaac   3120
gcttgtcttt gtctctgtca ctaaacactg gattattact cccaaatact tattttggac   3180
taatttaaat gatttcggat caacgttctt aatatcgctg aatcttccac aattgatgaa   3240
agtagctagg aagaggaatt ggtataaagt ttttgttttt gtaaatctcg aagtatactc   3300
aaacgaattt agtattttct cagtgatctc ccagatgctt tcaccctcac ttagaagtgc   3360
tttaagcatt tttttactgt ggctatttcc cttatctgct tcttccgatg attcgaactg   3420
taattgcaaa ctacttacaa tatcagtgat atcagattga tgtttttgtc catagtaagg   3480
aataattgta aattcccaag caggaatcaa tttctttaat gaggcttcca aaattgttgc   3540
tttttgcgtc ttgtatttaa actggagtga tttattgaca atatcgaaac tcaacgaatt   3600
gcttatgata gtattatagc tcatgaatgt ggctctcttg attgctgttc cgttatgtgt   3660
aatcatccaa cataaatagg ttagttcagc agcacataat gctattttct cacctgaagg   3720
tctttcaaac ctttccacaa actgacgaac aagcacctta ggtggtgttt tacataatat   3780
atcaaattgt ggcatgtcga cgattattag ttaaaccact gcaaaaagtt ggggaaaatt   3840
```

```
ttgcccattt ttataccgtg tcttcgtcta tcgcctcccc cactccccaa tctttgaatt   3900

attccgaaat attcagcgaa cggggtgtac acaaaaacta acattctcaa ctgcataatt   3960

tgaaaaatgg cgtgggacaa gaaaaaaaaa aaattctcaa ccatagcaat catggaatac   4020

ggtaaatttg tgttgttcgg tgactccatc acccagttta gttgtaccca gtatggcttt   4080

catccagcat tacagaatgt gtatatccga aaattggatg ttattaaccg tggtttcagt   4140

ggctacaact cagagcacgc tagacaaatt cttccaaaaa ttttagagtc ggaaaccaat   4200

atcaaattga tgacaatatt ttttggaact aacgatgcat acgactacat caatgaaatc   4260

cagacagtcg agttagacag atataaagat aatttaagtg taatggtaca gatggtacta   4320

gacaaaaata tcaaaccaat cattattgga tccgaagttc ctattctcta gaaagtatag   4380

gaacttcctc gaggagtacg ttagaccatt gggtaaggtt gttttggttg gtttgccagc   4440

tggctccaag gtcactgctg gtgttttcga agccgttgtc aagtccattg aaatcaaggg   4500

ttcctatgtc ggtaacagaa aggataccgc cgaagccgtt gactttttct ccagaggctt   4560

gatcaagtgt ccaatcaaga ttgttggctt ggagacg                            4597
```

<210> SEQ ID NO 46
<211> LENGTH: 445
<212> TYPE: DNA
<213> ORGANISM: Artificial Sequence
<220> FEATURE:
<223> OTHER INFORMATION: Pre-targeting construct for Candida tropicalis ADH-A4B

<400> SEQUENCE: 46

```
cgtctctgtc aacaaggtgc tgaaccaaac tgtggtgagg ccgacttgtc tggttacacc     60

cacgatggtt ctttcgaaca atacgccact gctgatgctg ttcaagccgc cagaatccca    120

gctggtactg atttggccga agttgcccca atcttgtgtg cgggtgtcac cgtctacaaa    180

gccttgaaga ctgccgactt ggcctaggcg gccgctagat cttgcgaagc tccatctcga    240

gggtttgggt tccttggctg tccaatacgc cgtcgccatg ggcttgagag tcgttgccat    300

tgacggtggt gacgaaaagg gtgcctttgt caagtccttg ggtgctgaag cctacattga    360

tttcctcaag gaaaaggaca ttgtctctgc tgtcaagaag gccaccgatg gaggtccaca    420

cggtgctatc aatgtttccg agacg                                          445
```

<210> SEQ ID NO 47
<211> LENGTH: 4597
<212> TYPE: DNA
<213> ORGANISM: Artificial Sequence
<220> FEATURE:
<223> OTHER INFORMATION: Targeting construct for deletion of Candida tropicalis ADH-A4B

<400> SEQUENCE: 47

```
cgtctctgtc aacaaggtgc tgaaccaaac tgtggtgagg ccgacttgtc tggttacacc     60

cacgatggtt ctttcgaaca atacgccact gctgatgctg ttcaagccgc cagaatccca    120

gctggtactg atttggccga agttgcccca atcttgtgtg cgggtgtcac cgtctacaaa    180

gccttgaaga ctgccgactt ggcctaggcg gccgctctag aactagtgga tctgaagttc    240

ctattctcta gaaagtatag gaacttcctg caggaccacc tttgattgta aatagtaata    300

attaccaccc ttatctaatt atttatttaa cttatttatt tatttattat acatatatac    360

aaatctaata aagtgaaaat ctcccccttc acacttcaca tatgttaggc gtcatcctgt    420

gctcccgaga accagtacca gtacatcgct gtttcgttcg agacttgagg tctagtttta    480
```

```
tacgtgaaga ggtcaatgcc gccgagagta aagccacatt ttgcgtacaa attgcaggca    540
ggtacattgt tcgtttgtgt ctctaatcgt atgccaagga gctgtctgct tagtgcccac    600
tttttcgcaa attcgatgag actgtgcgcg actcctttgc ctcggtgcgt gtgcgacaca    660
acaatgtgtt cgatagaggc tagatcgttc catgttgagt tgagttcaat cttcccgaca    720
agctcttggt cgatgaatgc gccatagcaa gcagagtctt catcagagtc atcatccgag    780
atgtaatcct tccggtaggg gctcacactt ctggtagata gttcaaagcc ttggtcggat    840
aggtgcacat cgaacacttc acgaacaatg aaatggttct cagcatccaa tgtttccgcc    900
acctgctcag ggatcaccga aattttcata tgagaaccgt tatcgataac taaagcagca    960
acttcttcta taaaaatggg ttagtatgac agtcatttaa ataaggaatt tttcagttgg   1020
cttggtttca attcaatgtt cgtttttttt ttttcttgct gtgtttgtgt ttgtgttgtt   1080
tatagttgtg tgcactgagc gtcgaaaaaa aaaattcata gtgagccggg aaatctgtat   1140
agcccagata acaacacaag tccaaactag aaactcgtca aacaccaaaa gcaatgttga   1200
atcaattgcc ttgcacaagt acacgtagga aaacataaaa cattgcaatt ttgaatattg   1260
agccttttgt cgtaacattg attgatagga ttactcaccg aatggttttg aaaccactgc   1320
cgacagatca atcaatcaat caaaaaacgt gaactttgaa aaaggggaag aacagataca   1380
ttgaagttag ccatttccat tgatcgtcac aacatatctg ataaattact ttcaaaatta   1440
taagctgatg tgtgtgtatt attaatgtga cagtaacatc ccaaacgaga aatattatgt   1500
cgacaacaaa aaagtttgat ctgaattgaa aatgaagttt tcccacccta cccatttgtc   1560
atattgaaac caatcaactg attaatcaat caattagaat tgaagctaaa ctaaaacata   1620
ccaccgtcca ttttgaatga ttatattttt ttaatattaa tatcgagata atgtttctaa   1680
gaaagaaaga aaaccaggag tgaaaattag aaaaggaaag gaaaggaaaa aaagaaaaat   1740
ctgaaaatat ataaaaaaaa attgtttcgt tggcaataaa tcttggtgag aacagcgacc   1800
gaaagcaaat aagaacaaaa tatgagtgta ttacgttgaa caactaatta acgtgtgtgt   1860
atggatcttt ttttcttttt tctctttaac cgactataaa caacaaacat ttttgggcag   1920
tgcacacact acttaatata cacagcataa attacacgat tagaaacaaa ttagcttatt   1980
aaaataacct aatcaaaccg aatattttat ggtattatga gtaaactata taatataaat   2040
agcacacacc cacaacaaca acaaaggaaa actaaaaggt tttttctttt tgaaaagatc   2100
gttttcttta ttattctcta gttttgacgc tcgacatttt atgatggaat gaatgggatg   2160
aatcatcaaa caagagaaaa tacccgtgac gaaaataata aaataagttc ctctgataca   2220
gaagatgaaa acaacaacaa caagatatag aaatgccttg ggtggctatt ttatagtctt   2280
aactttttaa tgtatatttg ttttgttttt ttacataata atactttata aaagctaagc   2340
taaattcaag taaaatttca atctctcaaa taaaacattt ttctcttttt cttaaattta   2400
gttttatata tttataaaat atacaaagat ttttttaaaa aagtaacaag ttatatatgt   2460
aataacaaaa agaagaataa caagaataca aaaccagatt tccagatttc cagaatttca   2520
ctcttatatg cgtctattta tgtaggatga aaggtagtct agtacctcct gtgatattat   2580
cccattccat gcggggtatc gtatgcttcc ttcagcacta ccctttagct gttctatatg   2640
ctgccactcc tcaattggat tagtctcatc cttcaatgct atcatttcct ttgatattgg   2700
atcatatgca tagtaccgag aaactagtgc gaagtagtga tcaggtattg ctgttatctg   2760
atgagtatac gttgtcctgg ccacggcaga agcacgctta tcgctccaat ttcccacaac   2820
attagtcaac tccgttaggc ccttcattga aagaaatgag gtcatcaaat gtcttccaat   2880
```

```
gtgagatttt gggccatttt ttatagcaaa gattgaataa ggcgcatttt tcttcaaagc   2940

tttattgtac gatctgacta agttatcttt taataattgg tattcctgtt tattgcttga   3000

agaattgccg gtcctattta ctcgttttag gactggttca gaattcctca aaaattcatc   3060

caaatataca agtggatcga tcctacccct tgcgctaaag aagtatatgt gcctactaac   3120

gcttgtcttt gtctctgtca ctaaacactg gattattact cccaaatact tattttggac   3180

taatttaaat gatttcggat caacgttctt aatatcgctg aatcttccac aattgatgaa   3240

agtagctagg aagaggaatt ggtataaagt ttttgttttt gtaaatctcg aagtatactc   3300

aaacgaattt agtattttct cagtgatctc ccagatgctt tcaccctcac ttagaagtgc   3360

tttaagcatt tttttactgt ggctatttcc cttatctgct tcttccgatg attcgaactg   3420

taattgcaaa ctacttacaa tatcagtgat atcagattga tgtttttgtc catagtaagg   3480

aataattgta aattcccaag caggaatcaa tttctttaat gaggcttcca aaattgttgc   3540

tttttgcgtc ttgtatttaa actggagtga tttattgaca atatcgaaac tcaacgaatt   3600

gcttatgata gtattatagc tcatgaatgt ggctctcttg attgctgttc cgttatgtgt   3660

aatcatccaa cataaatagg ttagttcagc agcacataat gctattttct cacctgaagg   3720

tctttcaaac ctttccacaa actgacgaac aagcacctta ggtggtgttt tacataatat   3780

atcaaattgt ggcatgtcga cgattattag ttaaaccact gcaaaaagtt ggggaaaatt   3840

ttgcccattt ttataccgtg tcttcgtcta tcgcctcccc cactccccaa tctttgaatt   3900

attccgaaat attcagcgaa cggggtgtac acaaaaacta acattctcaa ctgcataatt   3960

tgaaaaatgg cgtgggacaa gaaaaaaaaa aaattctcaa ccatagcaat catggaatac   4020

ggtaaatttg tgttgttcgg tgactccatc acccagttta gttgtaccca gtatggcttt   4080

catccagcat tacagaatgt gtatatccga aaattggatg ttattaaccg tggtttcagt   4140

ggctacaact cagagcacgc tagacaaatt cttccaaaaa ttttagagtc ggaaaccaat   4200

atcaaattga tgacaatatt ttttggaact aacgatgcat acgactacat caatgaaatc   4260

cagacagtcg agttagacag atataaagat aatttaagtg taatggtaca gatggtacta   4320

gacaaaaata tcaaaccaat cattattgga tccgaagttc ctattctcta gaaagtatag   4380

gaacttcctc gagggtttgg gttccttggc tgtccaatac gccgtcgcca tgggcttgag   4440

agtcgttgcc attgacggtg gtgacgaaaa gggtgccttt gtcaagtcct tgggtgctga   4500

agcctacatt gatttcctca aggaaaagga cattgtctct gctgtcaaga aggccaccga   4560

tggaggtcca cacggtgcta tcaatgtttc cgagacg                            4597
```

<210> SEQ ID NO 48
<211> LENGTH: 445
<212> TYPE: DNA
<213> ORGANISM: Artificial Sequence
<220> FEATURE:
<223> OTHER INFORMATION: Pre-targeting construct for Candida tropicalis ADH-B4

<400> SEQUENCE: 48

```
cgtctcaagc caaagccaaa cgaattgctc atcaacgtca agtactccgg tgtctgccac     60

actgatttac acgcctggaa gggtgactgg ccattggaca ccaagttgcc attggtgggt    120

ggtcacgaag gtgctggtgt tgttgttgcc attggtgaca atgtcaaggg atggaaggtc    180

ggtgatttgg ccggtgtcaa gtggtaggcg gccgctagat cttgcgaagc tccatctcga    240

ggactacgtt agaaccttgg gtaaggttgt cttggtcggt ttgccagctg gctccaaggt    300
```

```
ttctgctcca gtctttgact ccgtcgtcaa gtccatccaa atcaagggtt cctatgtcgg    360

taacagaaag gacactgccg aagctgttga ctttttctcc agaggcttga tcaagtgtcc    420

aatcaaggtt gtcggtttgg agacg                                          445


<210> SEQ ID NO 49
<211> LENGTH: 4597
<212> TYPE: DNA
<213> ORGANISM: Artificial Sequence
<220> FEATURE:
<223> OTHER INFORMATION: Targeting construct for deletion of Candida
      tropicalis ADH-B4

<400> SEQUENCE: 49

cgtctcaagc caaagccaaa cgaattgctc atcaacgtca agtactccgg tgtctgccac     60

actgatttac acgcctggaa gggtgactgg ccattggaca ccaagttgcc attggtgggt    120

ggtcacgaag gtgctggtgt tgttgttgcc attggtgaca atgtcaaggg atggaaggtc    180

ggtgatttgg ccggtgtcaa gtggtaggcg gccgctctag aactagtgga tctgaagttc    240

ctattctcta gaaagtatag gaacttcctg caggaccacc tttgattgta aatagtaata    300

attaccaccc ttatctaatt atttatttaa cttatttatt tatttattat acatatatac    360

aaatctaata aagtgaaaat ctcccccttc acacttcaca tatgttaggc gtcatcctgt    420

gctcccgaga accagtacca gtacatcgct gtttcgttcg agacttgagg tctagtttta    480

tacgtgaaga ggtcaatgcc gccgagagta aagccacatt ttgcgtacaa attgcaggca    540

ggtacattgt tcgtttgtgt ctctaatcgt atgccaagga gctgtctgct tagtgcccac    600

tttttcgcaa attcgatgag actgtgcgcg actcctttgc ctcggtgcgt gtgcgacaca    660

acaatgtgtt cgatagaggc tagatcgttc catgttgagt tgagttcaat cttcccgaca    720

agctcttggt cgatgaatgc gccatagcaa gcagagtctt catcagagtc atcatccgag    780

atgtaatcct tccggtaggg gctcacactt ctggtagata gttcaaagcc ttggtcggat    840

aggtgcacat cgaacacttc acgaacaatg aaatggttct cagcatccaa tgtttccgcc    900

acctgctcag ggatcaccga aattttcata tgagaaccgt tatcgataac taaagcagca    960

acttcttcta taaaaatggg ttagtatgac agtcatttaa ataaggaatt tttcagttgg   1020

cttggtttca attcaatgtt cgtttttttt ttttcttgct gtgtttgtgt ttgtgttgtt   1080

tatagttgtg tgcactgagc gtcgaaaaaa aaaattcata gtgagccggg aaatctgtat   1140

agcccagata acaacacaag tccaaactag aaactcgtca aacaccaaaa gcaatgttga   1200

atcaattgcc ttgcacaagt acacgtagga aaacataaaa cattgcaatt ttgaatattg   1260

agccttttgt cgtaacattg attgatagga ttactcaccg aatggttttg aaaccactgc   1320

cgacagatca atcaatcaat caaaaaacgt gaactttgaa aaaggggaag aacagataca   1380

ttgaagttag ccatttccat tgatcgtcac aacatatctg ataaattact ttcaaaatta   1440

taagctgatg tgtgtgtatt attaatgtga cagtaacatc ccaaacgaga aatattatgt   1500

cgacaacaaa aaagtttgat ctgaattgaa aatgaagttt tcccacccta cccatttgtc   1560

atattgaaac caatcaactg attaatcaat caattagaat tgaagctaaa ctaaaacata   1620

ccaccgtcca ttttgaatga ttatattttt ttaatattaa tatcgagata atgtttctaa   1680

gaaagaaaga aaaccaggag tgaaaattag aaaaggaaag gaaaggaaaa aaagaaaaat   1740

ctgaaaatat ataaaaaaaa attgtttcgt tggcaataaa tcttggtgag aacagcgacc   1800

gaaagcaaat aagaacaaaa tatgagtgta ttacgttgaa caactaatta acgtgtgtgt   1860

atggatcttt ttttcttttt tctctttaac cgactataaa caacaaacat tttgggcag    1920
```

```
tgcacacact acttaatata cacagcataa attacacgat tagaaacaaa ttagcttatt   1980
aaaataacct aatcaaaccg aatattttat ggtattatga gtaaactata taatataaat   2040
agcacacacc cacaacaaca acaaaggaaa actaaaaggt tttttctttt tgaaaagatc   2100
gttttcttta ttattctcta gttttgacgc tcgacatttt atgatggaat gaatgggatg   2160
aatcatcaaa caagagaaaa tacccgtgac gaaaataata aaataagttc ctctgataca   2220
gaagatgaaa acaacaacaa caagatatag aaatgccttg ggtggctatt ttatagtctt   2280
aactttttaa tgtatatttg ttttgttttt ttacataata atactttata aaagctaagc   2340
taaattcaag taaaatttca atctctcaaa taaaacattt ttctcttttt cttaaattta   2400
gttttatata tttataaaat atacaaagat ttttttaaaa aagtaacaag ttatatatgt   2460
aataacaaaa agaagaataa caagaataca aaaccagatt tccagatttc cagaatttca   2520
ctcttatatg cgtctattta tgtaggatga aaggtagtct agtacctcct gtgatattat   2580
cccattccat gcggggtatc gtatgcttcc ttcagcacta ccctttagct gttctatatg   2640
ctgccactcc tcaattggat tagtctcatc cttcaatgct atcatttcct ttgatattgg   2700
atcatatgca tagtaccgag aaactagtgc gaagtagtga tcaggtattg ctgttatctg   2760
atgagtatac gttgtcctgg ccacggcaga agcacgctta tcgctccaat ttcccacaac   2820
attagtcaac tccgttaggc ccttcattga aagaaatgag gtcatcaaat gtcttccaat   2880
gtgagatttt gggccatttt ttatagcaaa gattgaataa ggcgcatttt tcttcaaagc   2940
tttattgtac gatctgacta agttatcttt taataattgg tattcctgtt tattgcttga   3000
agaattgccg gtcctattta ctcgttttag gactggttca gaattcctca aaaattcatc   3060
caaatataca agtggatcga tcctacccct tgcgctaaag aagtatatgt gcctactaac   3120
gcttgtcttt gtctctgtca ctaaacactg gattattact cccaaatact tattttggac   3180
taatttaaat gatttcggat caacgttctt aatatcgctg aatcttccac aattgatgaa   3240
agtagctagg aagaggaatt ggtataaagt tttgttttt gtaaatctcg aagtatactc    3300
aaacgaattt agtattttct cagtgatctc ccagatgctt tcaccctcac ttagaagtgc   3360
tttaagcatt tttttactgt ggctatttcc cttatctgct tcttccgatg attcgaactg   3420
taattgcaaa ctacttacaa tatcagtgat atcagattga tgtttttgtc catagtaagg   3480
aataattgta aattcccaag caggaatcaa tttctttaat gaggcttcca aaattgttgc   3540
tttttgcgtc ttgtatttaa actggagtga tttattgaca atatcgaaac tcaacgaatt   3600
gcttatgata gtattatagc tcatgaatgt ggctctcttg attgctgttc cgttatgtgt   3660
aatcatccaa cataaatagg ttagttcagc agcacataat gctattttct cacctgaagg   3720
tctttcaaac ctttccacaa actgacgaac aagcacctta ggtggtgttt tacataatat   3780
atcaaattgt ggcatgtcga cgattattag ttaaaccact gcaaaaagtt ggggaaaatt   3840
ttgcccattt ttataccgtg tcttcgtcta tcgcctcccc cactccccaa tctttgaatt   3900
attccgaaat attcagcgaa cggggtgtac acaaaaacta acattctcaa ctgcataatt   3960
tgaaaaatgg cgtgggacaa gaaaaaaaaa aaattctcaa ccatagcaat catggaatac   4020
ggtaaatttg tgttgttcgg tgactccatc acccagttta gttgtaccca gtatggcttt   4080
catccagcat tacagaatgt gtatatccga aaattggatg ttattaaccg tggtttcagt   4140
ggctacaact cagagcacgc tagacaaatt cttccaaaaa ttttagagtc ggaaaccaat   4200
atcaaattga tgacaatatt ttttggaact aacgatgcat acgactacat caatgaaatc   4260
cagacagtcg agttagacag atataaagat aatttaagtg taatggtaca gatggtacta   4320
```

```
gacaaaaata tcaaaccaat cattattgga tccgaagttc ctattctcta gaaagtatag   4380

gaacttcctc gaggactacg ttagaacctt gggtaaggtt gtcttggtcg gtttgccagc   4440

tggctccaag gtttctgctc cagtctttga ctccgtcgtc aagtccatcc aaatcaaggg   4500

ttcctatgtc ggtaacagaa aggacactgc cgaagctgtt gactttttct ccagaggctt   4560

gatcaagtgt ccaatcaagg ttgtcggttt ggagacg                            4597
```

<210> SEQ ID NO 50
<211> LENGTH: 445
<212> TYPE: DNA
<213> ORGANISM: Artificial Sequence
<220> FEATURE:
<223> OTHER INFORMATION: Pre-targeting construct for Candida tropicalis ADH-B4B

<400> SEQUENCE: 50

```
cgtctctgtc aacagggtgc cgaaccaaac tgtccacagg ctgacttgtc tggttacacc     60

cacgacggtt ctttccagca atacgccact gcagatgccg tgcaagccgc tagaattcca    120

gctggtactg atttagccaa cgttgccccc atcttgtgtg ctggtgtcac tgtttacaag    180

gccttgaaga ccgccgactt gcagtaggcg gccgctagat cttgcgaagc tccatctcga    240

gggtttgggt tctttggccg ttcaatacgc caaggccatg ggctacagag ttgtcgccat    300

cgatggtggt gccgacaagg gtgagttcgt caagtctttg ggcgctgagg tctttgttga    360

tttcctcaag gaaaaggaca ttgttggtgc tgtcaagaag gcaaccgatg gtggcccaca    420

cggtgccgtt aacgtttccg agacg                                          445
```

<210> SEQ ID NO 51
<211> LENGTH: 4597
<212> TYPE: DNA
<213> ORGANISM: Artificial Sequence
<220> FEATURE:
<223> OTHER INFORMATION: Targeting construct for deletion of Candida tropicalis ADH-B4B

<400> SEQUENCE: 51

```
cgtctctgtc aacagggtgc cgaaccaaac tgtccacagg ctgacttgtc tggttacacc     60

cacgacggtt ctttccagca atacgccact gcagatgccg tgcaagccgc tagaattcca    120

gctggtactg atttagccaa cgttgccccc atcttgtgtg ctggtgtcac tgtttacaag    180

gccttgaaga ccgccgactt gcagtaggcg gccgctctag aactagtgga tctgaagttc    240

ctattctcta gaaagtatag gaacttcctg caggaccacc tttgattgta aatagtaata    300

attaccaccc ttatctaatt atttatttaa cttatttatt tatttattat acatatatac    360

aaatctaata aagtgaaaat ctcccccttc acacttcaca tatgttaggc gtcatcctgt    420

gctcccgaga accagtacca gtacatcgct gtttcgttcg agacttgagg tctagtttta    480

tacgtgaaga ggtcaatgcc gccgagagta aagccacatt ttgcgtacaa attgcaggca    540

ggtacattgt tcgtttgtgt ctctaatcgt atgccaagga gctgtctgct tagtgcccac    600

tttttcgcaa attcgatgag actgtgcgcg actcctttgc ctcggtgcgt gtgcgacaca    660

acaatgtgtt cgatagaggc tagatcgttc catgttgagt tgagttcaat cttcccgaca    720

agctcttggt cgatgaatgc gccatagcaa gcagagtctt catcagagtc atcatccgag    780

atgtaatcct tccggtaggg gctcacactt ctggtagata gttcaaagcc ttggtcggat    840

aggtgcacat cgaacacttc acgaacaatg aaatggttct cagcatccaa tgtttccgcc    900

acctgctcag ggatcaccga aattttcata tgagaaccgt tatcgataac taaagcagca    960
```

```
acttcttcta taaaaatggg ttagtatgac agtcatttaa ataaggaatt tttcagttgg   1020
cttggtttca attcaatgtt cgtttttttt ttttcttgct gtgtttgtgt ttgtgttgtt   1080
tatagttgtg tgcactgagc gtcgaaaaaa aaaattcata gtgagccggg aaatctgtat   1140
agcccagata acaacacaag tccaaactag aaactcgtca aacaccaaaa gcaatgttga   1200
atcaattgcc ttgcacaagt acacgtagga aaacataaaa cattgcaatt ttgaatattg   1260
agccttttgt cgtaacattg attgatagga ttactcaccg aatggttttg aaaccactgc   1320
cgacagatca atcaatcaat caaaaaacgt gaactttgaa aaaggggaag aacagataca   1380
ttgaagttag ccatttccat tgatcgtcac aacatatctg ataaattact ttcaaaatta   1440
taagctgatg tgtgtgtatt attaatgtga cagtaacatc ccaaacgaga aatattatgt   1500
cgacaacaaa aaagtttgat ctgaattgaa aatgaagttt tcccacccta cccatttgtc   1560
atattgaaac caatcaactg attaatcaat caattagaat tgaagctaaa ctaaaacata   1620
ccaccgtcca ttttgaatga ttatattttt ttaatattaa tatcgagata atgtttctaa   1680
gaaagaaaga aaaccaggag tgaaaattag aaaaggaaag gaaaggaaaa aaagaaaaat   1740
ctgaaaatat ataaaaaaaa attgtttcgt tggcaataaa tcttggtgag aacagcgacc   1800
gaaagcaaat aagaacaaaa tatgagtgta ttacgttgaa caactaatta acgtgtgtgt   1860
atggatcttt ttttcttttt tctctttaac cgactataaa caacaaacat ttttgggcag   1920
tgcacacact acttaatata cacagcataa attacacgat tagaaacaaa ttagcttatt   1980
aaaataacct aatcaaaccg aatattttat ggtattatga gtaaactata taatataaat   2040
agcacacacc cacaacaaca acaaaggaaa actaaaaggt tttttctttt tgaaaagatc   2100
gttttcttta ttattctcta gttttgacgc tcgacatttt atgatggaat gaatgggatg   2160
aatcatcaaa caagagaaaa tacccgtgac gaaaataata aaataagttc ctctgataca   2220
gaagatgaaa acaacaacaa caagatatag aaatgccttg ggtggctatt ttatagtctt   2280
aactttttaa tgtatatttg ttttgttttt ttacataata atactttata aaagctaagc   2340
taaattcaag taaaatttca atctctcaaa taaaacattt ttctcttttt cttaaattta   2400
gttttatata tttataaaat atacaaagat ttttttaaaa aagtaacaag ttatatatgt   2460
aataacaaaa agaagaataa caagaataca aaaccagatt tccagatttc cagaatttca   2520
ctcttatatg cgtctattta tgtaggatga aaggtagtct agtacctcct gtgatattat   2580
cccattccat gcggggtatc gtatgcttcc ttcagcacta ccctttagct gttctatatg   2640
ctgccactcc tcaattggat tagtctcatc cttcaatgct atcatttcct ttgatattgg   2700
atcatatgca tagtaccgag aaactagtgc gaagtagtga tcaggtattg ctgttatctg   2760
atgagtatac gttgtcctgg ccacggcaga agcacgctta tcgctccaat ttcccacaac   2820
attagtcaac tccgttaggc ccttcattga aagaaatgag gtcatcaaat gtcttccaat   2880
gtgagatttt gggccatttt ttatagcaaa gattgaataa ggcgcatttt tcttcaaagc   2940
tttattgtac gatctgacta agttatcttt taataattgg tattcctgtt tattgcttga   3000
agaattgccg gtcctattta ctcgttttag gactggttca gaattcctca aaaattcatc   3060
caaatataca agtggatcga tcctacccct tgcgctaaag aagtatatgt gcctactaac   3120
gcttgtcttt gtctctgtca ctaaacactg gattattact cccaaatact tattttggac   3180
taatttaaat gatttcggat caacgttctt aatatcgctg aatcttccac aattgatgaa   3240
agtagctagg aagaggaatt ggtataaagt ttttgttttt gtaaatctcg aagtatactc   3300
aaacgaattt agtattttct cagtgatctc ccagatgctt tcaccctcac ttagaagtgc   3360
```

```
tttaagcatt tttttactgt ggctatttcc cttatctgct tcttccgatg attcgaactg   3420

taattgcaaa ctacttacaa tatcagtgat atcagattga tgtttttgtc catagtaagg   3480

aataattgta aattcccaag caggaatcaa tttctttaat gaggcttcca aaattgttgc   3540

tttttgcgtc ttgtatttaa actggagtga tttattgaca atatcgaaac tcaacgaatt   3600

gcttatgata gtattatagc tcatgaatgt ggctctcttg attgctgttc cgttatgtgt   3660

aatcatccaa cataaatagg ttagttcagc agcacataat gctattttct cacctgaagg   3720

tctttcaaac ctttccacaa actgacgaac aagcacctta ggtggtgttt tacataatat   3780

atcaaattgt ggcatgtcga cgattattag ttaaaccact gcaaaaagtt ggggaaaatt   3840

ttgcccattt ttataccgtg tcttcgtcta tcgcctcccc cactccccaa tctttgaatt   3900

attccgaaat attcagcgaa cggggtgtac acaaaaacta acattctcaa ctgcataatt   3960

tgaaaaatgg cgtgggacaa gaaaaaaaaa aaattctcaa ccatagcaat catggaatac   4020

ggtaaatttg tgttgttcgg tgactccatc acccagttta gttgtaccca gtatggcttt   4080

catccagcat tacagaatgt gtatatccga aaattggatg ttattaaccg tggtttcagt   4140

ggctacaact cagagcacgc tagacaaatt cttccaaaaa ttttagagtc ggaaaccaat   4200

atcaaattga tgacaatatt ttttggaact aacgatgcat acgactacat caatgaaatc   4260

cagacagtcg agttagacag atataaagat aatttaagtg taatggtaca gatggtacta   4320

gacaaaaata tcaaaccaat cattattgga tccgaagttc ctattctcta gaaagtatag   4380

gaacttcctc gagggtttgg gttctttggc cgttcaatac gccaaggcca tgggctacag   4440

agttgtcgcc atcgatggtg gtgccgacaa gggtgagttc gtcaagtctt tgggcgctga   4500

ggtctttgtt gatttcctca aggaaaagga cattgttggt gctgtcaaga aggcaaccga   4560

tggtggccca cacggtgccg ttaacgtttc cgagacg                            4597
```

<210> SEQ ID NO 52
<211> LENGTH: 445
<212> TYPE: DNA
<213> ORGANISM: Artificial Sequence
<220> FEATURE:
<223> OTHER INFORMATION: Pre-targeting construct for Candida tropicalis ADH-A10

<400> SEQUENCE: 52

```
cgtctcgtcc ctaaacccaa cgaattgctt gtcaacgtca agtactcggg tgtgtgtcat     60

tctgacttgc atgtctggaa aggcgactgg cccattcctg ccaagttgcc cttggtggga    120

ggtcacgaag gtgctggtgt cgttgtcggc atgggtgaca acgtcaaggg ctggaaggtg    180

ggggacttgg ctggtatcaa gtggtaggcg gccgctagat cttgcgaagc tccatctcga    240

ggagtacgtc agaactttgg ggaaagtggt tttagttagc ttgccggcag gtggtaaact    300

cactgctcct cttttcgagt ctgttgctag atcaatccag attagaacta cgtgtgttgg    360

caacagaaag gatactactg aagctattga tttctttgtt agagggttga tcgattgccc    420

aattaaagtc gctggtttag agacg                                          445
```

<210> SEQ ID NO 53
<211> LENGTH: 4597
<212> TYPE: DNA
<213> ORGANISM: Artificial Sequence
<220> FEATURE:
<223> OTHER INFORMATION: Targeting construct for deletion of Candida tropicalis ADH-A10

<400> SEQUENCE: 53

```
cgtctcgtcc ctaaacccaa cgaattgctt gtcaacgtca agtactcggg tgtgtgtcat     60
tctgacttgc atgtctggaa aggcgactgg cccattcctg ccaagttgcc cttggtggga    120
ggtcacgaag gtgctggtgt cgttgtcggc atgggtgaca acgtcaaggg ctggaaggtg    180
ggggacttgg ctggtatcaa gtggtaggcg gccgctctag aactagtgga tctgaagttc    240
ctattctcta gaaagtatag gaacttcctg caggaccacc tttgattgta aatagtaata    300
attaccaccc ttatctaatt atttatttaa cttatttatt tatttattat acatatatac    360
aaatctaata aagtgaaaat ctcccccttc acacttcaca tatgttaggc gtcatcctgt    420
gctcccgaga accagtacca gtacatcgct gtttcgttcg agacttgagg tctagtttta    480
tacgtgaaga ggtcaatgcc gccgagagta aagccacatt ttgcgtacaa attgcaggca    540
ggtacattgt tcgtttgtgt ctctaatcgt atgccaagga gctgtctgct tagtgcccac    600
tttttcgcaa attcgatgag actgtgcgcg actcctttgc ctcggtgcgt gtgcgacaca    660
acaatgtgtt cgatagaggc tagatcgttc catgttgagt tgagttcaat cttcccgaca    720
agctcttggt cgatgaatgc gccatagcaa gcagagtctt catcagagtc atcatccgag    780
atgtaatcct tccggtaggg gctcacactt ctggtagata gttcaaagcc ttggtcggat    840
aggtgcacat cgaacacttc acgaacaatg aaatggttct cagcatccaa tgtttccgcc    900
acctgctcag ggatcaccga aattttcata tgagaaccgt tatcgataac taaagcagca    960
acttcttcta taaaaatggg ttagtatgac agtcatttaa ataaggaatt tttcagttgg   1020
cttggtttca attcaatgtt cgtttttttt ttttcttgct gtgtttgtgt ttgtgttgtt   1080
tatagttgtg tgcactgagc gtcgaaaaaa aaaattcata gtgagccggg aaatctgtat   1140
agcccagata acaacacaag tccaaactag aaactcgtca aacaccaaaa gcaatgttga   1200
atcaattgcc ttgcacaagt acacgtagga aaacataaaa cattgcaatt ttgaatattg   1260
agccttttgt cgtaacattg attgatagga ttactcaccg aatggttttg aaaccactgc   1320
cgacagatca atcaatcaat caaaaaacgt gaactttgaa aaaggggaag aacagataca   1380
ttgaagttag ccatttccat tgatcgtcac aacatatctg ataaattact ttcaaaatta   1440
taagctgatg tgtgtgtatt attaatgtga cagtaacatc ccaaacgaga aatattatgt   1500
cgacaacaaa aaagtttgat ctgaattgaa aatgaagttt tcccacccta cccatttgtc   1560
atattgaaac caatcaactg attaatcaat caattagaat tgaagctaaa ctaaaacata   1620
ccaccgtcca ttttgaatga ttatattttt ttaatattaa tatcgagata atgtttctaa   1680
gaaagaaaga aaaccaggag tgaaaattag aaaaggaaag gaaaggaaaa aaagaaaaat   1740
ctgaaaatat ataaaaaaaa attgtttcgt tggcaataaa tcttggtgag aacagcgacc   1800
gaaagcaaat aagaacaaaa tatgagtgta ttacgttgaa caactaatta acgtgtgtgt   1860
atggatcttt ttttcttttt tctctttaac cgactataaa caacaaacat ttttgggcag   1920
tgcacacact acttaatata cacagcataa attacacgat tagaaacaaa ttagcttatt   1980
aaaataacct aatcaaaccg aatattttat ggtattatga gtaaactata taatataaat   2040
agcacacacc cacaacaaca acaaaggaaa actaaaaggt tttttctttt tgaaaagatc   2100
gttttcttta ttattctcta gttttgacgc tcgacatttt atgatggaat gaatgggatg   2160
aatcatcaaa caagagaaaa tacccgtgac gaaaataata aaataagttc ctctgataca   2220
gaagatgaaa acaacaacaa caagatatag aaatgccttg ggtggctatt ttatagtctt   2280
aactttttaa tgtatatttg ttttgttttt ttacataata atactttata aaagctaagc   2340
taaattcaag taaaatttca atctctcaaa taaaacattt ttctcttttt cttaaattta   2400
```

```
gttttatata tttataaaat atacaaagat ttttttaaaa aagtaacaag ttatatatgt   2460
aataacaaaa agaagaataa caagaataca aaaccagatt tccagatttc cagaatttca   2520
ctcttatatg cgtctattta tgtaggatga aaggtagtct agtacctcct gtgatattat   2580
cccattccat gcggggtatc gtatgcttcc ttcagcacta ccctttagct gttctatatg   2640
ctgccactcc tcaattggat tagtctcatc cttcaatgct atcatttcct ttgatattgg   2700
atcatatgca tagtaccgag aaactagtgc gaagtagtga tcaggtattg ctgttatctg   2760
atgagtatac gttgtcctgg ccacggcaga agcacgctta tcgctccaat ttcccacaac   2820
attagtcaac tccgttaggc ccttcattga aagaaatgag gtcatcaaat gtcttccaat   2880
gtgagatttt gggccatttt ttatagcaaa gattgaataa ggcgcatttt tcttcaaagc   2940
tttattgtac gatctgacta agttatcttt taataattgg tattcctgtt tattgcttga   3000
agaattgccg gtcctattta ctcgttttag gactggttca gaattcctca aaaattcatc   3060
caaatataca agtggatcga tcctacccct tgcgctaaag aagtatatgt gcctactaac   3120
gcttgtcttt gtctctgtca ctaaacactg gattattact cccaaatact tattttggac   3180
taatttaaat gatttcggat caacgttctt aatatcgctg aatcttccac aattgatgaa   3240
agtagctagg aagaggaatt ggtataaagt ttttgttttt gtaaatctcg aagtatactc   3300
aaacgaattt agtattttct cagtgatctc ccagatgctt tcaccctcac ttagaagtgc   3360
tttaagcatt tttttactgt ggctatttcc cttatctgct tcttccgatg attcgaactg   3420
taattgcaaa ctacttacaa tatcagtgat atcagattga tgtttttgtc catagtaagg   3480
aataattgta aattcccaag caggaatcaa tttctttaat gaggcttcca aaattgttgc   3540
tttttgcgtc ttgtatttaa actggagtga tttattgaca atatcgaaac tcaacgaatt   3600
gcttatgata gtattatagc tcatgaatgt ggctctcttg attgctgttc cgttatgtgt   3660
aatcatccaa cataaatagg ttagttcagc agcacataat gctattttct cacctgaagg   3720
tctttcaaac ctttccacaa actgacgaac aagcacctta ggtggtgttt tacataaatat   3780
atcaaattgt ggcatgtcga cgattattag ttaaaccact gcaaaaagtt ggggaaaatt   3840
ttgcccattt ttataccgtg tcttcgtcta tcgcctcccc cactccccaa tctttgaatt   3900
attccgaaat attcagcgaa cggggtgtac acaaaaacta acattctcaa ctgcataatt   3960
tgaaaaatgg cgtgggacaa gaaaaaaaaa aaattctcaa ccatagcaat catggaatac   4020
ggtaaatttg tgttgttcgg tgactccatc acccagttta gttgtaccca gtatggcttt   4080
catccagcat tacagaatgt gtatatccga aaattggatg ttattaaccg tggtttcagt   4140
ggctacaact cagagcacgc tagacaaatt cttccaaaaa ttttagagtc ggaaaccaat   4200
atcaaattga tgacaatatt ttttggaact aacgatgcat acgactacat caatgaaatc   4260
cagacagtcg agttagacag atataaagat aatttaagtg taatggtaca gatggtacta   4320
gacaaaaata tcaaaccaat cattattgga tccgaagttc ctattctcta gaaagtatag   4380
gaacttcctc gaggagtacg tcagaacttt ggggaaagtg gttttagtta gcttgccggc   4440
aggtggtaaa ctcactgctc ctcttttcga gtctgttgct agatcaatcc agattagaac   4500
tacgtgtgtt ggcaacagaa aggatactac tgaagctatt gatttctttg ttagagggtt   4560
gatcgattgc ccaattaaag tcgctggttt agagacg                              4597
```

<210> SEQ ID NO 54
<211> LENGTH: 445
<212> TYPE: DNA
<213> ORGANISM: Artificial Sequence
<220> FEATURE:
<223> OTHER INFORMATION: Pre-targeting construct for Candida tropicalis ADH-B11

<400> SEQUENCE: 54

```
cgtctcgtcc ctaagccaaa cgaattgctc gtccacgtca aatactccgg tgtttgtcac     60

tcagatatac acgtctggaa gggtgactgg ttcccagcat cgaaattgcc cgttgttggt    120

ggtcacgaag gtgccggtgt tgtcgttgcc attggtgaaa acgtccaagg ctggaaagta    180

ggtgacttgg caggtataaa gatgtaggcg gccgctagat cttgcgaagc tccatctcga    240

ggaatatgtt agaactttgg gaactgttgt cttggttggt ttgccagctg gtgcaaagct    300

cgaagctcct atcttcaatg ccgttgccaa atccatccaa atcaaaggtt cttacgtggg    360

aaacagaaga gacactgctg aggctgttga tttcttcgct agaggtttgg tcaaatgtcc    420

aattaaggtt gttgggttgg agacg                                           445
```

<210> SEQ ID NO 55
<211> LENGTH: 4597
<212> TYPE: DNA
<213> ORGANISM: Artificial Sequence
<220> FEATURE:
<223> OTHER INFORMATION: Targeting construct for deletion of Candida tropicalis ADH-B11

<400> SEQUENCE: 55

```
cgtctcgtcc ctaagccaaa cgaattgctc gtccacgtca aatactccgg tgtttgtcac     60

tcagatatac acgtctggaa gggtgactgg ttcccagcat cgaaattgcc cgttgttggt    120

ggtcacgaag gtgccggtgt tgtcgttgcc attggtgaaa acgtccaagg ctggaaagta    180

ggtgacttgg caggtataaa gatgtaggcg gccgctctag aactagtgga tctgaagttc    240

ctattctcta gaaagtatag gaacttcctg caggaccacc tttgattgta aatagtaata    300

attaccaccc ttatctaatt atttatttaa cttatttatt tatttattat acatatatac    360

aaatctaata aagtgaaaat ctccccccttc acacttcaca tatgttaggc gtcatcctgt    420

gctcccgaga accagtacca gtacatcgct gtttcgttcg agacttgagg tctagtttta    480

tacgtgaaga ggtcaatgcc gccgagagta aagccacatt ttgcgtacaa attgcaggca    540

ggtacattgt tcgtttgtgt ctctaatcgt atgccaagga gctgtctgct tagtgcccac    600

tttttcgcaa attcgatgag actgtgcgcg actcctttgc ctcggtgcgt gtgcgacaca    660

acaatgtgtt cgatagaggc tagatcgttc catgttgagt tgagttcaat cttcccgaca    720

agctcttggt cgatgaatgc gccatagcaa gcagagtctt catcagagtc atcatccgag    780

atgtaatcct tccggtaggg gctcacactt ctggtagata gttcaaagcc ttggtcggat    840

aggtgcacat cgaacacttc acgaacaatg aaatggttct cagcatccaa tgtttccgcc    900

acctgctcag ggatcaccga aattttcata tgagaaccgt tatcgataac taaagcagca    960

acttcttcta taaaaatggg ttagtatgac agtcatttaa ataaggaatt tttcagttgg   1020

cttggtttca attcaatgtt cgtttttttt ttttcttgct gtgtttgtgt ttgtgttgtt   1080

tatagttgtg tgcactgagc gtcgaaaaaa aaaattcata gtgagccggg aaatctgtat   1140

agcccagata acaacacaag tccaaactag aaactcgtca aacaccaaaa gcaatgttga   1200

atcaattgcc ttgcacaagt acacgtagga aaacataaaa cattgcaatt ttgaatattg   1260

agccttttgt cgtaacattg attgatagga ttactcaccg aatggttttg aaaccactgc   1320

cgacagatca atcaatcaat caaaaaacgt gaactttgaa aaaggggaag aacagataca   1380

ttgaagttag ccatttccat tgatcgtcac aacatatctg ataaattact ttcaaaatta   1440
```

```
taagctgatg tgtgtgtatt attaatgtga cagtaacatc ccaaacgaga aatattatgt   1500

cgacaacaaa aaagtttgat ctgaattgaa aatgaagttt tcccacccta cccatttgtc   1560

atattgaaac caatcaactg attaatcaat caattagaat tgaagctaaa ctaaaacata   1620

ccaccgtcca ttttgaatga ttatattttt ttaatattaa tatcgagata atgtttctaa   1680

gaaagaaaga aaaccaggag tgaaaattag aaaaggaaag gaaaggaaaa aaagaaaaat   1740

ctgaaaatat ataaaaaaaa attgtttcgt tggcaataaa tcttggtgag aacagcgacc   1800

gaaagcaaat aagaacaaaa tatgagtgta ttacgttgaa caactaatta acgtgtgtgt   1860

atggatcttt ttttcttttt tctctttaac cgactataaa caacaaacat ttttgggcag   1920

tgcacacact acttaatata cacagcataa attacacgat tagaaacaaa ttagcttatt   1980

aaaataacct aatcaaaccg aatattttat ggtattatga gtaaactata taatataaat   2040

agcacacacc cacaacaaca acaaaggaaa actaaaaggt tttttctttt tgaaaagatc   2100

gttttcttta ttattctcta gttttgacgc tcgacatttt atgatggaat gaatgggatg   2160

aatcatcaaa caagagaaaa tacccgtgac gaaaataata aaataagttc ctctgataca   2220

gaagatgaaa acaacaacaa caagatatag aaatgccttg ggtggctatt ttatagtctt   2280

aactttttaa tgtatatttg ttttgttttt ttacataata atactttata aaagctaagc   2340

taaattcaag taaaatttca atctctcaaa taaaacattt ttctcttttt cttaaattta   2400

gttttatata tttataaaat atacaaagat ttttttaaaa aagtaacaag ttatatatgt   2460

aataacaaaa agaagaataa caagaataca aaaccagatt tccagatttc cagaatttca   2520

ctcttatatg cgtctattta tgtaggatga aaggtagtct agtacctcct gtgatattat   2580

cccattccat gcggggtatc gtatgcttcc ttcagcacta ccctttagct gttctatatg   2640

ctgccactcc tcaattggat tagtctcatc cttcaatgct atcatttcct ttgatattgg   2700

atcatatgca tagtaccgag aaactagtgc gaagtagtga tcaggtattg ctgttatctg   2760

atgagtatac gttgtcctgg ccacggcaga agcacgctta tcgctccaat ttcccacaac   2820

attagtcaac tccgttaggc ccttcattga aagaaatgag gtcatcaaat gtcttccaat   2880

gtgagatttt gggccatttt ttatagcaaa gattgaataa ggcgcatttt tcttcaaagc   2940

tttattgtac gatctgacta agttatcttt taataattgg tattcctgtt tattgcttga   3000

agaattgccg gtcctattta ctcgttttag gactggttca gaattcctca aaaattcatc   3060

caaatataca agtggatcga tcctacccct tgcgctaaag aagtatatgt gcctactaac   3120

gcttgtcttt gtctctgtca ctaaacactg gattattact cccaaatact tattttggac   3180

taatttaaat gatttcggat caacgttctt aatatcgctg aatcttccac aattgatgaa   3240

agtagctagg aagaggaatt ggtataaagt ttttgttttt gtaaatctcg aagtatactc   3300

aaacgaattt agtattttct cagtgatctc ccagatgctt tcaccctcac ttagaagtgc   3360

tttaagcatt tttttactgt ggctatttcc cttatctgct tcttccgatg attcgaactg   3420

taattgcaaa ctacttacaa tatcagtgat atcagattga tgtttttgtc catagtaagg   3480

aataattgta aattcccaag caggaatcaa tttctttaat gaggcttcca aaattgttgc   3540

tttttgcgtc ttgtatttaa actggagtga tttattgaca atatcgaaac tcaacgaatt   3600

gcttatgata gtattatagc tcatgaatgt ggctctcttg attgctgttc cgttatgtgt   3660

aatcatccaa cataaatagg ttagttcagc agcacataat gctattttct cacctgaagg   3720

tctttcaaac ctttccacaa actgacgaac aagcacctta ggtggtgttt tacataatat   3780

atcaaattgt ggcatgtcga cgattattag ttaaaccact gcaaaaagtt ggggaaaatt   3840
```

```
ttgcccattt ttataccgtg tcttcgtcta tcgcctcccc cactccccaa tctttgaatt   3900

attccgaaat attcagcgaa cggggtgtac acaaaaacta acattctcaa ctgcataatt   3960

tgaaaaatgg cgtgggacaa gaaaaaaaaa aaattctcaa ccatagcaat catggaatac   4020

ggtaaatttg tgttgttcgg tgactccatc acccagttta gttgtaccca gtatggcttt   4080

catccagcat tacagaatgt gtatatccga aaattggatg ttattaaccg tggtttcagt   4140

ggctacaact cagagcacgc tagacaaatt cttccaaaaa ttttagagtc ggaaaccaat   4200

atcaaattga tgacaatatt ttttggaact aacgatgcat acgactacat caatgaaatc   4260

cagacagtcg agttagacag atataaagat aatttaagtg taatggtaca gatggtacta   4320

gacaaaaata tcaaaccaat cattattgga tccgaagttc ctattctcta gaaagtatag   4380

gaacttcctc gaggaatatg ttagaacttt gggaactgtt gtcttggttg gtttgccagc   4440

tggtgcaaag ctcgaagctc ctatcttcaa tgccgttgcc aaatccatcc aaatcaaagg   4500

ttcttacgtg ggaaacagaa gagacactgc tgaggctgtt gatttcttcg ctagaggttt   4560

ggtcaaatgt ccaattaagg ttgttgggtt ggagacg                            4597
```

<210> SEQ ID NO 56
<211> LENGTH: 460
<212> TYPE: DNA
<213> ORGANISM: Candida tropicalis

<400> SEQUENCE: 56

```
tgaactgtga gttttgccaa cagggcgctg aacctaattg tccaagagcc gacatgtctg     60

gatataccca cgatgggact ttccaacaat atgctaccgc cgatgccgtc caagctgcca    120

agatcccaga aggcgcagac atggctagta tcgccccgat cttgtgtgct ggtgtgaccg    180

tgtacaaggc tttgaagaac gccgacttgt tggctggcca atgggtggct atctctggtg    240

ctggtggtgg tttgggctcc ttgggtgtgc agtacgctaa agccatgggt tacagagtgt    300

tagccatcga tggtggtgat gagagaggag agtttgtcaa gtcattgggc gccgaagtgt    360

acattgactt ccttaaggaa caggacattg ttagtgccat tagaaaggca actggtggtg    420

gcccacacgg tgttattaac gtctcggtgt ccgaaaaggc                          460
```

<210> SEQ ID NO 57
<211> LENGTH: 445
<212> TYPE: DNA
<213> ORGANISM: Artificial Sequence
<220> FEATURE:
<223> OTHER INFORMATION: Pre-targeting construct for Candida tropicalis ADH-A10B

<400> SEQUENCE: 57

```
cgtctctgcc aacagggcgc tgaacctaat tgtccaagag ccgacatgtc tggatatacc     60

cacgatggga ctttccaaca atatgctacc gccgatgccg tccaagctgc caagatccca    120

gaaggcgcag acatggctag tatcgccccg atcttgtgtg ctggtgtgac cgtgtacaag    180

gctttgaaga acgccgactt gttgtaggcg gccgctagat cttgcgaagc tccatctcga    240

gggtttgggc tccttgggtg tgcagtacgc taaagccatg ggttacagag tgttagccat    300

cgatggtggt gatgagagag gagagtttgt caagtcattg ggcgccgaag tgtacattga    360

cttccttaag gaacaggaca ttgttagtgc cattagaaag gcaactggtg gtggcccaca    420

cggtgttatt aacgtgtcgg agacg                                          445
```

<210> SEQ ID NO 58

<211> LENGTH: 4597
<212> TYPE: DNA
<213> ORGANISM: Artificial Sequence
<220> FEATURE:
<223> OTHER INFORMATION: Targeting construct for deletion of Candida tropicalis ADH-A10B

<400> SEQUENCE: 58

```
cgtctctgcc aacagggcgc tgaacctaat tgtccaagag ccgacatgtc tggatatacc     60
cacgatggga ctttccaaca atatgctacc gccgatgccg tccaagctgc caagatccca    120
gaaggcgcag acatggctag tatcgccccg atcttgtgtg ctggtgtgac cgtgtacaag    180
gctttgaaga acgccgactt gttgtaggcg gccgctctag aactagtgga tctgaagttc    240
ctattctcta gaaagtatag gaacttcctg caggaccacc tttgattgta aatagtaata    300
attaccaccc ttatctaatt atttatttaa cttatttatt tatttattat acatatatac    360
aaatctaata aagtgaaaat ctcccccttc acacttcaca tatgttaggc gtcatcctgt    420
gctcccgaga accagtacca gtacatcgct gtttcgttcg agacttgagg tctagtttta    480
tacgtgaaga ggtcaatgcc gccgagagta aagccacatt ttgcgtacaa attgcaggca    540
ggtacattgt tcgtttgtgt ctctaatcgt atgccaagga gctgtctgct tagtgcccac    600
tttttcgcaa attcgatgag actgtgcgcg actcctttgc ctcggtgcgt gtgcgacaca    660
acaatgtgtt cgatagaggc tagatcgttc catgttgagt tgagttcaat cttcccgaca    720
agctcttggt cgatgaatgc gccatagcaa gcagagtctt catcagagtc atcatccgag    780
atgtaatcct tccggtaggg gctcacactt ctggtagata gttcaaagcc ttggtcggat    840
aggtgcacat cgaacacttc acgaacaatg aaatggttct cagcatccaa tgtttccgcc    900
acctgctcag ggatcaccga aattttcata tgagaaccgt tatcgataac taaagcagca    960
acttcttcta taaaaatggg ttagtatgac agtcatttaa ataaggaatt tttcagttgg   1020
cttggtttca attcaatgtt cgtttttttt ttttcttgct gtgtttgtgt ttgtgttgtt   1080
tatagttgtg tgcactgagc gtcgaaaaaa aaaattcata gtgagccggg aaatctgtat   1140
agcccagata acaacacaag tccaaactag aaactcgtca aacaccaaaa gcaatgttga   1200
atcaattgcc ttgcacaagt acacgtagga aaacataaaa cattgcaatt ttgaatattg   1260
agccttttgt cgtaacattg attgatagga ttactcaccg aatggttttg aaaccactgc   1320
cgacagatca atcaatcaat caaaaaacgt gaactttgaa aaaggggaag aacagataca   1380
ttgaagttag ccatttccat tgatcgtcac aacatatctg ataaattact ttcaaaatta   1440
taagctgatg tgtgtgtatt attaatgtga cagtaacatc ccaaacgaga aatattatgt   1500
cgacaacaaa aaagtttgat ctgaattgaa aatgaagttt tcccacccta cccatttgtc   1560
atattgaaac caatcaactg attaatcaat caattagaat tgaagctaaa ctaaaacata   1620
ccaccgtcca ttttgaatga ttatattttt ttaatattaa tatcgagata atgtttctaa   1680
gaaagaaaga aaaccaggag tgaaaattag aaaaggaaag gaaaggaaaa aaagaaaaat   1740
ctgaaaatat ataaaaaaaa attgtttcgt tggcaataaa tcttggtgag aacagcgacc   1800
gaaagcaaat aagaacaaaa tatgagtgta ttacgttgaa caactaatta acgtgtgtgt   1860
atggatcttt ttttcttttt tctctttaac cgactataaa caacaaacat ttttgggcag   1920
tgcacacact acttaatata cacagcataa attacacgat tagaaacaaa ttagcttatt   1980
aaaataacct aatcaaaccg aatattttat ggtattatga gtaaactata taatataaat   2040
agcacacacc cacaacaaca acaaaggaaa actaaaaggt tttttctttt tgaaaagatc   2100
gttttcttta ttattctcta gttttgacgc tcgacatttt atgatggaat gaatgggatg   2160
```

```
aatcatcaaa caagagaaaa tacccgtgac gaaaataata aaataagttc ctctgataca   2220
gaagatgaaa acaacaacaa caagatatag aaatgccttg ggtggctatt ttatagtctt   2280
aactttttaa tgtatatttg ttttgttttt ttacataata atactttata aaagctaagc   2340
taaattcaag taaaatttca atctctcaaa taaaacattt ttctcttttt cttaaattta   2400
gttttatata tttataaaat atacaaagat ttttttaaaa aagtaacaag ttatatatgt   2460
aataacaaaa agaagaataa caagaataca aaaccagatt tccagatttc cagaatttca   2520
ctcttatatg cgtctattta tgtaggatga aaggtagtct agtacctcct gtgatattat   2580
cccattccat gcggggtatc gtatgcttcc ttcagcacta ccctttagct gttctatatg   2640
ctgccactcc tcaattggat tagtctcatc cttcaatgct atcatttcct ttgatattgg   2700
atcatatgca tagtaccgag aaactagtgc gaagtagtga tcaggtattg ctgttatctg   2760
atgagtatac gttgtcctgg ccacggcaga agcacgctta tcgctccaat ttcccacaac   2820
attagtcaac tccgttaggc ccttcattga aagaaatgag gtcatcaaat gtcttccaat   2880
gtgagatttt gggccatttt ttatagcaaa gattgaataa ggcgcatttt tcttcaaagc   2940
tttattgtac gatctgacta agttatcttt taataattgg tattcctgtt tattgcttga   3000
agaattgccg gtcctattta ctcgttttag gactggttca gaattcctca aaaattcatc   3060
caaatataca agtggatcga tcctacccct tgcgctaaag aagtatatgt gcctactaac   3120
gcttgtcttt gtctctgtca ctaaacactg gattattact cccaaatact tattttggac   3180
taatttaaat gatttcggat caacgttctt aatatcgctg aatcttccac aattgatgaa   3240
agtagctagg aagaggaatt ggtataaagt ttttgttttt gtaaatctcg aagtatactc   3300
aaacgaattt agtattttct cagtgatctc ccagatgctt tcaccctcac ttagaagtgc   3360
tttaagcatt tttttactgt ggctatttcc cttatctgct tcttccgatg attcgaactg   3420
taattgcaaa ctacttacaa tatcagtgat atcagattga tgtttttgtc catagtaagg   3480
aataattgta aattcccaag caggaatcaa tttctttaat gaggcttcca aaattgttgc   3540
tttttgcgtc ttgtatttaa actggagtga tttattgaca atatcgaaac tcaacgaatt   3600
gcttatgata gtattatagc tcatgaatgt ggctctcttg attgctgttc cgttatgtgt   3660
aatcatccaa cataaatagg ttagttcagc agcacataat gctattttct cacctgaagg   3720
tctttcaaac ctttccacaa actgacgaac aagcacctta ggtggtgttt tacataatat   3780
atcaaattgt ggcatgtcga cgattattag ttaaaccact gcaaaaagtt ggggaaaatt   3840
ttgcccattt ttataccgtg tcttcgtcta tcgcctcccc cactccccaa tctttgaatt   3900
attccgaaat attcagcgaa cggggtgtac acaaaaacta acattctcaa ctgcataatt   3960
tgaaaaatgg cgtgggacaa gaaaaaaaaa aaattctcaa ccatagcaat catggaatac   4020
ggtaaatttg tgttgttcgg tgactccatc acccagttta gttgtaccca gtatggcttt   4080
catccagcat tacagaatgt gtatatccga aaattggatg ttattaaccg tggtttcagt   4140
ggctacaact cagagcacgc tagacaaatt cttccaaaaa ttttagagtc ggaaaccaat   4200
atcaaattga tgacaatatt ttttggaact aacgatgcat acgactacat caatgaaatc   4260
cagacagtcg agttagacag atataaagat aatttaagtg taatggtaca gatggtacta   4320
gacaaaaata tcaaaccaat cattattgga tccgaagttc ctattctcta gaaagtatag   4380
gaacttcctc gagggtttgg gctccttggg tgtgcagtac gctaaagcca tgggttacag   4440
agtgttagcc atcgatggtg gtgatgagag aggagagttt gtcaagtcat tgggcgccga   4500
agtgtacatt gacttcctta aggaacagga cattgttagt gccattagaa aggcaactgg   4560
```

tggtggccca cacggtgtta ttaacgtgtc ggagacg 4597

<210> SEQ ID NO 59
<211> LENGTH: 948
<212> TYPE: DNA
<213> ORGANISM: Candida tropicalis

<400> SEQUENCE: 59
ccattgcaat acaccgatat cccagttcca gtccctaagc caaacgattt gctcgtcaat 60
gtcaaatact ccggtctttg tcactcagat atacacctct ggaagggtga ctgattccca 120
gcatcaaaat tgccagttgt tggtggtcac gaaggtgcca gtgttgtcgt tgctattggt 180
gaaaacgtcc agggctggaa agtaggtgcc ttggcgggca taaagatgtt gaatggttcc 240
tgtatgaact gtgaattctg tcaacaaagt gcttaaccaa gctgtcccca tgctgatgtc 300
tcgggttact cccacgacgg cactttccaa cagtacgcta ccgctgatgc tgctcaagct 360
gctaaattcc cagctggttc tgatttagct agcatcgcac ctatatcctg tgccggtgtt 420
actgtttaca aagcattgaa gactgctggc ttgcatccgg gccaatgggt tgccatctcc 480
gatgctggtg gtggtttggg ttctttggcc gtgcaatacg ccaaggccat gggctacaga 540
gtggtggcca ttgactgcgg cggcgaaaat ggagtgtttg tcagatcgtt gggtactgaa 600
gctttcgttg attccaccaa ggaggccaat gtctctgagg ctatcatcaa ggctaccgac 660
ggtggtgtcc atggtgtcat caacgtttcc atttctgaaa aagccatcaa ccagtctgtt 720
gaaaatgtca gaactttggg tactgttgtc ttggttggtt tgccagctgg tgccaagctc 780
gaagcaccta tcttcaatgc cgttgccaaa tccatctaaa tcaaggattc ttacgtgggt 840
aaccgaagag acactgctga ggctgttgat ttcttcgcga aaggtttggt caagtgtcca 900
attaaggttg ttgagttgag tgaattgcca gagattttca aattgttg 948

<210> SEQ ID NO 60
<211> LENGTH: 445
<212> TYPE: DNA
<213> ORGANISM: Artificial Sequence
<220> FEATURE:
<223> OTHER INFORMATION: Pre-targeting construct for Candida tropicalis ADH-B11B

<400> SEQUENCE: 60
cgtctctgtc aacaaagtgc ttaaccaagc tgtccccatg ctgatgtctc gggttactcc 60
cacgacggca ctttccaaca gtacgctacc gctgatgctg ctcaagctgc taaattccca 120
gctggttctg atttagctag catcgcacct atatcctgtg ccggtgttac tgtttacaaa 180
gcattgaaga ctgctggctt gcattaggcg gccgctagat cttgcgaagc tccatctcga 240
gggtttgggt tctttggccg tgcaatacgc caaggccatg ggctacagag tggtggccat 300
tgactgcggc ggcgaaaatg gagtgtttgt cagatcgttg ggtactgaag ctttcgttga 360
ttccaccaag gaggccaatg tctctgaggc tatcatcaag gctaccgacg gtggtgtcca 420
tggtgtcatc aacgtttccg agacg 445

<210> SEQ ID NO 61
<211> LENGTH: 4597
<212> TYPE: DNA
<213> ORGANISM: Artificial Sequence
<220> FEATURE:
<223> OTHER INFORMATION: Targeting construct for deletion of Candida tropicalis ADH-B11B

<400> SEQUENCE: 61

```
cgtctctgtc aacaaagtgc ttaaccaagc tgtccccatg ctgatgtctc gggttactcc     60
cacgacggca ctttccaaca gtacgctacc gctgatgctg ctcaagctgc taaattccca    120
gctggttctg atttagctag catcgcacct atatcctgtg ccggtgttac tgtttacaaa    180
gcattgaaga ctgctggctt gcattaggcg gccgctctag aactagtgga tctgaagttc    240
ctattctcta gaaagtatag gaacttcctg caggaccacc tttgattgta aatagtaata    300
attaccaccc ttatctaatt atttatttaa cttatttatt tatttattat acatatatac    360
aaatctaata aagtgaaaat ctcccccttc acacttcaca tatgttaggc gtcatcctgt    420
gctcccgaga accagtacca gtacatcgct gtttcgttcg agacttgagg tctagtttta    480
tacgtgaaga ggtcaatgcc gccgagagta aagccacatt ttgcgtacaa attgcaggca    540
ggtacattgt tcgtttgtgt ctctaatcgt atgccaagga gctgtctgct tagtgcccac    600
tttttcgcaa attcgatgag actgtgcgcg actcctttgc ctcggtgcgt gtgcgacaca    660
acaatgtgtt cgatagaggc tagatcgttc catgttgagt tgagttcaat cttcccgaca    720
agctcttggt cgatgaatgc gccatagcaa gcagagtctt catcagagtc atcatccgag    780
atgtaatcct tccggtaggg gctcacactt ctggtagata gttcaaagcc ttggtcggat    840
aggtgcacat cgaacacttc acgaacaatg aaatggttct cagcatccaa tgtttccgcc    900
acctgctcag ggatcaccga aattttcata tgagaaccgt tatcgataac taaagcagca    960
acttcttcta taaaaatggg ttagtatgac agtcatttaa ataaggaatt tttcagttgg   1020
cttggtttca attcaatgtt cgtttttttt ttttcttgct gtgtttgtgt ttgtgttgtt   1080
tatagttgtg tgcactgagc gtcgaaaaaa aaaattcata gtgagccggg aaatctgtat   1140
agcccagata acaacacaag tccaaactag aaactcgtca aacaccaaaa gcaatgttga   1200
atcaattgcc ttgcacaagt acacgtagga aaacataaaa cattgcaatt ttgaatattg   1260
agccttttgt cgtaacattg attgatagga ttactcaccg aatggttttg aaaccactgc   1320
cgacagatca atcaatcaat caaaaaacgt gaactttgaa aaaggggaag aacagataca   1380
ttgaagttag ccatttccat tgatcgtcac aacatatctg ataaattact ttcaaaatta   1440
taagctgatg tgtgtgtatt attaatgtga cagtaacatc ccaaacgaga aatattatgt   1500
cgacaacaaa aaagtttgat ctgaattgaa aatgaagttt tcccacccta cccatttgtc   1560
atattgaaac caatcaactg attaatcaat caattagaat tgaagctaaa ctaaaacata   1620
ccaccgtcca ttttgaatga ttatattttt ttaatattaa tatcgagata atgtttctaa   1680
gaaagaaaga aaaccaggag tgaaaattag aaaaggaaag gaaaggaaaa aaagaaaaat   1740
ctgaaaatat ataaaaaaaa attgtttcgt tggcaataaa tcttggtgag aacagcgacc   1800
gaaagcaaat aagaacaaaa tatgagtgta ttacgttgaa caactaatta acgtgtgtgt   1860
atggatcttt ttttcttttt tctctttaac cgactataaa caacaaacat ttttgggcag   1920
tgcacacact acttaatata cacagcataa attacacgat tagaaacaaa ttagcttatt   1980
aaaataacct aatcaaaccg aatattttat ggtattatga gtaaactata taatataaat   2040
agcacacacc cacaacaaca acaaaggaaa actaaaaggt tttttctttt tgaaaagatc   2100
gttttcttta ttattctcta gttttgacgc tcgacatttt atgatggaat gaatgggatg   2160
aatcatcaaa caagagaaaa tacccgtgac gaaaataata aaataagttc ctctgataca   2220
gaagatgaaa acaacaacaa caagatatag aaatgccttg ggtggctatt ttatagtctt   2280
aactttttaa tgtatatttg ttttgttttt ttacataata atactttata aaagctaagc   2340
taaattcaag taaaatttca atctctcaaa taaaacattt ttctcttttt cttaaattta   2400
```

```
gttttatata tttataaaat atacaaagat ttttttaaaa aagtaacaag ttatatatgt   2460
aataacaaaa agaagaataa caagaataca aaaccagatt tccagatttc cagaatttca   2520
ctcttatatg cgtctattta tgtaggatga aaggtagtct agtacctcct gtgatattat   2580
cccattccat gcggggtatc gtatgcttcc ttcagcacta ccctttagct gttctatatg   2640
ctgccactcc tcaattggat tagtctcatc cttcaatgct atcatttcct ttgatattgg   2700
atcatatgca tagtaccgag aaactagtgc gaagtagtga tcaggtattg ctgttatctg   2760
atgagtatac gttgtcctgg ccacggcaga agcacgctta tcgctccaat ttcccacaac   2820
attagtcaac tccgttaggc ccttcattga aagaaatgag gtcatcaaat gtcttccaat   2880
gtgagatttt gggccatttt ttatagcaaa gattgaataa ggcgcatttt tcttcaaagc   2940
tttattgtac gatctgacta agttatcttt taataattgg tattcctgtt tattgcttga   3000
agaattgccg gtcctattta ctcgttttag gactggttca gaattcctca aaaattcatc   3060
caaatataca agtggatcga tcctacccct tgcgctaaag aagtatatgt gcctactaac   3120
gcttgtcttt gtctctgtca ctaaacactg gattattact cccaaatact tattttggac   3180
taatttaaat gatttcggat caacgttctt aatatcgctg aatcttccac aattgatgaa   3240
agtagctagg aagaggaatt ggtataaagt ttttgttttt gtaaatctcg aagtatactc   3300
aaacgaattt agtattttct cagtgatctc ccagatgctt tcaccctcac ttagaagtgc   3360
tttaagcatt tttttactgt ggctatttcc cttatctgct tcttccgatg attcgaactg   3420
taattgcaaa ctacttacaa tatcagtgat atcagattga tgtttttgtc catagtaagg   3480
aataattgta aattcccaag caggaatcaa tttctttaat gaggcttcca aaattgttgc   3540
tttttgcgtc ttgtatttaa actggagtga tttattgaca atatcgaaac tcaacgaatt   3600
gcttatgata gtattatagc tcatgaatgt ggctctcttg attgctgttc cgttatgtgt   3660
aatcatccaa cataaatagg ttagttcagc agcacataat gctattttct cacctgaagg   3720
tctttcaaac ctttccacaa actgacgaac aagcacctta ggtggtgttt tacataatat   3780
atcaaattgt ggcatgtcga cgattattag ttaaaccact gcaaaaagtt ggggaaaatt   3840
ttgcccattt ttataccgtg tcttcgtcta tcgcctcccc cactccccaa tctttgaatt   3900
attccgaaat attcagcgaa cggggtgtac acaaaaacta acattctcaa ctgcataatt   3960
tgaaaaatgg cgtgggacaa gaaaaaaaaa aaattctcaa ccatagcaat catggaatac   4020
ggtaaatttg tgttgttcgg tgactccatc acccagttta gttgtaccca gtatggcttt   4080
catccagcat tacagaatgt gtatatccga aaattggatg ttattaaccg tggtttcagt   4140
ggctacaact cagagcacgc tagacaaatt cttccaaaaa ttttagagtc ggaaaccaat   4200
atcaaattga tgacaatatt ttttggaact aacgatgcat acgactacat caatgaaatc   4260
cagacagtcg agttagacag atataaagat aatttaagtg taatggtaca gatggtacta   4320
gacaaaaata tcaaaccaat cattattgga tccgaagttc ctattctcta gaaagtatag   4380
gaacttcctc gagggtttgg gttctttggc cgtgcaatac gccaaggcca tgggctacag   4440
agtggtggcc attgactgcg gcggcgaaaa tggagtgttt gtcagatcgt tgggtactga   4500
agctttcgtt gattccacca aggaggccaa tgtctctgag gctatcatca aggctaccga   4560
cggtggtgtc catggtgtca tcaacgtttc cgagacg                             4597
```

<210> SEQ ID NO 62
<211> LENGTH: 1484
<212> TYPE: DNA
<213> ORGANISM: Candida tropicalis

<400> SEQUENCE: 62

```
tattaggcga agaggcatct agtagtagtg gcagtggtga gaacgtgggc gctgctatag      60
tgaacaatct ccagtcgatg gttaagaaga agagtgacaa accagcagtg aatgacttgt     120
ctgggtccgt gaggaaaaga aagaagcccg acacaaagga cagtaacgtc aagaaaccca     180
agaaataggg gggacctgtt tagatgtata ggaataaaaa ctccgagatg atctcaatgt     240
gtaatggagt tgtaatattg caaaggggga aaatcaagac tcaaacgtgt gtatgagtga     300
gcgtacgtat atctccgaga gtagtatgac ataatgatga ctgtgaatca tcgtaatctc     360
acacaaaaac cccattgtcg gccatatacc acaccaagca acaccacata tcccccggaa     420
aaaaaaacgt gaaaaaaaga aacaatcaaa actacaacct actccttgat cacacagtca     480
ttgatcaagt tacagttcct gctagggaat gaccaaggta caaatcagca ccttaatggt     540
tagcacgctc tcttactctc tctcacagtc ttccggcccc tattcaaaat tctgcacttc     600
catttgaccc cagggttggg aaacagggcc acaaaagaaa aacccgacgt gaatgaaaaa     660
actaagaaaa gaaaaaaaat tatcacacca gaaatttacc taattgggta attcccatcg     720
gtgtttttcc tggattgtcg cacgcacgca tgctgaaaaa agtgttcgag ttttgctttt     780
gcctcggagt ttcacgcaag tttttcgatc tcggaaccgg agggcggtcg ccttgttgtt     840
tgtgatgtcg tgctttgggt gttctaatgt gctgttattg tgctcttttt ttttcttctt     900
tttttggtga tcatatgata ttgctcggta gattactttc gtgtgtaggt attcttttag     960
acgtttggtt attgggtaga tatgagagag agagagtggg tgggggagga gttggttgta    1020
ggagggaccc ctgggaggaa gtgtagttga gttttccctg acgaatgaaa atacgttttt    1080
gagaagataa tacaggaaag gtgtgtcggt gaatttccat ctatccgagg atatgagtgg    1140
aggagagtcg tgtgcgtgtg gttaatttag gatcagtgga acacacaaag taactaagac    1200
agagagacag agagaaaaat ctggggaaga gacaaagagt cagagtgtgt gagttattct    1260
gtattgtgaa attttttttgc ccaactacat aatattgctg aaactaattt tacttaaaaa    1320
gaaaagccaa caacgtcccc agtaaaactt ttctataaat atcagcagtt ttccctttcc    1380
tccattcctc ttcttgtctt ttttcttact ttccctttttt tataccttttt cattatcatc    1440
ctttataatt gtctaaccaa caactatata tctatcaacc atgg                     1484
```

<210> SEQ ID NO 63
<211> LENGTH: 319
<212> TYPE: DNA
<213> ORGANISM: Candida tropicalis

<400> SEQUENCE: 63

```
aagaaaaaag aaaaggtaaa gaacttcatt tgagatgaac ttttgtatat gacttttagt      60
ttctactttt ttttttattt attgcttaat tttctttatt tcaatccccc atagtttgtg     120
tagaatatat ttattcattc tggtaactca aacacgtagc aagctcgttg catctcgcct     180
cgtcacgggt acagctctgg aaccaaagac aaaaaaaaaa gttgatccga accctctcgc     240
tattccttgc tatgctatcc acgagatggg gtttatcagc ccaggcaagt cactaaagag     300
acaaagaccc agaaagaat                                                  319
```

<210> SEQ ID NO 64
<211> LENGTH: 412
<212> TYPE: DNA
<213> ORGANISM: Saccharomyces cerevisiae

<400> SEQUENCE: 64

```
cccacacacc atagcttcaa aatgtttcta ctcctttttt actcttccag attttctcgg     60

actccgcgca tcgccgtacc acttcaaaac acccaagcac agcatactaa attttccctc    120

tttcttcctc tagggtgtcg ttaattaccc gtactaaagg tttggaaaag aaaaaagaga    180

ccgcctcgtt tctttttctt cgtcgaaaaa ggcaataaaa atttttatca cgtttctttt    240

tcttgaaatt ttttttttta gtttttttct ctttcagtga cctccattga tatttaagtt    300

aataaacggt cttcaatttc tcaagtttca gtttcatttt tcttgttcta ttacaacttt    360

ttttacttct tgttcattag aaagaaagca tagcaatcta atctaagggg cg            412


<210> SEQ ID NO 65
<211> LENGTH: 68
<212> TYPE: DNA
<213> ORGANISM: Artificial sequence
<220> FEATURE:
<223> OTHER INFORMATION: EM7 promoter

<400> SEQUENCE: 65

gtgttgacaa ttaatcatcg gcatagtata tcggcatagt ataatacgac aaggtgagga     60

actaaacc                                                              68


<210> SEQ ID NO 66
<211> LENGTH: 375
<212> TYPE: DNA
<213> ORGANISM: Artificial Sequence
<220> FEATURE:
<223> OTHER INFORMATION: Zeocin-resistance gene optimized for Candida
      tropicali

<400> SEQUENCE: 66

atgtctaaat taacctctgc tgttccagtg ttaaccgccc gtgatgttgc cggtgcagtg     60

gaattttgga ctgaccgttt gggtttctca cgtgactttg tcgaagatga ttttgctggc    120

gttgtgcgtg atgacgtcac tttgttcatc tctgctgttc aggatcaggt cgtcccagac    180

aacactttgg cctgggtctg ggttcgtggt ttggacgaat tgtacgctga gtggagtgaa    240

gttgtgtcta caaactttcg tgatgcatca ggtccagcta tgaccgaaat tggcgaacaa    300

ccttggggcc gtgagttcgc tttacgtgat ccagccggta attgcgtgca cttcgttgct    360

gaggagcaag attag                                                     375


<210> SEQ ID NO 67
<211> LENGTH: 230
<212> TYPE: DNA
<213> ORGANISM: Artificial Sequence
<220> FEATURE:
<223> OTHER INFORMATION: CYC1 transcription terminator

<400> SEQUENCE: 67

cacgtccgac ggcggcccac gggtcccagg cctcggagat ccgtccccct tttcctttgt     60

cgatatcatg taattagtta tgtcacgctt acattcacgc cctcccccca catccgctct    120

aaccgaaaag gaaggagtta gacaacctga agtctaggtc cctatttatt tttttatagt    180

tatgttagta ttaagaacgt tatttatatt tcaaattttt cttttttttc               230


<210> SEQ ID NO 68
<211> LENGTH: 805
<212> TYPE: DNA
<213> ORGANISM: Artificial Sequence
<220> FEATURE:
<223> OTHER INFORMATION: pUC bacterial origin of replication
```

<400> SEQUENCE: 68

```
ctcatgacca aaatccctta acgtgagtta cgcgcgcgtc gttccactga gcgtcagacc     60
ccgtagaaaa gatcaaagga tcttcttgag atcctttttt tctgcgcgta atctgctgct    120
tgcaaacaaa aaaaccaccg ctaccagcgg tggtttgttt gccggatcaa gagctaccaa    180
ctctttttcc gaaggtaact ggcttcagca gagcgcagat accaaatact gttcttctag    240
tgtagccgta gttagcccac cacttcaaga actctgtagc accgcctaca tacctcgctc    300
tgctaatcct gttaccagtg gctgctgcca gtggcgataa gtcgtgtctt accgggttgg    360
actcaagacg atagttaccg gataaggcgc agcggtcggg ctgaacgggg ggttcgtgca    420
cacagcccag cttggagcga acgacctaca ccgaactgag atacctacag cgtgagctat    480
gagaaagcgc cacgcttccc gaagggagaa aggcggacag gtatccggta agcggcaggg    540
tcggaacagg agagcgcacg agggagcttc caggggggaaa cgcctggtat ctttatagtc    600
ctgtcgggtt tcgccacctc tgacttgagc gtcgattttt gtgatgctcg tcaggggggc    660
ggagcctatg gaaaaacgcc agcaacgcgg cctttttacg gttcctggcc ttttgctggc    720
cttttgctca catgttcttt cctgcgttat cccctgattc tgtggataac cgtattaccg    780
cctttgagtg agctgatacc gctcg                                          805
```

<210> SEQ ID NO 69
<211> LENGTH: 1554
<212> TYPE: DNA
<213> ORGANISM: Candida tropicalis

<400> SEQUENCE: 69

```
atggctgagc aattgttgga atattggtac gttgtggtgc cagttttgta tatcattaag     60
caattattgg cctacaccaa gaccagagtc ttaatgaaga agttgggtgc cgccccagtt    120
actaacaaat tgtacgacaa cgctttcgga attgtcaacg gatggaaggc tttgcaattt    180
aagaaggagg gtagagccca agaatacaat gattataagt ttgatcacag taaaaaccct    240
tccgtcggta cttacgtgtc cattttgttt ggcactagaa ttgtcgtcac caaagaccca    300
gaaaatatca aagctatctt ggctacacaa tttggtgact tctccttggg caaaagacac    360
accttattta agccattgtt gggagatggt attttcacct tagacggcga aggttggaaa    420
cactccagag ccatgttgcg tccacaattt gcaagagaac aggttgctca cgttacctct    480
ttggaaccac attttcaatt attgaagaaa cacattttga aacacaaggg tgagtacttc    540
gacatccaag aattattctt tagattcacc gttgactccg ccactgagtt tttgtttggt    600
gagtccgttc attccttgaa agacgaaagt attggtatta accaagacga catcgacttc    660
gctggaagaa aggacttcgc tgaatccttt aataaggccc aggaatactt ggctatcaga    720
actttggtcc agacctttta ctggttggtg aacaataagg aatttagaga ctgtaccaaa    780
agtgtccata aattcaccaa ttattacgtc caaaaggcct tagacgcttc accagaggaa    840
ttagaaaagc aatccggtta cgtgttctta tatgagttgg tgaagcaaac acgtgatcca    900
aacgtcttga gagatcaaag tttaaacatt ttattggctg gtagagatac tactgctggc    960
ttgttgtctt ttgctgtttt tgaattggcc agacatccag agatttgggc taaattgaga   1020
gaagaaattg agcaacagtt cggtttgggt gaagattctc gtgttgagga gatcactttc   1080
gaatcattga agagatgtga atatttgaag gctttcttga acgaaacctt gagaatttat   1140
ccatctgttc caagaaactt tagaatcgca accaaaaaca caacattgcc aagaggaggt   1200
ggaagtgatg gcacctctcc aattttgatt caaaaaggtg aagctgtctc ttatggtatt   1260
```

-continued

```
aattccactc acttggaccc agtttattat ggtccagatg ccgccgaatt tagaccagaa   1320

agatggtttg aaccatctac caagaagttg ggatgggctt atttgccatt caacggtggt   1380

cctagaatct gcttgggtca acaattcgct ttgaccgaag ctggctacgt tttggttaga   1440

ttggtccagg agttctcaca cgtgagatcc gacccagacg aggtttatcc accaaagaga   1500

ttaactaact tgaccatgtg tttgcaagac ggtgctattg ttaagttcga ctag         1554
```

```
<210> SEQ ID NO 70
<211> LENGTH: 5268
<212> TYPE: DNA
<213> ORGANISM: Artificial Sequence
<220> FEATURE:
<223> OTHER INFORMATION: Genomic integration vector for integrating
      CYP52A17 under control of the isocitrate lyase promoter

<400> SEQUENCE: 70

agatctgaat tctattaggc gaagaggcat ctagtagtag tggcagtggt gagaacgtgg     60

gcgctgctat agtgaacaat ctccagtcga tggttaagaa gaagagtgac aaaccagcag    120

tgaatgactt gtctgggtcc gtgaggaaaa gaaagaagcc cgacacaaag gacagtaacg    180

tcaagaaacc caagaaatag gggggacctg tttagatgta taggaataaa aactccgaga    240

tgatctcaat gtgtaatgga gttgtaatat tgcaaagggg gaaaatcaag actcaaacgt    300

gtgtatgagt gagcgtacgt atatctccga gagtagtatg acataatgat gactgtgaat    360

catcgtaatc tcacacaaaa accccattgt cggccatata ccacaccaag caacaccaca    420

tatccccccgg aaaaaaaaac gtgaaaaaaa gaaacaatca aaactacaac ctactccttg    480

atcacacagt cattgatcaa gttacagttc ctgctaggga atgaccaagg tacaaatcag    540

caccttaatg gttagcacgc tctcttactc tctctcacag tcttccggcc cctattcaaa    600

attctgcact tccatttgac cccagggttg ggaaacaggg ccacaaaaga aaaacccgac    660

gtgaatgaaa aaactaagaa aagaaaaaaa attatcacac cagaaattta cctaattggg    720

taattcccat cggtgttttt cctggattgt cgcacgcacg catgctgaaa aaagtgttcg    780

agttttgctt ttgcctcgga gtttcacgca agtttttcga tctcggaacc ggagggcggt    840

cgccttgttg tttgtgatgt cgtgctttgg gtgttctaat gtgctgttat tgtgctcttt    900

tttttcttc ttttttggt gatcatatga tattgctcgg tagattactt tcgtgtgtag    960

gtattctttt agacgtttgg ttattgggta gatatgagag agagagagtg ggtgggggag   1020

gagttggttg taggagggac ccctgggagg aagtgtagtt gagttttccc tgacgaatga   1080

aaatacgttt ttgagaagat aatacaggaa aggtgtgtcg gtgaatttcc atctatccga   1140

ggatatgagt ggaggagagt cgtgtgcgtg tggttaattt aggatcagtg gaacacacaa   1200

agtaactaag acagagagac agagagaaaa atctggggaa gagacaaaga gtcagagtgt   1260

gtgagttatt ctgtattgtg aaattttttt gcccaactac ataatattgc tgaaactaat   1320

tttacttaaa aagaaaagcc aacaacgtcc ccagtaaaac ttttctataa atatcagcag   1380

ttttcccttt cctccattcc tcttcttgtc ttttttctta ctttcccttt tttatacctt   1440

ttcattatca tcctttataa ttgtctaacc aacaactata tatctatcaa ccatggctga   1500

gcaattgttg gaatattggt acgttgtggt gccagttttg tatatcatta agcaattatt   1560

ggcctacacc aagaccagag tcttaatgaa gaagttgggt gccgccccag ttactaacaa   1620

attgtacgac aacgctttcg gaattgtcaa cggatggaag gctttgcaat ttaagaagga   1680

gggtagagcc caagaataca atgattataa gtttgatcac agtaaaaacc cttccgtcgg   1740

tacttacgtg tccattttgt ttggcactag aattgtcgtc accaaagacc cagaaaatat   1800
```

```
caaagctatc ttggctacac aatttggtga cttctccttg ggcaaaagac acaccttatt   1860
taagccattg ttgggagatg gtattttcac cttagacggc gaaggttgga aacactccag   1920
agccatgttg cgtccacaat ttgcaagaga acaggttgct cacgttacct ctttggaacc   1980
acattttcaa ttattgaaga aacacatttt gaaacacaag ggtgagtact tcgacatcca   2040
agaattattc tttagattca ccgttgactc cgccactgag tttttgtttg gtgagtccgt   2100
tcattccttg aaagacgaaa gtattggtat taaccaagac gacatcgact tcgctggaag   2160
aaaggacttc gctgaatcct ttaataaggc ccaggaatac ttggctatca gaactttggt   2220
ccagaccttt tactggttgg tgaacaataa ggaatttaga gactgtacca aaagtgtcca   2280
taaattcacc aattattacg tccaaaaggc cttagacgct tcaccagagg aattagaaaa   2340
gcaatccggt tacgtgttct tatatgagtt ggtgaagcaa acacgtgatc caaacgtctt   2400
gagagatcaa agtttaaaca ttttattggc tggtagagat actactgctg gcttgttgtc   2460
ttttgctgtt tttgaattgg ccagacatcc agagatttgg gctaaattga gagaagaaat   2520
tgagcaacag ttcggtttgg gtgaagattc tcgtgttgag gagatcactt tcgaatcatt   2580
gaagagatgt gaatatttga aggctttctt gaacgaaacc ttgagaattt atccatctgt   2640
tccaagaaac tttagaatcg caaccaaaaa cacaacattg ccaagaggag gtggaagtga   2700
tggcacctct ccaattttga ttcaaaaagg tgaagctgtc tcttatggta ttaattccac   2760
tcacttggac ccagtttatt atggtccaga tgccgccgaa tttagaccag aaagatggtt   2820
tgaaccatct accaagaagt tgggatgggc ttatttgcca ttcaacggtg gtcctagaat   2880
ctgcttgggt caacaattcg ctttgaccga agctggctac gttttggtta gattggtcca   2940
ggagttctca cacgtgagat ccgacccaga cgaggtttat ccaccaaaga gattaactaa   3000
cttgaccatg tgtttgcaag acggtgctat tgttaagttc gactaggcgg ccgcaagaaa   3060
aaagaaaagg taaagaactt catttgagat gaacttttgt atatgacttt tagtttctac   3120
ttttttttt atttattgct taattttctt tatttcaatc ccccatagtt tgtgtagaat   3180
atatttattc attctggtaa ctcaaacacg tagcaagctc gttgcatctc gcctcgtcac   3240
gggtacagct ctggaaccaa agacaaaaaa aaaagttgat ccgaaccctc tcgctattcc   3300
ttgctatgct atccacgaga tggggtttat cagcccaggc aagtcactaa aggatccccc   3360
acacaccata gcttcaaaat gtttctactc ctttttttact cttccagatt ttctcggact   3420
ccgcgcatcg ccgtaccact tcaaaacacc caagcacagc atactaaatt ttccctcttt   3480
cttcctctag ggtgtcgtta attacccgta ctaaaggttt ggaaaagaaa aaagagaccg   3540
cctcgtttct tttcttcgt cgaaaaaggc aataaaaatt tttatcacgt ttctttttct   3600
tgaaattttt ttttttagtt tttttctctt tcagtgacct ccattgatat ttaagttaat   3660
aaacggtctt caatttctca agtttcagtt tcatttttct tgttctatta caactttttt   3720
tacttcttgt tcattagaaa gaaagcatag caatctaatc taaggggcgg tgttgacaat   3780
taatcatcgg catagtatat cggcatagta taatacgaca aggtgaggaa ctaaaccatg   3840
tctaaattaa cctctgctgt tccagtgtta accgcccgtg atgttgccgg tgcagtggaa   3900
ttttggactg accgtttggg tttctcacgt gactttgtcg aagatgattt tgctggcgtt   3960
gtgcgtgatg acgtcacttt gttcatctct gctgttcagg atcaggtcgt cccagacaac   4020
actttggcct gggtctgggt tcgtggtttg gacgaattgt acgctgagtg gagtgaagtt   4080
gtgtctacaa actttcgtga tgcatcaggt ccagctatga ccgaaattgg cgaacaacct   4140
tggggccgtg agttcgcttt acgtgatcca gccggtaatt gcgtgcactt cgttgctgag   4200
```

```
gagcaagatt agcacgtccg acggcggccc acgggtccca ggcctcggag atccgtcccc   4260
cttttccttt gtcgatatca tgtaattagt tatgtcacgc ttacattcac gccctccccc   4320
cacatccgct ctaaccgaaa aggaaggagt tagacaacct gaagtctagg tccctattta   4380
ttttttata gttatgttag tattaagaac gttatttata tttcaaattt ttcttttttt   4440
tctgtacaga cgcgtgtacg catgtaacat tatactgaaa accttgcttg agaaggtttt   4500
gggacgctcg aaggctttaa tttgcaagct ggagaccaac atgtgagcaa aaggccagca   4560
aaaggccagg aaccgtaaaa aggccgcgtt gctggcgttt ttccataggc tccgcccccc   4620
tgacgagcat cacaaaaatc gacgctcaag tcagaggtgg cgaaacccga caggactata   4680
aagataccag gcgtttcccc ctggaagctc cctcgtgcgc tctcctgttc cgaccctgcc   4740
gcttaccgga tacctgtccg cctttctccc ttcgggaagc gtggcgcttt ctcaatgctc   4800
acgctgtagg tatctcagtt cggtgtaggt cgttcgctcc aagctgggct gtgtgcacga   4860
accccccgtt cagcccgacc gctgcgcctt atccggtaac tatcgtcttg agtccaaccc   4920
ggtaagacac gacttatcgc cactggcagc agccactggt aacaggatta gcagagcgag   4980
gtatgtaggc ggtgctacag agttcttgaa gtggtggcct aactacggct acactagaag   5040
gacagtattt ggtatctgcg ctctgctgaa gccagttacc ttcggaaaaa gagttggtag   5100
ctcttgatcc ggcaaacaaa ccaccgctgg tagcggtggt ttttttgttt gcaagcagca   5160
gattacgcgc agaaaaaaag gatctcaaga agatcctttg atcttttcta cggggtctga   5220
cgctcagtgg aacgaaaact cacgttaagg gattttggtc atgagatc               5268
```

<210> SEQ ID NO 71
<211> LENGTH: 1569
<212> TYPE: DNA
<213> ORGANISM: Candida tropicalis

<400> SEQUENCE: 71

```
atgactgttc acgacattat tgctacctac tttactaagt ggtacgtcat tgttccattg     60
gccttaatcg cctatagagt tttggattac ttttacggta gatacttgat gtacaaattg    120
ggtgctaaac cattctttca gaaacaaact gacggttgtt ttggttttaa ggccccttta    180
gaattattga agaaaaagtc tgacggtaca ttgatcgatt ttaccttgca aagaatccac    240
gacttggaca gaccagatat cccaaccttt acctttcctg ttttctcaat caatttggtg    300
aatactttgg aacctgaaaa catcaaggct atcttggcta cccagttcaa tgattttagt    360
ttgggcacca gacactcaca ttttgcacca ttgttgggag atggtatctt tacattggat    420
ggtgctggtt ggaagcattc aagatccatg ttaagaccac aatttgcaag agagcagatt    480
tcccatgtta agttgttgga accacatgtt caagtcttct tcaagcatgt tagaaaagcc    540
caaggtaaga cttttgatat tcaggagttg ttctttagat tgactgttga ttctgccacc    600
gaatttttgt ttggtgaatc cgtcgaatcc ttgagagacg aatctattgg tatgtctatt    660
aacgctttgg attttgatgg taaggctgga tttgcagatg catttaacta ttcccaaaac    720
tatttagctt ctagagctgt catgcaacaa ttatactggg ttttaaatgg taaaaagttc    780
aaggaatgta atgctaaggt ccacaagttc gctgactatt atgtcaacaa ggctttagac    840
ttaactccag agcaattaga aaagcaggat ggttacgtct tcttatatga attggtcaaa    900
cagactagag ataagcaagt tttgagagat cagttattga atatcatggt cgctggtaga    960
gacacaactg ctggtttgtt gtcctttgtc ttctttgaat tggccagaaa cccagaagtc   1020
accaacaaat taagagagga aatcgaagat aaatttggat taggcgaaaa tgcaagtgtc   1080
```

```
gaggacattt cctttgagtc tttgaagtct tgtgaatatt tgaaagctgt tttgaacgag   1140

acattgcgtt tgtacccttc agttccacag aactttagag ttgcaaccaa gaacaccaca   1200

ttgcctagag gcggtggtaa agatggtttg tctcctgttt tggtgagaaa gggtcaaacc   1260

gttatttacg gtgtctacgc cgcccacaga aacccagcag tctatggtaa agatgctttg   1320

gaattcagac cagagcgttg gttcgaacct gaaaccaaaa agttgggttg ggccttctta   1380

cctttcaacg gaggtccaag aatctgtttg ggtcagcaat tcgccttgac agaagcctca   1440

tatgtgactg tgagattgtt gcaagaattc gctcacttgt ctatggaccc tgacactgaa   1500

taccctccta aaaagatgtc ccatttgacc atgtcattat ttgacggtgc taatattgaa   1560

atgtattag                                                           1569
```

```
<210> SEQ ID NO 72
<211> LENGTH: 5283
<212> TYPE: DNA
<213> ORGANISM: Artificial Sequence
<220> FEATURE:
<223> OTHER INFORMATION: Genomic integration vector for integrating
      CYP52A13 under control of the isocitrate lyase promoter

<400> SEQUENCE: 72

agatctgaat tctattaggc gaagaggcat ctagtagtag tggcagtggt gagaacgtgg     60

gcgctgctat agtgaacaat ctccagtcga tggttaagaa gaagagtgac aaaccagcag    120

tgaatgactt gtctgggtcc gtgaggaaaa gaaagaagcc cgacacaaag gacagtaacg    180

tcaagaaacc caagaaatag gggggacctg tttagatgta taggaataaa aactccgaga    240

tgatctcaat gtgtaatgga gttgtaatat tgcaaagggg gaaaatcaag actcaaacgt    300

gtgtatgagt gagcgtacgt atatctccga gagtagtatg acataatgat gactgtgaat    360

catcgtaatc tcacacaaaa accccattgt cggccatata ccacaccaag caacaccaca    420

tatcccccgg aaaaaaaaac gtgaaaaaaa gaaacaatca aaactacaac ctactccttg    480

atcacacagt cattgatcaa gttacagttc ctgctaggga atgaccaagg tacaaatcag    540

caccttaatg gttagcacgc tctcttactc tctctcacag tcttccggcc cctattcaaa    600

attctgcact tccatttgac cccagggttg ggaaacaggg ccacaaaaga aaaacccgac    660

gtgaatgaaa aaactaagaa aagaaaaaaa attatcacac cagaaattta cctaattggg    720

taattcccat cggtgttttt cctggattgt cgcacgcacg catgctgaaa aaagtgttcg    780

agttttgctt ttgcctcgga gtttcacgca agtttttcga tctcggaacc ggagggcggt    840

cgccttgttg tttgtgatgt cgtgctttgg gtgttctaat gtgctgttat tgtgctcttt    900

tttttcttc ttttttggt gatcatatga tattgctcgg tagattactt tcgtgtgtag     960

gtattctttt agacgtttgg ttattgggta gatatgagag agagagagtg ggtgggggag   1020

gagttggttg taggagggac ccctgggagg aagtgtagtt gagttttccc tgacgaatga   1080

aaatacgttt ttgagaagat aatacaggaa aggtgtgtcg gtgaatttcc atctatccga   1140

ggatatgagt ggaggagagt cgtgtgcgtg tggttaattt aggatcagtg gaacacacaa   1200

agtaactaag acagagagac agagagaaaa atctggggaa gagacaaaga gtcagagtgt   1260

gtgagttatt ctgtattgtg aaattttttt gcccaactac ataatattgc tgaaactaat   1320

tttacttaaa aagaaaagcc aacaacgtcc ccagtaaaac ttttctataa atatcagcag   1380

ttttcccttt cctccattcc tcttcttgtc ttttttctta ctttcccttt tttatacctt   1440

ttcattatca tcctttataa ttgtctaacc aacaactata tatctatcaa ccatgactgt   1500
```

```
tcacgacatt attgctacct actttactaa gtggtacgtc attgttccat tggccttaat   1560
cgcctataga gttttggatt acttttacgg tagatacttg atgtacaaat tgggtgctaa   1620
accattcttt cagaaacaaa ctgacggttg ttttggtttt aaggcccctt tagaattatt   1680
gaagaaaaag tctgacggta cattgatcga ttttaccttg caaagaatcc acgacttgga   1740
cagaccagat atcccaacct ttacctttcc tgttttctca atcaatttgg tgaatacttt   1800
ggaacctgaa aacatcaagg ctatcttggc tacccagttc aatgatttta gtttgggcac   1860
cagacactca cattttgcac cattgttggg agatggtatc tttacattgg atggtgctgg   1920
ttggaagcat tcaagatcca tgttaagacc acaatttgca agagagcaga tttcccatgt   1980
taagttgttg gaaccacatg ttcaagtctt cttcaagcat gttagaaaag cccaaggtaa   2040
gacttttgat attcaggagt tgttctttag attgactgtt gattctgcca ccgaattttt   2100
gtttggtgaa tccgtcgaat ccttgagaga cgaatctatt ggtatgtcta ttaacgcttt   2160
ggattttgat ggtaaggctg gatttgcaga tgcatttaac tattcccaaa actatttagc   2220
ttctagagct gtcatgcaac aattatactg ggttttaaat ggtaaaaagt tcaaggaatg   2280
taatgctaag gtccacaagt tcgctgacta ttatgtcaac aaggctttag acttaactcc   2340
agagcaatta gaaaagcagg atggttacgt cttcttatat gaattggtca aacagactag   2400
agataagcaa gttttgagag atcagttatt gaatatcatg gtcgctggta gagacacaac   2460
tgctggtttg ttgtcctttg tcttctttga attggccaga aacccagaag tcaccaacaa   2520
attaagagag gaaatcgaag ataaatttgg attaggcgaa aatgcaagtg tcgaggacat   2580
ttcctttgag tctttgaagt cttgtgaata tttgaaagct gttttgaacg agacattgcg   2640
tttgtaccct tcagttccac agaactttag agttgcaacc aagaacacca cattgcctag   2700
aggcggtggt aaagatggtt tgtctcctgt tttggtgaga aagggtcaaa ccgttattta   2760
cggtgtctac gccgcccaca gaaacccagc agtctatggt aaagatgctt tggaattcag   2820
accagagcgt tggttcgaac ctgaaaccaa aaagttgggt tgggccttct acctttcaa    2880
cggaggtcca agaatctgtt tgggtcagca attcgccttg acagaagcct catatgtgac   2940
tgtgagattg ttgcaagaat tcgctcactt gtctatggac cctgacactg aataccctcc   3000
taaaaagatg tcccatttga ccatgtcatt atttgacggt gctaatattg aaatgtatta   3060
ggcggccgca agaaaaaaga aaaggtaaag aacttcattt gagatgaact tttgtatatg   3120
acttttagtt tctacttttt tttttattta ttgcttaatt ttctttattt caatcccca    3180
tagtttgtgt agaatatatt tattcattct ggtaactcaa acacgtagca agctcgttgc   3240
atctcgcctc gtcacgggta cagctctgga accaaagaca aaaaaaaaag ttgatccgaa   3300
ccctctcgct attccttgct atgctatcca cgagatgggg tttatcagcc caggcaagtc   3360
actaaaggat cccccacaca ccatagcttc aaaatgtttc tactcctttt ttactcttcc   3420
agattttctc ggactccgcg catcgccgta ccacttcaaa acacccaagc acagcatact   3480
aaattttccc tctttcttcc tctagggtgt cgttaattac ccgtactaaa ggtttggaaa   3540
agaaaaaaga gaccgcctcg tttctttttc ttcgtcgaaa aaggcaataa aaatttttat   3600
cacgtttctt tttcttgaaa tttttttttt tagttttttt ctctttcagt gacctccatt   3660
gatatttaag ttaataaacg gtcttcaatt tctcaagttt cagtttcatt tttcttgttc   3720
tattacaact ttttttactt cttgttcatt agaaagaaag catagcaatc taatctaagg   3780
ggcggtgttg acaattaatc atcggcatag tatatcggca tagtataata cgacaaggtg   3840
aggaactaaa ccatgtctaa attaacctct gctgttccag tgttaaccgc ccgtgatgtt   3900
```

```
gccggtgcag tggaattttg gactgaccgt ttgggtttct cacgtgactt tgtcgaagat   3960

gattttgctg gcgttgtgcg tgatgacgtc actttgttca tctctgctgt tcaggatcag   4020

gtcgtcccag acaacacttt ggcctgggtc tgggttcgtg gtttggacga attgtacgct   4080

gagtggagtg aagttgtgtc tacaaacttt cgtgatgcat caggtccagc tatgaccgaa   4140

attggcgaac aaccttgggg ccgtgagttc gctttacgtg atccagccgg taattgcgtg   4200

cacttcgttg ctgaggagca agattagcac gtccgacggc ggcccacggg tcccaggcct   4260

cggagatccg tcccccttt cctttgtcga tatcatgtaa ttagttatgt cacgcttaca   4320

ttcacgccct ccccccacat ccgctctaac cgaaaaggaa ggagttagac aacctgaagt   4380

ctaggtccct atttattttt ttatagttat gttagtatta agaacgttat ttatatttca   4440

aatttttctt ttttttctgt acagacgcgt gtacgcatgt aacattatac tgaaaacctt   4500

gcttgagaag gttttgggac gctcgaaggc tttaatttgc aagctggaga ccaacatgtg   4560

agcaaaaggc cagcaaaagg ccaggaaccg taaaaaggcc gcgttgctgg cgtttttcca   4620

taggctccgc ccccctgacg agcatcacaa aaatcgacgc tcaagtcaga ggtggcgaaa   4680

cccgacagga ctataaagat accaggcgtt tccccctgga agctccctcg tgcgctctcc   4740

tgttccgacc ctgccgctta ccggatacct gtccgccttt ctcccttcgg gaagcgtggc   4800

gctttctcaa tgctcacgct gtaggtatct cagttcggtg taggtcgttc gctccaagct   4860

gggctgtgtg cacgaacccc ccgttcagcc cgaccgctgc gccttatccg gtaactatcg   4920

tcttgagtcc aacccggtaa gacacgactt atcgccactg gcagcagcca ctggtaacag   4980

gattagcaga gcgaggtatg taggcggtgc tacagagttc ttgaagtggt ggcctaacta   5040

cggctacact agaaggacag tatttggtat ctgcgctctg ctgaagccag ttaccttcgg   5100

aaaaagagtt ggtagctctt gatccggcaa acaaaccacc gctggtagcg gtggtttttt   5160

tgtttgcaag cagcagatta cgcgcagaaa aaaaggatct caagaagatc ctttgatctt   5220

ttctacgggg tctgacgctc agtggaacga aaactcacgt taagggattt tggtcatgag   5280

atc                                                                 5283
```

<210> SEQ ID NO 73
<211> LENGTH: 1572
<212> TYPE: DNA
<213> ORGANISM: Candida tropicalis

<400> SEQUENCE: 73

```
atggcaaccc aggaaattat tgattctgtt ttaccttact tgaccaagtg gtatactgtc     60

attaccgccg ctgtgttggt gttcttgatt tctacaaaca ttaagaacta cgttaaagcc    120

aagaagttga agtgtgttga cccaccatac ttaaaagacg ctggtttgac cggtatttct    180

tcattgatcg ctgctattaa ggccaagaat gacggtcgtt tggccaactt tgccgacgag    240

gttttcgatg aataccctaa ccacaccttc tacttgtctg tggcaggagc tttgaagatt    300

gttatgaccg ttgacccaga aaatatcaaa gctgttttgg caacacagtt cacagacttt    360

tcattgggta ctcgtcatgc ccattttgct ccattgttgg gtgatggtat tttacttta    420

gacggtgaag gttggaagca ttcaagagcc atgttgcgtc cacagtttgc cagagatcaa    480

atcggtcatg tgaaagcctt agaaccacat atccaaatta tggccaagca aatcaagttg    540

aaccaaggaa agactttcga tatccaagaa ttgttcttca gatttacagt tgacacagct    600

actgaattct tgtttggtga atctgttcac agtttatatg acgaaaagtt gggtattcca    660

accccaaatg aaatcccagg tagagaaaat ttcgctgctg cattcaatgt ctctcaacac    720
```

```
tacttggcta caagatctta cagtcaaact ttctactttt tgactaaccc aaaggaattt    780

agagactgta acgccaaggt tcaccatttg gccaagtact ttgtgaataa agctttgaat    840

ttcaccccag aggaattaga agaaaagtct aaatccggct atgttttctt atacgaatta    900

gttaaacaaa caagagatcc taaggttttg caagaccaat tgttgaacat tatggtcgct    960

ggtagagaca ctactgctgg tttattgtcc tttgctttgt ttgaattggc tagacatcca   1020

gaaatgtggt caaagttgag agaggaaatc gaagttaact ttggcgtggg tgaagattca   1080

agagttgaag agattacctt tgaggccttg aaaagatgtg aatacttgaa ggctatcttg   1140

aacgagacat tgagaatgta tccatctgtt cctgttaact ttagaacagc cactagagat   1200

acaaccttgc caagaggtgg tggtgccaac ggtacagatc caatttacat tcctaagggt   1260

tccaccgtcg cttacgtcgt gtacaaaacc caccgtttgg aggaatatta cggtaaggac   1320

gctaacgatt tccgtcctga aagatggttt gaaccaagta ctaagaagtt gggatgggcc   1380

tatgttcctt ttaacggtgg tccaagagtt tgtttgggtc agcagtttgc tttgactgaa   1440

gccagttacg ttatcaccag attagcccaa atgttcgaaa ccgtttcatc tgacccagga   1500

ttggagtatc caccaccaaa gtgtattcat ttgacaatgt cccataatga tggtgttttt   1560

gtcaagatgt ag                                                       1572
```

```
<210> SEQ ID NO 74
<211> LENGTH: 5286
<212> TYPE: DNA
<213> ORGANISM: Artificial Sequence
<220> FEATURE:
<223> OTHER INFORMATION: Genomic integration vector for integrating
      CYP52A12 under control of the isocitrate lyase promoter

<400> SEQUENCE: 74
```

```
agatctgaat tctattaggc gaagaggcat ctagtagtag tggcagtggt gagaacgtgg     60

gcgctgctat agtgaacaat ctccagtcga tggttaagaa gaagagtgac aaaccagcag    120

tgaatgactt gtctgggtcc gtgaggaaaa gaaagaagcc cgacacaaag gacagtaacg    180

tcaagaaacc caagaaatag gggggacctg tttagatgta taggaataaa aactccgaga    240

tgatctcaat gtgtaatgga gttgtaatat tgcaaagggg gaaaatcaag actcaaacgt    300

gtgtatgagt gagcgtacgt atatctccga gagtagtatg acataatgat gactgtgaat    360

catcgtaatc tcacacaaaa accccattgt cggccatata ccacaccaag caacaccaca    420

tatcccccgg aaaaaaaaac gtgaaaaaaa gaaacaatca aaactacaac ctactccttg    480

atcacacagt cattgatcaa gttacagttc ctgctaggga atgaccaagg tacaaatcag    540

caccttaatg gttagcacgc tctcttactc tctctcacag tcttccggcc cctattcaaa    600

attctgcact tccatttgac cccagggttg ggaaacaggg ccacaaaaga aaaacccgac    660

gtgaatgaaa aaactaagaa aagaaaaaaa attatcacac cagaaattta cctaattggg    720

taattcccat cggtgttttt cctggattgt cgcacgcacg catgctgaaa aaagtgttcg    780

agttttgctt ttgcctcgga gtttcacgca agtttttcga tctcggaacc ggagggcggt    840

cgccttgttg tttgtgatgt cgtgctttgg gtgttctaat gtgctgttat tgtgctcttt    900

tttttcttc ttttttggt gatcatatga tattgctcgg tagattactt tcgtgtgtag     960

gtattctttt agacgtttgg ttattgggta gatatgagag agagagagtg ggtgggggag   1020

gagttggttg taggagggac ccctgggagg aagtgtagtt gagttttccc tgacgaatga   1080

aaatacgttt ttgagaagat aatacaggaa aggtgtgtcg gtgaatttcc atctatccga   1140

ggatatgagt ggaggagagt cgtgtgcgtg tggttaattt aggatcagtg gaacacacaa   1200
```

-continued

```
agtaactaag acagagagac agagagaaaa atctggggaa gagacaaaga gtcagagtgt   1260
gtgagttatt ctgtattgtg aaattttttt gcccaactac ataatattgc tgaaactaat   1320
tttacttaaa aagaaaagcc aacaacgtcc ccagtaaaac ttttctataa atatcagcag   1380
ttttcccttt cctccattcc tcttcttgtc tttttttctta ctttcccttt tttatacctt   1440
ttcattatca tcctttataa ttgtctaacc aacaactata tatctatcaa ccatggcaac   1500
ccaggaaatt attgattctg ttttacctta cttgaccaag tggtatactg tcattaccgc   1560
cgctgtgttg gtgttcttga tttctacaaa cattaagaac tacgttaaag ccaagaagtt   1620
gaagtgtgtt gacccaccat acttaaaaga cgctggtttg accggtattt cttcattgat   1680
cgctgctatt aaggccaaga atgacggtcg tttggccaac tttgccgacg aggttttcga   1740
tgaataccct aaccacacct tctacttgtc tgtggcagga gctttgaaga ttgttatgac   1800
cgttgaccca gaaaatatca aagctgtttt ggcaacacag ttcacagact tttcattggg   1860
tactcgtcat gcccattttg ctccattgtt gggtgatggt atttttactt tagacggtga   1920
aggttggaag cattcaagag ccatgttgcg tccacagttt gccagagatc aaatcggtca   1980
tgtgaaagcc ttagaaccac atatccaaat tatggccaag caaatcaagt tgaaccaagg   2040
aaagactttc gatatccaag aattgttctt cagatttaca gttgacacag ctactgaatt   2100
cttgtttggt gaatctgttc acagtttata tgacgaaaag ttgggtattc caaccccaaa   2160
tgaaatccca ggtagagaaa atttcgctgc tgcattcaat gtctctcaac actacttggc   2220
tacaagatct tacagtcaaa ctttctactt tttgactaac ccaaaggaat ttagagactg   2280
taacgccaag gttcaccatt tggccaagta ctttgtgaat aaagctttga atttcacccc   2340
agaggaatta gaagaaaagt ctaaatccgg ctatgttttc ttatacgaat tagttaaaca   2400
aacaagagat cctaaggttt tgcaagacca attgttgaac attatggtcg ctggtagaga   2460
cactactgct ggtttattgt cctttgcttt gtttgaattg gctagacatc cagaaatgtg   2520
gtcaaagttg agagaggaaa tcgaagttaa ctttggcgtg ggtgaagatt caagagttga   2580
agagattacc tttgaggcct tgaaaagatg tgaatacttg aaggctatct tgaacgagac   2640
attgagaatg tatccatctg ttcctgttaa ctttagaaca gccactagag atacaacctt   2700
gccaagaggt ggtggtgcca acggtacaga tccaatttac attcctaagg gttccaccgt   2760
cgcttacgtc gtgtacaaaa cccaccgttt ggaggaatat tacggtaagg acgctaacga   2820
tttccgtcct gaaagatggt ttgaaccaag tactaagaag ttgggatggg cctatgttcc   2880
ttttaacggt ggtccaagag tttgtttggg tcagcagttt gctttgactg aagccagtta   2940
cgttatcacc agattagccc aaatgttcga aaccgtttca tctgacccag gattggagta   3000
tccaccacca aagtgtattc atttgacaat gtcccataat gatggtgttt ttgtcaagat   3060
gtaggcggcc gcaagaaaaa agaaaaggta aagaacttca tttgagatga acttttgtat   3120
atgactttta gtttctactt ttttttttat ttattgctta attttcttta tttcaatccc   3180
ccatagtttg tgtagaatat atttattcat tctggtaact caaacacgta gcaagctcgt   3240
tgcatctcgc ctcgtcacgg gtacagctct ggaaccaaag acaaaaaaaa aagttgatcc   3300
gaaccctctc gctattcctt gctatgctat ccacgagatg ggtttatca gcccaggcaa   3360
gtcactaaag gatcccccac acaccatagc ttcaaaatgt ttctactcct tttttactct   3420
tccagatttt ctcggactcc gcgcatcgcc gtaccacttc aaaacaccca agcacagcat   3480
actaaatttt ccctctttct tcctctaggg tgtcgttaat tacccgtact aaaggtttgg   3540
aaaagaaaaa agagaccgcc tcgtttcttt ttcttcgtcg aaaaaggcaa taaaaatttt   3600
```

```
tatcacgttt ctttttcttg aaattttttt ttttagtttt tttctctttc agtgacctcc   3660

attgatattt aagttaataa acggtcttca atttctcaag tttcagtttc atttttcttg   3720

ttctattaca acttttttta cttcttgttc attagaaaga aagcatagca atctaatcta   3780

aggggcggtg ttgacaatta atcatcggca tagtatatcg gcatagtata atacgacaag   3840

gtgaggaact aaaccatgtc taaattaacc tctgctgttc cagtgttaac cgcccgtgat   3900

gttgccggtg cagtggaatt ttggactgac cgtttgggtt tctcacgtga ctttgtcgaa   3960

gatgattttg ctggcgttgt gcgtgatgac gtcactttgt tcatctctgc tgttcaggat   4020

caggtcgtcc cagacaacac tttggcctgg gtctgggttc gtggtttgga cgaattgtac   4080

gctgagtgga gtgaagttgt gtctacaaac tttcgtgatg catcaggtcc agctatgacc   4140

gaaattggcg aacaaccttg ggggccgtgag ttcgctttac gtgatccagc cggtaattgc   4200

gtgcacttcg ttgctgagga gcaagattag cacgtccgac ggcggcccac gggtcccagg   4260

cctcggagat ccgtccccct ttcctttgt cgatatcatg taattagtta tgtcacgctt   4320

acattcacgc cctcccccca catccgctct aaccgaaaag gaaggagtta gacaacctga   4380

agtctaggtc cctatttatt tttttatagt tatgttagta ttaagaacgt tatttatatt   4440

tcaaattttt cttttttttc tgtacagacg cgtgtacgca tgtaacatta tactgaaaac   4500

cttgcttgag aaggttttgg gacgctcgaa ggctttaatt tgcaagctgg agaccaacat   4560

gtgagcaaaa ggccagcaaa aggccaggaa ccgtaaaaag gccgcgttgc tggcgttttt   4620

ccataggctc cgcccccctg acgagcatca caaaaatcga cgctcaagtc agaggtggcg   4680

aaacccgaca ggactataaa gataccaggc gtttccccct ggaagctccc tcgtgcgctc   4740

tcctgttccg accctgccgc ttaccggata cctgtccgcc tttctccctt cgggaagcgt   4800

ggcgctttct caatgctcac gctgtaggta tctcagttcg gtgtaggtcg ttcgctccaa   4860

gctgggctgt gtgcacgaac cccccgttca gcccgaccgc tgcgccttat ccggtaacta   4920

tcgtcttgag tccaacccgg taagacacga cttatcgcca ctggcagcag ccactggtaa   4980

caggattagc agagcgaggt atgtaggcgg tgctacagag ttcttgaagt ggtggcctaa   5040

ctacggctac actagaagga cagtatttgg tatctgcgct ctgctgaagc cagttacctt   5100

cggaaaaaga gttggtagct cttgatccgg caaacaaacc accgctggta gcggtggttt   5160

ttttgtttgc aagcagcaga ttacgcgcag aaaaaaagga tctcaagaag atcctttgat   5220

cttttctacg gggtctgacg ctcagtggaa cgaaaactca cgttaaggga ttttggtcat   5280

gagatc                                                              5286
```

```
<210> SEQ ID NO 75
<211> LENGTH: 711
<212> TYPE: DNA
<213> ORGANISM: Artificial Sequence
<220> FEATURE:
<223> OTHER INFORMATION: Cloned into genomic integration and expression
      constructs to express mCherry

<400> SEQUENCE: 75

atggtttcta agggtgaaga agacaacatg gcaatcatca aggaatttat gcgttttaag     60

gtccatatgg aaggctccgt taacggccac gagttcgaga tcgagggaga aggtgagggt    120

agaccatacg aaggtactca aaccgccaag ttgaaagtta caaagggtgg tccattgcca    180

tttgcttggg atatcttgtc cccacaattt atgtacggat caaaggcata tgtcaagcat    240

cctgccgaca tcccagatta cttgaagtta tcctttccag aaggttttaa gtgggagaga    300
```

```
gttatgaact ttgaagatgg cggagttgtt actgttactc aggactcttc cttgcaagat    360

ggtgaattta tctataaagt gaaattgaga ggtactaact ttccatccga cggtccagtc    420

atgcaaaaga agacaatggg ttgggaggct tcttccgaaa gaatgtaccc agaagacggt    480

gcattgaaag gtgaaatcaa gcaacgttta aagttgaagg acggtggtca ctacgatgcc    540

gaggtcaaga ccacttataa ggctaagaag ccagtccaat tgccaggtgc ttataacgtt    600

aacatcaagt tagatattac ttcacacaac gaagactaca caatcgttga acaatatgaa    660

agagccgaag gtagacattc taccggcggc atggacgagt tatataagta g             711
```

<210> SEQ ID NO 76
<211> LENGTH: 4425
<212> TYPE: DNA
<213> ORGANISM: Artificial Sequence
<220> FEATURE:
<223> OTHER INFORMATION: Genomic integration vector for integrating mCherry under control of the isocitrate lyase promoter

<400> SEQUENCE: 76

```
agatctgaat tctattaggc gaagaggcat ctagtagtag tggcagtggt gagaacgtgg     60

gcgctgctat agtgaacaat ctccagtcga tggttaagaa gaagagtgac aaaccagcag    120

tgaatgactt gtctgggtcc gtgaggaaaa gaaagaagcc cgacacaaag gacagtaacg    180

tcaagaaacc caagaaatag gggggacctg tttagatgta taggaataaa aactccgaga    240

tgatctcaat gtgtaatgga gttgtaatat tgcaaagggg gaaaatcaag actcaaacgt    300

gtgtatgagt gagcgtacgt atatctccga gagtagtatg acataatgat gactgtgaat    360

catcgtaatc tcacacaaaa accccattgt cggccatata ccacaccaag caacaccaca    420

tatcccccgg aaaaaaaaac gtgaaaaaaa gaaacaatca aaactacaac ctactccttg    480

atcacacagt cattgatcaa gttacagttc ctgctaggga atgaccaagg tacaaatcag    540

caccttaatg gttagcacgc tctcttactc tctctcacag tcttccggcc cctattcaaa    600

attctgcact tccatttgac ccagggttg ggaaacaggg ccacaaaaga aaaacccgac    660

gtgaatgaaa aaactaagaa aagaaaaaaa attatcacac cagaaattta cctaattggg    720

taattcccat cggtgttttt cctggattgt cgcacgcacg catgctgaaa aaagtgttcg    780

agttttgctt ttgcctcgga gtttcacgca agtttttcga tctcggaacc ggagggcggt    840

cgccttgttg tttgtgatgt cgtgctttgg gtgttctaat gtgctgttat tgtgctcttt    900

tttttcttc tttttttggt gatcatatga tattgctcgg tagattactt tcgtgtgtag    960

gtattctttt agacgtttgg ttattgggta gatatgagag agagagagtg ggtgggggag   1020

gagttggttg taggagggac ccctgggagg aagtgtagtt gagttttccc tgacgaatga   1080

aaatacgttt ttgagaagat aatacaggaa aggtgtgtcg gtgaatttcc atctatccga   1140

ggatatgagt ggaggagagt cgtgtgcgtg tggttaattt aggatcagtg gaacacacaa   1200

agtaactaag acagagagac agagagaaaa atctggggaa gagacaaaga gtcagagtgt   1260

gtgagttatt ctgtattgtg aaattttttt gcccaactac ataatattgc tgaaactaat   1320

tttacttaaa aagaaaagcc aacaacgtcc ccagtaaaac ttttctataa atatcagcag   1380

ttttcccttt cctccattcc tcttcttgtc ttttttctta ctttcccttt tttatacctt   1440

ttcattatca tcctttataa ttgtctaacc aacaactata tatctatcaa ccatggtttc   1500

taagggtgaa gaagacaaca tggcaatcat caaggaattt atgcgtttta aggtccatat   1560

ggaaggctcc gttaacggcc acgagttcga gatcgaggga gaaggtgagg gtagaccata   1620

cgaaggtact caaaccgcca agttgaaagt tacaaagggt ggtccattgc catttgcttg   1680
```

```
ggatatcttg tccccacaat ttatgtacgg atcaaaggca tatgtcaagc atcctgccga   1740
catcccagat tacttgaagt tatcctttcc agaaggtttt aagtgggaga gagttatgaa   1800
ctttgaagat ggcggagttg ttactgttac tcaggactct tccttgcaag atggtgaatt   1860
tatctataaa gtgaaattga gaggtactaa ctttccatcc gacggtccag tcatgcaaaa   1920
gaagacaatg ggttgggagg cttcttccga aagaatgtac ccagaagacg gtgcattgaa   1980
aggtgaaatc aagcaacgtt taaagttgaa ggacggtggt cactacgatg ccgaggtcaa   2040
gaccacttat aaggctaaga agccagtcca attgccaggt gcttataacg ttaacatcaa   2100
gttagatatt acttcacaca acgaagacta cacaatcgtt gaacaatatg aaagagccga   2160
aggtagacat tctaccggcg gcatggacga gttatataag taggcggccg caagaaaaaa   2220
gaaaaggtaa agaacttcat ttgagatgaa cttttgtata tgacttttag tttctacttt   2280
tttttttatt tattgcttaa ttttctttat ttcaatcccc catagtttgt gtagaatata   2340
tttattcatt ctggtaactc aaacacgtag caagctcgtt gcatctcgcc tcgtcacggg   2400
tacagctctg gaaccaaaga caaaaaaaaa agttgatccg aaccctctcg ctattccttg   2460
ctatgctatc cacgagatgg ggtttatcag cccaggcaag tcactaaagg atcccccaca   2520
caccatagct tcaaaatgtt tctactcctt ttttactctt ccagattttc tcggactccg   2580
cgcatcgccg taccacttca aaacacccaa gcacagcata ctaaattttc cctctttctt   2640
cctctagggt gtcgttaatt acccgtacta aaggtttgga aaagaaaaaa gagaccgcct   2700
cgtttctttt tcttcgtcga aaaaggcaat aaaaattttt atcacgtttc tttttcttga   2760
aatttttttt tttagttttt ttctctttca gtgacctcca ttgatattta agttaataaa   2820
cggtcttcaa tttctcaagt ttcagtttca tttttcttgt tctattacaa cttttttttac  2880
ttcttgttca ttagaaagaa agcatagcaa tctaatctaa ggggcggtgt tgacaattaa   2940
tcatcggcat agtatatcgg catagtataa tacgacaagg tgaggaacta aaccatgtct   3000
aaattaacct ctgctgttcc agtgttaacc gcccgtgatg ttgccggtgc agtggaattt   3060
tggactgacc gtttgggttt ctcacgtgac tttgtcgaag atgattttgc tggcgttgtg   3120
cgtgatgacg tcactttgtt catctctgct gttcaggatc aggtcgtccc agacaacact   3180
ttggcctggg tctgggttcg tggtttggac gaattgtacg ctgagtggag tgaagttgtg   3240
tctacaaact ttcgtgatgc atcaggtcca gctatgaccg aaattggcga acaaccttgg   3300
ggccgtgagt tcgctttacg tgatccagcc ggtaattgcg tgcacttcgt tgctgaggag   3360
caagattagc acgtccgacg gcggcccacg ggtcccaggc ctcggagatc cgtcccccctt  3420
ttcctttgtc gatatcatgt aattagttat gtcacgctta cattcacgcc ctcccccccac  3480
atccgctcta accgaaaagg aaggagttag acaacctgaa gtctaggtcc ctatttattt   3540
ttttatagtt atgttagtat taagaacgtt atttatattt caaatttttc ttttttttct   3600
gtacagacgc gtgtacgcat gtaacattat actgaaaacc ttgcttgaga aggttttggg   3660
acgctcgaag gctttaattt gcaagctgga gaccaacatg tgagcaaaag gccagcaaaa   3720
ggccaggaac cgtaaaaagg ccgcgttgct ggcgtttttc cataggctcc gcccccctga   3780
cgagcatcac aaaaatcgac gctcaagtca gaggtggcga aacccgacag gactataaag   3840
ataccaggcg tttccccctg gaagctccct cgtgcgctct cctgttccga ccctgccgct   3900
taccggatac ctgtccgcct ttctcccttc gggaagcgtg gcgctttctc aatgctcacg   3960
ctgtaggtat ctcagttcgg tgtaggtcgt tcgctccaag ctgggctgtg tgcacgaacc   4020
ccccgttcag cccgaccgct gcgccttatc cggtaactat cgtcttgagt ccaacccggt   4080
```

```
aagacacgac ttatcgccac tggcagcagc cactggtaac aggattagca gagcgaggta   4140

tgtaggcggt gctacagagt tcttgaagtg gtggcctaac tacggctaca ctagaaggac   4200

agtatttggt atctgcgctc tgctgaagcc agttaccttc ggaaaaagag ttggtagctc   4260

ttgatccggc aaacaaacca ccgctggtag cggtggtttt tttgtttgca agcagcagat   4320

tacgcgcaga aaaaaaggat ctcaagaaga tcctttgatc ttttctacgg ggtctgacgc   4380

tcagtggaac gaaaactcac gttaagggat tttggtcatg agatc                   4425
```

<210> SEQ ID NO 77
<211> LENGTH: 25
<212> TYPE: DNA
<213> ORGANISM: Candida Tropicalis

<400> SEQUENCE: 77

```
tggcggaagt gcatgtgaca caacg                                           25
```

<210> SEQ ID NO 78
<211> LENGTH: 25
<212> TYPE: DNA
<213> ORGANISM: Candida Tropicalis

<400> SEQUENCE: 78

```
gtggttggtt tgtctgagtg gagag                                           25
```

<210> SEQ ID NO 79
<211> LENGTH: 25
<212> TYPE: DNA
<213> ORGANISM: Artificial Sequence
<220> FEATURE:
<223> OTHER INFORMATION: Primer for analysis of strains

<400> SEQUENCE: 79

```
tggtactggt tctcgggagc acagg                                           25
```

<210> SEQ ID NO 80
<211> LENGTH: 30
<212> TYPE: DNA
<213> ORGANISM: Candida tropicalis

<400> SEQUENCE: 80

```
cgctagacaa attcttccaa aaattttaga                                      30
```

<210> SEQ ID NO 81
<211> LENGTH: 25
<212> TYPE: DNA
<213> ORGANISM: Candida tropicalis

<400> SEQUENCE: 81

```
catgtggccg ctgaatgtgg gggca                                           25
```

<210> SEQ ID NO 82
<211> LENGTH: 30
<212> TYPE: DNA
<213> ORGANISM: Artificial sequence
<220> FEATURE:
<223> OTHER INFORMATION: Primer for analysis of strains

<400> SEQUENCE: 82

```
gccattttgt tttttttac ccctctaaca                                       30
```

<210> SEQ ID NO 83
<211> LENGTH: 25

<212> TYPE: DNA
<213> ORGANISM: Candida tropicalis

<400> SEQUENCE: 83
ggaagtgcat gtgacacaat accct 25

<210> SEQ ID NO 84
<211> LENGTH: 30
<212> TYPE: DNA
<213> ORGANISM: Artificial Sequence
<220> FEATURE:
<223> OTHER INFORMATION: Oligonucleotide primer for analysis of strains

<400> SEQUENCE: 84
ggtggtttgt ctgagtgaga acgtttaatt 30

<210> SEQ ID NO 85
<211> LENGTH: 25
<212> TYPE: DNA
<213> ORGANISM: Candida tropicalis

<400> SEQUENCE: 85
gacgtagccg atgaatgtgg ggtgc 25

<210> SEQ ID NO 86
<211> LENGTH: 30
<212> TYPE: DNA
<213> ORGANISM: Artificial Sequence
<220> FEATURE:
<223> OTHER INFORMATION: Oligonucleotide primer for analysis of strains

<400> SEQUENCE: 86
tgccatttat tttttattac ccctctaaat 30

<210> SEQ ID NO 87
<211> LENGTH: 25
<212> TYPE: DNA
<213> ORGANISM: Candidida tropicalis

<400> SEQUENCE: 87
attggcgtcg tggcattggc ggctc 25

<210> SEQ ID NO 88
<211> LENGTH: 20
<212> TYPE: DNA
<213> ORGANISM: Artificial Sequence
<220> FEATURE:
<223> OTHER INFORMATION: Oligonucleotide primers for analysis of strains

<400> SEQUENCE: 88
tgggcggaat caagtggctt 20

<210> SEQ ID NO 89
<211> LENGTH: 20
<212> TYPE: DNA
<213> ORGANISM: Candida tropicalis

<400> SEQUENCE: 89
cgtcgacacc cttatgttat 20

<210> SEQ ID NO 90
<211> LENGTH: 21
<212> TYPE: DNA
<213> ORGANISM: Candida tropicalis

<400> SEQUENCE: 90
cgttgactcc tatcaaggac a 21

<210> SEQ ID NO 91
<211> LENGTH: 22
<212> TYPE: DNA
<213> ORGANISM: Artificial Sequence
<220> FEATURE:
<223> OTHER INFORMATION: Primer used for analysis of strains

<400> SEQUENCE: 91
ggtcttctct tcctggataa tg 22

<210> SEQ ID NO 92
<211> LENGTH: 20
<212> TYPE: DNA
<213> ORGANISM: Candida tropicalis

<400> SEQUENCE: 92
ccagcagttg tttgttcttg 20

<210> SEQ ID NO 93
<211> LENGTH: 22
<212> TYPE: DNA
<213> ORGANISM: Artificial Sequence
<220> FEATURE:
<223> OTHER INFORMATION: Primer used for analysis of strains

<400> SEQUENCE: 93
aatcctgtgc tttgtcgtag gc 22

<210> SEQ ID NO 94
<211> LENGTH: 21
<212> TYPE: DNA
<213> ORGANISM: Candida tropicalis

<400> SEQUENCE: 94
tccttaacaa gaagggcatc g 21

<210> SEQ ID NO 95
<211> LENGTH: 20
<212> TYPE: DNA
<213> ORGANISM: Artificial Sequence
<220> FEATURE:
<223> OTHER INFORMATION: TTCTTGAATCCGGAGTTGAC

<400> SEQUENCE: 95
ttcttgaatc cggagttgac 20

<210> SEQ ID NO 96
<211> LENGTH: 20
<212> TYPE: DNA
<213> ORGANISM: Candida tropicalis

<400> SEQUENCE: 96
tcttagtcgt gataccacca 20

<210> SEQ ID NO 97
<211> LENGTH: 20
<212> TYPE: DNA
<213> ORGANISM: Artificial Sequence
<220> FEATURE:
<223> OTHER INFORMATION: Primer used for analysis of strains

<400> SEQUENCE: 97
ctaaggattc tcttggcacc 20

<210> SEQ ID NO 98
<211> LENGTH: 20
<212> TYPE: DNA
<213> ORGANISM: Artificial Sequence
<220> FEATURE:
<223> OTHER INFORMATION: Primer used for analysis of strains

<400> SEQUENCE: 98
gtgaccatag gattagcacc 20

<210> SEQ ID NO 99
<211> LENGTH: 30
<212> TYPE: DNA
<213> ORGANISM: Candida tropicalis

<400> SEQUENCE: 99
cttttctgat tcttgatttt cccttttcat 30

<210> SEQ ID NO 100
<211> LENGTH: 30
<212> TYPE: DNA
<213> ORGANISM: Artificial Sequence
<220> FEATURE:
<223> OTHER INFORMATION: Primer for analysis of strains

<400> SEQUENCE: 100
atacatctag tatataagtg tcgtatttcc 30

<210> SEQ ID NO 101
<211> LENGTH: 30
<212> TYPE: DNA
<213> ORGANISM: Candida tropicalis

<400> SEQUENCE: 101
tgcttttctg attcttgatc atccccttag 30

<210> SEQ ID NO 102
<211> LENGTH: 30
<212> TYPE: DNA
<213> ORGANISM: Artificial Sequence
<220> FEATURE:
<223> OTHER INFORMATION: Primer for analysis of strains

<400> SEQUENCE: 102
atacatctag tatataagtg tcgtatttct 30

<210> SEQ ID NO 103
<211> LENGTH: 25
<212> TYPE: DNA
<213> ORGANISM: Candida tropicalis

<400> SEQUENCE: 103
cgccagtctt tcctgattgg gcaag 25

<210> SEQ ID NO 104
<211> LENGTH: 25
<212> TYPE: DNA
<213> ORGANISM: Artificial Sequence
<220> FEATURE:
<223> OTHER INFORMATION: Analysis of constructs

<400> SEQUENCE: 104
ggacgttgtc gagtagaggg atgtg 25

<210> SEQ ID NO 105
<211> LENGTH: 20
<212> TYPE: DNA
<213> ORGANISM: Candida tropicalis

<400> SEQUENCE: 105
ctgtacttcc gtacttgacc 20

<210> SEQ ID NO 106
<211> LENGTH: 19
<212> TYPE: DNA
<213> ORGANISM: Artificial Sequence
<220> FEATURE:
<223> OTHER INFORMATION: Analysis of strains

<400> SEQUENCE: 106
gagacctgga tcagatgag 19

<210> SEQ ID NO 107
<211> LENGTH: 21
<212> TYPE: DNA
<213> ORGANISM: Candida albicans

<400> SEQUENCE: 107
gtttacaaag ccttaaagac t 21

<210> SEQ ID NO 108
<211> LENGTH: 21
<212> TYPE: DNA
<213> ORGANISM: Artificial Sequence
<220> FEATURE:
<223> OTHER INFORMATION: Analysis of strains

<400> SEQUENCE: 108
ttgaacggcc aaagaaccta a 21

<210> SEQ ID NO 109
<211> LENGTH: 27
<212> TYPE: DNA
<213> ORGANISM: Candida tropicalis

<400> SEQUENCE: 109
gaattagaat acaaagatat cccagtg 27

<210> SEQ ID NO 110
<211> LENGTH: 25
<212> TYPE: DNA
<213> ORGANISM: Artificial Sequence
<220> FEATURE:
<223> OTHER INFORMATION: Primer for analysis of strains

<400> SEQUENCE: 110
catcaacttg aagacctgtg gcaat 25

<210> SEQ ID NO 111
<211> LENGTH: 27
<212> TYPE: DNA
<213> ORGANISM: Candida tropicalis

<400> SEQUENCE: 111
gaacggttcc tgtatgtcct gtgagtt 27

<210> SEQ ID NO 112
<211> LENGTH: 26
<212> TYPE: DNA
<213> ORGANISM: Artificial sequence
<220> FEATURE:
<223> OTHER INFORMATION: Probe for analysis of strains

<400> SEQUENCE: 112
cggattggtc aatggctttt tcggaa 26

<210> SEQ ID NO 113
<211> LENGTH: 27
<212> TYPE: DNA
<213> ORGANISM: Candida tropicalis

<400> SEQUENCE: 113
aaattagaat acaaggacat cccagtt 27

<210> SEQ ID NO 114
<211> LENGTH: 25
<212> TYPE: DNA
<213> ORGANISM: Artificial sequence
<220> FEATURE:
<223> OTHER INFORMATION: Probe for analysis of strains

<400> SEQUENCE: 114
catcaacttg tagacttctg gcaat 25

<210> SEQ ID NO 115
<211> LENGTH: 27
<212> TYPE: DNA
<213> ORGANISM: Candida tropicalis

<400> SEQUENCE: 115
gaacggttcc tgtatgaact gtgagta 27

<210> SEQ ID NO 116
<211> LENGTH: 26
<212> TYPE: DNA
<213> ORGANISM: Artificial Sequence
<220> FEATURE:
<223> OTHER INFORMATION: Probe for analysis of strains

<400> SEQUENCE: 116
cagattggtt gatggccttt tcggag 26

<210> SEQ ID NO 117
<211> LENGTH: 27
<212> TYPE: DNA
<213> ORGANISM: Candida tropicalis

<400> SEQUENCE: 117
aagttagaat acaaagacgt gccggtc 27

<210> SEQ ID NO 118
<211> LENGTH: 25
<212> TYPE: DNA
<213> ORGANISM: Artificial Sequence
<220> FEATURE:
<223> OTHER INFORMATION: Primer for analysis of probes

<400> SEQUENCE: 118
catcaagtca aaaatctctg gcact 25

<210> SEQ ID NO 119
<211> LENGTH: 27
<212> TYPE: DNA
<213> ORGANISM: Candida tropicalis

<400> SEQUENCE: 119
ccattgcaat acaccgatat cccagtt 27

<210> SEQ ID NO 120
<211> LENGTH: 25
<212> TYPE: DNA
<213> ORGANISM: Artificial sequence
<220> FEATURE:
<223> OTHER INFORMATION: Primer for analysis of genes

<400> SEQUENCE: 120
caacaatttg aaaatctctg gcaat 25

<210> SEQ ID NO 121
<211> LENGTH: 27
<212> TYPE: DNA
<213> ORGANISM: Candida tropicalis

<400> SEQUENCE: 121
gaatggttcg tgtatgaact gtgagtt 27

<210> SEQ ID NO 122
<211> LENGTH: 26
<212> TYPE: DNA
<213> ORGANISM: Artificial Sequence
<220> FEATURE:
<223> OTHER INFORMATION: Probe for analysis of strains

<400> SEQUENCE: 122
ccgactggtt gattgccttt tcggac 26

<210> SEQ ID NO 123
<211> LENGTH: 26
<212> TYPE: DNA
<213> ORGANISM: Artificial Sequence
<220> FEATURE:
<223> OTHER INFORMATION: Probe for analysis of primers

<400> SEQUENCE: 123
cagactggtt gatggctttt tcagaa 26

<210> SEQ ID NO 124
<211> LENGTH: 26
<212> TYPE: DNA
<213> ORGANISM: Artificial sequence
<220> FEATURE:
<223> OTHER INFORMATION: Probe for analysis of strains

<400> SEQUENCE: 124
ggatccgtct gaagaaatca agaacc 26

<210> SEQ ID NO 125
<211> LENGTH: 48
<212> TYPE: DNA
<213> ORGANISM: Artificial sequence
<220> FEATURE:
<223> OTHER INFORMATION: Probe for analysis of strains

<400> SEQUENCE: 125
tggtgtaggc caataattgc ttaatgatat acaaaactgg caccacaa 48

<210> SEQ ID NO 126
<211> LENGTH: 49
<212> TYPE: DNA
<213> ORGANISM: Artificial sequence
<220> FEATURE:
<223> OTHER INFORMATION: Probe for analysis of strains

<400> SEQUENCE: 126
gagcaattgt tggaatattg gtacgttgtg gtgccagttt tgtatatca 49

<210> SEQ ID NO 127
<211> LENGTH: 49
<212> TYPE: DNA
<213> ORGANISM: Artificial sequence
<220> FEATURE:
<223> OTHER INFORMATION: Probe for analysis of strains

<400> SEQUENCE: 127
cgaacttaac aatagcaccg tcttgcaaac acatggtcaa gttagttaa 49

<210> SEQ ID NO 128
<211> LENGTH: 47
<212> TYPE: DNA
<213> ORGANISM: Artificial Sequence
<220> FEATURE:
<223> OTHER INFORMATION: Probe for analysis of strains

<400> SEQUENCE: 128
cgattaaggc caatggaaca atgacgtacc acttagtaaa gtaggta 47

<210> SEQ ID NO 129
<211> LENGTH: 49
<212> TYPE: DNA
<213> ORGANISM: Artificial sequence
<220> FEATURE:
<223> OTHER INFORMATION: Probe for analysis of strains

<400> SEQUENCE: 129
catgactgtt cacgacatta ttgctaccta ctttactaag tggtacgtc 49

<210> SEQ ID NO 130
<211> LENGTH: 48
<212> TYPE: DNA
<213> ORGANISM: Artificial Sequence
<220> FEATURE:
<223> OTHER INFORMATION: Probe for analysis of strains

<400> SEQUENCE: 130
acatttcaat attagcaccg tcaaataatg acatggtcaa atgggaca 48

<210> SEQ ID NO 131
<211> LENGTH: 24
<212> TYPE: DNA
<213> ORGANISM: Artificial sequence
<220> FEATURE:
<223> OTHER INFORMATION: Analysis of probes

<400> SEQUENCE: 131
atcaataatt tcctgggttg ccat 24

<210> SEQ ID NO 132
<211> LENGTH: 24
<212> TYPE: DNA
<213> ORGANISM: Artificial sequence
<220> FEATURE:
<223> OTHER INFORMATION: Analysis of probes

<400> SEQUENCE: 132
atggcaaccc aggaaattat tgat 24

<210> SEQ ID NO 133
<211> LENGTH: 27

<212> TYPE: DNA
<213> ORGANISM: Artificial sequence
<220> FEATURE:
<223> OTHER INFORMATION: CTACATCTTGACAAAAACACCATCATT

<400> SEQUENCE: 133
ctacatcttg acaaaaacac catcatt 27

<210> SEQ ID NO 134
<211> LENGTH: 709
<212> TYPE: PRT
<213> ORGANISM: Candida tropicalis

<400> SEQUENCE: 134

Met Thr Phe Thr Lys Lys Asn Val Ser Val Ser Gln Gly Pro Asp Pro
1 5 10 15

Arg Ser Ser Ile Gln Lys Glu Arg Asp Ser Ser Lys Trp Asn Pro Gln
20 25 30

Gln Met Asn Tyr Phe Leu Glu Gly Ser Val Glu Arg Ser Glu Leu Met
35 40 45

Lys Ala Leu Ala Gln Gln Met Glu Arg Asp Pro Ile Leu Phe Thr Asp
50 55 60

Gly Ser Tyr Tyr Asp Leu Thr Lys Asp Gln Gln Arg Glu Leu Thr Ala
65 70 75 80

Val Lys Ile Asn Arg Ile Ala Arg Tyr Arg Glu Gln Glu Ser Ile Asp
85 90 95

Thr Phe Asn Lys Arg Leu Ser Leu Ile Gly Ile Phe Asp Pro Gln Val
100 105 110

Gly Thr Arg Ile Gly Val Asn Leu Gly Leu Phe Leu Ser Cys Ile Arg
115 120 125

Gly Asn Gly Thr Thr Ser Gln Leu Asn Tyr Trp Ala Asn Glu Lys Glu
130 135 140

Thr Ala Asp Val Lys Gly Ile Tyr Gly Cys Phe Gly Met Thr Glu Leu
145 150 155 160

Ala His Gly Ser Asn Val Ala Gly Leu Glu Thr Thr Ala Thr Phe Asp
165 170 175

Lys Glu Ser Asp Glu Phe Val Ile Asn Thr Pro His Ile Gly Ala Thr
180 185 190

Lys Trp Trp Ile Gly Gly Ala Ala His Ser Ala Thr His Cys Ser Val
195 200 205

Tyr Ala Arg Leu Ile Val Asp Gly Gln Asp Tyr Gly Val Lys Thr Phe
210 215 220

Val Val Pro Leu Arg Asp Ser Asn His Asp Leu Met Pro Gly Val Thr
225 230 235 240

Val Gly Asp Ile Gly Pro Lys Met Gly Arg Asp Gly Ile Asp Asn Gly
245 250 255

Trp Ile Gln Phe Ser Asn Val Arg Ile Pro Arg Phe Phe Met Leu Gln
260 265 270

Lys Phe Cys Lys Val Ser Ala Glu Gly Glu Val Thr Leu Pro Pro Leu
275 280 285

Glu Gln Leu Ser Tyr Ser Ala Leu Leu Gly Gly Arg Val Met Met Val
290 295 300

Leu Asp Ser Tyr Arg Met Leu Ala Arg Met Ser Thr Ile Ala Leu Arg
305 310 315 320

Tyr Ala Ile Gly Arg Arg Gln Phe Lys Gly Asp Asn Val Asp Pro Asn
325 330 335

```
Asp Pro Asn Ala Leu Glu Thr Gln Leu Ile Asp Tyr Pro Leu His Gln
            340                 345                 350

Lys Arg Leu Phe Pro Tyr Phe Val Pro Pro Met Ser Ser Pro Ser Val
        355                 360                 365

Pro Ser Arg Leu Asn Thr Pro Ser Arg Pro Pro Trp Ser Asn Trp Thr
    370                 375                 380

Ser Pro Leu Lys Arg Thr Thr Pro Arg Leu Ile Phe Lys Ser Ile Asp
385                 390                 395                 400

Asp Met Lys Ser Leu Phe Val Asp Ser Gly Ser Leu Lys Ser Thr Ala
                405                 410                 415

Thr Trp Leu Gly Ala Glu Ala Ile Asp Gln Cys Arg Gln Ala Cys Gly
            420                 425                 430

Gly His Gly His Ser Ser Tyr Asn Gly Phe Gly Lys Ala Tyr Asn Asp
        435                 440                 445

Trp Val Val Gln Cys Thr Trp Glu Gly Asp Asn Asn Val Leu Gly Met
    450                 455                 460

Ser Val Gly Lys Pro Ile Val Lys Gln Val Ile Ser Ile Glu Asp Ala
465                 470                 475                 480

Gly Lys Thr Val Arg Gly Ser Thr Ala Phe Leu Asn Gln Leu Lys Glu
                485                 490                 495

Tyr Thr Gly Ser Asn Ser Ser Lys Val Val Leu Asn Thr Val Ala Asp
            500                 505                 510

Leu Asp Asp Ile Lys Thr Val Ile Lys Ala Ile Glu Val Ala Ile Ile
        515                 520                 525

Arg Leu Ser Gln Glu Ala Ala Ser Ile Val Lys Lys Glu Ser Phe Asp
    530                 535                 540

Tyr Val Gly Ala Glu Leu Val Gln Leu Ser Lys Leu Lys Ala His His
545                 550                 555                 560

Tyr Leu Leu Thr Glu Tyr Ile Arg Arg Ile Asp Thr Phe Asp Gln Lys
                565                 570                 575

Glu Leu Ala Pro Tyr Leu Ile Thr Leu Gly Lys Leu Tyr Ala Ala Thr
            580                 585                 590

Ile Val Leu Asp Arg Phe Ala Gly Val Phe Leu Thr Phe Asn Val Ala
        595                 600                 605

Ser Thr Glu Ala Ile Thr Ala Leu Ala Ser Val Gln Ile Pro Lys Leu
    610                 615                 620

Cys Ala Glu Val Arg Pro Asn Val Val Ala Tyr Thr Asp Ser Phe Gln
625                 630                 635                 640

Gln Ser Asp Met Ile Val Asn Ser Ala Ile Gly Arg Tyr Asp Gly Asp
                645                 650                 655

Ile Tyr Glu Asn Tyr Phe Asp Leu Val Lys Leu Gln Asn Pro Pro Ser
            660                 665                 670

Lys Thr Lys Ala Pro Tyr Ser Asp Ala Leu Glu Ala Met Leu Asn Arg
        675                 680                 685

Pro Thr Leu Asp Glu Arg Glu Arg Phe Gln Lys Ser Asp Glu Thr Ala
    690                 695                 700

Ala Ile Leu Ser Lys
705
```

<210> SEQ ID NO 135
<211> LENGTH: 662
<212> TYPE: PRT
<213> ORGANISM: Candida tropicalis

<400> SEQUENCE: 135

```
Met Pro Thr Glu Leu Gln Lys Glu Arg Glu Leu Thr Lys Phe Asn Pro
 1               5                  10                  15

Lys Glu Leu Asn Tyr Phe Leu Glu Gly Ser Gln Glu Arg Ser Glu Ile
            20                  25                  30

Ile Ser Asn Met Val Glu Gln Met Gln Lys Asp Pro Ile Leu Lys Val
        35                  40                  45

Asp Ala Ser Tyr Tyr Asn Leu Thr Lys Asp Gln Gln Arg Glu Val Thr
    50                  55                  60

Ala Lys Lys Ile Ala Arg Leu Ser Arg Tyr Phe Glu His Glu Tyr Pro
65                  70                  75                  80

Asp Gln Gln Ala Gln Arg Leu Ser Ile Leu Gly Val Phe Asp Pro Gln
                85                  90                  95

Val Phe Thr Arg Ile Gly Val Asn Leu Gly Leu Phe Val Ser Cys Val
            100                 105                 110

Arg Gly Asn Gly Thr Asn Ser Gln Phe Phe Tyr Trp Thr Ile Asn Lys
        115                 120                 125

Gly Ile Asp Lys Leu Arg Gly Ile Tyr Gly Cys Phe Gly Met Thr Glu
    130                 135                 140

Leu Ala His Gly Ser Asn Val Gln Gly Ile Glu Thr Thr Ala Thr Phe
145                 150                 155                 160

Asp Glu Asp Thr Asp Glu Phe Val Ile Asn Thr Pro His Ile Gly Ala
                165                 170                 175

Thr Lys Trp Trp Ile Gly Gly Ala Ala His Ser Ala Thr His Cys Ser
            180                 185                 190

Val Tyr Ala Arg Leu Lys Val Lys Gly Lys Asp Tyr Gly Val Lys Thr
        195                 200                 205

Phe Val Val Pro Leu Arg Asp Ser Asn His Asp Leu Glu Pro Gly Val
    210                 215                 220

Thr Val Gly Asp Ile Gly Ala Lys Met Gly Arg Asp Gly Ile Asp Asn
225                 230                 235                 240

Gly Trp Ile Gln Phe Ser Asn Val Arg Ile Pro Arg Phe Phe Met Leu
                245                 250                 255

Gln Lys Tyr Cys Lys Val Ser Arg Ser Gly Glu Val Thr Met Pro Pro
            260                 265                 270

Ser Glu Gln Leu Ser Tyr Ser Ala Leu Ile Gly Gly Arg Val Thr Met
        275                 280                 285

Met Met Asp Ser Tyr Arg Met Thr Ser Arg Phe Ile Thr Ile Ala Leu
    290                 295                 300

Arg Tyr Ala Ile His Arg Arg Gln Phe Lys Lys Lys Asp Thr Asp Thr
305                 310                 315                 320

Ile Glu Thr Lys Leu Ile Asp Tyr Pro Leu His Gln Lys Arg Leu Phe
                325                 330                 335

Pro Phe Leu Ala Ala Ala Tyr Leu Phe Ser Gln Gly Ala Leu Tyr Leu
            340                 345                 350

Glu Gln Thr Met Asn Ala Thr Asn Asp Lys Leu Asp Glu Ala Val Ser
        355                 360                 365

Ala Gly Glu Lys Glu Ala Ile Asp Ala Ala Ile Val Glu Ser Lys Lys
    370                 375                 380

Leu Phe Val Ala Ser Gly Cys Leu Lys Ser Thr Cys Thr Trp Leu Thr
385                 390                 395                 400

Ala Glu Ala Ile Asp Glu Ala Arg Gln Ala Cys Gly Gly His Gly Tyr
                405                 410                 415

Ser Ser Tyr Asn Gly Phe Gly Lys Ala Tyr Ser Asp Trp Val Val Gln
            420                 425                 430
```

```
Cys Thr Trp Glu Gly Asp Asn Asn Ile Leu Ala Met Asn Val Ala Lys
        435                 440                 445

Pro Met Val Arg Asp Leu Leu Lys Glu Pro Glu Gln Lys Gly Leu Val
    450                 455                 460

Leu Ser Ser Val Ala Asp Leu Asp Asp Pro Ala Lys Leu Val Lys Ala
465                 470                 475                 480

Phe Asp His Ala Leu Ser Gly Leu Ala Arg Asp Ile Gly Ala Val Ala
                485                 490                 495

Glu Asp Lys Gly Phe Asp Ile Thr Gly Pro Ser Leu Val Leu Val Ser
            500                 505                 510

Lys Leu Asn Ala His Arg Phe Leu Ile Asp Gly Phe Phe Lys Arg Ile
        515                 520                 525

Thr Pro Glu Trp Ser Glu Val Leu Arg Pro Leu Gly Phe Leu Tyr Ala
    530                 535                 540

Asp Trp Ile Leu Thr Asn Phe Gly Ala Thr Phe Leu Gln Tyr Gly Ile
545                 550                 555                 560

Ile Thr Pro Asp Val Ser Arg Lys Ile Ser Ser Glu His Phe Pro Ala
                565                 570                 575

Leu Cys Ala Lys Val Arg Pro Asn Val Val Gly Leu Thr Asp Gly Phe
            580                 585                 590

Asn Leu Thr Asp Met Met Thr Asn Ala Ala Ile Gly Arg Tyr Asp Gly
        595                 600                 605

Asn Val Tyr Glu His Tyr Phe Glu Thr Val Lys Ala Leu Asn Pro Pro
    610                 615                 620

Glu Asn Thr Lys Ala Pro Tyr Ser Lys Ala Leu Glu Asp Met Leu Asn
625                 630                 635                 640

Arg Pro Asp Leu Glu Val Arg Glu Arg Gly Glu Lys Ser Glu Glu Ala
                645                 650                 655

Ala Glu Ile Leu Ser Ser
            660


<210> SEQ ID NO 136
<211> LENGTH: 2845
<212> TYPE: DNA
<213> ORGANISM: Candida tropicalis

<400> SEQUENCE: 136

gagctccaat tgtaatattt cgggagaaat atcgttgggg taaaacaaca gagagagaga      60

gggagagatg gttctggtag aattataatc tggttgttgc aaatgctact gatcgactct     120

ggcaatgtct gtagctcgct agttgtatgc aacttaggtg ttatgcatac acacggttat     180

tcggttgaat tgtggagtaa aaattgtctg agttgtgtct tagctactgg ctggcccccc     240

gcgaaagata atcaaaatta cacttgtgaa tttttgcaca cacaccgatt aacatttccc     300

ttttttgtcc accgatacac gcttgcctct tcttttttt ctctgtgctt ccccctcctg      360

tgactttttc caccattgat ataaaatcaa ctccatttcc ctaaaatctc cccagattct     420

aaaaacaact tcttctcttc tgcttttcct tttttttgt tatatttatt taccatccct      480

ttttttgaa tagttattcc ccactaacat tgttcaaatc ttcacgacat aatgactttt      540

acaaagaaaa acgttagtgt atcacaaggt cctgacccta gatcatccat ccaaaaggaa     600

agagacagct ccaaatggaa ccctcaacaa atgaactact tcttggaagg ctccgtcgaa     660

agaagtgagt tgatgaaggc tttggcccaa caaatggaaa gagacccaat cttgttcaca     720

gacggctcct actacgactt gaccaaggac caacaaagag aattgaccgc cgtcaagatc     780
```

```
aacagaatcg ccagatacag agaacaagaa tccatcgaca ctttcaacaa gagattgtcc    840
ttgattggta tctttgaccc acaggtcggt accagaattg gtgtcaacct cggtttgttc    900
ctttcttgta tcagaggtaa cggtaccact tcccaattga actactgggc taacgaaaag    960
gaaaccgctg acgttaaagg tatctacggt tgtttcggta tgaccgaatt ggcccacggt   1020
tccaacgttg ctggtttgga aaccaccgcc acatttgaca aggaatctga cgagtttgtc   1080
atcaacaccc cacacattgg tgccaccaag tggtggattg gtggtgctgc tcactccgcc   1140
acccactgtt ctgtctacgc cagattgatt gttgacggtc aagattacgg tgtcaagact   1200
tttgttgtcc cattgagaga ctccaaccac gacctcatgc caggtgtcac tgttggtgac   1260
attggtgcca agatgggtag agatggtatc gataacggtt ggatccaatt ctccaacgtc   1320
agaatcccaa gattctttat gttgcaaaag ttctgtaagg tttctgctga aggtgaagtc   1380
accttgccac ctttggaaca attgtcttac tccgccttgt tgggtggtag agtcatgatg   1440
gttttggact cctacagaat gttggctaga atgtccacca ttgccttgag atacgccatt   1500
ggtagaagac aattcaaggg tgacaatgtc gatccaaaag atccaaacgc tttggaaacc   1560
caattgatag attacccatt gcaccaaaag agattgttcc catacttggc tgctgcctac   1620
gtcatctccg ctggtgccct caaggttgaa gacaccatcc ataacacctt ggctgaattg   1680
gacgctgccg ttgaaaagaa cgacaccaag gctatcttta agtctattga cgacatgaag   1740
tcattgtttg ttgactctgg ttccttgaag tccactgcca cttggttggg tgctgaagcc   1800
attgaccaat gtagacaagc ctgtggtggt cacggttact cgtcctacaa cggcttcggt   1860
aaagcctaca acgattgggt tgtccaatgt acttgggaag gtgacaacaa tgtcttggcc   1920
atgagtgttg gtaagccaat tgtcaagcaa gttatcagca ttgaagatgc cggcaagacc   1980
gtcagaggtt ccaccgcttt cttgaaccaa ttgaaggact acactggttc caacagctcc   2040
aaggttgttt tgaacactgt tgctgacttg gacgacatca agactgtcat caaggctatt   2100
gaagttgcca tcatcagatt gtcccaagaa gctgcttcta ttgtcaagaa ggaatctttc   2160
gactatgtcg gcgctgaatt ggttcaactc tccaagttga aggctcacca ctacttgttg   2220
actgaataca tcagaagaat tgacaccttt gaccaaaagg acttggttcc atacttgatc   2280
accctcggta agttgtacgc tgccactatt gtcttggaca gatttgccgg tgtcttcttg   2340
actttcaacg ttgcctccac cgaagccatc actgctttgg cctctgtgca aattccaaag   2400
ttgtgtgctg aagtcagacc aaacgttgtt gcttacaccg actccttcca acaatccgac   2460
atgattgtca attctgctat tggtagatac gatggtgaca tctatgagaa ctactttgac   2520
ttggtcaagt tgcagaaccc accatccaag accaaggctc cttactctga tgctttggaa   2580
gccatgttga acagaccaac cttggacgaa agagaaagat ttgaaaagtc tgatgaaacc   2640
gctgctatct tgtccaagta agaatagaag agagtgactc ttttgataag agtcgcaaat   2700
ttgatttcat aagtatatat tcattatgta aagtagtaaa tggaaaattc attaaaaaaa   2760
aagcaaattt ccgttgtatg catactccga acacaaaact agccccggaa aaacccttag   2820
ttgatagttg cgaatttagg tcgac                                          2845
```

<210> SEQ ID NO 137
<211> LENGTH: 640
<212> TYPE: DNA
<213> ORGANISM: Artificial Sequence
<220> FEATURE:
<223> OTHER INFORMATION: Pre-targeting construct for transformation of POX4 into Candida tropicalis

<400> SEQUENCE: 137
cgtctccaaa aggaaagaga cagctccaaa tggaaccctc aacaaatgaa ctacttcttg 60
gaaggctccg tcgaaagaag tgagttgatg aaggctttgg cccaacaaat ggaaagagac 120
ccaatcttgt tcacagacgg ctcctactac gacttgacca aggaccaaca aagagaattg 180
accgccgtca agatcaacag aatcgccaga tacagagaac aagaatccat cgacactttc 240
aacaagagat tgtccttgat tggtatcttt gacccacagg tcggtaccag aattggtgtc 300
aacgcggccg ctagatcttg cgaagctcca tctcgagact attgtcttgg acagatttgc 360
cggtgtcttc ttgactttca acgttgcctc caccgaagcc atcactgctt tggcctctgt 420
gcaaattcca aagttgtgtg ctgaagtcag accaaacgtt gttgcttaca ccgactcctt 480
ccaacaatcc gacatgattg tcaattctgc tattggtaga tacgatggtg acatctatga 540
gaactacttt gacttggtca agttgcagaa cccaccatcc aagaccaagg ctccttactc 600
tgatgctttg gaagccatgt tgaacagacc aaccgagacg 640

<210> SEQ ID NO 138
<211> LENGTH: 640
<212> TYPE: DNA
<213> ORGANISM: Artificial Sequence
<220> FEATURE:
<223> OTHER INFORMATION: pre-targeting construct for targeting POX4 in Candida tropicalis

<400> SEQUENCE: 138
cgtctcgcta acgaaaagga aaccgctgac gttaaaggta tctacggttg tttcggtatg 60
accgaattgg cccacggttc caacgttgct ggtttggaaa ccaccgccac atttgacaag 120
gaatctgacg agtttgtcat caacacccca cacattggtg ccaccaagtg gtggattggt 180
ggtgctgctc actccgccac ccactgttct gtctacgcca gattgattgt tgacggtcaa 240
gattacggtg tcaagacttt tgttgtccca ttgagagact ccaaccacga cctcatgcca 300
ggtgcggccg ctagatcttg cgaagctcca tctcgagcaa gttatcagca ttgaagatgc 360
cggcaagacc gtcagaggtt ccaccgcttt cttgaaccaa ttgaaggact acactggttc 420
caacagctcc aaggttgttt tgaacactgt tgctgacttg gacgacatca agactgtcat 480
caaggctatt gaagttgcca tcatcagatt gtcccaagaa gctgcttcta ttgtcaagaa 540
ggaatctttc gactatgtcg gcgctgaatt ggttcaactc tccaagttga aggctcacca 600
ctacttgttg actgaataca tcagaagaat tgacgagacg 640

<210> SEQ ID NO 139
<211> LENGTH: 4792
<212> TYPE: DNA
<213> ORGANISM: Artificial Sequence
<220> FEATURE:
<223> OTHER INFORMATION: Sequence of a first targeting construct for the deletion of a first allele of POX4 in Candida tropicalis

<400> SEQUENCE: 139
cgtctccaaa aggaaagaga cagctccaaa tggaaccctc aacaaatgaa ctacttcttg 60
gaaggctccg tcgaaagaag tgagttgatg aaggctttgg cccaacaaat ggaaagagac 120
ccaatcttgt tcacagacgg ctcctactac gacttgacca aggaccaaca aagagaattg 180
accgccgtca agatcaacag aatcgccaga tacagagaac aagaatccat cgacactttc 240
aacaagagat tgtccttgat tggtatcttt gacccacagg tcggtaccag aattggtgtc 300
aacgcggccg ctctagaact agtggatctg aagttcctat tctctagaaa gtataggaac 360
ttcctgcagg accacctttg attgtaaata gtaataatta ccacccttat ctaattattt 420

```
atttaactta tttatttatt tattatacat atatacaaat ctaataaagt gaaaatctcc    480
cccttcacac ttcacatatg ttaggcgtca tcctgtgctc ccgagaacca gtaccagtac    540
atcgctgttt cgttcgagac ttgaggtcta gttttatacg tgaagaggtc aatgccgccg    600
agagtaaagc cacattttgc gtacaaattg caggcaggta cattgttcgt ttgtgtctct    660
aatcgtatgc caaggagctg tctgcttagt gcccactttt tcgcaaattc gatgagactg    720
tgcgcgactc ctttgcctcg gtgcgtgtgc gacacaacaa tgtgttcgat agaggctaga    780
tcgttccatg ttgagttgag ttcaatcttc ccgacaagct cttggtcgat gaatgcgcca    840
tagcaagcag agtcttcatc agagtcatca tccgagatgt aatccttccg gtaggggctc    900
acacttctgg tagatagttc aaagccttgg tcggataggt gcacatcgaa cacttcacga    960
acaatgaaat ggttctcagc atccaatgtt tccgccacct gctcagggat caccgaaatt   1020
ttcatatgag aaccgttatc gataactaaa gcagcaactt cttctataaa aatgggttag   1080
tatgacagtc atttaaataa ggaatttttc agttggcttg gtttcaattc aatgttcgtt   1140
ttttttttt cttgctgtgt ttgtgtttgt gttgtttata gttgtgtgca ctgagcgtcg   1200
aaaaaaaaaa ttcatagtga gccgggaaat ctgtatagcc cagataacaa cacaagtcca   1260
aactagaaac tcgtcaaaca ccaaaagcaa tgttgaatca attgccttgc acaagtacac   1320
gtaggaaaac ataaaacatt gcaattttga atattgagcc ttttgtcgta acattgattg   1380
ataggattac tcaccgaatg gttttgaaac cactgccgac agatcaatca atcaatcaaa   1440
aaacgtgaac tttgaaaaag gggaagaaca gatacattga agttagccat ttccattgat   1500
cgtcacaaca tatctgataa attactttca aaattataag ctgatgtgtg tgtattatta   1560
atgtgacagt aacatcccaa acgagaaata ttatgtcgac aacaaaaaag tttgatctga   1620
attgaaaatg aagttttccc accctaccca tttgtcatat tgaaaccaat caactgatta   1680
atcaatcaat tagaattgaa gctaaactaa aacataccac cgtccatttt gaatgattat   1740
attttttaa tattaatatc gagataatgt ttctaagaaa gaaagaaaac caggagtgaa   1800
aattagaaaa ggaaaggaaa ggaaaaaaag aaaaatctga aaatatataa aaaaaaattg   1860
tttcgttggc aataaatctt ggtgagaaca gcgaccgaaa gcaaataaga acaaaatatg   1920
agtgtattac gttgaacaac taattaacgt gtgtgtatgg atcttttttt ctttttctc   1980
tttaaccgac tataaacaac aaacattttt gggcagtgca cacactactt aatatacaca   2040
gcataaatta cacgattaga aacaaattag cttattaaaa taacctaatc aaaccgaata   2100
ttttatggta ttatgagtaa actatataat ataaatagca cacacccaca acaacaacaa   2160
aggaaaacta aaaggttttt tctttttgaa aagatcgttt tctttattat tctctagttt   2220
tgacgctcga cattttatga tggaatgaat gggatgaatc atcaaacaag agaaaatacc   2280
cgtgacgaaa ataataaaat aagttcctct gatacagaag atgaaaacaa caacaacaag   2340
atatagaaat gccttgggtg gctattttat agtcttaact ttttaatgta tatttgtttt   2400
gttttttac ataataatac tttataaaag ctaagctaaa ttcaagtaaa atttcaatct   2460
ctcaaataaa acatttttct ctttttctta aatttagttt tatatattta taaaatatac   2520
aaagattttt ttaaaaaagt aacaagttat atatgtaata acaaaaagaa gaataacaag   2580
aatacaaaac cagatttcca gatttccaga atttcactct tatatgcgtc tatttatgta   2640
ggatgaaagg tagtctagta cctcctgtga tattatccca ttccatgcgg ggtatcgtat   2700
gcttccttca gcactaccct ttagctgttc tatatgctgc cactcctcaa ttggattagt   2760
ctcatccttc aatgctatca tttcctttga tattggatca tatgcatagt accgagaaac   2820
```

```
tagtgcgaag tagtgatcag gtattgctgt tatctgatga gtatacgttg tcctggccac   2880

ggcagaagca cgcttatcgc tccaatttcc cacaacatta gtcaactccg ttaggccctt   2940

cattgaaaga aatgaggtca tcaaatgtct tccaatgtga gattttgggc catttttat    3000

agcaaagatt gaataaggcg catttttctt caaagcttta ttgtacgatc tgactaagtt   3060

atcttttaat aattggtatt cctgtttatt gcttgaagaa ttgccggtcc tatttactcg   3120

ttttaggact ggttcagaat tcctcaaaaa ttcatccaaa tatacaagtg gatcgatcct   3180

accccttgcg ctaaagaagt atatgtgcct actaacgctt gtctttgtct ctgtcactaa   3240

acactggatt attactccca aatacttatt ttggactaat ttaaatgatt tcggatcaac   3300

gttcttaata tcgctgaatc ttccacaatt gatgaaagta gctaggaaga ggaattggta   3360

taaagttttt gtttttgtaa atctcgaagt atactcaaac gaatttagta ttttctcagt   3420

gatctcccag atgctttcac cctcacttag aagtgcttta agcatttttt tactgtggct   3480

atttccctta tctgcttctt ccgatgattc gaactgtaat tgcaaactac ttacaatatc   3540

agtgatatca gattgatgtt tttgtccata gtaaggaata attgtaaatt cccaagcagg   3600

aatcaatttc tttaatgagg cttccaaaat tgttgctttt tgcgtcttgt atttaaactg   3660

gagtgattta ttgacaatat cgaaactcaa cgaattgctt atgatagtat tatagctcat   3720

gaatgtggct ctcttgattg ctgttccgtt atgtgtaatc atccaacata aataggttag   3780

ttcagcagca cataatgcta ttttctcacc tgaaggtctt tcaaaccttt ccacaaactg   3840

acgaacaagc accttaggtg gtgttttaca taatatatca aattgtggca tgtcgacgat   3900

tattagttaa accactgcaa aaagttgggg aaaatttgc ccattttat accgtgtctt    3960

cgtctatcgc ctcccccact ccccaatctt tgaattattc cgaaatattc agcgaacggg   4020

gtgtacacaa aaactaacat tctcaactgc ataatttgaa aaatggcgtg ggacaagaaa   4080

aaaaaaaaat tctcaaccat agcaatcatg gaatacggta aatttgtgtt gttcggtgac   4140

tccatcaccc agtttagttg tacccagtat ggctttcatc cagcattaca gaatgtgtat   4200

atccgaaaat tggatgttat taaccgtggt ttcagtggct acaactcaga gcacgctaga   4260

caaattcttc caaaaatttt agagtcggaa accaatatca aattgatgac aatattttt    4320

ggaactaacg atgcatacga ctacatcaat gaaatccaga cagtcgagtt agacagatat   4380

aaagataatt taagtgtaat ggtacagatg gtactagaca aaaatatcaa accaatcatt   4440

attggatccg aagttcctat tctctagaaa gtataggaac ttcctcgaga ctattgtctt   4500

ggacagattt gccggtgtct tcttgacttt caacgttgcc tccaccgaag ccatcactgc   4560

tttggcctct gtgcaaattc caaagttgtg tgctgaagtc agaccaaacg ttgttgctta   4620

caccgactcc ttccaacaat ccgacatgat tgtcaattct gctattggta gatacgatgg   4680

tgacatctat gagaactact ttgacttggt caagttgcag aacccaccat ccaagaccaa   4740

ggctccttac tctgatgctt tggaagccat gttgaacaga ccaaccgaga cg           4792
```

<210> SEQ ID NO 140
<211> LENGTH: 4792
<212> TYPE: DNA
<213> ORGANISM: Artificial Sequence
<220> FEATURE:
<223> OTHER INFORMATION: Sequence of a resulting second targeting construct for the deletion of the second allele of POX4 in Candida tropicalis

<400> SEQUENCE: 140

```
cgtctcgcta acgaaaagga aaccgctgac gttaaaggta tctacggttg tttcggtatg     60
```

```
accgaattgg cccacggttc caacgttgct ggtttggaaa ccaccgccac atttgacaag    120
gaatctgacg agtttgtcat caacacccca cacattggtg ccaccaagtg gtggattggt    180
ggtgctgctc actccgccac ccactgttct gtctacgcca gattgattgt tgacggtcaa    240
gattacggtg tcaagacttt tgttgtccca ttgagagact ccaaccacga cctcatgcca    300
ggtgcggccg ctctagaact agtggatctg aagttcctat tctctagaaa gtataggaac    360
ttcctgcagg accacctttg attgtaaata gtaataatta ccacccttat ctaattattt    420
atttaactta tttatttatt tattatacat atatacaaat ctaataaagt gaaaatctcc    480
cccttcacac ttcacatatg ttaggcgtca tcctgtgctc ccgagaacca gtaccagtac    540
atcgctgttt cgttcgagac ttgaggtcta gttttatacg tgaagaggtc aatgccgccg    600
agagtaaagc cacattttgc gtacaaattg caggcaggta cattgttcgt ttgtgtctct    660
aatcgtatgc caaggagctg tctgcttagt gcccactttt tcgcaaattc gatgagactg    720
tgcgcgactc ctttgcctcg gtgcgtgtgc gacacaacaa tgtgttcgat agaggctaga    780
tcgttccatg ttgagttgag ttcaatcttc ccgacaagct cttggtcgat gaatgcgcca    840
tagcaagcag agtcttcatc agagtcatca tccgagatgt aatccttccg gtaggggctc    900
acacttctgg tagatagttc aaagccttgg tcggataggt gcacatcgaa cacttcacga    960
acaatgaaat ggttctcagc atccaatgtt tccgccacct gctcagggat caccgaaatt   1020
ttcatatgag aaccgttatc gataactaaa gcagcaactt cttctataaa aatgggttag   1080
tatgacagtc atttaaataa ggaatttttc agttggcttg gtttcaattc aatgttcgtt   1140
tttttttttt cttgctgtgt ttgtgtttgt gttgtttata gttgtgtgca ctgagcgtcg   1200
aaaaaaaaaa ttcatagtga gccgggaaat ctgtatagcc cagataacaa cacaagtcca   1260
aactagaaac tcgtcaaaca ccaaaagcaa tgttgaatca attgccttgc acaagtacac   1320
gtaggaaaac ataaaacatt gcaattttga atattgagcc ttttgtcgta acattgattg   1380
ataggattac tcaccgaatg gttttgaaac cactgccgac agatcaatca atcaatcaaa   1440
aaacgtgaac tttgaaaaag gggaagaaca gatacattga agttagccat ttccattgat   1500
cgtcacaaca tatctgataa attactttca aaattataag ctgatgtgtg tgtattatta   1560
atgtgacagt aacatcccaa acgagaaata ttatgtcgac aacaaaaaag tttgatctga   1620
attgaaaatg aagttttccc accctaccca tttgtcatat tgaaaccaat caactgatta   1680
atcaatcaat tagaattgaa gctaaactaa aacataccac cgtccatttt gaatgattat   1740
atttttttaa tattaatatc gagataatgt ttctaagaaa gaaagaaaac caggagtgaa   1800
aattagaaaa ggaaaggaaa ggaaaaaaag aaaaatctga aaatatataa aaaaaaattg   1860
tttcgttggc aataaatctt ggtgagaaca gcgaccgaaa gcaaataaga acaaaatatg   1920
agtgtattac gttgaacaac taattaacgt gtgtgtatgg atcttttttt cttttttctc   1980
tttaaccgac tataaacaac aaacattttt gggcagtgca cacactactt aatatacaca   2040
gcataaatta cacgattaga aacaaattag cttattaaaa taacctaatc aaaccgaata   2100
ttttatggta ttatgagtaa actatataat ataaatagca cacacccaca acaacaacaa   2160
aggaaaacta aaaggttttt tctttttgaa aagatcgttt tctttattat tctctagttt   2220
tgacgctcga cattttatga tggaatgaat gggatgaatc atcaaacaag agaaaatacc   2280
cgtgacgaaa ataataaaat aagttcctct gatacagaag atgaaaacaa caacaacaag   2340
atatagaaat gccttgggtg gctattttat agtcttaact ttttaatgta tatttgtttt   2400
gtttttttac ataataatac tttataaaag ctaagctaaa ttcaagtaaa atttcaatct   2460
```

```
ctcaaataaa acatttttct ctttttctta aatttagttt tatatattta taaaatatac   2520
aaagattttt ttaaaaaagt aacaagttat atatgtaata acaaaaagaa gaataacaag   2580
aatacaaaac cagatttcca gatttccaga atttcactct tatatgcgtc tatttatgta   2640
ggatgaaagg tagtctagta cctcctgtga tattatccca ttccatgcgg ggtatcgtat   2700
gcttccttca gcactaccct ttagctgttc tatatgctgc cactcctcaa ttggattagt   2760
ctcatccttc aatgctatca tttcctttga tattggatca tatgcatagt accgagaaac   2820
tagtgcgaag tagtgatcag gtattgctgt tatctgatga gtatacgttg tcctggccac   2880
ggcagaagca cgcttatcgc tccaatttcc cacaacatta gtcaactccg ttaggccctt   2940
cattgaaaga aatgaggtca tcaaatgtct tccaatgtga gattttgggc catttttttat   3000
agcaaagatt gaataaggcg catttttctt caaagcttta ttgtacgatc tgactaagtt   3060
atcttttaat aattggtatt cctgtttatt gcttgaagaa ttgccggtcc tatttactcg   3120
ttttaggact ggttcagaat tcctcaaaaa ttcatccaaa tatacaagtg gatcgatcct   3180
accccttgcg ctaaagaagt atatgtgcct actaacgctt gtctttgtct ctgtcactaa   3240
acactggatt attactccca aatacttatt ttggactaat ttaaatgatt tcggatcaac   3300
gttcttaata tcgctgaatc ttccacaatt gatgaaagta gctaggaaga ggaattggta   3360
taaagttttt gtttttgtaa atctcgaagt atactcaaac gaatttagta ttttctcagt   3420
gatctcccag atgctttcac cctcacttag aagtgcttta agcatttttt tactgtggct   3480
atttccctta tctgcttctt ccgatgattc gaactgtaat tgcaaactac ttacaatatc   3540
agtgatatca gattgatgtt tttgtccata gtaaggaata attgtaaatt cccaagcagg   3600
aatcaatttc tttaatgagg cttccaaaat tgttgctttt tgcgtcttgt atttaaactg   3660
gagtgattta ttgacaatat cgaaactcaa cgaattgctt atgatagtat tatagctcat   3720
gaatgtggct ctcttgattg ctgttccgtt atgtgtaatc atccaacata aataggttag   3780
ttcagcagca cataatgcta ttttctcacc tgaaggtctt tcaaaccttt ccacaaactg   3840
acgaacaagc accttaggtg gtgttttaca taatatatca aattgtggca tgtcgacgat   3900
tattagttaa accactgcaa aaagttgggg aaaattttgc ccatttttat accgtgtctt   3960
cgtctatcgc ctcccccact ccccaatctt tgaattattc cgaaatattc agcgaacggg   4020
gtgtacacaa aaactaacat tctcaactgc ataatttgaa aaatggcgtg ggacaagaaa   4080
aaaaaaaaat tctcaaccat agcaatcatg gaatacggta aatttgtgtt gttcggtgac   4140
tccatcaccc agtttagttg tacccagtat ggctttcatc cagcattaca gaatgtgtat   4200
atccgaaaat tggatgttat taaccgtggt ttcagtggct acaactcaga gcacgctaga   4260
caaattcttc caaaaatttt agagtcggaa accaatatca aattgatgac aatatttttt   4320
ggaactaacg atgcatacga ctacatcaat gaaatccaga cagtcgagtt agacagatat   4380
aaagataatt taagtgtaat ggtacagatg gtactagaca aaaatatcaa accaatcatt   4440
attggatccg aagttcctat tctctagaaa gtataggaac ttcctcgagc aagttatcag   4500
cattgaagat gccggcaaga ccgtcagagg ttccaccgct ttcttgaacc aattgaagga   4560
ctacactggt tccaacagct ccaaggttgt tttgaacact gttgctgact tggacgacat   4620
caagactgtc atcaaggcta ttgaagttgc catcatcaga ttgtcccaag aagctgcttc   4680
tattgtcaag aaggaatctt tcgactatgt cggcgctgaa ttggttcaac tctccaagtt   4740
gaaggctcac cactacttgt tgactgaata catcagaaga attgacgaga cg             4792
```

<210> SEQ ID NO 141
<211> LENGTH: 37
<212> TYPE: DNA
<213> ORGANISM: Candida tropicalis

<400> SEQUENCE: 141
atgactttta caaagaaaaa cgttagtgta tcacaag 37

<210> SEQ ID NO 142
<211> LENGTH: 27
<212> TYPE: DNA
<213> ORGANISM: Artificial Sequence
<220> FEATURE:
<223> OTHER INFORMATION: Oligonucleotide primer for evaluating contructs

<400> SEQUENCE: 142
ttacttggac aagatagcag cggtttc 27

<210> SEQ ID NO 143
<211> LENGTH: 2624
<212> TYPE: DNA
<213> ORGANISM: Candida tropicalis

<400> SEQUENCE: 143
gaattcacat ggctaatttg gcctcggttc cacaacgcac tcagcattaa aaaaaaaata 60
cgcaatggca gctcggtcga cgcagcagaa gcgccgacgt accgtcgcgt tgccccgccc 120
atgcctcgcc gacccctcca ccgccatcgt ttgcccattg tttgtggtag tgcgccgtga 180
cacaaaaact tgtcctgtca catgctgaag ttacaccaac ataactacta tgggattacg 240
taatcaaaaa tttcacagtt ttaacaaaaa aaaaatcata caatcaacat tgggacatct 300
tgccctcccc cacaaaactt gcttctgcat caatcatata taaacatcat gaaataagcc 360
taaactcact tctttttttt tcatccttcc tacttcttct ttcatagtaa ctactttttt 420
tttattacca cacttattca ttcataccac gctatcatgc ctaccgaact tcaaaaagaa 480
agagaactca ccaagttcaa cccaaaggag ttgaactact tcttggaagg ttcccaagaa 540
agatccgaga tcatcagcaa catggtcgaa caaatgcaaa aagaccctat cttgaaggtc 600
gacgcttcat actacaactt gaccaaagac caacaaagag aagtcaccgc caagaagatt 660
gccagactct ccagatactt tgagcacgag tacccagacc aacaggccca gagattgtcg 720
atcctcggtg tctttgaccc acaagtcttc accagaatcg gtgtcaactt gggtttgttt 780
gtttcctgtg tccgtggtaa cggtaccaac tcccagttct tctactggac cataaataag 840
ggtatcgaca agttgagagg tatctatggt tgttttggta tgactgagtt ggcccacggt 900
tccaacgtcc aaggtattga aaccaccgcc acttttgacg aagacactga cgagtttgtc 960
atcaacaccc cacacattgg tgccaccaag tggtggatcg gtggtgctgc gcactccgcc 1020
acccactgct ccgtctacgc cagattgaag gtcaaaggaa aggactacgg tgtcaagacc 1080
tttgttgtcc cattgagaga ctccaaccac gacctcgagc caggtgtgac tgttggtgac 1140
attggtgcca agatgggtag agacggtatc gataacggtt ggatccagtt ctccaacgtc 1200
agaatcccaa gattctttat gttgcaaaag tactgtaagg tttcccgtct gggtgaagtc 1260
accatgccac catctgaaca attgtcttac tcggctttga ttggtggtag agtcaccatg 1320
atgatggact cctacagaat gaccagtaga ttcatcacca ttgccttgag atacgccatc 1380
cacagaagac aattcaagaa gaaggacacc gataccattg aaaccaagtt gattgactac 1440
ccattgcatc aaaagagatt gttcccattc ttggctgccg cttacttgtt ctcccaaggt 1500
gccttgtact tagaacaaac catgaacgca accaacgaca agttggacga agctgtcagt 1560

```
gctggtgaaa aggaagccat tgacgctgcc attgtcgaat ccaagaaatt gttcgtcgct   1620
tccggttgtt tgaagtccac ctgtacctgg ttgactgctg aagccattga cgaagctcgt   1680
caagcttgtg gtggtcacgg ttactcgtct tacaacggtt tcggtaaagc ctactccgac   1740
tgggttgtcc aatgtacctg ggaaggtgac aacaacatct tggccatgaa cgttgccaag   1800
ccaatggtta gagacttgtt gaaggagcca gaacaaaagg gattggttct ctccagcgtt   1860
gccgacttgg acgacccagc caagttggtt aaggctttcg accacgccct ttccggcttg   1920
gccagagaca ttggtgctgt tgctgaagac aagggtttcg acattaccgg tccaagtttg   1980
gttttggttt ccaagttgaa cgctcacaga ttcttgattg acggtttctt caagcgtatc   2040
accccagaat ggtctgaagt cttgagacct ttgggtttct tgtatgccga ctggatcttg   2100
accaactttg gtgccacctt cttgcagtac ggtatcatta ccccagatgt cagcagaaag   2160
atttcctccg agcacttccc agccttgtgt gccaaggtta gaccaaacgt tgttggtttg   2220
actgatggtt tcaacttgac tgacatgatg accaatgctg ctattggtag atatgatggt   2280
aacgtctacg aacactactt cgaaactgtc aaggctttga acccaccaga aaacaccaag   2340
gctccatact ccaaggcttt ggaagacatg ttgaaccgtc cagaccttga agtcagagaa   2400
agaggtgaaa agtccgaaga agctgctgaa atcttgtcca gttaatagag cactaggttt   2460
tgataatttg gttcttacag tttatgtatt ttgattcttc ctttttttaga tactttttttt   2520
tatattttat tattccttat tgatgtaacg acagtcccac tataattaac ttaaactttg   2580
ctgtaaatca gatgacaagt gtttccctgt ttgcagggga gctc                    2624
```

<210> SEQ ID NO 144
<211> LENGTH: 640
<212> TYPE: DNA
<213> ORGANISM: Artificial Sequence
<220> FEATURE:
<223> OTHER INFORMATION: Pretargeting construct for deletion of POX5 allele from Candida tropicalis

<400> SEQUENCE: 144

```
cgtctctact tcttggaagg ttcccaagaa agatccgaga tcatcagcaa catggtcgaa     60
caaatgcaaa aagaccctat cttgaaggtc gacgcttcat actacaactt gaccaaagac    120
caacaaagag aagtcaccgc caagaagatt gccagactct ccagatactt tgagcacgag    180
tacccagacc aacaggccca gagattgtcg atcctcggtg tctttgaccc acaagtcttc    240
accagaatcg gtgtcaactt gggtttgttt gtttcctgtg tccgtggtaa cggtaccaac    300
tccgcggccg ctagatcttg cgaagctcca tctcgaggac tggatcttga ccaactttgg    360
tgccaccttc ttgcagtacg gtatcattac cccagatgtc agcagaaaga tttcctccga    420
gcacttccca gccttgtgtg ccaaggttag accaaacgtt gttggtttga ctgatggttt    480
caacttgact gacatgatga ccaatgctgc tattggtaga tatgatggta acgtctacga    540
acactacttc gaaactgtca aggctttgaa cccaccagaa aacaccaagg ctccatactc    600
caaggctttg gaagacatgt tgaaccgtcc agacgagacg                          640
```

<210> SEQ ID NO 145
<211> LENGTH: 640
<212> TYPE: DNA
<213> ORGANISM: Artificial Sequence
<220> FEATURE:
<223> OTHER INFORMATION: Second POX5 Pre-Targeting Sequence for deletion of POX5 allele from Candida tropicalis

<400> SEQUENCE: 145

```
cgtctctttg gtatgactga gttggcccac ggttccaacg tccaaggtat tgaaaccacc     60

gccacttttg acgaagacac tgacgagttt gtcatcaaca ccccacacat tggtgccacc    120

aagtggtgga tcggtggtgc tgcgcactcc gccacccact gctccgtcta cgccagattg    180

aaggtcaaag gaaaggacta cggtgtcaag acctttgttg tcccattgag agactccaac    240

cacgacttcg agccaggtgt gactgttggt gacattggtg ccaagatggg taaagacggt    300

atcgcggccg ctagatcttg cgaagctcca tctcgagtac tccgactggg ttgtccaatg    360

tacctgggaa ggtgacaaca acatcttggc catgaacgtt gccaagccaa tggttagaga    420

cttgttgaag gagccagaac aaaagggatt ggttctctcc agcgttgccg acttggacga    480

cccagccaag ttggttaagg ctttcgacca cgccctttcc ggcttggcca gagacattgg    540

tgctgttgct gaagacaagg gtttcgacat taccggtcca agtttggttt tggtttccaa    600

gttgaacgct cacagattct tgattgacgg tttcgagacg                          640
```

<210> SEQ ID NO 146
<211> LENGTH: 4792
<212> TYPE: DNA
<213> ORGANISM: Artificial Sequence
<220> FEATURE:
<223> OTHER INFORMATION: Sequence of resulting first targeting construct for deletion of a first allele of POX5 in Candida tropicalis

<400> SEQUENCE: 146

```
cgtctctact tcttggaagg ttcccaagaa agatccgaga tcatcagcaa catggtcgaa     60

caaatgcaaa aagaccctat cttgaaggtc gacgcttcat actacaactt gaccaaagac    120

caacaaagag aagtcaccgc caagaagatt gccagactct ccagatactt tgagcacgag    180

tacccagacc aacaggccca gagattgtcg atcctcggtg tctttgaccc acaagtcttc    240

accagaatcg gtgtcaactt gggtttgttt gtttcctgtg tccgtggtaa cggtaccaac    300

tccgcggccg ctctagaact agtggatctg aagttcctat tctctagaaa gtataggaac    360

ttcctgcagg accacctttg attgtaaata gtaataatta ccacccttat ctaattattt    420

atttaactta tttatttatt tattatacat atatacaaat ctaataaagt gaaaatctcc    480

cccttcacac ttcacatatg ttaggcgtca tcctgtgctc ccgagaacca gtaccagtac    540

atcgctgttt cgttcgagac ttgaggtcta gttttatacg tgaagaggtc aatgccgccg    600

agagtaaagc cacattttgc gtacaaattg caggcaggta cattgttcgt ttgtgtctct    660

aatcgtatgc caaggagctg tctgcttagt gcccactttt tcgcaaattc gatgagactg    720

tgcgcgactc ctttgcctcg gtgcgtgtgc gacacaacaa tgtgttcgat agaggctaga    780

tcgttccatg ttgagttgag ttcaatcttc ccgacaagct cttggtcgat gaatgcgcca    840

tagcaagcag agtcttcatc agagtcatca tccgagatgt aatccttccg gtaggggctc    900

acacttctgg tagatagttc aaagccttgg tcggataggt gcacatcgaa cacttcacga    960

acaatgaaat ggttctcagc atccaatgtt tccgccacct gctcagggat caccgaaatt   1020

ttcatatgag aaccgttatc gataactaaa gcagcaactt cttctataaa aatgggttag   1080

tatgacagtc atttaaataa ggaatttttc agttggcttg gtttcaattc aatgttcgtt   1140

ttttttttt cttgctgtgt ttgtgtttgt gttgtttata gttgtgtgca ctgagcgtcg    1200

aaaaaaaaaa ttcatagtga gccgggaaat ctgtatagcc cagataacaa cacaagtcca   1260

aactagaaac tcgtcaaaca ccaaaagcaa tgttgaatca attgccttgc acaagtacac   1320

gtaggaaaac ataaaacatt gcaattttga atattgagcc ttttgtcgta acattgattg   1380
```

```
ataggattac tcaccgaatg gttttgaaac cactgccgac agatcaatca atcaatcaaa   1440
aaacgtgaac tttgaaaaag gggaagaaca gatacattga agttagccat ttccattgat   1500
cgtcacaaca tatctgataa attactttca aaattataag ctgatgtgtg tgtattatta   1560
atgtgacagt aacatcccaa acgagaaata ttatgtcgac aacaaaaaag tttgatctga   1620
attgaaaatg aagttttccc accctaccca tttgtcatat tgaaaccaat caactgatta   1680
atcaatcaat tagaattgaa gctaaactaa aacataccac cgtccatttt gaatgattat   1740
attttttaa tattaatatc gagataatgt ttctaagaaa gaaagaaaac caggagtgaa    1800
aattagaaaa ggaaaggaaa ggaaaaaaag aaaaatctga aaatatataa aaaaaaattg   1860
tttcgttggc aataaatctt ggtgagaaca gcgaccgaaa gcaaataaga acaaaatatg   1920
agtgtattac gttgaacaac taattaacgt gtgtgtatgg atcttttttt ctttttctc    1980
tttaaccgac tataaacaac aaacattttt gggcagtgca cacactactt aatatacaca   2040
gcataaatta cacgattaga aacaaattag cttattaaaa taacctaatc aaaccgaata   2100
ttttatggta ttatgagtaa actatataat ataaatagca cacacccaca acaacaacaa   2160
aggaaaacta aaaggttttt tctttttgaa aagatcgttt tctttattat tctctagttt   2220
tgacgctcga cattttatga tggaatgaat gggatgaatc atcaaacaag agaaaatacc   2280
cgtgacgaaa ataataaaat aagttcctct gatacagaag atgaaaacaa caacaacaag   2340
atatagaaat gccttgggtg gctattttat agtcttaact ttttaatgta tatttgtttt   2400
gtttttttac ataataatac tttataaaag ctaagctaaa ttcaagtaaa atttcaatct   2460
ctcaaataaa acatttttct ctttttctta aatttagttt tatatattta taaaatatac   2520
aaagattttt ttaaaaaagt aacaagttat atatgtaata acaaaaagaa gaataacaag   2580
aatacaaaac cagatttcca gatttccaga atttcactct tatatgcgtc tatttatgta   2640
ggatgaaagg tagtctagta cctcctgtga tattatccca ttccatgcgg ggtatcgtat   2700
gcttccttca gcactaccct ttagctgttc tatatgctgc cactcctcaa ttggattagt   2760
ctcatccttc aatgctatca tttcctttga tattggatca tatgcatagt accgagaaac   2820
tagtgcgaag tagtgatcag gtattgctgt tatctgatga gtatacgttg tcctggccac   2880
ggcagaagca cgcttatcgc tccaatttcc cacaacatta gtcaactccg ttaggccctt   2940
cattgaaaga aatgaggtca tcaaatgtct tccaatgtga gattttgggc catttttat    3000
agcaaagatt gaataaggcg catttttctt caaagcttta ttgtacgatc tgactaagtt   3060
atcttttaat aattggtatt cctgtttatt gcttgaagaa ttgccggtcc tatttactcg   3120
ttttaggact ggttcagaat tcctcaaaaa ttcatccaaa tatacaagtg gatcgatcct   3180
accccttgcg ctaaagaagt atatgtgcct actaacgctt gtctttgtct ctgtcactaa   3240
acactggatt attactccca aatacttatt ttggactaat ttaaatgatt tcggatcaac   3300
gttcttaata tcgctgaatc ttccacaatt gatgaaagta gctaggaaga ggaattggta   3360
taaagttttt gtttttgtaa atctcgaagt atactcaaac gaatttagta ttttctcagt   3420
gatctcccag atgctttcac cctcacttag aagtgcttta agcatttttt tactgtggct   3480
atttccctta tctgcttctt ccgatgattc gaactgtaat tgcaaactac ttacaatatc   3540
agtgatatca gattgatgtt tttgtccata gtaaggaata attgtaaatt cccaagcagg   3600
aatcaatttc tttaatgagg cttccaaaat tgttgctttt tgcgtcttgt atttaaactg   3660
gagtgattta ttgacaatat cgaaactcaa cgaattgctt atgatagtat tatagctcat   3720
gaatgtggct ctcttgattg ctgttccgtt atgtgtaatc atccaacata aataggttag   3780
```

```
ttcagcagca cataatgcta ttttctcacc tgaaggtctt tcaaaccttt ccacaaactg   3840

acgaacaagc accttaggtg gtgttttaca taatatatca aattgtggca tgtcgacgat   3900

tattagttaa accactgcaa aaagttgggg aaaattttgc ccatttttat accgtgtctt   3960

cgtctatcgc ctcccccact ccccaatctt tgaattattc cgaaatattc agcgaacggg   4020

gtgtacacaa aaactaacat tctcaactgc ataatttgaa aaatggcgtg ggacaagaaa   4080

aaaaaaaaat tctcaaccat agcaatcatg gaatacggta aatttgtgtt gttcggtgac   4140

tccatcaccc agtttagttg tacccagtat ggctttcatc cagcattaca gaatgtgtat   4200

atccgaaaat tggatgttat taaccgtggt ttcagtggct acaactcaga gcacgctaga   4260

caaattcttc caaaaatttt agagtcggaa accaatatca aattgatgac aatatttttt   4320

ggaactaacg atgcatacga ctacatcaat gaaatccaga cagtcgagtt agacagatat   4380

aaagataatt taagtgtaat ggtacagatg gtactagaca aaaatatcaa accaatcatt   4440

attggatccg aagttcctat tctctagaaa gtataggaac ttcctcgagg actggatctt   4500

gaccaacttt ggtgccacct tcttgcagta cggtatcatt accccagatg tcagcagaaa   4560

gatttcctcc gagcacttcc cagccttgtg tgccaaggtt agaccaaacg ttgttggttt   4620

gactgatggt ttcaacttga ctgacatgat gaccaatgct gctattggta gatatgatgg   4680

taacgtctac gaacactact tcgaaactgt caaggctttg aacccaccag aaaacaccaa   4740

ggctccatac tccaaggctt tggaagacat gttgaaccgt ccagacgaga cg           4792
```

```
<210> SEQ ID NO 147
<211> LENGTH: 4792
<212> TYPE: DNA
<213> ORGANISM: Artificial sequence
<220> FEATURE:
<223> OTHER INFORMATION: Sequence of resulting second targeting
      construct for the deletion of a second allele of POX5 in Candida
      tropicalis

<400> SEQUENCE: 147
```

```
cgtctctttg gtatgactga gttggcccac ggttccaacg tccaaggtat tgaaaccacc     60

gccacttttg acgaagacac tgacgagttt gtcatcaaca ccccacacat tggtgccacc    120

aagtggtgga tcggtggtgc tgcgcactcc gccacccact gctccgtcta cgccagattg    180

aaggtcaaag gaaaggacta cggtgtcaag acctttgttg tcccattgag agactccaac    240

cacgacttcg agccaggtgt gactgttggt gacattggtg ccaagatggg taaagacggt    300

atcgcggccg ctctagaact agtggatctg aagttcctat tctctagaaa gtataggaac    360

ttcctgcagg accacctttg attgtaaata gtaataatta ccacccttat ctaattattt    420

atttaactta tttatttatt tattatacat atatacaaat ctaataaagt gaaaatctcc    480

cccttcacac ttcacatatg ttaggcgtca tcctgtgctc ccgagaacca gtaccagtac    540

atcgctgttt cgttcgagac ttgaggtcta gttttatacg tgaagaggtc aatgccgccg    600

agagtaaagc cacattttgc gtacaaattg caggcaggta cattgttcgt ttgtgtctct    660

aatcgtatgc caaggagctg tctgcttagt gcccactttt tcgcaaattc gatgagactg    720

tgcgcgactc ctttgcctcg gtgcgtgtgc gacacaacaa tgtgttcgat agaggctaga    780

tcgttccatg ttgagttgag ttcaatcttc ccgacaagct cttggtcgat gaatgcgcca    840

tagcaagcag agtcttcatc agagtcatca tccgagatgt aatccttccg gtaggggctc    900

acacttctgg tagatagttc aaagccttgg tcggataggt gcacatcgaa cacttcacga    960

acaatgaaat ggttctcagc atccaatgtt tccgccacct gctcagggat caccgaaatt   1020
```

```
ttcatatgag aaccgttatc gataactaaa gcagcaactt cttctataaa aatgggttag   1080
tatgacagtc atttaaataa ggaatttttc agttggcttg gtttcaattc aatgttcgtt   1140
ttttttttt cttgctgtgt ttgtgtttgt gttgtttata gttgtgtgca ctgagcgtcg   1200
aaaaaaaaaa ttcatagtga gccgggaaat ctgtatagcc cagataacaa cacaagtcca   1260
aactagaaac tcgtcaaaca ccaaaagcaa tgttgaatca attgccttgc acaagtacac   1320
gtaggaaaac ataaaacatt gcaattttga atattgagcc ttttgtcgta acattgattg   1380
ataggattac tcaccgaatg gttttgaaac cactgccgac agatcaatca atcaatcaaa   1440
aaacgtgaac tttgaaaaag gggaagaaca gatacattga agttagccat ttccattgat   1500
cgtcacaaca tatctgataa attactttca aaattataag ctgatgtgtg tgtattatta   1560
atgtgacagt aacatcccaa acgagaaata ttatgtcgac aacaaaaaag tttgatctga   1620
attgaaaatg aagttttccc accctaccca tttgtcatat tgaaaccaat caactgatta   1680
atcaatcaat tagaattgaa gctaaactaa aacataccac cgtccatttt gaatgattat   1740
attttttaa tattaatatc gagataatgt ttctaagaaa gaaagaaaac caggagtgaa   1800
aattagaaaa ggaaaggaaa ggaaaaaaag aaaaatctga aaatatataa aaaaaaattg   1860
tttcgttggc aataaatctt ggtgagaaca gcgaccgaaa gcaaataaga acaaaatatg   1920
agtgtattac gttgaacaac taattaacgt gtgtgtatgg atcttttttt ctttttctc   1980
tttaaccgac tataaacaac aaacattttt gggcagtgca cacactactt aatatacaca   2040
gcataaatta cacgattaga aacaaattag cttattaaaa taacctaatc aaaccgaata   2100
ttttatggta ttatgagtaa actatataat ataaatagca cacacccaca acaacaacaa   2160
aggaaaacta aaaggttttt tctttttgaa aagatcgttt tctttattat tctctagttt   2220
tgacgctcga cattttatga tggaatgaat gggatgaatc atcaaacaag agaaaatacc   2280
cgtgacgaaa ataataaaat aagttcctct gatacagaag atgaaaacaa caacaacaag   2340
atatagaaat gccttgggtg gctattttat agtcttaact ttttaatgta tatttgtttt   2400
gttttttac ataataatac tttataaaag ctaagctaaa ttcaagtaaa atttcaatct   2460
ctcaaataaa acatttttct ctttttctta aatttagttt tatatattta taaaatatac   2520
aaagattttt ttaaaaaagt aacaagttat atatgtaata acaaaaagaa gaataacaag   2580
aatacaaaac cagatttcca gatttccaga atttcactct tatatgcgtc tatttatgta   2640
ggatgaaagg tagtctagta cctcctgtga tattatccca ttccatgcgg ggtatcgtat   2700
gcttccttca gcactaccct ttagctgttc tatatgctgc cactcctcaa ttggattagt   2760
ctcatccttc aatgctatca tttcctttga tattggatca tatgcatagt accgagaaac   2820
tagtgcgaag tagtgatcag gtattgctgt tatctgatga gtatacgttg tcctggccac   2880
ggcagaagca cgcttatcgc tccaatttcc cacaacatta gtcaactccg ttaggccctt   2940
cattgaaaga aatgaggtca tcaaatgtct tccaatgtga gattttgggc catttttat   3000
agcaaagatt gaataaggcg catttttctt caaagcttta ttgtacgatc tgactaagtt   3060
atcttttaat aattggtatt cctgtttatt gcttgaagaa ttgccggtcc tatttactcg   3120
ttttaggact ggttcagaat tcctcaaaaa ttcatccaaa tatacaagtg gatcgatcct   3180
accccttgcg ctaaagaagt atatgtgcct actaacgctt gtctttgtct ctgtcactaa   3240
acactggatt attactccca aatacttatt ttggactaat ttaaatgatt tcggatcaac   3300
gttcttaata tcgctgaatc ttccacaatt gatgaaagta gctaggaaga ggaattggta   3360
taaagttttt gtttttgtaa atctcgaagt atactcaaac gaatttagta ttttctcagt   3420
```

```
gatctcccag atgctttcac cctcacttag aagtgcttta agcatttttt tactgtggct   3480

atttccctta tctgcttctt ccgatgattc gaactgtaat tgcaaactac ttacaatatc   3540

agtgatatca gattgatgtt tttgtccata gtaaggaata attgtaaatt cccaagcagg   3600

aatcaatttc tttaatgagg cttccaaaat tgttgctttt tgcgtcttgt atttaaactg   3660

gagtgattta ttgacaatat cgaaactcaa cgaattgctt atgatagtat tatagctcat   3720

gaatgtggct ctcttgattg ctgttccgtt atgtgtaatc atccaacata aataggttag   3780

ttcagcagca cataatgcta ttttctcacc tgaaggtctt tcaaaccttt ccacaaactg   3840

acgaacaagc accttaggtg gtgttttaca taatatatca aattgtggca tgtcgacgat   3900

tattagttaa accactgcaa aaagttgggg aaaattttgc ccatttttat accgtgtctt   3960

cgtctatcgc ctcccccact ccccaatctt tgaattattc cgaaatattc agcgaacggg   4020

gtgtacacaa aaactaacat tctcaactgc ataatttgaa aaatggcgtg ggacaagaaa   4080

aaaaaaaaat tctcaaccat agcaatcatg gaatacggta aatttgtgtt gttcggtgac   4140

tccatcaccc agtttagttg tacccagtat ggctttcatc cagcattaca gaatgtgtat   4200

atccgaaaat tggatgttat taaccgtggt ttcagtggct acaactcaga gcacgctaga   4260

caaattcttc caaaaatttt agagtcggaa accaatatca aattgatgac aatatttttt   4320

ggaactaacg atgcatacga ctacatcaat gaaatccaga cagtcgagtt agacagatat   4380

aaagataatt taagtgtaat ggtacagatg gtactagaca aaaatatcaa accaatcatt   4440

attggatccg aagttcctat tctctagaaa gtataggaac ttcctcgagt actccgactg   4500

ggttgtccaa tgtacctggg aaggtgacaa caacatcttg gccatgaacg ttgccaagcc   4560

aatggttaga gacttgttga aggagccaga acaaaaggga ttggttctct ccagcgttgc   4620

cgacttggac gacccagcca agttggttaa ggctttcgac cacgcccttt ccggcttggc   4680

cagagacatt ggtgctgttg ctgaagacaa gggtttcgac attaccggtc caagtttggt   4740

tttggtttcc aagttgaacg ctcacagatt cttgattgac ggtttcgaga cg           4792
```

<210> SEQ ID NO 148
<211> LENGTH: 30
<212> TYPE: DNA
<213> ORGANISM: Candida Tropicalis

<400> SEQUENCE: 148

```
atgcctaccg aacttcaaaa agaaagagaa                                      30
```

<210> SEQ ID NO 149
<211> LENGTH: 30
<212> TYPE: DNA
<213> ORGANISM: Artificial Sequence
<220> FEATURE:
<223> OTHER INFORMATION: Probe for analysis of Candida tropicalis constructs

<400> SEQUENCE: 149

```
ttaactggac aagatttcag cagcttcttc                                      30
```

<210> SEQ ID NO 150
<211> LENGTH: 48
<212> TYPE: DNA
<213> ORGANISM: Artificial Sequence
<220> FEATURE:
<223> OTHER INFORMATION: primer 1759R33

<400> SEQUENCE: 150

```
accttaaaac gcataaattc cttgatgatt gccatgttgt cttcttca                  48
```

<210> SEQ ID NO 151
<211> LENGTH: 316
<212> TYPE: PRT
<213> ORGANISM: Candida tropicalis
<220> FEATURE:
<223> OTHER INFORMATION: ADH B11

<400> SEQUENCE: 151

```
Pro Leu Gln Tyr Thr Asp Ile Pro Val Pro Val Pro Lys Pro Asn Glu
 1               5                  10                  15

Leu Leu Val His Val Lys Tyr Ser Gly Val Cys His Ser Asp Ile His
            20                  25                  30

Val Trp Lys Gly Asp Trp Phe Pro Ala Ser Lys Leu Pro Val Val Gly
        35                  40                  45

Gly His Glu Gly Ala Gly Val Val Val Ala Ile Gly Glu Asn Val Gln
    50                  55                  60

Gly Trp Lys Val Gly Asp Leu Ala Gly Ile Lys Met Leu Asn Gly Ser
65                  70                  75                  80

Cys Met Asn Cys Glu Tyr Cys Gln Gln Gly Ala Glu Pro Asn Cys Pro
                85                  90                  95

His Ala Asp Val Ser Gly Tyr Ser His Asp Gly Thr Phe Gln Gln Tyr
            100                 105                 110

Ala Thr Ala Asp Ala Val Gln Ala Ala Lys Phe Pro Ala Gly Ser Asp
        115                 120                 125

Leu Ala Ser Ile Ala Pro Ile Ser Cys Ala Gly Val Thr Val Tyr Lys
    130                 135                 140

Ala Leu Lys Thr Ala Gly Leu Gln Pro Gly Gln Trp Val Ala Ile Ser
145                 150                 155                 160

Gly Ala Ala Gly Gly Leu Gly Ser Leu Ala Val Gln Tyr Ala Lys Ala
                165                 170                 175

Met Gly Leu Arg Val Val Ala Ile Asp Gly Gly Asp Glu Arg Gly Val
            180                 185                 190

Phe Val Lys Ser Leu Gly Ala Glu Val Phe Val Asp Phe Thr Lys Glu
        195                 200                 205

Ala Asn Val Ser Glu Ala Ile Ile Lys Ala Thr Asp Gly Gly Ala His
    210                 215                 220

Gly Val Ile Asn Val Ser Ile Ser Glu Lys Ala Ile Asn Gln Ser Val
225                 230                 235                 240

Glu Tyr Val Arg Thr Leu Gly Thr Val Val Leu Val Gly Leu Pro Ala
                245                 250                 255

Gly Ala Lys Leu Glu Ala Pro Ile Phe Asn Ala Val Ala Lys Ser Ile
            260                 265                 270

Gln Ile Lys Gly Ser Tyr Val Gly Asn Arg Arg Asp Thr Ala Glu Ala
        275                 280                 285

Val Asp Phe Phe Ala Arg Gly Leu Val Lys Cys Pro Ile Lys Val Val
    290                 295                 300

Gly Leu Ser Glu Leu Pro Glu Ile Phe Lys Leu Leu
305                 310                 315
```

<210> SEQ ID NO 152
<211> LENGTH: 316
<212> TYPE: PRT
<213> ORGANISM: Candida tropicalis
<220> FEATURE:
<223> OTHER INFORMATION: ADH A10

<400> SEQUENCE: 152

```
Lys Leu Glu Tyr Lys Asp Val Pro Val Pro Val Pro Lys Pro Asn Glu
 1               5                  10                  15

Leu Leu Val Asn Val Lys Tyr Ser Gly Val Cys His Ser Asp Leu His
            20                  25                  30

Val Trp Lys Gly Asp Trp Pro Ile Pro Ala Lys Leu Pro Leu Val Gly
        35                  40                  45

Gly His Glu Gly Ala Gly Val Val Val Gly Met Gly Asp Asn Val Lys
    50                  55                  60

Gly Trp Lys Val Gly Asp Leu Ala Gly Ile Lys Trp Leu Asn Gly Ser
65                  70                  75                  80

Cys Met Asn Cys Glu Phe Cys Gln Gln Gly Ala Glu Pro Asn Cys Ser
                85                  90                  95

Arg Ala Asp Met Ser Gly Tyr Thr His Asp Gly Thr Phe Gln Gln Tyr
            100                 105                 110

Ala Thr Ala Asp Ala Val Gln Ala Ala Lys Ile Pro Glu Gly Ala Asp
        115                 120                 125

Met Ala Ser Ile Ala Pro Ile Leu Cys Ala Gly Val Thr Val Tyr Lys
    130                 135                 140

Ala Leu Lys Asn Ala Asp Leu Leu Ala Gly Gln Trp Val Ala Ile Ser
145                 150                 155                 160

Gly Ala Gly Gly Gly Leu Gly Ser Leu Gly Val Gln Tyr Ala Lys Ala
                165                 170                 175

Met Gly Tyr Arg Val Leu Ala Ile Asp Gly Gly Asp Glu Arg Gly Glu
            180                 185                 190

Phe Val Lys Ser Leu Gly Ala Glu Val Tyr Ile Asp Phe Leu Lys Glu
        195                 200                 205

Gln Asp Ile Val Ser Ala Ile Arg Lys Ala Thr Gly Gly Gly Pro His
    210                 215                 220

Gly Val Ile Asn Val Ser Val Ser Glu Lys Ala Ile Asn Gln Ser Val
225                 230                 235                 240

Glu Tyr Val Arg Thr Leu Gly Lys Val Val Leu Val Ser Leu Pro Ala
                245                 250                 255

Gly Gly Lys Leu Thr Ala Pro Leu Phe Glu Ser Val Ala Arg Ser Ile
            260                 265                 270

Gln Ile Arg Thr Thr Cys Val Gly Asn Arg Lys Asp Thr Thr Glu Ala
        275                 280                 285

Ile Asp Phe Phe Val Arg Gly Leu Ile Asp Cys Pro Ile Lys Val Ala
    290                 295                 300

Gly Leu Ser Glu Val Pro Glu Ile Phe Asp Leu Met
305                 310                 315
```

```
<210> SEQ ID NO 153
<211> LENGTH: 152
<212> TYPE: PRT
<213> ORGANISM: Candida tropicalis
<220> FEATURE:
<223> OTHER INFORMATION: ADH A10B

<400> SEQUENCE: 153

Asn Cys Glu Phe Cys Gln Gln Gly Ala Glu Pro Asn Cys Pro Arg Ala
 1               5                  10                  15

Asp Met Ser Gly Tyr Thr His Asp Gly Thr Phe Gln Gln Tyr Ala Thr
            20                  25                  30

Ala Asp Ala Val Gln Ala Ala Lys Ile Pro Glu Gly Ala Asp Met Ala
        35                  40                  45
```

```
Ser Ile Ala Pro Ile Leu Cys Ala Gly Val Thr Val Tyr Lys Ala Leu
    50                  55                  60

Lys Asn Ala Asp Leu Leu Ala Gly Gln Trp Val Ala Ile Ser Gly Ala
65                  70                  75                  80

Gly Gly Gly Leu Gly Ser Leu Gly Val Gln Tyr Ala Lys Ala Met Gly
                85                  90                  95

Tyr Arg Val Leu Ala Ile Asp Gly Gly Asp Glu Arg Gly Glu Phe Val
            100                 105                 110

Lys Ser Leu Gly Ala Glu Val Tyr Ile Asp Phe Leu Lys Glu Gln Asp
        115                 120                 125

Ile Val Ser Ala Ile Arg Lys Ala Thr Gly Gly Gly Pro His Gly Val
    130                 135                 140

Ile Asn Val Ser Val Ser Glu Lys
145                 150


<210> SEQ ID NO 154
<211> LENGTH: 316
<212> TYPE: PRT
<213> ORGANISM: Candida tropicalis
<220> FEATURE:
<223> OTHER INFORMATION: ADH B4

<400> SEQUENCE: 154

Lys Leu Glu Tyr Lys Asp Ile Pro Val Pro Lys Pro Lys Pro Asn Glu
 1               5                  10                  15

Leu Leu Ile Asn Val Lys Tyr Ser Gly Val Cys His Thr Asp Leu His
            20                  25                  30

Ala Trp Lys Gly Asp Trp Pro Leu Asp Thr Lys Leu Pro Leu Val Gly
        35                  40                  45

Gly His Glu Gly Ala Gly Val Val Val Ala Ile Gly Asp Asn Val Lys
    50                  55                  60

Gly Trp Lys Val Gly Asp Leu Ala Gly Val Lys Trp Leu Asn Gly Ser
65                  70                  75                  80

Cys Met Asn Cys Glu Tyr Cys Gln Gln Gly Ala Glu Pro Asn Cys Pro
                85                  90                  95

Gln Ala Asp Leu Ser Gly Tyr Thr His Asp Gly Ser Phe Gln Gln Tyr
            100                 105                 110

Ala Thr Ala Asp Ala Val Gln Ala Ala Arg Ile Pro Ala Gly Thr Asp
        115                 120                 125

Leu Ala Asn Val Ala Pro Ile Leu Cys Ala Gly Val Thr Val Tyr Lys
    130                 135                 140

Ala Leu Lys Thr Ala Asp Leu Gln Pro Gly Gln Trp Val Ala Ile Ser
145                 150                 155                 160

Gly Ala Ala Gly Gly Leu Gly Ser Leu Ala Val Gln Tyr Ala Lys Ala
                165                 170                 175

Met Gly Tyr Arg Val Val Ala Ile Asp Gly Gly Ala Asp Lys Gly Glu
            180                 185                 190

Phe Val Lys Ser Leu Gly Ala Glu Val Phe Val Asp Phe Leu Lys Glu
        195                 200                 205

Lys Asp Ile Val Gly Ala Val Lys Lys Ala Thr Asp Gly Gly Pro His
    210                 215                 220

Gly Ala Val Asn Val Ser Ile Ser Glu Lys Ala Ile Asn Gln Ser Val
225                 230                 235                 240

Asp Tyr Val Arg Thr Leu Gly Lys Val Val Leu Val Gly Leu Pro Ala
                245                 250                 255

Gly Ser Lys Val Ser Ala Pro Val Phe Asp Ser Val Val Lys Ser Ile
```

```
            260                 265                 270

Gln Ile Lys Gly Ser Tyr Val Gly Asn Arg Lys Asp Thr Ala Glu Ala
        275                 280                 285

Val Asp Phe Phe Ser Arg Gly Leu Ile Lys Cys Pro Ile Lys Val Val
    290                 295                 300

Gly Leu Ser Glu Leu Pro Glu Val Tyr Lys Leu Met
305                 310                 315


<210> SEQ ID NO 155
<211> LENGTH: 316
<212> TYPE: PRT
<213> ORGANISM: Candida tropicalis
<220> FEATURE:
<223> OTHER INFORMATION: ADH A4

<400> SEQUENCE: 155

Glu Leu Glu Tyr Lys Asp Ile Pro Val Pro Thr Pro Lys Ala Asn Glu
 1               5                  10                  15

Leu Leu Ile Asn Val Lys Tyr Ser Gly Val Cys His Thr Asp Leu His
            20                  25                  30

Ala Trp Lys Gly Asp Trp Pro Leu Ala Thr Lys Leu Pro Leu Val Gly
        35                  40                  45

Gly His Glu Gly Ala Gly Val Val Val Gly Met Gly Glu Asn Val Lys
    50                  55                  60

Gly Trp Lys Ile Gly Asp Phe Ala Gly Ile Lys Trp Leu Asn Gly Ser
65                  70                  75                  80

Cys Met Ser Cys Glu Phe Cys Gln Gln Gly Ala Glu Pro Asn Cys Gly
                85                  90                  95

Glu Ala Asp Leu Ser Gly Tyr Thr His Asp Gly Ser Phe Glu Gln Tyr
            100                 105                 110

Ala Thr Ala Asp Ala Val Gln Ala Ala Arg Ile Pro Ala Gly Thr Asp
        115                 120                 125

Leu Ala Glu Val Ala Pro Ile Leu Cys Ala Gly Val Thr Val Tyr Lys
    130                 135                 140

Ala Leu Lys Thr Ala Asp Leu Ala Ala Gly Gln Trp Val Ala Ile Ser
145                 150                 155                 160

Gly Ala Gly Gly Gly Leu Gly Ser Leu Ala Val Gln Tyr Ala Val Ala
                165                 170                 175

Met Gly Leu Arg Val Val Ala Ile Asp Gly Gly Asp Glu Lys Gly Ala
            180                 185                 190

Phe Val Lys Ser Leu Gly Ala Glu Ala Tyr Ile Asp Phe Leu Lys Glu
        195                 200                 205

Lys Asp Ile Val Ser Ala Val Lys Lys Ala Thr Asp Gly Gly Pro His
    210                 215                 220

Gly Ala Ile Asn Val Ser Val Ser Glu Lys Ala Ile Asp Gln Ser Val
225                 230                 235                 240

Glu Tyr Val Arg Pro Leu Gly Lys Val Val Leu Val Gly Leu Pro Ala
                245                 250                 255

Gly Ser Lys Val Thr Ala Gly Val Phe Glu Ala Val Val Lys Ser Ile
            260                 265                 270

Glu Ile Lys Gly Ser Tyr Val Gly Asn Arg Lys Asp Thr Ala Glu Ala
        275                 280                 285

Val Asp Phe Phe Ser Arg Gly Leu Ile Lys Cys Pro Ile Lys Ile Val
    290                 295                 300

Gly Leu Ser Glu Leu Pro Gln Val Phe Lys Leu Met
305                 310                 315
```

<210> SEQ ID NO 156
<211> LENGTH: 8
<212> TYPE: PRT
<213> ORGANISM: Candida tropicalis
<220> FEATURE:
<223> OTHER INFORMATION: ADH P1

<400> SEQUENCE: 156

Val Lys Tyr Ser Gly Val Cys His
1 5

<210> SEQ ID NO 157
<211> LENGTH: 11
<212> TYPE: PRT
<213> ORGANISM: Candida tropicalis
<220> FEATURE:
<223> OTHER INFORMATION: ADH P2

<400> SEQUENCE: 157

Val Gly Gly His Glu Gly Ala Gly Val Val Val
1 5 10

<210> SEQ ID NO 158
<211> LENGTH: 11
<212> TYPE: PRT
<213> ORGANISM: Candida tropicalis
<220> FEATURE:
<223> OTHER INFORMATION: ADH P3

<400> SEQUENCE: 158

Gln Tyr Ala Thr Ala Asp Ala Val Gln Ala Ala
1 5 10

<210> SEQ ID NO 159
<211> LENGTH: 11
<212> TYPE: PRT
<213> ORGANISM: Candida tropicalis
<220> FEATURE:
<223> OTHER INFORMATION: ADH P4

<400> SEQUENCE: 159

Cys Ala Gly Val Thr Val Tyr Lys Ala Leu Lys
1 5 10

<210> SEQ ID NO 160
<211> LENGTH: 9
<212> TYPE: PRT
<213> ORGANISM: Candida tropicalis
<220> FEATURE:
<223> OTHER INFORMATION: ADH P5

<400> SEQUENCE: 160

Gly Gln Trp Val Ala Ile Ser Gly Ala
1 5

<210> SEQ ID NO 161
<211> LENGTH: 394
<212> TYPE: DNA
<213> ORGANISM: Candida tropicalis
<220> FEATURE:
<223> OTHER INFORMATION: ICL Core - Minimal isocitrate lyase promoter

<400> SEQUENCE: 161
ataatacagg aaaggtgtgt cggtgaattt ccatctatcc gaggatatga gtggaggaga 60
gtcgtgtgcg tgtggttaat ttaggatcag tggaacacac aaagtaacta agacagagag 120

```
acagagagaa aaatctgggg aagagacaaa gagtcagagt gtgtgagtta ttctgtattg    180

tgaaattttt ttgcccaact acataatatt gctgaaacta attttactta aaaagaaaag    240

ccaacaacgt ccccagtaaa acttttctat aaatatcagc agttttccct ttcctccatt    300

cctcttcttg tctttttctt tactttccct tttttatacc ttttcattat catcctttat    360

aattgtctaa ccaacaacta tatatctatc aacc                                394


<210> SEQ ID NO 162
<211> LENGTH: 18
<212> TYPE: PRT
<213> ORGANISM: Candida tropicalis
<220> FEATURE:
<221> NAME/KEY: VARIANT
<222> LOCATION: 9, 10, 11, 12, 13
<223> OTHER INFORMATION: Xaa = Any Amino Acid

<400> SEQUENCE: 162

Val Lys Tyr Ser Gly Val Cys His Xaa Xaa Xaa Xaa Xaa Trp Lys Gly
 1               5                   10                  15

Asp Trp


<210> SEQ ID NO 163
<211> LENGTH: 37
<212> TYPE: PRT
<213> ORGANISM: Candida tropicalis
<220> FEATURE:
<221> NAME/KEY: VARIANT
<222> LOCATION: 9, 10, 11, 12, 13, 19, 20, 21, 22, 26
<223> OTHER INFORMATION: Xaa = Any Amino Acid

<400> SEQUENCE: 163

Val Lys Tyr Ser Gly Val Cys His Xaa Xaa Xaa Xaa Xaa Trp Lys Gly
 1               5                   10                  15

Asp Trp Xaa Xaa Xaa Xaa Lys Leu Pro Xaa Val Gly Gly His Glu Gly
            20                  25                  30

Ala Gly Val Val Val
        35


<210> SEQ ID NO 164
<211> LENGTH: 21
<212> TYPE: PRT
<213> ORGANISM: Candida tropicalis
<220> FEATURE:
<221> NAME/KEY: VARIANT
<222> LOCATION: 4, 8, 10
<223> OTHER INFORMATION: Xaa = Any Amino Acid

<400> SEQUENCE: 164

Ser Gly Tyr Xaa His Asp Gly Xaa Phe Xaa Gln Tyr Ala Thr Ala Asp
 1               5                   10                  15

Ala Val Gln Ala Ala
            20


<210> SEQ ID NO 165
<211> LENGTH: 32
<212> TYPE: PRT
<213> ORGANISM: Candida tropicalis
<220> FEATURE:
<221> NAME/KEY: VARIANT
<222> LOCATION: 7, 8, 11, 15, 19, 21
<223> OTHER INFORMATION: Xaa = Any Amino Acid

<400> SEQUENCE: 165

Gly Ala Glu Pro Asn Cys Xaa Xaa Ala Asp Xaa Ser Gly Tyr Xaa His
 1               5                   10                  15
```

```
Asp Gly Xaa Phe Xaa Gln Tyr Ala Thr Ala Asp Ala Val Gln Ala Ala
            20                  25                  30


<210> SEQ ID NO 166
<211> LENGTH: 15
<212> TYPE: PRT
<213> ORGANISM: Candida tropicalis
<220> FEATURE:
<221> NAME/KEY: VARIANT
<222> LOCATION: 4
<223> OTHER INFORMATION: Xaa = Any Amino Acid

<400> SEQUENCE: 166

Ala Pro Ile Xaa Cys Ala Gly Val Thr Val Tyr Lys Ala Leu Lys
 1               5                  10                  15


<210> SEQ ID NO 167
<211> LENGTH: 16
<212> TYPE: PRT
<213> ORGANISM: Candida tropicalis
<220> FEATURE:
<221> NAME/KEY: VARIANT
<222> LOCATION: 10
<223> OTHER INFORMATION: Xaa = Any Amino Acid

<400> SEQUENCE: 167

Gly Gln Trp Val Ala Ile Ser Gly Ala Xaa Gly Gly Leu Gly Ser Leu
 1               5                  10                  15


<210> SEQ ID NO 168
<211> LENGTH: 21
<212> TYPE: PRT
<213> ORGANISM: Candida tropicalis
<220> FEATURE:
<221> NAME/KEY: VARIANT
<222> LOCATION: 10, 17
<223> OTHER INFORMATION: Xaa = Any Amino Acid

<400> SEQUENCE: 168

Gly Gln Trp Val Ala Ile Ser Gly Ala Xaa Gly Gly Leu Gly Ser Leu
 1               5                  10                  15

Xaa Val Gln Tyr Ala
            20


<210> SEQ ID NO 169
<211> LENGTH: 25
<212> TYPE: PRT
<213> ORGANISM: Candida tropicalis
<220> FEATURE:
<221> NAME/KEY: VARIANT
<222> LOCATION: 10, 17, 22
<223> OTHER INFORMATION: Xaa = Any Amino Acid

<400> SEQUENCE: 169

Gly Gln Trp Val Ala Ile Ser Gly Ala Xaa Gly Gly Leu Gly Ser Leu
 1               5                  10                  15

Xaa Val Gln Tyr Ala Xaa Ala Met Gly
            20                  25


<210> SEQ ID NO 170
<211> LENGTH: 34
<212> TYPE: PRT
<213> ORGANISM: Candida tropicalis
<220> FEATURE:
<221> NAME/KEY: VARIANT
<222> LOCATION: 10, 17, 22, 26, 29
<223> OTHER INFORMATION: Xaa = Any Amino Acid
```

<400> SEQUENCE: 170

```
Gly Gln Trp Val Ala Ile Ser Gly Ala Xaa Gly Gly Leu Gly Ser Leu
 1               5                  10                  15

Xaa Val Gln Tyr Ala Xaa Ala Met Gly Xaa Arg Val Xaa Ala Ile Asp
            20                  25                  30

Gly Gly
```

<210> SEQ ID NO 171
<211> LENGTH: 1530
<212> TYPE: DNA
<213> ORGANISM: Candida tropicalis
<220> FEATURE:
<223> OTHER INFORMATION: ICL(isocitrate lyase gene) promoter (GenBank accession no. S77426)

<400> SEQUENCE: 171

```
ggatccgtct gaagaaatca agaaccaaca gttggatatc atcaagggaa tattaggcga     60

agaggcatct agtagtagtg gcagtggtga gaacgtgggc gctgctatag tgaacaatct    120

ccagtcgatg gttaagaaga agagtgacaa accagcagtg aatgacttgt ctgggtccgt    180

gaggaaaaga aagaagcccg acacaaagga cagtaacgtc aagaaaccca agaaataggg    240

gggacctgtt tagatgtata ggaataaaaa ctccgagatg atctcaatgt gtaatggagt    300

tgtaatattg caaaggggga aaatcaagac tcaaacgtgt gtatgagtga gcgtacgtat    360

atctccgaga gtagtatgac ataatgatga ctgtgaatca tcgtaatctc acacaaaaac    420

cccattgtcg gccatatacc acaccaagca acaccacata tcccccggaa aaaaaaacgt    480

gaaaaaaaga aacaatcaaa actacaacct actccttgat cacacagtca ttgatcaagt    540

tacagttcct gctagggaat gaccaaggta caaatcagca ccttaatggt tagcacgctc    600

tcttactctc tctcacagtc ttccggcccc tattcaaaat tctgcacttc catttgaccc    660

cagggttggg aaacagggcc acaaaagaaa aacccgacgt gaatgaaaaa actaagaaaa    720

gaaaaaaaat tatcacacca gaaatttacc taattgggta attcccatcg gtgtttttcc    780

tggattgtcg cacgcacgca tgctgaaaaa agtgttcgag ttttgctttt gcctcggagt    840

ttcacgcaag tttttcgatc tcggaaccgg agggcggtcg ccttgttgtt tgtgatgtcg    900

tgctttgggt gttctaatgt gctgttattg tgctcttttt ttttcttctt tttttggtga    960

tcatatgata ttgctcggta gattactttc gtgtgtaggt attcttttag acgtttggtt   1020

attgggtaga tatgagagag agagagtggg tgggggagga gttggttgta ggagggaccc   1080

ctgggaggaa gtgtagttga gttttccctg acgaatgaaa atacgttttt gagaagataa   1140

tacaggaaag gtgtgtcggt gaatttccat ctatccgagg atatgagtgg aggagagtcg   1200

tgtgcgtgtg gttaatttag gatcagtgga acacacaaag taactaagac agagagacag   1260

agagaaaaat ctggggaaga gacaaagagt cagagtgtgt gagttattct gtattgtgaa   1320

atttttttgc ccaactacat aatattgctg aaactaattt tacttaaaaa gaaaagccaa   1380

caacgtcccc agtaaaactt ttctataaat atcagcagtt ttccctttcc tccattcctc   1440

ttcttgtctt ttttcttact ttccctttt tataccttt cattatcatc ctttataatt   1500

gtctaaccaa caactatata tctatcaacc                                    1530
```

<210> SEQ ID NO 172
<211> LENGTH: 434
<212> TYPE: PRT
<213> ORGANISM: Candida albicans
<220> FEATURE:
<223> OTHER INFORMATION: ADH1A (434 Amino acid sequence)

<400> SEQUENCE: 172

```
Met Gln Ala Ser Leu Phe Arg Ile Phe Arg Gly Ala Ser Leu Thr Thr
1               5                   10                  15

Thr Thr Ala Ala Ala Ser Phe Thr Ala Thr Ala Thr Ala Gly Ala Thr
            20                  25                  30

Thr Ala Lys Thr Leu Ser Gly Ser Thr Val Leu Arg Lys Ser Tyr Lys
        35                  40                  45

Arg Thr Tyr Ser Ser Ser Val Leu Ser Ser Pro Glu Leu Phe Phe Phe
    50                  55                  60

His Gln Phe Asn Asn Asn Lys Arg Tyr Cys His Thr Thr Thr Thr Thr
65                  70                  75                  80

Asn Thr Lys Thr Ile Met Ser Glu Gln Ile Pro Lys Thr Gln Lys Ala
                85                  90                  95

Val Val Phe Asp Thr Asn Gly Gly Gln Leu Val Tyr Lys Asp Tyr Pro
            100                 105                 110

Val Pro Thr Pro Lys Pro Asn Glu Leu Leu Ile His Val Lys Tyr Ser
        115                 120                 125

Gly Val Cys His Thr Asp Leu His Ala Trp Lys Gly Asp Trp Pro Leu
    130                 135                 140

Ala Thr Lys Leu Pro Leu Val Gly Gly His Glu Gly Ala Gly Val Val
145                 150                 155                 160

Val Gly Met Gly Glu Asn Val Lys Gly Trp Lys Ile Gly Asp Phe Ala
                165                 170                 175

Gly Ile Lys Trp Leu Asn Gly Ser Cys Met Ser Cys Glu Phe Cys Gln
            180                 185                 190

Gln Gly Ala Glu Pro Asn Cys Gly Glu Ala Asp Leu Ser Gly Tyr Thr
        195                 200                 205

His Asp Gly Ser Phe Glu Gln Tyr Ala Thr Ala Asp Ala Val Gln Ala
    210                 215                 220

Ala Lys Ile Pro Ala Gly Thr Asp Leu Ala Asn Val Ala Pro Ile Leu
225                 230                 235                 240

Cys Ala Gly Val Thr Val Tyr Lys Ala Leu Lys Thr Ala Asp Leu Ala
                245                 250                 255

Ala Gly Gln Trp Val Ala Ile Ser Gly Ala Gly Gly Gly Leu Gly Ser
            260                 265                 270

Leu Ala Val Gln Tyr Ala Arg Ala Met Gly Leu Arg Val Val Ala Ile
        275                 280                 285

Asp Gly Gly Asp Glu Lys Gly Glu Phe Val Lys Ser Leu Gly Ala Glu
    290                 295                 300

Ala Tyr Val Asp Phe Thr Lys Asp Lys Asp Ile Val Glu Ala Val Lys
305                 310                 315                 320

Lys Ala Thr Asp Gly Gly Pro His Gly Ala Ile Asn Val Ser Val Ser
                325                 330                 335

Glu Lys Ala Ile Asp Gln Ser Val Glu Tyr Val Arg Pro Leu Gly Lys
            340                 345                 350

Val Val Leu Val Gly Leu Pro Ala His Ala Lys Val Thr Ala Pro Val
        355                 360                 365

Phe Asp Ala Val Val Lys Ser Ile Glu Ile Lys Gly Ser Tyr Val Gly
    370                 375                 380

Asn Arg Lys Asp Thr Ala Glu Ala Ile Asp Phe Phe Ser Arg Gly Leu
385                 390                 395                 400

Ile Lys Cys Pro Ile Lys Ile Val Gly Leu Ser Asp Leu Pro Glu Val
                405                 410                 415
```

```
Phe Lys Leu Met Glu Glu Gly Lys Ile Leu Ser Arg Tyr Val Leu Asp
            420                 425                 430

Thr Ser


<210> SEQ ID NO 173
<211> LENGTH: 435
<212> TYPE: PRT
<213> ORGANISM: Candida albicans
<220> FEATURE:
<223> OTHER INFORMATION: ADH1B (435 Amino acid sequence)

<400> SEQUENCE: 173

Met Glu Ala Arg Phe Phe Arg Ile Phe Lys Gly Gly Ser Leu Thr Thr
 1               5                  10                  15

Thr Thr Ala Ala Ala Ser Phe Thr Ala Thr Ala Thr Ala Gly Ala Thr
            20                  25                  30

Thr Ala Lys Thr Leu Ser Gly Ser Thr Val Leu Arg Lys Ser Tyr Lys
        35                  40                  45

Arg Thr Tyr Ser Ser Ser Val Leu Ser Ser Pro Glu Leu Phe Phe Phe
    50                  55                  60

His Gln Phe Asn Asn Asn Lys Arg Tyr Cys His Thr Thr Thr Thr Thr
65                  70                  75                  80

Asn Thr Lys Thr Ile Met Ser Glu Gln Ile Pro Lys Thr Gln Lys Ala
                85                  90                  95

Val Val Phe Asp Thr Asn Gly Gly Gln Leu Val Tyr Lys Asp Tyr Pro
            100                 105                 110

Val Pro Thr Pro Lys Pro Asn Glu Leu Leu Ile Asn Val Lys Tyr Ser
        115                 120                 125

Gly Val Cys His Thr Asp Leu His Ala Trp Lys Gly Asp Trp Pro Leu
    130                 135                 140

Ala Thr Lys Leu Pro Leu Val Gly Gly His Glu Gly Ala Gly Val Val
145                 150                 155                 160

Val Gly Met Gly Glu Asn Val Lys Gly Trp Lys Ile Gly Asp Phe Ala
                165                 170                 175

Gly Ile Lys Trp Leu Asn Gly Ser Cys Met Ser Cys Glu Phe Cys Gln
            180                 185                 190

Gln Gly Ala Glu Pro Asn Cys Gly Glu Ala Asp Leu Ser Gly Tyr Thr
        195                 200                 205

His Asp Gly Ser Phe Glu Gln Tyr Ala Thr Ala Asp Ala Val Gln Ala
    210                 215                 220

Ala Lys Ile Pro Ala Gly Thr Asp Leu Ala Asn Val Ala Pro Ile Leu
225                 230                 235                 240

Cys Ala Gly Val Thr Val Tyr Lys Ala Leu Lys Thr Ala Asp Leu Ala
                245                 250                 255

Ala Gly Gln Trp Val Ala Ile Ser Gly Ala Gly Gly Gly Leu Gly Ser
            260                 265                 270

Leu Ala Val Gln Tyr Ala Arg Ala Met Gly Leu Arg Val Val Ala Ile
        275                 280                 285

Asp Gly Gly Asp Glu Lys Gly Glu Phe Val Lys Ser Leu Gly Ala Glu
    290                 295                 300

Ala Tyr Val Asp Phe Thr Lys Asp Lys Asp Ile Val Glu Ala Val Lys
305                 310                 315                 320

Lys Ala Thr Asp Gly Gly Pro His Gly Ala Ile Asn Val Ser Val Ser
                325                 330                 335

Glu Lys Ala Ile Asp Gln Ser Val Glu Tyr Val Arg Pro Leu Gly Lys
```

```
            340                 345                 350

Val Val Leu Val Gly Leu Pro Ala His Ala Lys Val Thr Ala Pro Val
        355                 360                 365

Phe Asp Ala Val Val Lys Ser Ile Glu Ile Lys Gly Ser Tyr Val Gly
    370                 375                 380

Asn Arg Lys Asp Thr Ala Glu Ala Ile Asp Phe Phe Ser Arg Gly Leu
385                 390                 395                 400

Ile Lys Cys Pro Ile Lys Ile Val Gly Leu Ser Asp Leu Pro Glu Val
                405                 410                 415

Phe Lys Leu Met Glu Glu Gly Lys Ile Leu Gly Arg Tyr Val Leu Asp
            420                 425                 430

Thr Ser Lys
        435


<210> SEQ ID NO 174
<211> LENGTH: 348
<212> TYPE: PRT
<213> ORGANISM: Candida albicans
<220> FEATURE:
<223> OTHER INFORMATION: ADH2A (348 Amino acid sequence)

<400> SEQUENCE: 174

Met Ser Val Pro Thr Thr Gln Lys Ala Val Ile Phe Glu Thr Asn Gly
 1               5                  10                  15

Gly Lys Leu Glu Tyr Lys Asp Ile Pro Val Pro Lys Pro Lys Ala Asn
            20                  25                  30

Glu Leu Leu Ile Asn Val Lys Tyr Ser Gly Val Cys His Thr Asp Leu
        35                  40                  45

His Ala Trp Lys Gly Asp Trp Pro Leu Ala Thr Lys Leu Pro Leu Val
    50                  55                  60

Gly Gly His Glu Gly Ala Gly Val Val Val Ala Leu Gly Glu Asn Val
65                  70                  75                  80

Lys Gly Trp Lys Val Gly Asp Tyr Ala Gly Val Lys Trp Leu Asn Gly
                85                  90                  95

Ser Cys Leu Asn Cys Glu Tyr Cys Gln Ser Gly Ala Glu Pro Asn Cys
            100                 105                 110

Ala Glu Ala Asp Leu Ser Gly Tyr Thr His Asp Gly Ser Phe Gln Gln
        115                 120                 125

Tyr Ala Thr Ala Asp Ala Val Gln Ala Ala Arg Ile Pro Ala Gly Thr
    130                 135                 140

Asp Leu Ala Asn Val Ala Pro Ile Leu Cys Ala Gly Val Thr Val Tyr
145                 150                 155                 160

Lys Ala Leu Lys Thr Ala Glu Leu Glu Ala Gly Gln Trp Val Ala Ile
                165                 170                 175

Ser Gly Ala Ala Gly Gly Leu Gly Ser Leu Ala Val Gln Tyr Ala Lys
            180                 185                 190

Ala Met Gly Tyr Arg Val Leu Ala Ile Asp Gly Gly Glu Asp Lys Gly
        195                 200                 205

Glu Phe Val Lys Ser Leu Gly Ala Glu Thr Phe Ile Asp Phe Thr Lys
    210                 215                 220

Glu Lys Asp Val Val Glu Ala Val Lys Lys Ala Thr Asn Gly Gly Pro
225                 230                 235                 240

His Gly Val Ile Asn Val Ser Val Ser Glu Arg Ala Ile Gly Gln Ser
                245                 250                 255

Thr Glu Tyr Val Arg Thr Leu Gly Lys Val Val Leu Val Gly Leu Pro
            260                 265                 270
```

```
Ala Gly Ala Lys Ile Ser Thr Pro Val Phe Asp Ala Val Ile Lys Thr
        275                 280                 285

Ile Gln Ile Lys Gly Ser Tyr Val Gly Asn Arg Lys Asp Thr Ala Glu
    290                 295                 300

Ala Val Asp Phe Phe Thr Arg Gly Leu Ile Lys Cys Pro Ile Lys Ile
305                 310                 315                 320

Val Gly Leu Ser Glu Leu Pro Glu Val Tyr Lys Leu Met Glu Glu Gly
                325                 330                 335

Lys Ile Leu Gly Arg Tyr Val Leu Asp Asn Asp Lys
            340                 345


<210> SEQ ID NO 175
<211> LENGTH: 348
<212> TYPE: PRT
<213> ORGANISM: Candida albicans
<220> FEATURE:
<223> OTHER INFORMATION: AADH2B (348 amin acid sequence)

<400> SEQUENCE: 175

Met Ser Val Pro Thr Thr Gln Lys Ala Val Ile Phe Glu Thr Asn Gly
 1               5                  10                  15

Gly Lys Leu Glu Tyr Lys Asp Ile Pro Val Pro Lys Pro Lys Ala Asn
            20                  25                  30

Glu Leu Leu Ile Asn Val Lys Tyr Ser Gly Val Cys His Thr Asp Leu
        35                  40                  45

His Ala Trp Lys Gly Asp Trp Pro Leu Ala Thr Lys Leu Pro Leu Val
    50                  55                  60

Gly Gly His Glu Gly Ala Gly Val Val Val Ala Leu Gly Glu Asn Val
65                  70                  75                  80

Lys Gly Trp Lys Val Gly Asp Tyr Ala Gly Val Lys Trp Leu Asn Gly
                85                  90                  95

Ser Cys Leu Asn Cys Glu Tyr Cys Gln Ser Gly Ala Glu Pro Asn Cys
            100                 105                 110

Ala Glu Ala Asp Leu Ser Gly Tyr Thr His Asp Gly Ser Phe Gln Gln
        115                 120                 125

Tyr Ala Thr Ala Asp Ala Val Gln Ala Ala Arg Ile Pro Ala Gly Thr
    130                 135                 140

Asp Leu Ala Asn Val Ala Pro Ile Leu Cys Ala Gly Val Thr Val Tyr
145                 150                 155                 160

Lys Ala Leu Lys Thr Ala Glu Leu Glu Ala Gly Gln Trp Val Ala Ile
                165                 170                 175

Ser Gly Ala Ala Gly Gly Leu Gly Ser Leu Ala Val Gln Tyr Ala Lys
            180                 185                 190

Ala Met Gly Tyr Arg Val Leu Ala Ile Asp Gly Gly Glu Asp Lys Gly
        195                 200                 205

Glu Phe Val Lys Ser Leu Gly Ala Glu Thr Phe Ile Asp Phe Thr Lys
    210                 215                 220

Glu Lys Asp Val Val Glu Ala Val Lys Lys Ala Thr Asn Gly Gly Pro
225                 230                 235                 240

His Gly Val Ile Asn Val Ser Val Ser Glu Arg Ala Ile Gly Gln Ser
                245                 250                 255

Thr Glu Tyr Val Arg Thr Leu Gly Lys Val Val Leu Val Gly Leu Pro
            260                 265                 270

Ala Gly Ala Lys Ile Ser Thr Pro Val Phe Asp Ala Val Ile Lys Thr
        275                 280                 285
```

-continued

```
Ile Gln Ile Lys Gly Ser Tyr Val Gly Asn Arg Lys Asp Thr Ala Glu
    290                 295                 300

Ala Val Asp Phe Phe Thr Arg Gly Leu Ile Lys Cys Pro Ile Lys Ile
305                 310                 315                 320

Val Gly Leu Ser Glu Leu Pro Glu Val Tyr Lys Leu Met Glu Glu Gly
                325                 330                 335

Lys Ile Leu Gly Arg Tyr Val Leu Asp Asn Asp Lys
            340                 345
```